United States Patent
Igawa et al.

(10) Patent No.: US 11,891,434 B2
(45) Date of Patent: Feb. 6, 2024

(54) ANTIGEN-BINDING MOLECULE CAPABLE OF BINDING TO PLURALITY OF ANTIGEN MOLECULES REPEATEDLY

(71) Applicant: Chugai Seiyaku Kabushiki Kaisha, Tokyo (JP)

(72) Inventors: Tomoyuki Igawa, Shizuoka (JP); Shinya Ishii, Shizuoka (JP); Miho Funaki, Shizuoka (JP); Naoka Hironiwa, Shizuoka (JP); Atsuhiko Maeda, Shizuoka (JP); Junichi Nezu, Shizuoka (JP); Yoshinao Ruike, Shizuoka (JP); Takeshi Baba, Shizuoka (JP); Shun Shimizu, Shizuoka (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

(21) Appl. No.: 15/988,348

(22) Filed: May 24, 2018

(65) Prior Publication Data
US 2018/0258161 A1    Sep. 13, 2018

Related U.S. Application Data

(62) Division of application No. 13/990,158, filed as application No. PCT/JP2011/077619 on Nov. 30, 2011, now abandoned.

(30) Foreign Application Priority Data

Nov. 30, 2010 (JP) .................................. 2010-266121
Sep. 30, 2011 (JP) .................................. 2011-217886

(51) Int. Cl.
C07K 16/18       (2006.01)
C07K 16/24       (2006.01)
C07K 16/28       (2006.01)
C07K 16/42       (2006.01)
G01N 33/53       (2006.01)

(52) U.S. Cl.
CPC ............ *C07K 16/18* (2013.01); *C07K 16/248* (2013.01); *C07K 16/2866* (2013.01); *C07K 16/4291* (2013.01); *G01N 33/53* (2013.01); *C07K 2317/565* (2013.01)

(58) Field of Classification Search
None
See application file for complete search history.

(56) References Cited

U.S. PATENT DOCUMENTS

| 4,689,299 | A | 8/1987 | Insel et al. |
|---|---|---|---|
| 4,801,687 | A | 1/1989 | Ngo |
| 5,126,250 | A | 6/1992 | Mcdonough et al. |
| 5,202,253 | A | 4/1993 | Esmon et al. |
| 5,322,678 | A | 6/1994 | Morgan et al. |
| 5,468,634 | A | 11/1995 | Liu |
| 5,501,854 | A | 3/1996 | Raso |
| 5,585,089 | A | 12/1996 | Queen et al. |
| 5,670,373 | A | 9/1997 | Kishimoto |
| 5,747,422 | A | 5/1998 | Schafer et al. |
| 5,795,965 | A | 8/1998 | Tsuchiya et al. |
| 5,817,790 | A | 10/1998 | Tsuchiya et al. |
| 5,827,733 | A | 10/1998 | Lee et al. |
| 5,830,478 | A | 11/1998 | Raso et al. |
| 5,935,935 | A | 8/1999 | Connelly et al. |
| 5,945,311 | A | 8/1999 | Lindhofer et al. |
| 5,994,524 | A | 11/1999 | Matsushima et al. |
| 6,018,032 | A | 1/2000 | Koike et al. |
| 6,024,956 | A | 2/2000 | Matsushima et al. |
| 6,025,158 | A | 2/2000 | Gonzalez et al. |
| 6,074,642 | A | 6/2000 | Wang et al. |
| 6,096,506 | A | 8/2000 | Lee et al. |
| 6,165,745 | A | 12/2000 | Ward et al. |

(Continued)

FOREIGN PATENT DOCUMENTS

| AR | 068564 | 11/2009 |
|---|---|---|
| AU | 2007255753 | 12/2007 |

(Continued)

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Ito et al., FEBS Letters 309(1): 85-88 (Year: 2008).*
Rudikoff et al., Proc. Natl. Acad. Sci. USA vol. 79 p. 1979 (Year: 1982).*

(Continued)

*Primary Examiner* — Phuong Huynh
(74) *Attorney, Agent, or Firm* — Fish & Richardson P.C.

(57) ABSTRACT

An objective of the present invention is to provide methods for promoting antigen uptake into cells by antigen-binding molecules, methods for increasing the number of times of antigen binding by one antigen-binding molecule, methods for promoting reduction of the antigen concentration in plasma by administering antigen-binding molecules, and methods for improving the plasma retention of an antigen-binding molecule, as well as antigen-binding molecules that allow enhanced antigen uptake into cells, antigen-binding molecules having an increased number of times of antigen binding, antigen-binding molecules that can promote reduction of the antigen concentration in plasma when administered, antigen-binding molecules with improved plasma retention, pharmaceutical compositions comprising the above antigen-binding molecules, and methods for producing them. The present inventors revealed that the above objective can be achieved by using antigen-binding molecules that show calcium-dependent antigen-antibody reaction.

32 Claims, 56 Drawing Sheets

Specification includes a Sequence Listing.

(56) References Cited

U.S. PATENT DOCUMENTS

| | | |
|---|---|---|
| 6,245,894 B1 | 6/2001 | Matsushima et al. |
| 6,309,636 B1 | 10/2001 | do Couto et al. |
| 6,329,511 B1 | 12/2001 | Vasquez et al. |
| 6,355,245 B1 | 3/2002 | Evans et al. |
| 6,458,355 B1 | 10/2002 | Hsei et al. |
| 6,723,319 B1 | 4/2004 | Ito et al. |
| 6,737,056 B1 | 5/2004 | Presta |
| 6,821,505 B2 | 11/2004 | Ward |
| 7,052,873 B2 | 5/2006 | Tsuchiya |
| 7,247,302 B1 | 7/2007 | Rosok et al. |
| 7,261,893 B2 | 8/2007 | Geertruida et al. |
| 7,276,585 B2 | 10/2007 | Lazar et al. |
| 7,282,568 B2 | 10/2007 | Teeling et al. |
| 7,320,789 B2 | 1/2008 | Aghajanian et al. |
| 7,371,826 B2 | 5/2008 | Presta |
| 7,432,356 B2 | 10/2008 | Fung et al. |
| 7,479,543 B2 | 1/2009 | Tsuchiya et al. |
| 7,482,440 B2 | 1/2009 | Maeda et al. |
| 7,632,497 B2 | 12/2009 | Stavenhagen et al. |
| 7,632,499 B2 | 12/2009 | Davies et al. |
| 7,662,925 B2 | 2/2010 | Lazar et al. |
| 7,670,600 B2 | 3/2010 | Dall Acqua et al. |
| 7,785,791 B2 | 8/2010 | Presta |
| 7,807,159 B2 | 10/2010 | Chin et al. |
| 7,888,486 B2 | 2/2011 | Walsh et al. |
| 7,960,512 B2 | 6/2011 | Stavenhagen et al. |
| 8,062,635 B2 | 11/2011 | Hattori et al. |
| 8,101,720 B2 | 1/2012 | Lazar et al. |
| 8,147,829 B2 | 4/2012 | Hariharan et al. |
| 8,188,231 B2 | 5/2012 | Lazar et al. |
| 8,323,962 B2 | 12/2012 | Dall Acqua et al. |
| 8,329,867 B2 | 12/2012 | Lazar et al. |
| 8,367,805 B2 | 2/2013 | Chamberlain et al. |
| 8,388,955 B2 | 3/2013 | Lazar et al. |
| 8,415,459 B2 | 4/2013 | La Vallie et al. |
| 8,562,991 B2 | 10/2013 | Igawa et al. |
| 8,568,726 B2 | 10/2013 | Beaumont et al. |
| 8,604,174 B2 | 12/2013 | Babcook et al. |
| 8,637,641 B2 | 1/2014 | Dahiyat et al. |
| 8,753,629 B2 | 6/2014 | Lazar et al. |
| 8,802,820 B2 | 8/2014 | Chamberlain et al. |
| 9,029,515 B2 | 5/2015 | Pons et al. |
| 9,051,373 B2 | 6/2015 | Lazar et al. |
| 9,079,949 B1 | 7/2015 | Andrien et al. |
| 9,605,061 B2 | 3/2017 | Lazar et al. |
| 9,701,759 B2 | 7/2017 | Desjarlais et al. |
| 9,765,135 B2 | 9/2017 | Ruike et al. |
| 9,868,948 B2 | 1/2018 | Igawa et al. |
| 9,890,377 B2 | 2/2018 | Igawa et al. |
| 9,969,800 B2 | 5/2018 | Igawa et al. |
| 10,000,560 B2 | 6/2018 | Ruike et al. |
| 10,023,630 B2 | 7/2018 | Ruike et al. |
| 10,024,867 B2 | 7/2018 | Igawa |
| 10,253,100 B2 | 4/2019 | Igawa et al. |
| 10,385,122 B2 | 8/2019 | Ruike et al. |
| 10,472,623 B2 | 11/2019 | Igawa et al. |
| 10,519,229 B2 | 12/2019 | Igawa et al. |
| 10,618,965 B2 | 4/2020 | Igawa et al. |
| 10,662,245 B2 | 5/2020 | Igawa et al. |
| 10,738,111 B2 | 8/2020 | Ruike et al. |
| 10,774,148 B2 | 9/2020 | Kakehi et al. |
| 11,053,308 B2 | 7/2021 | Kakiuchi et al. |
| 11,180,548 B2 | 11/2021 | Igawa et al. |
| 11,359,009 B2 | 6/2022 | Ruike et al. |
| 11,359,194 B2 | 6/2022 | Igawa et al. |
| 11,371,039 B2 | 6/2022 | Igawa et al. |
| 11,454,633 B2 | 9/2022 | Ruike et al. |
| 2001/0001663 A1 | 5/2001 | Kishimoto et al. |
| 2002/0082396 A1 | 6/2002 | Matsushima et al. |
| 2002/0098193 A1 | 7/2002 | Ward |
| 2002/0142374 A1 | 10/2002 | Gallo et al. |
| 2002/0187150 A1 | 12/2002 | Mihara et al. |
| 2003/0059937 A1 | 3/2003 | Ruben et al. |
| 2003/0077283 A1 | 4/2003 | Ye |
| 2003/0125520 A1 | 7/2003 | Maeda et al. |
| 2003/0215838 A1 | 11/2003 | Sprecher et al. |
| 2003/0224487 A1 | 12/2003 | Sprecher et al. |
| 2004/0058393 A1 | 3/2004 | Fukishima et al. |
| 2004/0071706 A1 | 4/2004 | Ito et al. |
| 2004/0081651 A1 | 4/2004 | Karpusas et al. |
| 2004/0110226 A1 | 6/2004 | Lazar et al. |
| 2004/0133357 A1 | 7/2004 | Zhong et al. |
| 2004/0223970 A1 | 11/2004 | Afar et al. |
| 2004/0236080 A1 | 11/2004 | Aburatani et al. |
| 2005/0014934 A1 | 1/2005 | Hinton et al. |
| 2005/0130224 A1 | 6/2005 | Saito et al. |
| 2005/0142635 A1 | 6/2005 | Tsuchiya et al. |
| 2005/0191293 A1 | 9/2005 | Deshpande et al. |
| 2005/0260711 A1 | 11/2005 | Datta et al. |
| 2005/0261229 A1 | 11/2005 | Gillies et al. |
| 2006/0014156 A1 | 1/2006 | Rabbani et al. |
| 2006/0019342 A1 | 1/2006 | Dall Acqua et al. |
| 2006/0134709 A1 | 6/2006 | Stavenhagen et al. |
| 2006/0141456 A1 | 6/2006 | Edwards et al. |
| 2006/0153860 A1 | 7/2006 | Cho et al. |
| 2006/0182743 A1 | 8/2006 | Bilsborough |
| 2006/0194280 A1 | 8/2006 | Dillon et al. |
| 2006/0275282 A1 | 12/2006 | Moore et al. |
| 2006/0292147 A1 | 12/2006 | Yoshizaki et al. |
| 2007/0009523 A1 | 1/2007 | Presta |
| 2007/0036785 A1 | 2/2007 | Kishimoto et al. |
| 2007/0037734 A1 | 2/2007 | Rossi et al. |
| 2007/0041978 A1 | 2/2007 | Hattori et al. |
| 2007/0110747 A1 | 5/2007 | Paszty et al. |
| 2007/0135620 A1 | 6/2007 | Chamberlain et al. |
| 2007/0148164 A1 | 6/2007 | Farrington et al. |
| 2007/0160598 A1 | 7/2007 | Dennis et al. |
| 2007/0160611 A1 | 7/2007 | Yao et al. |
| 2007/0190056 A1 | 8/2007 | Kambadur et al. |
| 2007/0224188 A1 | 9/2007 | Allan et al. |
| 2007/0231329 A1 | 10/2007 | Lazar et al. |
| 2007/0237767 A1 | 10/2007 | Lazar et al. |
| 2007/0253951 A1 | 11/2007 | Ng et al. |
| 2007/0269371 A1 | 11/2007 | Krummen et al. |
| 2007/0280945 A1 | 12/2007 | Stevens et al. |
| 2008/0050370 A1 | 2/2008 | Glaser et al. |
| 2008/0075712 A1 | 3/2008 | Hattori et al. |
| 2008/0089892 A1 | 4/2008 | Allan et al. |
| 2008/0125579 A1 | 5/2008 | Owens et al. |
| 2008/0166756 A1 | 7/2008 | Tsuchiya et al. |
| 2008/0219971 A1 | 9/2008 | Smith et al. |
| 2009/0041770 A1 | 2/2009 | Chamberlain et al. |
| 2009/0053240 A1 | 2/2009 | Lazar et al. |
| 2009/0060924 A1 | 3/2009 | Korytko et al. |
| 2009/0117097 A1 | 5/2009 | Igawa et al. |
| 2009/0136485 A1 | 5/2009 | Chu et al. |
| 2009/0263392 A1 | 10/2009 | Igawa et al. |
| 2009/0291076 A1 | 11/2009 | Morichika et al. |
| 2009/0324589 A1 | 12/2009 | Igawa et al. |
| 2010/0003254 A1 | 1/2010 | Hattori et al. |
| 2010/0004429 A1 | 1/2010 | Kai et al. |
| 2010/0008907 A1 | 1/2010 | Nishimoto et al. |
| 2010/0015133 A1 | 1/2010 | Igawa et al. |
| 2010/0055092 A1 | 3/2010 | Hasegawa et al. |
| 2010/0098730 A1 | 4/2010 | Lowman et al. |
| 2010/0099147 A1 | 4/2010 | Hariharan et al. |
| 2010/0129365 A1 | 5/2010 | Kim et al. |
| 2010/0166748 A1 | 7/2010 | Guild et al. |
| 2010/0184959 A1 | 7/2010 | Guler-Gane et al. |
| 2010/0216187 A1 | 8/2010 | Lasters et al. |
| 2010/0239577 A1 | 9/2010 | Igawa et al. |
| 2010/0247523 A1 | 9/2010 | Kano et al. |
| 2010/0249482 A1 | 9/2010 | Chung et al. |
| 2010/0292443 A1 | 11/2010 | Sabbadini et al. |
| 2010/0297697 A1 | 11/2010 | Ambrosius et al. |
| 2010/0298542 A1 | 11/2010 | Igawa et al. |
| 2010/0316636 A1 | 12/2010 | Radin et al. |
| 2011/0002931 A1 | 1/2011 | Tamburini |
| 2011/0044986 A1 | 2/2011 | Biere-Citron et al. |
| 2011/0059093 A1 | 3/2011 | Bohrmann et al. |
| 2011/0076275 A1 | 3/2011 | Igawa et al. |
| 2011/0098450 A1 | 4/2011 | Igawa et al. |
| 2011/0105724 A1 | 5/2011 | Clegg et al. |
| 2011/0111406 A1 | 5/2011 | Igawa et al. |

(56) References Cited

U.S. PATENT DOCUMENTS

| | | |
|---|---|---|
| 2011/0129459 A1 | 6/2011 | Kuramochi et al. |
| 2011/0135662 A1 | 6/2011 | Finney et al. |
| 2011/0150888 A1 | 6/2011 | Foltz et al. |
| 2011/0229459 A1 | 9/2011 | Kuramochi et al. |
| 2011/0229489 A1 | 9/2011 | Pons et al. |
| 2011/0236374 A1 | 9/2011 | Shitara et al. |
| 2011/0245473 A1 | 10/2011 | Igawa et al. |
| 2012/0009188 A1 | 1/2012 | Behrens et al. |
| 2012/0065379 A1 | 3/2012 | Igawa et al. |
| 2012/0071634 A1 | 3/2012 | Igawa et al. |
| 2012/0121587 A1 | 5/2012 | Maeda et al. |
| 2012/0189639 A1 | 7/2012 | Schebye et al. |
| 2012/0237517 A1 | 9/2012 | Hattori et al. |
| 2012/0238729 A1 | 9/2012 | Kuramochi et al. |
| 2012/0253016 A1 | 10/2012 | Igawa et al. |
| 2012/0301460 A1 | 11/2012 | Bao et al. |
| 2012/0301488 A1 | 11/2012 | Zhang et al. |
| 2012/0303083 A1 | 11/2012 | Agnetti et al. |
| 2013/0011866 A1 | 1/2013 | Igawa et al. |
| 2013/0018174 A1 | 1/2013 | Igawa et al. |
| 2013/0022624 A1 | 1/2013 | Weaver et al. |
| 2013/0064820 A1 | 3/2013 | Magro |
| 2013/0064836 A1 | 3/2013 | Diefenback-Streiber et al. |
| 2013/0085074 A1 | 4/2013 | Walker et al. |
| 2013/0101581 A1 | 4/2013 | Kuramochi et al. |
| 2013/0131319 A1 | 5/2013 | Igawa et al. |
| 2013/0142788 A1 | 6/2013 | Ashman et al. |
| 2013/0209489 A1 | 8/2013 | Han et al. |
| 2013/0247236 A1 | 9/2013 | Mcwhirter et al. |
| 2013/0302399 A1 | 11/2013 | Feldhaus et al. |
| 2013/0303396 A1 | 11/2013 | Igawa et al. |
| 2013/0317203 A1 | 11/2013 | Igawa et al. |
| 2013/0336963 A1 | 12/2013 | Igawa et al. |
| 2014/0056878 A1 | 2/2014 | Mcconnell et al. |
| 2014/0105889 A1 | 4/2014 | Igawa et al. |
| 2014/0127209 A1 | 5/2014 | Grabstein et al. |
| 2014/0227292 A1 | 8/2014 | Flanagan et al. |
| 2014/0234340 A1 | 8/2014 | Igawa et al. |
| 2014/0255398 A1 | 9/2014 | Igawa et al. |
| 2014/0271459 A1 | 9/2014 | Dutzar et al. |
| 2014/0335089 A1 | 11/2014 | Igawa et al. |
| 2014/0363426 A1 | 12/2014 | Moore et al. |
| 2014/0363428 A1 | 12/2014 | Igawa et al. |
| 2015/0050269 A1 | 2/2015 | Igawa et al. |
| 2015/0056182 A1 | 2/2015 | Igawa et al. |
| 2015/0079088 A1 | 3/2015 | Lowman et al. |
| 2015/0166654 A1 | 6/2015 | Igawa et al. |
| 2015/0166666 A1 | 6/2015 | Igawa et al. |
| 2015/0239966 A1 | 8/2015 | Baciu et al. |
| 2015/0247849 A1 | 9/2015 | Tamburini |
| 2015/0299305 A1 | 10/2015 | Andrien et al. |
| 2015/0299313 A1 | 10/2015 | Igawa et al. |
| 2015/0353630 A1 | 12/2015 | Igawa et al. |
| 2016/0039912 A1 | 2/2016 | Mimoto et al. |
| 2016/0046693 A1 | 2/2016 | Igawa et al. |
| 2016/0068592 A1 | 3/2016 | Chung et al. |
| 2016/0176954 A1 | 6/2016 | Ruike et al. |
| 2016/0200807 A1 | 7/2016 | Ruike et al. |
| 2016/0229908 A1 | 8/2016 | Igawa et al. |
| 2016/0244526 A1 | 8/2016 | Igawa et al. |
| 2017/0022270 A1 | 1/2017 | Igawa et al. |
| 2017/0174778 A1 | 6/2017 | Shusta et al. |
| 2017/0181987 A1 | 6/2017 | Camilla et al. |
| 2017/0226206 A1 | 8/2017 | Igawa et al. |
| 2018/0016327 A1 | 1/2018 | Murata et al. |
| 2018/0148509 A1 | 5/2018 | Kakehi et al. |
| 2019/0085085 A1 | 3/2019 | Igawa et al. |
| 2019/0085095 A1 | 3/2019 | Natarajan et al. |
| 2019/0185557 A1 | 6/2019 | Igawa et al. |
| 2019/0218309 A1* | 7/2019 | Igawa ................ C07K 16/4291 |
| 2019/0233525 A1 | 8/2019 | Igawa et al. |
| 2020/0199241 A1 | 6/2020 | Igawa et al. |
| 2020/0231688 A1 | 7/2020 | Igawa et al. |
| 2021/0017286 A1 | 1/2021 | Kakehi et al. |
| 2021/0206862 A1 | 7/2021 | Igawa et al. |
| 2022/0041741 A1 | 2/2022 | Igawa et al. |
| 2022/0306755 A1 | 9/2022 | Igawa et al. |
| 2023/0159648 A1 | 5/2023 | Igawa et al. |

FOREIGN PATENT DOCUMENTS

| | | |
|---|---|---|
| AU | 2008332271 | 6/2009 |
| AU | 2009290162 | 4/2010 |
| AU | 2010/206050 | 8/2010 |
| AU | 2011/244851 | 11/2011 |
| AU | 2014/250434 | 10/2014 |
| AU | 2015/227424 | 10/2015 |
| CA | 1 332 367 | 10/1994 |
| CA | 2 203 182 | 5/1996 |
| CA | 2 443 294 | 10/2002 |
| CA | 2 523 577 | 11/2004 |
| CA | 2 549 467 | 7/2005 |
| CA | 2 560 953 | 9/2005 |
| CA | 2 603 264 | 10/2006 |
| CA | 2 625 773 | 4/2007 |
| CA | 2 626 688 | 4/2007 |
| CA | 2 648 644 | 10/2007 |
| CA | 2 911 000 | 10/2007 |
| CA | 2 700 394 | 4/2009 |
| CA | 2 700 498 | 4/2009 |
| CA | 2 708 065 | 6/2009 |
| CA | 2 708 532 | 6/2009 |
| CA | 2 721 052 | 10/2009 |
| CA | 2 831 770 | 10/2012 |
| CA | 2 899 589 | 8/2014 |
| CN | 1156460 | 8/1997 |
| CN | 1274289 | 11/2000 |
| CN | 1763097 | 4/2006 |
| CN | 101098890 | 1/2008 |
| CN | 101230102 | 7/2008 |
| CN | 101277976 | 10/2008 |
| CN | 101282992 | 10/2008 |
| CN | 100455598 | 1/2009 |
| CN | 101479381 | 7/2009 |
| CN | 101511871 | 8/2009 |
| CN | 101849006 | 9/2010 |
| CN | 102056946 | 5/2011 |
| CN | 102271703 | 12/2011 |
| CN | 102325793 | 1/2012 |
| CN | 102597005 | 7/2012 |
| CN | 102844332 | 12/2012 |
| CN | 102918057 | 2/2013 |
| CN | 102993304 | 3/2013 |
| CN | 103097415 | 5/2013 |
| CN | 103221426 | 7/2013 |
| CN | 103328632 | 9/2013 |
| CN | 103476793 | 12/2013 |
| CN | 103492565 | 1/2014 |
| CN | 103975060 | 8/2014 |
| CN | 104302169 | 1/2015 |
| CN | 106459189 | 2/2017 |
| CN | 107108726 | 8/2017 |
| CO | 07124506 | 11/2007 |
| CO | 11080753 | 6/2011 |
| CO | 13047993 | 3/2013 |
| CO | 15075851 | 4/2015 |
| EA | 2008/01027 | 10/2008 |
| EA | 2011/00300 | 12/2011 |
| EP | 0 091 539 A | 10/1983 |
| EP | 0 182 495 | 5/1986 |
| EP | 0 361 902 | 4/1990 |
| EP | 0 628 639 A | 12/1994 |
| EP | 0 783 893 | 7/1997 |
| EP | 0 791 359 | 8/1997 |
| EP | 0 983 767 | 3/2000 |
| EP | 1 004 315 | 5/2000 |
| EP | 1 074 268 | 2/2001 |
| EP | 1 188 830 | 3/2002 |
| EP | 1 334 731 | 8/2003 |
| EP | 1 374 900 | 1/2004 |
| EP | 1 510 943 | 3/2005 |
| EP | 1 690 550 | 8/2006 |
| EP | 1 693 448 | 8/2006 |
| EP | 0 770 628 | 9/2006 |

(56) References Cited

FOREIGN PATENT DOCUMENTS

| | | |
|---|---|---|
| EP | 1 707 215 | 10/2006 |
| EP | 1 728 801 | 12/2006 |
| EP | 1 733 740 | 12/2006 |
| EP | 1 601 697 | 5/2007 |
| EP | 009026 | 10/2007 |
| EP | 1 870 459 | 12/2007 |
| EP | 1 941 907 | 7/2008 |
| EP | 1 941 908 | 7/2008 |
| EP | 1 967 207 | 9/2008 |
| EP | 1 967 209 | 9/2008 |
| EP | 1 990 060 | 11/2008 |
| EP | 1 992 692 A | 11/2008 |
| EP | 2 006 381 | 12/2008 |
| EP | 2 031 064 | 3/2009 |
| EP | 2 047 863 | 4/2009 |
| EP | 2 123 302 | 11/2009 |
| EP | 2 174 667 | 4/2010 |
| EP | 2 194 066 | 6/2010 |
| EP | 2 196 220 | 6/2010 |
| EP | 2 196 541 | 6/2010 |
| EP | 2 202 245 | 6/2010 |
| EP | 2 206 775 | 7/2010 |
| EP | 2 236 604 | 10/2010 |
| EP | 2 241 332 | 10/2010 |
| EP | 2 275 443 | 1/2011 |
| EP | 2 305 306 | 4/2011 |
| EP | 2 314 618 | 4/2011 |
| EP | 2 330 193 | 8/2011 |
| EP | 2 366 713 | 9/2011 |
| EP | 2 431 393 | 3/2012 |
| EP | 12764620.6 | 3/2012 |
| EP | 2 471 813 A | 7/2012 |
| EP | 2 578 233 | 4/2013 |
| EP | 2 647 706 | 10/2013 |
| EP | 2 679 681 | 1/2014 |
| EP | 2 698 431 | 2/2014 |
| EP | 1 509 770 B | 7/2014 |
| EP | 2 760 890 A | 8/2014 |
| EP | 2 762 166 A | 8/2014 |
| EP | 2 762 493 A | 8/2014 |
| EP | 2 762 564 | 8/2014 |
| EP | 2 818 183 A | 12/2014 |
| EP | 2 853 898 | 4/2015 |
| EP | 2 889 377 | 7/2015 |
| EP | 2 940 043 | 11/2015 |
| EP | 2 975 055 | 1/2016 |
| EP | 3 042 912 A | 7/2016 |
| EP | 3 240 804 | 11/2017 |
| EP | 3 263 132 A | 1/2018 |
| JP | S61-117457 | 6/1986 |
| JP | S63-52890 | 3/1988 |
| JP | H01-144991 | 6/1989 |
| JP | 2-028200 | 1/1990 |
| JP | H02-501112 | 4/1990 |
| JP | 2-163096 | 6/1990 |
| JP | H02-163085 | 6/1990 |
| JP | H03-504332 A | 9/1991 |
| JP | H05-504579 | 7/1993 |
| JP | H08-217799 | 8/1996 |
| JP | 09-506001 | 6/1997 |
| JP | 11-500915 | 1/1999 |
| JP | 2002-514406 | 5/2002 |
| JP | 2003-055398 | 2/2003 |
| JP | 2003-512019 | 4/2003 |
| JP | 2004-073210 | 3/2004 |
| JP | 2004-511426 | 4/2004 |
| JP | 2005-510212 | 4/2005 |
| JP | 2005-532805 | 11/2005 |
| JP | 2005-537009 | 12/2005 |
| JP | 2006-517525 | 7/2006 |
| JP | 2006-519583 | 8/2006 |
| JP | 2007-252368 | 10/2007 |
| JP | 2007-532139 | 11/2007 |
| JP | 2008-510466 | 4/2008 |
| JP | 2008-519860 | 6/2008 |
| JP | 2009-541352 | 11/2009 |
| JP | 2010-500020 | 1/2010 |
| JP | 2010-505436 | 2/2010 |
| JP | 2010-079667 | 3/2010 |
| JP | 2010-081866 | 4/2010 |
| JP | 2010-521194 | 6/2010 |
| JP | 2010-250830 | 11/2010 |
| JP | 2011-504096 | 2/2011 |
| JP | 2011-507963 | 3/2011 |
| JP | 4652414 | 3/2011 |
| JP | 2011-184418 | 9/2011 |
| JP | 2011-529700 | 12/2011 |
| JP | 2012-505833 | 3/2012 |
| JP | 2012-512641 | 6/2012 |
| JP | 4961501 | 6/2012 |
| JP | 5048866 | 10/2012 |
| JP | 2012-531418 | 12/2012 |
| JP | 2013-518131 | 5/2013 |
| JP | 2013-518606 | 5/2013 |
| JP | 2013-521772 | 6/2013 |
| JP | 2013-531486 | 8/2013 |
| JP | 2013-537425 | 10/2013 |
| JP | 2013-541594 | 11/2013 |
| JP | 2014-055145 | 3/2014 |
| JP | 2014-528906 | 10/2014 |
| JP | 2014-257647 | 12/2014 |
| JP | 2015-510769 | 4/2015 |
| JP | 2016-026190 | 2/2016 |
| JP | 2017-501706 | 1/2017 |
| JP | 6088703 | 3/2017 |
| JP | 2017-509312 | 4/2017 |
| JP | 2017-113013 | 6/2017 |
| JP | 2018-123125 | 8/2018 |
| JP | 2018-141025 | 9/2018 |
| JP | 2019-523295 | 8/2019 |
| KR | 1997/0704785 | 7/1997 |
| KR | 2006/0010765 | 2/2006 |
| KR | 2007/0035482 | 3/2007 |
| KR | 2010/0074220 | 7/2010 |
| KR | 2011/0103431 | 9/2011 |
| KR | 2012-0035192 | 4/2012 |
| KR | 2014/0005864 | 1/2014 |
| KR | 2014/0069332 | 6/2014 |
| KR | 2017/0092449 | 8/2017 |
| MX | 2013/006109 | 1/2014 |
| RU | 2147442 | 4/2000 |
| RU | 2195960 | 1/2003 |
| RU | 2225721 | 3/2004 |
| RU | 2337107 | 10/2008 |
| RU | 2007/121679 | 12/2008 |
| RU | 2360925 | 7/2009 |
| RU | 2367667 | 9/2009 |
| RU | 2008/128133 | 1/2010 |
| RU | 2399381 | 9/2010 |
| RU | 2009/112723 | 10/2010 |
| RU | 2422460 | 6/2011 |
| RU | 2430111 | 9/2011 |
| RU | 2010/116152 | 11/2011 |
| RU | 2434882 | 11/2011 |
| RU | 2445975 | 3/2012 |
| RU | 2010/150931 | 6/2012 |
| RU | 2477137 | 3/2013 |
| SG | 183867 | 10/2012 |
| TW | 416960 | 1/2001 |
| TW | 2010/00127 | 1/2010 |
| TW | 2012/02419 | 1/2012 |
| TW | 2012/06466 | 2/2012 |
| TW | 2013/02219 | 1/2013 |
| TW | 2016/32557 | 9/2016 |
| TW | 2016/42902 | 12/2016 |
| TW | 2016/43190 | 12/2016 |
| TW | 2017/12032 | 4/2017 |
| TW | I605057 | 11/2017 |
| TW | 2018/08331 | 3/2018 |
| TW | 2018/08992 | 3/2018 |
| TW | 2018/19409 | 6/2018 |
| TW | I656133 | 4/2019 |
| TW | 2020/39553 | 11/2020 |
| WO | WO 83/03678 | 10/1983 |

(56) References Cited

FOREIGN PATENT DOCUMENTS

| | | |
|---|---|---|
| WO | WO 88/04692 | 6/1988 |
| WO | WO 91/12023 | 8/1991 |
| WO | WO 91/13631 | 9/1991 |
| WO | WO 92/07084 | 4/1992 |
| WO | WO 92/19759 | 11/1992 |
| WO | WO 93/17105 | 9/1993 |
| WO | WO 94/10354 | 5/1994 |
| WO | WO 94/12215 | 6/1994 |
| WO | WO 94/21681 | 9/1994 |
| WO | WO 95/02187 | 1/1995 |
| WO | WO 95/14710 | 6/1995 |
| WO | WO 95/29697 | 11/1995 |
| WO | WO 95/33844 | 12/1995 |
| WO | WO 96/01653 | 1/1996 |
| WO | WO 96/02576 | 2/1996 |
| WO | WO 96/11020 | 4/1996 |
| WO | WO 96/12503 | 5/1996 |
| WO | WO 96/23071 | 8/1996 |
| WO | WO 96/27011 | 9/1996 |
| WO | WO 97/10354 | 3/1997 |
| WO | WO 97/20858 | 6/1997 |
| WO | WO 97/34631 | 9/1997 |
| WO | WO 98/03546 | 1/1998 |
| WO | WO 98/05787 | 2/1998 |
| WO | WO 98/42377 | 10/1998 |
| WO | WO 98/46257 | 10/1998 |
| WO | WO 98/50431 | 11/1998 |
| WO | WO 99/03495 | 1/1999 |
| WO | WO 99/08707 | 2/1999 |
| WO | WO 99/18212 | 4/1999 |
| WO | WO 99/47140 | 9/1999 |
| WO | WO 99/47170 | 9/1999 |
| WO | WO 99/51642 | 10/1999 |
| WO | WO 99/58572 | 11/1999 |
| WO | WO 2000/0014220 | 3/2000 |
| WO | WO 00/34317 | 6/2000 |
| WO | WO 00/42072 | 7/2000 |
| WO | WO 00/75314 | 12/2000 |
| WO | WO 01/82899 | 11/2001 |
| WO | WO 02/09641 | 2/2002 |
| WO | WO 02/30985 | 4/2002 |
| WO | WO 02/34292 | 5/2002 |
| WO | WO 02/060919 | 8/2002 |
| WO | WO 02/080969 | 10/2002 |
| WO | WO 03/000883 | 1/2003 |
| WO | WO 03/015819 | 2/2003 |
| WO | WO 03/027248 | 4/2003 |
| WO | WO 03/057881 | 7/2003 |
| WO | WO 03/060090 | 7/2003 |
| WO | WO 2003/070760 | 8/2003 |
| WO | WO 03/074679 | 9/2003 |
| WO | WO 03/105757 | 12/2003 |
| WO | WO 2003/107009 | 12/2003 |
| WO | WO 2004/007553 | 1/2004 |
| WO | WO 2004/008147 | 1/2004 |
| WO | WO 2004/020579 | 3/2004 |
| WO | WO 2004/024890 | 3/2004 |
| WO | WO 2004/029207 | 4/2004 |
| WO | WO 2004/035752 | 4/2004 |
| WO | WO 2004/037861 | 5/2004 |
| WO | WO 2004/039826 | 5/2004 |
| WO | WO 2004/058797 | 7/2004 |
| WO | WO 2004/063351 | 7/2004 |
| WO | WO 2004/085476 | 10/2004 |
| WO | WO 2004/091543 | 10/2004 |
| WO | WO 2004/092219 | 10/2004 |
| WO | WO 2004/096273 | 11/2004 |
| WO | WO 2004/099249 | 11/2004 |
| WO | WO 2004/108157 | 12/2004 |
| WO | WO 2004/113387 | 12/2004 |
| WO | WO 2005/020936 | 3/2005 |
| WO | WO 2005/023193 | 3/2005 |
| WO | WO 2005/035753 | 4/2005 |
| WO | WO 2005/035754 | 4/2005 |
| WO | WO 2005/035756 | 4/2005 |
| WO | WO 2005/037315 | 4/2005 |
| WO | WO 2005/037867 | 4/2005 |
| WO | WO 2005/047307 | 5/2005 |
| WO | WO 2005/047327 | 5/2005 |
| WO | WO 2005/056606 | 6/2005 |
| WO | WO 2005/056759 | 6/2005 |
| WO | WO 2005/061000 | 7/2005 |
| WO | WO 2005/066204 | 7/2005 |
| WO | WO 2005/070963 | 8/2005 |
| WO | WO 2005/074607 | 8/2005 |
| WO | WO 2005/077981 | 8/2005 |
| WO | WO 2005/080429 | 9/2005 |
| WO | WO 2005/090405 | 9/2005 |
| WO | WO 2005/092925 | 10/2005 |
| WO | WO 2005/094446 | 10/2005 |
| WO | WO 2005/115452 | 12/2005 |
| WO | WO 2005/123780 | 12/2005 |
| WO | WO 2006/004663 | 1/2006 |
| WO | WO 2006/019447 | 2/2006 |
| WO | WO 2006/020114 | 2/2006 |
| WO | WO 2006/023144 | 3/2006 |
| WO | WO 2006/023403 | 3/2006 |
| WO | WO 2006/031370 | 3/2006 |
| WO | WO 2006/047350 | 5/2006 |
| WO | WO 2006/050166 | 5/2006 |
| WO | WO 2006/053301 | 5/2006 |
| WO | WO 2006/066598 | 6/2006 |
| WO | WO 2006/067913 | 6/2006 |
| WO | WO 2006/070286 | 7/2006 |
| WO | WO 2006/071877 | 7/2006 |
| WO | WO 2006/082052 | 8/2006 |
| WO | WO 2006/083182 | 8/2006 |
| WO | WO 2006/083183 | 8/2006 |
| WO | WO 2006/085967 | 8/2006 |
| WO | WO 2006/088855 | 8/2006 |
| WO | WO 2006/102095 | 9/2006 |
| WO | WO 2006/105338 | 10/2006 |
| WO | WO 2006/106903 | 10/2006 |
| WO | WO 2006/106905 | 10/2006 |
| WO | WO 2006/109592 | 10/2006 |
| WO | WO 2006/113643 | 10/2006 |
| WO | WO 2006/116260 | 11/2006 |
| WO | WO 2006/116269 | 11/2006 |
| WO | WO 2006/118959 | 11/2006 |
| WO | WO 2006/119062 | 11/2006 |
| WO | WO 2006/119107 | 11/2006 |
| WO | WO 2006/119115 | 11/2006 |
| WO | WO 2006/130834 | 12/2006 |
| WO | WO 2007/001422 | 1/2007 |
| WO | WO 2007/008943 | 1/2007 |
| WO | WO 2007/012614 | 2/2007 |
| WO | WO 2007/021841 | 2/2007 |
| WO | WO 2007/024249 | 3/2007 |
| WO | WO 2007/024535 | 3/2007 |
| WO | WO 2007/041635 | 4/2007 |
| WO | WO 2007 043641 | 4/2007 |
| WO | WO 2007/044411 | 4/2007 |
| WO | WO 2007/044616 | 4/2007 |
| WO | WO 2007/046489 | 4/2007 |
| WO | WO 2007/047112 | 4/2007 |
| WO | WO 2007/058194 | 5/2007 |
| WO | WO 2007/060411 | 5/2007 |
| WO | WO 2007/061029 | 5/2007 |
| WO | WO 2007/068411 | 6/2007 |
| WO | WO 2007/074880 | 7/2007 |
| WO | WO 2007/076524 | 7/2007 |
| WO | WO 2007/084253 | 7/2007 |
| WO | WO 2007/086490 | 8/2007 |
| WO | WO 2007/092772 | 8/2007 |
| WO | WO 2007/103134 | 9/2007 |
| WO | WO 2007/103549 | 9/2007 |
| WO | WO 2007/106585 | 9/2007 |
| WO | WO 2007/108559 | 9/2007 |
| WO | WO 2007/114319 | 10/2007 |
| WO | WO 2007/114325 | 10/2007 |
| WO | WO 2007/133816 | 11/2007 |
| WO | WO 2007/137984 | 12/2007 |
| WO | WO 2007/142325 | 12/2007 |
| WO | WO 2007/143168 | 12/2007 |

(56) References Cited

FOREIGN PATENT DOCUMENTS

| | | |
|---|---|---|
| WO | WO 2007/150015 | 12/2007 |
| WO | WO 2007/150016 | 12/2007 |
| WO | WO 2008/002933 | 1/2008 |
| WO | WO 2008/017963 | 2/2008 |
| WO | WO 2008/022152 | 2/2008 |
| WO | WO 2008/030706 | 3/2008 |
| WO | WO 2008/036688 | 3/2008 |
| WO | WO 2008/043822 | 4/2008 |
| WO | WO 2008/060785 | 5/2008 |
| WO | WO 2008/069889 | 6/2008 |
| WO | WO 2008/090901 | 7/2008 |
| WO | WO 2008/090960 | 7/2008 |
| WO | WO 2008/091798 | 7/2008 |
| WO | WO 2008/091954 | 7/2008 |
| WO | WO 2008/092117 | 7/2008 |
| WO | WO 2008/098115 | 8/2008 |
| WO | WO 2008/103432 | 8/2008 |
| WO | WO 2008/113834 | 9/2008 |
| WO | WO 2008/115732 | 9/2008 |
| WO | WO 2008/031056 | 10/2008 |
| WO | WO 2008/121160 | 10/2008 |
| WO | WO 2008/130969 | 10/2008 |
| WO | WO 2008/132453 | 11/2008 |
| WO | WO 2008/143954 | 11/2008 |
| WO | WO 2008/145141 | 12/2008 |
| WO | WO 2008/150494 | 12/2008 |
| WO | WO 2009/000098 | 12/2008 |
| WO | WO 2009/000099 | 12/2008 |
| WO | WO 2009/006338 | 1/2009 |
| WO | WO 2009/014263 | 1/2009 |
| WO | WO 2009/026117 | 2/2009 |
| WO | WO 2009/032145 | 3/2009 |
| WO | WO 2009/032782 | 3/2009 |
| WO | WO 2009/039175 | 3/2009 |
| WO | WO 2009/041062 | 4/2009 |
| WO | WO 2009/041613 | 4/2009 |
| WO | WO 2009/041621 | 4/2009 |
| WO | WO 2009/041643 | 4/2009 |
| WO | WO 2009/041734 | 4/2009 |
| WO | WO 2009/044774 | 4/2009 |
| WO | WO 2009/047356 | 4/2009 |
| WO | WO 2009/053358 | 4/2009 |
| WO | WO 2009/058346 | 5/2009 |
| WO | WO 2009/058492 | 5/2009 |
| WO | WO 2009/063965 | 5/2009 |
| WO | WO 2009/072598 | 6/2009 |
| WO | WO 2009/072604 | 6/2009 |
| WO | WO 2009/086320 | 7/2009 |
| WO | WO 2009/089846 | 7/2009 |
| WO | WO 2009/095235 | 8/2009 |
| WO | WO 2009/125825 | 10/2009 |
| WO | WO 2009/137880 | 11/2009 |
| WO | WO 2009/139822 | 11/2009 |
| WO | WO 2009/148148 | 12/2009 |
| WO | WO 2010/015608 | 2/2010 |
| WO | WO 2010/033736 | 3/2010 |
| WO | WO 2010/035769 | 4/2010 |
| WO | WO 2010/045193 | 4/2010 |
| WO | WO 2010/054403 | 5/2010 |
| WO | WO 2010/058860 | 5/2010 |
| WO | WO 2010/065078 | 6/2010 |
| WO | WO 2010/070094 | 6/2010 |
| WO | WO 2010/081173 | 7/2010 |
| WO | WO 2010/085682 | 7/2010 |
| WO | WO 2010/106180 | 9/2010 |
| WO | WO 2010/106812 | 9/2010 |
| WO | WO 2010/151338 | 12/2010 |
| WO | WO 2010/151526 | 12/2010 |
| WO | WO 2010/151792 | 12/2010 |
| WO | WO 2011/021009 | 2/2011 |
| WO | PCT/JP2011/001888 | 3/2011 |
| WO | WO 2011/043643 | 4/2011 |
| WO | WO 2011/044368 | 4/2011 |
| WO | WO 2011/063980 | 6/2011 |
| WO | WO 2011/094593 | 8/2011 |
| WO | WO 2011/100271 | 8/2011 |
| WO | WO 2011/109338 | 9/2011 |
| WO | WO 2011/111007 | 9/2011 |
| WO | WO 2011/122011 | 10/2011 |
| WO | WO 2011/137362 | 11/2011 |
| WO | WO 2011/149046 | 12/2011 |
| WO | WO 2011/150008 | 12/2011 |
| WO | WO 2011/151432 | 12/2011 |
| WO | WO 2012/016227 | 2/2012 |
| WO | WO 2012/024242 | 2/2012 |
| WO | WO 2012/033953 | 3/2012 |
| WO | WO 2012/064627 | 5/2012 |
| WO | WO 2012/073992 | 6/2012 |
| WO | WO 2012/088247 | 6/2012 |
| WO | WO 2012/093704 | 7/2012 |
| WO | 2012/115241 | 8/2012 |
| WO | WO 2012/115241 | 8/2012 |
| WO | WO 2012/118903 | 9/2012 |
| WO | 2012/132067 | 10/2012 |
| WO | WO 2012/132067 | 10/2012 |
| WO | WO 2012/133782 | 10/2012 |
| WO | WO 2012/145417 | 10/2012 |
| WO | WO 2012/151481 | 11/2012 |
| WO | WO 2012/162067 | 11/2012 |
| WO | WO 2012/177653 | 12/2012 |
| WO | WO 2013/004842 | 1/2013 |
| WO | WO 2013/012733 | 1/2013 |
| WO | WO 2013/046704 | 4/2013 |
| WO | WO 2013/046722 | 4/2013 |
| WO | WO 2013/047748 | 4/2013 |
| WO | WO 2013/047752 | 4/2013 |
| WO | WO 2013/081143 | 6/2013 |
| WO | WO 2013/125667 | 8/2013 |
| WO | WO 2013/138400 | 9/2013 |
| WO | WO 2013/138680 | 9/2013 |
| WO | WO 2013/149111 | 10/2013 |
| WO | WO 2013/152001 | 10/2013 |
| WO | WO 2013/166099 | 11/2013 |
| WO | WO 2013/186719 | 12/2013 |
| WO | WO 2014/006217 | 1/2014 |
| WO | WO 2014/028354 | 2/2014 |
| WO | WO 2014/030728 | 2/2014 |
| WO | WO 2014/043344 | 3/2014 |
| WO | WO 2014/047500 | 3/2014 |
| WO | WO 2014/074532 | 5/2014 |
| WO | WO 2014/100689 | 6/2014 |
| WO | WO 2014/114651 | 7/2014 |
| WO | WO 2014/119969 | 8/2014 |
| WO | WO 2014/144080 | 9/2014 |
| WO | WO 2014/144575 | 9/2014 |
| WO | WO 2014/144903 | 9/2014 |
| WO | WO 2014/145159 | 9/2014 |
| WO | WO 2014/145806 | 9/2014 |
| WO | WO 2014/160958 | 10/2014 |
| WO | WO 2014/163101 | 10/2014 |
| WO | WO 2014/182676 | 11/2014 |
| WO | WO 2014/184384 | 11/2014 |
| WO | WO 2014/190441 | 12/2014 |
| WO | WO 2015/022658 | 2/2015 |
| WO | WO 2015/023972 | 2/2015 |
| WO | WO 2015/034000 | 3/2015 |
| WO | WO 2015/091738 | 6/2015 |
| WO | WO 2015/111008 | 7/2015 |
| WO | WO 2015/127134 | 8/2015 |
| WO | WO 2015/134894 | 9/2015 |
| WO | WO 2015/162590 | 10/2015 |
| WO | WO 2016/000813 | 1/2016 |
| WO | WO 2016/073853 | 5/2016 |
| WO | WO 2016/073879 | 5/2016 |
| WO | WO 2016/073906 | 5/2016 |
| WO | WO 2016/092439 | 6/2016 |
| WO | WO 2016/098356 | 6/2016 |
| WO | WO 2016/098357 | 6/2016 |
| WO | WO 2016/117346 | 7/2016 |
| WO | WO 2016/125495 | 8/2016 |
| WO | WO 2016/136933 | 9/2016 |
| WO | WO 2016/160756 | 10/2016 |
| WO | WO 2016/168613 | 10/2016 |
| WO | WO 2016/178980 | 11/2016 |

(56) References Cited

FOREIGN PATENT DOCUMENTS

| | | |
|---|---|---|
| WO | WO 2016/209956 | 12/2016 |
| WO | WO 2017/046994 | 3/2017 |
| WO | WO 2017/049011 | 3/2017 |
| WO | WO 2017/064615 | 4/2017 |
| WO | WO 2017/104779 | 6/2017 |
| WO | WO 2017/104783 | 6/2017 |
| WO | WO 2017/110981 | 6/2017 |
| WO | WO 2017/120523 | 7/2017 |
| WO | WO 2017/123636 | 7/2017 |
| WO | WO 2017/217524 | 12/2017 |
| WO | WO 2017/217525 | 12/2017 |
| WO | WO 2017/218515 | 12/2017 |
| WO | WO 2017/218592 | 12/2017 |
| WO | WO 2018/025982 | 2/2018 |
| WO | WO 2018/139623 | 8/2018 |
| WO | WO 2018/143266 | 8/2018 |
| WO | WO 2018/167322 | 9/2018 |
| WO | WO 2018/169993 | 9/2018 |
| WO | WO 2018/184739 | 10/2018 |
| WO | WO 2019/084438 | 5/2019 |
| WO | WO 2019/112984 | 6/2019 |
| WO | WO 2020/027279 | 2/2020 |
| WO | WO 2020/209318 | 10/2020 |

OTHER PUBLICATIONS

Kussie et al., J. Immunol. 152: 146-152 (Year: 1994).*
Wu et al., J. Mol. Biol. 294: 151-162 (Year: 1999).*
U.S. Appl. No. 14/520,423, Igawa et al., filed Oct. 22, 2014.
U.S. Appl. No. 14/007,947, Igawa et al., filed Sep. 26, 2013.
U.S. Appl. No. 15/553,609, Kakehi et al., filed Aug. 25, 2017.
U.S. Appl. No. 13/595,139, Igawa et al., filed Aug. 27, 2012.
U.S. Appl. No. 15/952,945, Igawa et al., filed Apr. 13, 2018.
U.S. Appl. No. 15/688,004, Ruike et al., filed Aug. 28, 2017.
U.S. Appl. No. 16/019,752, Ruike et al., filed Jun. 22, 2018.
U.S. Appl. No. 15/963,449, Ruike et al., filed Apr. 26, 2018.
Sondermann et al., "The 3.2-Å crystal structure of the human IgG1 Fc fragment-FcγRIII complex," Nature, Jul. 20, 2000, 406(6793): 267-273.
Yarilin, Fundamentals of Immunology, M: Medicina, 1999, pp. 181-184 (with English translation).
U.S. Appl. No. 15/976,288, Igawa et al., filed May 10, 2018.
Ferl et al., "A Predictive Model of Therapeutic Monoclonal Antibody Dynamics and Regulation by the Neonatal Fc Receptor (FcRn)," Ann Biomed Eng, Nov. 2005, 33(11):1640-52.
Ferl et al., Erratum to: A Predictive Model of Therapeutic Monoclonal Antibody Dynamics and Regulation by the Neonatal Fc Receptor (FcRn), Ann Biomed Eng, Oct. 2011, 39(10):2668.
U.S. Appl. No. 14/007,947, Igawa et al., filed Dec. 30, 2013.
U.S. Appl. No. 15/230,904, Igawa et al., filed Aug. 8, 2016.
U.S. Appl. No. 16/480,047, filed Jul. 23, 2019, Shinomiya et al.
U.S. Appl. No. 16/480,765, filed Jul. 25, 2019, Sampei.
U.S. Appl. No. 16/514,467, filed Jul. 19, 2019, Ruike et al.
Interleukin 6, Wikipedia, Feb. 22, 2019, XP055598802, (URL:https://en.wikipedia.org/wiki/Interleukin_6), retrieved on Jun. 24, 2019, 20 pages.
Aboud-Pirak et al., "Binding and Endocytosis of a Monoclonal Antibody to a High Molecular Weight Human Milk Fat Globule Membrane-associated Antigen by Cultured MCF-7 Breast Carcinoma Cells," Cancer Res, Jun. 1, 1988, 48(11):3188-96.
Anchin et al., "Recognition of Superpotent Sweetener Ligands by a Library of Monoclonal Antibodies," J Mol Recognit, Sep.-Oct. 1997, 10(5):235-42.
Avsian-Kretchmer et al., "Comparative Genomic Analysis of the Eight-Membered Ring Cystine Knot-Containing Bone Morphogenetic Protein Antagonists," Mol Endocrinol, Jan. 2004, 18(1):1-12. Epub Oct. 2, 2003.
Balemans et al., "Increased bone density in sclerosteosis is due to the deficiency of a novel secreted protein (SOST)," Hum Mol Genet, Mar. 1, 2001, 10(5):537-43.

Binding data for Rituximab (submitted by the Opponent during EP opposition procedure for EP 2 708 558 and posted by EPO on Jan. 15, 2019), 6 pages.
Brunkow et al., "Bone Dysplasia Sclerosteosis Results from Loss of the SOST Gene Product, a Novel Cystine Knot-Containing Protein," Am J Hum Genet, Mar. 2001, 68(3):577-89. Epub Feb. 9, 2001.
Chang et al., "Practical Approaches to Protein Formulation Development," Pharm Biotechnol, 2002, 13:1-25.
Cleland et al., Chapter 15 "Drug Delivery from Bioerodible Polymers," Formulation and Delivery of Proteins and Peptides, American Chemical Society, 1994, pp. 242-277.
Declaration by Madhusudan Natarajan, Ph.D. (submitted by the Opponent during EP opposition procedure for EP 2 708 558 and posted by EPO on Jan. 15, 2019), 3 pages.
Edwards et al., "The Remarkable Flexibility of the Human Antibody Repertoire; Isolation of Over One Thousand Different Antibodies to a Single Protein, BLyS," J Mol Biol, Nov. 14, 2003, 334(1):103-18.
Fisher et al., "Affinity purification of antibodies using antigens immobilized on solid supports," Biochem Soc Trans, Apr. 1988, 16(2):134-8.
Goel et al., "Plasticity within the Antigen-Combining Site May Manifest as Molecular Mimicry in the Humoral Immune Response," J Immunol, Dec. 15, 2004, 173(12):7358-67.
Hughes-Jones et al., "The Effect of pH and Ionic Strength on the Reaction between Anti-D and Erythrocytes," Immunology, Jan. 1964, 7:72-81.
Huse et al., "Purification of antibodies by affinity chromatography," J Biochem Biophys Methods, May 31, 2002, 51(3):217-31.
Jain et al., "Engineering antibodies for clinical applications," Trends Biotechnol, Jul. 2007, 25(7):307-16. Epub May 21, 2007.
Kakita et al., "Isolation of a Human Monoclonal Antibody with Strong Neutralizing Activity against Diphtheria Toxin," Infect Immun, Jun. 2006, 74(6):3682-3.
Kamata et al., "Comparison of pH and Ionic Strength Dependence of Interactions between Monoclonal Antibodies and Bovine β-Lactoglobulin," Biosci Biotechnol Biochem, Jan. 1996, 60(1):25-9.
Kanyavuz et al., "Breaking the law: unconventional strategies for antibody diversification," Nat Rev Immunol, Jun. 2019, 19(6):355-368. doi: 10.1038/s41577-019-0126-7.
Keller et al., "SOST is a target gene for PTH in bone," Bone, Aug. 2005, 37(2):148-58.
Khosla et al., "Concise Review for Primary-Care Physicians—Treatment Options for Osteoporosis," Mayo Clin Proc, Oct. 1995, 70(10):978-82.
King, "Antibody engineering: design for specific applications," Applications and Engineering of Monoclonal Antibodies, 1998, pp. 27-75.
Kipriyanov et al., "Generation of Recombinant Antibodies," Mol Biotechnol, Sep. 1999, 12(2):173-201.
Kranz et al., "Mechanisms of Ligand Binding by Monoclonal Anti-fluorescyl Antibodies," J Biol Chem, Jun. 25, 1982, 257(12):6987-95.
Lloyd et al., "Modelling the human immune response: performance of a $10^{11}$ human antibody repertoire against a broad panel of therapeutically relevant antigens," Protein Eng Des Sel, Mar. 2009, 22(3):159-68. doi: 10.1093/protein/gzn058. Epub Oct. 29, 2008.
Medesan et al., "Comparative studies of rat IgG to further delineate the Fc:FcRn interaction site," Eur J Immunol, Jul. 1998, 28(7):2092-100.
Narhi et al., "Effect of Three Elution Buffers on the Recovery and Structure of Monoclonal Antibodies," Anal Biochem, Nov. 15, 1997, 253(2):236-45.
Originally Filed Claims of EP Application No. 13195713.6 (EP Publication No. 2 708 558) (submitted by the Opponent during EP opposition procedure for EP 2 708 558 and posted by EPO on Jan. 15, 2019), 2 pages.
Originally Filed Description of EP Application No. 13195713.6 (EP Publication No. 2708558) (submitted by the Opponent during EP opposition procedure for EP 2 708 558 and posted by EPO on Jan. 15, 2019), 153 pages.

(56) References Cited

OTHER PUBLICATIONS

Patel et al., "A Forgotten Cause of Kidney Injury in Chronic Myelomonocytic Leukemia," Am J Kidney Dis, Jul. 2009, 54(1):159-64. doi: 10.1053/j.ajkd.2008.11.013. Epub Jan. 29, 2009.
Pirruccello-Straub, "Blocking extracellular activation of myostatin as a strategy for treating muscle wasting," Scientific Reports, 2018, 8:2292.
Product Information Sheet from SIGMA—H—Y Medium (1998) and document establishing that it was published in 1998 (submitted by the Opponent during EP opposition procedure for EP 2 708 558 and posted by EPO on Jan. 15, 2019), 4 pages.
Promega Protocols and Applications Guide, 1991, 2nd Edition (submitted by the Opponent during EP opposition procedure for EP 2 708 558 and posted by EPO on Jan. 14, 2019), 3 pages.
Raso et al., "Antibodies Capable of Releasing Diphtheria Toxin in Response to the Low pH Found in Endosomes," J Biol Chem, Oct. 31, 1997, 272(44):27618-22.
Raso et al., "Intracellular Targeting with Low pH-triggered Bispecific Antibodies," J Biol Chem, Oct. 31, 1997, 272(44):27623-8.
Raso, "Intracellular Targeting Using Bispecific Antibodies," Methods in Molecular Medicine, 2000, vol. 25, pp. 37-50.
Rituximab biologic license application approval, dated Nov. 26, 1997 (submitted by the Opponent during EP opposition procedure for EP 2 708 558 and posted by EPO on Jan. 15, 2019), 2 pages.
Rituximab product information, IDEC, 1997 (submitted by the Opponent during EP opposition procedure for EP 2 708 558 and posted by EPO on Jan. 15, 2019), 2 pages.
Rituximab (Wikipedia), accessed on Oct. 24, 2018 (with English translation) (submitted by the Opponent during EP opposition procedure for EP 2 708 558 and posted by EPO on Jan. 15, 2019), 7 pages.
Roitt et al., Chapter 3 "Antibodies," Immunology, Moscow: Mir, 2000, pp. 97-113 (including what are believed to be corresponding pages from an English language edition of Immunology).
Sada et al., "Effect of histidine residues in antigenic sites on pH dependence of immuno-adsorption equilibrium," Appl Microbiol Biotechnol, 1988, 27:528-32.
Sampei et al., "Identification and Multidimensional Optimization of an Asymmetric Bispecific IgG Antibody Mimicking the Function of Factor VIII Cofactor Activity," PLoS One, 2013, 8(2):e57479. doi: 10.1371/journal.pone.0057479. Epub Feb. 28, 2013.
Shadduck et al., "Fractionation of Antibodies to L-Cell Colony-Stimulating Factor by Affinity Chromatography," Blood, Jun. 1979, 53(6): 1182-90.
Singer et al., "The Genetic Molecules," Genes & Genomes, Moscow: Mir, 1998, pp. 1:63-64 (including what are believed to be corresponding pages from an English language edition of Genes & Genomes).
Venturi et al., "The Monoclonal Antibody 1F6 Identifies a pH-dependent Conformational Change in the Hydrophilic $NH_2$ Terminus of NhaA $Na^+/H^+$ Antiporter of *Escherichia coli*," J Biol Chem, Feb. 18, 2000, 275(7):4734-42.
Wang, "Instability, stabilization, and formulation of liquid protein pharmaceuticals," Int J Pharm, Aug. 20, 1999, 185(2):129-88.
USPTO Non-Final Office Action in U.S. Appl. No. 13/637,415, dated Jun. 10, 2019, 27 pages.
USPTO Restriction Requirement in U.S. Appl. No. 15/977,757, dated Jul. 25, 2019, 5 pages.
USPTO Non-Final Office Action in U.S. Appl. No. 15/952,945 dated Sep. 20, 2018, 32 pages.
USPTO Final Office Action in U.S. Appl. No. 15/952,945 dated Jun. 3, 2019, 190 pages.
USPTO Non-Final Office Action in U.S. Appl. No. 15/952,951 dated Oct. 1, 2018, 12 pages.
Harvey et al., Lippincott's Illustrated Reviews: Immunology, Second Edition (copyright 2013 and 2008), Chapter 2, "Antigens and Receptors," pp. 11-23 and Chapter 11, "Lymphocyte Effector Functions," pp. 141-157.
USPTO Non-Final Office Action in U.S. Appl. No. 16/028,140, dated Jul. 9, 2019, 95 pages.
USPTO Restriction Requirement in U.S. Appl. No. 13/990,158, dated Jan. 6, 2016, 9 pages.
USPTO Non-Final Office Action in U.S. Appl. No. 13/990,158, dated Aug. 19, 2016, 85 pages.
USPTO Final Office Action in U.S. Appl. No. 13/990,158, dated May 2, 2017, 57 pages.
U.S. Appl. No. 16/323,142, filed Feb. 4, 2019, Kakiuchi et al.
U.S. Appl. No. 14/347,187, Igawa et al., filed Mar. 25, 2014.
U.S. Appl. No. 14/974,488, Ruike et al., filed Dec. 18, 2015.
U.S. Appl. No. 15/015,287, Igawa et al., filed Feb. 4, 2016.
U.S. Appl. No. 15/495,026, filed Apr. 24, 2017, Igawa et al.
U.S. Appl. No. 15/553,609, filed Aug. 25 2017, Kakehi et al.
U.S. Appl. No. 15/688,004, filed Aug. 28, 2017, Ruike et al.
U.S. Appl. No. 15/963,449, filed Apr. 26, 2018, Ruike et al.
U.S. Appl. No. 15/963,455, filed Apr. 26, 2018, Ruike et al.
U.S. Appl. No. 16/028,140, filed Jul. 5, 2018, Igawa et al.
U.S. Appl. No. 16/041,976, filed Jul. 23, 2018, Igawa et al.
U.S. Appl. No. 16/065,192, filed Jun. 22, 2018, Ruike et al.
U.S. Appl. No. 61/313,102, filed Mar. 11, 2010, Pons.
[Anonymous] "Rabbit Antibody to Human pro-Myostatin (amino acids 79-92)", Meridian Life Science Inc., Nov. 13, 2015, XP055478289, Retrieved from the Internet: URL:https://meridianlifescience.com/biospecs/K24340R.pdf [retrieved on May 24, 2018].
[Anonymous] "Blog entry", Jun. 1, 2014, Retrieved from the Internet: URL:https://www.thundersplace.org/male-supplements/the-chemical-pe thread-7.html92 [retrieved on May 23, 2018].
[Anonymous] "polyclonal human pro-Myostatin (aa 79-92) antibody", Immun Diagnostik Antibodies Catalogue, Jun. 30, 2016, Retrieved from the Internet: URL:https://www.immundiagnostik.com/fileadmin/pdf/AK3004.pdf [retrieved on May 24, 2018].
[Anonymous] "Mouse GDF-8/Myostatin Propeptide Antibody",R&D Catalogue AF 1539, Feb. 6, 2018, XP055478493, Retrieved from the Internet: URL:https://resources.mdsystems.com/pdfs/datasheets/af1539.pdf [retrieved on May 25, 2018].
Akbarzadeh-Sharbaf et al., "In silico design, construction and cloning of Trastuzumab humanized monoclonal antibody: A possible biosimilar for Herceptin," Adv Biomed Res, Jan.-Mar. 2012, 1:21. doi: 10. 4103/ 2277-9175. 98122. Epub Jul. 6, 2012.
Akira et al., "Interleukin-6 in Biology and Medicine," Adv Immunol, 1993, 54:1-78.
Alignment of constant region sequences from WO 2009/125825 (document submitted in EP opposition and posted by EPO on Feb. 2, 2018); 1 page.
Alignment of the amino acid sequences of the Fc regions of antibodies exemplified in EP 2275443 (document submitted in EP opposition and posted by EPO on Feb. 2, 2018); 1 page.
Alignment of variable heavy and light chain amino acid sequences from WO 2009/125825 (document submitted in EP opposition and posted by EPO on Feb. 2, 2018); 2 pages.
Annual Report 2012 (Integrated Edition Including CSR Report) Mar. 27, 2013, 154 pages.
Araki et al., "Clinical improvement in a patient with neuromyelitis optica following therapy with the anti-IL-6 receptor monoclonal antibody tocilizumab," Mod Rheumatol, Jul. 2013, 23(4):827-31. doi: 10. 1007/s10165-012-0715-9. Epub Jul. 11, 2012.
Aricha et al., "Blocking of IL-6 suppresses experimental autoimmune myasthenia gravis," J Autoimmun, Mar. 2011, 36(2):135-41. doi: 10. 1016/j. jaut. 2010. 12. 001. Epub Dec. 30, 2010.
Atherton et al., "Acid-base balance: maintenance of plasma pH," Anaesthesia & Intensive Care Medicine, Nov. 2009, 10(11):557-61 (abstract).
Becker et al., "Prevention of postoperative abdominal adhesions by a sodium hyaluronate-based bioresorbable membrane: a prospective, randomized, double-blind multicenter study," J Am Coll Surg, Oct. 1996, 183(4):297-306.
Burmeister et al., "Crystal structure of the complex of rat neonatal Fc receptor with Fc," Nature, Nov. 24, 1994; 372(6504):379-83.
Besada, "Potential patient benefit of a subcutaneous formulation of a tocilizumab for the treatment of rheumatoid arthritis: a critical review," Patient Preference and Adherence, Aug. 1, 2014, 8:1051-9. doi: 10.2147/PPA. S34958. eCollection 2014.

(56) References Cited

OTHER PUBLICATIONS

Biasini et al., "Immunopurification of Pathological Prion Protein Aggregates," PLoS One, Nov. 12, 2009, 4(11):e7816. doi: 10.1371/journal.pone.0007816.

Borrok et al., "pH-dependent Binding Engineering Reveals an FcRn Affinity Threshold That Governs IgG Recycling," J Biol Chem, Feb. 13, 2015, 290(7):4282-90. doi: 10. 1074/ jbc. M114. 603712. Epub Dec. 23, 2014.

Breitbart et al., "Highly Specific Detection of Myostatin Prodomain by an Immunoradiometric Sandwich Assay in Serum of Healthy Individuals and Patients," PLoS One, Nov. 15, 2013, 8(11): e80454. doi: 10.1371/journal.pone. 0080454. eCollection 2013.

Bulun, "Endometriosis," New Eng J Med, Jan. 2009, 360(3):268-279.

Chihara et al., "Interleukin 6 signaling promotes anti-aquaporin 4 autoantibody production from plasmablasts in neuromyelitis optica," PNAS, Mar. 2011, 108(9):3701-3706.

Claims as granted for Publication No. EP 2275443, dated Jan. 19, 2011 (document submitted in EP opposition); 6 pages.

Cooper et al., "Variable domain-identical antibodies exhibit IgG subclass-related differences in affinity and kinetic constants as determined by surface plasmon resonance," Mol Immunol, Jun. 1994, 31(8): 577-84.

Datta-Mannan et al., "Humanized IgG1 Variants with Differential Binding Properties to the Neonatal Fc Receptor: Relationship to Pharmacokinetics in Mice and Primates," Drug Metab Dispos, Jan. 2007, 35(1):86-94. Epub Oct. 18, 2006.

Davydov, "Omalizuman (Xolair) for Treatment of Asthma," Am Fam Physician, Jan. 15, 2005, 71(2):341-2.

De Felice et al., "Formation of amyloid aggregates from human lysozyme and its disease-associated variants using hydrostatic pressure," FASEB J, Jul. 2004, 18(10):1099-101. (dol:10.1096/fj.03-1072fje; PMID 15155566).

Declaration of Nimish Gera, Ph.D., CV and Exhibits, Sep. 1, 2016 (submitted in the matter of EP 2275443, Opposition thereto by Alexion Pharmaceuticals, Inc); 24 pages.

Donnez et al., "Current thinking on the pathogenesis of endometriosis," Gynecol Obstet Invest, Dec. 2002, 54(Suppl 1):52-62.

EMA product information: Annexes to file of the tocilizumab preparation RoActemra (WC500054890).

Experimental data characterizing the binding of rituximab to its antigen CD20 and to human FcRn (document submitted in EP opposition and posted by EPO on Feb. 5, 2018); 6 pages.

Expert Declaration by Dr. Madhusudan Natarajan, submitted in EP opposition regarding EP 2552955 and posted by EPO on Feb. 5, 2018; 4 pages.

Fiedler et al., "An engineered IN-1 Fab fragment with improved affinity for the Nogo-A axonal growth inhibitor permits immunochemical detection and shows enhanced neutralizing activity," Protein Eng, Nov. 2002, 15(11):931-41.

Foote et al., "Antibody framework residues affecting the conformation of the hypervariable loops," J Mol Biol, Mar. 20, 1992, 224(2):487-99.

Fukuzawa et al., "Long lasting neutralization of C5 bgy SKY59, a novel recycling antibody, is a potential therapy for compliment-mediated diseases," Sci. Rep., Apr. 24, 2017, 7(1):1080. doi:10.1038/x41598-017-01087-7.

Gera et al., "Design of pH Sensitive Binding Proteins from the Hyperthermophilic Sso7d Scaffold," PLoS One, Nov. 2012, 7(11):e48928. doi: 10.1371/journal.pone.0048928. Epub Nov. 7, 2012.

Giclas et al., "Preparation and characterization of monoclonal antibodies against the fifth component of rabbit complement (C5)," J. Immunol. Methods, Dec. 24, 1987, 105(2):201-9.

Giudice et al., "Endometriosis," Lancet, Nov. 2004, 364(9447):1789-1799.

Glick et al., Molecular Biotechnology: Principles and Applications of Recombinant DNA, 3rd Edition, Chemical Industry Press, Mar. 2003, p. 168 (English Translation).

Goebl et al., "Neonatal Fc Receptor Mediates Internalization of Fc Transfected Human Endothelial Cells," Molecular Biology of the Cell, Dec. 2008, 19(12):5490-5505.

Guo, "Recurrence of endometriosis and its control," Hum Reprod Update, Jul.-Aug. 2009 (Epub Mar. 2009), 15(4):441-461.

Gurbaxani et al., "Analysis of a family of antibodies with different half-lives in mice fails to find a correlation between affinity for FcRn and serum half-life," Mol Immunol, Mar. 2006, 43(9):1462-73. Epub Sep. 1, 2005.

Hamers-Casterman et al., "Naturally occurring antibodies devoid of light chains," Nature, Jun. 3, 1993, 363(6428):446-8.

Han, et al., "Targeting the Myostatin Signaling Pathway to Treat Muscle Wasting Diseases," Curr Opin Support Palliat Care, Dec. 2011, 5(4):334-41. doi: 10.1097/SPC.0b013e32834bddf9.

Hill et al., "The Myostatin Propeptide and the Follistatin-related Gene Are Inhibitory Binding Proteins of Myostatin in Normal Serum," J Biol Chem, Oct. 25, 2002, 277(43):40735-41. Epub Aug. 22, 2002.

Hirano et al., "Complementary DNA for a novel human interleukin (BSF-2) that induces B lymphocytes to produce immunoglobulin," Nature, Nov. 1986, 324:73-76.

Hirata et al., "Characterization of IL-6 Receptor Expression by Monoclonal and Polyclonal Antibodies," J Immunol, Nov. 1, 1989, 143(9):2900-6.

Hoogenboom, "Selecting and screening recombinant antibody libraries," Nat Biotechnol, Sep. 2005, 23(9):1105-16.

Horiuchi et al., "Complement-targeted therapy: development of C5- and C5a-targeted inhibition," Inflammation and Regeneration, Jun. 3, 2016, 36:11.

Huang et al., "A Monoclonal Anti-Human IL-6 Receptor Antibody Inhibits the Proliferation of Human Myeloma Cells," Hybridoma, Oct. 1993, 12(5):621-30.

Huizinga et al., "Sarilumab, a fully human monoclonal antibody against IL-6Rα in patients with rheumatoid arthritis and an inadequate response to methotrexate: efficacy and safety results from the randomised SARIL-RA-MOBILITY Part A trial," Ann Rheum Dis, Sep. 2014, 73(9):1626-34. doi: 10. 1136/annrheumdis-2013-204405. Epub Dec. 2, 2013.

Irani et al., Molecular properties of human IgG subclasses and their implications for designing therapeutic monoclonal antibodies against infectious diseases, Mol Immunol, Oct. 2015, 67 (2 Pt A):171-82. doi : 10. 1016/ j. molimm. 2015. 03. 255. Epub Apr. 18, 2015.

Iwabe et al., "Pathogenetic significance of increased levels• of interleukin-a in the peritoneal fluid of patients with endometriosis," Fertil Steril, May 1998, 69(5):924-30.

Kim et al., "Production of a Polyclonal Anti-Myostatin Antibody and the Effects of In Ovo Administration of the Antibody on Posthatch Broiler Growth and Muscle Mass," Poult Sci, Jun. 2007, 86(6):1196-205.

Kim et al., "Production of a Polyclonal Anti-Myostatin Antibody and the Effects of In Ovo Administration of the Antibody on Posthatch Broiler Growth and Muscle Mass," Poult Sci, Jun. 2006, 85(6):1062-71.

King, Applications and Engineering of Monoclonal Antibodies, 1998, pp. 68-71.

Knappik et al., "Fully Synthetic Human Combinatorial Antibody Libraries (HuCAL) Based on Modular Consensus Frameworks and CDRs Randomized with Trinucleotides," J Mol Biol, Feb. 11, 2000, 296(1):57-86.

Krieckaert et al., "Immunogenicity of biologic therapies—we need tolerance," Nat Rev Rheumatol, Oct. 2010, 6(10):558-9. doi: 10. 1038/nrrheum. 2010. 153.

Kuroda et al., "Computer-aided antibody design," Protein Eng Des Sel, Oct. 2012, 25(10):507-21. Epub Jun. 2, 2012.

Lotz et al., "B Cell Stimulating Factor 2/Interleukin 6 is a Costimulant for Human Thymocytes and T Lymphocytes," J. Exp. Med., Mar. 1, 1988, 167(3):1253-1258.

Matsunaga et al., "A pH-dependent conformational transition of AP peptide and physicochemical properties of the conformers in the glial cell," Biochem J, Feb. 1, 2002, 361(Pt3):547-56.

(56) References Cited

OTHER PUBLICATIONS

Molina et al., "Trastuzumab (Herceptin), a Humanized Anti-HER2 Receptor Monoclonal Antibody, Inhibits Basal and Activated HER2 Ectodomain Cleavage in Breast Cancer Cells," Cancer Res, Jun. 15, 2001, 61(12):4744-9.
Muller et al., "VEGF and the Fab fragment of a humanized neutralizing antibody: crystal structure of the complex at 2.4 Å resolution and mutational analysis of the interface," Structure, Sep. 6, 1998, (9):1153-67.
Novick et al., "Monoclonal Antibodies to the Soluble Human IL-6 Receptor: Affinity Purification, ELISA, and Inhibition of Ligand Binding," Hybridoma, Feb. 1991, 10(1):137-46.
Ober et al., "Visualizing the Site and Dynamics of IgG Salvage by the MHC Class I-Related Receptor, FcRn," J Immunol, Feb. 15, 2004, 172(4):2021-9.
O'Donovan et al., "EGFR and HER-2 Antagonists in Breast Cancer," Anticancer Res, May-Jun. 2007, 27(3A):1285-94.
Official Action dated Oct. 13, 2016, issued for EP Application No. 11714860.1 and submitted as evidence during EP opposition; 3 pages.
Experimental information regarding off-rate of Xolair Fab for binding to human IgE at pH7.4 and pH5.5 (document submitted in EP opposition and posted by EPO on Feb. 2, 2018); 3 pages.
Okabe, Proprietary Innovative Antibody Engineering Technologies in Chugai Pharmaceutical, Dec. 18, 2012, 78 pages.
Osbourn et al., "Generation of a panel of related human scFv antibodies with high affinities for human CEA," Immunotechnology, Sep. 1996, 2(3):181-96.
Pancook et al., In Vitro Affinity Maturation of Human IgM Antibodies Reactive with Tumor-Associated Antigens, Hybrid Hybridomics, Oct. 2001, 20(5-6):383-96.
Presta at el., "Humanization of an Anti-Vascular Endothelial Growth Factor Monoclonal Antibody for the Therapy of Solid Tumors and Other Disorders," Cancer Res, Oct. 15, 1997, 57(20):4593-9.
Product labelling information for Rituxan (Rituximab), dated Nov. 1997.
Ragahavan et al., "Analysis of the pH Dependence of the Neonatal Fc Receptor/Immunoglobulin G Interaction Using Antibody and Receptor Variants," Biochemistry, Nov. 14, 1995, 34(45):14649-57.
Reichert, "Antibodies to watch in 2014," mAbs, Jul./Aug. 2014, 6(4):799-802 doi: 10.4161/mabs.29282. Epub May 19, 2014.
Rother et al., "Discovery and development of the complement inhibitor eculizumab for the treatment of paroxysmal nocturnal hemoglobinuria," Nature Biotechnol, Nov. 2007, 25(11):1256-64.
Russo et al., "The CXCL8/IL-8 chemokine family and its receptors in inflammatory diseases," Expert Rev Clin Immunol, May 2014, 10(5):593-619.
Schier et al., "Isolation of Picomolar Affinity Anti-c-erbB-2 Single-chain Fv by Molecular Evolution of the Complementarity Determining Regions in the Center of the Antibody Binding Site," J Mol Biol, Nov. 8, 1996, 263(4):551-67.
Supplementary data provided by opponent for EP Application No. 11714860.1 (document submitted in EP opposition and posted by EPO on Feb. 20, 2018); 3 pages.
Taga et al., "Interleukin-6 Triggers the Association of Its Receptor with a Possible Signal Transducer, gp130," Cell, Aug. 11, 1989, 58(3):573-581.
Taga et al., "Receptors for B Cell Stimulatory Factor 2," J. Exp. Med., Oct. 1, 1987, 166(4):967-981.
Tanzi et al., "Twenty years of the Alzheimer's disease amylold hypothesis: a genetic perspective," Cell, Feb. 2005, 120(4):545-55. (doi:10.1016/j.cell.2005.02.008; PMID 15734686).
Vaccaro et al., "Divergent activities of an engineered antibody in murine and human systems have implications for therapeutic antibodies," Proc Natl Acad Sci USA, Dec. 5, 2006, 103(49):18709-14. Epub Nov. 20, 2006.
Vercellini et al., "Postoperative oral contraceptive exposure and risk of endometrioma recurrence," Am J Obstet Gynecol, May 2008 (Epub Feb. 2008), 198(5):504.

Vidarsson et al., "IgG subclasses and allotypes: from structure to effector functions," Front immunol, Oct. 20, 2014, 5:520. doi: 10.3389/fimmu.2014.00520. eCollection 2014.
Waelbroeck et al., "The pH Dependence of Insulin Binding," J Biol Chem, Jul. 25, 1982, 257(14):8284-91.
Wang et al., "Monoclonal Antibodies with Identical Fc Sequences Can Bind to FcRn Differentially with Pharmacokinetic Consequences," Drug Metab Dispos, Sep. 2011, 39(9):1469-77. doi: 10.1124/dmd.111.039453. Epub May 24, 2011.
Ward et al., "Evidence to support the cellular mechanism involved in serum IgG homeostasis in humans," Int Immunol, Feb. 2003, 15(2):187-95.
Welch et al., "Adalimumab (Humira) for the Treatment of Rheumatoid Arthritis" Am Fam Physician, Dec. 15, 2008, 78(12):1406-1408.
Wu et al., "Stepwise in vitro affinity maturation of Vitaxin, an $\alpha v\beta 33$-specific humanized mAb," Proc Natl Acad Sci USA, May 26, 1998, 95(11):6037-42.
Xolair (omalizumab) Prescribing Information, https://www.gene.com/download/pdf/xolair_prescribing.pdf, Jul. 2016, 27 pages.
Yamasaki et al., "Cloning and Expression of the Human Interleukin-6 (BSF-2/IFNb 2) Receptor," Science, Aug. 12, 1988, 241(4867):825-8.
Yang et al., "Dataset of the binding kinetic rate constants of anti-PCSK9 antibodies obtained using the Biacore T100, Protean XPR36, Octet RED384, and IBIS MX96 biosensor platforms," Data Brief, Jul. 27, 2016, 8:1173-83. doi : 10. 1016/ J. dib. 2016.07.044. eCollection Sep. 2016.
Yang et al., "Maximizing in vivo target clearance by design of pH-dependent target binding antibodies with altered affinity to FcRn," mAbs, Oct. 2017, 9(7):1105-1117. doi : 10. 1080/ 19420862. 2017. 1359455. Epub Aug. 8, 2017.
Yeung et al., "A Therapeutic Anti-VEGF Antibody with Increased Potency Independent of Pharmacokinetic Half-life," Cancer Res, Apr. 15, 2010, 70(8):3269-77. doi : 10. 1158/0008-5472. CAN-09-4580. Epub Mar. 30, 2010.
Ying et al., Chinese Journal of Cell Biology, Oct. 2014, 36(10):1344-1349.
USPTO Amendment and Response to Non-Final Office Action in U.S. Appl. No. 14/404,051, dated Jun. 5, 2017, 55 pages.
USPTO Final Office Action in U.S. Appl. No. 14/404,051, dated Oct. 18, 2017, 15 pages.
USPTO Advisory Action Before the Filing of an Appeal Brief and Notice of Non-Compliant Amendment (37 CFR 1.121) in U.S. Appl. No. 14/404,051, dated Jun. 28, 2018, 4 pages.
USPTO Non-Final Office Action in U.S. Appl. No. 14/347,321, dated Nov. 13, 2017, 64 pages.
USPTO Non-Final Office Action in U.S. Appl. No. 13/637,415, dated May 23, 2017, 65 pages.
USPTO Final Office Action in U.S. Appl. No. 13/637,415, dated Mar. 2, 2018, 36 pages.
USPTO Notice of Allowance in U.S. Appl. No. 14/347,034, dated Sep. 22, 2016, 9 pages.
USPTO Non-Final Office Action in U.S. Appl. No. 14/347,034, dated May 25, 2017, 16 pages.
USPTO Non-Final Office Action in U.S. Appl. No. 14/347,034, dated Jan. 8, 2018, 15 pages.
USPTO Non-Final Office Action in U.S. Appl. No. 15/230,904, dated May 25, 2017, 9 pages.
Non-Final Office Action for U.S. Appl. No. 15/230,904, dated Jan. 8, 2018, 16 pages.
International Search Report for App. Ser. No. PCT/JP2016/003616, dated Nov. 25, 2016, 4 pages.
International Search Report for App. Ser. No. PCT/JP2015/006323, dated Jul. 12, 2018, 23 pages.
International Search Report for App. Ser. No. PCT/JP2017/028346, dated Oct. 31, 2017, 5 pages.
U.S. Appl. No. 15/230,904, Igawa el al., filed Aug. 8, 2016 (abandoned).
U.S. Appl. No. 16/028,140, Igawa el al., filed Jul. 5, 2018.
U.S. Appl. No. 16/264,735, Igawa el al., filed Feb. 1, 2019.
U.S. Appl. No. 15/553,609, Kakehi el al., filed Aug. 25, 2017.
GenBank Accession No. AAA51925.1, Oct. 31, 1994 (3 pages).

(56) References Cited

OTHER PUBLICATIONS

Tarantul, "Antibodies," Explanatory Biotechnological Dictionary, Moscow, 2009, p. 72 (with English translation).
U.S. Appl. No. 16/361,498, filed Mar. 22, 2019, Igawa et al.
Actemra (tocilizumab), Highlights of Prescribing Information, as revised in Aug. 2017 (1 page).
Ando et al., "Tocilizumab, a Proposed Therapy for the Cachexia of Interleukin6-Expressing Lung Cancer," PLOS One, Jul. 10, 2014, 9(7):e102436. doi: 10.1371/journal.pone.0102436. eCollection 2014.
Costa et al., "Efficacy of tocilizumab in a patient with refractory psoriatic arthritis," Clin Rheumatol, Sep. 2014, 33(9):1355-7.
Furuya et al., "Interleukin-6 as a Potential Therapeutic Target for Pulmonary Arterial Hypertension," Int J Rheumatol, Aug. 2010, 2010:720305:1-8. doi: 10.1155/2010/720305. Epub Aug. 2, 2010.
Hashizume et al., "Tocilizumab, a humanized anti-interleukin-6 receptor antibody, improved anemia in monkey arthritis by suppressing IL-6-induced hepcidin production," Rheumatol Int, May 2010, 30(7):917-23. doi: 10.1007/s00296-009-1075-4. Epub Jul. 29, 2009.
Honda et al., "Marginal zone B cells exacerbate endotoxic shock via interleukin-6 secretion induced by Fca/mR-coupled TLR4 signalling," Nat Commun, May 5, 2016, 7:11498. doi: 10.1038/ncomms11498.
Iijima et al., "Tocilizumab improves systemic rheumatoid vasculitis with necrotizing crescentic glomerulonephritis," Mod Rheumatol, Jan. 2015, 25(1):138-42. doi: 0.3109/14397595.2013.874748. Epub Feb. 18, 2014.
Kishimoto, "Interleukin-6 and its Receptor in Autoimmunity," J Autoimmun, Apr. 1992, 5 Suppl A:123-32.
Kondo et al., "A case of overlap syndrome successfully treated with tocilizumab: a hopeful treatment strategy for refractory dermatomyositis? ," Rheumatology (Oxford), Oct. 2014, 53(10):1907-8. doi: 10.1093/rheumatology/keu234. Epub May 23, 2014.
Mihara et al., "Anti-interleukin 6 receptor antibody inhibits murine AA-amyloidosis," J Rheumatol, Jun. 2004, 31(6):1132-8.
Mori et al., "Novel models of cancer-related anemia in mice inoculated with IL-6-producing tumor cells," Biomed Res, Feb. 2009, 30(1):47-51.
Motozawa et al., "Unique circumferential peripheral keratitis in relapsing polychondritis," Medicine (Baltimore), Oct. 2017, 96(41):e7951. doi: 10.1097/MD.0000000000007951.
Narazaki et al., "Therapeutic effect of tocilizumab on two patients with polymyositis," Rheumatology (Oxford), Jul. 2011, 50(7):1344-6. doi: 10.1093/rheumatology/ker152. Epub Apr. 2011.
Serada et al., "IL-6 blockade inhibits the induction of myelin antigen-specific Th17 cells and Th1 cells in experimental autoimmune encephalomyelitis," Proc Natl Acad Sci USA, Jul. 1, 2008, 105(26):9041-6. doi: 10.1073/pnas.0802218105. Epub Jun. 24, 2008.
Shima et al., "Tocilizumab, a humanized anti-interleukin-6 receptor antibody, ameliorated clinical symptoms and MRI findings of a patient with ankylosing spondylitis," Mod Rheumatol, Aug. 2011, 21(4):436-9. doi: 10.1007/s10165-011-0416-9. Epub Feb. 9, 2011.
Shimizu et al., "Successful treatment with tocilizumab for refractory scleritis associated with relapsing polychondritis," Scand J Rheumatol, Sep. 2017, 46(5):418-419. doi: 10.1080/03009742.2016.1275774. Epub Jan. 25, 2017.
Silpa-Archa et al., "Outcome of tocilizumab treatment in refractory ocular inflammatory diseases," Acta Ophthalmol, Sep. 2016, 94(6):e400-6. doi: 10.1111/aos.13015. Epub Mar. 24, 2016.
Suzuki et al., "Anti-murine IL-6 receptor antibody inhibits IL-6 effects in vivo," Immunol Lett, Sep. 1991, 30(1):17-21.
U.S. Appl. No. 13/889,484, filed May 8, 2013, Igawa et al.
U.S. Appl. No. 13/889,512, filed May 8, 2013, Igawa et al.
U.S. Appl. No. 13/959,489, filed Aug, 5, 2013, Igawa et al.
U.S. Appl. No. 14/007,947, filed Dec. 30, 2013, Igawa et al.
U.S. Appl. No. 15/210,353, filed Jul. 14, 2016, Igawa et al.
U.S. Appl. No. 15/210,360, filed Jul. 14, 2016, Igawa et al.
U.S. Appl. No. 15/230,904, filed Sep. 13, 2016, Igawa et al.
U.S. Appl. No. 15/263,617, filed Sep. 13, 2016, Igawa et al.
Abe et al., "Purification of monoclonal antibodies with light-chain heterogeneity produced by mouse hybridomas raised with NS-1 myelomas: application of hydrophobic interaction high-performance liquid chromatography," J. Biochem. Biophys. Methods, Oct. 1993, 27:215-227.
Adams et al., "Humanization of a recombinant monoclonal antibody to produce a therapeutic HER dimerization inhibitor, pertuzumab," Cancer Immunol. Immunother., Jun. 2006, 55:717-727.
Algonomics—Tripole® applications [online] Retrieved from the Internet on Feb. 29, 2012: http://web.archive.org/web20090221052902/http://www.algonomics.com/proteinengineering/tripole_applications.php, 2 pages (Feb. 21, 2009).
Allen et al., "Novel mechanism for gonadotropin-releasing hormone neuronal migration involving Gas6/Ark signaling to p38 mitogen-activated protein kinase," Mol. Cell. Biol., Jan. 2002, 22(2):599-613.
Alley et al., "Antibody-drug conjugates: targeted drug delivery for cancer," Curr Opin Chem Biol., Aug. 2010, 14(4):529-37. doi: 10.1016/j.cbpa.2010.06.170. Epub Jul. 17, 2010.
Almagro et al., "Humanization of antibodies," Front Biosci., Jan. 2008, 13:1619-33.
Amersham Biosciences, "Affinity Chromatography: Principles and Methods," Edition AD, 2002, pp. 16-18, 137.
Amersham Biosciences, "Antibody Purification Handbook," Edition 18-1037-46 [online], [retrieved on Nov. 5, 2015]. Retrieved from the Internet: http:///www.promix.ru/manuf/ge/chrom/lit/Antibody_Purification.pdf.
Amersham Biosciences, "Protein Purification Handbook," Edition AC, 2001, 98 pages.
Amigorena et al., "Cytoplasmic domain heterogeneity and functions of IgG Fc receptors in B lymphocytes," Science, Jun. 1992, 256(5065):1808-12.
Amigorena et al., "Fc gamma RII expression in resting and activated B lymphocytes," Eur J Immunol., Aug. 1989, 19(8):1379-85.
Araujo et al., "Increased rheumatoid factor interference observed during immunogenicity assessment of an Fc-engineered therapeutic antibody," J Pharm Biomed Anal., Jul. 15, 2011, 55(5):1041-9. doi: 10.1016/j.jpba.2011.03.008. Epub Mar. 11, 2011.
Armour et al., "Differential binding to human FcgammaRIIa and FcgammaRIIb receptors by human IgG wildtype and mutant antibodies," Mol Immunol., Dec. 2003, 40(9):585-93.
Armour et al., "Recombinant human IgG molecules lacking Fcgamma receptor I binding and monocyte triggering activities," Eur. J. Immunol., Aug. 1999, 29(8):2613-24.
Baeuerle et al., "BiTE: Teaching antibodies to engage T-cells for cancer therapy," Curr Opin Mol Ther., Feb. 1, 2009, 11(1):22-30.
Balint et al., "Antibody engineering by parsimonious mutagenesis," Gene., Dec. 27, 1993, 137(1):109-18.
Bartelds et al., "Clinical response to adalimumab: relationship to anti-adalimumab antibodies and serum adalimumab concentrations in rheumatoid arthritis," 2007, Ann Rheum. Dis., 66:921-926.
Bayry et al., "Immuno affinity purification of foot and mouth disease virus type specific antibodies using recombinant protein adsorbed to polystyrene wells," J. Virol. Methods, Aug. 1999, 81:21-30.
Beck et al., "Strategies and challenges for the next generation of therapeutic antibodies," Nat Rev Immunol., May 1, 2010, 10(5):345-52.
Bellosta et al., "Signaling through the ARK tyrosine kinase receptor protects from apoptosis in the absence of growth stimulation," Oncogene., Nov. 13, 1997, 15(20):2387-97.
Bender et al., "Immunogenicity, efficacy and adverse events of adalimumab in RA patients," Rheumatol. Int., 2007, 27:269-274.
Beringhelli et al., "pH and ionic strength dependence of protein (un)folding and ligand binding to bovine beta-lactoglobulins A and B," Biochemistry, Dec. 24, 2002;41(51):15415-22.
Bilsborough, "IL-31 is associated with cutaneous lymphocyte antigen-positive skin homing T cells in patients with atopic dermatitis," J. Allergy Clin. Immunol., 117(2):418-25 (2006).
Binz et al., "Engineering novel binding proteins from nonimmunoglobulin domains," Nat. Biotechnol., 23:1257-68 (2005).

(56) References Cited

OTHER PUBLICATIONS

Blank et al., Decreased transcription of the human FCGR2B gene mediated by the -343 G/C promoter polymorphism and association with systemic lupus erythematosus. Hum Genet., 117(2-3):220-7 (Jul. 2005). Epub May 14, 2005.
Blazar, "Infusion of Anti-B7.1 (CD80) and Anti-B7.2 (CD86) Monoclonal Antibodies Inhibits Murine Graft-Versus-Host Disease Lethality in Part Via Direct Effects on CD4+ and CD8+ T Cells," J. Immunol., 157:3250-59 (1996).
Bogdanovich et al., "Functional improvement of dystrophic muscle by myostatin blockade," Nature, Nov. 28, 2002, 420(6914):418-21.
Boruchov et al., "Activating and inhibitory IgG Fc receptors on human DCs mediate opposing functions," J Clin Invest., 115(10):2914-23 (Oct. 2005). Epub Sep. 15, 2005.
Boumpas et al., "A short course of BG9588 (anti-CD40 ligand antibody) improves serologic activity and decreases hematuria in patients with proliferative lupus glomerulonephritis," Arthritis Rheum., 48(3):719-27 (Mar. 2003).
Branden et al., "Recognition of Foreign Molecules by the Immune System," Introduction to Protein Structure, 2d Ed., Garland Publishing, pp. 299-323 (1999).
Brown et al., "A study of the interactions between an IgG-binding domain based on the B domain of staphylococcal protein A and rabbit IgG," Mol Biotechnol., Aug. 1998, 10(1):9-16.
Brown et al., "Tolerance of single, but not multiple, amino acid replacements in antibody $V_H$ CDR2: a means of minimizing B cell wastage from somatic hypermutation?," J. Immunol., 156(9):3285-91 (1996).
Bruhns et al., "Specificity and affinity of human Fcgamma receptors and their polymorphic variants for human IgG subclasses," Blood, Apr. 16, 2009, 113(16):3716-25. doi: 10.1182/blood-2008-09-179754. Epub Nov. 18, 2008.
Budagian et al., "A promiscuous liaison between IL-15 receptor and Axl receptor tyrosine kinase in cell death control," EMBO J., 24(24):4260-70 (2005).
Burges et al., "Effective relief of malignant ascites in patients with advanced ovarian cancer by a trifunctional anti-EpCAM x anti-CD3 antibody: a phase I/II study," Clin. Cancer Res., 13(13):3899-905 (2007).
Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell. Biol., 111:2129-2138 (1990).
CALBIOCHEM® Buffers, "A guide for the preparation and use of buffers in biological systems," by Chandra Mohan, Ph.D., Copyright © 2003 EMD Biosciences, Inc., an Affiliate of Merck KGaA, Darmstadt, Germany, 37 pages.
Carter, "Bispecific human IgG by design," J. Immunol. Methods, 248:7-15 (2001).
Cemerski et al., "Suppression of mast cell degranulation through a dual-targeting tandem IgE-IgG Fc domain biologic engineered to bind with high affinity to FcγRIIb," Immunol Lett., 143(1):34-43 (Mar. 2012). Doi: 10.1016/j.imlet.2012.01.008. Epub Jan. 25, 2012.
Chamow et al., "A humanized, bispecific immunoadhesin-antibody that retargets CD3+ effectors to kill HIV-1-infected cells," J. Immunol., 153(9):4268-80 (1994).
Chaparro-Riggers et al., "Increasing serum half-life and extending cholesterol lowering in vivo by engineering antibody with pH-sensitive binding to PCSK9," J Biol Chem., 287(14):11090-7 (2012).
Chau et al., "HuM291(Nuvion), a humanized Fc receptor-nonbinding antibody against CD3, anergizes peripheral blood T cells as partial agonist of the T cell receptor," Transplantation., 71(7):941-50 (2001).
Chen et al., "Enhancement and destruction of antibody function by somatic mutation: unequal occurrence is controlled by V gene combinatorial associations," EMBO J., Jun. 15, 1995, 14(12):2784-94.
Chen et al., "Association of a transmembrane polymorphism of Fcgamma receptor IIb (FCGR2B) with systemic lupus erythematosus in Taiwanese patients," Arthritis Rheum., 54(12):3908-17 (Dec. 2006).
Chen et al., "Defective secretion of an immunoglobulin caused by mutations in the heavy chain complementarity determining region 2," J. Exp. Med., 180(2):577-86 (1994).
Chen et al., "Generation and analysis of random point mutations in an antibody CDR2 sequence: many mutated antibodies lose their ability to bind antigen," J. Exp. Med., 176(3):855-66 (1992).
Chen et al., "Selection and analysis of an optimized anti-VEGF antibody: crystal structure of an affinity-matured Fab in complex with antigen," J Mol Biol., Nov. 5, 1999, 293(4):865-81.
Chien et al., "Significant structural and functional change of an antigen-binding site by a distant amino acid substitution: proposal of a structural mechanism," Proc. Natl. Acad. Sci. USA, 86(14):5532-6 (1989).
Chirino et al., "Minimizing the immunogenicity of protein therapeutics," Drug Discov. Today., 9:82-90 (2004).
Chu et al., "Accumulation of succinimide in a recombinant monoclonal antibody in mildly acidic buffers under elevated temperatures," Pharm. Res., 24(6):1145-56 (2007).
Chu et al., "Inhibition of B cell receptor-mediated activation of primary human B cells by coengagement of CD19 and FcgammaRIIb with Fc-engineered antibodies," Mol Immunol., 45(15):3926-33 (Sep. 2008). Doi: 10.1016/j.molimm.2008.06.027. Epub Aug. 8, 2008.
Chu et al., "Reduction of total IgE by targeted coengagement of IgE B-cell receptor and FcγRIIb with Fc-engineered antibody," J Allergy Clin Immunol., 129(4):1102-15 (Apr. 2012). Doi: 10.1016/j.jaci.2011.11.029. Epub Jan. 16, 2012.
Chung et al., "Expression of the proto-oncogene Axl in renal cell carcinoma," DNA Cell Biol., 22(8):533-40 (2003).
Chuntharapai et al., "Isotype-dependent inhibition of tumor growth in vivo by monoclonal antibodies to death receptor 4," J Immunol., 166(8):4891-8 (Apr. 2001).
Clark, "An alignment of IgG sequences from Human, Mouse and Rat," Part II Immunoglobulin lectures (v4), pp. 5(i)-(ii) [retrieved on Jul. 25, 2014]. Retrieved from the Internet: http://www.path.cam.ac.uk/~mrc7/lecturenotes/handoutla.pdf.
Clark, "IgG effector mechanisms," Chem Immunol., 65:88-110 (1997).
Clynes et al., "Fc receptors are required in passive and active immunity to melanoma," Proc Natl Acad Sci USA, Jan. 20, 1998, 95(2):652-6.
Clynes et al., "Inhibitory Fc receptors modulate in vivo cytotoxicity against tumor targets," Nat Med., Apr. 2000, 6(4):443-6.
Cole et al., "Human IgG2 variants of chimeric anti-CD3 are nonmitogenic to T cells," J. Immunol., 159(7):3613-21 (1997).
Colman et al., "Effects of amino acid sequence changes on antibody-antigen interactions," Res Immunol. Jan. 1994, 145(1):33-6.
Comper et al., "Charge selectivity in kidney ultrafiltration," Kidney Int., 47:1242-51 (1995).
Cordoba et al., "Non-enzymatic hinge region fragmentation of antibodies in solution," J. Chromatogr. B. Analyt. Technol. Biomed. Life Sci., 818(2):115-21 (2005).
Couto et al., "Anti-BA46 Monoclonal Antibody Mc3: Humanization Using a Novel Positional Consensus and in Vivo and in Vitro Characterization," Cancer Res., 55:1717-22 (1995).
Craven et al., "Receptor tyrosine kinases expressed in metastatic colon cancer," Int. J. Cancer, 60(6):791-7 (1995).
Cuatrecasas et al., "Affinity Chromatography," Methods Enzymol., 1971, 12:345-78.
Dall'Acqua et al., "Antibody humanization by framework shuffling," Methods, 36(1):43-60 (2005).
Dall'Acqua et al., "Increasing the affinity of a human IgG1 for the neonatal Fc receptor: biological consequences," J. Immunol., Nov. 1, 2002, 169(9):5171-80.
Dall'Acqua et al., "Modulation of the effector functions of a human IgG1 through engineering of its hinge region," J. Immunol., 177(2):1129-38 (2006).

(56) References Cited

OTHER PUBLICATIONS

Dall'Acqua et al., "Properties of human IgG1s engineered for enhanced binding to the neonatal Fc receptor (FcRn)," J Biol Chem., Aug. 18, 2006, 281(33):23514-24. Epub Jun. 21, 2006.
Damschroder et al., "Framework shuffling of antibodies to reduce immunogenicity and manipulate functional and biophysical properties," Mol. Immunol., 44(11):3049-60 (2007).
Datta-Mannan et al., "Monoclonal antibody clearance. Impact of modulating the interaction of IgG with the neonatal Fc receptor," J Biol Chem., Jan. 19, 2007, 282(3):1709-17. Epub Nov. 29, 2006.
Davda et al., "Properties of a general PK/PD model of antibody-ligand interactions for therapeutic antibodies that bind to soluble endogenous targets," mAbs, Sep.-Oct. 2010, 2(5):576-88. doi: 10.4161/mabs.2.5.12833. Epub Sep. 1, 2010.
Davies et al., "Affinity improvement of single antibody VH domains: residues in all three hypervariable regions affect antigen binding." Immunotechnology, 2(3):169-79 (1996).
De Bono et al., "ING-1, a monoclonal antibody targeting Ep-CAM in patients with advanced adenocarcinomas," Clin Cancer Res., 10(22):7555-65 (2004).
De Groot et al., "Reducing risk, improving outcomes: bioengineering less immunogenic protein therapeutics," Clin Immunol., May 2009, 131(2):189-201. doi: 10.1016/j.clim.2009.01.009. Epub Mar. 6, 2009.
De Groot et al., "De-immunization of therapeutic proteins by T-cell epitope modification," Dev. Biol. (Basel), 122:171-94 (2005).
De Pascalis et al., "Grafting of "abbreviated" complementarity-determining regions containing specificity-determining residues essential for ligand contact to engineer a less immunogenic humanized monoclonal antibody," J. Immunol., 169(6):3076-84 (2002).
Declaration of Nimish Gera, Ph.D., CV and Exhibits, dated Sep. 1, 2016, 24 pages.
Deen et al., "Structural determinants of glomerular permeability," Am. J. Physiol. Renal. Physiol., 281:F579-F596 (2001).
Del Rio et al., "An Engineered Penicillin Acylase with Altered Surface Charge Is More Stable in Alkaline pH," Ann. NY Acad. Sci., 799:61-64 (1996).
Deng et al., "An Agonist Murine Monoclonal Antibody to the Human c-Mpl Receptor Stimulates Megakaryocytopoiesis," Blood, 92:1981-88 (1998).
Deng et al., "Pharmacokinetics of humanized monoclonal anti-tumor necrosis factor-{alpha} antibody and its neonatal Fc receptor variants in mice and cynomolgus monkeys," Drug Metab Dispos., Apr. 2010; 38(4):600-5. doi: 10.1124/dmd.109.031310. Epub Jan. 13, 2010.
Desai et al., "Fc gamma receptor IIB on dendritic cells enforces peripheral tolerance by inhibiting effector T cell responses," J Immunol., May 15, 2007, 178(10):6217-26.
Desjarlais et al., "Optimizing engagement of the immune system by anti-tumor antibodies: an engineer's perspective," Drug Discov Today, Nov. 2007, 12(21-22):898-910. Epub Oct. 22, 2007.
Devanaboyina et al., "The effect of pH dependence of antibody-antigen interactions on subcellular trafficking dynamics," mAbs, 5(6):851-9 (2013).
Dhodapkar et al., "Selective blockade of inhibitory Fcgamma receptor enables human dendritic cell maturation with IL-12p70 production and immunity to antibody-coated tumor cells," Proc Natl Acad Sci USA, 102(8):2910-5 (Feb. 2005). Epub Feb. 9, 2005.
Dillon et al., "Interleukin 31, a cytokine produced by activated T cells, induces dermatitis in mice," Nat. Immunol., 5(7):752-760 (2004).
Dillon et al., "Structural and functional characterization of disulfide isoforms of the human IgG2 subclass," J. Biol. Chem., 283:16206-15 (2008).
Diveu et al., "GPL, a novel cytokine receptor related to GP130 and leukemia inhibitory factor receptor," J. Biol. Chem., 278(50):49850-49859 (2003).

Dmytrijuk et al., "FDA report: eculizumab (Soliris) for the treatment of patients with paroxysmal nocturnal hemoglobinuria," Oncologist, Sep. 2008, 13(9):993-1000. doi: 10.1634/theoncologist.2008-0086. Epub Sep. 10, 2008.
Drake et al., "Chapter 5: Biophysical Considerations for Development of Antibody-Based Therapeutics," Biophysical Considerations for Development of Antibody-Based Therapeutics, Springer Springer Science + Business Media New York, 95-7 (2012).
Duffau et al., "Platelet CD154 potentiates interferon-alpha secretion by plasmacytoid dendritic cells in systemic lupus erythematosus," Sci Transl Med., 2(47):47ra63 (Sep. 2010). Doi: 10.1126/scitranslmed.3001001.
Dufner et al., "Harnessing phage and ribosome display for antibody optimization," Trends Biotechnol., Nov. 2006;24(11), 523-9. Epub Sep. 26, 2006.
Durkee et al., "Immunoaffinity chromatographic purification of Russell's viper venom factor X activator using elution in high concentrations of magnesium chloride," Protein Expr Purif., Oct. 1993, 4(5):405-11.
Ejima et al., "Effective elution of antibodies by arginine and arginine derivatives in affinity column chromatography," Anal Biochem., Oct. 15, 2005, 345(2):250-7.
Elliott et al., "Activation of the erythropoietin (EPO) receptor by bivalent anti-EPO receptor antibodies," J. Biol. Chem., 271(40):24691-7 (1996).
Epstein, "Non-randomness of amino-acid changes in the evolution of homologous proteins," Nature, Jul. 22, 1967, 215(5099):355-9.
Ewert et al., "Stability improvement of antibodies for extracellular and intracellular applications: CDR grafting to stable frameworks and structure-based framework engineering," Methods, 34:184-199 (2004).
Feinberg et al., "Mechanism of pH-dependent N-acetylgalactosamine binding by a functional mimic of the hepatocyte asialoglycoprotein receptor," J Biol Chem., 275(45):35176-84 (2000).
Fillipovich, Biochemical basis of human life, VLADOS, 2005:49-50 (with English translation).
Finkelman et al., "Anti-cytokine antibodies as carrier proteins. Prolongation of in vivo effects of exogenous cytokines by injection of cytokine-anti-cytokine antibody complexes," J Immunol., 151(3):1235-44 (1993).
Floto et al., "Loss of function of a lupus-associated FcgammaRIIb polymorphism through exclusion from lipid rafts," Nat Med., 11(10):1056-8 (Oct. 2005). Epub Sep. 18, 2005.
Fournier et al., "Activation of human peripheral IgM+ B cells is transiently inhibited by BCR-independent aggregation of Fc gammaRIIB," J Immunol., 181(8):5350-9 (Oct. 2008).
Fridell et al., "GAS6 induces Axl-mediated chemotaxis of vascular smooth muscle cells," J. Biol. Chem., 273(12):7123-6 (1998).
Fujii, "Antibody affinity maturation by random mutagenesis," Methods Mol. Biol., 248:345-59 (2004).
GE Healthcare. Application note 28-9277-92 AA. "High-throughput screening of elution pH for monoclonal antibodies on MabSelect SuRe using PreDictor plates" [online], [retrieved on Nov. 5, 2015]. Retrieved from the Internet: https://www.gelifesciences.com/gehcls_images/GELS/Related%20Content/Files/1314787424814/litdoc28927792AA_20110831131840.pdf.
Gelderman et al., "The inhibitory effect of CD46, CD55, and CD59 on complement activation after immunotherapeutic treatment of cervical carcinoma cells with monoclonal antibodies or bispecific monoclonal antibodies," Lab Invest., 82(4):483-93 (2002).
Gerstner et al., "Sequence plasticity in the antigen-binding site of a therapeutic anti-HER2 antibody," J. Mol. Biol., 321(5):851-62 (2002).
Gessner et al., "The IgG Fc receptor family," Ann. Hematol., 76:231-248 (1998).
Ghetie et al., "FcRn: the MHC class I-related receptor that is more than an IgG transporter," Immunol. Today, 18:592-598 (1997).
Ghetie et al., "Increasing the serum persistence of an IgG fragment by random mutagenesis," Nat. Biotechnol., 15(7):637-40 (1997).
Ghetie et al., "Multiple roles for the major histocompatibility complex class I-related receptor FcRn," Annu. Rev. Immunol., 18:739-766 (2000).

(56) References Cited

OTHER PUBLICATIONS

Gobburu et al., "Pharmacokinetics/dynamics of 5c8, a monoclonal antibody to CD154 (CD40 ligand) suppression of an immune response in monkeys," J. Pharmacol. Exp. Ther., 286:925-930 (1998).
Goode et al., "The glomerular basement membrane charge-selectivity barrier: an oversimplified concept?" Nephrol. Dial. Transplant., 11:1714-16 (1996).
Goruppi et al., "Requirement of phosphatidylinositol 3-kinase-dependent pathway and Src for Gas6-Axl mitogenic and survival activities in NIH 3T3 fibroblasts," Mol. Cell Biol., 17(8):4442-53 (1997).
Graves et al., "Molecular modeling and preclinical evaluation of the humanized NR-LU-13 antibody," Clin. Cancer Res., 5:899-908 (1999).
Greenwood et al., "Structural motifs involved in human IgG antibody effector functions," Eur J Immunol., 23(5):1098-104 (May 1993).
Gupta et al., "Affinity chromatography and co-chromatography of bispecific monoclonal antibody immunoconjugates," J. Biochem. Biophys. Methods, 51:203-216 (2002).
Guyre et al., "Increased potency of Fc-receptor-targeted antigens," Cancer Immunol. Immunother., 45(3-4):146-8 (1997).
Hafizi et al., "Interaction of Axl receptor tyrosine kinase with C1-TEN, a novel C1 domain-containing protein with homology to tensin," Biochem. Biophys. Res. Commun., 299(5):793-800 (2002).
Hafizi et al., "Signalling and functional diversity within the Axl subfamily of receptor tyrosine kinases," Cytokine Growth Factor Rev., 17(4):295-304 (2006).
Hamilton, "Molecular engineering: applications to the clinical laboratory," Clin. Chem., 39(9):1988-97 (1993).
Hanes et al., "Picomolar affinity antibodies from a fully synthetic naive library selected and evolved by ribosome display," Nat. Biotechnol., 18(12):1287-1292 (2000).
Hanson et al., "Catalytic antibodies and their applications," Curr. Opin. Biotechnol., 16:631-636 (2005).
Haringman et al., "A randomized controlled trial with an anti-CCL2 (anti-monocyte chemotactic protein 1) monoclonal antibody in patients with rheumatoid arthritis," Arthritis Rheum., 54(8):2387-92 (2006).
Haviland et al., "Complete cDNA sequence of human complement pro-C5. Evidence of truncated transcripts derived from a single copy gene," J Immunol., Jan. 1, 1991, 146(1):362-368.
He et al., "Humanization and pharmacokinetics of a monoclonal antibody with specificity for both E- and P-selectin," J. Immunol., 160:1029-35 (1998).
Heyman, "Feedback regulation by IgG antibodies," Immunol Lett., 88(2):157-61 (Aug. 2003).
Hinton et al., "An engineered human IgG1 antibody with longer serum half-life," J Immunol., Jan. 1, 2006, 176(1):346-56.
Hinton et al., "Engineered human IgG antibodies with longer serum half-lives in primates," J. Biol. Chem., 279(8):6213-6 (2004).
Hironiwa et al., "Calcium-dependent antigen binding as a novel modality for antibody recycling by endosomal antigen dissociation," mAbs, Jan. 2016, 8(1):65-73. doi: 10.1080/19420862.2015.1110660. Epub Oct. 23, 2015.
Holash et al., "VEGF-Trap: a VEGF blocker with potent antitumor effects," Proc Natl Acad Sci USA, Aug. 20, 2002, 99(17):11393-8. Epub Aug. 12, 2002.
Holers, "The spectrum of complement alternative pathway-mediated diseases," Immunol Rev., Jun. 2008, 223:300-16. doi: 10.1111/j.1600-065X.2008.00641.x.
Holland et al., "Multiple roles for the receptor tyrosine kinase axl in tumor formation," Cancer Res., Oct. 15, 2005, 65(20):9294-303.
Holt et al., "Domain antibodies: proteins for therapy," Trends Biotechnol., 21(11):484-90 (2003).
Hoodless et al., "Mechanism and function of signaling by the TGF beta superfamily," Curr Top Microbiol Immunol., 1998, 228:235-72.
Hwang et al., "Use of human germline genes in a CDR homology-based approach to antibody humanization," Methods, 36:35-42 (2005).
Igawa et al., "pH-dependent antigen-binding antibodies as a novel therapeutic modality," Biochim Biophys Acta., Nov. 30, 2014, 1844(11):1943-1950.
Igawa et al., "Antibody optimization technologies for developing next generation antibody therapeutics," Bio Industry, 28(7):15-21 (2011) (with English translation).
Igawa et al., "Antibody recycling by engineered pH-dependent antigen binding improves the duration of antigen neutralization," Nat Biotechnol., Nov. 2010, 28(11):1203-7. doi: 10.1038/nbt.1691. Epub Oct. 17, 2010.
Igawa et al., "Engineered monoclonal antibody with novel antigen-sweeping activity in vivo," PLoS One, 8(5):e63236 (2013).
Igawa et al., "Engineering the variable region of therapeutic IgG antibodies," mAbs, 3(3):243-52 (2011).
Igawa et al., "Reduced elimination of IgG antibodies by engineering the variable region," Protein Eng. Des. Sel., 23(5):385-92 (2010).
Ishii et al., "FcRn, a critical regulator of antibody pharmacokinetics," Folia Pharmacol. Jpn., 136(5):280-284 (2010) (with English translation).
Ito et al., "Expression of receptor-type tyrosine kinase, Axl, and its ligand, Gas6, in pediatric thyroid carcinomas around Chernobyl," Thyroid., 12(11):971-5 (2002).
Ito et al., "The His-probe method: effects of histidine residues introduced into the complementarity-determining regions of antibodies on antigen-antibody interactions at different pH values," FEBS Lett., 309:85-88 (1992).
Janeway et al., Immunobiology, The Immune System in Health and Disease, 3$^{rd}$ Edition, 1997 Garland Publishing Inc., pp. 3:1-3:11.
Jefferis et al., "Interaction sites on human IgG-Fc for FcgammaR: current Models," Immunol Lett., 82(1-2):57-65 (Jun. 2002).
Jefferis et al., "Recognition sites on human IgG for Fc gamma receptors: the role of glycosylation," Immunol. Lett., 44(2-3):111-7 (1995).
Johnson et al., "Cation exchange-HPLC and mass spectrometry reveal C-terminal amidation of an IgG1 heavy chain," Anal. Biochem., 360:75-83 (2007).
Jones et al., "Identification and removal of a promiscuous CD4+ T cell epitope from the C1 domain of factor VIII," Thromb. Haemost., 3:991-1000 (2005).
Junghans et al., "The protection receptor for IgG catabolism is the beta2-microglobulin-containing neonatal intestinal transport receptor," Proc Natl Acad Sci USA, May 28, 1996, 93(11):5512-6.
Juszczak et al., "Ipilimumab: a novel immunomodulating therapy causing autoimmune hypophysitis: a case report and review," Eur J Endocrinol., Jul. 2012, 167(1):1-5. doi: 10.1530/EJE-12-0167. Epub Apr. 10, 2012.
Kai et al., "Switching constant domains enhances agonist activities of antibodies to a thrombopoietin receptor," Nat. Biotechnol., 26(2):209-11 (2008).
Kamei et al., "Quantitative methods for developing Fc mutants with extended half-lives," Biotechnol Bioeng., Dec. 20, 2005, 92(6):748-60.
Kashmiri et al., "Generation, characterization, and in vivo studies of humanized anticarcinoma antibody CC49," Hybridoma, 14:461-473 (1995).
Katayose et al., "MUC1-specific targeting immunotherapy with bispecific antibodies: inhibition of xenografted human bile duct carcinoma growth," Cancer Res., 56(18):4205-12 (1996).
Khawli et al., "Improved tumor localization and radioimaging with chemically modified monoclonal antibodies," Cancer Biother. Radiopharm., 11:203-215 (1996).
Kim et al., "Antibody Engineering for the Development of Therapeutic Antibodies," Mol. Cells, 20:17-29 (2005).
Kim et al., "Chemical modification to reduce renal uptake of disulfide-bonded variable region fragment of anti-tac monoclonal antibody labeled with $^{99m}Tc$," Bioconjugate Chem., 10:447-453 (1999).
Kim et al., "Lowering of pI by acylation improves the renal uptake of 99mTc-labeled anti-Tac dsFv: effect of different acylating reagents," Nucl. Med. Biol., 29:795-801 (2002).

(56) References Cited

OTHER PUBLICATIONS

Kim et al., "Mapping the site on human IgG for binding of the MHC class I-related receptor, FcRn," Eur. J. Immunol., 29(9):2819-25 (1999).
Kingsley et al., "The TGF-beta superfamily: new members, new receptors, and new genetic tests of function in different organisms," Genes Dev., Jan. 1994, 8(2):133-46.
Kobayashi et al., "A monoclonal antibody specific for a distinct region of hen egg-white lysozyme," Mol. Immunol., 19:619-30 (1982).
Kobayashi et al., "The pharmacokinetic characteristics of glycolated humanized anti-Tac Fabs are determined by their isoelectric points," Cancer Res., 59:422-430 (1999).
Kohrt et al., "Stimulation of natural killer cells with a CD137-specific antibody enhances trastuzumab efficacy in xenotransplant models of breast cancer," J Clin Invest., 122(3):1066-75 (Mar. 2012). Doi: 10.1172/JCI61226. Epub Feb. 13, 2012.
Komissarov et al., "Site-specific mutagenesis of a recombinant anti-single-stranded DNA Fab. Role of heavy chain complementarity-determining region 3 residues in antigen interaction," J. Biol. Chem., 272(43):26864-70 (1997).
Kranenborg et al., "Development and characterization of anti-renal cell carcinoma x antichelate bispecific monoclonal antibodies for two-phase targeting of renal cell carcinoma," Cancer Res., 55:5864s-5867s (1995).
Krauss et al., "Impact of antibody framework residue VH-71 on the stability of a humanised anti-MUC1 scFv and derived immunoenzyme," Br. J. Cancer, 90:1863-70 (2004).
Kreutz et al., "Efficient bispecific monoclonal antibody purification using gradient thiophilic affinity chromatography." J. Chromatogr. B, 714:161-170 (1998).
Kurfis et al., "Role of Arg182 in the second extracellular loop of angiotensin II receptor AT2 in ligand binding," Biochem. Biophys. Res. Commun., 263:816-819 (1999).
Kussie et al., "A single engineered amino acid substitution changes antibody fine specificity," J Immunol. Jan. 1, 1994, 152(1):146-52.
Laitinen et al., "Brave new (strept)avidins in biotechnology," Trends Biotechnol., Jun. 2007, 25(6):269-77. Epub Apr. 12, 2007.
Lansdorp et al., "Purification and analysis of bispecific tetrameric antibody complexes," Mol. Immunol., 27:659-666 (1990).
Lay et al., "Sulfasalazine suppresses drug resistance and invasiveness of lung adenocarcinoma cells expressing AXL," Cancer Res., 67(8):3878-87 (2007).
Lazar et al., "Engineered antibody Fc variants with enhanced effector function," Proc Natl Acad Sci USA, Mar. 14, 2006, 103(11):4005-10. Epub Mar. 6, 2006.
Lazar et al., "Transforming growth factor alpha: mutation of aspartic acid 47 and leucine 48 results in different biological activities," Mol. Cell. Biol., 8:1247-1252 (1988).
Lederman et al., "A single amino acid substitution in a common African allele of the CD4 molecule ablates binding of the monoclonal antibody, OKT4," Mol Immunol. Nov. 1991, 28(11):1171-81.
Lee et al., "Genetic analysis of the role of proteolysis in the activation of latent myostatin," PLoS One, Feb. 20, 2008, 3(2):e1628. doi: 10.1371/journal.pone.0001628.
Lee et al., "High-affinity human antibodies from phage-displayed synthetic Fab libraries with a single framework scaffold," J Mol Biol., 340(5):1073-93 (2004).
Lee et al., "Regulation of myostatin activity and muscle growth," Proc Natl Acad Sci USA., Jul. 31, 2001, 98(16):9306-11. Epub Jul. 17, 2001.
Leong et al., "Adapting pharmacokinetic properties of a humanized anti-interleukin-8 antibody for therapeutic applications using site-specific pegylation," Cytokine, 16(3):106-19 (2001).
Levin et al., "Optimizing the affinity and specificity of proteins with molecular display," Mol. Biosyst., 2(1):49-57 (2006) (Epub Nov. 8, 2005).
Lewis et al., "Differential responses of human tumor cell lines to anti-p185HER2 monoclonal antibodies," Cancer Immunol Immunother., 37(4):255-63 (1993).

Li et al., "beta-Endorphin omission analogs: dissociation of immunoreactivity from other biological activities," Proc Natl Acad Sci USA, Jun. 1980, 77(6):3211-4.
Li et al., "Apoptotic and antitumor activity of death receptor antibodies require inhibitory Fcγ receptor engagement," Proc Natl Acad Sci USA., Jul. 3, 2012, 109(27):10966-71. doi: 10.1073/pnas.1208698109. Epub Jun. 20, 2012.
Li et al., "CD72 down-modulates BCR-induced signal transduction and diminishes survival in primary mature B lymphocytes," J Immunol., 176(9):5321-8 (May 2006).
Li et al., "Inhibitory Fcγ receptor engagement drives adjuvant and anti-tumor activities of agonistic CD40 antibodies," Science, 333(6045):1030-4 (Aug. 2011). Doi: 10.1126/science.1206954.
Liang et al., "Immunity against a therapeutic xenoprotein/Fc construct delivered by gene transfer is reduced through binding to the inhibitory receptor FcγRIIb," J Gene Med., 13(9):470-7 (2011).
Linder et al., "Design of a pH-dependent cellulose-binding domain," FEBS Lett., Mar. 19, 1999, 447(1):13-6.
Lindhofer et al., "Preferential Species-Restricted Heavy/Light Chain Pairing in Rat/Mouse Quadromas," J. Immunol., 155:219-225 (1995).
Liu et al., "Heterogeneity of monoclonal antibodies," J. Pharm. Sci., 97(7):2426-47 (2008).
Lobo et al., "Antibody pharmacokinetics and pharmacodynamics," J. Pharm. Sci., 93:2645-68 (2004).
Lund et al., "Expression and characterization of truncated forms of humanized L243 IgG1. Architectural features can influence synthesis of its oligosaccharide chains and affect superoxide production triggered through human Fcgamma receptor I," Eur. J. Biochem., 267:7246-57 (2000).
Lutterbuese et al., "T cell-engaging BiTE antibodies specific for EGFR potently eliminate KRAS- and BRAF-mutated colorectal cancer cells," Proc Natl Acad Sci USA, Jul. 13, 2010, 107(28):12605-10. doi: 10.1073/pnas.1000976107. Epub Jun. 28, 2010.
Luttrell et al., "Reaction coupling of chelation and antigen binding in the calcium ion-dependent antibody binding of cyclic AMP," J Biol Chem., Nov. 15, 1991, 266(32):21626-30.
MacCallum et al., "Antibody-antigen interactions: contact analysis and binding site topography," J. Mol. Biol., 262:732-45 (1996).
Mackay et al., "Selective dysregulation of the FcgammaIIB receptor on memory B cells in SLE," J Exp Med., 203(9):2157-64 (Sep. 2006). Epub Aug. 21, 2006.
Maeda et al., "pH-dependent receptor/ligand dissociation as a determining factor for intracellular sorting of ligands for epidermal growth factor receptors in rat hepatocytes," J. Control Release, 82(1):71-82 (2002).
Maier et al., "Assessment of fully automated antibody homology modeling protocols in molecular operating environment," Proteins, Aug. 2014, 82(8):1599-610. doi: 10.1002/prot.24576. Epub Apr. 23, 2014.
Maini et al., "Double-blind randomized controlled clinical trial of the interleukin-6 receptor antagonist, tocilizumab, in European patients with rheumatoid arthritis who had an incomplete response to methotrexate," Arthritis Rheum., 54:2817-29 (2006).
Malbec et al., "Antibodies against growth factor receptors can inhibit the proliferation of transformed cells via a cis-interaction with inhibitory FcR," Immunol Lett., Mar. 30, 2012, 143(1):28-33.
Manger et al., "Fcgamma receptor IIa polymorphism in Caucasian patients with systemic lupus erythematosus: association with clinical symptoms," Arthritis Rheum., 41(7):1181-9 (Jul. 1998).
Manzke et al., "Single-step purification of bispecific monoclonal antibodies for immunotherapeutic use by hydrophobic interaction chromatography," J. Immunol. Methods, 208:65-73 (1997).
Marks et al., "By-passing immunization: building high affinity human antibodies by chain shuffling," Biotechnology (N.Y.), 10(7):779-83 (1992).
Marshall et al., "Rational design and engineering of therapeutic proteins," Drug Discov Today., Mar. 1, 2003, 8(5):212-21.
Martin et al., "Crystal structure at 2.8 A of an FcRn/heterodimeric Fc complex: mechanism of pH-dependent binding," Mol. Cell, 7:867-877 (2001).
Martin et al., "Preclinical safety and immune-modulatng effects of therapeutic monoclonal antibodies to interleukin-6 and tumor necro-

(56) References Cited

OTHER PUBLICATIONS sis factor-α in cynomolgus macaques," J Immunotoxicol., Jul. 1, 2004, 1(3):131-9. doi: 10.1080/15476910490894904.
Martinez et al., "Disulfide connectivity of human immunoglobulin G2 structural isoforms," Biochemistry, 47(28):7496-7508 (2008).
Marvin et al., "Recombinant approaches to IgG-like bispecific antibodies," Acta. Pharmacol. Sin., 26:649-658 (2005).
Marvin et al., "Redesigning an antibody fragment for faster association with its antigen," Biochemistry, 42:7077-83 (2003).
Maxfield et al., "Endocytic recycling," Nat. Rev. Mol. Cell Biol., 5(2):121-32 (2004).
Maynard et al., "Antibody engineering," Annu. Rev. Biomed. Eng., 2:339-76 (2000).
Mazda et al., "Regulation of Muscle Homeostasis and Metabolism by the TGF-β Superfamily Cytokine, Myostatin/growth Differentiation Factor 8 (GDF8)," Journal of Kyoto prefectural university of medicine, 2013, 122(3):133-41.
McCloskey et al., "GAS6 mediates adhesion of cells expressing the receptor tyrosine kinase Axl," J. Biol. Chem., 272(37):23285-91 (1997).
McCroskery et al., "Improved muscle healing through enhanced regeneration and reduced fibrosis in myostatin-null mice," J Cell Sci., Aug. 1, 2005, 118(Pt 15):3531-41.
McPherron et al., "Double muscling in cattle due to mutations in the myostatin gene," Proc Natl Acad Sci USA., Nov. 11, 1997, 94(23):12457-61.
McPherron et al., "Regulation of skeletal muscle mass in mice by a new TGF-beta superfamily member," Nature, May 1, 1997, 387(6628):83-90.
Merchant et al., "An efficient route to human bispecific IgG," Nat. Biotechnol., 16:677-681 (1998).
Meric et al., "Expression profile of tyrosine kinases in breast cancer," Clin. Cancer Res., 8(2):361-7 (2002).
Meyer et al., "Bevacizumab immune complexes activate platelets and induce thrombosis in FCGR2A transgenic mice," J Thromb Haemost., Jan. 2009, 7(1):171-81. Epub Oct. 30, 2008.
Mi et al., "Targeting the neonatal fc receptor for antigen delivery using engineered fc fragments," J Immunol., 181(11):7550-61 (2008).
Mihara et al., "Tocilizumab inhibits signal transduction mediated by both mIL-6R and sIL-6R, but not by the receptors of other members of IL-6 cytokine family," Int. Immunopharmacol., 5(12):1731-40 (2005).
Mollnes et al., "Identification of a human C5 beta-chain epitope exposed in the native complement component but concealed in the SC5b-9 complex," Scand J Immunol., Sep. 1988, 28(3):307-312.
Montero-Julian et al., "Pharmacokinetic study of anti-interleukin-6 (IL-6) therapy with monoclonal antibodies: enhancement of IL-6 clearance by cocktails of anti-IL-6 antibodies," Blood, Feb. 15, 1995, 85(4):917-24.
Morell et al., "Metabolic properties of IgG subclasses in man," J. Clin. Invest., 49(4):673-80 (1970).
Morgan et al., "The N-terminal end of the CH2 domain of chimeric human IgG1 anti-HLA-DR is necessary for Clq, Fc gamma RI and Fc gamma RIII binding," Immunology., 86(2):319-24 (Oct. 1995).
Morimoto et al., "Single-step purification of F(ab')2 fragments of mouse monoclonal antibodies (immunoglobulins G1) by hydrophobic interaction high performance liquid chromatography using TSKgel Phenyl-5PW," J. Biochem. Biophys. Methods, 24:107-117 (1992).
Murtaugh et al., "A combinatorial histidine scanning library approach to engineer highly pH-dependent protein switches," Protein Sci., 20(9):1619-31 doi: 10.1002/pro 696 (2011).
Muta et al., "A 13-amino-acid motif in the cytoplasmic domain of Fc gamma RIIB modulates B-cell receptor signaling," Nature, 368(6466):70-3 (Mar. 1994).
Nakamura et al., "Fcgamma receptor IIB-deficient mice develop Goodpasture's syndrome upon immunization with type IV collagen: a novel murine model for autoimmune glomerular basement membrane disease," J Exp Med., 191(5):899-906 (Mar. 2000).
Nakano et al., "Prevention of growth arrest-induced cell death of vascular smooth muscle cells by a product of growth arrest-specific gene, gas6," FEBS Lett., 387(1):78-80 (1996).
Nakano et al., "Vascular smooth muscle cell-derived, Gla-containing growth-potentiating factor for Ca(2+)-mobilizing growth factors," J. Biol. Chem., 270(11):5702-5 (1995).
Nam et al., "Current evidence for the management of rheumatoid arthritis with biological disease-modifying antirheumatic drugs: a systematic literature review informing the EULAR recommendations for the management of RA," Ann Rheum Dis., Jun. 2010;69(6):976-86. doi: 10.1136/ard.2009.126573. Epub May 6, 2010.
Neis et al., "Enhanced expression levels of IL-31 correlate with IL-4 and IL-13 in atopic and allergic contact dermatitis," J. Allergy Clin. Immunol., 118(4):930-937 (2006).
Nesterova et al., "Glypican-3 as a novel target for an antibody-drug conjugate," AACR Abstract No. 656, Los Angeles, CA (Apr. 4-18, 2007).
Neubauer et al., "Expression of axl, a transforming receptor tyrosine kinase, in normal and malignant hematopoiesis," Blood, 84(6):1931-41 (1994).
Nicholas et al., "Regulation of the immune response. I. Reduction in ability of specific antibody to inhibit long-lasting IgG immunological priming after removal of the Fc fragment," J Exp Med., 129(6):1183-201 (Jun. 1969).
Niebecker et al., "Safety of therapeutic monoclonal antibodies," Curr Drug Saf., 5(4):275-86 (2010).
Nimmerjahn et al., "Fcgamma receptors as regulators of immune responses," Nat Rev Immunol., 8(1):34-47 (Jan. 2008).
Nishimoto et al., "Humanized anti-interleukin-6 receptor antibody treatment of multicentric Castleman disease," Blood, 106:2627-32 (2005).
Nishimoto et al., "Interleukin 6: from bench to bedside," Nat. Clin. Pract. Rheumatol., 2:619-626 (2006).
Nishimoto et al., "Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease," Blood, Nov. 15, 2008, 112(10):3959-64. doi: 10.1182/blood-2008-05-155846. Epub Sep. 10, 2008.
Nishimura et al., "Genetic variants in C5 and poor response to eculizumab," N Engl J Med., Feb. 13, 2014, 370(7):632-9. doi: 10.1056/NEJMoa1311084.
Nordlund et al., "Introduction of histidine residues into avidin subunit interfaces allows pH-dependent regulation of quaternary structure and biotin binding," FEBS Lett., Dec. 18, 2003, 555(3):449-54.
O'Bryan et al., "axl, a transforming gene isolated from primary human myeloid leukemia cells, encodes a novel receptor tyrosine kinase," Mol. Cell Biol., 11(10):5016-31 (1991).
Ohno et al., "Antigen-binding specificities of antibodies are primarily determined by seven residues of VH," Proc. Natl. Acad. Sci. USA, 82(9):2945-9 (1985).
Ohsugi et al., "Current Antibody Drugs ~ Developments/Manufacturing Technology/Scope of Patents," Pharm. Stage, 7:13-18 (2007) (with English translation).
Olferiev et al., "The role of activating protein 1 in the transcriptional regulation of the human FCGR2B promoter mediated by the -343 G → C polymorphism associated with systemic lupus erythematosus," J Biol Chem., 282(3):1738-46 (Jan. 2007). Epub Nov. 27, 2006.
Onda et al., "Lowering the Isoelectric Point of the Fv Portion of Recombinant Immunotoxins Leads to Decreased Nonspecific Animal Toxicity without Affecting Antitumor Activity," Cancer Res., 61:5070-77 (2001).
Ono et al., "The humanized anti-HM1.24 antibody effectively kills multiple myeloma cells by human effector cell-mediated cytotoxicity," Mol. Immunol., 36(6):387-95 (1999).
Ozhegov et al., Tolkovyi Slovar Russkogo iazyka: 2004, p. 292 (with an English translation of the relevant passage defining "control").
Padlan et al., "Identification of specificity-determining residues in antibodies," FASEB J., 9:133-139 (1995).

(56) References Cited

OTHER PUBLICATIONS

Padlan et al., "Structure of an antibody-antigen complex: crystal structure of the HyHEL-10 Fab-lysozyme complex," Proc. Natl. Acad. Sci. USA, 86:5938-5942 (1989).
Pakula et al., "Genetic analysis of protein stability and function," Annu Rev Genet., 1989;23:289-310.
Palladino et al., "Anti-TNF-alpha therapies: the next generation," Nat Rev Drug Discov., Sep. 2003, 2(9):736-46.
Panka et al., "Variable region framework differences result in decreased or increased affinity of variant anti-digoxin antibodies," Proc. Natl. Acad. Sci. USA, 85(9):3080-4 (1988).
Pardridge et al., "Enhanced endocytosis in cultured human breast carcinoma cells and in vivo biodistribution in rats of a humanized monoclonal antibody after cationization of the protein," J. Pharmacol. Exp. Ther., 286(1):548-54 (1998).
Patton et al., "An acid dissociation bridging ELISA for detection of antibodies directed against therapeutic proteins in the presence of antigen," J Immunol Methods, Sep. 2005, 304(1-2):189-95.
Pavlaki et al., "Matrix metalloproteinase inhibitors (MMPIs): the beginning of phase I or the termination of phase III clinical trials," Cancer Metastasis Rev., 22(2-3):177-203 (2003).
Pavlinkova et al., "Charge-modified single chain antibody constructs of monoclonal antibody CC49: Generation, characterization, pharmacokinetics, and biodistribution analysis," Nucl. Med. Biol., 26:27-34 (1999).
Pavlou et al., "The therapeutic antibodies market to 2008," Eur. J. Pharm. Biopharm., 59:389-396 (Apr. 2005).
Petkova et al., "Enhanced half-life of genetically engineered human IgG1 antibodies in a humanized FcRn mouse model: potential application in humorally mediated autoimmune disease," Int Immunol., Dec. 2006, 18(12):1759-69. Epub Oct. 31, 2006.
Pini et al., "Design and use of a phage display library. Human antibodies with subnanomolar affinity against a marker of angiogenesis eluted from a two-dimensional gel," J. Biol. Chem., 273(34):21769-76 (1998).
Poduslo et al., "Polyamine modification increases the permeability of proteins at the blood-nerve and blood-brain barriers," J. Neurochem., 66:1599-1609 (1996).
Pons et al., "Energetic analysis of an antigen/antibody interface: alanine scanning mutagenesis and double mutant cycles on the HyHEL-10/lysozyme interaction," Protein Sci., 8(5):958-68 (1999).
Presta et al., "Molecular engineering and design of therapeutic antibodies," Curr. Opin. Immunol., 20(4):460-70. doi: 10.1016/j.coi.2008.06.012 (2008).
Presta, "Engineering of therapeutic antibodies to minimize immunogenicity and optimize function," Adv. Drug Deliv. Rev., 58(5-6):640-56 (2006).
Qiao et al., "Dependence of antibody-mediated presentation of antigen on FcRn," Proc Natl Acad Sci USA, 105(27):9337-42 (2008).
Queen et al., "A humanized antibody that binds to the interleukin 2 receptor," Proc. Natl. Acad. Sci. USA, 86(24): 10029-10033 (1989).
R&D Systems (R&D Systems, Anti-human IL-31 RA Antibody, Catalog #AF2769, Oct. 2008), 1 page.
R&D Systems (R&D Systems, Biotinylated Anti-human IL-31 RA Antibody, Catalog #BAF2769, Nov. 2005), 1 page.
Raap et al., "Correlation of IL-31 serum levels with severity of atopic dermatitis," J. Allergy Clin. Immunol., 122(2):421-423 (2008).
Radaev et al., "The role of Fc glycosylation and the binding of peptide inhibitors," J Biol Chem., 276(19):16478-83 (May 2001). Epub Jan. 31, 2001.
Raffen et al., "Reengineering immunoglobulin domain interactions by introduction of charged residues," Protein Eng. 11:303-309 (1998).
Rajpal et al., A general method for greatly improving the affinity of antibodies by using combinatorial libraries, Proc. Natl. Acad. Sci. USA, 102:8466-71 (2005).
Rathanaswami et al., "Demonstration of an in vivo generated sub-picomolar affinity fully human monoclonal antibody to interleukin-8," Biochem. Biophys. Res. Commun., 334:1004-13 (2005).
Ravetch et al., "Immune inhibitory receptors," Science, 290(5489):84-9 (Oct. 2000).
Reddy et al., "Elimination of Fc receptor-dependent effector functions of a modified IgG4 monoclonal antibody to human CD4," J. Immunol., 164(4):1925-33 (2000).
Reichert et al., "Development trends for monoclonal antibody cancer therapeutics," Nat. Rev. Drug Discov., 6(5):349-56 (2007).
Reichert et al., "Monoclonal antibody successes in the clinic," Nat. Biotechnol., 23:1073-78 (Sep. 2005).
Reverberi et al., "Factors affecting the antigen-antibody reaction," Blood Transfus., Nov. 2007, 5(4):227-40. doi: 10.2450/2007.0047-07.
Rich et al., "Grading the commercial optical biosensor literature—Class of 2008: 'The Mighty Binders'," J. Mol. Recognit., 23(1):1-64 (2010). doi: 10.1002/jmr.1004.
Richards et al., "Optimization of antibody binding to FcgammaRIIa enhances macrophage phagocytosis of tumor cells," Mol Cancer Ther., 7(8):2517-27 (Aug. 2008). Doi: 10.1158/1535-7163.MCT-08-0201.
Riechelmann et al., "Phase I trial with the CD44v6-targeting immunoconjugate bivatuzumab mertansine in head and neck squamous cell carcinoma," Oral Oncol., Sep. 2008, 44(9):823-9. doi: 10.1016/j.oraloncology.2007.10.009. Epub Jan. 18, 2008.
Robles-Carrillo et al., "Anti-CD40L immune complexes potently activate platelets in vitro and cause thrombosis in FCGR2A transgenic mice," J Immunol., 185(3):1577-83 (Aug. 2010). Doi: 10.4049/jimmunol.0903888. Epub Jun. 28, 2010.
Roitt et al., Immunology, M., Mir, (2000), pp. 110, 150, and 537-9 (with English translation).
Rojas et al., "Formation, distribution, and elimination of infliximab and anti-infliximab immune complexes in cynomolgus monkeys," J Pharmacol Exp Ther., May 2005, 313(2):578-85. Epub Jan. 12, 2005.
Roopenian et al., "FcRn: the neonatal Fc receptor comes of age," Nat Rev Immunol., Sep. 2007, 7(9):715-25. Epub Aug. 17, 2007.
Rothe et al., "Ribosome display for improved biotherapeutic molecules," Expert Opin. Biol. Ther., 6:177-187 (2006).
Rudikoff et al., "Single amino acid substitution altering antigen-binding specificity," Proc. Natl. Acad. Sci. U.S.A., 79(6):1979-83 (1982).
Ruf et al., "Pharmacokinetics and in vivo stability of intraperitoneally administered therapeutic antibody catumaxomab," J. Clin. Oncol., 26 (May 20 suppl) (2008), abstr 14006.
Russo et al., "The CXCL8/IL-8 chemokine family and its receptors in inflammatory diseases," Expert Rev Clin Immunol., May 2014, 10(5):593-619. doi: 10.1586/1744666X.2014.894886. Epub Mar. 29, 2014.
Sainaghi et al., "Gas6 induces proliferation in prostate carcinoma cell lines expressing the Axl receptor," J. Cell. Physiol., 204(1):36-44 (2005).
Salfeld et al., "Isotype selection in antibody engineering," Nat. Biotechnol., 25:1369-72 (2007).
Sal-Man et al., "Arginine mutations within a transmembrane domain of Tar, an *Escherichia coli* aspartate receptor, can drive homodimer dissociation and heterodimer association in vivo," May 2014, 10(5):593-619. doi: 10.1586/1744666X.2014.894886. Epub Mar. 29, 2014.
Salmon et al., "Fc gamma RIIA alleles are heritable risk factors for lupus nephritis in African Americans," J Clin Invest., 97(5):1348-54 (Mar. 1996).
Sarkar et al., "Rational cytokine design for increased lifetime and enhanced potency using pH-activated histidine switching," Nat Biotechnol., 20(9):908-13 (2002).
Sarmay et al., "Mapping and comparison of the interaction sites on the Fc region of IgG responsible for triggering antibody dependent cellular cytotoxicity (ADCC) through different types of human Fc gamma receptor," Mol. Immunol., 29(5):633-9 (1992).
Sato et al., "Reshaping a human antibody to inhibit the interleukin 6-dependent tumor cell growth," Cancer Res., 53:851-856 (1993).
Satoh et al., "Non-fucosylated therapeutic antibodies as next-generation therapeutic antibodies," Expert Opin Biol Ther., 6(11):1161-73 (2006).

(56) References Cited

OTHER PUBLICATIONS

Sawabu et al., "Growth arrest-specific gene 6 and Axl signaling enhances gastric cancer cell survival via Akt pathway," Mol. Carcinog., 46(2):155-64 (2007).
Scappaticci et al., "Arterial thromboembolic events in patients with metastatic carcinoma treated with chemotherapy and bevacizumab," J Natl Cancer Inst., 99(16):1232-9 (Aug. 2007). Epub Aug. 8, 2007.
Schaeffer et al., "The Rat Glomerular Filtration Barrier Does Not Show Negative Charge Selectivity," Microcirculation, 9:329-342 (2002).
Schmidt et al., Human Physiology, Moscow, 2:431-436 (1996) (with English translation).
Schmidt et al., Human Physiology, Moscow, 3:764 (1996) (with English translation).
Schmitz et al., "Phage display: a molecular tool for the generation of antibodies—a review," Placenta., 21 Suppl A:S106-12 (2000).
Schroeder et al., "Similarity and divergence in the development and expression of the mouse and human antibody repertoires," Dev Comp Immunol., 2006, 30(1-2):119-35.
Schroter et al., "A generic approach to engineer antibody pH-switches using combinatorial histidine scanning libraries and yeast display," mAbs., 2015, 7(1):138-51. doi: 10.4161/19420862.2014.985993.
Schuster et al., "Signaling of human ciliary neurotrophic factor (CNTF) revisited. The interleukin-6 receptor can serve as an alpha-receptor for CTNF," J Biol Chem., Mar. 14, 2003, 278(11):9528-35.
Sebba et al., "Tocilizumab: the first interleukin-6-receptor inhibitor," Am J Health Syst Pharm., Aug. 1, 2008, 65(15):1413-8. doi: 10.2146/ajhp070449.
Seda et al., "B-cell receptor signalling and its crosstalk with other pathways in normal and malignant cells," Eur J Haematol., Mar. 2015, 94(3):193-205. doi: 10.1111/ejh.12427.
Segal et al., "Bispecific antibodies in cancer therapy," Curr. Opin. Immunol., 11:558-562 (1999).
Shaul, "Exploring the charge space of protein-protein association: a proteomic study," Proteins, 60:341-352 (2005).
Shieh et al., "Expression of axl in lung adenocarcinoma and correlation with tumor progression," Neoplasia., 7(12):1058-64 (2005).
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., Mar. 2, 2001, 276(9):6591-604. Epub Nov. 28, 2000.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem., Jan. 31, 2003, 278(5):3466-73. Epub Nov. 8, 2002.
Shire et al., "Challenges in the development of high protein concentration formulations," J. Pharm. Sci., 93:1390-1402 (2004).
Sigma-Aldrich, "Product Information: Monoclonal Anti-Flag ® M1, Clone M1 produced in mouse, purified immunoglobulin," Sigma-Aldrich.com, Catalog No. F3040. Retrieved from the Internet on Nov. 5, 2013 at: http://www.sigmaaldrich.com/content/dam/sigma-aldrich/does/Sigma/Datasheet/13040dat.pdf.
Sims et al., "HMGB1 and RAGE in inflammation and cancer," Annu Rev Immunol., 28:367-88 (2010).
Singer et al., Genes & Genomes 1:63 (1998) (with English translation).
Singer et al., Genes & Genomes, 1991, 67-69 (with English translation).
Sinha et al., "Electrostatics in protein binding and function," Curr. Protein Pept. Sci., 3(6):601-14 (2002).
Smith et al., "FcgammaRIIB in autoimmunity and infection: evolutionary and therapeutic implications," Nat Rev Immunol., May, 10(5):328-43 (May 2010). Doi: 10.1038/nri2762.
Sonkoly et al., "IL-31: a new link between T cells and pruritus in atopic skin inflammation," J. Allergy Clin. Immunol., 117:411-417 (2006).

Stearns et al., "The interaction of a Ca2+-dependent monoclonal antibody with the protein C activation peptide region. Evidence for obligatory Ca2+ binding to both antigen and antibody," J Biol Chem., Jan. 15, 1988, 263(2):826-32.
Stenhoff et al., "Vitamin K-dependent Gas6 activates ERK kinase and stimulates growth of cardiac fibroblasts," Biochem. Biophys. Res. Commun., 319(3):871-8 (2004).
Stewart et al., "Site-directed mutagenesis of a catalytic antibody: an arginine and a histidine residue play key roles," Biochemistry, 33(8):1994-2003 (1994).
Strand et al., "Biologic therapies in rheumatology: lessons learned, future directions," Nat. Rev. Drug Discov., 6:75-92 (2007).
Strohl, "Optimization of Fc-mediated effector functions of monoclonal antibodies," Curr Opin Biotechnol., Dec. 2009, 20(6):685-91. doi: 10.1016/j.copbio.2009.10.011. Epub Nov. 4, 2009.
Su et al., Expression profile of FcgammaRIIb on leukocytes and its dysregulation in systemic lupus erythematosus, J Immunol., 178(5):3272-80 (Mar. 2007).
Sun et al., "Coexpression of Gas6/Axl in human ovarian cancers," Oncology, 66(6):450-7 (2004).
Suresh et al., "Bispecific monoclonal antibodies from hybrid hybridomas," Methods Enzymol., 121:210-228 (1986).
Suzuki et al., "Importance of neonatal FcR in regulating the serum half-life of therapeutic proteins containing the Fc domain of human IgG1: a comparative study of the affinity of monoclonal antibodies and Fc-fusion proteins to human neonatal FcR," J. Immunol., 184(4):1968-76 (2010).
Szlama et al., "Latent myostatin has significant activity and this activity is controlled more efficiently by WFIKKN1 than by WFIKKN2," FEBS J., Aug. 2013, 280(16):3822-39. doi: 10.1111/febs.12377. Epub Jul. 5, 2013.
Tabrizi et al., "Elimination mechanisms of therapeutic monoclonal antibodies," Drug Discov Today, 11(1-2):81-8 (2006).
Takeuchi et al., "The Japanese experience with biologic therapies for rheumatoid arthritis," Nat Rev Rheumatol., Nov. 2010, 6(11):644-52. doi: 10.1038/nrrheum.2010.154. Epub Sep. 28, 2010.
Takkinen et al., "Affinity and Specificity Maturation by CDR Walking," Antibody Engineering, Springer Lab Manuals, pp. 540-545 (2001).
Tan et al., "Engineering the isoelectric point of a renal cell carcinoma targeting antibody greatly enhances scFv solubility," Immunotechnology, 4(2):107-114 (1998).
Tarditi et al., "Selective high-performance liquid chromatographic purification of bispecific monoclonal antibodies," J. Chromatogr., 599:13-20 (1992).
Teeling et al., "The biological activity of human CD20 monoclonal antibodies is linked to unique epitopes on CD20," J. Immunol., 177(1):362-71 (2006).
Ten Kate et al., "Effect of isoelectric point on biodistribution and inflammation: imaging with indium-111-labelled IgG," Eur. J. Nucl. Med., 17:305-309 (1990).
Trinh et al., "Ipilimumab in the treatment of melanoma," Expert Opin Biol Ther., Jun. 2012, 12(6):773-82. doi: 10.1517/14712598.2012.675325. Epub Apr. 14, 2012.
Tsuchiya, Credit Suisse Seminar, "Therapeutic Antibody," at Fuji-Gotemba Laboratories, p. 21 (2006) (with English translation).
Tsurushita et al., "Design of humanized antibodies: From anti-Tac to Zenapax," Methods, 36:69-83 (2005).
Vaccaro et al., "Engineering the Fc region of immunoglobulin G to modulate in vivo antibody levels," Nat Biotechnol., Oct. 2005, 23(10):1283-8. Epub Sep. 25, 2005.
Vaisitti et al., "Cationization of monoclonal antibodies: another step towards the "magic bullet"?," J. Biol. Regul. Homeost. Agents., 19(3-4):105-12 (2005).
Vajdos et al., "Comprehensive functional maps of the antigen-binding site of an anti-ErbB2 antibody obtained with shotgun scanning mutagenesis," J. Mol. Biol., 320(2):415-28 (2002).
Vajkoczy et al., "Dominant-negative inhibition of the Axl receptor tyrosine kinase suppresses brain tumor cell growth and invasion and prolongs survival," Proc. Natl. Acad. Sci. U.S.A., 103(15):5799-804 (2006).
Van Walle et al., Immunogenicity screening in protein drug development, Expert Opin. Biol. Ther., 7:405-418 (2007).

(56) References Cited

OTHER PUBLICATIONS

Varnum et al., "Axl receptor tyrosine kinase stimulated by the vitamin K-dependent protein encoded by growth-arrest-specific gene 6," Nature, 373(6515):623-6 (1995).
Vaughn et al., "Structural basis of pH-dependent antibody binding by the neonatal Fc receptor," Structure, 6(1):63-73 (1998).
Veri et al., "Monoclonal antibodies capable of discriminating the human inhibitory Fcgamma-receptor IIB (CD32B) from the activating Fcgamma-receptor IIA (CD32A): biochemical, biological and functional characterization," Immunology, 121(3):392-404 (2007).
Veri et al., "Therapeutic control of B cell activation via recruitment of Fcgamma receptor IIb (CD32B) inhibitory function with a novel bispecific antibody scaffold," Arthritis Rheum., 62(7):1933-43 (Jul. 2010). Doi: 10.1002/art.27477.
Wagner et al., "Loss of myostatin attenuates severity of muscular dystrophy in mdx mice," Ann Neurol., Dec. 2002, 52(6):832-6.
Wang et al., "HMG-1 as a late mediator of endotoxin lethality in mice," Science, 285(5425):248-51 (1999).
Wang et al., "Polyethylene Glycol-modified Chimeric Toxin Composed of Transforming Growth Factor alpha and Pseudomonas Exotoxin," Cancer. Res., 53:4588-4594 (1993).
Ward et al., "A calcium-binding monoclonal antibody that recognizes a non-calcium-binding epitope in the short consensus repeat units (SCRs) of complement Clr," Mol Immunol., Jan. 1992, 29(1):83-93.
Warmerdam et al., Molecular basis for a polymorphism of human Fc gamma receptor II (CD32), J Exp Med., 172(1):19-25 (Jul. 1990).
Warnaar et al., "Purification of bispecific F(ab')2 from murine trinoma OC/TR with specificity for CD3 and ovarian cancer," Hybridoma, 13:519-526 (1994).
Weiner et al., "Monoclonal antibodies: versatile platforms for cancer immunotherapy," Nat Rev Immunol., May 2010, 10(5):317-27. doi: 10.1038/nri2744.
Wenink et al., "The inhibitory Fc gamma IIb receptor dampens TLR4-mediated immune responses and is selectively up-regulated on dendritic cells from rheumatoid arthritis patients with quiescent disease," J Immunol., Oct. 1, 2009, 183(7):4509-20. doi: 10.4049/jimmonul.0900153. Epub Sep. 4, 2009.
Wernersson et al., "IgG-mediated enhancement of antibody responses is low in Fc receptor gamma chain-deficient mice and increased in Fc gamma RII-deficient mice," J Immunol., 163(2):618-22 (Jul. 1999).
Whittemore et al., "Inhibition of myostatin in adult mice increases skeletal muscle mass and strength," Biochem Biophys Res Commun., Jan. 24, 2003, 300(4):965-71.
Wiens et al., "Mutation of a single conserved residue in VH complementarity-determining region 2 results in a severe Ig secretion defect," J. Immunol., 167(4):2179-86 (2001).
Wiens et al., "Somatic mutation in VH complementarity-determining region 2 and framework region 2: differential effects on antigen binding and Ig secretion," J. Immunol., 159(3):1293-302 (1997).
Wikipedia, "Chaotropic agent" [online], [retrieved on Nov. 2, 2015]. Retrieved from the Internet: https://en.wikipedia.org/wiki/Chaotropic_agent.
Wilson et al., "An Fcγ receptor-dependent mechanism drives antibody-mediated target-receptor signaling in cancer cells," Cancer Cell, 19(1):101-13 (Jan. 2011). Doi: 10.1016/j.ccr.2010.11.012.
Wojciak et al., "The crystal structure of sphingosine-1-phosphate in complex with a Fab fragment reveals metal bridging of an antibody and its antigen," Proc Natl Acad Sci USA, 106(42):17717-22 (2009).
Wu et al., "Structure-based engineering of a monoclonal antibody for improved solubility," Protein Eng Des Sel., Aug. 2010, 23(8):643-51. doi: 10.1093/protein/gzq037. Epub Jun. 11, 2010.
Wu et al., "Development of motavizumab, an ultra-potent antibody for the prevention of respiratory syncytial virus infection in the upper and lower respiratory tract," J. Mol. Biol., 368:652-665 (2007).
Wu et al., "Humanization of a murine monoclonal antibody by simultaneous optimization of framework and CDR residues," J. Mol. Biol., 294(1):151-62 (1999).
Wypych et al., "Human IgG2 antibodies display disulfide-mediated structural isoforms," J. Biol. Chem., 283(23):16194-16205 (2008).
Xiang et al., "Study of B72.3 combining sites by molecular modeling and site-directed mutagenesis," Protein Eng., 13(5):339-44 (2000).
Xiao et al., "Pharmacokinetics of anti-hepcidin monoclonal antibody Ab 12B9m and hepcidin in cynomolgus monkeys," AAPS J., Dec. 2010, 12(4):646-57. doi: 10.1208/s12248-010-9222-0. Epub Aug. 25, 2010.
Xu et al., "Fc gamma Rs modulate cytotoxicity of anti-Fas antibodies: implications for agonistic antibody-based therapeutics," J Immunol., 171(2):562-8 (Jul. 2003).
Yagi et al., "Interleukin-31 stimulates production of inflammatory mediators from human colonic subepithelial myofibroblasts," Int. J. Mol. Med., 19(6):941-946 (2007).
Yamagata et al., "Synaptic adhesion molecules," Curr. Opin. Cell Biol., 15(5):621-32 (2003).
Yamamoto et al., "Molecular studies of pH-dependent ligand interactions with the low-density lipoprotein receptor," Biochemistry, 47(44):11647-52 (2008).
Yamasaki et al., "Pharmacokinetic analysis of in vivo disposition of succinylated proteins targeted to liver nonparenchymal cells via scavenger receptors: importance of molecular size and negative charge density for in vivo recognition by receptors," J. Pharmacol. Exp. Ther., 301:467-477 (2002).
Yang et al., "CDR walking mutagenesis for the affinity maturation of a potent human anti-HIV-1 antibody into the picomolar range," J. Mol. Biol., 254(3):392-403 (1995).
Yang et al., "Tailoring structure-function and pharmacokinetic properties of single-chain Fv proteins by site-specific PEGylation," Protein Eng., 16:761-770 (2003).
Yeung et al., "Engineering human IgG1 affinity to human neonatal Fc receptor: impact of affinity improvement on pharmacokinetics in primates," J. Immunol., Jun. 15, 2009, 182(12):7663-71. doi: 10.4049/jimmunol.0804182.
Yuasa et al., "Deletion of fcgamma receptor IIB renders H-2(b) mice susceptible to collagen-induced arthritis," J Exp Med., 189(1):187-94 (Jan. 1999).
Zalevsky et al., "Enhanced antibody half-life improves in vivo activity," Nat. Biotechnol., 28(2):157-9 (2010).
Zhang et al., "Effective therapy for a murine model of human anaplastic large-cell lymphoma with the anti-CD30 monoclonal antibody, HeFi-1,does not require activating Fc receptors," Blood, 108(2):705-10 (Jul. 2006). Epub Mar. 21, 2006.
Zhang et al., "Immune complex/Ig negatively regulate TLR4-triggered inflammatory response in macrophages through Fc gamma RIIb-dependent PGE2 production," J Immunol., Jan. 1, 2009, 182(1):554-62.
Zheng et al., "Translational pharmacokinetics and pharmacodynamics of an FcRn-variant anti-CD4 monoclonal antibody from preclinical model to phase I study," Clin Pharmacol Ther., Feb. 2011, 89(2):283-90. doi: 10.1038/clpt.2010.311. Epub Dec. 29, 2010.
Zhou et al., "Interfacial metal and antibody recognition," Proc Natl Acad Sci U S A., Oct. 11, 2005, 102(41):14575-80.
Zhu et al., "MHC class I-related neonatal Fc receptor for IgG is functionally expressed in monocytes, intestinal macrophages, and dendritic cells," J. Immunol., 166(5):3266-76 (2001).
Zimmers et al., "Induction of cachexia in mice by systemically administered myostatin," Science, May 24, 2002, 296(5572):1486-8.
Zuckier et al., "Chimeric human-mouse IgG antibodies with shuffled constant region exons demonstrate that multiple domains contribute to in vivo half-life," Cancer Res., 58:3905-08 (1998).
Zwick et al., "The long third complementarity-determining region of the heavy chain is important in the activity of the broadly neutralizing anti-human immunodeficiency virus type 1 antibody 2F5," J. Virol., 78(6):3155-61 (2004).
International Search Report for App. Ser. No. PCT/JP2011/077619, dated Feb. 28, 2012, 4 pages.

(56) References Cited

OTHER PUBLICATIONS

International Preliminary Report on Patentability for App. Ser. No. PCT/JP2011/077619, dated Jun. 4, 2013, 8 pages.
International Search Report for App. Ser. No. PCT/JP2008/067534, dated Oct. 21, 2008, 4 pages.
International Preliminary Report on Patentability for App. Ser. No. PCT/JP2008/067534, dated Apr. 7, 2010, 7 pages.
International Search Report for App. Ser. No. PCT/JP2009/066590, dated Oct. 20, 2009, 2 pages.
International Preliminary Report on Patentability for App. Ser. No. PCT/JP2009/066590, dated May 10, 2011, 6 pages.
International Preliminary Report on Patentability for App. Ser. No. PCT/JP2008/067499, dated Apr. 7, 2010, 6 pages.
International Preliminary Report on Patentability for App. Ser. No. PCT/JP2007/057036, dated Oct. 21, 2008, 6 pages.
International Search Report for App. Ser. No. PCT/JP2007/057036, dated May 1, 2007, 2 pages.
European Search Report for App. Ser. No. 07 74 0494, dated Sep. 3, 2009, 3 pages.
International Search Report for App. Ser. No. PCT/JP2009/057309, dated Jul. 7, 2009, 8 pages.
International Preliminary Report on Patentability for App. Ser. No. PCT/JP2009/057309, dated Nov. 30, 2010, 7 pages.
European Search Report for App. Ser. No. EP 09 72 9337, dated Nov. 3, 2011, 3 pages.
International Preliminary Report on Patentability for App. Ser. No. PCT/JP2007/057058, dated Oct. 21, 2008, 11 pages.
International Search Report App. Ser. No. PCT/JP2007/057058, dated May 7, 2001, 2 pages.
European Search Report for App. Ser. No. 07 74 0474, dated Mar. 16, 2009, 5 pages.
International Preliminary Report on Patentability for App. Ser. No. PCT/JP2009/070376, dated Jul. 5, 2011, 11 pages.
International Preliminary Report on Patentability for App. Ser. No. PCT/JP2010/058166, dated Dec. 16, 2011, 15 pages.
International Search Report for App. Ser. No. PCT/JP2010/066490, dated Nov. 9, 2010, 5 pages.
International Preliminary Report on Patentability for App. Ser. No. PCT/JP2010/066490, dated Apr. 11, 2012, 6 pages.
International Preliminary Report on Patentability for App. Ser. No. PCT/JP2010/073361, dated Aug. 14, 2012, 7 pages.
International Search Report for App. Ser. No. PCT/JP2011/055101, dated May 10, 2011, 4 pages.
International Preliminary Report on Patentability for App. Ser. No. PCT/JP2011/055101, dated Oct. 2, 2012, 6 pages.
International Search Report for App. Ser. No. PCT/JP2011/001888, dated Nov. 2, 2011, 7 pages.
International Preliminary Report on Patentability for App. Ser. No. PCT/JP2012/058603, dated Oct. 8, 2013, 11 pages.
International Search Report for App. Ser. No. PCT/JP2012/058603, dated May 29, 2012, 2 pages.
International Search Report for App. Ser. No. PCT/JP2012/075083, dated Oct. 23, 2012, 2 pages.
International Preliminary Report on Patentability for App. Ser. No. PCT/JP2012/075083, dated Apr. 1, 2014, 8 pages.
International Search Report for App. Ser. No. PCT/JP2012/006218, dated Mar. 26, 2013, 11 pages.
USPTO Restriction Requirement in U.S. Appl. No. 13/637,415, dated Dec. 31, 2014, 8 pages.
Fish & Richardson P.C., Reply to Restriction Requirement dated Dec. 31, 2014 in U.S. Appl. No. 13/637,415, filed Feb. 25, 2015, 1 page.
USPTO Non-Final Office Action in U.S. Appl. No. 13/637,415, dated May 13, 2015, 24 pages.
Fish & Richardson P.C., Reply to Non-Final Office Action dated May 13, 2015 in U.S. Appl. No. 13/637,415, filed Aug. 13, 2015, 21 pages.
USPTO Final Office Action in U.S. Appl. No. 13/637,415, dated Nov. 13, 2015, 20 pages.
Fish & Richardson P.C., Reply to Final Office Action dated Nov. 13, 2015 in U.S. Appl. No. 13/637,415, filed May 12, 2016, 22 pages.
USPTO Restriction Requirement in U.S. Appl. No. 14/347,034, dated Dec. 18, 2014, 9 pages.
Fish & Richardson P.C., Reply to Restriction Requirement dated Dec. 18, 2014 in U.S. Appl. No. 14/347,034, filed Mar. 18, 2015, 2 pages.
USPTO Non-Final Office Action in U.S. Appl. No. 14/347,034, dated Apr. 16, 2015, 9 pages.
USPTO Interview Summary in U.S. Appl. No. 14/347,034, dated Aug. 17, 2015, 3 pages.
Fish & Richardson P.C., Reply to Non-Final Office Action dated Apr. 16, 2015 in U.S. Appl. No. 14/347,034, filed Sep. 16, 2015, 28 pages.
USPTO Final Office Action in U.S. Appl. No. 14/347,034, dated Oct. 16, 2015, 5 pages.
Fish & Richardson P.C., Reply to Final Office Action dated Oct. 16, 2015 in U.S. Appl. No. 14/347,034, filed Jan. 13, 2016, 28 pages.
USPTO Notice of Allowance in U.S. Appl. No. 14/347,034, dated Feb. 17, 2016, 6 pages.
USPTO Notice of Allowance in U.S. Appl. No. 14/347,034, dated Jun. 3, 2016, 5 pages.
USPTO Restriction Requirement in U.S. Appl. No. 14/404,051, dated Apr. 4, 2016, 13 pages.
Fish & Richardson P.C., Amendment and Response to Restriction Requirement dated Apr. 4, 2016, in U.S. Appl. No. 14/404,051, filed Sep. 6, 2016, 22 pages.
USPTO Non-Final Office Action in U.S. Appl. No. 14/404,051, dated Dec. 6, 2016, 22 pages.
USPTO Restriction Requirement in U.S. Appl. No. 14/347,321, dated Dec. 17, 2015, 10 pages.
Fish & Richardson P.C., Reply to Restriction Requirement dated Dec. 17, 2015 in U.S. Appl. No. 14/347,321, filed Feb. 16, 2016, 3 pages.
USPTO Office Action in U.S. Appl. No. 14/347,321, dated May 2, 2016, 35 pages.
Fish & Richardson P.C., Reply to Office Action dated May 2, 2016 in U.S. Appl. No. 14/347,321, filed Nov. 2, 2016, 35 pages.
USPTO Final Office Action in U.S. Appl. No. 14/347,321, dated Jan. 9, 2017, 60 pages.
USPTO Restriction Requirement in U.S. Appl. No. 13/637,415, dated Dec. 1, 2016, 8 pages.
U.S. Appl. No. 16/264,735, filed Feb. 1, 2019, Igawa et al.
Yada et al., Lippincott's Illustrated Reviews: Immunology, Second Edition, Nov. 30, 2013, Chapter 2, pp. 11-23 and Chapter 11, pp. 149-165 (in Japanese, with English equivalent).
U.S. Appl. No. 15/952,945, filed Apr. 13, 2018, Igawa et al.
U.S. Appl. No. 15/952,951, filed Apr. 13, 2018, Igawa et al.
U.S. Appl. No. 15/976,288, filed May 10, 2018, Igawa et al.
U.S. Appl. No. 16/019,752, filed Jun. 22, 2018, Ruike et al.
Alexion initiates simultaneous registration trials of ALXN1210 for patients with paroxysmal nocturnal hemoglobinuria (PNH) and atypical hemolytic uremic syndrome (aHUS), Press Release, Alexion Pharmaceuticals, Inc. [online] (retrieved on Jun. 6, 2018), retrieved from the Internet URL: http://ir.alexion.com/releasedetail.cfm?releaseid=995788>.
Antibodies from www.bioinf.org.uk: Dr. Andrew C.R. Martin's Group, downloaded Jul. 11, 2018, 9 pages.
Concordance table showing Kabat numbering for antibody Hyb C1, 6 pages.
Concordance table showing Kabat numbering for antibody 300N, 5 pages.
European Medicines Agency, No. WC500054212, Jun. 22, 2016, pp. 1-41, XP002780707 Retrieved from the Internet: URL:A210.
Feagan et al., "Ustekinumab as Induction and Maintenance Therapy for Crohn's Disease," N Engl J Med, Nov. 17, 2016, 375(20):1946-1960.
GE Healthcare, Biacore, Sensor Surface Handbook BR-1005-71, Edition AB, Feb. 2005, pp. 1-100.
Harvey et al., Lippincott's Illustrated Reviews: Immunology, Second Edition, Chapter 2 "Antigens and Receptors" pp. 11-23 and Chapter 11 "Lymphocyte Effector Functions," pp. 141-157.

(56) References Cited

OTHER PUBLICATIONS

Jaeger, Clinical Immunology and Allergology, 2nd edition, M.: Medicina, 1990, 2:484-5 (with English translation).
Kawahata, Alnylam Pharmaceuticals, Mar. 22, 2016, XP055471916 Retrieved from the Internet: URL: http://www.alnylam.com/web/assets/ERA-EDTA_CC5_Ph-1_052216.pdf.
King, Applications and Engineering of Monoclonal Antibodies, Taylor & Francis, ISBN 0-203-21169-3, 2005, pp. 1-236.
Mellman, "The importance of being acid: the role of acidification in intracellular membrane traffic," J Exp Biol, 1992, 172:39-45.
Okiyama et al., "Therapeutic Effects of Interleukin-6 Blockade in a Murine Model of Polymyositis That Does Not Require Interleukin-17A," Arthritis Rheum, Aug. 2009, 60(8):2505-12.
OriGene Technologies, Inc., AP02123SU-N, Polyclonal Antibody to Myostatin (79-92)—Serum, Mar. 19, 2013, https://ml.acris-antibodies.com/pdf/AP02123SU-N.pdf.
Popov et al., "The Stoichiometry and Affinity of the Interaction of Murine Fc Fragments with the MHC Class I-Related Receptor, FcRn," Mol Immunol, Apr. 1996, 33(6):521-30.
Richter et al., "Special Section on DI\/IPK of Therapeutic Proteins≥Minireview—Subcutaneous Absorption of Biotherapeutics: Knowns and Unknowns," Drug Metab Dispos, Nov. 2014, 42(11):1881-9. doi: 10.1124/dmd.114.059238. Epub Aug. 6, 2014.
Roitt et al., Immunology, M., Mir, 2000, pp. 373-374 (with English translation).
Sal-Man et al., "Arginine mutations within a transmembrane domain of Tar, an *Escherichia coli* aspartate receptor, can drive homodimer dissociation and heterodimer association in vivo," Biochem J, Jan. 1, 2005, 385 (Pt 1):29-36.
Scappaticci et al., J Natl Cancer Inst, Jan. 16, 2008, 100(2):156, doi: 10.1093/jnci/djm319. Epub Jan. 8, 2008 (Erratum related to Scappaticci et al., "Arterial thromboembolic events in patients with metastatic carcinoma treated with chemotherapy and bevacizumab," J Natl Cancer Inst., 99(16):1232-9 (Aug. 2007), Epub Aug. 8, 2007, cited in IDS filed on Aug. 23, 2018).
Schmidt et al., "Enzymes of the pancreatic juice," Human Physiology, Second Completely Revised Edition, Springer-Verlag, 1989, p. 716 (with English translation).
Schmidt et al., Section 18.6 "Hemostasis and Coagulation," Human Physiology, Second Completely Revised Edition, Springer-Verlag, 1989, pp. 418-423 (with English translation).
Soliris® (eculizumab) injection, for intravenous use, BLA:125166, Jan. 13, 2017, Suppl-417, Label, Drugs@FDA[online](retrieved on Jun. 6, 2018), retrieved from the internet URL:https://www.accessdata.fda.gov/scripts/cder/daf/index.cfm?event=overview.process&applno=125166>.
Technical Data Sheet, Polyclonal Antisera: Anti-Human C5, Quidel online catalogue, Jan. 1, 2010, 1 page.
Yada et al., Lippincott's Illustrated Reviews: Immunology Second Edition, Nov. 30, 2013, pp. 18, 19, 152, 153.
Yarilin, Fundamentals of Immunology, M: Medicina, 1999, pp. 175, 182 (with English translation).
Yarilin, Fundamentals of Immunology, M: Medicina, 1999, pp. 172-174 (with English translation).
Zheng et al., Minipig as a potential translatable model for monoclonal antibody pharmacokinetics after intravenous and subcutaneous administration, mAbs, Mar.-Apr. 2012, 4(2):243-55. doi:10.4161/mabs.4.2.19387. Epub Mar. 1, 2012.
USPTO Advisory Action Before the Filing of an Appeal Brief in U.S. Appl. No. 14/404,051, dated Aug. 30, 2018, 3 pages.
USPTO Restriction Requirement in U.S. Appl. No. 15/210,353, dated Oct. 6, 2016, 5 pages.
USPTO Non-Final Office Action in U.S. Appl. No. 15/210,353, dated Mar. 9, 2017, 16 pages.
USPTO Non-Final Office Action in U.S. Appl. No. 15/210,360 dated Mar. 10, 2017, 18 pages.
USPTO Restriction Requirement in U.S. Appl. No. 15/210,360 dated Oct. 19, 2016, 5 pages.
U.S. Appl. No. 16/041,976, Igawa et al., filed Jul. 23, 2018.
U.S. Appl. No. 16/480,047, Shinomiya et al., filed Jul. 23, 2019.
U.S. Appl. No. 16/697,310, filed Nov. 27, 2019, Igawa et al.
U.S. Appl. No. 16/806,027, filed Mar. 2, 2020, Igawa et al.
U.S. Appl. No. 16/838,415, filed Apr. 2, 2020, Igawa et al.
U.S. Appl. No. 16/889,066, filed Jun. 1, 2020, Ruike.
U.S. Appl. No. 16/928,129, filed Jul. 14, 2020, Shinomiya et al.
U.S. Appl. No. 16/983,115, filed Aug. 3, 2020, Kakehi et al.
U.S. Appl. No. 17/020,497, filed Sep. 14, 2020, Igawa et al.
U.S. Appl. No. 17/020,543, filed Sep. 14, 2020, Igawa et al.
Aleshin et al., "Crystal Structure of C5b-6 Suggests Structural Basis for Priming Assembly of the Membrane Attack Complex," J Biol Chem, Jun. 1, 2012, 287(23):19642-19652. doi: 10.1074/jbc.M112.361121. Epub Apr. 12, 2012.
Altshuler et al., "Production of Recombinant Antibodies and Methods for Increasing Their Affinity," Progress of Biological Chemistry, 2010, 50:207 (with English translation).
Annotated amino acid sequence of the variable heavy (VH) and variable light (VL) domains of the monoclonal antibodies bevacizumab/Avastin, adalimumab/Humira, omalizumab/Xolair, and rituximab/Mabthera, dated Jul. 2019, 10 pages (submitted to the EPO with the written submission to attend oral proceedings on Sep. 6, 2019 by Opponent 1 in EP 11714860.1).
Arici, "Local Cytokines in Endometrial Tissue: The Role of Interleukin-8 in the Pathogenesis of Endometriosis," Ann NY Acad Sci, Mar. 2002, 955:101-109; discussion 118, pp. 396-406.
Buckler, vol. 4 "Molecular Medicine and Medicinal Chemistry," Section 2.4 "Library Selection," Antibody Drug Discovery, edited by Clive Wood, 2012, pp. 49-57.
Chugai NMO Clinical Trial Webinar, Sakura Star Study, dated Dec. 12, 2014, downloaded on Sep. 5, 2019 from https://s3.amazonaws.com/gjcf-wp-ploads/wpcontent/uploads/2016/05/16162202/12_12_14_Chugai_Webinar_PPT_Complete_Deck_FINAL.pdf, 18 pages.
Chugai Pharmaceutical, A phase I, multiple-dose study of SA237, Study JapicCTI—No. 121786; submitted to Clinicaltrials.jp on Jan. 31, 2014; downloaded from clinicaltrials.jp archive on Sep. 5, 2019 as https://www.clinicaltrials.jp/cti-user/trial/Show.jsp, 5 pages.
Chugai Pharmaceutical, A phase I, multiple-dose study of SA237, Study JapicCTI—No. 121786; submitted to Clinicaltrials.jp on Jun. 19, 2012; downloaded from clinicaltrials.jp archive on Sep. 5, 2019 as https://www.clinicaltrials.jp/cti-user/trial/Show.jsp, 5 pages.
Chugai Pharmaceutical, A phase I, multiple-dose study of SA237, Study JapicCTI—No. 121786; submitted to Clinicaltrials.jp on Mar. 19, 2012; downloaded from clinicaltrials.jp archive on Sep. 5, 2019 as https://www.clinicaltrials.jp/cti-user/trial/Show.jsp, 5 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 1; submitted to ClinicalTrials.gov on Jan. 6, 2014; downloaded from ClinicalTrials.gov archive on Sep. 4, 2019 as https://clinicaltrials.gov/ct2/history/NCT02028884?V_1=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 2; submitted to ClinicalTrials.gov on Feb. 25, 2014; downloaded from ClinicalTrials.gov archive on Sep. 4, 2019 as https://clinicaltrials.gov/ct2/history/NCT02028884?V_2=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 3; submitted to ClinicalTrials.gov on Sep. 4, 2015; downloaded from ClinicalTrials.gov archive on Sep. 4, 2019 as https://clinicaltrials.gov/ct2/history/NCT02028884?V_3=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 4; submitted to ClinicalTrials.gov on Dec. 8, 2015; downloaded from ClinicalTrials.gov archive on Sep. 4, 2019 as https://clinicaltrials.gov/ct2/history/NCT02028884?V_4=View#StudyPageTop, 6 pages.
Chugai Pharmaceutical, Efficacy and Safety Study of Satralizumab (SA237) as Monotherapy to Treat Participants With Neuromyelitis

(56) References Cited

OTHER PUBLICATIONS

Optica (NMO) and Neuromyelitis Optica Spectrum Disorder (NMOSD), Study NCT02073279, version 1; submitted to ClinicalTrials.gov on Feb. 25, 2014; downloaded from ClinicalTrials.gov archive on Sep. 4, 2019 as https://clinicaltrials.gov/ct2/history/NCT02073279?V_1=View#StudyPageTop, 6 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 2; submitted to ClinicalTrials.gov on Jul. 22, 2014; downloaded from ClinicalTrials.gov archive on Sep. 5, 2019 as https://clinicaltrials.gov/ct2/history/NCT02073279?V_2=View#StudyPageTop, 6 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 3; submitted to ClinicalTrials.gov on Dec. 15, 2014; downloaded from ClinicalTrials.gov archive on Sep. 5, 2019 as https://clinicaltrials.gov/ct2/history/NCT02073279?V_3=View#StudyPageTop, 7 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 4; submitted to ClinicalTrials.gov on Feb. 5, 2015; downloaded from ClinicalTrials.gov archive on Sep. 5, 2019 as https://clinicaltrials.gov/ct2/history/NCT02073279?V_4=View#StudyPageTop, 8 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 5; submitted to ClinicalTrials.gov on Feb. 6, 2015; downloaded from ClinicalTrials.gov archive on Sep. 5, 2019 as https://clinicaltrials.gov/ct2/history/NCT02073279?V_5=View#StudyPageTop, 8 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 6; submitted to ClinicalTrials.gov on Mar. 4, 2015; downloaded from ClinicalTrials.gov archive on Sep. 5, 2019 as https://clinicaltrials.gov/ct2/history/NCT02073279?V_6=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 7; submitted to ClinicalTrials.gov on Apr. 1, 2015; downloaded from ClinicalTrials.gov archive on Sep. 5, 2019 as https://clinicaltrials.gov/ct2/history/NCT02073279?V_7=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 8; submitted to ClinicalTrials.gov on May 7, 2015; downloaded from ClinicalTrials.gov archive on Sep. 5, 2019 as https://clinicaltrials.gov/ct2/history/NCT02073279?V_8=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 9; submitted to ClinicalTrials.gov on Jun. 5, 2015; downloaded from ClinicalTrials.gov archive on Sep. 5, 2019 as https://clinicaltrials.gov/ct2/history/NCT02073279?V_9=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 10; submitted to ClinicalTrials.gov on Jul. 7, 2015; downloaded from ClinicalTrials.gov archive on Sep. 5, 2019 as https://clinicaltrials.gov/ct2/history/NCT02073279?V_10=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 11; submitted to ClinicalTrials.gov on Aug. 3, 2015; downloaded from ClinicalTrials.gov archive on Sep. 5, 2019 as https://clinicaltrials.gov/ct2/history/NCT02073279?V_11=View#StudyPageTop, 10 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 12; submitted to ClinicalTrials.gov on Sep. 3, 2015; downloaded from ClinicalTrials.gov archive on Sep. 5, 2019 as https://clinicaltrials.gov/ct2/history/NCT02073279?V_12=View#StudyPageTop, 10 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 13; submitted to ClinicalTrials.gov on Oct. 5, 2015; downloaded from ClinicalTrials.gov archive on Sep. 5, 2019 as https://clinicaltrials.gov/ct2/history/NCT02073279?V_13=View#StudyPageTop, 10 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 14; submitted to ClinicalTrials.gov on Dec. 8, 2015; downloaded from ClinicalTrials.gov archive on Sep. 5, 2019 as https://clinicaltrials.gov/ct2/history/NCT02073279?V_14=View#StudyPageTop, 10 pages.

Coico et al., Chapter 4 "Antibody Structure and Function," Immunology: Manual, M.: Publishing Center Academy, 2008, pp. 61-62 (with English translation).

Cunningham et al., "The Covalent Structure of a Human γG-Immunoglobulin. VII. Amino Acid Sequence of Heavy-Chain Cyanogen Bromide Fragments $H_1$-$H_4$," Biochemistry, Aug. 4, 1970, 9(16):3161-3170.

Curtiss, "Selectivity and Specificity Are the Keys to Cost-Effective Use of Omalizumab for Allergic Asthma," J Manag Care Pharm, Nov.-Dec. 2005, 11(9):774-776.

Decision of the Opposition Division dated Dec. 19, 2019 in EP 2 552 955 (document submitted by Patentee (Chugai Seiyaku Kabushiki Kaisha) in the grounds of appeal on Apr. 28, 2020 in EP 2 552 955).

Evidence for the publication date of Zalevsky et al., Nat Biotechnol, Feb. 2010, 28(2):157-9, 1 page (submitted to the EPO with the written submission to attend oral proceedings on Sep. 6, 2019 by Opponent 1 in EP 11714860.1).

Expert Declaration of Joachim Boucneau, dated Mar. 11, 2020, 6 pages (submitted by Opponents in Mar. 2020 in Oppositions of EP 2 708 558 and EP 2 708 559).

Expert Declaration of Joachim Boucneau, dated Sep. 6, 2019, 13 pages (submitted to the EPO with the written submission to attend oral proceedings on Sep. 6, 2019 by Opponent 1 in EP 11714860.1).

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Germany; submitted to clinicaltrialsregister.eu on Dec. 20, 2013; downloaded from clinicaltrialsregister.eu archive on Sep. 5, 2019 as https://www.clinicaltrialsregister.eu/ctr-search/trial/2013-003752-21/DE, 7 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Hungary; submitted to clinicaltrialsregister.eu on Feb. 25, 2015; downloaded from clinicaltrialsregister.eu archive on Sep. 5, 2019 as https://www.clinicaltrialsregister.eu/ctr-search/trial/2013-003752-21/HU, 6 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Italy; submitted to clinicaltrialsregister.eu on Feb. 6, 2014; downloaded from

(56) References Cited

OTHER PUBLICATIONS clinicaltrialsregister.eu archive on Sep. 5, 2019 as https://www.clinicaltrialsregister.eu/ctr-search/trial/2013-003752-21/IT, 5 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Poland; submitted to clinicaltrialsregister.eu on Oct. 15, 2013; downloaded from clinicaltrialsregister.eu archive on Sep. 5, 2019 as https://www.clinicaltrialsregister.eu/ctr-search/trial/2013-003752-21/PL, 7 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Spain; submitted to clinicaltrialsregister.eu on Mar. 11, 2015; downloaded from clinicaltrialsregister.eu archive on Sep. 5, 2019 as https://www.clinicaltrialsregister.eu/ctr-search/trial/2013-003752-21/ES, 7 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in the United Kingdom; submitted to clinicaltrialsregister.eu on Oct. 15, 2013; downloaded from clinicaltrialsregister.eu archive on Sep. 5, 2019 as https://www.clinicaltrialsregister.eu/ctr-search/trial/2013-003752-21/GB, 6 pages.
F. Hoffmann-La Roche Ltd., A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder (NMOSD), Study EudraCT 2015-005431-41 in Croatia; submitted to clinicaltrialsregister.eu on Dec. 15, 2016; downloaded from clinicaltrialsregister.eu archive on Sep. 5, 2019 as https://www.clinicaltrialsregister.eu/ctr-search/trial/2015-005431-41/HR, 6 pages.
F. Hoffmann-La Roche Ltd., A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder (NMOSD), Study EudraCT 2015-005431-41 in Poland; submitted to clinicaltrialsregister.eu on Apr. 7, 2016; downloaded from clinicaltrialsregister.eu archive on Sep. 5, 2019 as https://www.clinicaltrialsregister.eu/ctr-search/trial/2015-005431-41/PL, 6 pages.
"FDA grants supplemental approval for ACTEMRA," Roche Media Release, 4 pages (retrieved from https://www.roche.com/media/releases/med-cor-2011-01-0 (submitted by the Opponents in Mar. 2020 in the Oppositions of EP 2 708 558 and EP 2 708 559).
Gonzalez et al., "BMP-1/Tolloid-like Metalloproteases Process Endorepellin, the Angiostatic C-terminal Fragment of Perlecan," J Biol Chem, Feb. 25, 2005, 280(8):7080-7087. Epub Dec. 9, 2004.
Guidance on the use of International Nonproprietary Names (INNs) for Pharmaceutical Substances, World Health Organization, 2017, 55 pages (submitted by the Opponents in Mar. 2020 in Oppositions of EP 2 708 558 and EP 2 708 559).
Igawa et al., "Sweeping antibody as a novel therapeutic antibody modality capable of eliminating soluble antigens from circulation," Immunol Rev, Mar. 2016, 270(1):132-151.
Ishii et al., "Molecular design of antibody drugs," Journal of Pharmaceutical Science and Technology, Japan, 2014, 74(1):4-11 (with English translation).
Kurki et al., "Desmin antibodies in acute infectious myopericarditis," APMIS, Jun. 1989, 97(6):527-532.
Mariuzza et al., "The Structural Basis of Antigen-Antibody Recognition," Annu Rev Biophys Biophys Chem, Jun. 1987, 16:139-159.
Marri et al., Chapter 4, Human Biochemistry, Moscow, Mir, 1993, 1:34 (with English translation).

Muramatsu, "Latent myostatin specific elimination by sweeping antibody® is a novel therapeutic approach to improve muscle strength," Neuromuscular Disorders, Oct. 1, 2019, 29(Supplement 1):S86, 1 page.
Perng et al., "Desmin Aggregate Formation by R120G αB-Crystallin Is Caused by Altered Filament Interactions and Is Dependent upon Network Status in Cells," Mol Biol Cell, May 2004, 15(5):2335-2346. Epub Mar. 5, 2004.
Proprietor's (Chugai Seiyaku Kabushiki Kaisha) Submission dated Sep. 5, 2016 in EP11714860.1, 6 pages (submitted to the EPO with the written submission to attend oral proceedings on Sep. 6, 2019 by Opponent 1 in EP 11714860.1).
Proprietor's (Chugai Seiyaku Kabushiki Kaisha) Submission dated Sep. 19, 2016 in EP11714860.1, 3 pages (submitted to the EPO with the written submission to attend oral proceedings on Sep. 6, 2019 by Opponent 1 EP 11714860.1).
Proprietor's (Chugai Seiyaku Kabushiki Kaisha) Submission dated Feb. 20, 2017 in EP 2 275 443, 35 pages (submitted to the EPO with the written submission to attend oral proceedings on Sep. 6, 2019 by Opponent 5 in EP 11714860.1).
Rich et al., A global benchmark study using affinity-based biosensors, Anal Biochem, Mar. 15, 2009, 386(2):194-216. doi: 10.1016/j.ab.2008.11.021. Epub Nov. 27, 2008.
Roitt et al., "Antibodies and their Receptors," Immunology, 1998, pp. 80-81 (with what are believed to be the corresponding pages from an English version of Immunology).
Sigma product information for ACES buffer, 1 page (submitted to the EPO with the written submission to attend oral proceedings on Sep. 6, 2019 by Opponent 1 in EP 11714860.1).
Table summarizing alleged lack of novelty over WO 2009/086320A, dated Jul. 9, 2009, 4 pages (submitted to the EPO with the written submission to attend oral proceedings on Sep. 6, 2019 by Opponent 1 in EP 11714860.1).
Van Assche et al., "Adalimumab in Crohn's disease," Biologics, Dec. 2007, 1(4):355-365.
Wang et al., "Complement C5a, C5a receptor and their antagonists: research advances," J Int Pharm Res, 2010, 37(3):181-186 (with English translation).
Wolfman et al., "Activation of latent myostatin by the BMP-1/tolloid family of metalloproteinases," Proc Natl Acad Sci USA, Dec. 23, 2003, 100(26):15842-15846. Epub Dec. 11, 2003.
Yang et al., "Comparison of biosensor platforms in the evaluation of high affinity antibody-antigen binding kinetics," Anal Biochem, Sep. 1, 2016, 508:78-96. doi: 10.1016/j.ab.2016.06.024. Epub Jun. 27, 2016.
Yu et al., "Development and Validation of a Cell-Based Fluorescent Method for Measuring Antibody Affinity," J Immunol Methods, Mar. 2017, 442:49-53. doi: 10.1016/j.jim.2016.12.004. Epub Dec. 24, 2016.
USPTO Final Office Action in U.S. Appl. No. 14/404,051, dated Jul. 14, 2020, 31 pages.
USPTO Final Office Action in U.S. Appl. No. 13/637,415, dated Mar. 3, 2020, 26 pages.
USPTO Final Office Action in U.S. Appl. No. 15/952,951 dated Jun. 3, 2019, 21 pages.
USPTO Advisory Action in U.S. Appl. No. 15/952,951 dated Aug. 19, 2019, 5 pages.
Abelev, "Monoclonal Antibodies," Sorosovkii Educational Journal No. 1, 1998, pp. 16-20 (with English translation).
Arduin et al., "Highly reduced binding to high and low affinity mouse Fc gamma receptors by L234A/L235A and N297A Fc mutations engineered into mouse IgG2a," Mol Immunol, Feb. 2015, 63(2):456-463.
Datta-Mannan et al., "FcRn Affinity-Pharmacokinetic Relationship of Five Human IgG4 Antibodies Engineered for Improved In Vitro FcRn Binding Properties in Cynomolgus Monkeys," Drug Metab Dispos, Aug. 2012, 40(8):1545-55.
Moore et al., "Engineered Fc variant antibodies with enhanced ability to recruit complement and mediate effector functions," mAbs, Mar.-Apr. 2010, 2(2):181-189.

(56) References Cited

OTHER PUBLICATIONS

Wong et al., "Anticomplement C5 therapy with eculizumab for the treatment of paroxysmal nocturnal hemoglobinuria and atypical hemolytic uremic syndrome," Transl Res, Feb. 2015, 165(2):306-320.
U.S. Appl. No. 16/539,765, filed Aug. 13, 2019, Igawa et al.
U.S. Appl. No. 17/144,342, filed Jan. 8, 2021, Igawa et al.
Submission of Proprietor (Chugai Seiyaku Kabushiki Kaisha) in the opposition-appeal case against EP 2 275 443, dated Feb. 20, 2017, 35 pages.
Gershoni et al., "Epitope Mapping—The First Step in Developing Epitope-Based Vaccines," BioDrugs, 2007, 21(3):145-156.
English translation of PCT/JP2012/054624, 110 pages, corresponding to WO 2012/115241. The document was submitted in the opposition proceeding for EP 2 698 431 on Jun. 23, 2021.
English translation of PCT/JP2011/072550, 283 pages, corresponding to WO 2012/132067. The translation was submitted in the opposition proceeding for EP 2 698 431 on Jun. 23, 2021.
Han et al., "Monoclonal antibodies: interspecies scaling with minimal preclinical information," Ther Deliv, Mar. 2011, 2(3):359-368.
Jung et al., "Aglycosylated IgG variants expressed in bacteria that selectively bind FcKRI potentiate tumor cell killing by monocyte-dendritic cells," Proc Natl Acad Sci USA, Jan. 12, 2010, 107(2):604-609.
Mimoto et al., "Engineered antibody Fc variant with selectively enhanced FcγRIIb binding over both FcγRIIa$^{R131}$ and FcγRIIa$^{H131}$," Protein Eng Des Sel, Oct. 2013, 26(10):589-598. doi: 10.1093/protein/gzt022. Epub Jun. 5, 2013.
Presta et al., "Engineering therapeutic antibodies for improved function," Biochem Soc Trans, Aug. 2002, 30(4):487-490.
U.S. Appl. No. 13/524,528, Igawa et al., filed Jun. 15, 2012 (abandoned).
U.S. Appl. No. 16/838,415, Igawa et al., filed Apr. 2, 2020.
U.S. Appl. No. 12/680,112, Igawa et al., filed Jun. 23, 2010 (abandoned).
U.S. Appl. No. 13/959,489, Igawa et al., filed Aug. 5, 2013 (abandoned).
U.S. Appl. No. 15/263,617, Igawa et al., filed Sep. 13, 2016 (abandoned).
U.S. Appl. No. 16/041,976, Igawa et al., filed Jul. 23, 2018 (abandoned).
U.S. Appl. No. 17/097,298, Igawa et al., filed Nov. 13, 2020.
U.S. Appl. No. 13/990,158, Igawa et al., filed Mar. 28, 2014 (abandoned).
U.S. Appl. No. 16/806,027, Igawa et al., filed Mar. 2, 2020.
U.S. Appl. No. 14/347,034, Igawa et al., filed Mar. 25, 2014 (abandoned).
U.S. Appl. No. 15/230,904, Igawa et al., filed Aug. 8, 2016 (abandoned).
U.S. Appl. No. 16/028,140, Igawa et al., filed Jul. 5, 2018.
U.S. Appl. No. 16/264,735, Igawa et al., filed Feb. 1, 2019.
U.S. Appl. No. 16/983,115, Kakehi et al., filed Aug. 3, 2020.
U.S. Appl. No. 13/637,415, Igawa et al., filed Feb. 4, 2013.
U.S. Appl. No. 15/050,145, Igawa et al., filed Feb. 22, 2016.
U.S. Appl. No. 15/210,353, Igawa et al., filed Jul. 14, 2016.
U.S. Appl. No. 15/210,360, Igawa et al., filed Jul. 14, 2016.
U.S. Appl. No. 15/495,026, Igawa et al., filed Apr. 24, 2017.
U.S. Appl. No. 12/936,587, Igawa et al., filed Jan. 3, 2011 (abandoned).
U.S. Appl. No. 13/595,139, Igawa et al., filed Aug. 27, 2012 (abandoned).
U.S. Appl. No. 15/952,951, Igawa et al., filed Apr. 13, 2018.
U.S. Appl. No. 15/544,930, Murata et al., filed Jul. 20, 2017.
U.S. Appl. No. 15/963,455, Ruike et al., filed Apr. 26, 2018.
U.S. Appl. No. 16/065,192, Ruike et al., filed Jun. 22, 2018.
U.S. Appl. No. 16/323,142, Kakiuchi et al., filed Feb. 4, 2019.
U.S. Appl. No. 16/361,498, Igawa et al., filed Mar. 22, 2019.
U.S. Appl. No. 16/480,047, Shinomiya et al., filed Jul. 23, 2019 (abandoned).
U.S. Appl. No. 16/480,765, Sampei, filed Jul. 25, 2019.
U.S. Appl. No. 16/514,467, Ruike et al., filed Jul. 19, 2019.
U.S. Appl. No. 16/928,129, Shinomiya et al., filed Jul. 14, 2020.
U.S. Appl. No. 16/889,066, Ruike, filed Jun. 1, 2020.
U.S. Appl. No. 16/697,310, Igawa et al., Nov. 27, 2019.
U.S. Appl. No. 17/020,497, Igawa et al., filed Sep. 14, 2020.
U.S. Appl. No. 17/020,543, Igawa et al., filed Sep. 14, 2020.
U.S. Appl. No. 17/263,691, Shinomiya et al., filed Jan. 27, 2021.
U.S. Appl. No. 17/097,298, filed Nov. 13, 2020, Igawa et al.
U.S. Appl. No. 17/263,691, filed Jan. 27, 2021, Shinomiya et al.
Abe et al., "Effect of $\beta_2$-microglobulin adsorption column on dialysis-related amyloidosis," Kidney Int, Oct. 2003, 64(4):1522-1528. doi: 10.1046/j.1523-1755.2003.00235.x.
Alignment sequences 1047 and 30, Jan. 26, 2021, 1 page (cited in an office action dated Feb. 2, 2021 for EP 15869566.8).
Alignment sequences 472 and 24, Jan. 26, 2021, 1 page (cited in an office action dated Feb. 2, 2021 for EP 15869566.8).
Altshuler et al., "Production of Recombinant Antibodies and Methods to Increase Their Affinity," Advances in Biological Chemistry, 2010, vol. 50, pp. 203-204, 215, 219-228 (with English translation).
Annex 1 accompanying Response to Statement of Grounds of Appeal of Opponent 2 (Alexion Pharmaceuticals, Inc.), dated Sep. 16, 2020 in opposition against EP 2 552 955, 29 pages.
Bork, "Powers and Pitfalls in Sequence Analysis: The 70% Hurdle," Genome Res, Apr. 2000, 10(4):398-400.
Bowie et al., "Deciphering the Message in Protein Sequences: Tolerance to Amino Acid Substitutions," Science, Mar. 16, 1990, 247(4948):1306-1310.
Burmester et al., "Efficacy and safety of subcutaneous tocilizumab versus intravenous tocilizumab in combination with traditional DMARDs in patients with RA at week 97 (SUMMACTA)," Ann Rheum Dis, Jan. 2016, 75(1):68-74. doi: 10.1136/annrheumdis-2015-207281. Epub Jun. 8, 2015. PMID: 26056119; PMCID: PMC4717437.
Dagbay et al., "Structural basis of specific inhibition of extracellular activation of pro- or latent myostatin by the monoclonal antibody SRK-015," J Biol Chem, Apr. 17, 2020, 295(16):5404-5418.
D'Angelo et al., "Many Routes to an Antibody Heavy-Chain CDR3: Necessary, Yet Insufficient, for Specific Binding," Front Immunol, Mar. 8, 2018, 9:395. doi:10.3389/fimmu.2018.00395.
Decision of the Opposition Division in EP 2 275 443, dated Apr. 26, 2018, 29 pages.
Declaration of Muramatsu Hiroyasu, signed Oct. 21, 2020, 5 pages (cited in an office action dated Feb. 2, 2021 for EP 15869566.8).
Di Stefano et al., "Role of Interleukin-8 in the Pathogenesis and Treatment of COPD," Chest, Sep. 2004, 126(3):676-678. doi: 10.1378/chest.126.3.676.
Diamond et al., "Somatic mutation of the T15 heavy chain gives rise to an antibody with autoantibody specificity," Proc Natl Acad Sci USA, Sep. 1984, 81(18):5841-5844.
EUTM register extract—Biacore 4 pages (document downloaded on Aug. 26, 2020, submitted in Opposition of EP 2 552 955, and posted by EPO on Sep. 15, 2020).
Example antibody family tree, 4 pages (submitted on Mar. 12, 2020 by an opposer in the opposition proceeding against EP 2 708 558).
Fakhouri et al., "C3 glomerulopathy: a new classification," Nat Rev Nephrol, Aug. 2010, 6(8):494-499. doi: 10.1038/nrneph.2010.85. Epub Jul. 6, 2010. PMID: 20606628.
Finlay et al., "Affinity Maturation of a Humanized Rat Antibody for Anti-RAGE Therapy: Comprehensive Mutagenesis Reveals a High Level of Mutational Plasticity Both Inside and Outside the Complementarity-Determining Regions," J Mol Biol, May 8, 2009, 388(3):541-558. doi: 10.1016/j.jmb.2009.03.019.
Kabat et al., "Sequences of Proteins of Immunological Interest," 1991, National Institute of Health Publication No. 91-3242, pp. 103, 310.
Kontermann et al., Chapter 4 "Mouse Immune Libraries for the Generation of ScFv Fragments Directed Against Human Cell Surface Antigens," 1:47-62; and Chapter 27 "Engineering of the Fc Region for Improved PK (FcRn Interaction)," 1:415-427, Antibody Engineering, 2010.

(56) References Cited

OTHER PUBLICATIONS

Krieg et al., "Functional Analysis of B and T Lymphocyte Attenuator Engagement on CD4+ and CD8+ T Cells," J Immunol, Nov. 15, 2005, 175(10):6420-6427. doi: 10.4049/jimmunol.175.10.6420. PMID: 16272294.
Kroetsch et al., "Engineered pH-dependent recycling antibodies enhance elimination of Staphylococcal enterotoxin B superantigen in mice," mAbs, Feb./Mar. 2019, 11(2):411-421.
Makarova et al., "Experience of using eculizumab in children with atypical hemolytic-uremic syndrome," Nephrology, 2014, 18(3):84-88 (with English translation).
Mayilyan, "Complement genetics, deficiencies, and disease associations," Protein Cell, Jul. 2012, 3(7):487-496. doi: 10.1007/s13238-012-2924-6. Epub Jul. 10, 2012. PMID: 22773339; PMCID: PMC4875391.
Mease et al., "Secukinumab Inhibition of Interleukin-17A in Patients with Psoriatic Arthritis," N Engl J Med, Oct. 2015, 373(14):1329-1339.
Morris, "Epitope Mapping of Protein Antigens by Competition ELISA," The Protein Protocols Handbook, Jan. 1, 1996, pp. 595-600.
Notice of Opposition by Opponent 1 (Ablynx N.V.), dated Feb. 2, 2018, submitted in opposition against EP 2 552 955, 50 pages.
Statement of Facts and Arguments in Support of Opposition by Opponent 2 (Alexion Pharmaceuticals, Inc.), dated Feb. 2, 2018, submitted in opposition against EP 2 552 955, 39 pages.
Opposition Statement of Opponent 5 (Shire Human Genetic Therapies, Inc.), dated Feb. 5, 2018, submitted in opposition against EP 2 552 955, 70 pages.
Piche-Nicholas et al., "Changes in complementarity-determining regions significantly alter IgG binding to the neonatal Fc receptor (FcRn) and pharmacokinetics," mAbs, 2018, 10(1):81-94. doi: 10.1080/19420862.2017.1389355.
Rachner, "New Horizons in Osteoporosis," Lancet, Apr. 9, 2011, 377(9773):1276-1287. doi: 10.1016/S0140-6736(10)62349-5. Epub Mar. 28, 2011. PMID: 21450337; PMCID: PMC3555696.
Roitt et al., Immunology, Moscow, Mir, 2000, 110-111, 151 (with corresponding pages from an English version of Immunology (Roitt et al., Immunology, 2006, 62-68)).
Schrama et al., "Antibody targeted drugs as cancer therapeutics," Nat Rev Drug Discov, Feb. 2006, 5(2):147-159.
Siberil et al., "Molecular aspects of human FcKR interactions with IgG: Functional and therapeutic consequences," Immunol Lett, Aug. 15, 2006, 106(2):111-118. Epub Jun. 12, 2006.
Sikkink et al., "Biochemical and aggregation analysis of Bence Jones proteins from different light chain diseases," Amyloid, Mar. 2008, 15(1):29-39.
Stavenhagen et al., "Enhancing the potency of therapeutic monoclonal antibodies via Fc optimization," Adv Enzyme Regul, 2008, 48:152-64.
Response by Opponent 1 (Ablynx N.V.), dated Sep. 6, 2019, submitted in opposition against EP 2 552 955, 57 pages.
Final Written Submissions of Opponent 2 (Alexion Pharmaceuticals, Inc.), dated Sep. 6, 2019, submitted in opposition against EP 2 552 955, 26 pages.
Reply from Opponent 5 (Shire Human Genetic Therapies, Inc.), dated Sep. 6, 2019, submitted in opposition against EP 2 552 955, 15 pages.
Submission of Proprietor (Chugai Seiyaku Kabushiki Kaisha) in the opposition-appeal case against EP 2 275 443, dated Feb. 20, 2017.
Tarantul, "Denaturation," Explanatory Biotechnological Dictionary, Russian-English, Languages of Slavic Cultures, Moscow, 2009, p. 228 (with English translation).
Watts et al., "Gene silencing by siRNAs and antisense oligonucleotides in the laboratory and the clinic," J Pathol, Jan. 2012, 226(2):365-379. doi: 10.1002/path.2993.
WHO Drug Information, vol. 32 No. 2, 2018, International Nonproprietary Names (INN), p. 283, 303-304.
Yang et al., "Effect of anti-CD20 antibody Fab' fragment on apoptosis of B lymphoma cells and intracellular calcium," Tumor, Feb. 2006, 26(2):116-119 (with English translation).
Zhang et al., "Monoclonal antibodies as therapeutic agents in oncology and antibody gene therapy," Cell Res, Feb. 2007, 17(2):89-99.
USPTO Non-Final Office Action in U.S. Appl. No. 14/404,051, dated Oct. 11, 2019, 30 pages.
U.S. Appl. No. 17/333,256, Kakiuchi et al., filed May 28, 2021.
U.S. Appl. No. 17/494,199, Igawa et al., filed Oct. 5, 2021.
U.S. Appl. No. 17/509,128 Igawa et al., filed Oct. 26, 2021.
U.S. Appl. No. 17/602,196, Wakabayashi et al., filed Oct. 7, 2021.
U.S. Appl. No. 17/742,824, Ruike et al., filed May 12, 2022.
U.S. Appl. No. 17/829,641, Igawa et al., filed Jun. 1, 2022.
U.S. Appl. No. 17/333,256, filed May 28, 2021, Kakiuchi et al.
U.S. Appl. No. 17/494,199, filed Oct. 5, 2021, Igawa et al.
U.S. Appl. No. 17/509,128, filed Oct. 26, 2021, Igawa et al.
U.S. Appl. No. 17/602,196, filed Oct. 7, 2021, Wakabayashi et al.
U.S. Appl. No. 17/742,824, filed May 12, 2022, Ruike et al.
U.S. Appl. No. 17/829,641, filed Jun. 1, 2022, Igawa et al.
Almagro et al., "Design and validation of a synthetic $V_H$ repertoire with tailored diversity for protein recognition," J Mol Recognit, Sep.-Oct. 2006, 19(5):413-422.
Anderson et al., "Perspective—FcRn transports albumin: relevance to immunology and medicine," Trends Immunol, Jul. 2006, 27(7):343-348. Epub May 30, 2006.
Application as filed for EP 2 698 431, 375 pages (document cited during EPO opposition proceedings of EP 2 698 431 on Jun. 23, 2021).
Bazin et al., "Use of hu-IgG-SCID mice to evaluate the in vivo stability of human monoclonal IgG antibodies," J Immunol Methods, Jun. 24, 1994, 172(2):209-217.
Beranger et al., "IMGT Scientific Chart," Jun. 8, 2016, 7 pages.
Birn et al., "Renal albumin absorption in physiology and pathology," Kidney Int, Feb. 2006, 69(3):440-449.
Chaudhury et al., "The Major Histocompatibility Complex-related Fc Receptor for IgG (FcRn) Binds Albumin and Prolongs Its Lifespan," J Exp Med, Feb. 3, 2003, 197(3):315-322.
Chilukuri et al., "Polyethylene glycosylation prolongs the circulatory stability of recombinant human butyrylcholinesterase," Chem Biol Interact, Dec. 15, 2005, 157-158:115-121. Epub Oct. 25, 2005.
Chuang et al., "Pharmaceutical Strategies Utilizing Recombinant Human Serum Albumin," Pharm Res, May 2002, 19(5):569-577.
Coloma et al., "Design and production of novel tetravalent bispecific antibodies," Nat Biotechnol, Feb. 1997, 15(2):159-163.
Declaration of Susannah Davis with Curriculum Vitae, dated Dec. 13, 2017, 6 pages (document submitted in the EPO opposition proceedings of EP 2 275 443 on Dec. 20, 2017).
Declaration of Dr. Roland Kontermann with Curriculum Vitae, dated Nov. 20, 2017, 24 pages (document submitted in the EPO opposition proceedings of EP 2 275 443 on Dec. 20, 2017).
Declaration of Jan-Terje Andersen with Curriculum Vitae, dated Dec. 12, 2012, 5 pages (document submitted in the EPO opposition proceedings of EP 2 275 443 on Dec. 20, 2017).
Dennis et al., "Albumin Binding as a General Strategy for Improving the Pharmacokinetics of Proteins," J Biol Chem, Sep. 20, 2002, 277(38):35035-35043. Epub Jul. 15, 2002.
Dirnberger et al., "Secretion of biologically active glycoforms of bovine follicle stimulating hormone in plants," Eur J Biochem, Aug. 2001, 268(16):4570-4579.
Fillipovic, Biochemical basis of human life, VLADOS, 2005, 407:49-50, 70 (with English translation).
Fischer et al., "Bispecific Antibodies: Molecules That Enable Novel Therapeutic Strategies," Pathobiology, 2007, 74(1):3-14.
Franks, Chapter 11 "Conformational Stability of Proteins," Protein biotechnology, 1993, pp. 395-436.
Gekle, "Renal Tubule Albumin Transport," Annu Rev Physiol, 2005, 67:573-594.
Guasch et al., "Charge Selectively of the Glomerular Filtration Barrier in Healthy and Nephrotic Humans," J Clin Invest, Nov. 1993, 92(5):2274-2282.

(56) References Cited

OTHER PUBLICATIONS

Holt et al., "Anti-serum albumin domain antibodies for extending the half-lives of short lived drugs," Protein Eng Des Sel, May 2008, 21(5):283-288. doi: 10.1093/protein/gzm067. Epub Apr. 2, 2008.
Huang et al., "Recombinant human butyrylcholinesterase from milk of transgenic animals to protect against organophosphase poisoning," Proc Natl Acad Sci USA, Aug. 21, 2007, 104(34):13603-13608. Epub Jul. 27, 2007.
Igawa et al., "Antibody recycling by engineered pH-dependent antigen binding improves the duration of antigen neutralization," Nat Biotechnol, Nov. 2010, 28(11):1203-1208, including Online Methods page. doi: 10.1038/nbt.1691.
Inoue et al., "Synthesis of a Superoxide Dismutase Derivative That Circulates Bound to Albumin and Accumulates in Tissues Whose pH Is Deceased," Biochemistry, Aug. 8, 1989, 28(16):6619-6624.
Jakubke et al., "Physicochemical properties," Amino Acids, Peptides and Proteins, Moscow, Mir, 1985, pp. 356-363 (with English translation).
Janeway et al., Immunobiology, 2001, $5^{th}$ ed., p. 122.
Kawamoto et al., "Circulatory Stability and Plasma Lidocaine Levels during Continuous and Intermittent Thoracic Epidural Analgesia," J Anesth, Apr. 1991, 5(2):166-171.
Kim et al., "The Glycosylation and Pharmacokinetics of CTLA4Ig Produced in Rice Cells," Biol Pharm Bull, Oct. 2007, 30(10):1913-1917.
Knudsen et al., "Potent Derivatives of Glucagon-like Peptide-1 with Pharmacokinetic Properties Suitable for Once Daily Administration," J Med Chem, May 4, 2000, 43(9):1664-1669.
Kratz, "Albumin as a drug carrier: Design of prodrugs, drug conjugates and nanoparticles," J Control Release, Dec. 18, 2008, 132(3):171-183. doi: 10.1016/j.jconrel.2008.05.010. Epub May 17, 2008.
Kurtzhals et al., "Albumin Binding and Time Action of Acylated Insulins in Various Species," J Pharm Sci, Mar. 1996, 85(3):304-308.
Kurtzhals et al., "Effect of Fatty Acids and Selected Drugs on the Albumin Binding of a Long-Acting, Acylated Insulin Analogue," J Pharm Sci, Dec. 1997, 86(12):1365-1368.
Lescar et al., "Crystal Structure of a Cross-reaction Complex between Fab F9.13.7 and Guinea Fowl Lysozyme," Biol Chem, Jul. 28, 1995, 270(30):18067-18076.
Makrides et al., "Extended in Vivo Half-Life of Human Soluble Complement Receptor Type 1 Fused to a Serum Albumin-Binding Receptor," J Pharmacol Exp Ther, Apr. 1996, 277(1):534-542.
Manning et al., "Stability of Protein Pharmaceuticals," Pharm Res, Nov. 1989, 6(11):903-918.
Muller et al., Chapter 2 "Bispecific Antibodies," Handbook of Therapeutic Antibodies, 2007, 2:345-378.
Nair et al., "Epitope Recognition by Diverse Antibodies Suggests Conformational Convergence in an Antibody Response," J Immunol, Mar. 1, 2002, 168(5):2371-2382.
Nishimura et al., "An Optimized Crovalimab Dose and Regimen Reduced the Formation of Drug-Target-Drug Complexes in Patients with Paroxysmal Nocturnal Hemoglobinuria from the Phase I/II Composer Trial," Blood, 2020, 136 (Supplement 1):2-3.
O'Hear et al., "Antibody buffering of a ligand in vivo," Proc Natl Acad Sci USA, Jan. 4, 2005, 102(1):40-44. Epub Dec. 22, 2004.
Padlan, "Anatomy of the Antibody Molecule," Mol Immunol, Feb. 1994, 31(3):169-217.
Patentee's explanation in the submission of Apr. 28, 2020 in Annex A made in the appeal case for EP 2 552 955.
Patentee's response to Article 94(3) EPC communication on EP 3 521 311 filed on Oct. 20, 2020.
Peters et al., Chapter 3 "Ligand Binding by Albumin," Academic Press, 1996, pp. 76-79.
Rabia et al., "Understanding and overcoming trade-offs between antibody affinity, specificity, stability and solubility," Biochem Eng J, Sep. 15, 2018, 137:365-374.
Radaev et al., "The structure of a human type III Fcgamma receptor in complex with Fc," J Biol Chem, May 11, 2001, 276(19):16469-16477. Epub Jan. 31, 2001.
Rehlaender et al., "Antibodies as Carrier Proteins," Pharm Res, Nov. 1998, 15(11):1652-1656.
Roitt et al., Immunology, 2006, pp. 62-68.
Roth et al., "The complement C5 inhibitor crovalimab in paroxysmal nocturnal hemoglobinuria," Blood, Mar. 19, 2020, 135(12):912-920. doi: 10.1182/blood.2019003399.
Saxena et al., "Role of Oligosaccharides in the Pharmacokinetics of Tissue-Derived and Genetically Engineered Cholinesterases," Mol Pharmacol, Jan. 1998, 53(1):112-122.
Schultze et al., "Turnover of Plasma Proteins," Molecular Biology of Human Proteins with Special Reference to Plasma Proteins, Nature and Metabolism of Extracellular Proteins, Elsevier, 1996, 1:476-477.
Smith et al., "Prolonged in Vivo Residence Times of Antibody Fragments Associated with Albumin," Bioconjug Chem, Sep.-Oct. 2001, 12(5):750-756.
Stork et al., "A novel tri-functional antibody fusion protein with improved pharmacokinetic properties generated by fusing a bispecific single-chain diabody with an albumin-binding domain from streptococcal protein G," Protein Eng Des Sel, Nov. 2007, 20(11):569-576. Epub Nov. 3, 2007.
Third-Party Submission Under 37 C.F.R. 1.290 submitted Apr. 2, 2019 in U.S. Appl. No. 15/952,951.
Third-Party Submission Under 37 C.F.R. 1.290 submitted Jan. 17, 2019 in U.S. Appl. No. 15/952,951.
Wang et al., "Applications of Eculizumab, a humanized anti-complement factor C5 monoclonal antibody," Chinese Journal of Clinical Pharmacology and Therapeutics, 2015, 20(4):455-459 (with English abstract).
Xu, editor, Part III "Medicated Bath for Common Disease—Correct Medicated Bath Can Treat Various Diseases," Chinese Medicated Bath Encyclopedia, Golden Shield Press, Beijing, Oct. 31, 2013, p. 177.
Yoon et al., "Construction, Affinity Maturation, and Biological Characterization of an Anti-tumor-associated Glycoprotein-72 Humanized Antibody," J Biol Chem, Mar. 17, 2006, 281(11):6985-6992.
Fish & Richardson P.C., Reply to Final Office Action dated May 30, 2017 in U.S. Appl. No. 13/595,139, dated Sep. 21, 2017, 36 pages (document submitted in EPO opposition proceedings of EP 2 275 443 on Dec. 20, 2017).
Fish & Richardson P.C., Amendment and Reply to Restriction Requirement dated Jan. 6, 2016 in U.S. Appl. No. 13/990,158, filed Jul. 1, 2016, 7 pages.
Fish & Richardson P.C, Reply to Non-Final Office Action dated Aug. 19, 2016 in U.S. Appl. No. 13/990,158, filed Feb. 17, 2017, 19 pages.
USPTO Non-Final Office Action in U.S. Appl. No. 13/637,415, dated Feb. 10, 2021, 32 pages.
USPTO Final Office Action in U.S. Appl. No. 15/952,951 dated Jul. 16, 2021, 15 pages.
U.S. Appl. No. 17/854,023, filed Jun. 30, 2022, Igawa et al.
U.S. Appl. No. 18/052,258, filed Nov. 3, 2022, Igawa et al.
U.S. Appl. No. 18/059,677, filed Nov. 29, 2022, Murata et al.
U.S. Appl. No. 18/096,066, filed Jan. 12, 2023, Igawa et al.
U.S. Appl. No. 18/156,138, filed Jan. 18, 2023, Igawa et al.
U.S. Appl. No. 18/157,320, filed Jan. 20, 2023, Ruike et al.
U.S. Appl. No. 18/166,211, filed Feb. 8, 2023, Sampei.
U.S. Appl. No. 18/181,641, filed Mar. 10, 2023, Shinomiya et al.
U.S. Appl. No. 18/298,743, filed Apr. 11, 2023, Igawa et al.
U.S. Appl. No. 18/330,420, filed Jun. 7, 2023, Kakehi et al.
Attwood, "The Babel of Bioinformatics," Science, Oct. 20, 2000, 290(5491):471-473. doi: 10.1126/science.290.5491.471. PMID: 11183771.
Harkevic, Pharmacology Textbook, Moscow, GEOTAR-Media, 2006, 9th ed., pp. 39, 63, and 569 (with English translation).
Hoffmann-La Roche, "Study to Assess Safety, Efficacy, Pharmacokinetics, and Pharmacodynamics of Crovalimab in Healthy Volunteers and Participants With Paroxysmal Nocturnal Hemoglobinuria," clinical trial NCT03157635, first posted on May 17, 2017 at

(56) References Cited

OTHER PUBLICATIONS

ClinicalTrials.gov (https://clinicaltrials.gov/ct2/home), 13 pages, retrieved from the internet on Sep. 24, 2021.
Huang et al., "Fully Humanized Neutralizing Antibodies to Interleukin-8 (ABX-IL8) Inhibit Angiogenesis, Tumor Growth, and Metastasis of Human Melanoma," Am J Pathol, Jul. 2002, 161(1):125-134.
Perrakis et al., "AI revolutions in biology," EMBO Rep, Nov. 4, 2021, 22(11):e54046, 6 pages.
Skolnick et al., "From genes to protein structure and function: novel applications of computational approaches in the genomic era," Trends Biotechnol, Jan. 2000, 18(1):34-39. doi: 10.1016/s0167-7799(99)01398-0. PMID: 10631780.
Zwolak et al., "Rapid Purification of Human Bispecific Antibodies via Selective Modulation of Protein A Binding," Sci Rep, Nov. 14, 2017, 7(1):15521.
USPTO Final Office Action in U.S. Appl. No. 13/637,415, dated Oct. 4, 2021, 32 pages.
U.S. Appl. No. 18/052,258, Igawa et al., filed Nov. 3, 2022.
U.S. Appl. No. 18/059,677, Murata et al., filed Nov. 29, 2022.
U.S. Appl. No. 18/096,066, Igawa et al., filed Jan. 12, 2023.
U.S. Appl. No. 18/156,138, Igawa et al., filed Jan. 18, 2023.
U.S. Appl. No. 18/157,320, Ruike et al., filed Jan. 20, 2023.
U.S. Appl. No. 18/166,211, Sampei, filed Feb. 8, 2023.
U.S. Appl. No. 18/181,641, Shinomiya et al., filed Mar. 10, 2023.
U.S. Appl. No. 18/298,743, Igawa et al., filed Apr. 11, 2023.
U.S. Appl. No. 18/330,420, Kakehi et al., filed Jun. 7, 2023.

\* cited by examiner

ANTIGEN-BINDING MOLECULE CAPABLE OF BINDING TO PLURALITY OF ANTIGEN MOLECULES REPEATEDLY

CROSS-REFERENCE TO RELATED APPLICATIONS

This application is a divisional of patent application Ser. No. 13/990,158, now abandoned, filed on Mar. 28, 2014, which is the National Stage of International Patent Application Serial No. PCT/JP2011/077619, filed on Nov. 30, 2011, which claims the benefit of Japanese Patent Application Serial No. 2010-266121, filed on Nov. 30, 2010, and Japanese Patent Application Serial No. 2011-217886, filed on Sep. 30, 2011.

SEQUENCE LISTING

This application contains a Sequence Listing that has been submitted electronically in ASCII format and is hereby incorporated by reference in its entirety. The name of the text file is SequenceListing.txt, and the size of the text file is 296.106 kilobytes. The text file was created on May 24, 2018.

BACKGROUND ART

Antibodies are drawing attention as pharmaceuticals as they are highly stable in plasma and have few side effects. At present, a number of IgG-type antibody pharmaceuticals are available on the market and many antibody pharmaceuticals are currently under development (Non-patent Documents 1 and 2). Meanwhile, various technologies applicable to second-generation antibody pharmaceuticals have been reported, including those that enhance effector function, antigen-binding ability, pharmacokinetics, and stability, and those that reduce the risk of immunogenicity (Non-patent Document 3). In general, the requisite dose of an antibody pharmaceutical is very high. This in turn has led to problems such as high production cost, as well as the difficulty in producing subcutaneous formulations. In theory, the dose of an antibody pharmaceutical may be reduced by improving antibody pharmacokinetics or improving the affinity between antibodies and antigens.

The literature has reported methods for improving antibody pharmacokinetics using artificial substitution of amino acids in constant regions (Non-patent Documents 4 and 5). Similarly, affinity maturation has been reported as a technology for enhancing antigen-binding ability or antigen-neutralizing activity (Non-patent Document 6). This technology enables enhancement of antigen-binding activity by introducing amino acid mutations into the CDR region of a variable region or such. The enhancement of antigen-binding ability enables improvement of in vitro biological activity or reduction of dosage, and further enables improvement of in vivo efficacy (Non-patent Document 7).

Meanwhile, the antigen-neutralizing capacity of a single antibody molecule depends on its affinity. By increasing the affinity, an antigen can be neutralized by a smaller amount of an antibody. Various methods can be used to enhance antibody affinity (Non-patent Document 6). Furthermore, if the affinity could be made infinite by covalently binding the antibody to the antigen, a single antibody molecule could neutralize one antigen molecule (a divalent antibody can neutralize two antigen molecules). However, the stoichiometric neutralization of one antibody against one antigen (one divalent antibody against two antigens) is the limit of pre-existing methods, and thus it was impossible to completely neutralize antigen with an amount of antibody smaller than the amount of antigen. In other words, the affinity-enhancing effect has a limit (Non-Patent Document 9). To prolong the neutralization effect of a neutralizing antibody for a certain period, the antibody must be administered at a dose higher than the amount of antigen produced in the body during the same period. Therefore, with just the above-described improvement of antibody pharmacokinetics or affinity maturation technology, there were limitations when it comes to reduction of the required antibody dose. Accordingly, in order to sustain antibody's antigen-neutralizing effect for a target period with an amount of the antibody smaller than the amount of antigen, a single antibody must neutralize multiple antigens.

An antibody that binds to an antigen in a pH-dependent manner has recently been reported as a novel method for achieving the above objective (Patent Document 1). The antibodies with pH-dependent antigen binding, which strongly bind to an antigen under the neutral conditions in plasma and dissociate from the antigen under acidic conditions in the endosome, can dissociate from the antigen in the endosome. When an antibody with pH-dependent antigen binding dissociates from the antigen is recycled to the plasma by FcRn, it can bind to another antigen again. Thus, a single antibody can repeatedly bind to a number of antigens.

In addition, plasma retention of the antigen is very short as compared to antibodies recycled via FcRn binding. When an antibody with long plasma retention binds to such an antigen with a short plasma retention, the plasma retention time of the antigen-antibody complex is prolonged to the same as that of the antibody. Thus, the plasma retention of the antigen is prolonged by binding to the antibody, and thus the plasma antigen concentration is increased. In such cases, even if the antigen affinity of the antibody is improved, antigen elimination from the plasma cannot be enhanced. The above-described antibodies with pH-dependent antigen binding have been reported to be more effective as a method for enhancing antigen elimination from the plasma as compared to common antibodies (Patent Document 1).

Thus, a single antibody with pH-dependent antigen binding binds to a number of antigens and is capable of facilitating antigen elimination from the plasma as compared to common antibodies. Accordingly, the antibodies with pH-dependent antigen binding have effects not achieved by common antibodies. However, the only known method for achieving the effect of repeated binding of an antibody with pH-dependent antigen binding to antigen, and the effect of promoting antigen elimination from plasma, was to confer pH dependency on the antigen-antibody reaction using the pH difference between plasma and endosome.

Prior art documents related to the present invention are shown below:

PRIOR ART DOCUMENTS

Patent Documents

[Patent Document 1] WO 2009/125825, ANTIGEN-BINDING MOLECULE CAPABLE OF BINDING TO TWO OR MORE ANTIGEN MOLECULES REPEATEDLY Non-Patent Documents

[Non-patent Document 1] Monoclonal antibody successes in the clinic, Janice M Reichert, Clark J Rosensweig, Laura B Faden & Matthew C Dewitz, Nature Biotechnology 23, 1073-1078 (2005)

[Non-patent Document 2] Pavlou A K, Belsey M J., The therapeutic antibodies market to 2008., Eur J Pharm Biopharm. 2005 April; 59(3): 389-96

[Non-patent Document 3] Kim S J, Park Y, Hong H J., Antibody engineering for the development of therapeutic antibodies., Mol Cells. 2005 Aug. 31; 20(1): 17-29. Review

[Non-patent Document 4] Hinton P R, Xiong J M, Johlfs M G, Tang M T, Keller S, Tsurushita N., An engineered human IgG1 antibody with longer serum half-life., J Immunol. 2006 Jan. 1; 176(1): 346-56

[Non-patent Document 5] Ghetie V, Popov S, Borvak J, Radu C, Matesoi D, Medesan C, Ober R J, Ward E S., Increasing the serum persistence of an IgG fragment by random mutagenesis., Nat Biotechnol. 1997 July; 15(7): 637-40

[Non-patent Document 6] Proc Natl Acad Sci USA. 2005 Jun. 14; 102(24): 8466-71. Epub 2005 Jun. 6. A general method for greatly improving the affinity of antibodies by using combinatorial libraries. Rajpal A, Beyaz N, Haber L, Cappuccilli G, Yee H, Bhatt R R, Takeuchi T, Lerner R A, Crea R

[Non-patent Document 7] Wu H, Pfarr D S, Johnson S, Brewah Y A, Woods R M, Patel N K, White W I, Young J F, Kiener P A. Development of Motavizumab, an Ultra-potent Antibody for the Prevention of Respiratory Syncytial Virus Infection in the Upper and Lower Respiratory Tract. J Mol Biol. (2007) 368: 652-665

[Non-patent Document 8] Hanson C V, Nishiyama Y, Paul S. Catalytic antibodies and their applications. Curr Opin Biotechnol. 2005 December; 16(6): 631-6

[Non-patent Document 9] Rathanaswami P, Roalstad S, Roskos L, Su Q J, Lackie S, Babcook J. Demonstration of an in vivo generated sub-picomolar affinity fully human monoclonal antibody to interleukin-8. Biochem Biophys Res Commun. 2005 Sep. 9; 334(4): 1004-13

SUMMARY OF THE INVENTION

Problems to be Solved by the Invention

The present invention was achieved in view of the above circumstances. An objective of the present invention is to provide methods for promoting antigen uptake into cells by using antigen-binding molecules, methods for increasing the number of times of antigen binding by one antigen-binding molecule, methods for promoting the reduction of plasma antigen concentration by administering antigen-binding molecules, methods for improving plasma retention of antigen-binding molecules, antigen-binding molecules that facilitate antigen uptake into cells, antigen-binding molecules that have an increased number of times of antigen binding, antigen-binding molecules capable of promoting the reduction of plasma antigen concentration by administration, antigen-binding molecules with improved plasma retention, pharmaceutical compositions comprising the antigen-binding molecules, and methods for producing those described above.

Means for Solving the Problems

The present inventors conducted dedicated studies on methods for promoting antigen uptake into cells by antigen-binding molecules (molecules such as polypeptides having the antigen-binding activity), methods for increasing the number of times of antigen binding by one antigen-binding molecule, methods for promoting the reduction of plasma antigen concentration by administering antigen-binding molecules, and methods for improving the plasma retention of an antigen-binding molecule. As a result, the present inventors focused on the difference in the calcium concentration between plasma and early endosome, and then discovered that: antigen uptake into cells by antigen-binding molecules could be promoted by using antigen-binding molecules that have antigen-antibody reactivity in a calcium dependent manner; the number of times of antigen binding by one antigen-binding molecule could be increased by repetitive antigen binding of an antigen-binding molecule; the reduction of antigen concentration in plasma could be promoted by administering antigen-binding molecules; and that the plasma retention of antigen-binding molecule could be improved.

Specifically, the present invention relates to methods for promoting antigen uptake into cells by using antigen-binding molecules that have antigen-antibody reactivity in a calcium dependent manner, methods for increasing the number of times of antigen binding by one antigen-binding molecule, methods for promoting the reduction of plasma antigen concentration by administering antigen-binding molecules, and methods for improving the plasma retention of antigen-binding molecules, as well as antigen-binding molecules that allow enhanced antigen uptake into cells, antigen-binding molecules with an increased number of times of antigen binding, antigen-binding molecules that can promote the reduction of plasma antigen concentration when administered, antigen-binding molecules with improved plasma retention, pharmaceutical compositions comprising the above antigen-binding molecules, and methods for producing them. More specifically, the present invention relates to the following:

[1] an antigen-binding molecule comprising an antigen-binding domain and a human FcRn-binding domain, whose antigen-binding activity is different under two different calcium concentration conditions and is lower under a low calcium concentration condition than under a high calcium concentration condition, and which has binding activity to human FcRn under a neutral pH condition;

[2] the antigen-binding molecule of [1], wherein the low calcium concentration is an ionized calcium concentration of 0.1 to 30 μM;

[3] the antigen-binding molecule of [1], wherein the high calcium concentration is an ionized calcium concentration of 100 μM to 10 mM;

[4] the antigen-binding molecule of [1] or [2], wherein the low calcium concentration is an intraendosomal concentration of ionized calcium;

[5] the antigen-binding molecule of [1] or [3], wherein the high calcium concentration is a plasma concentration of ionized calcium;

[6] the antigen-binding molecule of any of [1] to [5], wherein the FcRn-binding domain is an Fc region;

[7] the antigen-binding molecule of any of [1] to [6], further wherein the antigen-binding activity is lower under an acidic pH condition than under a neutral pH condition;

[8] the antigen-binding molecule of [7], wherein at least one amino acid is substituted with histidine, or at least one histidine is inserted into the antigen-binding molecule;

[9] the antigen-binding molecule of any of [1] to [8], which binds to a membrane antigen or soluble antigen;

[10] the antigen-binding molecule of any of [1] to [9], wherein the antigen is an antigen selected from the group consisting of IL-6R, IL-6, IgA, human glypican 3, and IgE;

[11] an antigen-binding molecule comprising an antigen-binding domain and a human FcRn-binding domain, whose antigen-binding activity is different between two different calcium concentration conditions and is lower under a low calcium concentration condition than under a high calcium concentration condition, and wherein a light chain or heavy chain of the antigen-binding domain comprises a calcium-binding motif derived from a human antibody;

[12] the antigen-binding molecule of [11], wherein the calcium-binding motif is comprised in the light chain CDR1, CDR2, and/or CDR3 of the antigen-binding domain;

[13] the antigen-binding molecule of [12], wherein the calcium-binding motif is comprised at positions 30, 31, and/or 32 according to Kabat's numbering in the light chain CDR1;

[14] the antigen-binding molecule of [12] or [13], wherein the calcium-binding motif is comprised at position 50 according to Kabat's numbering in the light chain CDR2;

[15] the antigen-binding molecule of any of [12] to [14], wherein the calcium-binding motif is comprised at position 92 according to Kabat's numbering in the light chain CDR3;

[16] the antigen-binding molecule of any of [12] to [15], which is either IgA or human glypican 3;

[17] the antigen-binding molecule of [11], wherein the calcium-binding motif is comprised in the heavy chain CDR1, CDR2, and/or CDR3 of the antigen-binding domain;

[18] the antigen-binding molecule of [16], wherein the calcium-binding motif is comprised at positions 95, 96, 100a, and/or 101 according to Kabat's numbering in the heavy chain CDR3;

[19] the antigen-binding molecule of [17] or [18], which is either IL-6R or IL-6;

[20] the antigen-binding molecule of any of [11] to [19], which comprises an FcRn-binding domain that has FcRn-binding activity in the neutral pH range;

[21] the antigen-binding molecule of [20], wherein the FcRn-binding domain is an Fc region;

[22] the antigen-binding molecule of any of [1] to [10], [20], or [21], wherein one or more amino acids at positions 248, 250, 252, 254, 255, 256, 257, 258, 265, 286, 289, 297, 303, 305, 307, 308, 309, 311, 312, 314, 315, 317, 332, 334, 360, 376, 380, 382, 384, 385, 386, 387, 389, 424, 428, 433, 434, and 436 (EU numbering) in the amino acid sequence of the Fc region are different from those of the natural Fc region;

[23] the antigen-binding molecule of [22], which comprises any one or combination of:
Met at amino acid position 237;
Ile at amino acid position 248;
Ala, Phe, Ile, Met, Gln, Ser, Val, Trp, or Tyr at amino acid position 250;
Phe, Trp, or Tyr at amino acid position 252;
Thr at amino acid position 254;
Glu at amino acid position 255;
Asp, Glu, or Gln at amino acid position 256;
Ala, Gly, Ile, Leu, Met, Asn, Ser, Thr, or Val at amino acid position 257;
His at amino acid position 258;
Ala at amino acid position 265;
Ala or Glu at amino acid position 286;
His at amino acid position 289;
Ala at amino acid position 297;
Ala at amino acid position 303;
Ala at amino acid position 305;
Ala, Asp, Phe, Gly, His, Ile, Lys, Leu, Met, Asn, Pro, Gln, Arg, Ser, Val, Trp, or Tyr at amino acid position 307;
Ala, Phe, Ile, Leu, Met, Pro, Gln, or Thr at amino acid position 308;
Ala, Asp, Glu, Pro, or Arg at amino acid position 309;
Ala, His, or Ile at amino acid position 311;
Ala or His at amino acid position 312;
Lys or Arg at amino acid position 314;
Ala, Asp, or His at amino acid position 315;
Ala at amino acid position 317;
Val at amino acid position 332;
Leu at amino acid position 334;
His at amino acid position 360;
Ala at amino acid position 376;
Ala at amino acid position 380;
Ala at amino acid position 382;
Ala at amino acid position 384;
Asp or His at amino acid position 385;
Pro at amino acid position 386;
Glu at amino acid position 387;
Ala or Ser at amino acid position 389;
Ala at amino acid position 424;
Ala, Asp, Phe, Gly, His, Ile, Lys, Leu, Asn, Pro, Gln, Ser, Thr, Val, Trp, or Tyr at amino acid position 428;
Lys at amino acid position 433;
Ala, Phe, His, Ser, Trp, or Tyr at amino acid position 434; or
His, Ile, Leu, or Val at amino acid position 436;
according to EU numbering in the Fc region;

[24] the antigen-binding molecule of any of [1] to [23], wherein the antigen-binding molecule is an antibody;

[25] a method of producing an antigen-binding molecule having at least one function selected from:
(i) function of promoting uptake of an antigen into cells,
(ii) function of binding to an antigen two or more times,
(iii) function of promoting the reduction of plasma antigen concentration, and
(iv) function of excellence in plasma retention,
wherein the method comprises the steps of (a) to (e) below:
(a) determining the antigen-binding activity of an antigen-binding molecule under a low calcium concentration condition;
(b) determining the antigen-binding activity of the antigen-binding molecule under a high calcium concentration condition;
(c) selecting an antigen-binding molecule that has a lower antigen-binding activity under the low calcium concentration condition than under the high calcium concentration condition;
(d) obtaining a gene encoding the antigen-binding molecule selected in step (c); and
(e) producing the antigen-binding molecule using the gene obtained in step (d);

[26] a method of producing an antigen-binding molecule having at least one function selected from:
(i) function of promoting uptake of an antigen into cells,
(ii) function of binding to an antigen two or more times, (iii) function of promoting the reduction of plasma antigen concentration, and
(iv) function of excellence in plasma retention,
wherein the method comprises the steps of (a) to (e) below:
  (a) contacting an antigen with an antigen-binding molecule or a library of antigen-binding molecules under a high calcium concentration condition;
  (b) placing an antigen-binding molecule that binds to the antigen in step (a) under a low calcium concentration condition;
  (c) obtaining an antigen-binding molecule that dissociates in step (b);
  (d) obtaining a gene encoding the antigen-binding molecule obtained in step (c); and
  (e) producing the antigen-binding molecule using the gene obtained in step (d);
[27] a method of producing an antigen-binding molecule having at least one function selected from:
  (i) function of promoting uptake of an antigen into cells,
  (ii) function of binding to an antigen two or more times,
  (iii) function of promoting the reduction of plasma antigen concentration, and
  (iv) function of excellence in plasma retention,
wherein the method comprises the steps of (a) to (f) below:
  (a) contacting an antigen with an antigen-binding molecule or a library of antigen-binding molecules under a low calcium concentration condition;
  (b) selecting an antigen-binding molecule that does not bind to the antigen in step (a);
  (c) allowing the antigen-binding molecule selected in step (b) to bind to the antigen under a high calcium concentration condition;
  (d) obtaining an antigen-binding molecule that bound to the antigen in step (c);
  (e) obtaining a gene encoding the antigen-binding molecule obtained in step (d); and
  (f) producing the antigen-binding molecule using the gene obtained in step (e);
[28] the production method of any of [25] to [27], which additionally comprises the step of conferring or increasing the human FcRn-binding activity under a neutral pH condition by modifying an amino acid in the antigen-binding molecule;
[29] the production method of any of [25] to [27], which additionally comprises the step of reducing the antigen-binding activity under an acidic pH condition to be lower than that under a neutral pH condition by modifying an amino acid in the antigen-binding molecule;
[30] the production method of any one of [25] to [27], wherein the low calcium concentration is an ionized calcium concentration of 0.1 to 30 μM;
[31] the production method of any of [25] to [27], wherein the high calcium concentration is an ionized calcium concentration of 100 μM to 10 mM;
[32] the production method of any of [25] to [27], wherein the low calcium concentration is an intraendosomal concentration of ionized calcium;
[33] the production method of any of [25] to [27], wherein the high calcium concentration is a plasma concentration of ionized calcium;
[34] the production method of [29], wherein the amino acid modification in the antigen-binding molecule is modification by substituting at least one amino acid with histidine, or inserting at least one histidine into the antigen-binding molecule;
[35] the production method of any of [25] to [34], wherein an antigen bound by the antigen-binding molecule is an antigen selected from the group consisting of IL-6R, IL-6, IgA, human glypican 3, and IgE;
[36] the production method of any of [25] to [35], wherein the antigen-binding molecule is an antibody;
[37] a pharmaceutical composition comprising:
the antigen-binding molecule of any of [1] to [24] or an antigen-binding molecule produced by the production method of any of [25] to [36], and a pharmaceutically acceptable carrier;
[38] the pharmaceutical composition of [37] for use in promoting internalization of the antigen into cells;
[39] the pharmaceutical composition of [37] for use in promoting reduction of the antigen concentration in plasma;
[40] a pharmaceutical composition for use in promoting antigen uptake into cells or reduction of plasma antigen concentration, which comprises an antigen-binding molecule comprising an antigen-binding domain and a human FcRn-binding domain, whose antigen-binding activity is different between two different calcium concentrations and is lower under a low calcium concentration condition than under a high calcium concentration condition;
[41] the pharmaceutical composition of [40], wherein the low calcium concentration is an ionized calcium concentration of 0.1 to 30 μM;
[42] the pharmaceutical composition of [40], wherein the high calcium concentration is an ionized calcium concentration of 100 μM to 10 mM;
[43] the pharmaceutical composition of [40] or [41], wherein the low calcium concentration is an intraendosomal concentration of ionized calcium;
[44] the pharmaceutical composition of [40] or [42], wherein the high calcium concentration is a plasma concentration of ionized calcium;
[45] the pharmaceutical composition of any of [40] to [44], wherein the FcRn-binding domain comprised in the antigen-binding molecule is an Fc region;
[46] the pharmaceutical composition of any of [40] to [45], wherein the antigen-binding activity of the antigen-binding molecule is lower under an acidic pH condition than under a neutral pH condition;
[47] the pharmaceutical composition of [46], wherein the amino acid modification in the antigen-binding molecule is modification by substituting at least one amino acid with histidine, or inserting at least one histidine into the antigen-binding molecule;
[48] the pharmaceutical composition of any of [40] to [47], wherein the antigen to which the antigen-binding molecule binds is an antigen selected from the group consisting of IL-6R, IL-6, IgA, human glypican 3, and IgE;
[49] a method of screening for an antigen-binding molecule that has at least one function selected from:
  (i) function of promoting uptake of an antigen into cells,
  (ii) function of binding to an antigen two or more times,
  (iii) function of promoting the reduction of plasma antigen concentration, and
  (iv) function of excellence in plasma retention, wherein the method comprises the steps of (a) to (c) below:
- (a) determining the antigen-binding activity of an antigen-binding molecule under a low calcium concentration condition;
- (b) determining the antigen-binding activity of an antigen-binding molecule under a high calcium concentration condition; and
- (c) selecting an antigen-binding molecule whose antigen-binding activity is lower under the low calcium concentration condition than under the high calcium concentration condition;

[50] a method of screening for an antigen-binding molecule that comprises at least one function selected from:
- (i) function of promoting uptake of an antigen into cells,
- (ii) function of binding to an antigen two or more times,
- (iii) function of promoting the reduction of plasma antigen concentration, and
- (iv) function of excellence in plasma retention, wherein the method comprises the steps of (a) to (c) below:
- (a) contacting an antigen with an antigen-binding molecule or a library of antigen-binding molecules under a high calcium concentration condition;
- (b) placing an antigen-binding molecule that binds to the antigen in step (a) under a low calcium concentration condition; and
- (c) obtaining an antigen-binding molecule that dissociates in step (b);

[51] a method of screening for an antigen-binding molecule that comprises at least one function selected from:
- (i) function of promoting uptake of an antigen into cells,
- (ii) function of binding to an antigen two or more times,
- (iii) function of promoting the reduction of plasma antigen concentration, and
- (iv) function of excellence in plasma retention, wherein the method comprises the steps of (a) to (d) below:
- (a) contacting an antigen with an antigen-binding molecule or a library of antigen-binding molecules under a low calcium concentration condition;
- (b) selecting an antigen-binding molecule that does not bind to the antigen in step (a);
- (c) allowing the antigen-binding molecule selected in step (b) to bind to the antigen under a high calcium concentration condition; and
- (d) obtaining an antigen-binding molecule bound to the antigen in step (c);

[52] the screening method of any of [49] to [51], wherein the low calcium concentration is an ionized calcium concentration of 0.1 to 30 μM;

[53] the screening method of any of [49] to [51], wherein the high calcium concentration is an ionized calcium concentration of 100 μM to 10 mM;

[54] the screening method of any of [49] to [52], wherein the low calcium concentration is an intraendosomal concentration of ionized calcium;

[55] the screening method of any of [49] to [51], or [53], wherein the high calcium concentration is a plasma concentration of ionized calcium;

[56] the screening method of any of [49] to [55], wherein the antigen to which the antigen-binding molecule binds is an antigen selected from the group consisting of IL-6R, IL-6, IgA, human glypican 3, and IgE;

[57] the screening method of any of [49] to [56], wherein the antigen-binding molecule is an antibody;

[58] a method for promoting antigen uptake into a cell by an antigen-binding molecule by administering the antigen-binding molecule of any of [1] to [24] or an antigen-binding molecule produced by the production method of any of [25] to [36];

[59] a method for promoting the reduction of plasma antigen concentration by administering the antigen-binding molecule of any of [1] to [24] or an antigen-binding molecule produced by the production method of any of [25] to [36];

[60] a method for increasing the number of times of antigen binding by one antigen-binding molecule by using the antigen-binding molecule of any of [1] to [24] or an antigen-binding molecule produced by the production method of any of [25] to [36];

[61] a method for improving plasma retention of an antigen-binding molecule by using the antigen-binding molecule of any of [1] to [24] or an antigen-binding molecule produced by the production method of any of [25] to [36];

[62] a method for promoting antigen uptake into a cell by an antigen-binding molecule by administering an antigen-binding molecule comprising an antigen-binding domain and a human FcRn-binding domain, whose antigen-binding activity is different between two different calcium concentrations and is lower under a low calcium concentration condition than under a high calcium concentration condition;

[63] a method for promoting the reduction of plasma antigen concentration by administering an antigen-binding molecule comprising an antigen-binding domain and a human FcRn-binding domain, whose antigen-binding activity is different between two different calcium concentrations and is lower under a low calcium concentration condition than under a high calcium concentration condition;

[64] a method for increasing the number of times of antigen binding by one antigen-binding molecule by using an antigen-binding molecule comprising an antigen-binding domain and a human FcRn-binding domain, whose antigen-binding activity is different between two different calcium concentrations and is lower under a low calcium concentration condition than under a high calcium concentration condition;

[65] a method for improving plasma retention of an antigen-binding molecule by using an antigen-binding molecule comprising an antigen-binding domain and a human FcRn-binding domain, whose antigen-binding activity is different between two different calcium concentrations and is lower under a low calcium concentration condition than under a high calcium concentration condition;

[66] the method of any of [62] to [65], wherein the low calcium concentration is an ionized calcium concentration of 0.1 to 30 μM;

[67] the method of any of [62] to [66], wherein the high calcium concentration is an ionized calcium concentration of 100 μM to 10 mM;

[68] the method of any of [62] to [67], wherein the low calcium concentration is an intraendosomal concentration of ionized calcium;

[69] the method of any of [62] to [68], wherein the high calcium concentration is a plasma concentration of ionized calcium;

[70] the method of any of [62] to [69], wherein an FcRn-binding domain of the antigen-binding molecule is an Fc region;

[71] the method of any of [62] to [70], wherein additionally the antigen-binding activity of the antigen-binding molecule is lower under an acidic pH condition than under a neutral pH condition;

[72] the method of [71], wherein the amino acid modification in the antigen-binding molecule is modification by substituting at least one amino acid with histidine, or inserting at least one histidine into the antigen-binding molecule;

[73] the method of any of [62] to [72], wherein the antigen to which the antigen-binding molecule binds is an antigen selected from the group consisting of IL-6R, IL-6, IgA, human glypican 3, and IgE; and

[74] the method of any of [62] to [73], wherein the antigen-binding molecule is an antibody.

Furthermore, the present invention relates to kits for use in the methods of the present invention, which comprise an antigen-binding molecule of the present invention or an antigen-binding molecule produced by production methods of the present invention. The present invention also relates to agents for promoting antigen uptake into cells by an antigen-binding molecule, agents for promoting the reduction of plasma antigen concentration, agents for increasing the number of times of antigen binding by one antigen-binding molecule, and agents for improving plasma retention of an antigen-binding molecule, all of which comprise as an active ingredient an antigen-binding molecule of the present invention or an antigen-binding molecule produced by the production method of the present invention. Furthermore, the present invention relates to the use of an antigen-binding molecule of the present invention or an antigen-binding molecule produced by the production methods of the present invention in the production of agents for promoting antigen uptake into cells by an antigen-binding molecule, agents for promoting reduction of plasma antigen concentration, agents for increasing the number of times of antigen binding by an antigen-binding molecule, or agents for improving plasma retention of an antigen-binding molecule. The present invention also relates to antigen-binding molecules of the present invention or antigen-binding molecules produced by production methods of the present invention for use in the methods of the present invention.

Effects of the Invention

The present invention provides methods for promoting antigen uptake into cells by antigen-binding molecules, methods for increasing the number of times of antigen binding by one antigen-binding molecule, methods for promoting the reduction of plasma antigen concentration by administering antigen-binding molecules, and methods for improving the plasma retention of an antigen-binding molecule. Promotion of antigen uptake into cells by antigen-binding molecules enables one to promote reduction of plasma antigen concentration by administering the antigen-binding molecules and also to promote the plasma retention of an antigen-binding molecule. This can increase the number of times of antigen binding by one antigen-binding molecule. Thus, such antigen-binding molecules can produce more superior in vivo effects as compared to typical antigen-binding molecules.

Figure 17:
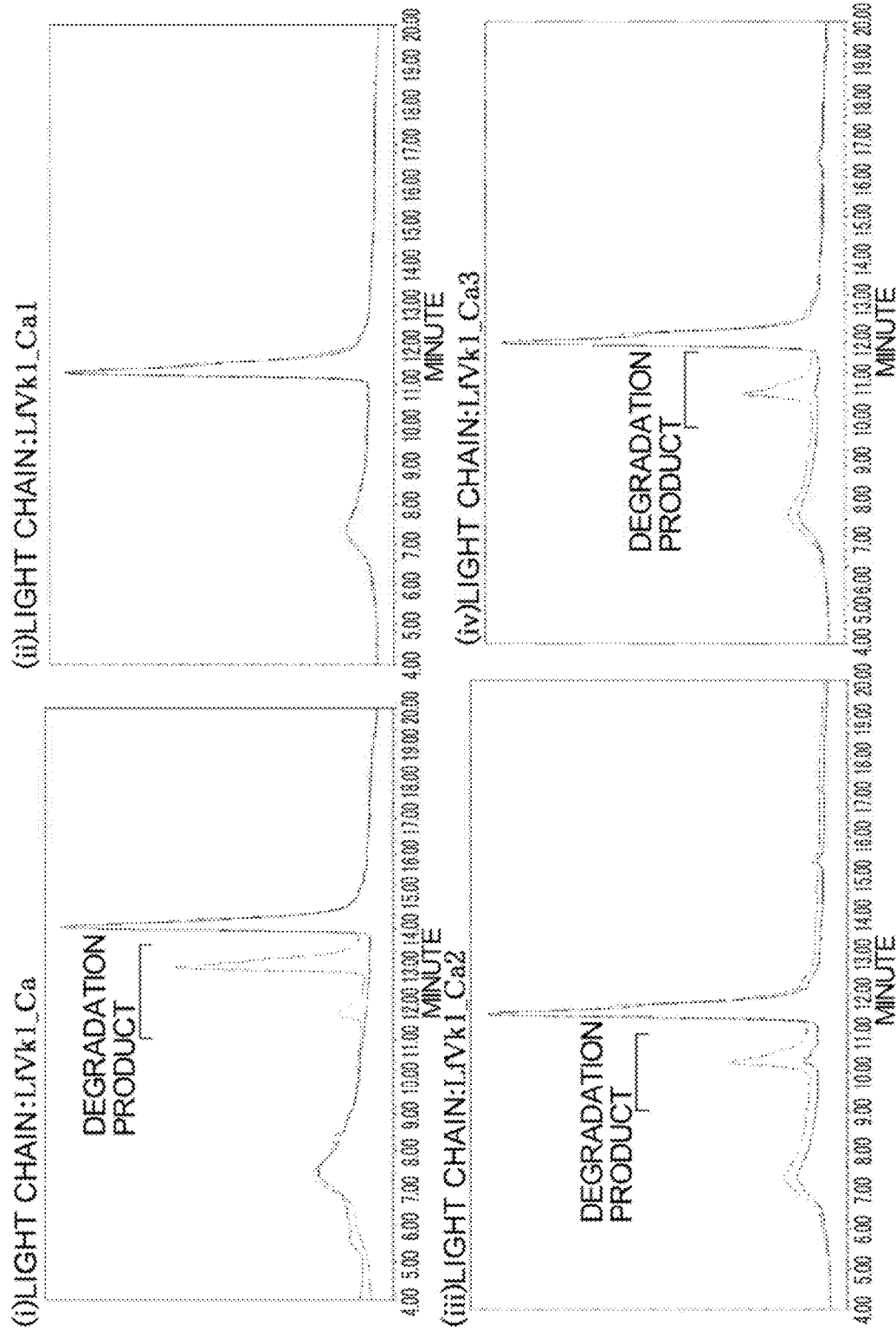

FIG. 17 shows ion-exchange chromatograms for an antibody having LfVk1_Ca sequence (heavy chain: GC_H, SEQ ID NO: 102; light chain: LfVk1_Ca, SEQ ID NO: 61) and an antibody having a sequence in which Asp (D) in the LfVk1_Ca sequence is substituted with Ala (A) after storage at 5° C. (solid line) or 50° C. (dotted line). After storage at 5° C., the highest peak in the chromatogram for each antibody is defined as a main peak, and the y axis of each ion-exchange chromatogram was normalized to the main peak.

Figure 18:
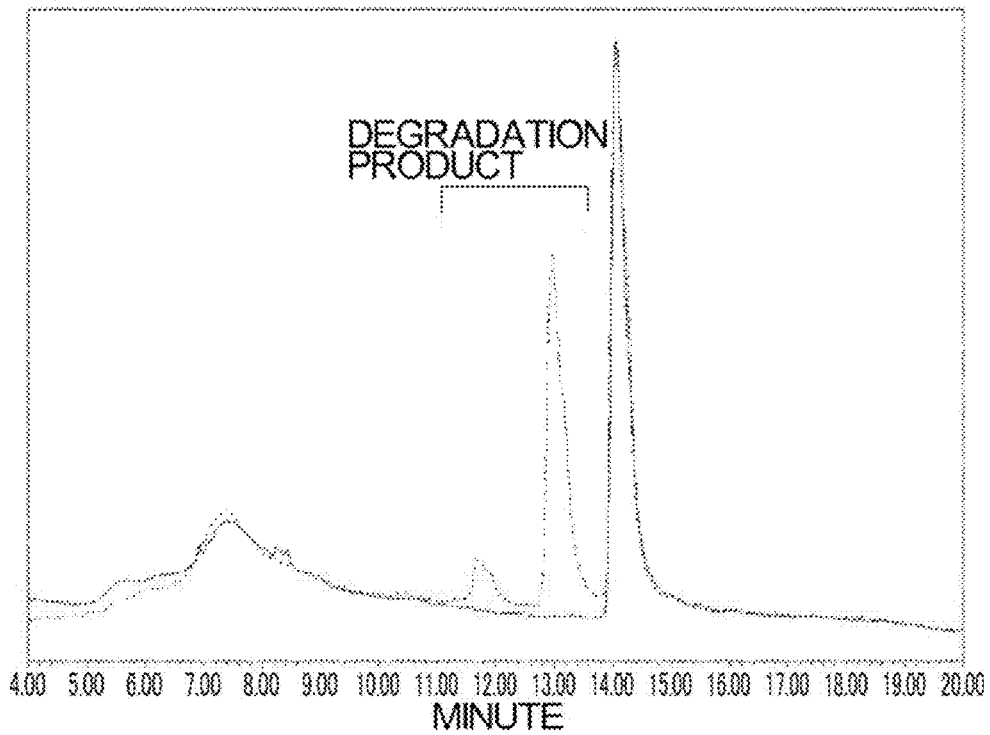
Figure 18:
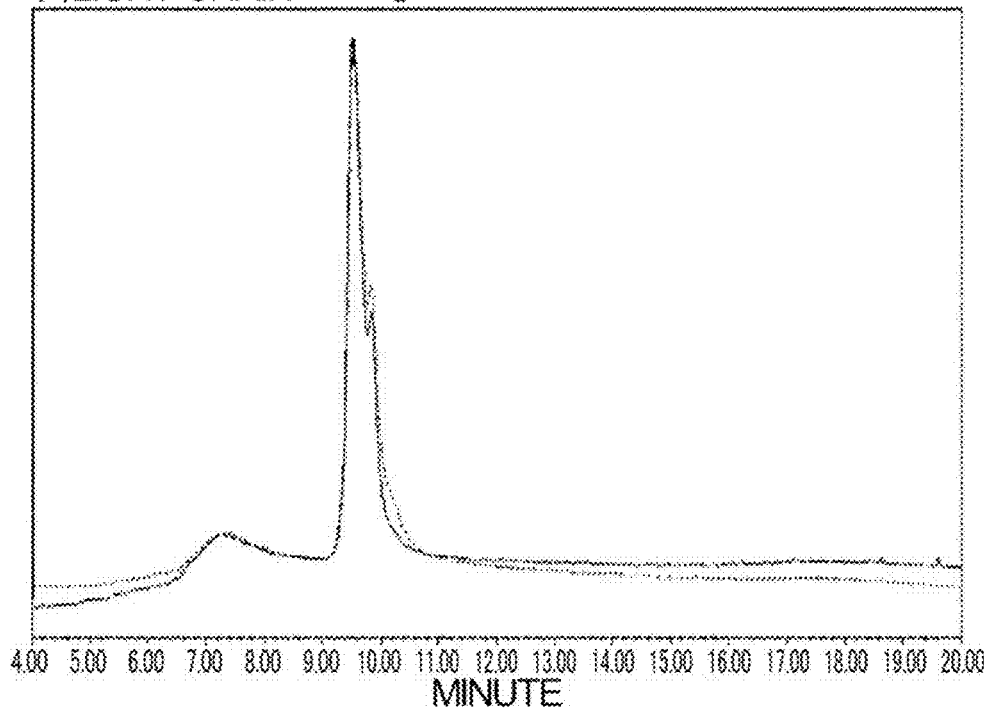

FIG. 18 shows ion-exchange chromatograms for an antibody having LfVk1_Ca sequence (heavy chain: GC_H, SEQ ID NO: 102; light chain: LfVk1_Ca, SEQ ID NO: 61) and an antibody having LfVk1_Ca6 sequence (heavy chain: GC_H, SEQ ID NO: 102; light chain: LfVk1_Ca6, SEQ ID NO: 75) in which Asp (D) at position 30 (Kabat's numbering system) in the LfVk1_Ca sequence is substituted with Ser (S) after storage at 5° C. (solid line) or 50° C. (dotted line). After storage at 5° C., the highest peak in the chromatogram for each antibody is defined as a main peak, and the y axis of each ion-exchange chromatogram was normalized to the main peak.

Figure 19:
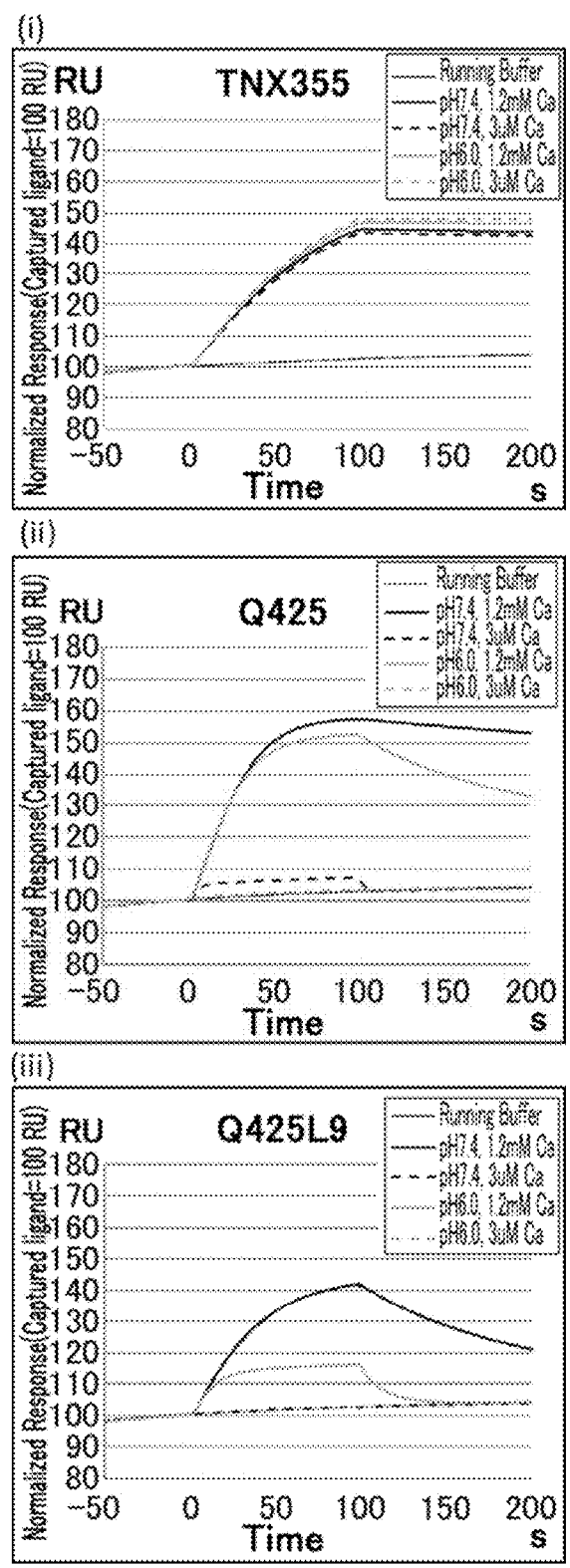

FIG. 19 presents Biacore™ sensorgrams showing the interaction of anti-human CD4 antibodies with soluble human CD4 under the conditions of ($Ca^{2+}$ 1.2 mM) and ($Ca^{2+}$ 3 μM).

Figure 20:
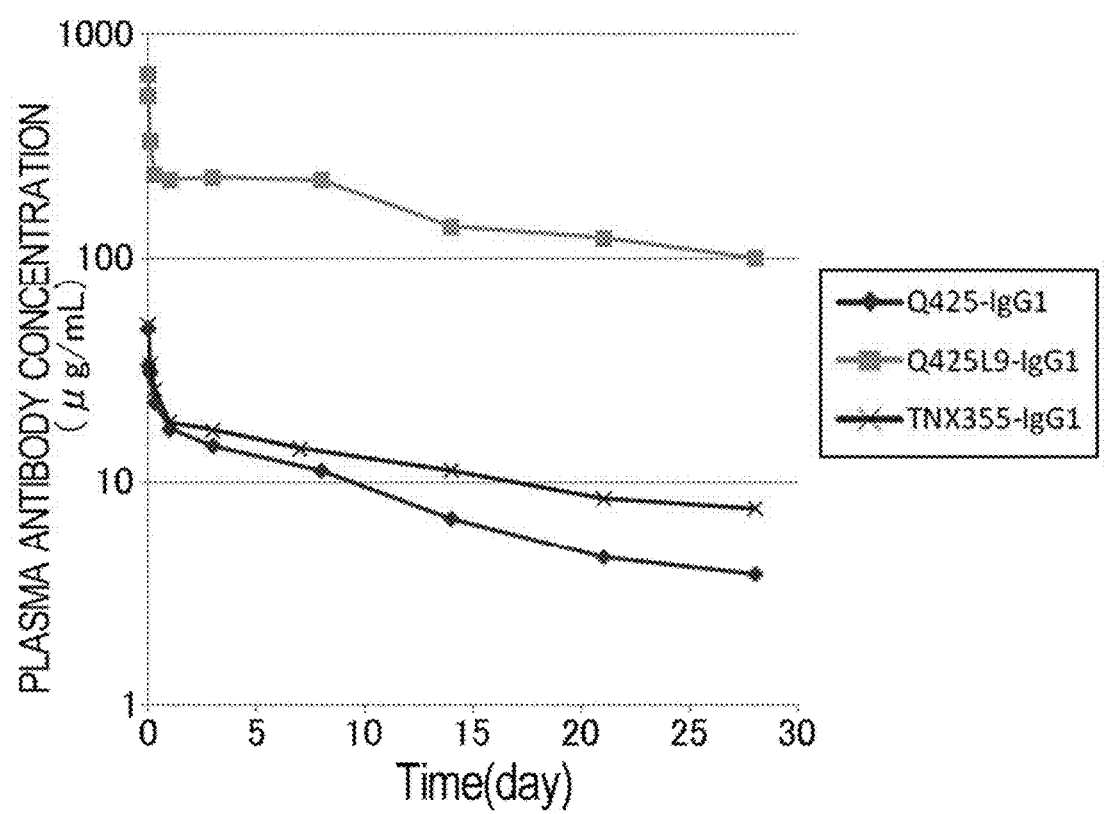

FIG. 20 describes a time course of the plasma concentration of anti-human CD4 antibodies in normal mice.

Figure 21:
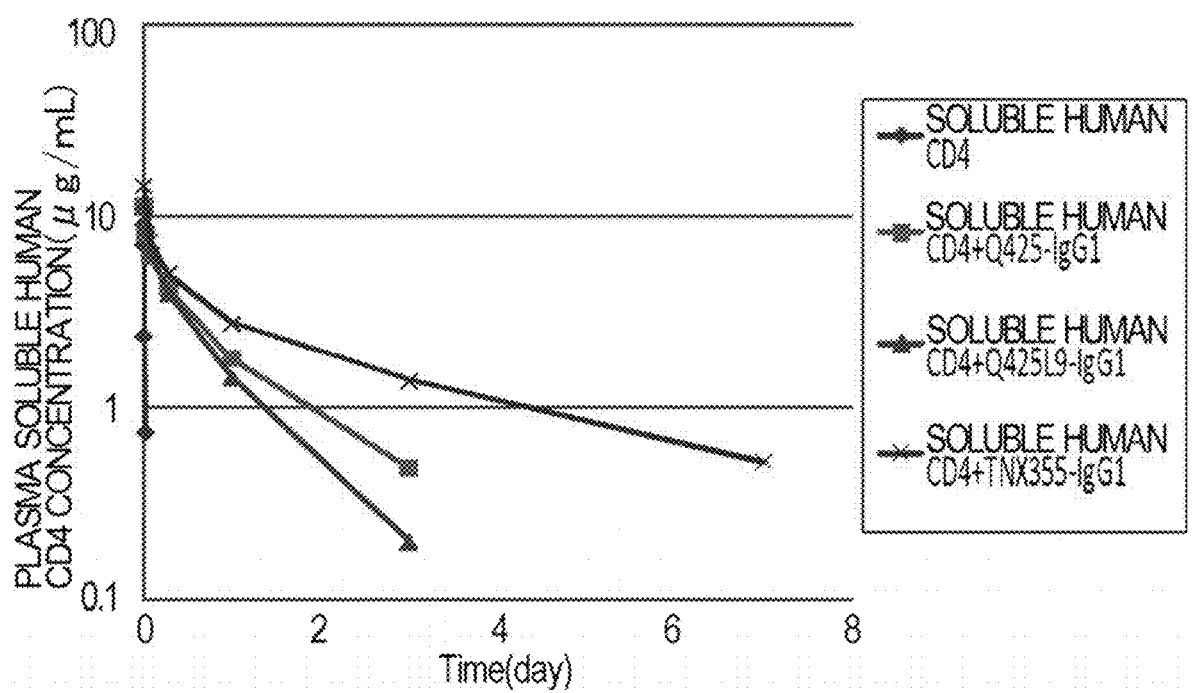

FIG. 21 describes a time course of the plasma concentration of soluble human CD4 in the group administered with soluble human CD4 alone, the antibody TNX355-IgG1-administered group, the antibody Q425-administered group, and the antibody Q425L9-administered group of normal mice.

Figure 22:
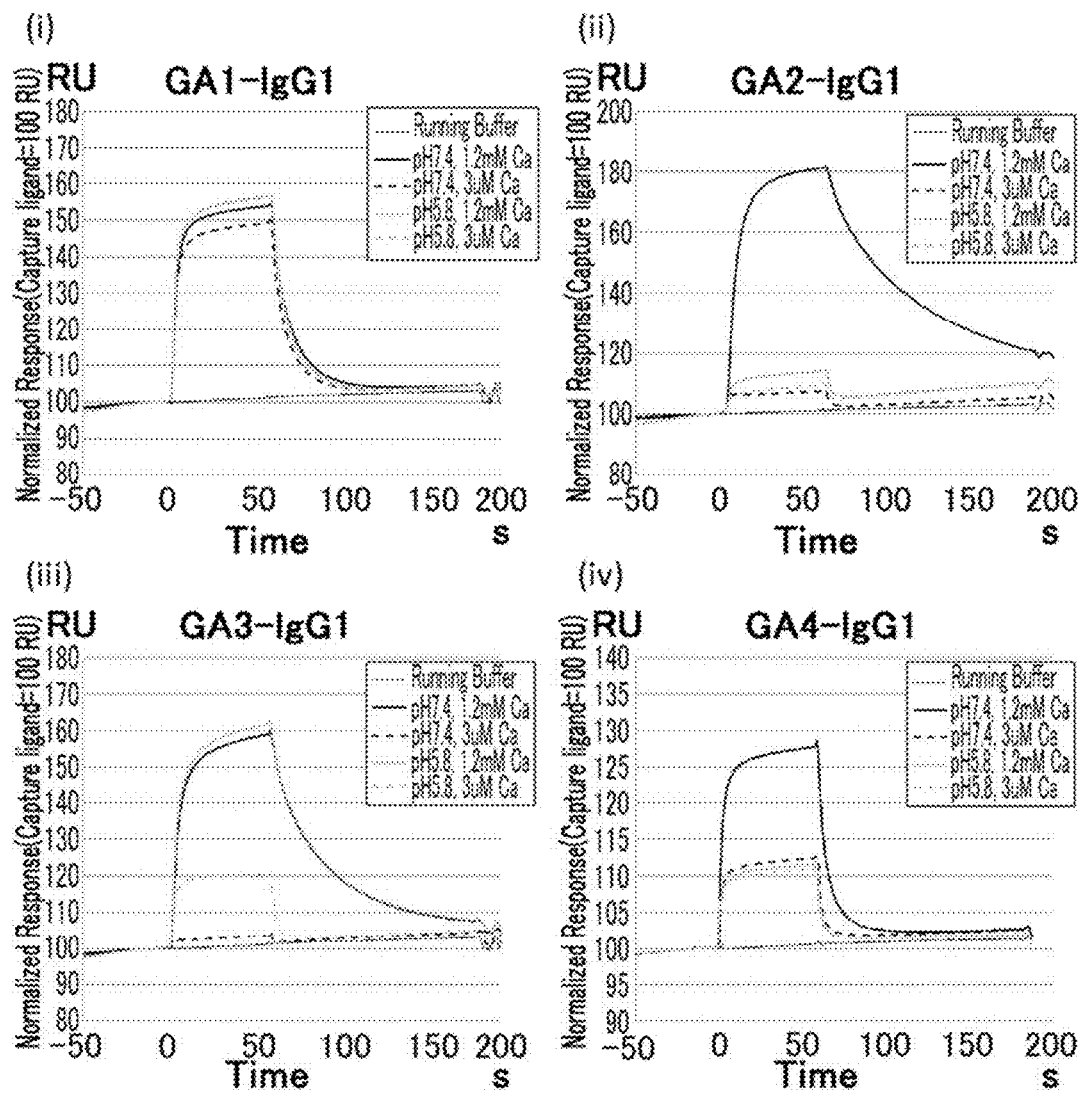

FIG. 22 presents Biacore™ sensorgrams showing the interaction of anti-human IgA antibodies with human IgA under the conditions of ($Ca^{2+}$ 1.2 mM) and ($Ca^{2+}$ 3 μM).

Figure 23:
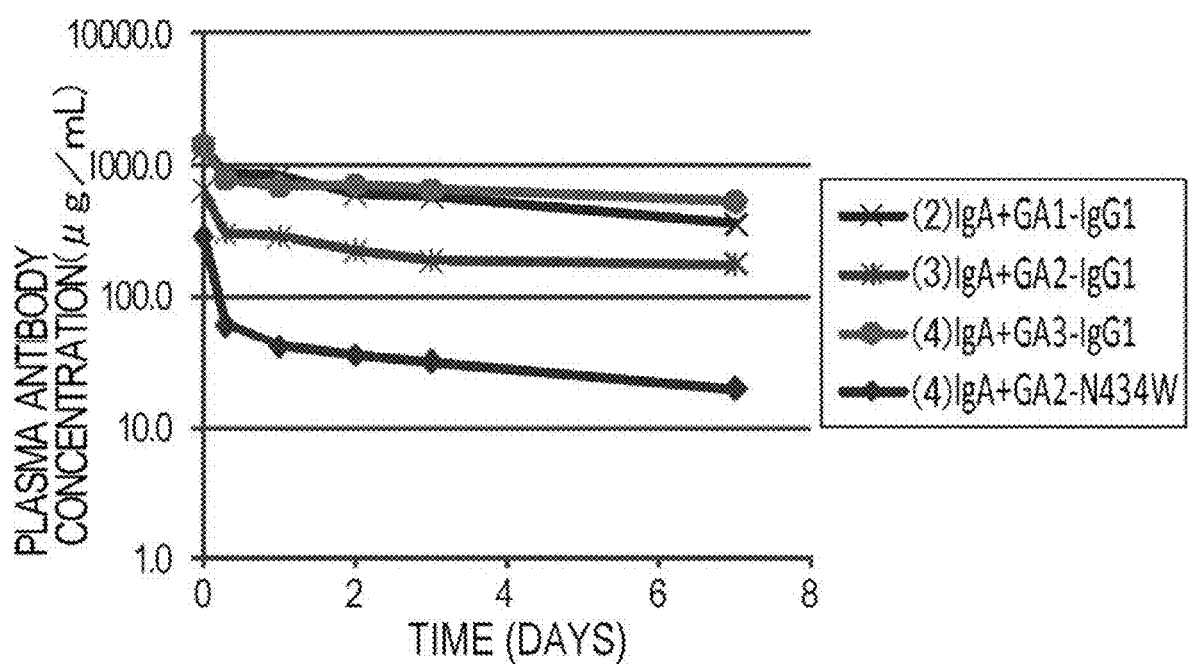

FIG. 23 describes a time course of plasma antibody concentrations in normal mice for the antibody GA1-IgG1-administered group, the antibody GA2-IgG1-administered group, the antibody GA3-IgG1-administered group, and the GA2-N434W-administered group.

Figure 24:
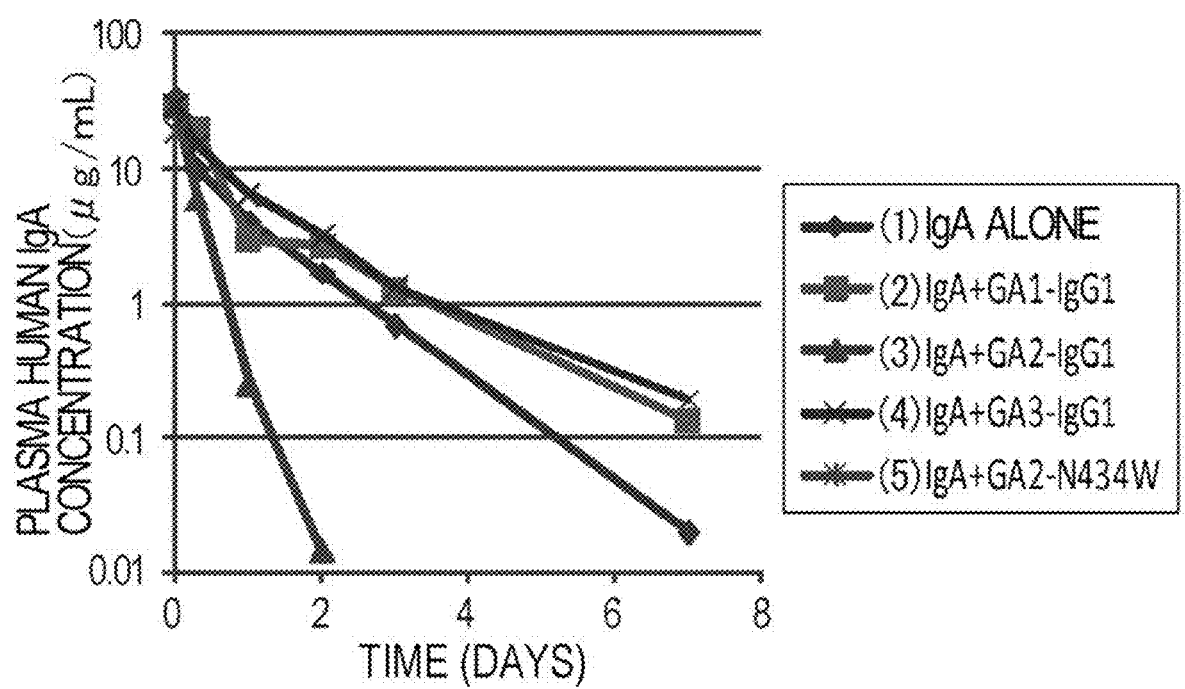

FIG. 24 describes a time course of the plasma human IgA concentration in normal mice for the group administered with human IgA alone, the antibody GA1-IgG1-administered group, the antibody GA2-IgG1-administered group, the antibody GA3-IgG1-administered group, and the antibody GA2-N434W-administered group.

Figure 25:
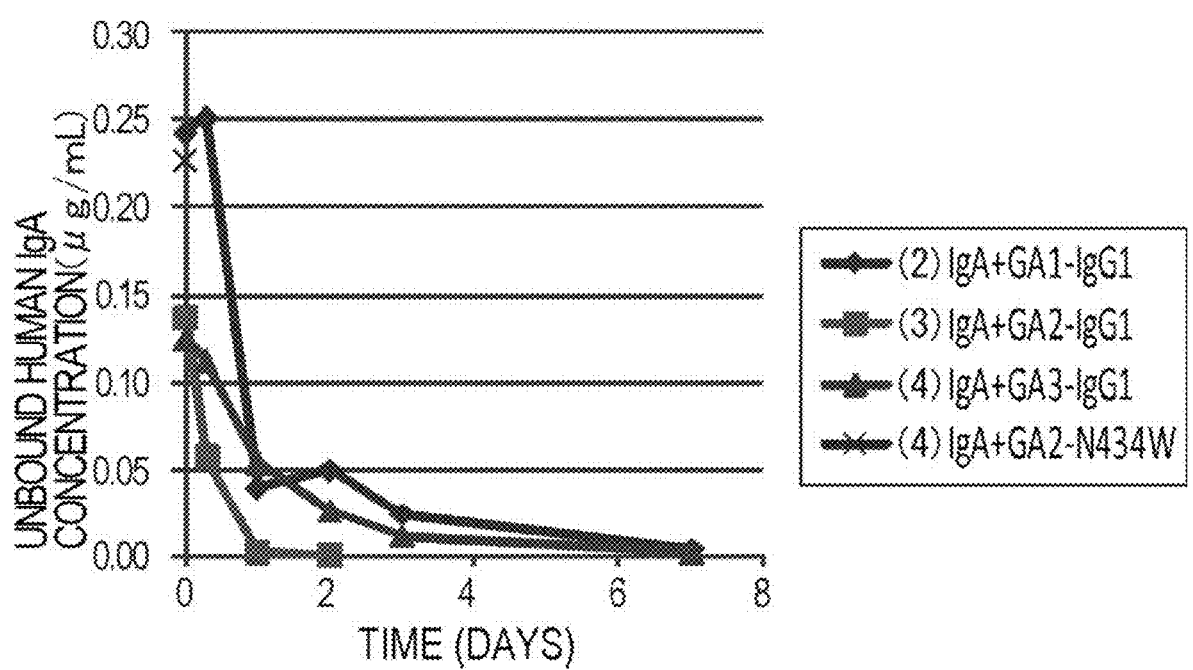

FIG. 25 describes a time course of the plasma concentration of unbound human IgA in normal mice for the antibody GA1-IgG1-administered group, the antibody GA2-IgG1-administered group, the antibody GA3-IgG1-administered group, and the antibody GA2-N434W-administered group.

Figure 26:
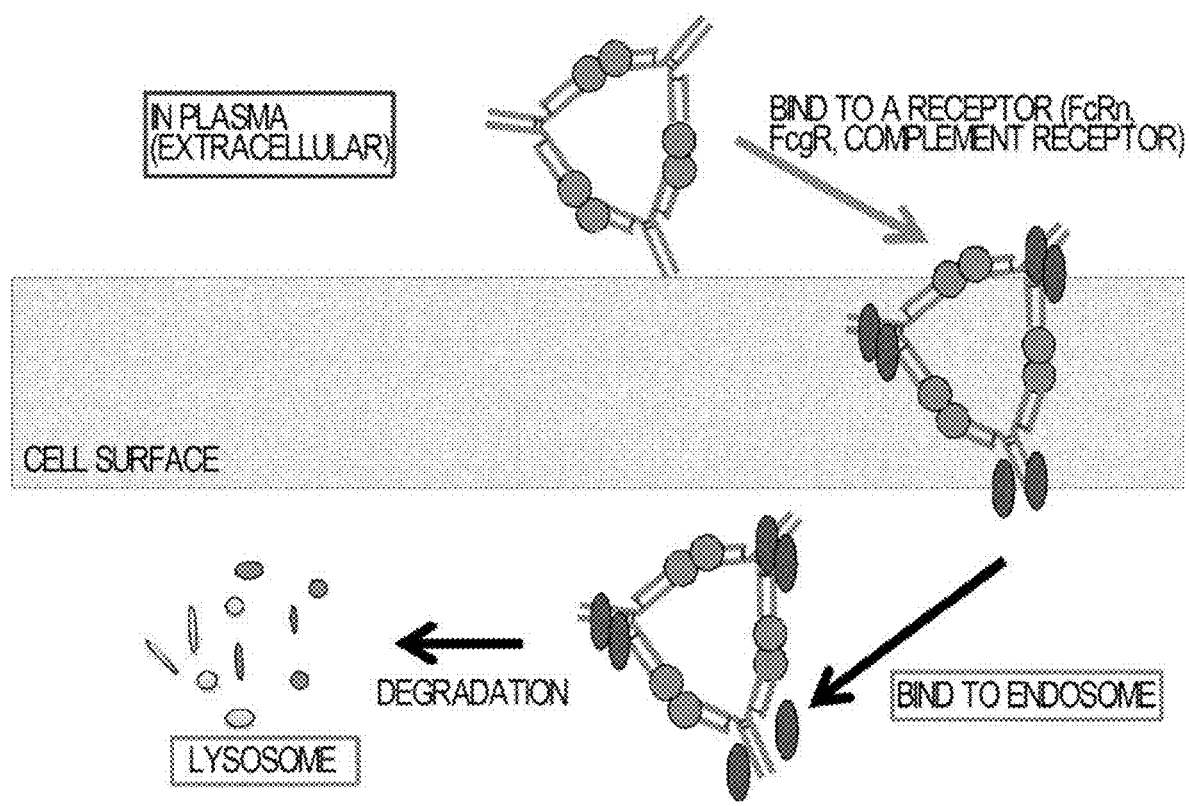

FIG. 26 is an illustrative diagram showing the efficiency of antigen elimination per antibody molecule for a general antibody that forms a large immune complex with a multimeric antigen.

Figure 27:
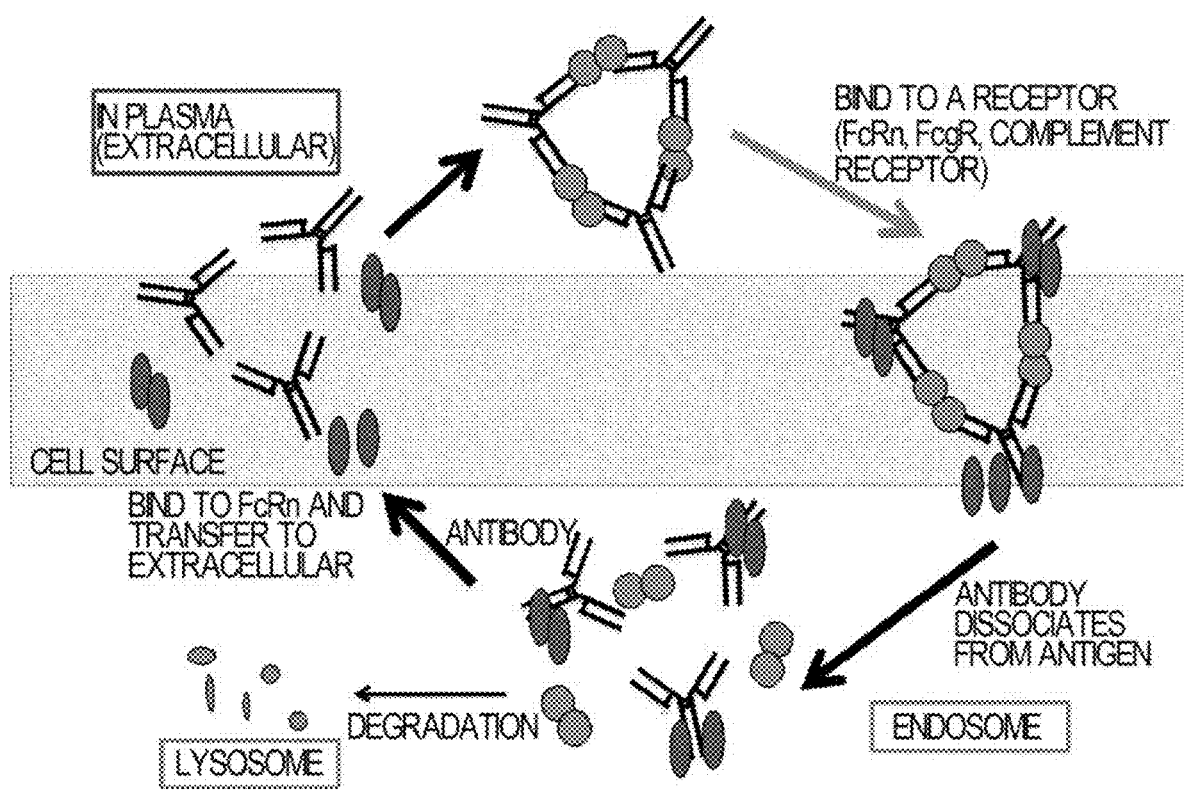

FIG. 27 is an illustrative diagram showing the efficiency of antigen elimination per antibody molecule for a pH/Ca-dependent antibody having the constant region of natural IgG1 which forms a large immune complex with a multimeric antigen.

Figure 28:
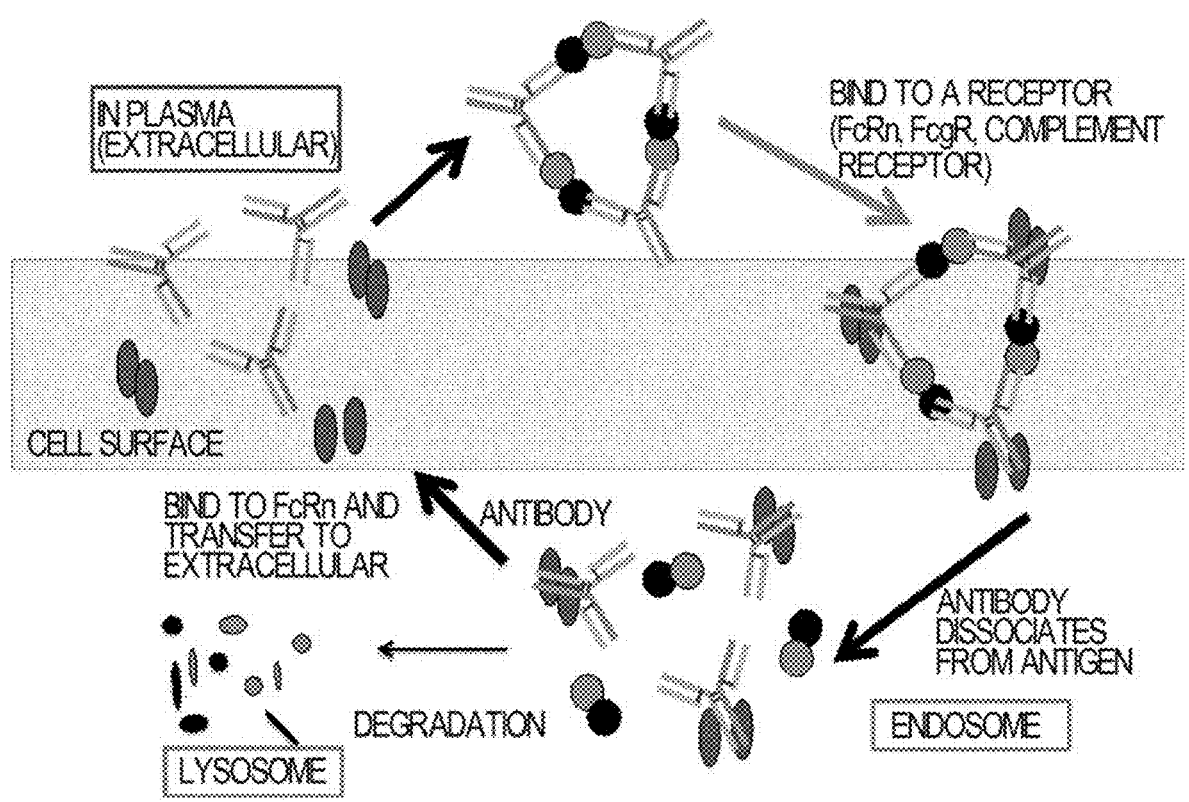

FIG. 28 is an illustrative diagram showing the efficiency of antigen elimination per antibody molecule for a pH/Ca-dependent multispecific antibody that recognizes two or more epitopes in a monomeric antigen and is suitable for formation of a large immune complex.

Figure 29:
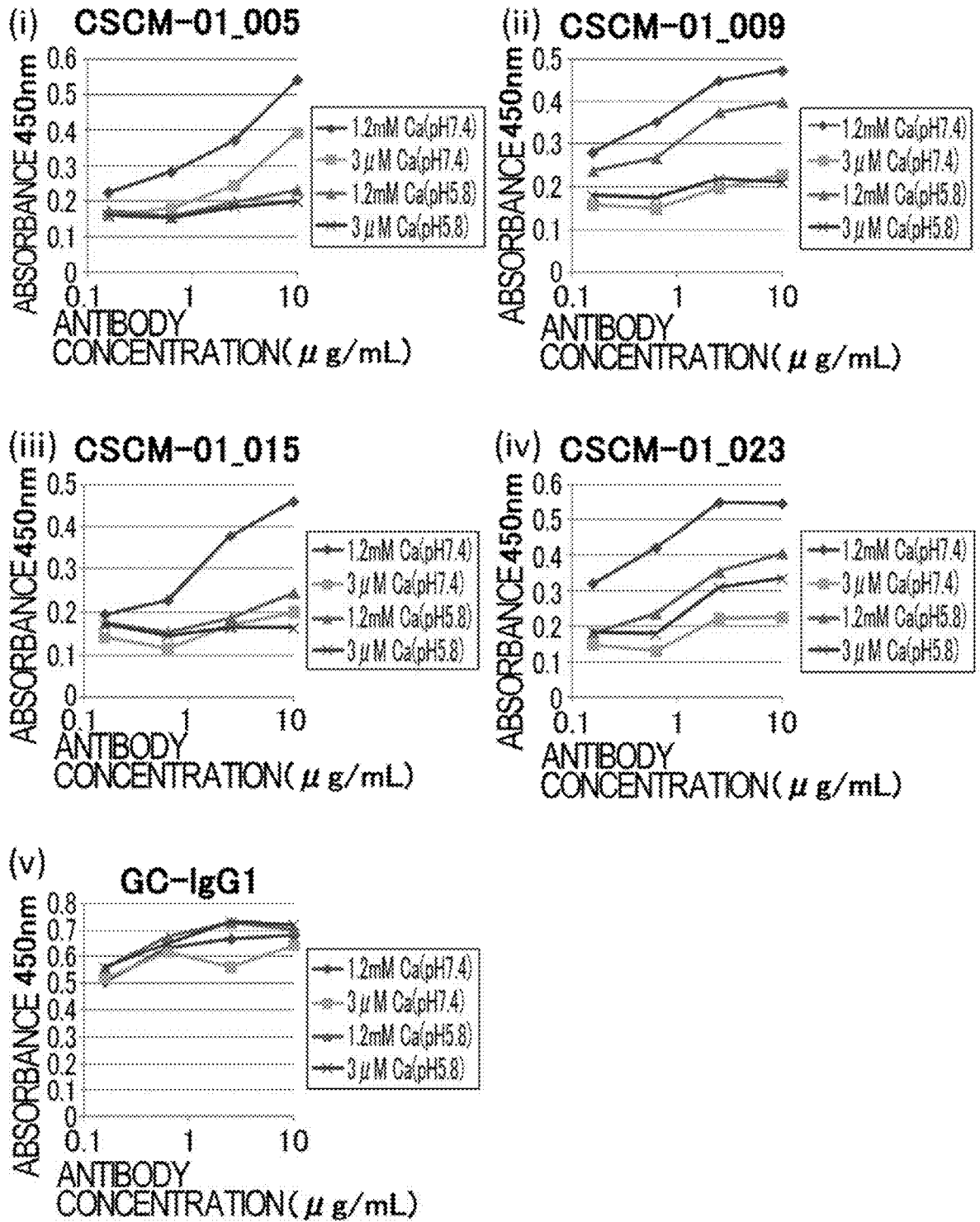

FIG. 29 describes the interaction of anti-human glypican 3 antibodies with recombinant human glypican 3 under the conditions of ($Ca^{2+}$ 1.2 mM) and ($Ca^{2+}$ 3 μM) by ELISA.

Figure 30:
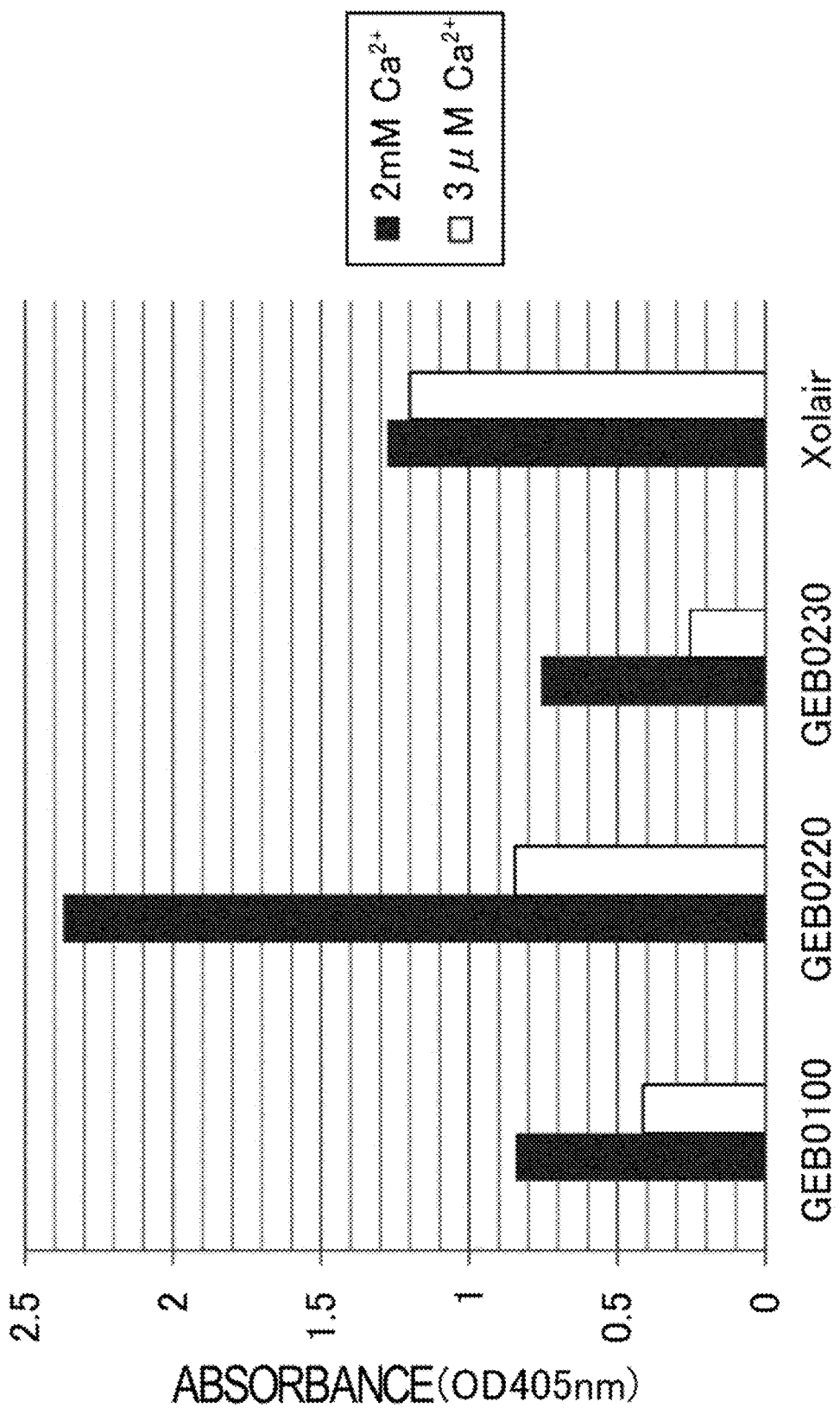

FIG. 30 describes the interaction of anti-human IgE antibodies with recombinant human IgE under the conditions of ($Ca^{2+}$ 2 mM) and ($Ca^{2+}$ 3 μM) by ELISA.

Figure 31:
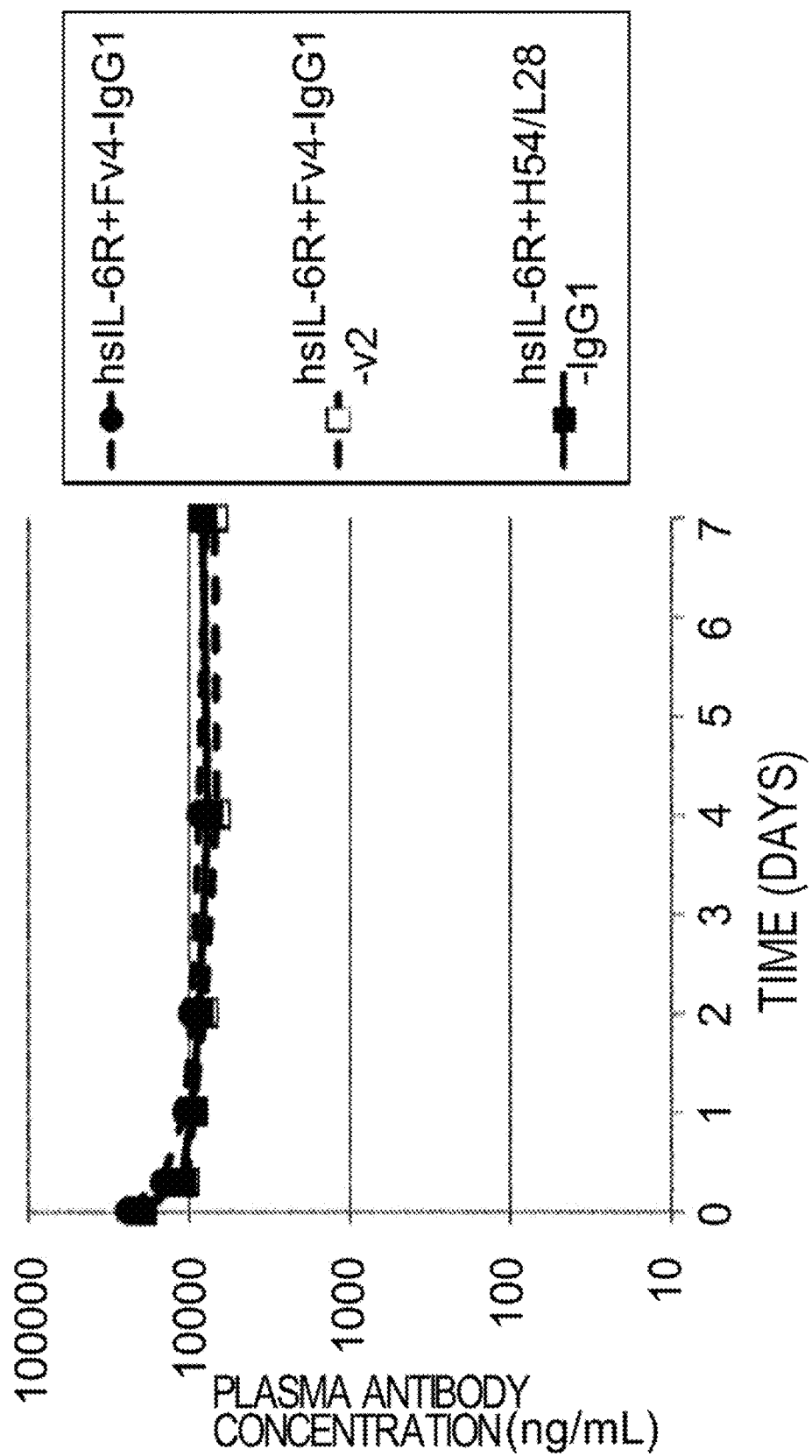

FIG. 31 describes a time course of plasma antibody concentrations in human FcRn transgenic mice.

Figure 32:
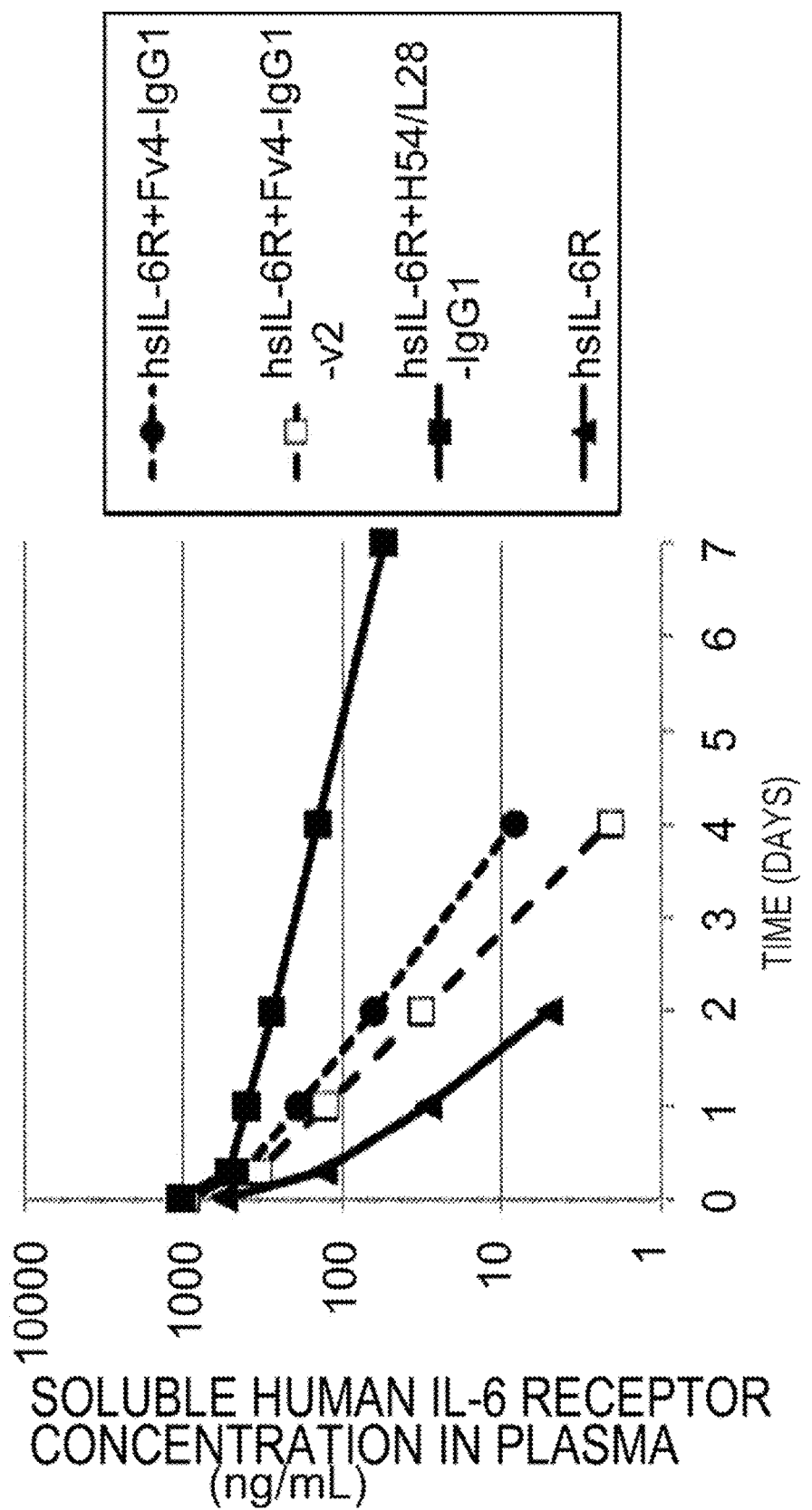

FIG. 32 describes a time course of the plasma concentration of soluble human IL-6 receptor in human FcRn transgenic mice.

Figure 33:
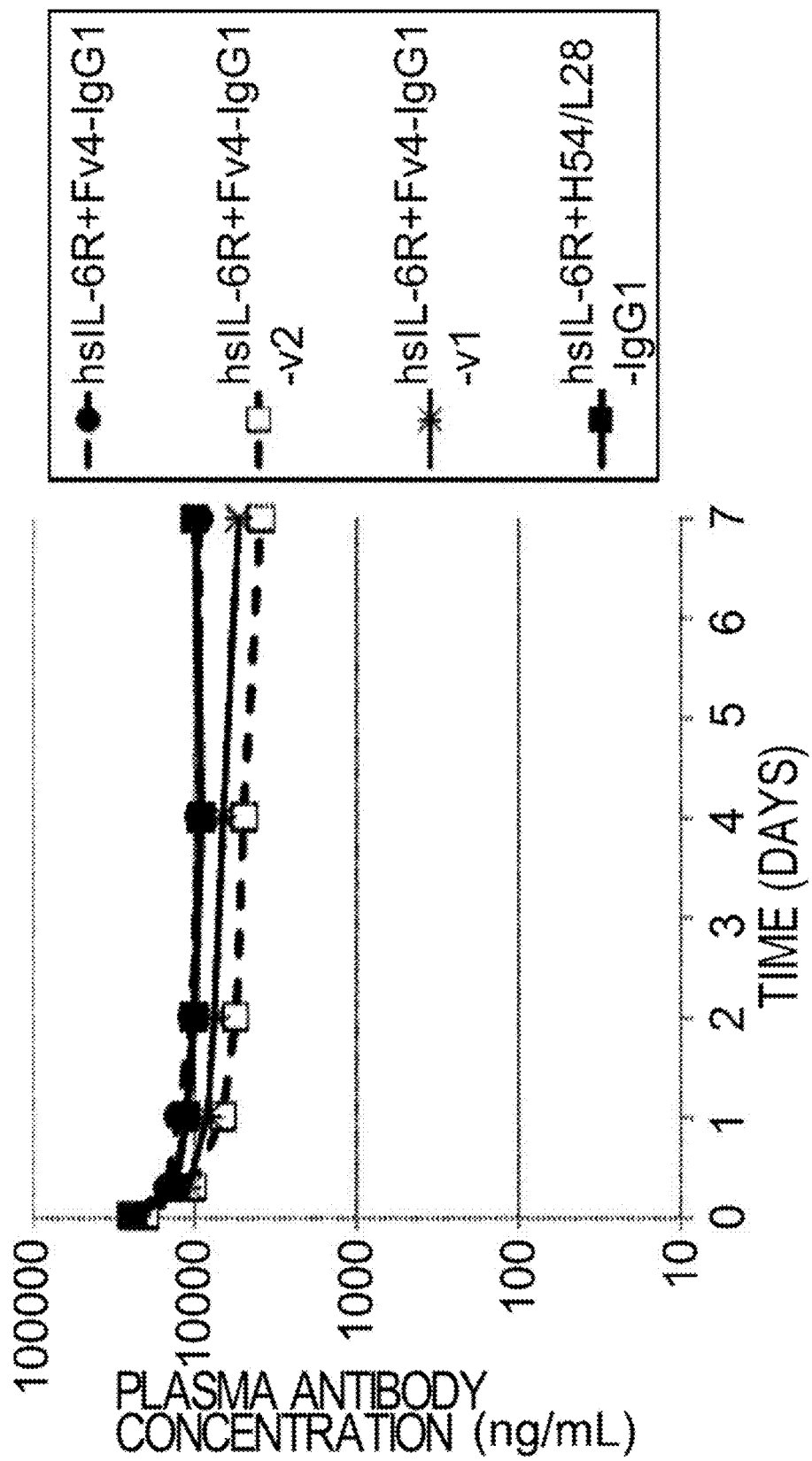

FIG. 33 describes a time course of plasma antibody concentrations in normal mice.

Figure 34:
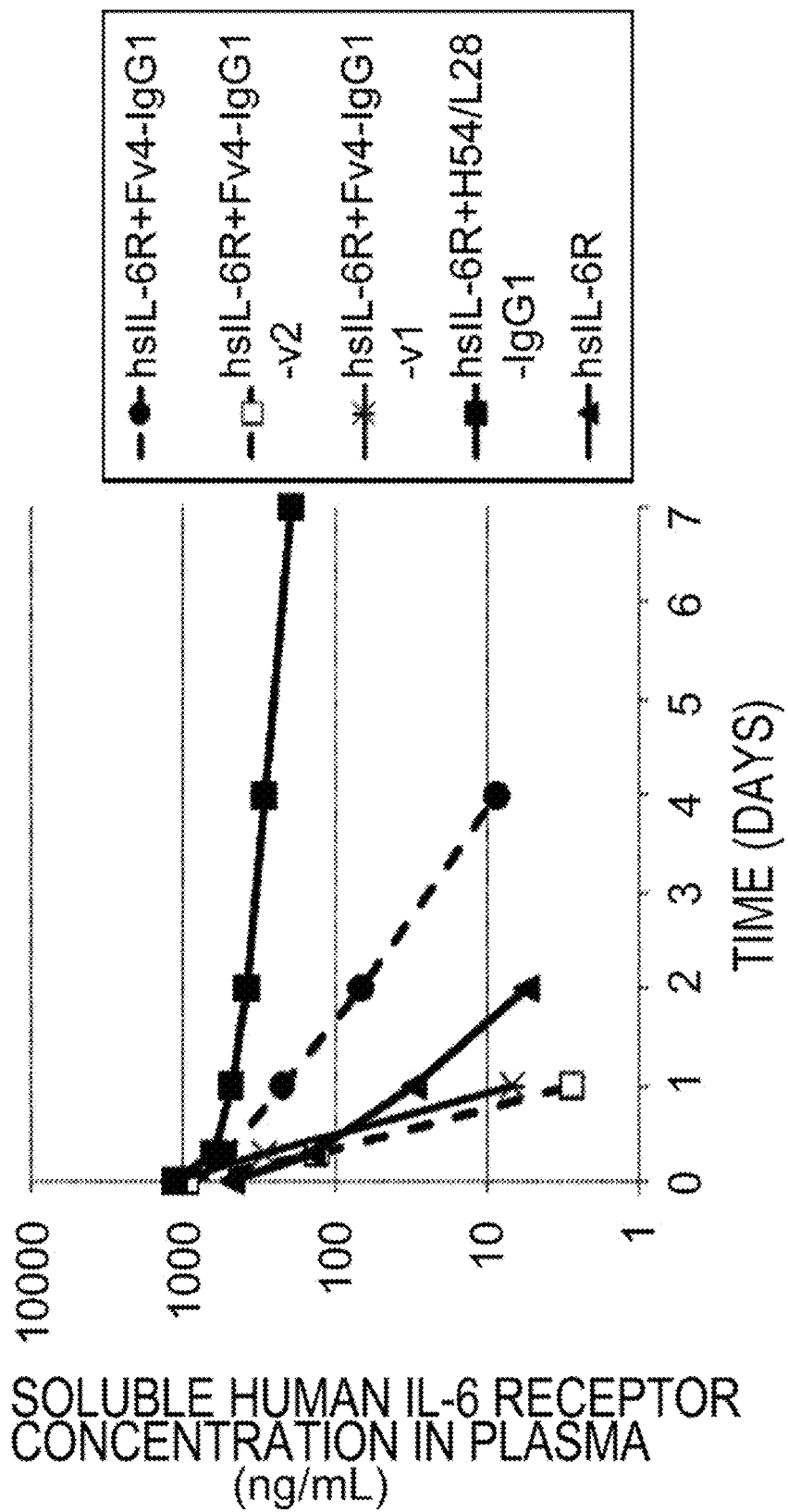

FIG. 34 describes a time course of the plasma concentration of soluble human IL-6 receptor in normal mice.

Figure 35:
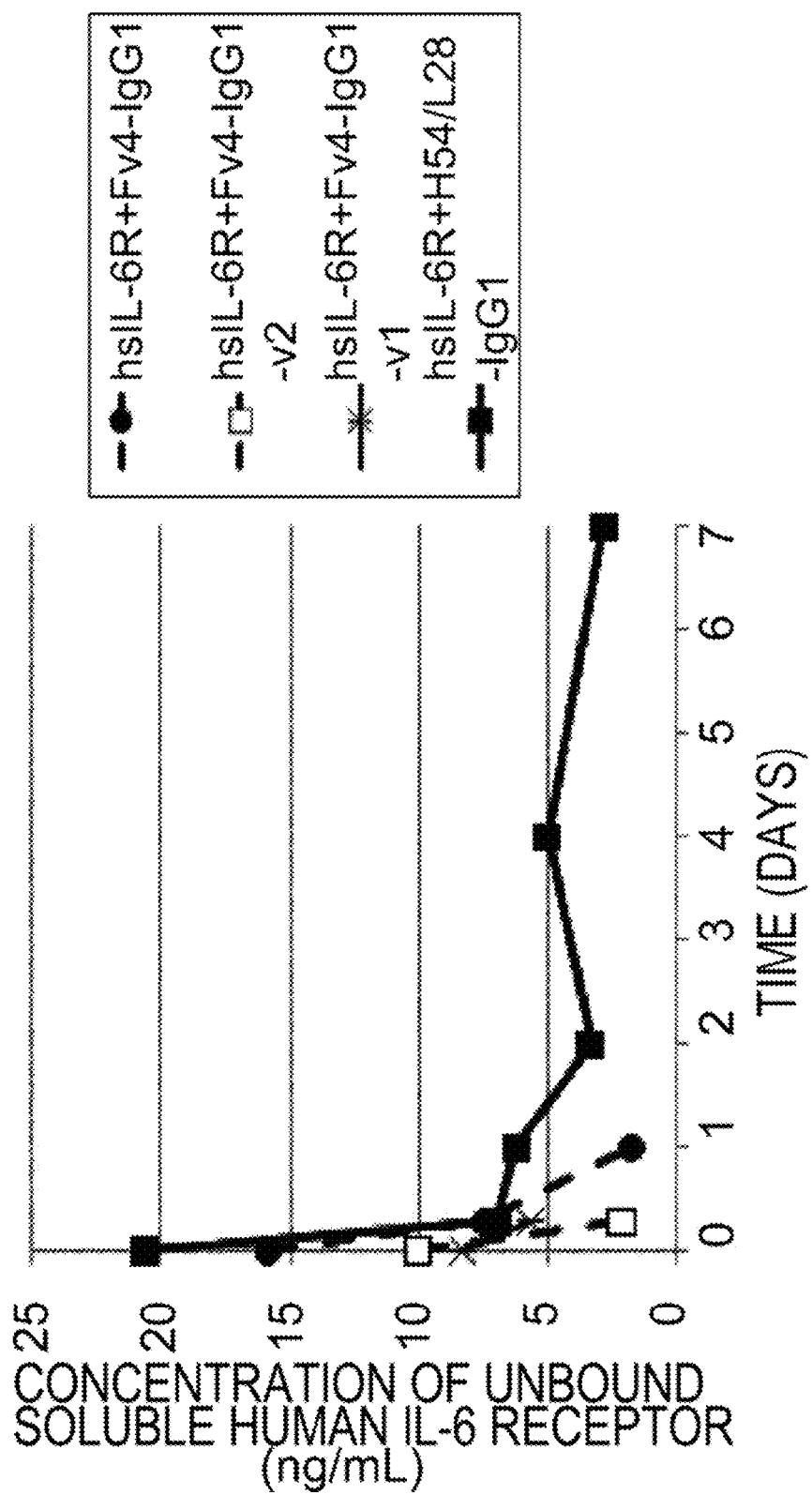

FIG. 35 describes a time course of the plasma concentration of unbound soluble human IL-6 receptor in normal mice.

Figure 36:
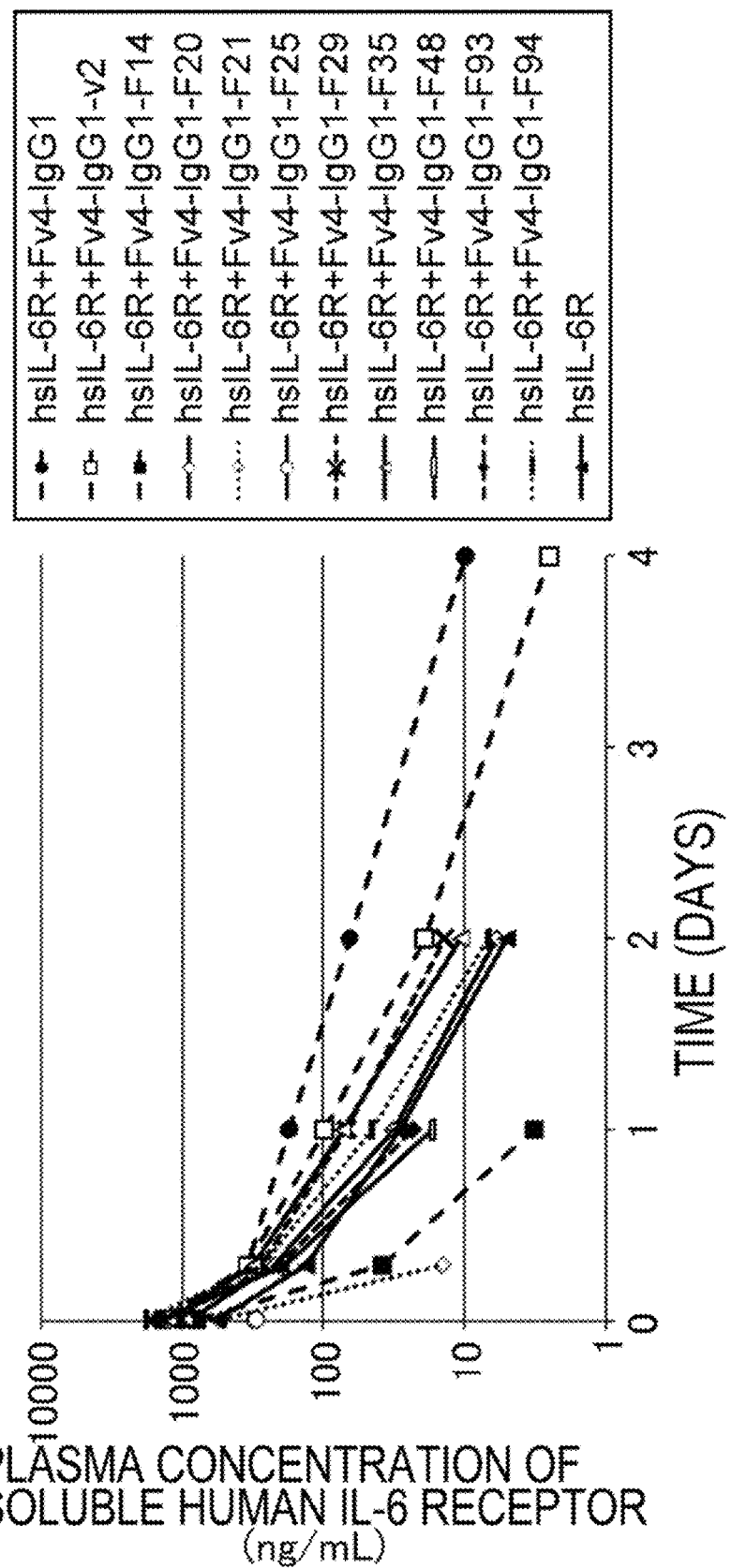

FIG. 36 describes a time course of the plasma concentration of soluble human IL-6 receptor in human FcRn transgenic mice.

Figure 37:
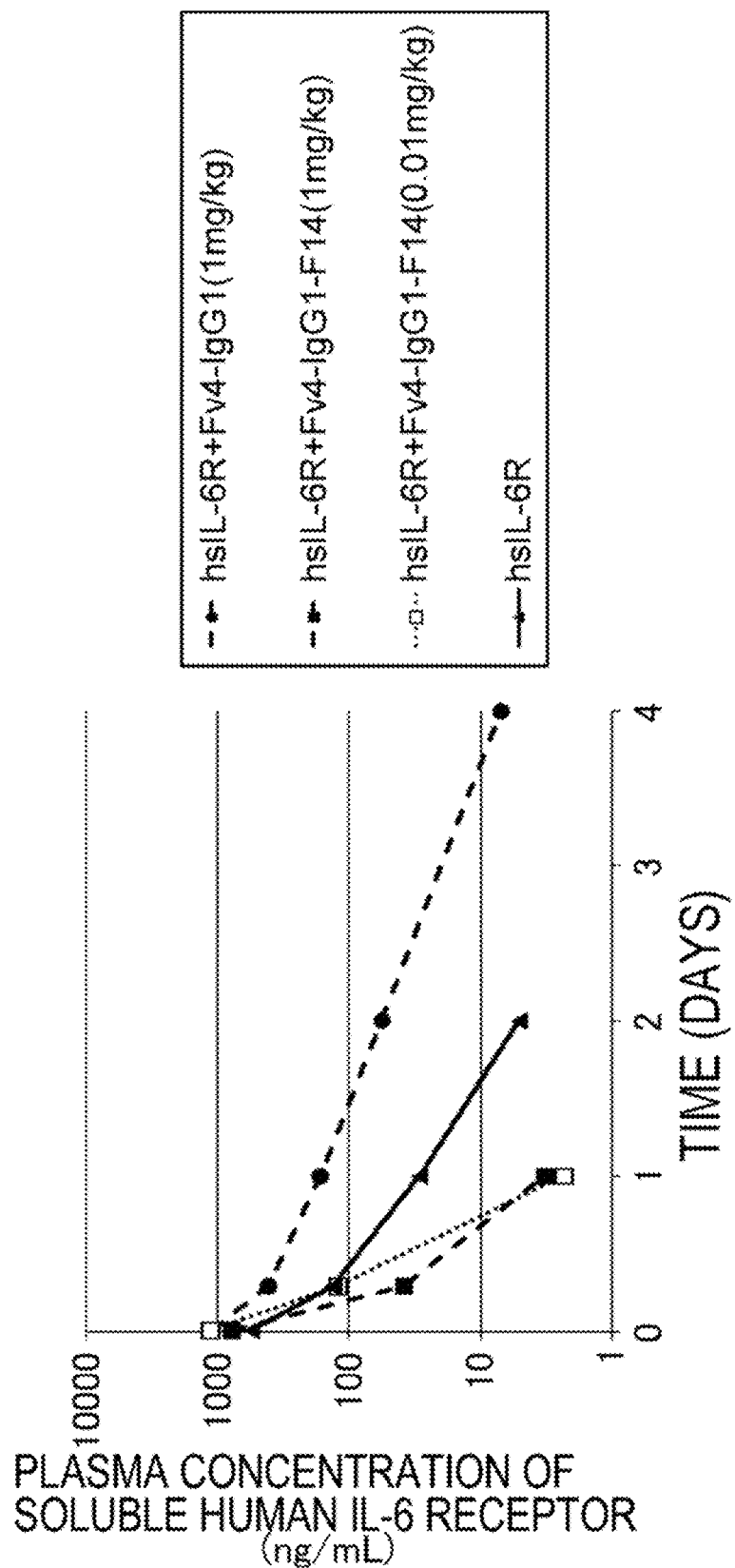

FIG. 37 describes a time course of the plasma concentration of soluble human IL-6 receptor after administration of Fv4-IgG1-F14 at a lower dose (0.01 mg/kg) or 1 mg/kg.

Figure 38:
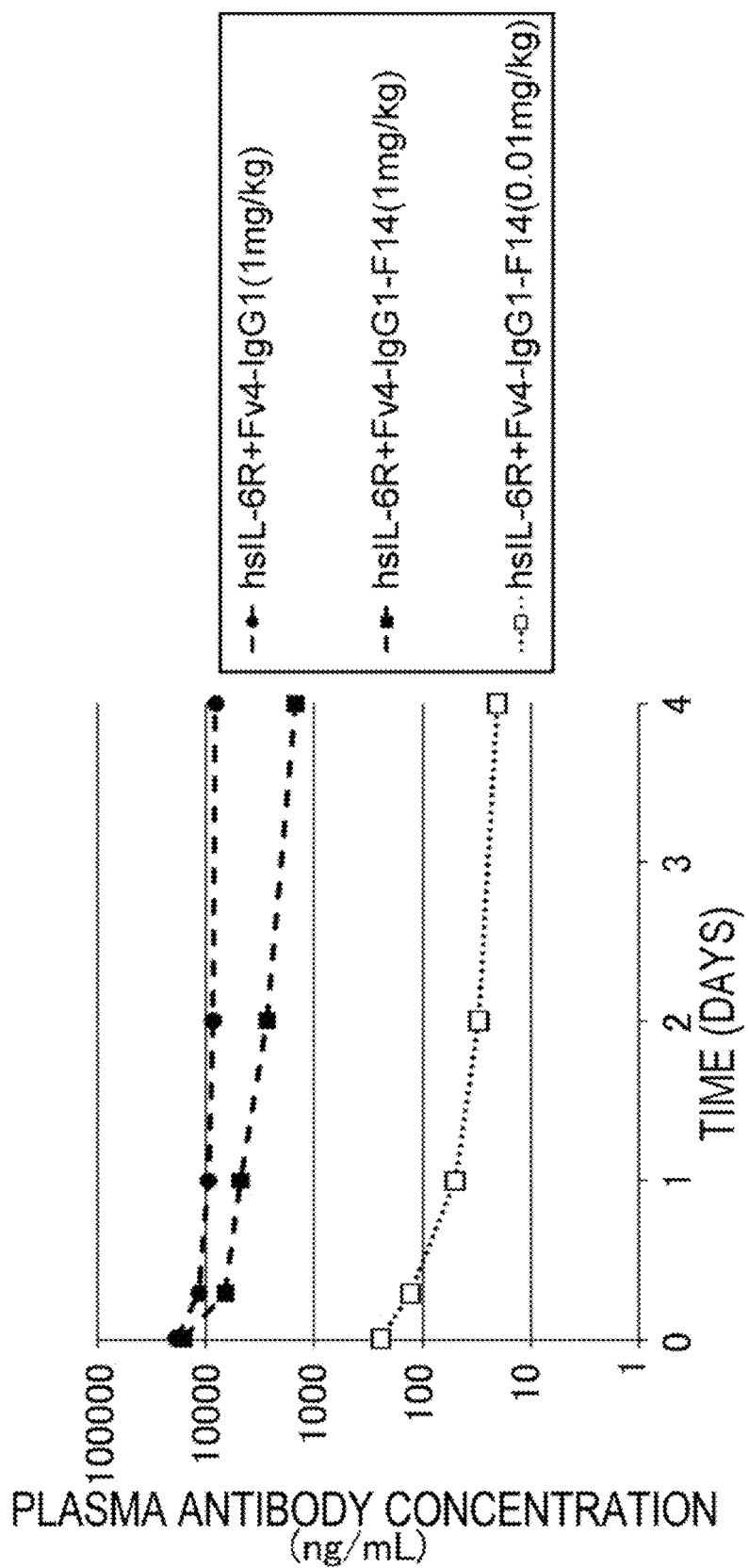

FIG. 38 describes a time course of plasma antibody concentrations after administration of Fv4-IgG1-F14 at a lower dose (0.01 mg/kg) or 1 mg/kg.

Figure 39:
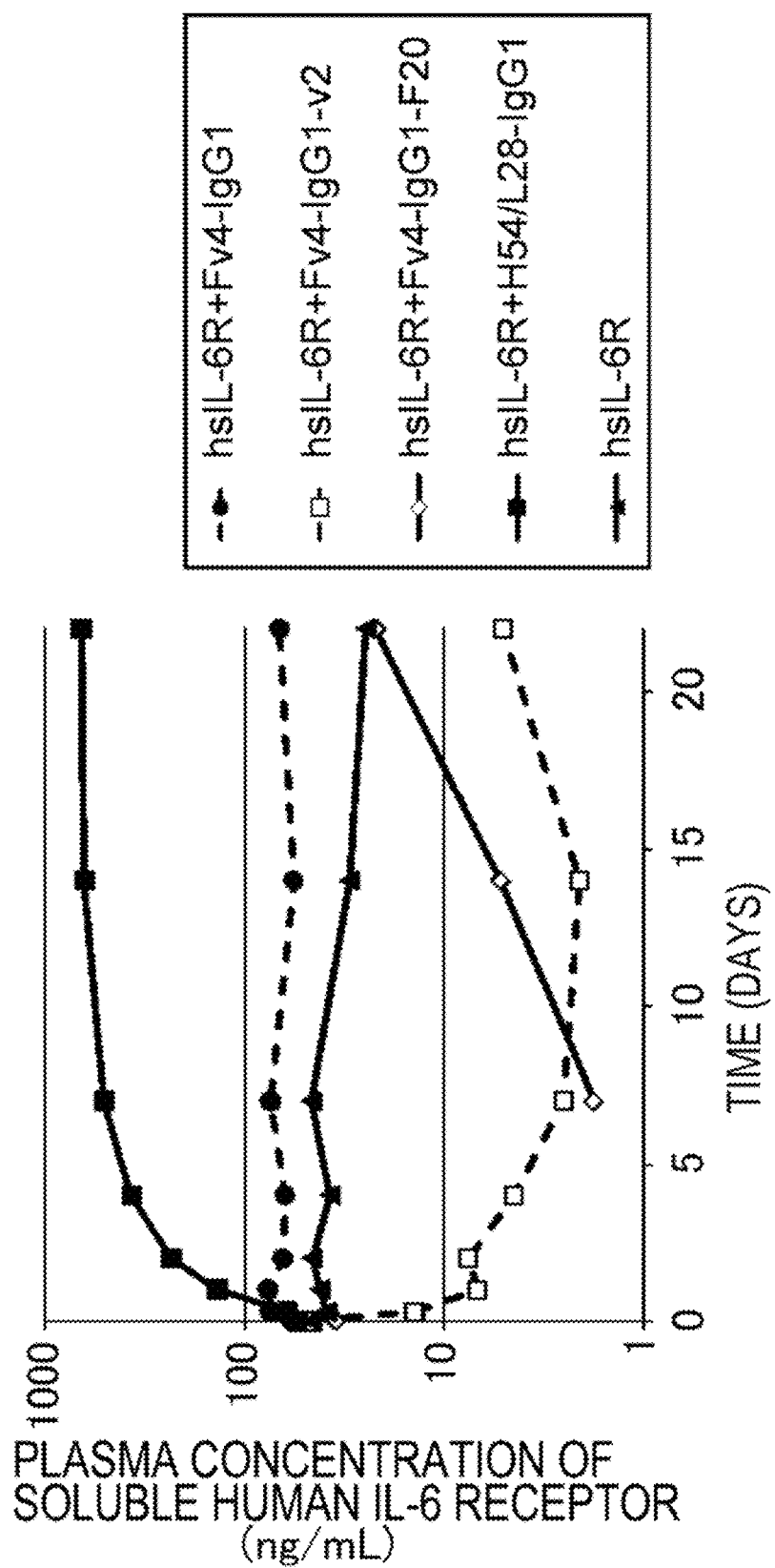

FIG. 39 describes a time course of the plasma concentration of soluble human IL-6 receptor after administration of anti-human IL-6 receptor antibodies to normal mice in which the plasma concentration of soluble human IL-6 receptor is constant.

Figure 40:
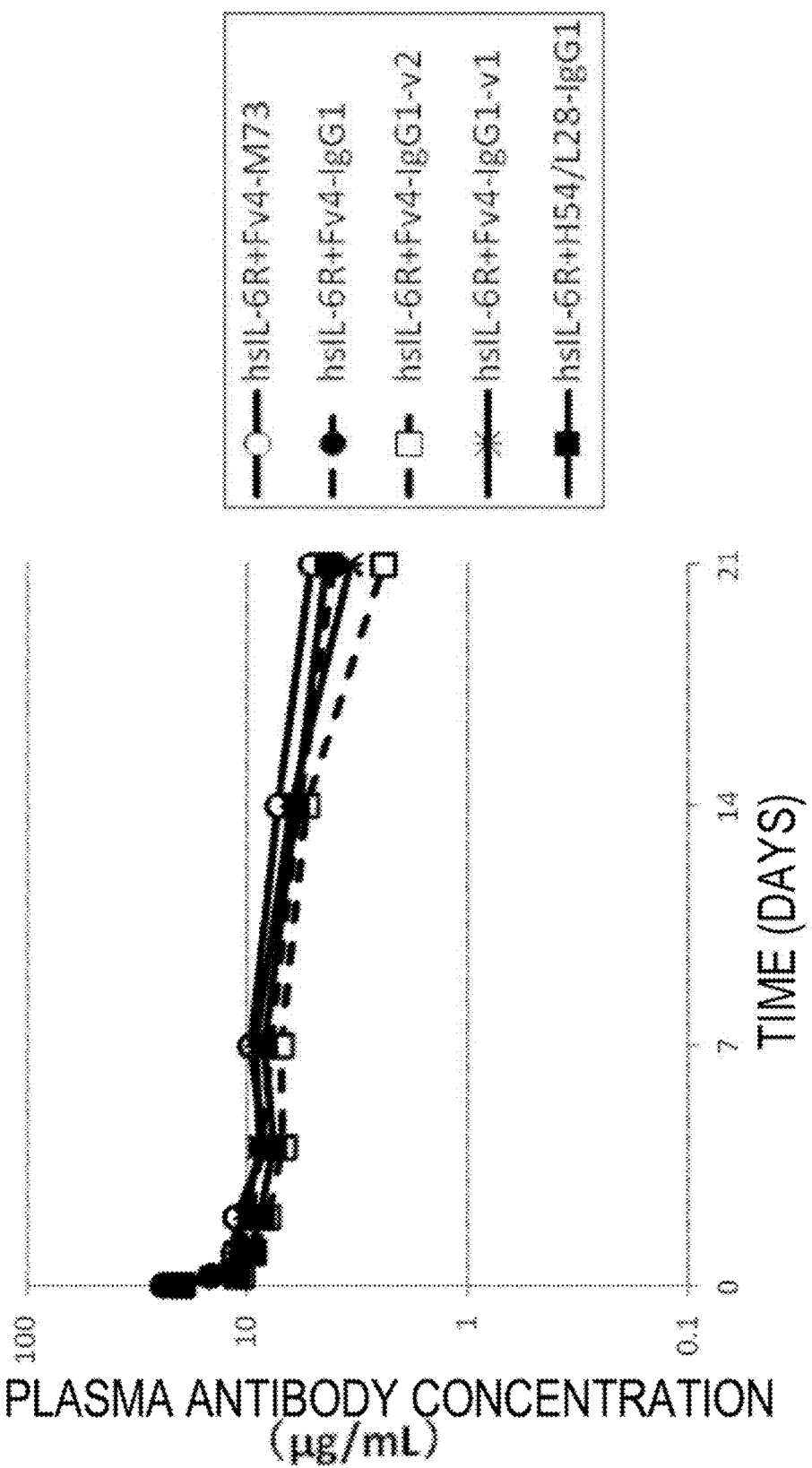

FIG. 40 describes a time course of plasma antibody concentration after co-administration of hsIL-6R and an anti-human IL-6 receptor antibody to human FcRn transgenic mice (lineage 276).

Figure 41:
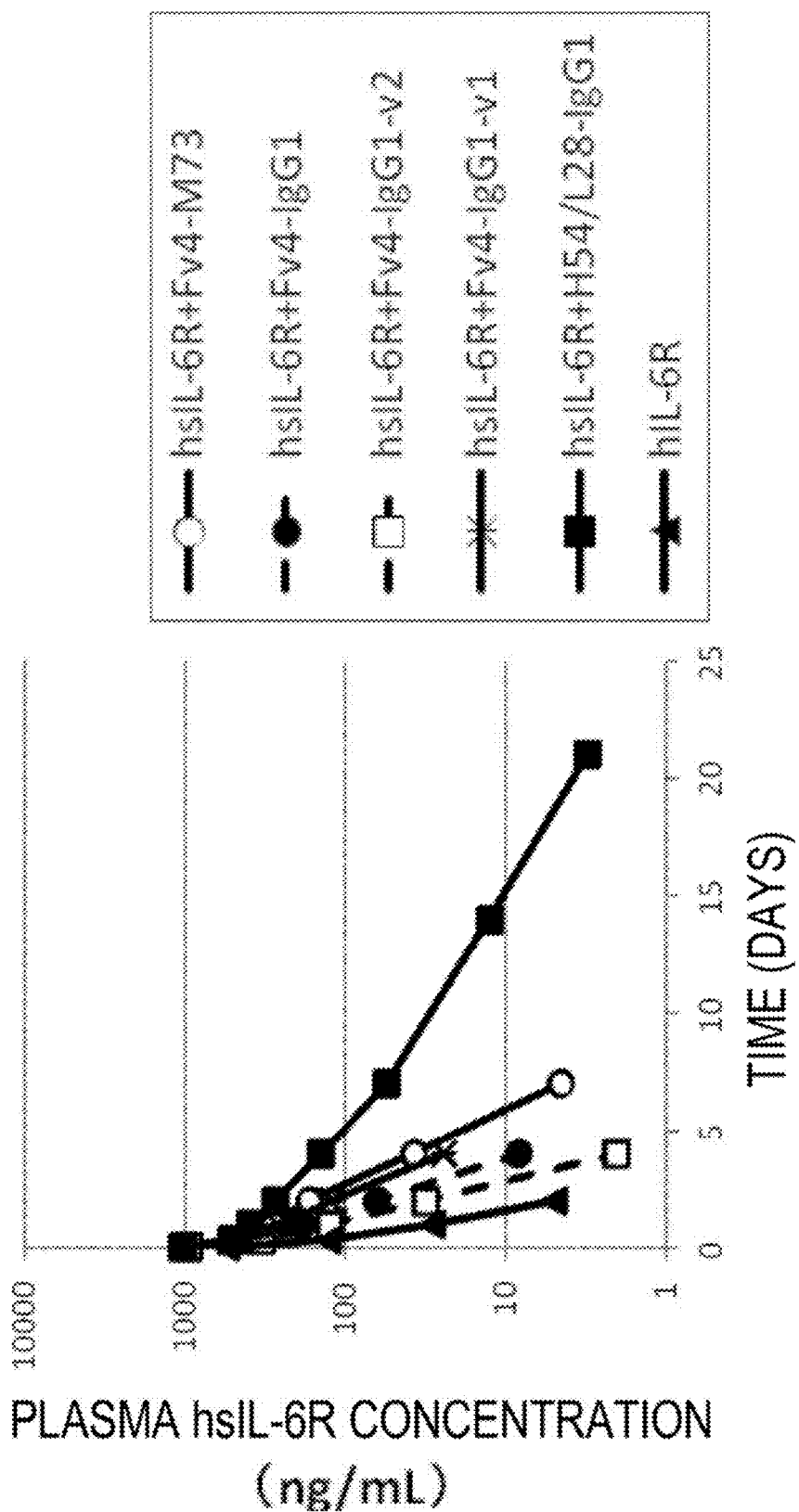

FIG. 41 describes a time course of the plasma concentration of soluble human IL-6 receptor after co-administration of hsIL-6R and an anti-human IL-6 receptor antibody to human FcRn transgenic mice (lineage 276).

Figure 42:
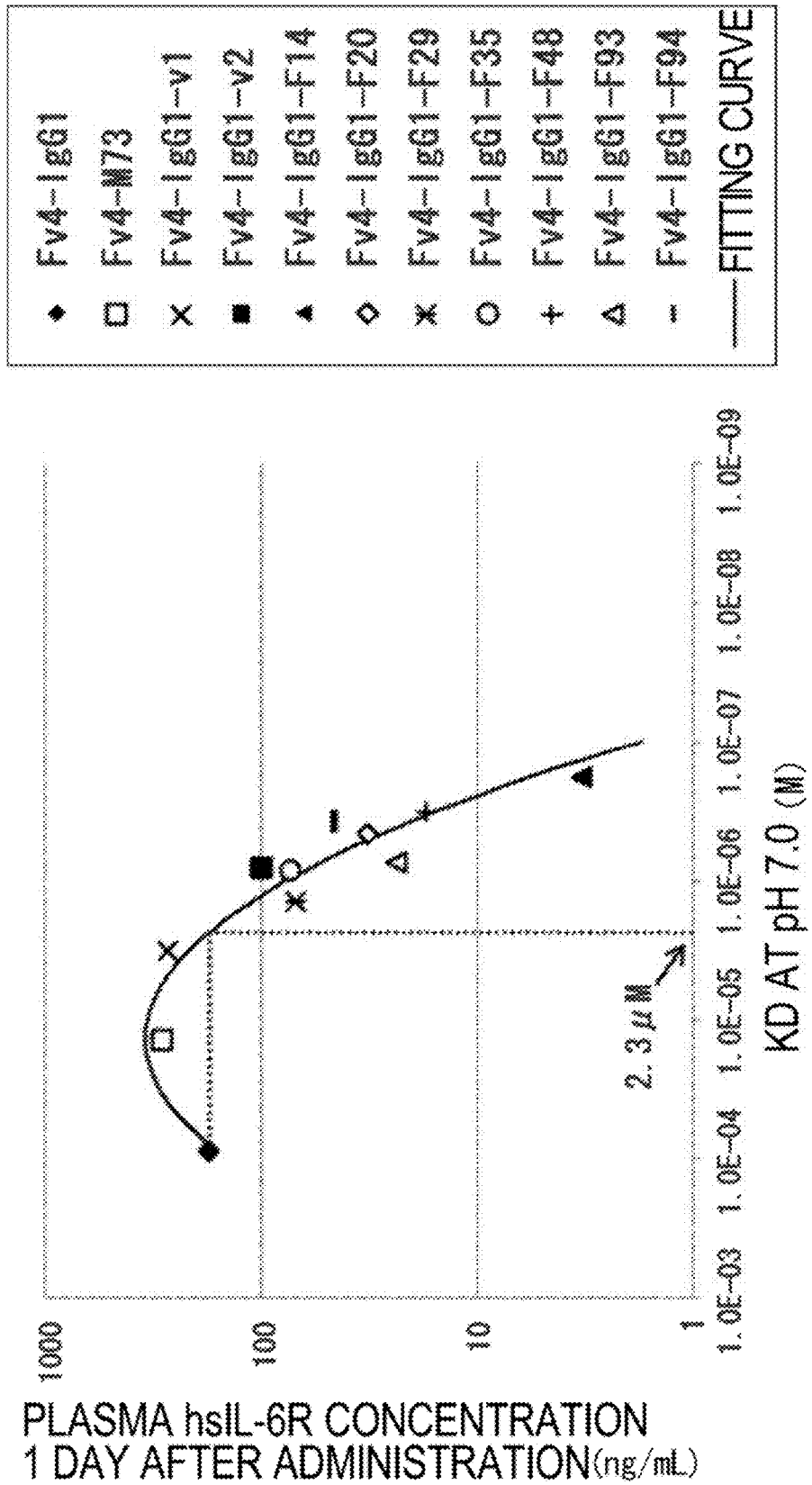

FIG. 42 describes the relationship between the binding affinity of Fc variants to human FcRn at pH 7.0 and plasma hsIL-6R concentration one day after co-administration of hsIL-6R and an anti-human IL-6 receptor antibody to human FcRn transgenic mice (lineage 276).

Figure 43:
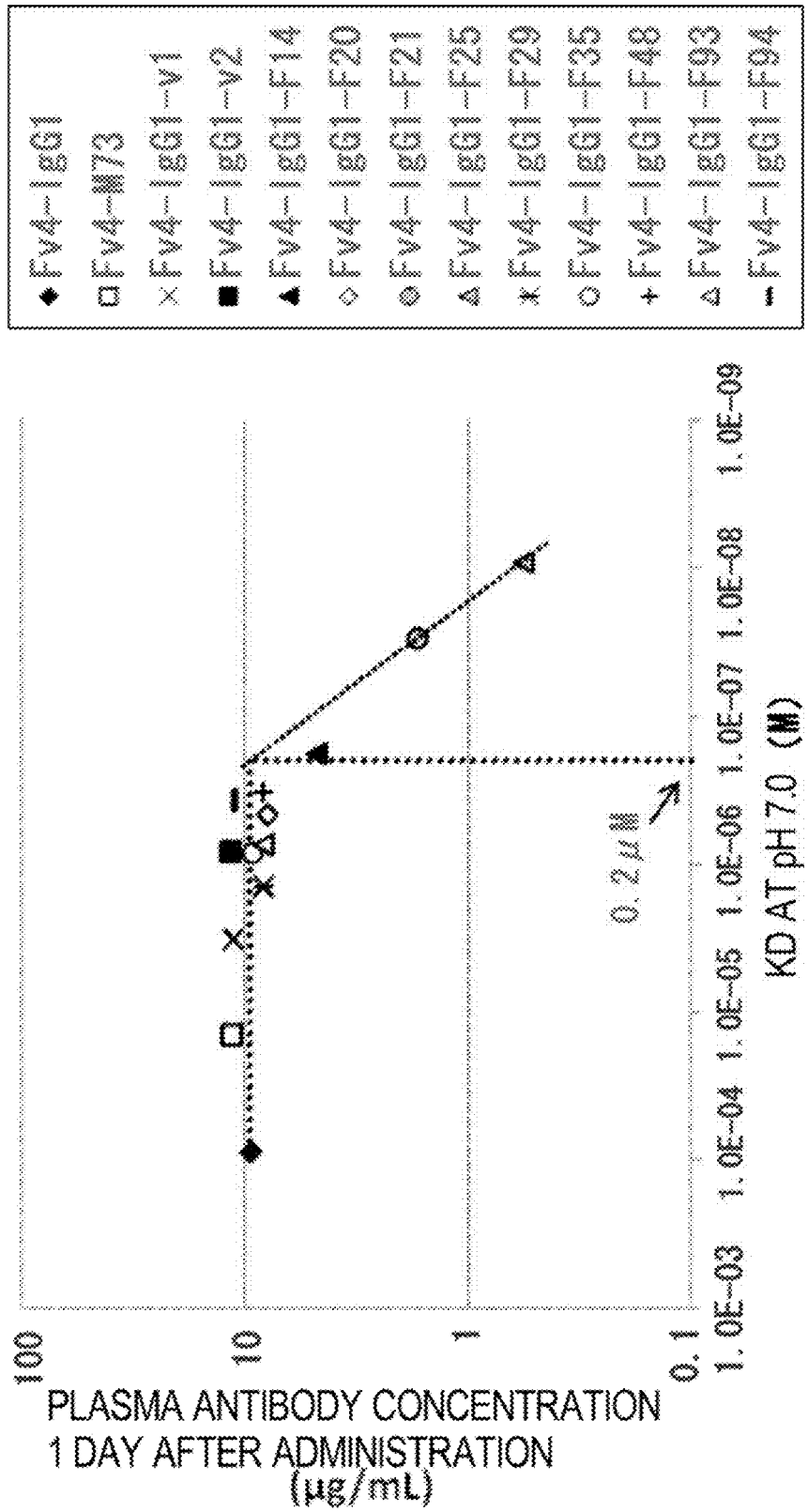

FIG. 43 describes the relationship between the binding affinity of Fc variants to human FcRn at pH 7.0 and plasma antibody concentration one day after co-administration of hsIL-6R and an anti-human IL-6 receptor antibody to human FcRn transgenic mice (lineage 276).

Figure 44:
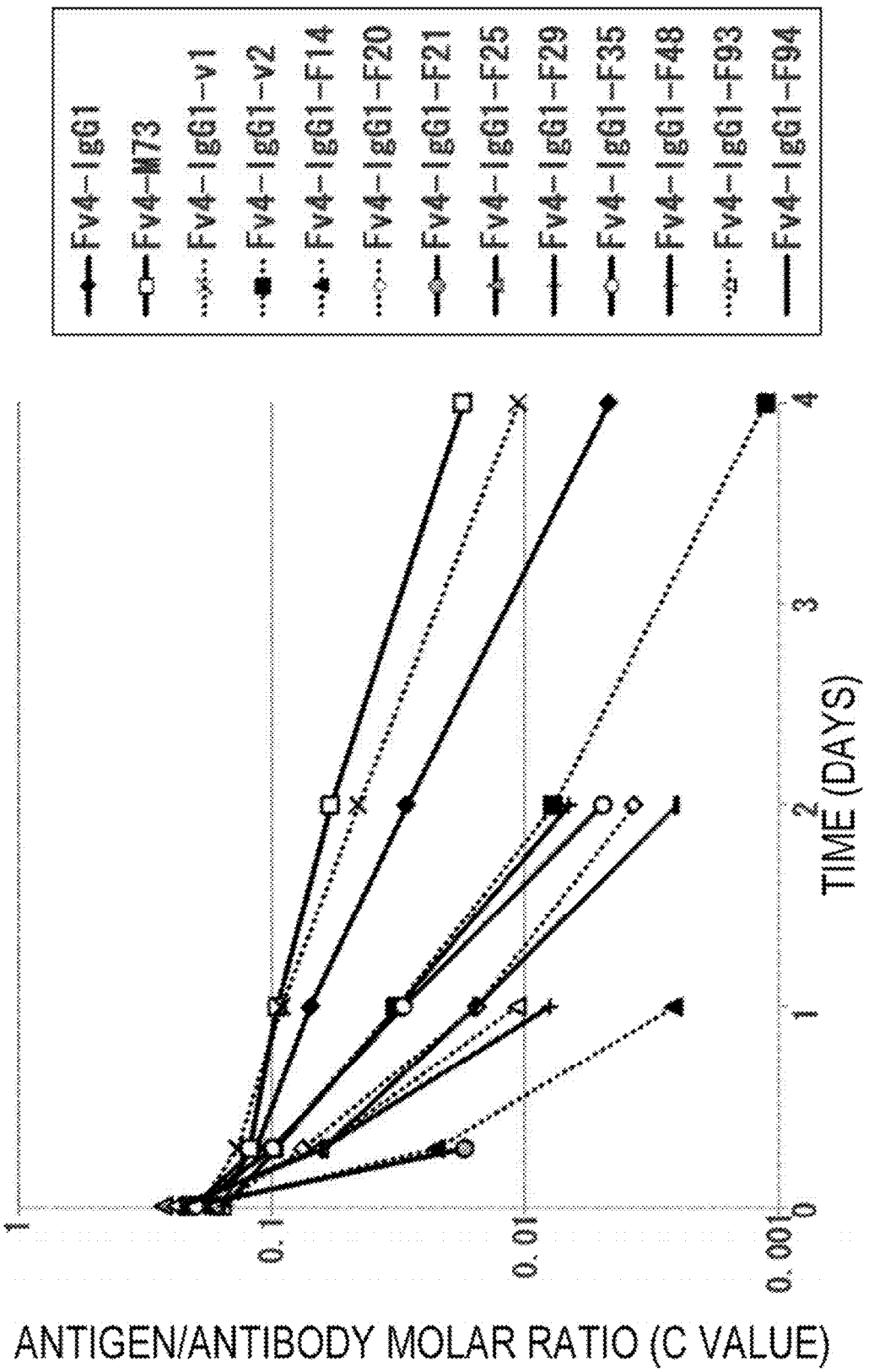

FIG. 44 describes a time course of the molar antigen/antibody ratio (C value) after co-administration of hsIL-6R and an anti-human IL-6 receptor antibody to human FcRn transgenic mice (lineage 276).

Figure 45:
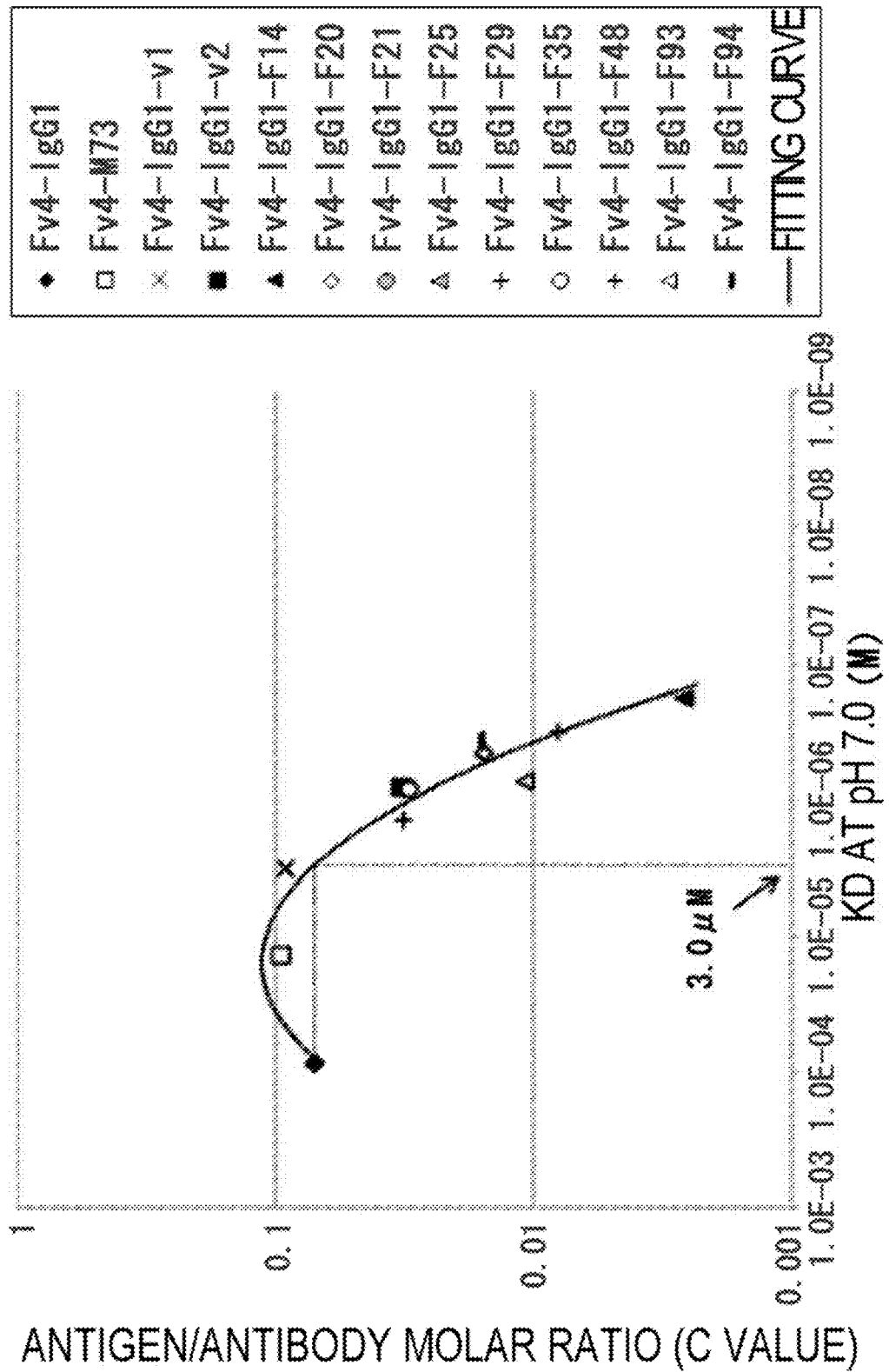

FIG. 45 describes the relationship between the binding affinity of Fc variants to human FcRn at pH 7.0 and the molar antigen/antibody ratio (C value) at day 1 after co-administration of hsIL-6R and an anti-human IL-6 receptor antibody to human FcRn transgenic mice (lineage 276).

Figure 46:
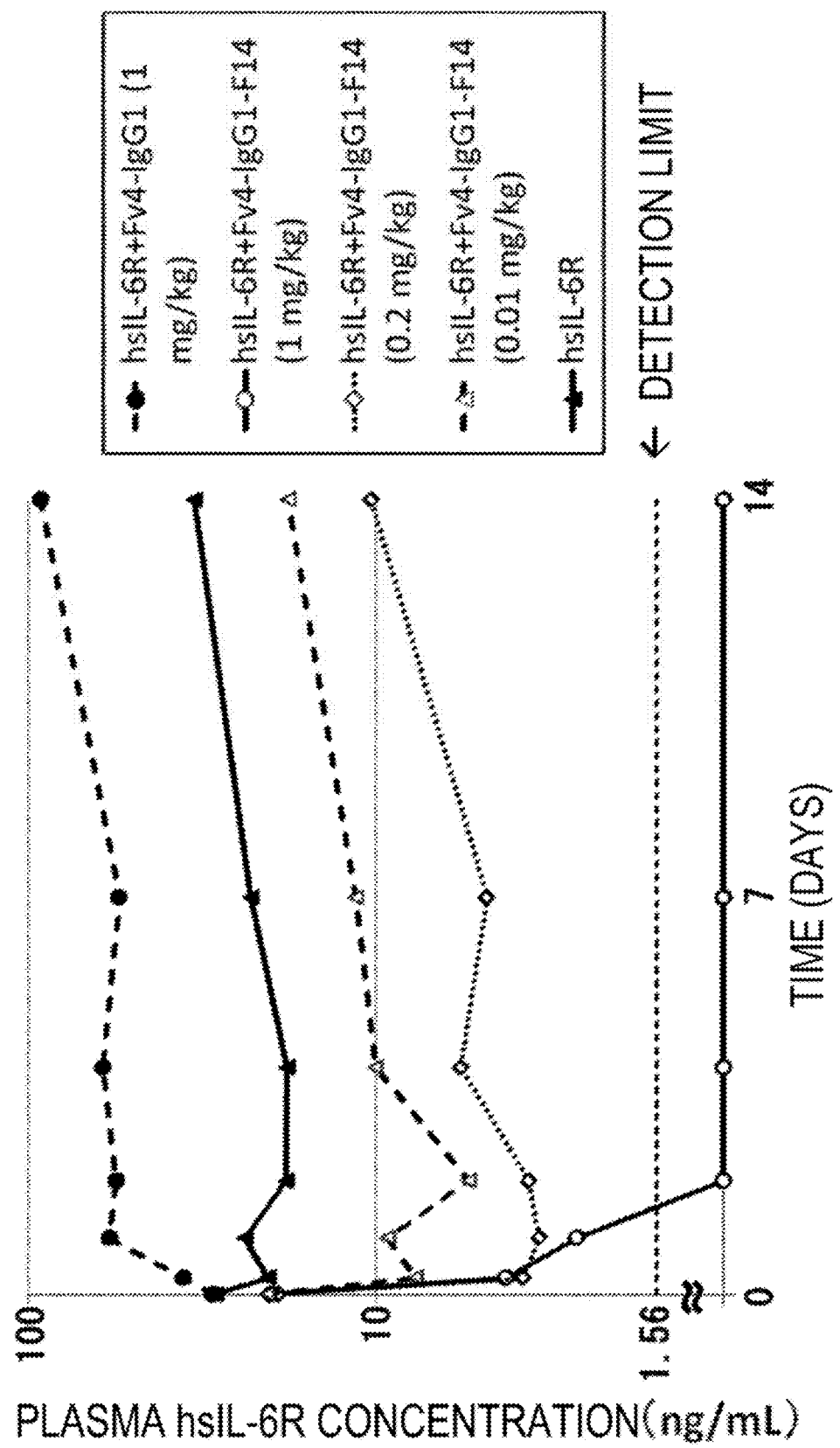

FIG. 46 describes a time course of the plasma concentration of hsIL-6R after administration of Fv4-IgG1-F14 at lower doses (0.01 or 0.2 mg/kg) or 1 mg/kg to human FcRn transgenic mice (lineage 276) in which the plasma concentration of hsIL-6R is constant (steady-state infusion model).

Figure 47:
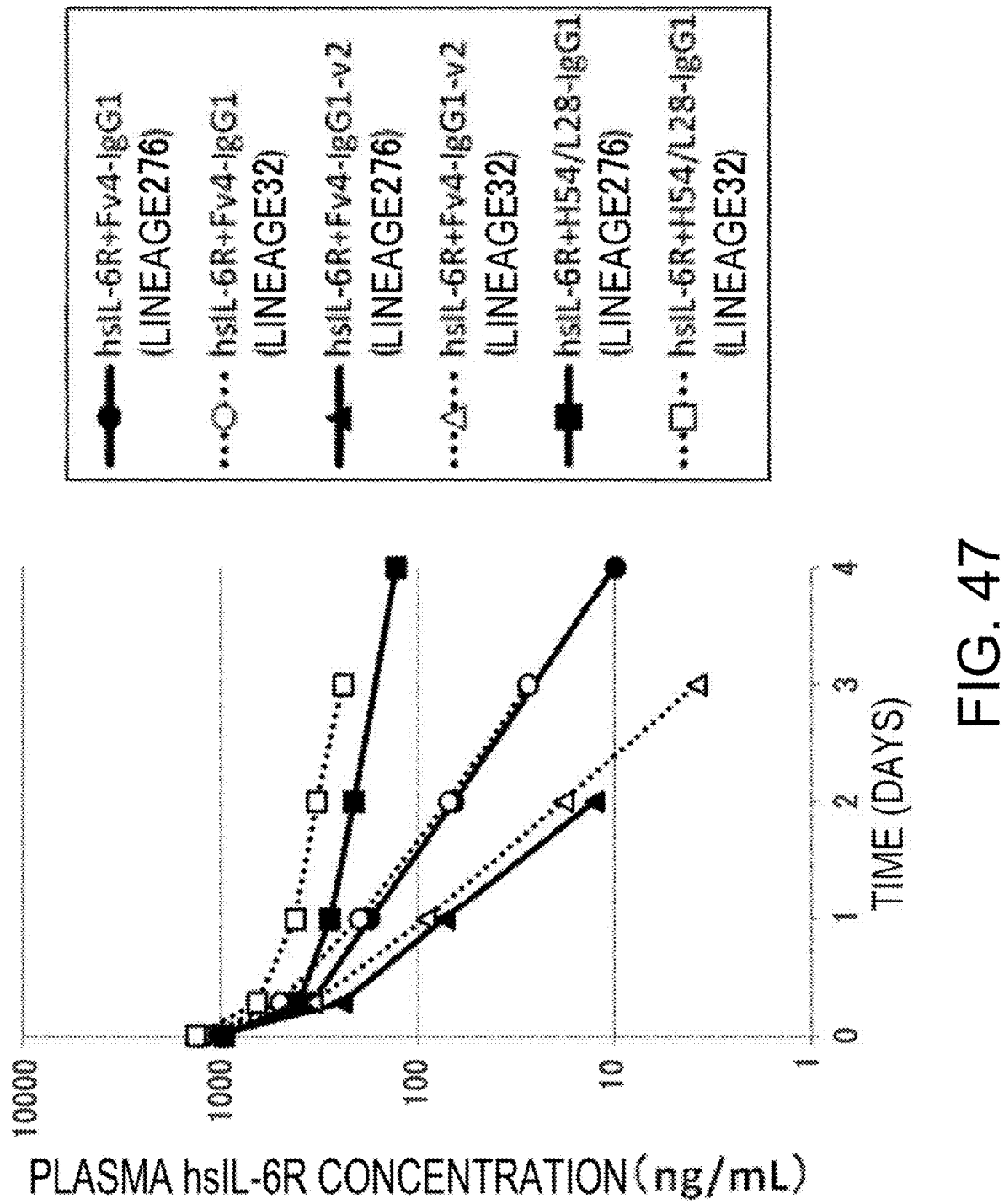

FIG. 47 describes a time course of the plasma hsIL-6R concentration in human FcRn transgenic mouse lineage 276 and lineage 32 after co-administration of hsIL-6R and anti-human IL-6 receptor antibody to human FcRn transgenic mice (lineages 276 and 32).

Figure 48:
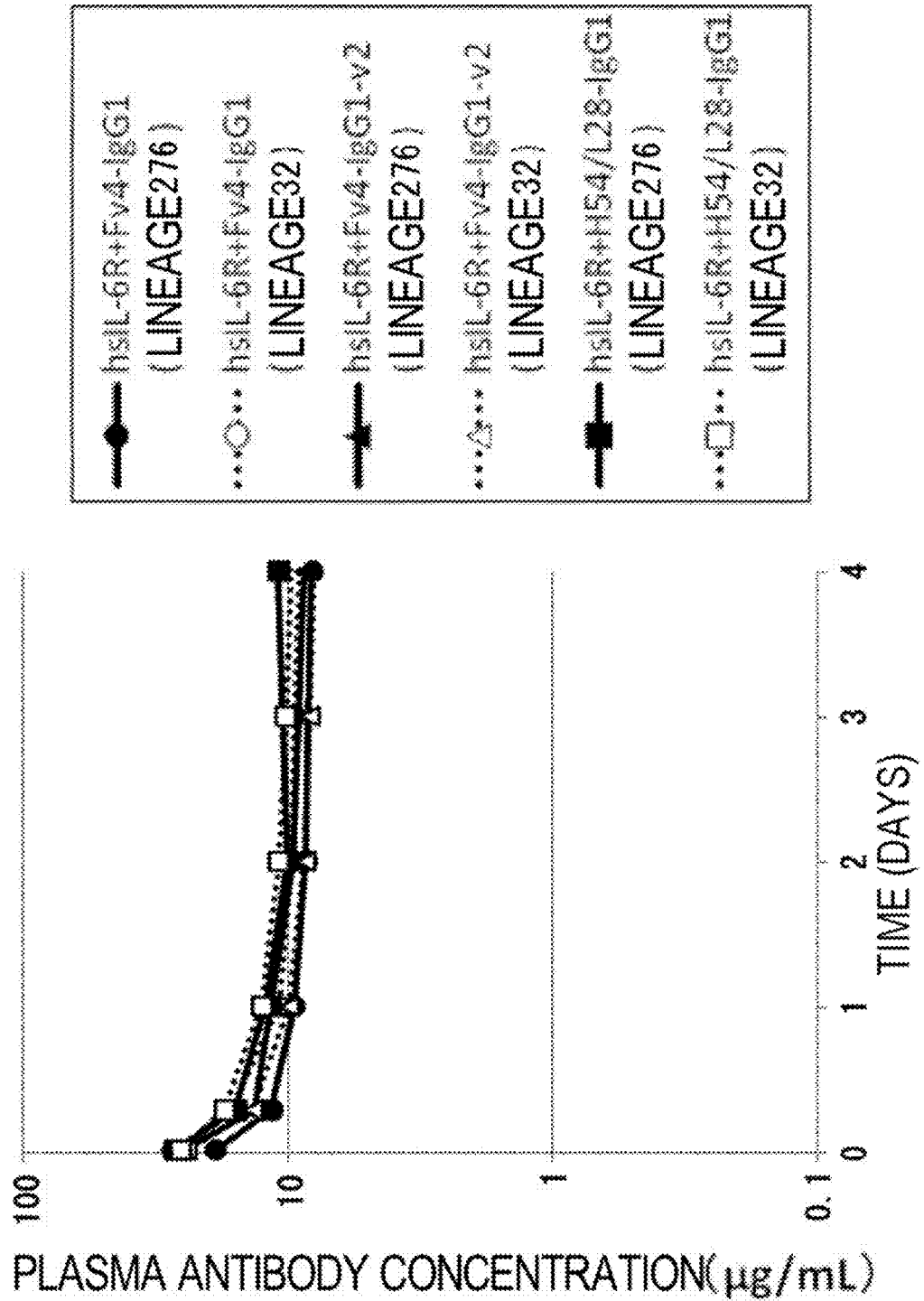

FIG. 48 describes a time course of plasma antibody concentration in human FcRn transgenic mouse lineage 276 and lineage 32 after co-administration of hsIL-6R and anti-human IL-6 receptor antibody to human FcRn transgenic mice (lineages 276 and 32).

Figure 49:
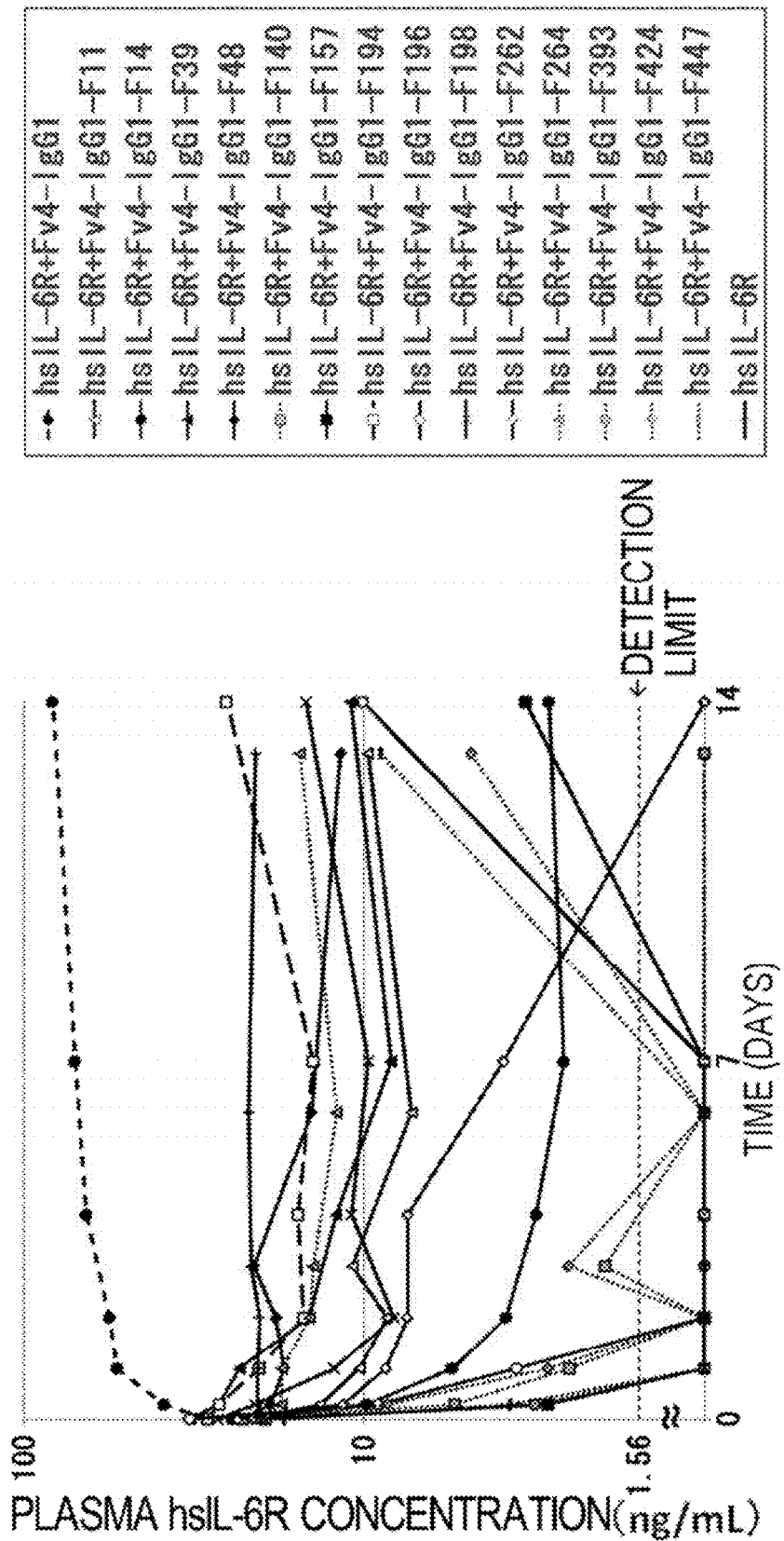

FIG. 49 describes a time course of the plasma concentration of hsIL-6R after administration of anti-human IL-6 receptor antibody to human FcRn transgenic mice in which the plasma concentration of hsIL-6R is constant (lineage 32) (steady-state infusion model).

Figure 50:
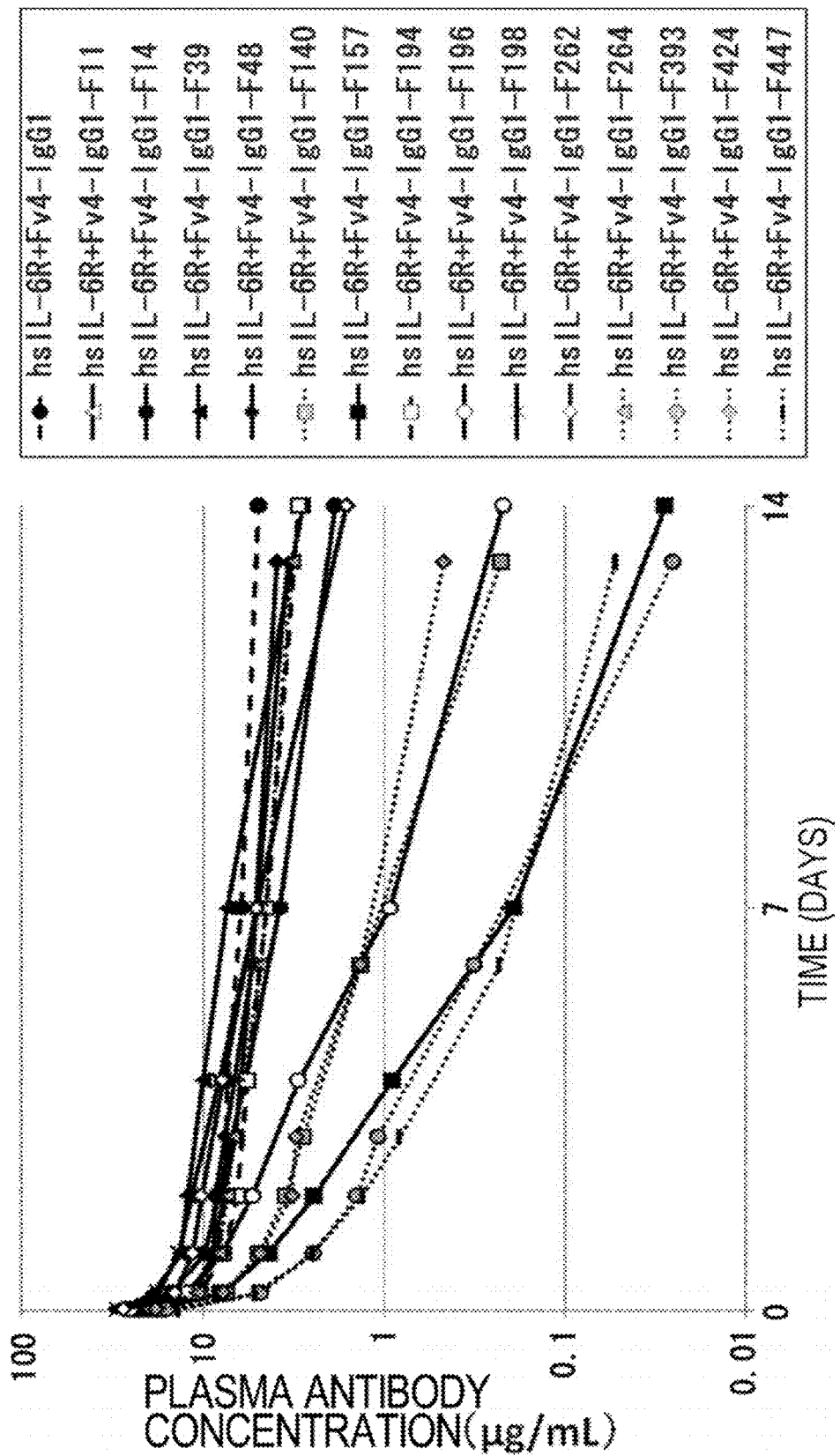

FIG. 50 describes a time course of plasma antibody concentration after administration of anti-human IL-6 receptor antibody to human FcRn transgenic mice in which the plasma concentration of hsIL-6R is constant (lineage 32) (steady-state infusion model).

Figure 51:
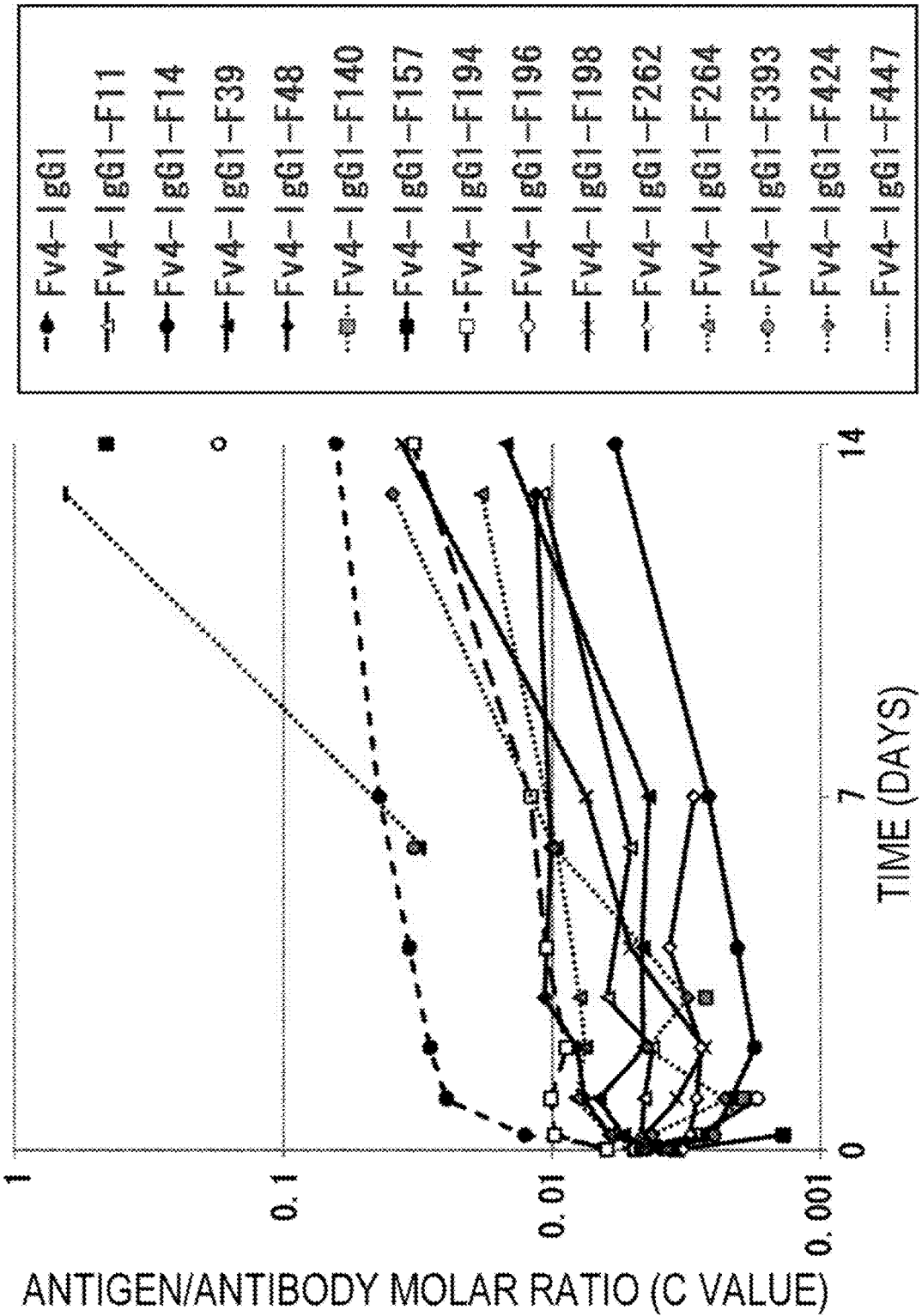

FIG. 51 describes time courses of the molar antigen/antibody ratio (value C) after administration of anti-human IL-6 receptor antibody to human FcRn transgenic mice in which the plasma concentration of hsIL-6R is constant (lineage 32) (steady-state infusion model).

Figure 52:
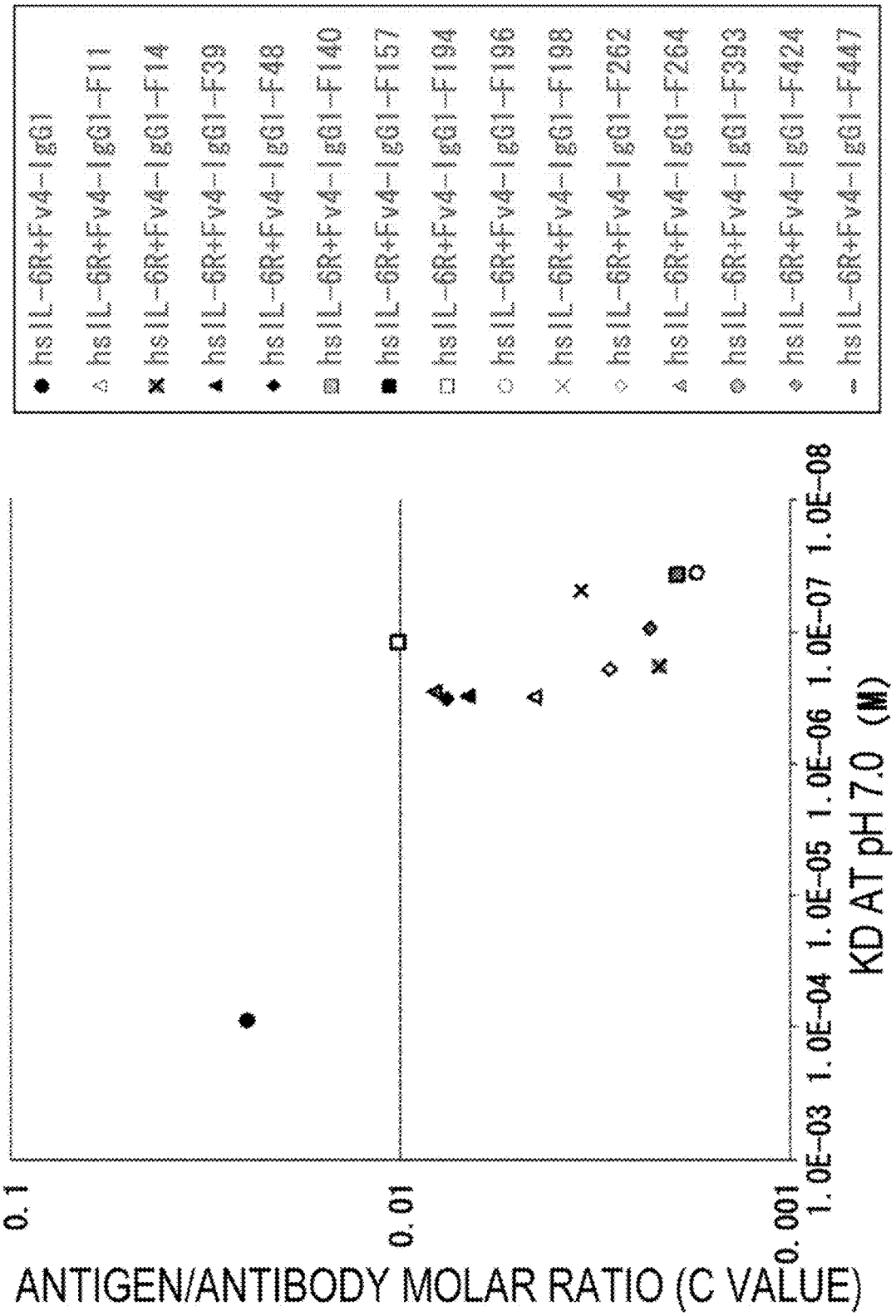

FIG. 52 describes the relationship between the binding affinity of Fc variants to human FcRn at pH 7.0 and molar antigen/antibody ratio (value C) at day 1 after administration of anti-human IL-6 receptor antibody to human FcRn transgenic mice (lineage 32) in which the plasma concentration of hsIL-6R is constant (steady-state infusion model).

Figure 53:
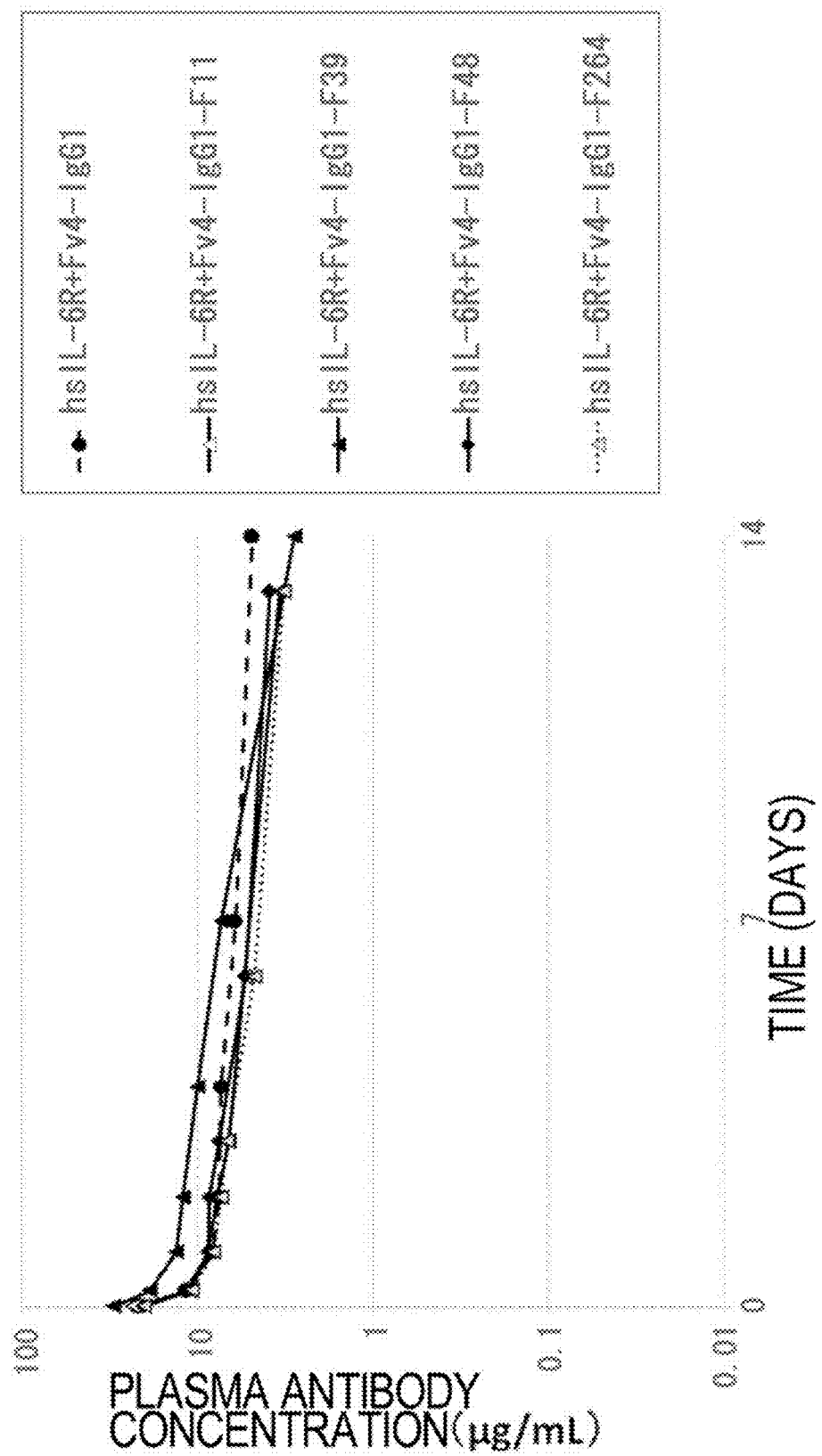

FIG. 53 shows in a graph a time course of plasma antibody concentration after administration of anti-human IL-6 receptor antibodies having Fc variant of F11, F39, F48, and F264 to human FcRn transgenic mice in which the plasma concentration of hsIL-6R is constant (lineage 32) (steady-state infusion model).

Figure 54:
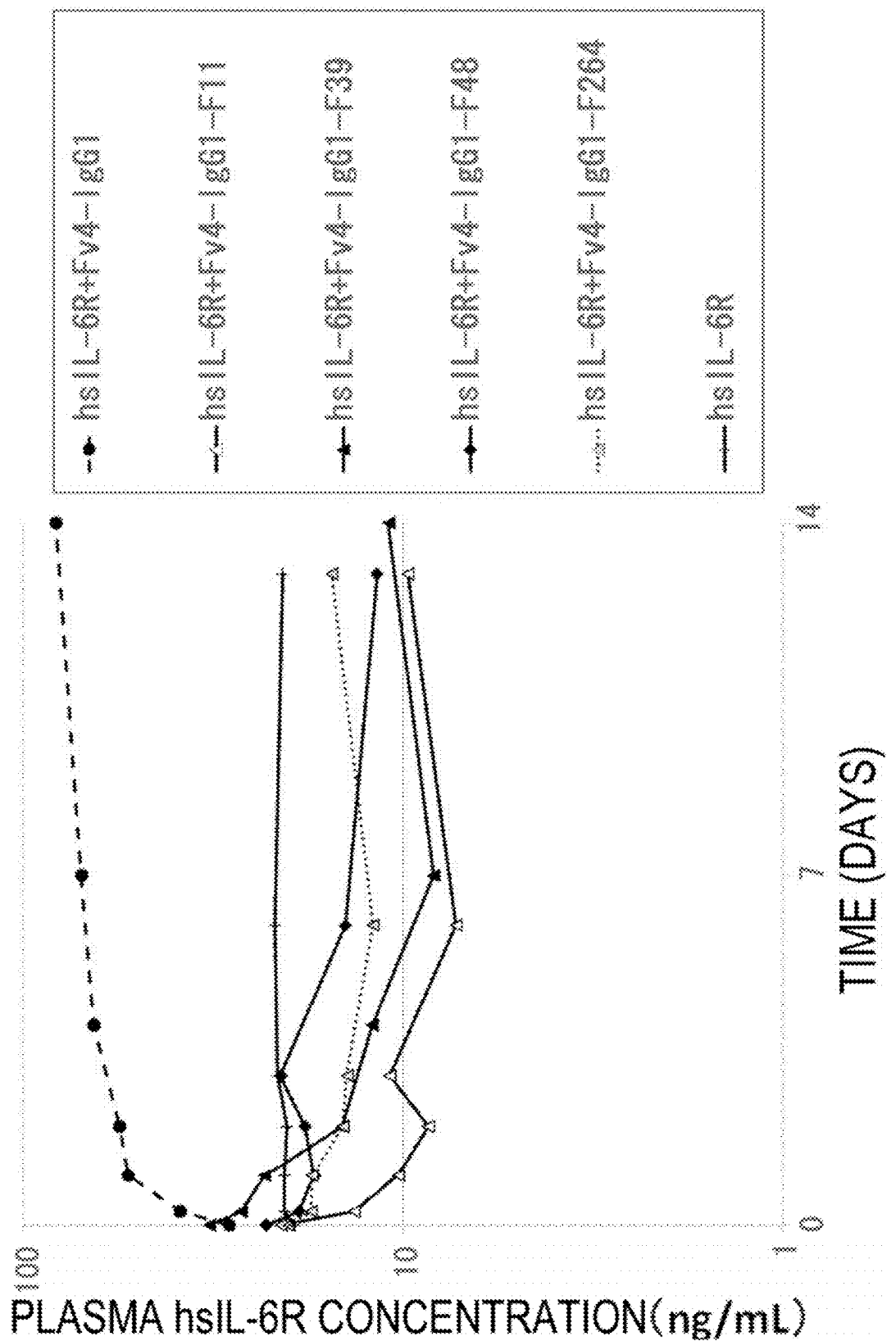

FIG. 54 shows in a graph a time course of the plasma concentration of hsIL-6R after administration of anti-human IL-6 receptor antibodies having Fc variant of F11, F39, F48, and F264 to human FcRn transgenic mice in which the plasma concentration of hsIL-6R is constant (lineage 32) (steady-state infusion model).

Figure 55:
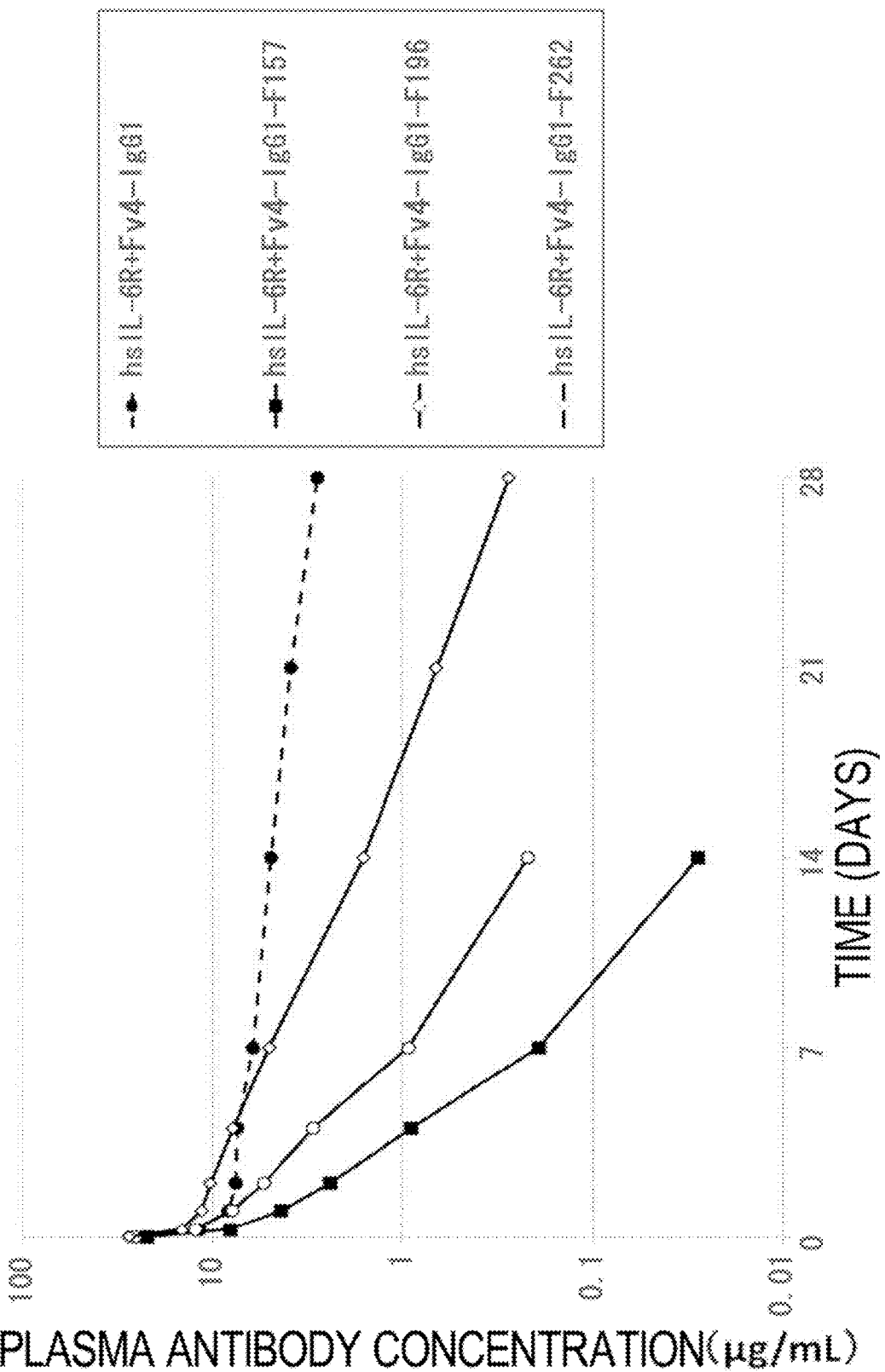

FIG. 55 describes a time course of plasma antibody concentration after administration of anti-human IL-6 receptor antibodies having Fc variant of F157, F196, and F262 to human FcRn transgenic mice in which the plasma concentration of hsIL-6R is constant (lineage 32) (steady-state infusion model).

Figure 56:
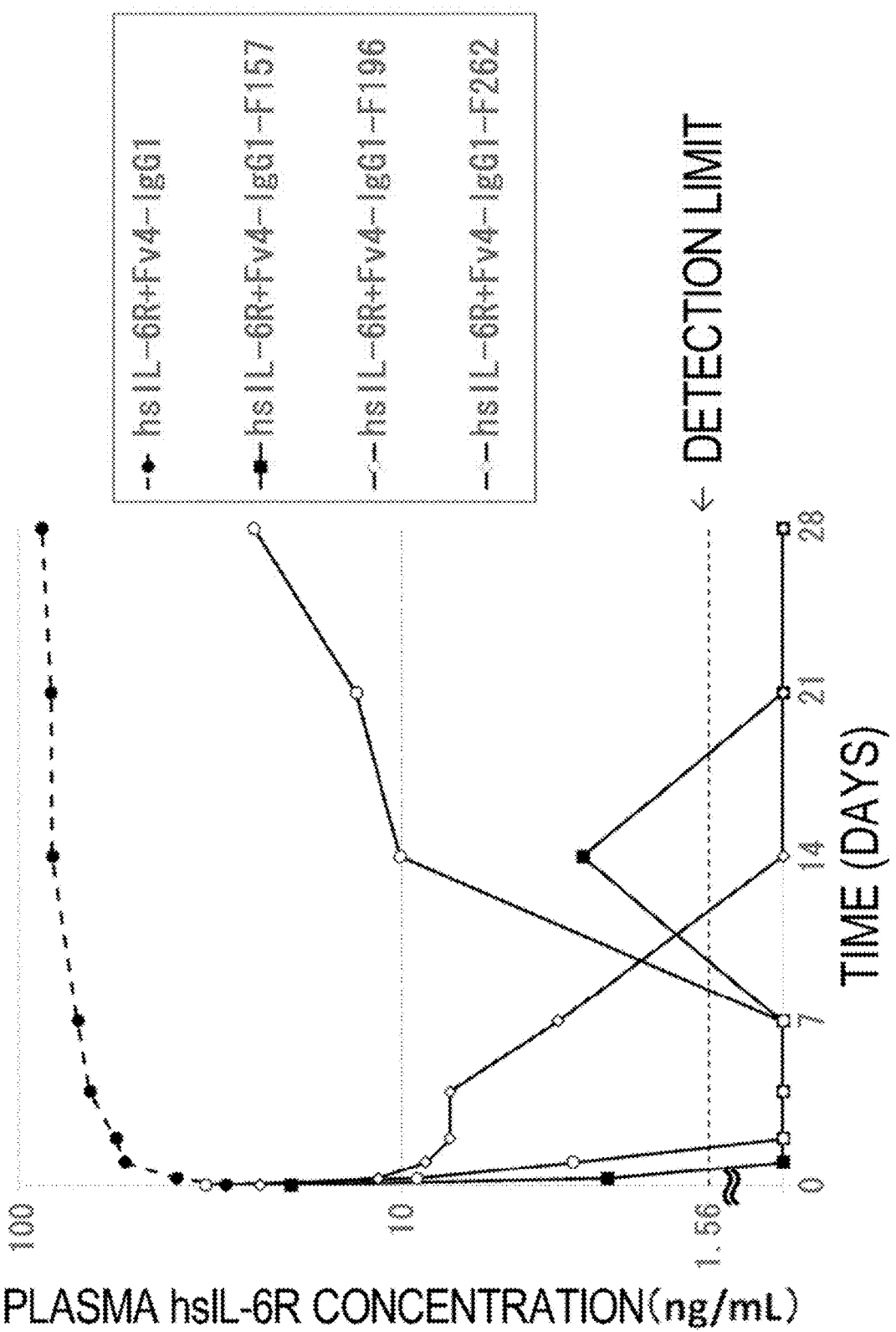

FIG. 56 describes a time course of the plasma concentration of hsIL-6R after administration of anti-human IL-6 receptor antibodies having Fc variant of F157, F196, and F262 to human FcRn transgenic mice in which the plasma concentration of hsIL-6R is constant (lineage 32) (steady-state infusion model).

MODE FOR CARRYING OUT THE INVENTION

The present invention provides methods for promoting antigen uptake into cells by antigen-binding molecules, methods for increasing the number of times of antigen binding by one antigen-binding molecule, methods for promoting the reduction of plasma antigen concentration by administering antigen-binding molecules, and methods for improving the plasma retention of an antigen-binding molecule. Specifically, the present invention provides methods for promoting antigen uptake into cells by antigen-binding molecules, methods for increasing the number of times of antigen binding by one antigen-binding molecule, methods for promoting the reduction of plasma antigen concentration by administering antigen-binding molecules, and methods for improving the plasma retention of antigen-binding molecules, all of which use an antigen-binding molecule that has a lower antigen-binding activity (herein, sometimes referred to as "binding activity") under a low calcium concentration condition than under a high calcium concentration condition.

Amino Acids

Herein, amino acids are described in one- or three-letter codes or both, for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/Q Trp/W, His/H, Tyr/Y, Ile/I, or Val/V.

Antigens

Herein, "antigens" are not particularly limited in their structure, as long as they comprise epitopes to which antigen-binding domains bind. In other words, antigens can be inorganic or organic substances; and alternatively, antigens can be foreign or endogenous substances to organisms subjected to the administration of the present invention. Examples of antigens bound by the antigen-binding domains of antigen-binding molecules whose pharmacokinetics is improved by methods of the present invention preferably include membrane antigens such as receptor proteins (membrane-bound receptors and soluble receptors) and cell surface markers; soluble antigens such as cytokines; and antigens with epitopes present only in foreign organisms. Such antigens include, for example, the following molecules: 17-IA, 4-1 BB, 4Dc, 6-keto-PGF1a, 8-iso-PGF2a, 8-oxo-dG, A1 Adenosine Receptor, A33, ACE, ACE-2, Activin, Activin A, Activin A B, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAM8, ADAM9, ADAMTS, ADAMTS4, ADAMTS5, Addressins, adiponectin, ADP ribosyl cyclase-1, aFGF, AGE, ALCAM, ALK, ALK-1, ALK-7, allergen, α1-anticymotrypsin, α1-antitrypsin, α-synuclein, α-V/β-1 antagonist, aminin, amylin, amyloid s, amyloid immunoglobulin heavy-chain variable region, amyloid immunoglobulin light-chain variable region, Androgen, ANG, angiotensinogen, Angiopoietin ligand-2, anti-Id, anti-thrombinIII, Anthrax, APAF-1, APE, APJ, apo A1, apo serum amyloid A, Apo-SAA, APP, APRIL, AR, ARC, ART, Artemin, ASPARTIC, Atrial natriuretic factor, Atrial natriuretic peptide, atrial natriuretic peptides A, atrial natriuretic peptides B, atrial natriuretic peptides C, av/b3 integrin, Ax1, B7-1, B7-2, B7-H, BACE, BACE-1, *Bacillus anthracis* protective antigen, Bad, BAFF, BAFF-R, Bag-1, BAK, Bax, BCA-1, BCAM, Bcl, BCMA, BDNF, b-ECGF, β-2-microglobulin, β lactamase, bFGF, BID, Bik, BIM, BLC, BL-CAM, BLK, B-lymphocyte Stimulator (BlyS), BMP, BMP-2 (BMP-2a), BMP-3 (Osteogenin), BMP-4 (BMP-2b), BMP-5, BMP-6 (Vgr-1), BMP-7 (OP-1), BMP-8 (BMP-8a), BMPR, BMPR-IA (ALK-3), BMPR-IB (ALK-6), BMPR-II (BRK-3), BMPs, BOK, Bombesin, Bone-derived neurotrophic factor, bovine growth hormone, BPDE, BPDE-DNA, BRK-2, BTC, B-lymphocyte cell adhesion molecule, C10, C1-inhibitor, C1q, C3, C3a, C4, C5, C5a (complement 5a), CA125, CAD-8, Cadherin-3, Calcitonin, cAMP, Carbonic anhydrase-IX, carcinoembryonic antigen (CEA), carcinoma-associated antigen, Cardiotrophin-1, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CCI, CCK2, CCL, CCL1/I-309, CCL11/Eotaxin, CCL12/MCP-5, CCL13/MCP-4, CCL14/HCC-1, CCL15/HCC-2, CCL16/HCC-4, CCL17/TARC, CCL18/PARC, CCL19/ELC, CCL2/MCP-1, CCL20/MIP-3-α, CCL21/SLC, CCL22/MDC, CCL23/MPIF-1, CCL24/Eotaxin-2, CCL25/TECK, CCL26/Eotaxin-3, CCL27/CTACK, CCL28/MEC, CCL3/M1P-1-α, CCL3L1/LD-78-β, CCL4/MIP-1-β, CCL5/RANTES, CCL6/C10, CCL7/MCP-3, CCL8/MCP-2, CCL9/10/MTP-1-γ, CCR, CCR1, CCR10, CCR2, CCR3, CCR4, CCR5, CCR6, CCR7, CCR8, CCR9, CD1, CD10, CD105, CD11a, CD11b, CD11c, CD123, CD13, CD137, CD138, CD14, CD140a, CD146, CD147, CD148, CD15, CD152, CD16, CD164, CD18, CD19, CD2, CD20, CD21, CD22, CD23, CD25, CD26, CD27L, CD28, CD29, CD3, CD30, CD30L, CD32, CD33 (p67 proteins), CD34, CD37, CD38, CD3E, CD4, CD40, CD40L, CD44, CD45, CD46, CD49a, CD49b, CD5, CD51, CD52, CD54, CD55, CD56, CD6, CD61, CD64, CD66e, CD7, CD70, CD74, CD8, CD80 (B7-1), CD89, CD95, CD105, CD158a, CEA, CEACAM5, CFTR, cGMP, CGRP receptor, CINC, CKb8-1, Claudini8, CLC, *Clostridium botulinum* toxin, *Clostridium difficile* toxin, *Clostridium perfringens* toxin, c-Met, CMV, CMV UL, CNTF, CNTN-1, complement factor 3 (C3), complement factor D, corticosteroid-binding globulin, Colony stimulating factor-1 receptor, COX, C-Ret, CRG-2, CRTH2, CT-1, CTACK, CTGF, CTLA-4, CX3CL1/Fractalkine, CX3CR1, CXCL, CXCL1/Gro-α, CXCL10, CXCL11/I-TAC, CXCL12/SDF-1-α/β, CXCL13/BCA-1, CXCL14/BRAK, CXCL15/Lungkine, CXCL16, CXCL16, CXCL2/Gro-β CXCL3/Gro-γ, CXCL3, CXCL4/PF4, CXCL5/ENA-78, CXCL6/GCP-2, CXCL7/NAP-2, CXCL8/IL-8, CXCL9/Mig, CXCL10/IP-10, CXCR, CXCR1, CXCR2, CXCR3, CXCR4, CXCR5, CXCR6, cystatin C, cytokeratin tumor-associated antigen, DAN, DCC, DcR3, DC-SIGN, Decay accelerating factor, Delta-like protein ligand 4, des(1-3)-IGF-1 (brain IGF-1), Dhh, DHICA oxidase, Dickkopf-1, digoxin, Dipeptidyl peptidase IV, DK1, DNAM-1, Dnase, Dpp, DPPIV/CD26, Dtk, ECAD, EDA, EDA-A1, EDA-A2, EDAR, EGF, EGFR (ErbB-1), EGF like domain containing protein 7, Elastase, elastin, EMA, EMMPRIN, ENA, ENA-78, Endosialin, endothelin receptor, endotoxin, Enkephalinase, eNOS, Eot, Eotaxin, Eotaxin-2, eotaxini, EpCAM, Ephrin B2/EphB4, Epha2 tyrosine kinase receptor, epidermal growth factor receptor (EGFR), ErbB2 receptor, ErbB3 tyrosine kinase receptor, ERCC, erythropoietin (EPO), Erythropoietin receptor, E-selectin, ET-1, Exodus-2, F protein of RSV, F10, F11, F12, F13, F5, F9, Factor Ia, Factor IX, Factor Xa, Factor VII, factor VIII, Factor VIIc, Fas, FcαR, FcepsilonRI, FcγIIb, FcγRI, FcγRIIa, FcγRIIIa, FcγRIIIb, FcRn, FEN-1, Ferritin, FGF, FGF-19, FGF-2, FGF-2 receptor, FGF-3, FGF-8, FGF-acidic, FGF-basic, FGFR, FGFR-3, Fibrin, fibroblast activation protein (FAP), fibroblast growth factor, fibroblast growth factor-10, fibronectin, FL, FLIP, Flt-3, FLT3 ligand, Folate receptor, follicle stimulating hormone (FSH), Fractalkine (CX3C), free heavy chain, free light chain, FZD1, FZD10, FZD2, FZD3, FZD4, FZD5, FZD6, FZD7, FZD8, FZD9, G250, Gas 6, GCP-2, GCSF, G-CSF, G-CSF receptor, GD2, GD3, GDF, GDF-1, GDF-15 (MIC-1), GDF-3 (Vgr-2), GDF-5 (BMP-14/CDMP-1), GDF-6 (BMP-13/CDMP-2), GDF-7 (BMP-12/CDMP-3), GDF-8 (Myostatin), GDF-9, GDNF, Gelsolin, GFAP, GF-CSF, GFR-α1, GFR-α2, GFR-α3, GF-β1, gH envelope glycoprotein, GITR, Glucagon, Glucagon receptor, Glucagon-like peptide 1 receptor, Glut 4, Glutamate carboxypeptidase II, glycoprotein hormone receptors, glycoprotein IIb/IIIa (GP IIb/IIIa), Glypican-3, GM-CSF, GM-CSF receptor, gp130, gp140, gp72, granulocyte-CSF (G-CSF), GRO/MGSA, Growth hormone releasing factor, GRO-β, GRO-γ, *H. pylori*, Hapten (NP-cap or NIP-cap), HB-EGF, HCC, HCC 1, HCMV gB envelope glycoprotein, HCMV UL, Hemopoietic growth factor (HGF), Hep B gp120, heparanase, heparin cofactor II, hepatic growth factor, *Bacillus anthracis* protective antigen, Hepatitis C virus E2 glycoprotein, Hepatitis E, Hepcidin, Her1, Her2/neu (ErbB-2), Her3 (ErbB-3), Her4 (ErbB-4), herpes simplex virus (HSV) gB glycoprotein, HGF, HGFA, High molecular weight melanoma-associated antigen (HMW-MAA), HIV envelope proteins such as GP120, HIV MIB gp 120 V3 loop, HLA, HLA-DR, HM1.24, HMFG PEM, HMGB-1, HRG, Hrk, HSP47, Hsp90, HSV gD glycoprotein, human cardiac myosin, human cytomegalovirus (HCMV), human growth hormone (hGH), human serum albumin, human tissue-type plasminogen activator (t-PA), Huntingtin, HVEM, IAP, ICAM, ICAM-1, ICAM-3, ICE, ICOS, IFN-α, IFN-β, IFN-γ, IgA, IgA receptor, IgE, IGF, IGF binding proteins, IGF-1, IGF-1R, IGF-2, IGFBP, IGFR, IL, IL-1, IL-10, IL-10 receptors, IL-11, IL-11 receptors, IL-12, IL-12 receptors, IL-13, IL-13 receptors, IL-15, IL-15 receptors, IL-16, IL-16 receptors, IL-17, IL-17 receptors, IL-18 (IGIF), IL-18 receptors, IL-1α, IL-1β, IL-1 receptors, IL-2, IL-2 receptors, IL-20, IL-20 receptors, IL-21, IL-21 receptors, IL-23, IL-23 receptors, IL-2 receptors, IL-3, IL-3 receptors, IL-31, IL-31 receptors, IL-3 receptors, IL-4, IL-4 receptors IL-5, IL-5 receptors, IL-6, IL-6 receptors, IL-7, IL-7 receptors, IL-8, IL-8 receptors, IL-9, IL-9 receptors, immunoglobulin immune complex, immunoglobulins, INF-α, INF-α receptors, INF—P, INF-β receptors, INF-γ, INF-γ receptors, IFN type-I, IFN type-I receptor, influenza, inhibin, Inhibin α, Inhibin β, iNOS, insulin, Insulin A-chain, Insulin B-chain, Insulin-like growth factor 1, insulin-like growth factor 2, insulin-like growth factor binding proteins, integrin, integrin α2, integrin α3, integrin α4, integrin α4/β1, integrin α-V/β-3, integrin α-V/β-6, integrin α4/β7, integrin α5/β1, integrin α5/β, integrin α5/β6, integrin α-δ (αV), integrin α-θ, integrin β1, integrin β2, integrin β3(GPIIb-IIIa), IP-10, I-TAC, JE, kalliklein, Kallikrein 11, Kallikrein 12, Kallikrein 14, Kallikrein 15, Kallikrein 2, Kallikrein 5, Kallikrein 6, Kallikrein L1, Kallikrein L2, Kallikrein L3, Kallikrein L4, kallistatin, KC, KDR, Keratinocyte Growth Factor (KGF), Keratinocyte Growth Factor-2 (KGF-2), KGF, killer immunoglobulin-like receptor, kit ligand (KL), Kit tyrosine kinase, laminin 5, LAMP, LAPP (Amylin, islet-amyloid polypeptide), LAP (TGF-1), latency associated peptide, Latent TGF-1, Latent TGF-1 bpi, LBP, LDGF, LDL, LDL receptor, LECT2, Lefty, Leptin, leutinizing hormone (LH), Lewis-Y antigen, Lewis-Y related antigen, LFA-1, LFA-3, LFA-3 receptors, Lfo, LIF, LIGHT, lipoproteins, LIX, LKN, Lptn, L-Selectin, LT-a, LT-b, LTB4, LTBP-1, Lung surfactant, Luteinizing hormone, Lymphotactin, Lymphotoxin β Receptor, Lysosphingolipid receptor, Mac-1, macrophage-CSF (M-CSF), MAdCAM, MAG, MAP2, MARC, maspin, MCAM, MCK-2, MCP, MCP-1, MCP-2, MCP-3, MCP-4, MCP-I (MCAF), M-CSF, MDC, MDC (67 a.a.), MDC (69 a.a.), megsin, Mer, MET tyrosine kinase receptor family, METALLOPROTEASES, Membrane glycoprotein OX2, Mesothelin, MGDF receptor, MGMT, MHC (HLA-DR), microbial protein, MIF, MIG, MIP, MIP-1α, MIP-Iβ, MIP-3α, MIP-3β, MIP-4, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, monocyte attractant protein, monocyte colony inhibitory factor, mouse gonadotropin-associated peptide, MPIF, Mpo, MSK, MSP, MUC-16, MUC18, mucin (Mud), Muellerian-inhibiting substance, Mug, MuSK, Myelin associated glycoprotein, myeloid progenitor inhibitor factor-1 (MPIF-I), NAIP, Nanobody, NAP, NAP-2, NCA 90, NCAD, N-Cadherin, NCAM, Neprilysin, Neural cell adhesion molecule, neroserpin, Neuronal growth factor (NGF), Neurotrophin-3, Neurotrophin-4, Neurotrophin-6, Neuropilin 1, Neurturin, NGF-β, NGFR, NKG20, N-methionyl human growth hormone, nNOS, NO, Nogo-A, Nogo receptor, non-structural protein type 3 (NS3) from the hepatitis C virus, NOS, Npn, NRG-3, NT, NT-3, NT-4, NTN, OB, OGG1, Oncostatin M, OP-2, OPG, OPN, OSM, OSM receptors, osteoinductive factors, osteopontin, OX40L, OX40R, oxidized LDL, p150, p95, PADPr, parathyroid hormone, PARC, PARP, PBR, PBSF, PCAD, P-Cadherin, PCNA, PCSK9, PDGF, PDGF receptor, PDGF-AA, PDGF-AB, PDGF-BB, PDGF-D, PDK-1, PECAM, PEDF, PEM, PF-4, PGE, PGF, PGI2, PGJ2, PIGF, PIN, PLA2, Placenta growth factor, placental alkaline phosphatase (PLAP), placental lactogen, plasminogen activator inhibitor-1, platelet-growth factor, plgR, PLP, poly glycol chains of different size(e.g. PEG-20, PEG-30, PEG40), PP14, prekallikrein, prion protein, procalcitonin, Programmed cell death protein 1, proinsulin, prolactin, Proprotein convertase PC9, prorelaxin, prostate specific membrane antigen (PSMA), Protein A, Protein C, Protein D, Protein S, Protein Z, PS, PSA, PSCA, PsmAr, PTEN, PTHrp, Ptk, PTN, P-selectin glycoprotein ligand-1, R51, RAGE, RANK, RANKL, RANTES, relaxin, Relaxin A-chain, Relaxin B-chain, renin, respiratory syncytial virus (RSV) F, Ret, reticulon 4, Rheumatoid factors, RLI P76, RPA2, RPK-1, RSK, RSV Fgp, S100, RON-8, SCF/KL, SCGF, Sclerostin, SDF-1, SDF1α, SDF1β, SERINE, Serum Amyloid P, Serum albumin, sFRP-3, Shh, Shiga like toxin II, SIGIRR, SK-1, SLAM, SLPI, SMAC, SMDF, SMOH, SOD, SPARC, sphingosine 1-phosphate receptor 1, Staphylococcal lipoteichoic acid, Stat, STEAP, STEAP-II, stem cell factor (SCF), streptokinase, superoxide dismutase, syndecan-1, TACE, TACI, TAG-72 (tumor-associated glycoprotein-72), TARC, TB, TCA-3, T-cell receptor α/β, TdT, TECK, TEM1, TEM5, TEM7, TEM8, Tenascin, TERT, testicular PLAP-like alkaline phosphatase, TfR, TGF, TGF-α, TGFβ, TGFβ Pan Specific, TGF-β RII, TGF-β RIIb, TGF-β RIII, TGF-β RI (ALK-5), TGF-β1, TGF-β2, TGF-β3, TGF-β4, TGF-β5, TGF-I, Thrombin, thrombopoietin (TPO), Thymic stromal lymphoprotein receptor, Thymus Ck-1, thyroid stimulating hormone (TSH), thyroxine, thyroxine-binding globulin, Tie, TIMP, TIQ, Tissue Factor, tissue factor protease inhibitor, tissue factor protein, TMEFF2, Tmpo, TMPRSS2, TNF receptor I, TNF receptor II, TNF-α, TNF-β, TNF-β2, TNFc, TNF-RI, TNF-RII, TNFRSF10A (TRAIL R1 Apo-2/DR4), TNFRSF10B (TRAIL R2 DR5/KILLER/TRICK-2A/TRICK-B), TNFRSF10C (TRAIL R3 DcR1/LIT/TRID), TNFRSF10D (TRAIL R4 DcR2/TRUNDD), TNFRSF11A (RANK ODF R/TRANCE R), TNFRSF11B(OPG OCIF/TR1), TNFRSF12 (TWEAK R FN14), TNFRSF12A, TNFRSF13B (TACI), TNFRSF13C(BAFF R), TNFRSF14 (HVEM ATAR/HveA/LIGHT R/TR2), TNFRSF16 (NGFR p75NTR), TNFRSF17 (BCMA), TNFRSF18 (GITR AITR), TNFRSF19 (TROY TAJ/TRADE), TNFRSF19L (RELT), TNFRSF1A (TNF R1 CD120a/p55-60), TNFRSF1B (TNF RII CD120b/p75-80), TNFRSF21 (DR6), TNFRSF22 (Dc-TRAIL R2 TNFRH2), TNFRSF25 (DR3 Apo-3/LARD/TR-3/TRAMP/WSL-1), TNFRSF26 (TNFRH3), TNFRSF3 (LTbR TNF RIII/TNFC R), TNFRSF4 (OX40 ACT35/ TXGP1R), TNFRSF5 (CD40 p50), TNFRSF6 (Fas Apo-1/APT1/CD95), TNFRSF6B (DcR3 M68/TR6), TNFRSF7 (CD27), TNFRSF8 (CD30), TNFRSF9 (4-1 BB CD137/ILA), TNFRST23 (DcTRAIL R1 TNFRH1), TNFSF10 (TRAIL Apo-2 Ligand/TL2), TNFSF11 (TRANCE/RANK Ligand ODF/OPG Ligand), TNFSF12 (TWEAK Apo-3 Ligand/DR3 Ligand), TNFSF13 (APRIL TALL2), TNFSF13B (BAFF BLYS/TALL1/THANK/TNFSF20), TNFSF14 (LIGHT HVEM Ligand/LTg), TNFSF15 (TL1A/VEGI), TNFSF18 (GITR Ligand AITR Ligand/TL6), TNFSF1A (TNF-a Conectin/DIF/TNFSF2), TNFSF1B (TNF-b LTa/TNFSF1), TNFSF3 (LTb TNFC/p33), TNFSF4 (OX40 Ligand gp34/TXGP1), TNFSF5 (CD40 Ligand CD154/gp39/HIGM1/IMD3/TRAP), TNFSF6 (Fas Ligand Apo-1 Ligand/APT1 Ligand), TNFSF7 (CD27 Ligand CD70), TNFSF8 (CD30 Ligand CD153), TNFSF9 (4-1 BB Ligand CD137 Ligand), TNFα, TNF-β, TNIL-I, toxic metabolite, TP-1, t-PA, Tpo, TRAIL, TRAIL R, TRAIL-R1, TRAIL-R2, TRANCE, transferrin receptor, transforming growth factors (TGF) such as TGF-α and TGF-β, Transmembrane glycoprotein NMB, Transthyretin, TRF, Trk, TROP-2, Trophoblast glycoprotein, TSG, TSLP, Tumor Necrosis Factor (TNF), tumor-associated antigen CA 125, tumor-associated antigen expressing Lewis Y related carbohydrate, TWEAK, TXB2, Ung, uPAR, uPAR-1, Urokinase, VAP-1, vascular endothelial growth factor (VEGF), vaspin, VCAM, VCAM-1, VECAD, VE-Cadherin, VE-Cadherin-2, VEFGR-1 (flt-1), VEFGR-2, VEGF receptor (VEGFR), VEGFR-3 (fit-4), VEGI, VIM, Viral antigens, VitB12 receptor, Vitronectin receptor, VLA, VLA-I, VLA-4, VNR integrin, von Willebrand Factor (vWF), WIF-1, WNT1, WNT10A, WNT10B, WNT11, WNT16, WNT2, WNT2B/13, WNT3, WNT3A, WNT4, WNT5A, WNT5B, WNT6, WNT7A, WNT7B, WNT8A, WNT8B, WNT9A, WNT9B, XCL1, XCL2/SCM-1-β, XCL1/Lymphotactin, XCR1, XEDAR, XIAP, XPD, HMGB1, IgA, As, CD81, CD97, CD98, DDR1, DKK1, EREG, Hsp90, IL-17/IL-17R, IL-20/IL-20R, oxidized LDL, PCSK9, prekallikrein, RON, TMEM16F, SODI, Chromogranin A, Chromogranin B, tau, VAPI, high-molecular-weight kininogen, IL-31, IL-31R, Nav1.1, Nav1.2, Nav1.3, Nav1.4, Nav1.5, Nav1.6, Nav1.7, Nav1.8, Nav1.9, EPCR, C1, C1q, C1r, C1s, C2, C2a, C2b, C3, C3a, C3b, C4, C4a, C4b, C5, C5a, C5b, C6, C7, C8, C9, factor B, factor D, factor H, properdin, sclerostin, fibrinogen, fibrin, prothrombin, thrombin, tissue factor, factor V, factor Va, factor VII, factor VIIa, factor VIII, factor VIIIa, factor IX, factor IXa, factor X, factor Xa, factor XI, factor XIa, factor XII, factor XIIa, factor XIII, factor XIIIa, TFPI, antithrombin III, EPCR, thrombomodulin, TAPI, tPA, plasminogen, plasmin, PAI-I, PAI-2, GPC3, Syndecan-1, Syndecan-2, Syndecan-3, Syndecan-4, LPA, and SIP and soluble receptor molecules for a hormone or growth factor, which are not anchored to cells in the body fluid of organisms.

"Epitope" means an antigenic determinant in an antigen, and refers to an antigen site to which the antigen-binding domain of an antigen-binding molecule disclosed herein binds. Thus, for example, the epitope can be defined according to its structure. Alternatively, the epitope may be defined according to the antigen-binding activity of an antigen-binding molecule that recognizes the epitope. When the antigen is a peptide or polypeptide, the epitope can be specified by the amino acid residues forming the epitope. Alternatively, when the epitope is a sugar chain, the epitope can be specified by its specific sugar chain structure.

A linear epitope is an epitope that contains an epitope whose primary amino acid sequence is recognized. Such a linear epitope typically contains at least three and most commonly at least five, for example, about 8 to 10 or 6 to 20 amino acids in its specific sequence.

In contrast to the linear epitope, "conformational epitope" is an epitope in which the primary amino acid sequence containing the epitope is not the only determinant of the recognized epitope (for example, the primary amino acid sequence of a conformational epitope is not necessarily recognized by an epitope-defining antibody). Conformational epitopes may contain a greater number of amino acids compared to linear epitopes. A conformational epitope-recognizing antibody recognizes the three-dimensional structure of a peptide or protein. For example, when a protein molecule folds and forms a three-dimensional structure, amino acids and/or polypeptide main chains that form a conformational epitope become aligned, and the epitope is made recognizable by the antibody. Methods for determining epitope conformations include, for example, X ray crystallography, two-dimensional nuclear magnetic resonance, site-specific spin labeling, and electron paramagnetic resonance, but are not limited thereto. See, for example, Epitope Mapping Protocols in Methods in Molecular Biology (1996), Vol. 66, Morris (ed.).

Binding Activity

Examples of a method for assessing the epitope binding by a test antigen-binding molecule containing an IL-6R antigen-binding domain are described below. According to the examples below, methods for assessing the epitope binding by a test antigen-binding molecule containing an antigen-binding domain for an antigen other than IL-6R, can also be appropriately conducted.

For example, whether a test antigen-binding molecule containing an IL-6R antigen-binding domain recognizes a linear epitope in the IL-6R molecule can be confirmed for example as mentioned below. A linear peptide comprising an amino acid sequence forming the extracellular domain of IL-6R is synthesized for the above purpose. The peptide can be synthesized chemically, or obtained by genetic engineering techniques using a region encoding the amino acid sequence corresponding to the extracellular domain in an IL-6R cDNA. Then, a test antigen-binding molecule containing an IL-6R antigen-binding domain is assessed for its binding activity towards a linear peptide comprising the amino acid sequence forming the extracellular domain. For example, an immobilized linear peptide can be used as an antigen by ELISA to evaluate the binding activity of the antigen-binding molecule towards the peptide. Alternatively, the binding activity towards a linear peptide can be assessed based on the level that the linear peptide inhibits the binding of the antigen-binding molecule to IL-6R-expressing cells. These tests can demonstrate the binding activity of the antigen-binding molecule towards the linear peptide.

Whether a test antigen-binding molecule containing an IL-6R antigen-binding domain recognizes a conformational epitope can be assessed as follows. IL-6R-expressing cells are prepared for the above purpose. A test antigen-binding molecule containing an IL-6R antigen-binding domain can be determined to recognize a conformational epitope when it strongly binds to IL-6R-expressing cells upon contact, but does not substantially bind to an immobilized linear peptide comprising an amino acid sequence forming the extracellular domain of IL-6R. Herein, "not substantially bind" means that the binding activity is 80% or less, generally 50% or less, preferably 30% or less, and particularly preferably 15% or less compared to the binding activity towards cells expressing human IL-6R.

Methods for assaying the binding activity of a test antigen-binding molecule containing an IL-6R antigen-binding domain towards IL-6R-expressing cells include, for example, the methods described in Antibodies: A Laboratory Manual (Ed Harlow, David Lane, Cold Spring Harbor Laboratory (1988) 359-420). Specifically, the assessment can be performed based on the principle of ELISA or fluorescence activated cell sorting (FACS) using IL-6R-expressing cells as antigen.

In the ELISA format, the binding activity of a test antigen-binding molecule containing an IL-6R antigen-binding domain towards IL-6R-expressing cells can be assessed quantitatively by comparing the levels of signal generated by enzymatic reaction. Specifically, a test antigen-binding molecule is added to an ELISA plate onto which IL-6R-expressing cells are immobilized.

Then, the test antigen-binding molecule bound to the cells is detected using an enzyme-labeled antibody that recognizes the test antigen-binding molecule. Alternatively, when FACS is used, a dilution series of a test antigen-binding molecule is prepared, and the antibody binding titer for IL-6R-expressing cells can be determined to compare the binding activity of the test antigen-binding molecule towards IL-6R-expressing cells.

The binding of a test antigen-binding molecule towards an antigen expressed on the surface of cells suspended in buffer or the like can be detected using a flow cytometer. Known flow cytometers include, for example, the following devices:

FACSCanto™ II
FACSAria™
FACSArray™
FACSVantage™ SE
FACSCalibur™ (all are trade names of BD Biosciences)
EPICS ALTRA HyPerSort
Cytomics FC 500
EPICS XL-MCL ADC EPICS XL ADC
Cell Lab Quanta/Cell Lab Quanta SC (all are trade names of Beckman Coulter).

Preferable methods for assaying the binding activity of a test antigen-binding molecule containing an IL-6R antigen-binding domain towards an antigen include, for example, the following method. First, IL-6R-expressing cells are reacted with a test antigen-binding molecule, and then this is stained with an FITC-labeled secondary antibody that recognizes the antigen-binding molecule. The test antigen-binding molecule is appropriately diluted with a suitable buffer to prepare the molecule at a desired concentration. For example, the molecule can be used at a concentration within the range of 10 µg/ml to 10 ng/ml. Then, the fluorescence intensity and cell count are determined using FACSCalibur (BD). The fluorescence intensity obtained by analysis using the CELL QUEST Software (BD), i.e., the Geometric Mean value, reflects the quantity of antibody bound to cells. That is, the binding activity of a test antigen-binding molecule, which is represented by the quantity of the test antigen-binding molecule bound, can be determined by measuring the Geometric Mean value.

Whether a test antigen-binding molecule containing an IL-6R antigen-binding domain shares a common epitope with another antigen-binding molecule can be assessed based on the competition between the two molecules for the same epitope. The competition between antigen-binding molecules can be detected by cross-blocking assay or the like. For example, the competitive ELISA assay is a preferred cross-blocking assay.

Specifically, in cross-blocking assay, the IL-6R protein immobilized to the wells of a microtiter plate is pre-incubated in the presence or absence of a candidate competitor antigen-binding molecule, and then a test antigen-binding molecule is added thereto. The quantity of test antigen-binding molecule bound to the IL-6R protein in the wells is indirectly correlated with the binding ability of a candidate competitor antigen-binding molecule that competes for the binding to the same epitope. That is, the greater the affinity of the competitor antigen-binding molecule for the same epitope, the lower the binding activity of the test antigen-binding molecule towards the IL-6R protein-coated wells.

The quantity of the test antigen-binding molecule bound to the wells via the IL-6R protein can be readily determined by labeling the antigen-binding molecule in advance. For example, a biotin-labeled antigen-binding molecule is measured using an avidin/peroxidase conjugate and appropriate substrate. In particular, cross-blocking assay that uses enzyme labels such as peroxidase is called "competitive ELISA assay". The antigen-binding molecule can also be labeled with other labeling substances that enable detection or measurement. Specifically, radiolabels, fluorescent labels, and such are known.

When the candidate competitor antigen-binding molecule can block the binding by a test antigen-binding molecule containing an IL-6R antigen-binding domain by at least 20%, preferably at least 20 to 50%, and more preferably at least 50% compared to the binding activity in a control experiment conducted in the absence of the competitor antigen-binding molecule, the test antigen-binding molecule is determined to substantially bind to the same epitope bound by the competitor antigen-binding molecule, or compete for the binding to the same epitope.

When the structure of an epitope bound by a test antigen-binding molecule containing an IL-6R antigen-binding domain has already been identified, whether the test and control antigen-binding molecules share a common epitope can be assessed by comparing the binding activities of the two antigen-binding molecules towards a peptide prepared by introducing amino acid mutations into the peptide forming the epitope.

To measure the above binding activities, for example, the binding activities of test and control antigen-binding molecules towards a linear peptide into which a mutation is introduced are compared in the above ELISA format. Besides the ELISA methods, the binding activity towards the mutant peptide bound to a column can be determined by flowing test and control antigen-binding molecules in the column, and then quantifying the antigen-binding molecule eluted in the elution solution. Methods for adsorbing a mutant peptide to a column, for example, in the form of a GST fusion peptide, are known.

Alternatively, when the identified epitope is a conformational epitope, whether test and control antigen-binding molecules share a common epitope can be assessed by the following method. First, IL-6R-expressing cells and cells expressing IL-6R with a mutation introduced into the epitope are prepared. The test and control antigen-binding molecules are added to a cell suspension prepared by suspending these cells in an appropriate buffer such as PBS. Then, the cell suspensions are appropriately washed with a buffer, and an FITC-labeled antibody that recognizes the test and control antigen-binding molecules is added thereto. The fluorescence intensity and number of cells stained with the labeled antibody are determined using FACSCalibur (BD). The test and control antigen-binding molecules are appropriately diluted using a suitable buffer, and used at desired concentrations. For example, they may be used at a concentration within the range of 10 µg/ml to 10 ng/ml. The fluorescence intensity determined by analysis using the CELL QUEST Software (BD), i.e., the Geometric Mean value, reflects the quantity of labeled antibody bound to cells. That is, the binding activities of the test and control antigen-binding molecules, which are represented by the quantity of labeled antibody bound, can be determined by measuring the Geometric Mean value.

In the above method, whether an antigen-binding molecule does "not substantially bind to cells expressing mutant IL-6R" can be assessed, for example, by the following method. First, the test and control antigen-binding molecules bound to cells expressing mutant IL-6R are stained with a labeled antibody. Then, the fluorescence intensity of the cells is determined.

When FACSCalibur is used for fluorescence detection by flow cytometry, the determined fluorescence intensity can be analyzed using the CELL QUEST Software. From the Geometric Mean values in the presence and absence of the antigen-binding molecule, the comparison value (ΔGeo-Mean) can be calculated according to the following formula to determine the ratio of increase in fluorescence intensity as a result of the binding by the antigen-binding molecule.

$$\Delta Geo\text{-}Mean = Geo\text{-}Mean(\text{in the presence of the antigen-binding molecule})/Geo\text{-}Mean(\text{in the absence of the antigen-binding molecule})$$

The Geometric Mean comparison value (ΔGeo-Mean value for the mutant IL-6R molecule) determined by the above analysis, which reflects the quantity of a test antigen-binding molecule bound to cells expressing mutant IL-6R, is compared to the ΔGeo-Mean comparison value that reflects the quantity of the test antigen-binding molecule bound to IL-6R-expressing cells. In this case, the concentrations of the test antigen-binding molecule used to determine the ΔGeo-Mean comparison values for IL-6R-expressing cells and cells expressing mutant IL-6R are particularly preferably adjusted to be equal or substantially equal. An antigen-binding molecule that has been confirmed to recognize an epitope in IL-6R is used as a control antigen-binding molecule.

If the ΔGeo-Mean comparison value of a test antigen-binding molecule for cells expressing mutant IL-6R is smaller than the ΔGeo-Mean comparison value of the test antigen-binding molecule for IL-6R-expressing cells by at least 80%, preferably 50%, more preferably 30%, and particularly preferably 15%, then the test antigen-binding molecule "does not substantially bind to cells expressing mutant IL-6R". The formula for determining the Geo-Mean (Geometric Mean) value is described in the CELL QUEST Software User's Guide (BD biosciences). When the comparison shows that the comparison values are substantially equivalent, the epitope for the test and control antigen-binding molecules can be determined to be the same.

Antigen-Binding Domain

Herein, an "antigen-binding domain" may be of any structure as long as it binds to an antigen of interest. Such domains preferably include, for example:

antibody heavy-chain and light-chain variable regions;
    a module of about 35 amino acids called A domain which is contained in the in vivo cell membrane protein Avimer (WO 2004/044011, WO 2005/040229);
    Adnectin containing the 10Fn3 domain which binds to the protein moiety of fibronectin, a glycoprotein expressed on cell membrane (WO 2002/032925);
    Affibody which is composed of a 58-amino acid three-helix bundle based on the scaffold of the IgG-binding domain of Protein A (WO 1995/001937);

Designed Ankyrin Repeat proteins (DARPins) which are a region exposed on the molecular surface of ankyrin repeats (AR) having a structure in which a subunit consisting of a turn comprising 33 amino acid residues, two antiparallel helices, and a loop is repeatedly stacked (WO 2002/020565);

Anticalins and such, which are domains consisting of four loops that support one side of a barrel structure composed of eight circularly arranged antiparallel strands that are highly conserved among lipocalin molecules such as neutrophil gelatinase-associated lipocalin (NGAL) (WO 2003/029462); and the concave region formed by the parallel-sheet structure inside the horseshoe-shaped structure constituted by stacked repeats of the leucine-rich-repeat (LRR) module of the variable lymphocyte receptor (VLR) which does not have the immunoglobulin structure and is used in the system of acquired immunity in jawless vertebrate such as lampery and hagfish (WO 2008/016854). Preferred antigen-binding domains of the present invention include, for example, those having antibody heavy-chain and light-chain variable regions. Preferred examples of antigen-binding domains include "single chain Fv (scFv)", "single chain antibody", "Fv", "single chain Fv 2 (scFv2)", "Fab", and "F(ab')2".

The antigen-binding domains of antigen-binding molecules of the present invention can bind to an identical epitope. Such epitope can be present, for example, in a protein comprising the amino acid sequence of SEQ ID NO: 15. Alternatively, the epitope can be present in the protein comprising the amino acids at positions 20 to 365 in the amino acid sequence of SEQ ID NO: 15. Alternatively, each of the antigen-binding domains of antigen-binding molecules of the present invention can bind to a different epitope. Herein, the different epitope can be present in, for example, a protein comprising the amino acid sequence of SEQ ID NO: 15. Alternatively, the epitope can be present in the protein comprising the amino acids at positions 20 to 365 in the amino acid sequence of SEQ ID NO: 15.

Calcium-Binding Motif

The antigen-binding domain of an antigen-binding molecule of the present invention comprises a calcium-binding motif. The calcium-binding motif can be located anywhere within the antigen-binding domain as long as the antigen-binding activity is lower under a low calcium concentration condition than under a high calcium concentration condition. When the antigen-binding domain is an antibody variable region, the calcium-binding motif can be contained in the heavy-chain variable region or light-chain variable region. Alternatively, the calcium-binding motif can be contained in both heavy chains and light chains. In another non-limiting embodiment, the calcium-binding motif can be contained in the framework or CDR sequence of the variable region. Alternatively, the calcium-binding motif can be contained in both framework and CDR sequences.

In a non-limiting embodiment of the present invention, the calcium-binding motif comprises an amino acid residue(s) that alters the antigen-binding activity of the antigen-binding molecule depending on the calcium-ion concentration condition. Such amino acid residues preferably include, for example, amino acids having a metal-chelating activity. Amino acids having a metal-chelating activity preferably include, for example, serine (Ser (S)), threonine (Thr (T)), asparagine (Asn (N)), glutamine (Gln (Q)), aspartic acid (Asp (D)), glutamic acid (Glu (E)), histidine (His (H)), and tyrosine (Tyr (Y)). The calcium-binding motifs in existing antigen-binding domains that have a lower antigen-binding activity under a low calcium concentration condition than under a high calcium concentration condition can be used as a suitable calcium-binding motif of the present invention. As examples of such existing antigen-binding domains, calcium-binding motifs in the variable regions of antibodies that have a lower antigen-binding activity under a low calcium concentration condition than under a high calcium concentration condition can be preferably used; but are not limited thereto. Such antibodies include, but are not limited to, for example, IL-6 receptor antibodies comprising SEQ ID NOs: 1 and 2 and IL-6 antibodies comprising SEQ ID NOs: 25 and 26. Furthermore, troponin C, calmodulin, parvalbumin, myosin light chain, and such, which have several calcium ion-binding sites and are assumed to be derived from a common origin in their molecular evolution, are known. Their binding motifs can also be used as a calcium-binding motif of the present invention.

When an antigen-binding domain of the present invention is an antibody variable region, the calcium-binding motif can be contained in its heavy-chain variable region or light-chain variable region. Alternatively, the calcium-binding motif can be contained in both heavy chains and light chains. In another non-limiting embodiment, the calcium-binding motif can be contained in the framework or CDR sequence of the variable region. Alternatively, the calcium-binding motif can be contained in both framework and CDR sequences. The heavy chain or light chain CDR1, CDR2, and/or CDR3 can be designed so that they comprise such calcium-binding motifs. For example, in a non-limiting embodiment of the present invention, the light-chain variable region of an antigen-binding molecule of the present invention can be designed so as to contain the calcium-binding motif of the human antibody light chain variable region of SEQ ID NO: 41, 63, or 64. Such calcium-binding motifs include those in which any one or more of the amino acids at positions 30, 31, 32, 50, and/or 92 according to Kabat's numbering have a metal-chelating activity. In a non-limiting embodiment, such calcium-binding motifs preferably include those in which the same amino acids as one to four amino acids selected from the five amino acids at positions 30, 31, 32, 50, and/or 92 according to Kabat's numbering system in the human antibody light chain variable region of SEQ ID NO: 41, 63, or 64 are contained at the corresponding amino acid positions according to Kabat's numbering system. In this case, it is preferable that amino acids having a metal-chelating activity are contained in the human antibody light chain variable region of SEQ ID NO: 41, 63, or 64 at amino acid positions where amino acids at the corresponding amino acid positions of the five amino acid positions 30, 31, 32, 50, and/or 92 according to Kabat's numbering system in the light chain variable region are not identical to the amino acids at these positions. In another non-limiting embodiment of the present invention, the heavy-chain variable region of an antigen-binding molecule of the present invention can be designed to have, for example, the calcium-binding motif of the heavy-chain variable region of SEQ ID NO: 1. Such calcium-binding motifs include those in which the amino acids at positions 95, 96, and/or 100a according to Kabat's numbering system have a metal-chelating activity. In another non-limiting embodiment of the present invention, the heavy-chain variable region of an antigen-binding molecule of the present invention can be designed to have, for example, the calcium-binding motif of the heavy-chain variable region of SEQ ID NO: 25. Such calcium-binding motifs include those in which the amino acids at positions 95 and/or 101 according to Kabat's numbering system have a metal-chelating activity.

Amino acids having a metal-chelating activity include, for example, serine (Ser (S)), threonine (Thr (T)), asparagine (Asn (N)), glutamine (Gln (Q)), aspartic acid (Asp (D)), glutamic acid (Glu (E)), histidine (His (H)), and tyrosine (Tyr (Y)). Furthermore, the main chain carbonyl groups of amino acids at the positions described above may participate in the calcium ion binding. Surprisingly, as described in the Examples below, calcium ion-binding activity can be conferred to an antigen-binding domain of interest by grafting amino acids from a calcium-binding motif to the antigen-binding domain. It is also possible to appropriately use an EF hand, which is contained in the cadherin domain and calmodulin; C2 domain, which is contained in Protein kinase C; Gla domain, which is contained in blood coagulation protein Factor IX; C-type lectin, which is contained in acyaroglycoprotein receptor and mannose-binding receptor; A domain, which is contained in LDL receptor; Annexin, thrombospondin type-3 domain, and EGF-like domain.

Specificity

"Specific" means that a molecule does not show any significant binding to molecules other than a single or a number of binding partner molecules. Furthermore, "specific" is also used when an antigen-binding domain is specific to a particular epitope among multiple epitopes in an antigen. When an epitope bound by an antigen-binding domain is contained in multiple different antigens, antigen-binding molecules containing the antigen-binding domain can bind to various antigens that have the epitope.

Antibody

Herein, "antibody" refers to a natural immunoglobulin or an immunoglobulin produced by partial or complete synthesis. Antibodies can be isolated from natural sources such as naturally-occurring plasma and serum, or culture supernatants of antibody-producing hybridomas. Alternatively, antibodies can be partially or completely synthesized using techniques such as genetic recombination. Preferred antibodies include, for example, antibodies of an immunoglobulin isotype or subclass belonging thereto. Known human immunoglobulins include antibodies of the following nine classes (isotypes): IgG1, IgG2, IgG3, IgG4, IgA1, IgA2, IgD, IgE, and IgM. Of these isotypes, antibodies of the present invention include IgG1, IgG2, IgG3, and IgG4.

Methods for producing an antibody with desired binding activity are known to those skilled in the art. Below is an example that describes a method for producing an antibody that binds to IL-6R (anti-IL-6R antibody). Antibodies that bind to an antigen other than IL-6R can also be produced according to the example described below.

Anti-IL-6R antibodies can be obtained as polyclonal or monoclonal antibodies using known methods. The anti-IL-6R antibodies preferably produced are monoclonal antibodies derived from mammals. Such mammal-derived monoclonal antibodies include antibodies produced by hybridomas or host cells transformed with an expression vector carrying an antibody gene by genetic engineering techniques. "Humanized antibodies" or "chimeric antibodies" are included in the monoclonal antibodies of the present invention.

Monoclonal antibody-producing hybridomas can be produced using known techniques, for example, as described below. Specifically, mammals are immunized by conventional immunization methods using an IL-6R protein as a sensitizing antigen. Resulting immune cells are fused with known parental cells by conventional cell fusion methods. Then, hybridomas producing an anti-IL-6R antibody can be selected by screening for monoclonal antibody-producing cells using conventional screening methods.

Specifically, monoclonal antibodies are prepared as mentioned below. First, the IL-6R gene whose nucleotide sequence is disclosed in SEQ ID NO: 16 can be expressed to produce an IL-6R protein shown in SEQ ID NO: 15, which will be used as a sensitizing antigen for antibody preparation. That is, a gene sequence encoding IL-6R is inserted into a known expression vector, and appropriate host cells are transformed with this vector. The desired human IL-6R protein is purified from the host cells or their culture supernatants by known methods. In order to obtain soluble IL-6R from culture supernatants, for example, a protein consisting of the amino acids at positions 1 to 357 in the IL-6R polypeptide sequence of SEQ ID NO: 15, such as described in Mullberg et al. (J. Immunol. (1994) 152 (10), 4958-4968), is expressed as a soluble IL-6R, instead of the IL-6R protein of SEQ ID NO: 15. Purified natural IL-6R protein can also be used as a sensitizing antigen.

The purified IL-6R protein can be used as a sensitizing antigen for immunization of mammals. A partial IL-6R peptide may also be used as a sensitizing antigen. In this case, a partial peptide can be prepared by chemical synthesis based on the amino acid sequence of human IL-6R, or by inserting a partial IL-6R gene into an expression vector for expression. Alternatively, a partial peptide can be produced by degrading an IL-6R protein with a protease. The length and region of the partial IL-6R peptide are not limited to particular embodiments. A preferred region can be arbitrarily selected from the amino acid sequence at amino acid positions 20 to 357 in the amino acid sequence of SEQ ID NO: 15. The number of amino acids forming a peptide to be used as a sensitizing antigen is preferably at least five or more, six or more, or seven or more. More specifically, a peptide of 8 to 50 residues, more preferably 10 to 30 residues can be used as a sensitizing antigen.

For sensitizing antigen, alternatively it is possible to use a fusion protein prepared by fusing a desired partial polypeptide or peptide of the IL-6R protein with a different polypeptide. For example, antibody Fc fragments and peptide tags are preferably used to produce fusion proteins to be used as sensitizing antigens. Vectors for expression of such fusion proteins can be constructed by fusing in frame genes encoding two or more desired polypeptide fragments and inserting the fusion gene into an expression vector as described above. Methods for producing fusion proteins are described in Molecular Cloning 2nd ed. (Sambrook, J et al., Molecular Cloning 2nd ed., 9.47-9.58 (1989) Cold Spring Harbor Lab. Press). Methods for preparing IL-6R to be used as a sensitizing antigen, and immunization methods using IL-6R are specifically described in WO 2003/000883, WO 2004/022754, WO 2006/006693, and such.

There is no particular limitation on the mammals to be immunized with the sensitizing antigen. However, it is preferable to select the mammals by considering their compatibility with the parent cells to be used for cell fusion. In general, rodents such as mice, rats, and hamsters, rabbits, and monkeys are preferably used.

The above animals are immunized with a sensitizing antigen by known methods. Generally performed immunization methods include, for example, intraperitoneal or subcutaneous administration of a sensitizing antigen into mammals. Specifically, a sensitizing antigen is appropriately diluted with PBS (Phosphate-Buffered Saline), physiological saline, or the like. If desired, a conventional adjuvant such as Freund's complete adjuvant is mixed with the antigen, and the mixture is emulsified. Then, the sensitizing antigen is administered to a mammal several times at 4-to 21-day intervals. Appropriate carriers may be used in immunization with the sensitizing antigen. In particular, when a low-molecular-weight partial peptide is used as the sensitizing antigen, it is sometimes desirable to couple the sensitizing antigen peptide to a carrier protein such as albumin or keyhole limpet hemocyanin for immunization.

Alternatively, hybridomas producing a desired antibody can be prepared using DNA immunization as mentioned below. DNA immunization is an immunization method that confers immunostimulation by expressing a sensitizing antigen in an animal immunized as a result of administering a vector DNA constructed to allow expression of an antigen protein-encoding gene in the animal. As compared to conventional immunization methods in which a protein antigen is administered to animals to be immunized, DNA immunization is expected to be superior in that:

immunostimulation can be provided while retaining the structure of a membrane protein such as IL-6R; and there is no need to purify the antigen for immunization.

In order to prepare a monoclonal antibody of the present invention using DNA immunization, first, a DNA expressing an IL-6R protein is administered to an animal to be immunized. The IL-6R-encoding DNA can be synthesized by known methods such as PCR. The obtained DNA is inserted into an appropriate expression vector, and then this is administered to an animal to be immunized. Preferably used expression vectors include, for example, commercially-available expression vectors such as pcDNA3.1. Vectors can be administered to an organism using conventional methods. For example, DNA immunization is performed by using a gene gun to introduce expression vector-coated gold particles into cells in the body of an animal to be immunized. Antibodies that recognized IL-6R can also be produced by the methods described in WO 2003/104453.

After immunizing a mammal as described above, an increase in the titer of an IL-6R-binding antibody is confirmed in the serum. Then, immune cells are collected from the mammal, and then subjected to cell fusion. In particular, splenocytes are preferably used as immune cells.

A mammalian myeloma cell is used as a cell to be fused with the above-mentioned immune cells. The myeloma cells preferably comprise a suitable selection marker for screening. A selection marker confers characteristics to cells for their survival (or death) under a specific culture condition. Hypoxanthine-guanine phosphoribosyltransferase deficiency (hereinafter abbreviated as HGPRT deficiency) and thymidine kinase deficiency (hereinafter abbreviated as TK deficiency) are known as selection markers. Cells with HGPRT or TK deficiency have hypoxanthine-aminopterin-thymidine sensitivity (hereinafter abbreviated as HAT sensitivity). HAT-sensitive cells cannot synthesize DNA in a HAT selection medium, and are thus killed. However, when the cells are fused with normal cells, they can continue DNA synthesis using the salvage pathway of the normal cells, and therefore they can grow even in the HAT selection medium.

HGPRT-deficient and TK-deficient cells can be selected in a medium containing 6-thioguanine, 8-azaguanine (hereinafter abbreviated as 8AG), or 5'-bromodeoxyuridine, respectively. Normal cells are killed because they incorporate these pyrimidine analogs into their DNA. Meanwhile, cells that are deficient in these enzymes can survive in the selection medium, since they cannot incorporate these pyrimidine analogs. In addition, a selection marker referred to as G418 resistance provided by the neomycin-resistant gene confers resistance to 2-deoxystreptamine antibiotics (gentamycin analogs). Various types of myeloma cells that are suitable for cell fusion are known.

For example, myeloma cells including the following cells can be preferably used:

P3(P3x63Ag8.653) (J. Immunol. (1979) 123 (4), 1548-1550);

P3x63Ag8U.1 (Current Topics in Microbiology and Immunology (1978)81, 1-7);

NS-1 (C. Eur. J. Immunol. (1976)6 (7), 511-519);

MPC-11 (Cell (1976) 8 (3), 405-415);

SP2/0 (Nature (1978) 276 (5685), 269-270);

FO (J. Immunol. Methods (1980) 35 (1-2), 1-21);

S194/5.XX0.BU.1 (J. Exp. Med. (1978) 148 (1), 313-323);

R210 (Nature (1979) 277 (5692), 131-133), etc.

Cell fusions between the immunocytes and myeloma cells are essentially carried out using known methods, for example, a method by Kohler and Milstein et al. (Methods Enzymol. (1981) 73: 3-46).

More specifically, cell fusion can be carried out, for example, in a conventional culture medium in the presence of a cell fusion-promoting agent. The fusion-promoting agents include, for example, polyethylene glycol (PEG) and Sendai virus (HVJ). If required, an auxiliary substance such as dimethyl sulfoxide is also added to improve fusion efficiency.

The ratio of immune cells to myeloma cells may be determined at one's own discretion, preferably, for example, one myeloma cell for every one to ten immunocytes. Culture media to be used for cell fusions include, for example, media that are suitable for the growth of myeloma cell lines, such as RPMI1640 medium and MEM medium, and other conventional culture medium used for this type of cell culture. In addition, serum supplements such as fetal calf serum (FCS) may be preferably added to the culture medium.

For cell fusion, predetermined amounts of the above immune cells and myeloma cells are mixed well in the above culture medium. Then, a PEG solution (for example, the average molecular weight is about 1,000 to 6,000) prewarmed to about 37° C. is added thereto at a concentration of generally 30% to 60% (w/v). This is gently mixed to produce desired fusion cells (hybridomas). Then, an appropriate culture medium mentioned above is gradually added to the cells, and this is repeatedly centrifuged to remove the supernatant. Thus, cell fusion agents and such which are unfavorable to hybridoma growth can be removed.

The hybridomas thus obtained can be selected by culture using a conventional selective medium, for example, HAT medium (a culture medium containing hypoxanthine, aminopterin, and thymidine). Cells other than the desired hybridomas (non-fused cells) can be killed by continuing culture in the above HAT medium for a sufficient period of time. Typically, the period is several days to several weeks. Then, hybridomas producing the desired antibody are screened and singly cloned by conventional limiting dilution methods.

The hybridomas thus obtained can be selected using a selection medium based on the selection marker possessed by the myeloma used for cell fusion. For example, HGPRT- or TK-deficient cells can be selected by culture using the HAT medium (a culture medium containing hypoxanthine, aminopterin, and thymidine). Specifically, when HAT-sensitive myeloma cells are used for cell fusion, cells successfully fused with normal cells can selectively proliferate in the HAT medium. Cells other than the desired hybridomas (non-fused cells) can be killed by continuing culture in the above HAT medium for a sufficient period of time. Specifically, desired hybridomas can be selected by culture for generally several days to several weeks. Then, hybridomas producing the desired antibody are screened and singly cloned by conventional limiting dilution methods.

Desired antibodies can be preferably selected and singly cloned by screening methods based on known antigen/antibody reaction. For example, an IL-6R-binding monoclonal antibody can bind to IL-6R expressed on the cell surface. Such a monoclonal antibody can be screened by fluorescence activated cell sorting (FACS). FACS is a system that assesses the binding of an antibody to cell surface by analyzing cells contacted with a fluorescent antibody using laser beam, and measuring the fluorescence emitted from individual cells.

To screen for hybridomas that produce a monoclonal antibody of the present invention by FACS, IL-6R-expressing cells are first prepared. Cells preferably used for screening are mammalian cells in which IL-6R is forcedly expressed. As control, the activity of an antibody to bind to cell-surface IL-6R can be selectively detected using non-transformed mammalian cells as host cells. Specifically, hybridomas producing an anti-IL-6R monoclonal antibody can be isolated by selecting hybridomas that produce an antibody which binds to cells forced to express IL-6R, but not to host cells.

Alternatively, the activity of an antibody to bind to immobilized IL-6R-expressing cells can be assessed based on the principle of ELISA. For example, IL-6R-expressing cells are immobilized to the wells of an ELISA plate. Culture supernatants of hybridomas are contacted with the immobilized cells in the wells, and antibodies that bind to the immobilized cells are detected. When the monoclonal antibodies are derived from mouse, antibodies bound to the cells can be detected using an anti-mouse immunoglobulin antibody. Hybridomas producing a desired antibody having the antigen-binding ability are selected by the above screening, and they can be cloned by a limiting dilution method or the like.

Monoclonal antibody-producing hybridomas thus prepared can be passaged in a conventional culture medium, and stored in liquid nitrogen for a long period.

The above hybridomas are cultured by a conventional method, and desired monoclonal antibodies can be prepared from the culture supernatants. Alternatively, the hybridomas are administered to and grown in compatible mammals, and monoclonal antibodies are prepared from the ascites. The former method is suitable for preparing antibodies with high purity.

Antibodies encoded by antibody genes that are cloned from antibody-producing cells such as the above hybridomas can also be preferably used. A cloned antibody gene is inserted into an appropriate vector, and this is introduced into a host to express the antibody encoded by the gene. Methods for isolating antibody genes, inserting the genes into vectors, and transforming host cells have already been established, for example, by Vandamme et al. (Eur. J. Biochem. (1990) 192(3), 767-775). Methods for producing recombinant antibodies are also known as described below.

For example, a cDNA encoding the variable region (V region) of an anti-IL-6R antibody is prepared from hybridoma cells expressing the anti-IL-6R antibody. For this purpose, total RNA is first extracted from hybridomas. Methods used for extracting mRNAs from cells include, for example:
the guanidine ultracentrifugation method (Biochemistry (1979) 18(24), 5294-5299), and
the AGPC method (Anal. Biochem. (1987) 162(1), 156-159)

Extracted mRNAs can be purified using the mRNA Purification Kit (GE Healthcare Bioscience) or such. Alternatively, kits for extracting total mRNA directly from cells, such as the QuickPrep mRNA Purification Kit (GE Healthcare Bioscience), are also commercially available. mRNAs can be prepared from hybridomas using such kits. cDNAs encoding the antibody V region can be synthesized from the prepared mRNAs using a reverse transcriptase. cDNAs can be synthesized using the AMV Reverse Transcriptase First-strand cDNA Synthesis Kit (Seikagaku Co.) or such. Furthermore, the SMART RACE cDNA amplification kit (Clontech) and the PCR-based 5'-RACE method (Proc. Natl. Acad. Sci. USA (1988) 85(23), 8998-9002; Nucleic Acids Res. (1989) 17(8), 2919-2932) can be appropriately used to synthesize and amplify cDNAs. In such a cDNA synthesis process, appropriate restriction enzyme sites described below may be introduced into both ends of a cDNA.

The cDNA fragment of interest is purified from the resulting PCR product, and then this is ligated to a vector DNA. A recombinant vector is thus constructed, and introduced into E. coli or such. After colony selection, the desired recombinant vector can be prepared from the colony-forming E. coli. Then, whether the recombinant vector has the cDNA nucleotide sequence of interest is tested by a known method such as the dideoxy nucleotide chain termination method.

The 5'-RACE method which uses primers to amplify the variable region gene is conveniently used for isolating the gene encoding the variable region. First, a 5'-RACE cDNA library is constructed by cDNA synthesis using RNAs extracted from hybridoma cells as a template. A commercially available kit such as the SMART RACE cDNA amplification kit is appropriately used to synthesize the 5'-RACE cDNA library.

The antibody gene is amplified by PCR using the prepared 5'-RACE cDNA library as a template. Primers for amplifying the mouse antibody gene can be designed based on known antibody gene sequences. The nucleotide sequences of the primers vary depending on the immunoglobulin subclass. Therefore, it is preferable that the subclass is determined in advance using a commercially available kit such as the Iso Strip mouse monoclonal antibody isotyping kit (Roche Diagnostics).

Specifically, for example, primers that allow amplification of genes encoding γ1, γ2a, γ2b, and γ3 heavy chains and x and X light chains are used to isolate mouse IgG-encoding genes. In general, a primer that anneals to a constant region site close to the variable region is used as a 3'-side primer to amplify an IgG variable region gene. Meanwhile, a primer attached to a 5' RACE cDNA library construction kit is used as a 5'-side primer.

PCR products thus amplified are used to reshape immunoglobulins composed of a combination of heavy and light chains. A desired antibody can be selected using the IL-6R-binding activity of a reshaped immunoglobulin as an indicator. For example, when the objective is to isolate an antibody against IL-6R, it is more preferred that the binding of the antibody to IL-6R is specific. An IL-6R-binding antibody can be screened, for example, by the following steps:
(1) contacting an IL-6R-expressing cell with an antibody comprising the V region encoded by a cDNA isolated from a hybridoma;
(2) detecting the binding of the antibody to the IL-6R-expressing cell; and (3) selecting an antibody that binds to the IL-6R-expressing cell.

Methods for detecting the binding of an antibody to IL-6R-expressing cells are known. Specifically, the binding of an antibody to IL-6R-expressing cells can be detected by the above-described techniques such as FACS. Immobilized samples of IL-6R-expressing cells are appropriately used to assess the binding activity of an antibody.

Preferred antibody screening methods that use the binding activity as an indicator also include panning methods using phage vectors. Screening methods using phage vectors are advantageous when the antibody genes are isolated from heavy-chain and light-chain subclass libraries from a polyclonal antibody-expressing cell population. Genes encoding the heavy-chain and light-chain variable regions can be linked by an appropriate linker sequence to form a single-chain Fv (scFv). Phages presenting scFv on their surface can be produced by inserting a gene encoding scFv into a phage vector. The phages are contacted with an antigen of interest. Then, a DNA encoding scFv having the binding activity of interest can be isolated by collecting phages bound to the antigen. This process can be repeated as necessary to enrich scFv having the binding activity of interest.

After isolation of the cDNA encoding the V region of the anti-IL-6R antibody of interest, the cDNA is digested with restriction enzymes that recognize the restriction sites introduced into both ends of the cDNA. Preferred restriction enzymes recognize and cleave a nucleotide sequence that occurs in the nucleotide sequence of the antibody gene at a low frequency. Furthermore, a restriction site for an enzyme that produces a sticky end is preferably introduced into a vector to insert a single-copy digested fragment in the correct orientation. The cDNA encoding the V region of the anti-IL-6R antibody is digested as described above, and this is inserted into an appropriate expression vector to construct an antibody expression vector. In this case, if a gene encoding the antibody constant region (C region) and a gene encoding the above V region are fused in-frame, a chimeric antibody is obtained. Herein, "chimeric antibody" means that the origin of the constant region is different from that of the variable region. Thus, in addition to mouse/human heterochimeric antibodies, human/human allochimeric antibodies are included in the chimeric antibodies of the present invention. A chimeric antibody expression vector can be constructed by inserting the above V region gene into an expression vector that already has the constant region. Specifically, for example, a recognition sequence for a restriction enzyme that excises the above V region gene can be appropriately placed on the 5' side of an expression vector carrying a DNA encoding a desired antibody constant region (C region). A chimeric antibody expression vector is constructed by fusing in frame the two genes digested with the same combination of restriction enzymes.

To produce an anti-IL-6R monoclonal antibody, antibody genes are inserted into an expression vector so that the genes are expressed under the control of an expression regulatory region. The expression regulatory region for antibody expression includes, for example, enhancers and promoters. Furthermore, an appropriate signal sequence may be attached to the amino terminus so that the expressed antibody is secreted to the outside of cells. For example, a peptide having the amino acid sequence MGWSCIILFL-VATATGVHS (SEQ ID NO: 113) can be used as a signal sequence. Meanwhile, other appropriate signal sequences may be attached. The expressed polypeptide is cleaved at the carboxyl terminus of the above sequence, and the resulting polypeptide is secreted to the outside of cells as a mature polypeptide. Then, appropriate host cells are transformed with the expression vector, and recombinant cells expressing the anti-IL-6R antibody-encoding DNA are obtained.

DNAs encoding the antibody heavy chain (H chain) and light chain (L chain) are separately inserted into different expression vectors to express the antibody gene. An antibody molecule having the H and L chains can be expressed by co-transfecting the same host cell with vectors into which the H-chain and L-chain genes are respectively inserted. Alternatively, host cells can be transformed with a single expression vector into which DNAs encoding the H and L chains are inserted (see WO 1994011523).

There are various known host cell/expression vector combinations for antibody preparation by introducing isolated antibody genes into appropriate hosts. All of these expression systems are applicable to isolation of the antigen-binding domains of the present invention. Appropriate eukaryotic cells used as host cells include animal cells, plant cells, and fungal cells. Specifically, the animal cells include, for example, the following cells.

(1) mammalian cells: CHO, COS, myeloma, baby hamster kidney (BHK), HeLa, Vero, or such;
(2) amphibian cells: *Xenopus* oocytes, or such; and
(3) insect cells: sf9, sf21, Tn5, or such.

In addition, as a plant cell, an antibody gene expression system using cells derived from the *Nicotiana* genus such as *Nicotiana tabacum* is known. Callus cultured cells can be appropriately used to transform plant cells.

Furthermore, the following cells can be used as fungal cells:

yeasts: the *Saccharomyces* genus such as *Saccharomyces cerevisiae*, and the *Pichia* genus such as *Pichia pastoris*; and filamentous fungi: the *Aspergillus* genus such as *Aspergillus niger*.

Furthermore, antibody gene expression systems that utilize prokaryotic cells are also known. For example, when using bacterial cells, *E. coli* cells, *Bacillus subtilis* cells, and such can suitably be utilized in the present invention. Expression vectors carrying the antibody genes of interest are introduced into these cells by transfection. The transfected cells are cultured in vitro, and the desired antibody can be prepared from the culture of transformed cells.

In addition to the above-described host cells, transgenic animals can also be used to produce a recombinant antibody. That is, the antibody can be obtained from an animal into which the gene encoding the antibody of interest is introduced. For example, the antibody gene can be constructed as a fusion gene by inserting in frame into a gene that encodes a protein produced specifically in milk. Goat β-casein or such can be used, for example, as the protein secreted in milk. DNA fragments containing the fused gene inserted with the antibody gene is injected into a goat embryo, and then this embryo is introduced into a female goat. Desired antibodies can be obtained as a protein fused with the milk protein from milk produced by the transgenic goat born from the embryo-recipient goat (or progeny thereof). In addition, to increase the volume of milk containing the desired antibody produced by the transgenic goat, hormones can be administered to the transgenic goat as necessary (Ebert, K. M. et al., Bio/Technology (1994) 12 (7), 699-702).

When an antigen-binding molecule described herein is administered to human, an antigen-binding domain derived from a genetically recombinant antibody that has been artificially modified to reduce the heterologous antigenicity against human and such, can be appropriately used as the antigen-binding domain of the complex. Such genetically recombinant antibodies include, for example, humanized antibodies. These modified antibodies are appropriately produced by known methods.

An antibody variable region used to produce the antigen-binding domain of an antigen-binding molecule described herein is generally formed by three complementarity-determining regions (CDRs) that are separated by four framework regions (FRs). CDR is a region that substantially determines the binding specificity of an antibody. The amino acid sequences of CDRs are highly diverse. On the other hand, the FR-forming amino acid sequences often have high identity even among antibodies with different binding specificities. Therefore, generally, the binding specificity of a certain antibody can be introduced to another antibody by CDR grafting.

A humanized antibody is also called a reshaped human antibody. Specifically, humanized antibodies prepared by grafting the CDR of a non-human animal antibody such as a mouse antibody to a human antibody and such are known. Common genetic engineering techniques for obtaining humanized antibodies are also known. Specifically, for example, overlap extension PCR is known as a method for grafting a mouse antibody CDR to a human FR. In overlap extension PCR, a nucleotide sequence encoding a mouse antibody CDR to be grafted is added to primers for synthesizing a human antibody FR. Primers are prepared for each of the four FRs. It is generally considered that when grafting a mouse CDR to a human FR, selecting a human FR that has high identity to a mouse FR is advantageous for maintaining the CDR function. That is, it is generally preferable to use a human FR comprising an amino acid sequence which has high identity to the amino acid sequence of the FR adjacent to the mouse CDR to be grafted.

Nucleotide sequences to be ligated are designed so that they will be connected to each other in frame. Human FRs are individually synthesized using the respective primers. As a result, products in which the mouse CDR-encoding DNA is attached to the individual FR-encoding DNAs are obtained. Nucleotide sequences encoding the mouse CDR of each product are designed so that they overlap with each other. Then, complementary strand synthesis reaction is conducted to anneal the overlapping CDR regions of the products synthesized using a human antibody gene as template. Human FRs are ligated via the mouse CDR sequences by this reaction.

The full length V region gene, in which three CDRs and four FRs are ultimately ligated, is amplified using primers that anneal to its 5'- or 3'-end, which are added with suitable restriction enzyme recognition sequences. An expression vector for humanized antibody can be produced by inserting the DNA obtained as described above and a DNA that encodes a human antibody C region into an expression vector so that they will ligate in frame. After the recombinant vector is transfected into a host to establish recombinant cells, the recombinant cells are cultured, and the DNA encoding the humanized antibody is expressed to produce the humanized antibody in the cell culture (see, European Patent Publication No. EP 239400 and International Patent Publication No. WO 1996/002576).

By qualitatively or quantitatively measuring and evaluating the antigen-binding activity of the humanized antibody produced as described above, one can suitably select human antibody FRs that allow CDRs to form a favorable antigen-binding site when ligated through the CDRs. Amino acid residues in FRs may be substituted as necessary, so that the CDRs of a reshaped human antibody form an appropriate antigen-binding site. For example, amino acid sequence mutations can be introduced into FRs by applying the PCR method used for grafting a mouse CDR into a human FR. More specifically, partial nucleotide sequence mutations can be introduced into primers that anneal to the FR. Nucleotide sequence mutations are introduced into the FRs synthesized by using such primers. Mutant FR sequences having the desired characteristics can be selected by measuring and evaluating the activity of the amino acid-substituted mutant antibody to bind to the antigen by the above-mentioned method (Cancer Res. (1993) 53: 851-856).

Alternatively, desired human antibodies can be obtained by immunizing transgenic animals having the entire repertoire of human antibody genes (see WO 1993/012227; WO 1992/003918; WO 1994/002602; WO 1994/025585; WO 1996/034096; WO 1996/033735) by DNA immunization.

Furthermore, techniques for preparing human antibodies by panning using human antibody libraries are also known. For example, the V region of a human antibody is expressed as a single-chain antibody (scFv) on phage surface by the phage display method. Phages expressing an scFv that binds to the antigen can be selected. The DNA sequence encoding the human antibody V region that binds to the antigen can be determined by analyzing the genes of selected phages. The DNA sequence of the scFv that binds to the antigen is determined. An expression vector is prepared by fusing the V region sequence in frame with the C region sequence of a desired human antibody, and inserting this into an appropriate expression vector. The expression vector is introduced into cells appropriate for expression such as those described above. The human antibody can be produced by expressing the human antibody-encoding gene in the cells. These methods are already known (see WO 1992/001047; WO 1992/020791; WO 1993/006213; WO 1993/011236; WO 1993/019172; WO 1995/001438; WO 1995/015388).

In addition to the techniques described above, techniques of B cell cloning (identification of each antibody-encoding sequence, cloning and its isolation; use in constructing expression vector in order to prepare each antibody (IgG1, IgG2, IgG3, or IgG4 in particular); and such) such as described in Bernasconi et al. (Science (2002) 298: 2199-2202) or in WO 2008/081008 can be appropriately used to isolate antibody genes.

EU Numbering System

According to the methods used in the present invention, amino acid positions assigned to antibody CDR and FR are specified according to Kabat's numbering (Sequences of Proteins of Immunological Interest (National Institute of Health, Bethesda, Md., 1987 and 1991)). Herein, when an antigen-binding molecule is an antibody or antigen-binding fragment, variable region amino acids are indicated according to Kabat's numbering system, while constant region amino acids are indicated according to EU numbering system based on Kabat's amino acid positions.

Antigen Uptake into Cells or Promoting the Antigen Uptake into Cells

Herein, "antigen uptake into cells" mediated by antigen-binding molecules means that antigens are incorporated into cells via endocytosis. Herein, "promoting the antigen uptake into cells" means increasing the rate of cellular uptake of an antigen-binding molecule that has bound to an antigen in plasma and/or decreasing the amount of antigen recycled to plasma after uptake. In the present invention, the rate of uptake into cells may be enhanced compared to that of the antigen-binding molecule before reducing its antigen-binding activity under a low calcium concentration condition to be lower than that under a high calcium concentration condition. Thus, in the present invention, whether antigen uptake into cells is facilitated by an antigen-binding molecule can be assessed based on an increase in the rate of antigen uptake into cells. The rate of antigen uptake into cells can be calculated, for example, by monitoring over time reduction in the antigen concentration in the culture medium containing human FcRn-expressing cells after adding the antigen and antigen-binding molecule to the medium, or monitoring over time the amount of antigen uptake into human FcRn-expressing cells.

Using methods of the present invention for facilitating the rate of antigen-binding molecule-mediated antigen uptake into cells, for example, the rate of antigen elimination from the plasma can be enhanced by administering antigen-binding molecules. Thus, whether antigen-binding molecule-mediated antigen uptake into cells is facilitated can also be assessed, for example, by testing whether the rate of antigen elimination from the plasma is accelerated or whether the plasma antigen concentration is reduced by administering an antigen-binding molecule. Specifically, the reduction of the antigen concentration in plasma can also be promoted by administering antigen-binding molecules of the present invention.

The Number of Times of Antigen Binding by One Antigen-Binding Molecule

Herein, "the number of times of antigen binding by one antigen-binding molecule" means the number of times of antigen binding that can be achieved by one antigen-binding molecule until it is eliminated due to degradation. Herein, "increasing the number of times of antigen binding by one antigen-binding molecule" means increasing the number of cycles that can be achieved by one antigen-binding molecule until it is eliminated due to degradation when defining as "one cycle" the process in which the antigen-binding molecule binds to an antigen in plasma, and the antigen-binding molecule bound to the antigen is taken up into cells, and dissociates from the antigen in an endosome, and then the antigen-binding molecule returns to plasma. In the present invention, the number of cycles may be increased compared to that of an antigen-binding molecule whose antigen-binding activity under a low calcium concentration condition is not lower than that under a high calcium concentration condition, or that of the antigen-binding molecule before reducing its antigen-binding activity under a low calcium concentration condition to be lower than that under a high calcium concentration condition. Thus, whether the number of cycles is increased can be assessed by testing whether "the uptake into cells is promoted" as described above or whether "the plasma retention is improved" as described below.

Improvement of Plasma Retention

Herein, "improvement of the plasma retention" is interchangeable with "enhancement of the pharmacokinetics", "improvement of the pharmacokinetics", "superior pharmacokinetics", "enhancement of the plasma retention", "excellence in plasma retention", or "prolongation of the plasma retention". These phrases are synonymous.

Herein, "improvement of plasma retention" means not only prolongation of the period until elimination from the plasma (for example, until the antigen-binding molecule is degraded intracellularly or the like and cannot return to the plasma) after administration of the antigen-binding molecule to animals such as humans, mice, rats, monkeys, rabbits, and dogs, but also prolongation of the plasma retention of the antigen-binding molecule in a form that allows antigen binding (for example, in an antigen-free form of the antigen-binding molecule) during the period of administration to elimination due to degradation. Specifically, "improvement of plasma retention" also includes prolongation of the period until elimination due to degradation of the antigen-binding molecule not bound to antigens (the antigen-free form of antigen-binding molecule).

The antigen-binding molecule in plasma cannot bind to a new antigen if the antigen-binding molecule has already bound to an antigen. Thus, the longer the period that the antigen-binding molecule is not bound to an antigen, the longer the period that it can bind to a new antigen (the higher the chance of binding to another antigen). This enables reduction of the time period that an antigen is free of the antigen-binding molecule in vivo and prolongation of the period that an antigen is bound to the antigen-binding molecule. The plasma concentration of the antigen-free form of antigen-binding molecule can be increased and the period that the antigen is bound to the antigen-binding molecule can be prolonged by accelerating the antigen elimination from the plasma by administration of the antigen-binding molecule. Specifically, as used herein, "improvement of the plasma retention of an antigen-binding molecule" includes improvement of any pharmacokinetic parameter (such as prolongation of half-life in plasma, prolongation of mean plasma retention time, or reduction of clearance in plasma) of an antigen-free antigen-binding molecule of the present invention, prolongation of the period where an antigen is bound to the antigen-binding molecule after administration of the antigen-binding molecule, and enhancement of antigen elimination from plasma by the antigen-binding molecule, as compared to an antigen-free antigen-binding molecule whose antigen-binding activity under a low calcium concentration condition is not lower than that under a high calcium concentration condition, or an antigen-free antigen-binding molecule before reducing its antigen-binding activity under a low calcium concentration condition to be lower than that under a high calcium concentration condition.

Whether the pharmacokinetics parameters are improved can be assessed by determining any one of the parameters, half-life in plasma, mean plasma retention time, and plasma clearance for the antigen-binding molecule or the antigen-free form thereof ("Pharmacokinetics: Enshu-niyoru Rikai (Understanding through practice)" Nanzando). For example, the plasma concentration of the antigen-binding molecule or antigen-free form thereof is determined after administration of the antigen-binding molecule to mice, rats, monkeys, rabbits, dogs, or humans. Then, each parameter is determined. When the plasma half-life or mean plasma retention time is prolonged, the plasma retention of the antigen-binding molecule can be judged to be improved. The parameters can be determined by methods known to those skilled in the art. The parameters can be appropriately assessed, for example, by noncompartmental analysis using the pharmacokinetics analysis software WinNonlin (Pharsight) according to the appended instruction manual. The plasma concentration of antigen-free form of antigen-binding molecule can be determined by methods known to those skilled in the art, for example, using the assay method described in Clin Pharmacol. 2008 April; 48(4): 406-17.

Herein, "improvement of the plasma retention" also includes prolongation of the period where an antigen is bound to an antigen-binding molecule after administration of the antigen-binding molecule. Whether the period where an antigen is bound to an antigen-binding molecule after administration of the antigen-binding molecule is prolonged can be assessed based on the time until the increase in the concentration (ratio) by measuring the plasma concentration of the antigen-binding molecule-unbound antigen (free antigen), or the ratio of the concentration of the antigen-binding molecule-unbound antigen (concentration of the free antigen) to the total antigen concentration.

In the present invention, the "antigen concentration in plasma" can be determined by measuring the plasma concentration of an antigen-binding molecule-free antigen, or the ratio of the concentration of the antigen-binding molecule-free antigen to the total antigen concentration, using methods known to those skilled in the art, for example, measurement methods described in Pharm Res. 2006 January; 23(1): 95-103.

Alternatively, when an antigen exhibits a particular function in vivo, whether the antigen is bound to an antigen-binding molecule that neutralizes the antigen function (antagonistic molecule) can be assessed by testing whether the antigen function is neutralized. Whether the antigen function is neutralized can be assessed by assaying an in vivo marker that reflects the antigen function. Whether the antigen is bound to an antigen-binding molecule that activates the antigen function (agonistic molecule) can be assessed by assaying an in vivo marker that reflects the antigen function.

Determination of the plasma concentration of antigen-binding molecule-free antigen and ratio of the concentration of antigen-binding molecule-free antigen to the total antigen concentration, in vivo marker assay, and such measurements are not particularly limited; however, the assays are preferably carried out after a certain period of time has passed after administration of the antigen-binding molecule. In the present invention, the period after administration of the antigen-binding molecule is not particularly limited; those skilled in the art can determine the appropriate period depending on the properties and the like of the administered antigen-binding molecule. Such periods include, for example, one day after administration of the antigen-binding molecule, three days after administration of the antigen-binding molecule, seven days after administration of the antigen-binding molecule, 14 days after administration of the antigen-binding molecule, and 28 days after administration of the antigen-binding molecule.

In the present invention, improvement of plasma retention in human is preferred. When the plasma retention in human is difficult to determine, it may be predicted based on the plasma retention in mice (for example, normal mice, human antigen-expressing transgenic mice, human FcRn-expressing transgenic mice) or monkeys (for example, cynomolgus monkeys).

Dissociation of an Antigen within a Cell from an Extracellularly-Bound Antigen-Binding Molecule The present invention is also applicable as a method for promoting the dissociation of an antigen within a cell from an extracellularly-bound antigen-binding molecule. In the present invention, the antigen may dissociate from the antigen-binding molecule anywhere in a cell; however, it is preferred that the antigen dissociates within an early endosome. In the present invention, "an antigen dissociates within a cell from an extracellularly-bound antigen-binding molecule" does not necessarily mean that every antigen which has been taken up into a cell by extracellularly binding to the antigen-binding molecule dissociates from the antigen-binding molecule within the cell. It is acceptable that the proportion of the antigen that dissociates from the antigen-binding molecule within a cell is higher compared to an antigen-binding molecule whose antigen-binding activity under a low calcium concentration condition is not lower than that under a high calcium concentration condition, or the antigen-binding molecule before reducing the antigen-binding activity under a low calcium concentration condition to be lower than that under a high calcium concentration condition. The method for promoting the dissociation of an antigen within a cell from an extracellularly-bound antigen-binding molecule can also be referred to as a method for conferring to an antigen-binding molecule a property that facilitates promotion of the intracellular uptake of the antigen-binding molecule bound to an antigen, and promotion of the intracellular dissociation of the antigen from the antigen-binding molecule.

Extracellular Release in an Antigen-Free Form of an Antigen-Binding Molecule that has been Taken Up into a Cell in an Antigen-Bound Form The present invention is also applicable as a method for enhancing the extracellular release in an antigen-free form of an antigen-binding molecule that has been taken up into a cell in an antigen-bound form. In the present invention, "extracellular release in an antigen-free form of an antigen-binding molecule that has been taken up into a cell in an antigen-bound form" does not necessarily mean that every antigen-binding molecule that has been bound to an antigen and taken up into a cell is released in an antigen-free form to the outside of a cell. It is acceptable that the proportion of the antigen-binding molecule that is released in an antigen-free form to the outside of cells is higher compared to an antigen-binding molecule whose antigen-binding activity under a low calcium concentration condition is not lower than that under a high calcium concentration condition, or the antigen-binding molecule before reducing its antigen-binding activity under a low calcium concentration condition to be lower than that under a high calcium concentration condition. It is preferred that the antigen-binding molecule released to the outside of a cell retains the antigen-binding activity. The method for promoting the extracellular release in an antigen-free form of an antigen-binding molecule that has been taken up into a cell in an antigen-bound form can also be referred to as a method for conferring to an antigen-binding molecule a property that facilitates promotion of the intracellular uptake of the antigen-binding molecule bound to an antigen, and promotion of the extracellular release of the antigen-binding molecule in an antigen-free form.

Calcium concentration condition Herein, the low calcium concentration condition typically means the concentration of ionized calcium is 0.1 µM to 30 µM, preferably 0.5 µM to 10 µM, and particularly preferably 1 µM to 5 µM, which is comparable to the concentration of ionized calcium in the early endosome in vivo. Meanwhile, herein, the high calcium concentration condition typically means that the concentration of ionized calcium is 100 µM to 10 mM, preferably 200 µM to 5 mM, and particularly preferably 0.5 mM to 2.5 mM, which is comparable to the concentration of ionized calcium in plasma (blood) in vivo.

Thus, herein, "the antigen-binding activity of an antigen-binding molecule is lower under a low calcium concentration condition than under a high calcium concentration condition" means that the antigen-binding activity of an antigen-binding molecule is lower at an ionized calcium concentration of 0.1 µM to 30 µM than at an ionized calcium concentration of 100 µM to 10 mM. It preferably means that the antigen-binding activity of an antigen-binding molecule is lower at an ionized calcium concentration of 0.5 µM to 10 µM than at an ionized calcium concentration of 200 µM to 5 mM. Particularly preferably, it means that the antigen-binding activity is lower at the concentration of ionized calcium in the early endosome in vivo than at the concentration of ionized calcium in plasma in vivo; specifically, it means that the antigen-binding activity of an antigen-binding molecule is lower at an ionized calcium concentration of 1 μM to 5 μM than at an ionized calcium concentration of 0.5 mM to 2.5 mM.

Meanwhile, as used herein, the phrase "the antigen-binding activity of an antigen-binding molecule is lower under a low calcium concentration condition than under a high calcium concentration condition" is interchangeable with the phrase "the antigen-binding activity of an antigen-binding molecule is higher under a high calcium concentration condition than under a low calcium concentration condition". The phrase "the antigen-binding activity of an antigen-binding molecule is lower under a low calcium concentration condition than under a high calcium concentration condition" also means that the antigen-binding activity of an antigen-binding molecule under a low calcium concentration condition is reduced to be lower than that under a high calcium concentration condition or the antigen-binding activity of an antigen-binding molecule under a high calcium concentration condition is increased to be higher than that under a low calcium concentration condition, by modifying an amino acid sequence in the antigen-binding molecule, etc. That is, in the present invention, the ratio between the antigen-binding activity of an antigen-binding molecule under a low calcium concentration condition and that under a high calcium concentration condition may be increased. For example, in an embodiment, the ratio of KD (Ca 3 μM)/KD (Ca 2 mM) may be increased as described below.

The ratio between the antigen-binding activity of an antigen-binding molecule under a low calcium concentration condition and that under a high calcium concentration condition may be increased, for example, by lowering the antigen-binding activity under a low calcium concentration condition through selection of an antigen-binding molecule with low antigen-binding activity under a low calcium concentration condition, or through modification of an amino acid sequence in the antigen-binding molecule; or by increasing the antigen-binding activity under a high calcium concentration condition through selection of an antigen-binding molecule with high antigen-binding activity under a high calcium concentration condition, or through modification of an amino acid sequence in the antigen-binding molecule; or by both of them.

Herein, the expression "the antigen-binding ability is weaker under a low calcium concentration condition than under a high calcium concentration condition", is sometimes used instead of the phrase "the antigen-binding activity is lower under a low calcium concentration condition than under a high calcium concentration condition". Furthermore, the expression, "weakening the antigen-binding ability under a low calcium concentration condition to be lower than that under a high calcium concentration condition", is sometimes used instead of the phrase "reducing the antigen-binding activity under a low calcium concentration condition to be lower than that under a high calcium concentration condition".

FcRn

Unlike Fcγ receptor belonging to the immunoglobulin superfamily, FcRn, particularly human FcRn, is structurally similar to polypeptides of major histocompatibility complex (MHC) class I, exhibiting 22% to 29% sequence identity to class I MHC molecules (Ghetie el al., Immunol. Today (1997) 18 (12): 592-598). FcRn is expressed as a heterodimer consisting of soluble β or light chain (β2 microglobulin) complexed with transmembrane a or heavy chain. Like MHC, FcRn α chain comprises three extracellular domains (α1, α2, and α3) and its short cytoplasmic domain anchors the protein onto the cell surface. α1 and α2 domains interact with the FcRn-binding domain of the antibody Fc region (Raghavan et al., Immunity (1994) 1: 303-315).

FcRn is expressed in maternal placenta and york sac of mammals, and is involved in mother-to-fetus IgG transfer. In addition, in neonatal small intestine of rodents, where FcRn is expressed, FcRn is involved in transfer of maternal IgG across brush border epithelium from ingested colostrum or milk. FcRn is expressed in a variety of other tissues and endothelial cell systems of various species. FcRn is also expressed in adult human endothelia, muscular blood vessels, and hepatic sinusoidal capillaries. FcRn is believed to play a role in maintaining the plasma IgG concentration by mediating recycling of IgG to serum upon binding to IgG Typically, binding of FcRn to IgG molecules is strictly pH dependent. The optimal binding is observed in an acidic pH range below 7.0.

Human FcRn whose precursor is a polypeptide having the signal sequence of SEQ ID NO: 17 (the polypeptide with the signal sequence is shown in SEQ ID NO: 18) forms a complex with human β2-microglobulin in vivo. Soluble human FcRn complexed with β2-microglobulin is produced by using conventional recombinant expression techniques. FcRn-binding domains of the present invention can be assessed for their binding activity to such a soluble human FcRn complexed with β2-microglobulin. Herein, unless otherwise specified, human FcRn refers to a form capable of binding to an FcRn-binding domain of the present invention. Examples include a complex between human FcRn and human β2-microglobulin.

FcRn-Binding Domain

The antigen-binding molecules of the present invention have an antigen-binding domain and a human FcRn-binding domain. The human FcRn-binding domain is not particularly limited, as long as the antigen-binding molecules exhibit the human FcRn-binding activity at acidic pH and/or neutral pH. Alternatively, the domain may have a direct or indirect human FcRn-binding activity. Such domains include, for example, the Fc region of IgG-type immunoglobulin, albumin, albumin domain 3, anti-human FcRn antibodies, anti-human FcRn peptides, and anti-human FcRn scaffold molecules, all of which have the activity to directly bind to human FcRn; and molecules that bind to IgG or albumin, which have the activity to indirectly bind to human FcRn. Such preferred domains of the present invention have human FcRn-binding activity in the acidic and neutral pH ranges. It is possible to use the domains without any alteration as long as they already have human FcRn-binding activity in the acidic and neutral pH ranges. When the domains have only weak or no human FcRn-binding activity in the acidic and/or neutral pH ranges, the human FcRn-binding activity may be conferred by altering amino acids in the antigen-binding molecules. However, it is preferred that human FcRn-binding activity in the acidic and/or neutral pH ranges is conferred by altering amino acids in the human FcRn-binding domain. Alternatively, amino acids in the domains that already have human FcRn-binding activity in the acidic and/or neutral pH ranges may be altered to increase the human FcRn-binding activity. Desired amino acid alterations in the human FcRn-binding domain can be selected by comparing the human FcRn-binding activity in the acidic and/or neutral pH ranges before and after amino acid alteration.

The preferred human FcRn-binding domain is a region that directly binds to human FcRn. Such preferred human FcRn-binding regions include, for example, antibody Fc regions. Meanwhile, regions capable of binding to a polypeptide such as albumin or IgG, which has human FcRn-binding activity, can indirectly bind to human FcRn via albumin, IgG, or such. Thus, such a human FcRn-binding region of the present invention may be a region that binds to a polypeptide having an activity of binding to albumin or IgG. In particular, a human-FcRn-binding domain with a greater human FcRn-binding activity at neutral pH is preferred. A human-FcRn-binding domain with a greater human FcRn-binding activity at neutral pH may be selected in advance. Alternatively, the human FcRn-binding activity at neutral pH may be conferred or increased by modifying an amino acid in an antigen-binding molecule.

Appropriate conditions, other than the pH at which the human FcRn-binding activity is determined, can be selected by those skilled in the art. The conditions are not particularly limited. For example, the measurements can be conducted at 37° C. using MES buffer, as described in WO 2009/125825. Meanwhile, the human FcRn-binding activity of an antigen-binding molecule can be determined by methods known to those skilled in the art, for example, by using a Biacore™ (GE Healthcare) surface plasmon resonance (SPR) assay or the like. The activity of binding between an antigen-binding molecule and human FcRn can be assessed by loading human FcRn or the antigen-binding molecule as an analyte to a chip onto which the antigen-binding molecule or human FcRn is immobilized, respectively.

Herein, the human FcRn-binding activity at acidic pH means the human FcRn-binding activity at pH 4.0 to 6.5, preferably the human FcRn-binding activity at pH 5.5 to 6.5, and particularly preferably the human FcRn-binding activity at pH 5.8 to 6.0, which is comparable to pH in the early endosome in vivo. Meanwhile, the human FcRn-binding activity at neutral pH means the human FcRn-binding activity at pH 6.7 to 10.0, preferably the human FcRn-binding activity at pH 7.0 to pH 8.0, and particularly preferably the human FcRn-binding activity at pH 7.4, which is comparable to pH in plasma in vivo.

The human FcRn-binding activity at neutral pH can be conferred to or increased in an antigen-binding molecule by modifying an amino acid in the molecule. For example, when the Fc region of an IgG-type immunoglobulin is used as the human-FcRn-binding domain, the human FcRn-binding activity at neutral pH can be conferred to or increased in an antigen-binding molecule by modifying an amino acid in the human-FcRn-binding domain. Preferred Fc region of IgG-type immunoglobulin to be altered includes, for example, the Fc region of a human natural IgG (IgG1, IgG2, IgG3, or IgG4). Amino acids at any sites may be altered to other amino acids as long as the human FcRn-binding activity is conferred or increased at neutral pH. When the antigen-binding molecule has a human IgG1 Fc region as the human FcRn-binding domain, it is preferred that the molecule has alterations that potentiate the binding to human FcRn at neutral pH as compared to that of the human natural IgG1. Amino acids where such alteration can be achieved include, for example, amino acids at positions 221 to 225, 227, 228, 230, 232, 233 to 241, 243 to 252, 254 to 260, 262 to 272, 274, 276, 278 to 289, 291 to 312, 315 to 320, 324, 325, 327 to 339, 341, 343, 345, 360, 362, 370, 375 to 378, 380, 382, 385 to 387, 389, 396, 414, 416, 423, 424, 426 to 438, 440, and 442 (EU numbering). More specifically, such amino acid alterations include, for example, those listed in Table 1. The human FcRn binding of the Fc region of an IgG-type immunoglobulin at neutral pH can be enhanced (potentiated) by using the alterations described above. Furthermore, alterations that can potentiate the binding to human FcRn in the acidic pH range as compared to the human natural IgG1 are shown as an example in Table 2. When appropriate alterations that can also potentiate the binding to human FcRn at neutral pH range are selected from the above-described alterations, they are applicable to the present invention.

"Alteration of amino acids" or "amino acid alteration" of an FcRn-binding domain comprises alteration of an amino acid sequence in a parent FcRn-binding domain to a different amino acid sequences. Any FcRn-binding domain can be used as a parent FcRn-binding domain, as long as variants prepared by modifying the parent FcRn-binding domain can bind to human FcRn in the neutral pH range. Furthermore, an FcRn-binding domain modified from a parent FcRn-binding domain which has been already modified can also be used preferably as an FcRn-binding domain of the present invention. The "parent FcRn-binding domain" can refer to the polypeptide itself, a composition comprising the parent FcRn-binding domain, or a polynucleotide sequence encoding the parent FcRn-binding domain. Parent FcRn-binding domains can comprise a known Fc region produced via recombination described briefly in section "Antibodies". The origin of parent FcRn-binding domains is not limited, and they may be obtained from human or any nonhuman organisms. Such organisms preferably include mice, rats, guinea pigs, hamsters, gerbils, cats, rabbits, dogs, goats, sheep, bovines, horses, camels and organisms selected from nonhuman primates. In another embodiment, parent FcRn-binding domains can also be obtained from cynomolgus monkeys, marmosets, rhesus monkeys, chimpanzees, or humans. Parent FcRn-binding domains can be obtained preferably from human IgG1; however, they are not limited to any particular IgG class. This means that an Fc region of human IgG1, IgG2, IgG3, or IgG4 can be used appropriately as a parent FcRn-binding domain, and herein also means that an Fc region of an arbitrary IgG class or subclass derived from any organisms described above can be preferably used as a parent FcRn-binding domain. Examples of naturally-occurring IgG mutants or modified forms are described in published documents (Curr. Opin. Biotechnol. (2009) 20 (6): 685-91; Curr. Opin. Immunol. (2008) 20 (4), 460-470; Protein Eng. Des. Sel. (2010) 23 (4): 195-202; WO 2009/086320; WO 2008/092117; WO 2007/041635; and WO 2006/105338); however, they are not limited to the examples.

Examples of alterations include those with one or more mutations, for example, mutations by substitution of different amino acid residues for amino acids of parent FcRn-binding domains, by insertion of one or more amino acid residues into parent FcRn-binding domains, or by deletion of one or more amino acids from parent FcRn-binding domains. Preferably, the amino acid sequences of altered FcRn-binding domains comprise at least a part of the amino acid sequence of a non-natural FcRn-binding domain. Such variants necessarily have sequence identity or similarity less than 100% to their parent FcRn-binding domain. In a preferred embodiment, the variants have amino acid sequence identity or similarity about 75% to less than 100%, more preferably about 80% to less than 100%, even more preferably about 85% to less than 100%, still more preferably about 90% to less than 100%, and yet more preferably about 95% to less than 100% to the amino acid sequence of their parent FcRn-binding domain. In a non-limiting embodiment of the present invention, at least one amino acid is different between a modified FcRn-binding domain of the present invention and its parent FcRn-binding domain. Amino acid difference between a modified FcRn-binding domain of the present invention and its parent FcRn-binding domain can also be preferably specified based on amino acid differences at above-described particular amino acid positions according to EU numbering system.

Furthermore, alterations that can potentiate the binding to human FcRn in the acidic pH range as compared to the parent human IgG are shown as an example in Table 2. When appropriate alterations that can also potentiate the binding to human FcRn in the neutral pH range are selected from the above-described alterations, they are applicable to the present invention. Meanwhile, combinations of alterations that can potentiate the binding of Fv4-IgG1 to human FcRn under acidic conditions are shown in Tables 6-1 and 6-2. Particularly preferred amino acids to be altered in the parent human IgG Fc region include, for example, amino acids at positions 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434, and 436 (EU numbering).

Particularly preferred alterations include, for example,
an amino acid substitution of Met for Gly at position 237;
an amino acid substitution of Ala for Pro at position 238;
an amino acid substitution of Lys for Ser at position 239;
an amino acid substitution of Ile for Lys at position 248;
an amino acid substitution of Ala, Phe, Ile, Met, Gln, Ser, Val, Trp, or Tyr for Thr at position 250;
an amino acid substitution of Phe, Trp, or Tyr for Met at position 252;
an amino acid substitution of Thr for Ser at position 254;
an amino acid substitution of Glu for Arg at position 255;
an amino acid substitution of Asp, Glu, or Gln for Thr at position 256;
an amino acid substitution of Ala, Gly, Ile, Leu, Met, Asn, Ser, Thr, or Val for Pro at position 257;
an amino acid substitution of His for Glu at position 258;
an amino acid substitution of Ala for Asp at position 265;
an amino acid substitution of Phe for Asp at position 270;
an amino acid substitution of Ala, or Glu for Asn at position 286;
an amino acid substitution of His for Thr at position 289;
an amino acid substitution of Ala for Asn at position 297;
an amino acid substitution of Gly for Ser at position 298;
an amino acid substitution of Ala for Val at position 303;
an amino acid substitution of Ala for Val at position 305;
an amino acid substitution of Ala, Asp, Phe, Gly, His, Ile, Lys, Leu, Met, Asn, Pro, Gln, Arg, Ser, Val, Trp, or Tyr for Thr at position 307;
an amino acid substitution of Ala, Phe, Ile, Leu, Met, Pro, Gln, or Thr for Val at position 308; an amino acid substitution of Ala, Asp, Glu, Pro, or Arg for Leu or Val at position 309; an amino acid substitution of Ala, His, or Ile for Gln at position 311;
an amino acid substitution of Ala, or His for Asp at position 312;
an amino acid substitution of Lys, or Arg for Leu at position 314;
an amino acid substitution of Ala, or His for Asn at position 315;
an amino acid substitution of Ala for Lys at position 317;
an amino acid substitution of Gly for Asn at position 325;
an amino acid substitution of Val for Ile at position 332;
an amino acid substitution of Leu for Lys at position 334;
an amino acid substitution of His for Lys at position 360;
an amino acid substitution of Ala for Asp at position 376;
an amino acid substitution of Ala for Glu at position 380;
an amino acid substitution of Ala for Glu at position 382;
an amino acid substitution of Ala for Asn or Ser at position 384;
an amino acid substitution of Asp, or His for Gly at position 385;
an amino acid substitution of Pro for Gln at position 386;
an amino acid substitution of Glu for Pro at position 387;
an amino acid substitution of Ala, or Ser for Asn at position 389;
an amino acid substitution of Ala for Ser at position 424;
an amino acid substitution of Ala, Asp, Phe, Gly, His, Ile, Lys, Leu, Asn, Pro, Gln, Ser, Thr, Val, Trp, or Tyr for Met at position 428;
an amino acid substitution of Lys for His at position 433;
an amino acid substitution of Ala, Phe, His, Ser, Trp, or Tyr for Asn at position 434; and an amino acid substitution of His for Tyr or Phe at position 436 (EU numbering) in the parent IgG Fc region.

Meanwhile, the number of amino acids to be altered is not particularly limited; and it is possible to alter amino acids at only a single site or at two or more sites. Combinations of two or more amino acid alterations include, for example, those shown in Table 3. Meanwhile, combinations of alterations that can potentiate the binding to human FcRn in the acidic pH range as compared to the parent human IgG are shown in Tables 4-1 to 4-5. When appropriate combinations of alterations that can also potentiate the binding to human FcRn in the neutral pH range are selected from the above-described alterations, they are applicable to the present invention. Furthermore, combinations of alterations that can potentiate the binding of Fv4-IgG1 to human FcRn under neutral conditions are shown in Tables 5-1 and 5-2.

The human FcRn-binding activity of an antigen-binding molecule in the neutral pH range can be increased by substituting at least one amino acid selected from these amino acids with a different amino acid.

TABLE 1

| POSITION | AMINO ACID ALTERATION |
|---|---|
| 256 | P |
| 280 | K |
| 339 | T |
| 385 | H |
| 428 | L |
| 434 | W, Y, F, A, H |

TABLE 2

| POSITION | AMINO ACID ALTERATION |
|---|---|
| 221 | Y, K |
| 222 | Y |
| 223 | E, K |
| 224 | Y, E |
| 225 | E, K, W |
| 227 | K, E, G |
| 228 | Y, K, G |
| 230 | E, G |
| 232 | K |
| 233 | R, S, M, T, W, Y, G |
| 234 | H, R, E, I, V, F, D, Y, G |
| 235 | Y, V, N, S, T, Q, D |
| 236 | I, V, K, P, E, Q, H, W, Y, D, T, M, A, F, S, N, R |
| 237 | I, W, S, T, E, R, N, Q, K, H, D, P, L, M |
| 238 | A, L, D, S, T, H, W, V, I, G, M, F, E, K |
| 239 | M, R, T, G, V, E, D, L, A |
| 240 | I, M, T |
| 241 | E, W, L |
| 243 | E, W |
| 244 | L |

TABLE 2-continued

| POSITION | AMINO ACID ALTERATION |
|---|---|
| 245 | R |
| 246 | Y, H |
| 247 | D |
| 248 | Y |
| 249 | P, Q, Y, H |
| 250 | I, E, Q |
| 251 | T, D |
| 252 | Y, W, Q |
| 254 | H |
| 255 | E, Y, H |
| 256 | A |
| 257 | A, I, M, N, S, V, T, L, Y, C |
| 258 | D, Y, H, A |
| 259 | I, F, N |
| 260 | S, D, E, H, Y |
| 262 | L, E |
| 263 | I |
| 264 | F, A, I, T, N, S, D |
| 265 | R, P, G, A |
| 266 | I |
| 267 | K, E, A |
| 268 | E, M |
| 269 | M, W, K, P, I, S, G, V, F, Y, A |
| 270 | K, S, I, A |
| 271 | A, V, S, Y, I, T |
| 272 | A, L, R, I, D, H, V, W, Y, P, T |
| 274 | M, F, G, E, I, T, N |
| 276 | D, F, H, R, L, V, W, A |
| 278 | R, S, V, M, N, I, L, D |
| 279 | A, D, G, H, M, N, Q, R, S, T, W, Y, C, I |
| 281 | D, Y |
| 282 | G, K, E, Y |
| 283 | A, D, F, G, H, I, K, L, N, P, Q, R, S, T, W, Y |
| 284 | T, L, Q, E |
| 285 | N, Y, W, Q, K, E, D, Y |
| 286 | F, L, Y, E, P, D, K, A |
| 287 | S, H |
| 288 | N, P, Y, H, D, I, V, C, E, G, L, Q, R |
| 289 | H |
| 291 | Q, H |
| 292 | Y, E, D |
| 293 | V |
| 294 | I, K, G |
| 295 | V, T |
| 296 | E, I, L |
| 298 | F, E, T, H |
| 299 | W, F, H, Y |
| 300 | K, A, G, V, M, Q, N, E |
| 301 | E |
| 302 | I |
| 303 | Y, E, A |
| 304 | N, T |
| 305 | A, H |
| 306 | Y |
| 307 | A, E, M, G, Q, H |
| 308 | A, R, F, C, Y, W, N, H |
| 311 | A, I, K, L, M, V, W, T, H |
| 312 | A, P, H |
| 315 | T, H |
| 316 | K |
| 317 | A, P, H |
| 318 | N, T, R, L, Y |
| 319 | L, I, W, H, M, V, A |
| 320 | L, W, H, N |
| 324 | T, D |
| 325 | F, M, D |
| 326 | A |
| 327 | D, K, M, Y, H, L |
| 328 | G, A, W, R, F |
| 329 | K, R, W |
| 330 | G, W, V, P, H, F |
| 331 | L, F, Y |
| 332 | F, H, K, L, M, R, S, W, T, Q, E, Y, D, N, V |
| 333 | L, F, M, A |
| 334 | A |
| 335 | H, F, N, V, M, W, I, S, P, L |
| 336 | E, K |
| 337 | A |
| 338 | A |
| 339 | N, W |
| 341 | P |
| 343 | E, H, K, Q, R, T, Y |
| 360 | H, A |
| 362 | A |
| 375 | R |
| 376 | A, G, I, M, P, T, V |
| 377 | K |
| 378 | Q, D, N, W |
| 380 | A, N, S, T, Q, R, H |
| 382 | A, F, H, I, K, L, M, N, Q, R, S, T, V, W, Y |
| 385 | N, E |
| 386 | H |
| 387 | H, Q |
| 414 | A |
| 423 | N |
| 424 | A |
| 426 | H, L, V, R |
| 427 | N |
| 428 | F |
| 429 | Q |
| 430 | A, F, G, H, I, K, L, M, N, Q, R, S, T, V, Y |
| 431 | H, K |
| 432 | H |
| 433 | P |
| 434 | G, T, M, S |
| 435 | K |
| 436 | I, L, T |
| 437 | H |
| 438 | K, L, T, W |
| 440 | K |
| 442 | K |

TABLE 3

| COMBINATION OF AMINO ACID ALTERATION |
|---|
| M252Y/S254T/T256E |
| M252Y/S254T/T256E/H433K/N434F/Y436H |
| H433K/N434F/Y436H |
| T307A/E380A |
| T307A/E380A/N434H |
| T307A/E380A/N434A |
| N434H/N315H |
| N434H/T289H |
| N434H/T370A/E380A |
| T250Q/M428L |
| T250Q/N434A |
| M252W/N434A |
| M252Y/N434A |
| T256A/N434A |
| T256D/N434A |
| T256E/N434A |
| T256S/N434A |
| P257I/Q311I |
| T307A/N434A |
| T307E/N434A |
| T307Q/N434A |
| V308P/N434A |
| L309G/N434A |
| Q311H/N434A |
| Q311R/N434A |
| N315D/N434A |
| A378V/N434A |
| E380S/N434A |
| E382V/N434A |
| S424E/N434A |
| M428L/N434A |
| N434A/Y436I |
| T437Q/N434A |
| T437R/N434A |

TABLE 4-1

| COMBINATION OF AMINO ACID ALTERATION |
| --- |
| L234I/L235D |
| G236A/V308F/I332E |
| G236R/L328R |
| G236A/I332E/N434S |
| S239E/V264I/A330Y/I332E |
| S239E/V264I/I332E |
| S239E/V264I/S298A/A330Y/I332E |
| S239D/D265H/N297D/I332E |
| S239D/E272Y/I332E |
| S239D/E272S/I332E |
| S239D/E272I/I332E |
| S239D/N297D/I332E |
| S239D/K326T/I332E |
| S239Q/I332Q |
| S239Q/I332N |
| S239D/I332D |
| S239D/I332E |
| S239Q/I332E |
| S239E/I332E |
| F241W/F243W |
| F241Y/F243Y/V262T/V264T |
| F241W/F243W/V262A/V264A |
| F241L/V262I |
| F243L/V262I/V264W |
| F243L/K288D/R292P/Y300L/V305I/P396L/H435K |
| F243L/K288D/R292P/Y300L/H435K |
| F243L/R292P/Y300L/V305I/P396L/H435K |
| P245G/V308F |
| T250I/V259I/V308F |
| T250I/V308F |
| T250I/V308F/N434S |
| T250Q/V308F/M428L |
| T250Q/M428L |
| L251I/N434S |
| L251N/N434S |
| L251F/N434S |
| L251V/N434S |
| L251M/N434S |
| T252L/T254S/T256F |
| M252Y/S254T/T256E/N434M |
| M252Y/S254T/T256E/M428L/N434S |
| M252Y/S254T/T256E |
| M252Y/S254T/T256E/V308F |
| M252Y/S254T/T256E/N434S |
| M252Y/S254T/T256E/N434A |
| M252Y/S254T/T256E/M428L |
| M252Y/S254T/T256E/T307Q |
| M252F/T256D |
| M252Y/T256Q |
| M252Y/P257L |
| M252Y/P257N |
| M252Y/V259I |
| M252Y/V279Q |
| M252Y/V308P/N434Y |
| M252Q/V308F |
| M252Y/V308F |

TABLE 4-2

| |
| --- |
| M252Q/V308F/N434S |
| M252Y/V308F/M428L |
| M252Y/V308F/N434M |
| M252Y/V308F/N434S |
| M252Y/Y319I |
| M252Q/M428L/N434S |
| M252Y/M428L |
| M252Y/N434M |
| M252Y/N434S |
| M252Y/N434A |
| M252Y/N434Y |
| S254T/V308F |
| R255H/N434A |
| R255Q/N434S |
| R255H/N434S |
| T256V/V308F |

TABLE 4-2-continued

| |
| --- |
| T256P/Q311I |
| T256P/I332E |
| T256P/I332E/S440Y |
| T256P/E430Q |
| T256P/N434H |
| T256E/N434Y |
| T256P/S440Y |
| P257Y/V279Q |
| P257L/V279E |
| P257N/V279Q |
| P257N/V279E |
| P257N/V279Y |
| P257L/V279Q |
| P257N/^281S |
| P257L/^281S |
| P257N/V284E |
| P257N/L306Y |
| P257L/V308Y |
| P257L/V308F |
| P257N/V308Y |
| P257I/Q311I/N434H |
| P257L/Q311V |
| P257L/G385N |
| P257L/M428L |
| P257I/E430Q |
| P257I/N434H |
| P257L/N434H |
| P257L/N434Y |
| E258H/N434A |
| E258H/N434H |
| V259I/T307Q/V308F |
| V259I/V308F |
| V259I/V308F/Y319L |
| V259I/V308F/Y319I |
| V259A/V308F |
| V259I/V308F/N434M |
| V259I/V308F/N434S |
| V259I/V308F/M428L/N434S |
| V259I/V308F/M428L |
| V259I/Y319I |
| V259I/Y319I/N434S |
| V259I/M428L |
| V259I/M428L/N434S |
| V259I/N434S |

Table 4-3 is a continuation of Table 4-2.

TABLE 4-3

| |
| --- |
| V259I/N434Y |
| V264I/A330L/I332E |
| V264I/I332E |
| D265F/N297E/I332E |
| S267L/A327S |
| E272R/V279L |
| V279E/V284E |
| V279Q/L306Y |
| V279Y/V308F |
| V279Q/V308F |
| V279Q/G385H |
| ^281S/V308Y |
| ^281S/V308F |
| ^281S/N434Y |
| E283F/V284E |
| V284E/V308F |
| V284E/G385H |
| K288A/N434A |
| K288D/H435K |
| K288V/H435D |
| T289H/N434A |
| T289H/N434H |
| L306I/V308F |
| T307P/V308F |
| T307Q/V308F/N434S |
| T307Q/V308F/Y319L |
| T307S/V308F |
| T307Q/V308F |
| T307A/E310A/N434A |
| T307Q/E380A/N434A |

TABLE 4-3-continued

T307Q/M428L
T307Q/N434M
T307I/N434S
T307V/N434S
T307Q/N434S
T307Q/N434Y
V308T/L309P/Q311S
V308F/L309Y
V308F/Q311V
V308F/Y319F
V308F/Y319I/N434M
V308F/Y319I
V308F/Y319L
V308F/Y319I/M428L
V308F/Y319I/M428L/N434S
V308F/Y319L/N434S
V308F/I332E
V308F/G385H
V308F/M428L/N434M
V308F/M428L
V308F/M428L/N434S
V308P/N434Y
V308F/N434M
V308F/N434S
V308F/N434Y
Q311G/N434S
Q311D/N434S
Q311E/N434S
Q311N/N434S

Table 4-4 is a continuation of Table 4-3.

TABLE 4-4

Q311Y/N434S
Q311F/N434S
Q311W/N434S
Q311A/N434S
Q311K/N434S
Q311T/N434S
Q311R/N434S
Q311L/N434S
Q311M/N434S
Q311V/N434S
Q311I/N434S
Q311A/N434Y
D312H/N434A
D312H/N434H
L314Q/N434S
L314V/N434S
L314M/N434S
L314F/N434S
L314I/N434S
N315H/N434A
N315H/N434H
Y319I/V308F
Y319I/M428L
Y319I/M428L/N434S
Y319I/N434M
Y319I/N434S
L328H/I332E
L328N/I332E
L328E/I332E
L328I/I332E
L328Q/I332E
L328D/I332E
L328R/M428L/N434S
A330L/I332E
A330Y/I332E
I332E/D376V
I332E/N434S
P343R/E345D
D376V/E430Q
D376V/E430R
D376V/N434H
E380A/N434A
G385R/Q386T/P387R/N389P
G385D/Q386P/N389S

TABLE 4-4-continued

N414F/Y416H
M428L/N434M
M428L/N434S
M428L/N434A
M428L/N434Y
M429N/N434S
E430D/N434S
E430T/N434S
E430S/N434S
E430A/N434S
E430F/N434S
E430Q/N434S
E430L/N434S
E430I/N434S
A431T/N434S

Table 4-5 is a continuation of Table 4-4.

TABLE 4-5

A431S/N434S
A431G/N434S
A431V/N434S
A431N/N434S
A431F/N434S
A431H/N434S
L432F/N434S
L432N/N434S
L432Q/N434S
L432H/N434S
L432G/N434S
L432I/N434S
L432V/N434S
L432A/N434S
H433K/N434F
H433L/N434S
H433M/N434S
H433A/N434S
H433V/N434S
H433K/N434S
H433S/N434S
H433P/N434S
N434S/M428L
N434S/Y436D
N434S/Y436Q
N434S/Y436M
N434S/Y436G
N434S/Y436E
N434S/Y436F
N434S/Y436T
N434S/Y436R
N434S/Y436S
N434S/Y436H
N434S/Y436K
N434S/Y436L
N434S/Y436V
N434S/Y436W
N434S/Y436I
N434S/T437I

TABLE 5-1

| VARIANT NAME | KD (M) | AMINO ACID ALTERATION |
|---|---|---|
| IgG1 | ND | NONE |
| IgG1-v1 | 3.2E−06 | M252Y/S254T/T256E |
| IgG1-v2 | 8.1E−07 | N434W |
| IgG1-F3 | 2.5E−06 | N434Y |
| IgG1-F4 | 5.8E−06 | N434S |
| IgG1-F5 | 6.8E−06 | N434A |
| IgG1-F7 | 5.6E−06 | M252Y |
| IgG1-F8 | 4.2E−06 | M252W |
| IgG1-F9 | 1.4E−07 | M252Y/S254T/T256E/N434Y |
| IgG1-F10 | 6.9E−08 | M252Y/S254T/T256E/N434W |
| IgG1-F11 | 3.1E−07 | M252Y/N434Y |
| IgG1-F12 | 1.7E−07 | M252Y/N434W |

TABLE 5-1-continued

| VARIANT NAME | KD (M) | AMINO ACID ALTERATION |
|---|---|---|
| IgG1-F13 | 3.2E−07 | M252W/N434Y |
| IgG1-F14 | 1.8E−07 | M252W/N434W |
| IgG1-F19 | 4.6E−07 | P257L/N434Y |
| IgG1-F20 | 4.6E−07 | V308F/N434Y |
| IgG1-F21 | 3.0E−08 | M252Y/V308P/N434Y |
| IgG1-F22 | 2.0E−06 | M428L/N434S |
| IgG1-F25 | 9.2E−09 | M252Y/S254T/T256E/V308P/N434W |
| IgG1-F26 | 1.0E−06 | I332V |
| IgG1-F27 | 7.4E−06 | G237M |
| IgG1-F29 | 1.4E−06 | I332V/N434Y |
| IgG1-F31 | 2.8E−06 | G237M/V308F |
| IgG1-F32 | 8.0E−07 | S254T/N434W |
| IgG1-F33 | 2.3E−06 | S254T/N434Y |
| IgG1-F34 | 2.8E−07 | T256E/N434W |
| IgG1-F35 | 8.4E−07 | T256E/N434Y |
| IgG1-F36 | 3.6E−07 | S254T/T256E/N434W |
| IgG1-F37 | 1.1E−06 | S254T/T256E/N434Y |
| IgG1-F38 | 1.0E−07 | M252Y/S254T/N434W |
| IgG1-F39 | 3.0E−07 | M252Y/S254T/N434Y |
| IgG1-F40 | 8.2E−08 | M252Y/T256E/N434W |
| IgG1-F41 | 1.5E−07 | M252Y/T256E/N434Y |
| IgG1-F42 | 1.0E−06 | M252Y/S254T/T256E/N434A |
| IgG1-F43 | 1.7E−06 | M252Y/N434A |
| IgG1-F44 | 1.1E−06 | M252W/N434A |
| IgG1-F47 | 2.4E−07 | M252Y/T256Q/N434W |
| IgG1-F48 | 3.2E−07 | M252Y/T256Q/N434Y |
| IgG1-F49 | 5.1E−07 | M252F/T256D/N434W |
| IgG1-F50 | 1.2E−06 | M252F/T256D/N434Y |
| IgG1-F51 | 8.1E−06 | N434F/Y436H |
| IgG1-F52 | 3.1E−06 | H433K/N434F/Y436H |
| IgG1-F53 | 1.0E−06 | I332V/N434W |
| IgG1-F54 | 8.4E−08 | V308P/N434W |
| IgG1-F56 | 9.4E−07 | I332V/M428L/N434Y |

TABLE 5-2

| IgG1-F57 | 1.1E−05 | G385D/Q386P/N389S |
| IgG1-F58 | 7.7E−07 | G385D/Q386P/N389S/N434W |
| IgG1-F59 | 2.4E−06 | G385D/Q386P/N389S/N434Y |
| IgG1-F60 | 1.1E−05 | G385H |
| IgG1-F61 | 9.7E−07 | G385H/N434W |
| IgG1-F62 | 1.9E−06 | G385H/N434Y |
| IgG1-F63 | 2.5E−06 | N434F |
| IgG1-F64 | 5.3E−06 | N434H |
| IgG1-F65 | 2.9E−07 | M252Y/S254T/T256E/N434F |
| IgG1-F66 | 4.3E−07 | M252Y/S254T/T256E/N434H |
| IgG1-F67 | 6.3E−07 | M252Y/N434F |
| IgG1-F68 | 9.3E−07 | M252Y/N434H |
| IgG1-F69 | 5.1E−07 | M428L/N434W |
| IgG1-F70 | 1.5E−06 | M428L/N434Y |
| IgG1-F71 | 8.3E−08 | M252Y/S254T/T256E/M428L/N434W |
| IgG1-F72 | 2.0E−07 | M252Y/S254T/T256E/M428L/N434Y |
| IgG1-F73 | 1.7E−07 | M252Y/M428L/N434W |
| IgG1-F74 | 4.6E−07 | M252Y/M428L/N434Y |
| IgG1-F75 | 1.4E−06 | M252Y/M428L/N434A |
| IgG1-F76 | 1.0E−06 | M252Y/S254T/T256E/M428L/N434A |
| IgG1-F77 | 9.9E−07 | T256E/M428L/N434Y |
| IgG1-F78 | 7.8E−07 | S254T/M428L/N434W |
| IgG1-F79 | 5.9E−06 | S254T/T256E/N434A |
| IgG1-F80 | 2.7E−06 | M252Y/T256Q/N434A |
| IgG1-F81 | 1.6E−06 | M252Y/T256E/N434A |
| IgG1-F82 | 1.1E−06 | T256Q/N434W |
| IgG1-F83 | 2.6E−06 | T256Q/N434Y |
| IgG1-F84 | 2.8E−07 | M252W/T256Q/N434W |
| IgG1-F85 | 5.5E−07 | M252W/T256Q/N434Y |
| IgG1-F86 | 1.5E−06 | S254T/T256Q/N434W |
| IgG1-F87 | 4.3E−06 | S254T/T256Q/N434Y |
| IgG1-F88 | 1.9E−07 | M252Y/S254T/T256Q/N434W |
| IgG1-F89 | 3.6E−07 | M252Y/S254T/T256Q/N434Y |
| IgG1-F90 | 1.9E−08 | M252Y/T256E/V308P/N434W |
| IgG1-F91 | 4.8E−08 | M252Y/V308P/M428L/N434Y |
| IgG1-F92 | 1.1E−08 | M252Y/S254T/T256E/V308P/M428L/N434W |
| IgG1-F93 | 7.4E−07 | M252W/M428L/N434W |

TABLE 5-2-continued

| IgG1-F94 | 3.7E−07 | P257L/M428L/N434Y |
| IgG1-F95 | 2.6E−07 | M252Y/S254T/T256E/M428L/N434F |
| IgG1-F99 | 6.2E−07 | M252Y/T256E/N434H |

TABLE 6-1

| VARIANT NAME | KD (M) | AMINO ACID ALTERATION |
|---|---|---|
| IgG1 | ND | NONE |
| IgG1-v1 | 3.2E−06 | M252Y/S254T/T256E |
| IgG1-v2 | 8.1E−07 | N434W |
| IgG1-F3 | 2.5E−06 | N434Y |
| IgG1-F4 | 5.8E−06 | N434S |
| IgG1-F5 | 6.8E−06 | N434A |
| IgG1-F7 | 5.6E−06 | M252Y |
| IgG1-F8 | 4.2E−06 | M252W |
| IgG1-F9 | 1.4E−07 | M252Y/S254T/T256E/N434Y |
| IgG1-F10 | 6.9E−08 | M252Y/S254T/T256E/N434W |
| IgG1-F11 | 3.1E−07 | M252Y/N434Y |
| IgG1-F12 | 1.7E−07 | M252Y/N434W |
| IgG1-F13 | 3.2E−07 | M252W/N434Y |
| IgG1-F14 | 1.8E−07 | M252W/N434W |
| IgG1-F19 | 4.6E−07 | P257L/N434Y |
| IgG1-F20 | 4.6E−07 | V308F/N434Y |
| IgG1-F21 | 3.0E−08 | M252Y/V308P/N434Y |
| IgG1-F22 | 2.0E−06 | M428L/N434S |
| IgG1-F25 | 9.2E−09 | M252Y/S254T/T256E/V308P/N434W |
| IgG1-F26 | 1.0E−06 | I332V |
| IgG1-F27 | 7.4E−06 | G237M |
| IgG1-F29 | 1.4E−06 | I332V/N434Y |
| IgG1-F31 | 2.8E−06 | G237M/V308F |
| IgG1-F32 | 8.0E−07 | S254T/N434W |
| IgG1-F33 | 2.3E−06 | S254T/N434Y |
| IgG1-F34 | 2.8E−07 | T256E/N434W |
| IgG1-F35 | 8.4E−07 | T256E/N434Y |
| IgG1-F36 | 3.6E−07 | S254T/T256E/N434W |
| IgG1-F37 | 1.1E−06 | S254T/T256E/N434Y |
| IgG1-F38 | 1.0E−07 | M252Y/S254T/N434W |
| IgG1-F39 | 3.0E−07 | M252Y/S254T/N434Y |
| IgG1-F40 | 8.2E−08 | M252Y/T256E/N434W |
| IgG1-F41 | 1.5E−07 | M252Y/T256E/N434Y |
| IgG1-F42 | 1.0E−06 | M252Y/S254T/T256E/N434A |
| IgG1-F43 | 1.7E−06 | M252Y/N434A |
| IgG1-F44 | 1.1E−06 | M252W/N434A |
| IgG1-F47 | 2.4E−07 | M252Y/T256Q/N434W |
| IgG1-F48 | 3.2E−07 | M252Y/T256Q/N434Y |
| IgG1-F49 | 5.1E−07 | M252F/T256D/N434W |
| IgG1-F50 | 1.2E−06 | M252F/T256D/N434Y |
| IgG1-F51 | 8.1E−06 | N434F/Y436H |
| IgG1-F52 | 3.1E−06 | H433K/N434F/Y436H |
| IgG1-F53 | 1.0E−06 | I332V/N434W |
| IgG1-F54 | 8.4E−08 | V308P/N434W |
| IgG1-F56 | 9.4E−07 | I332V/M428L/N434Y |
| IgG1-F57 | 1.1E−05 | G385D/Q386P/N389S |
| IgG1-F58 | 7.7E−07 | G385D/Q386P/N389S/N434W |
| IgG1-F59 | 2.4E−06 | G385D/Q386P/N389S/N434Y |
| IgG1-F60 | 1.1E−05 | G385H |
| IgG1-F61 | 9.7E−07 | G385H/N434W |
| IgG1-F62 | 1.9E−06 | G385H/N434Y |
| IgG1-F63 | 2.5E−06 | N434F |
| IgG1-F64 | 5.3E−06 | N434H |

Table 6-2 is a continuation of Table 6-1.

TABLE 6-2

| IgG1-F65 | 2.9E−07 | M252Y/S254T/T256E/N434F |
| IgG1-F66 | 4.3E−07 | M252Y/S254T/T256E/N434H |
| IgG1-F67 | 6.3E−07 | M252Y/N434F |
| IgG1-F68 | 9.3E−07 | M252Y/N434H |
| IgG1-F69 | 5.1E−07 | M428L/N434W |
| IgG1-F70 | 1.5E−06 | M428L/N434Y |
| IgG1-F71 | 8.3E−08 | M252Y/S254T/T256E/M428L/N434W |
| IgG1-F72 | 2.0E−07 | M252Y/S254T/T256E/M428L/N434Y |
| IgG1-F73 | 1.7E−07 | M252Y/M428L/N434W |
| IgG1-F74 | 4.6E−07 | M252Y/M428L/N434Y |

TABLE 6-2-continued

| | | |
|---|---|---|
| IgG1-F75 | 1.4E−06 | M252Y/M428L/N434A |
| IgG1-F76 | 1.0E−06 | M252Y/S254T/T256E/M428L/N434A |
| IgG1-F77 | 9.9E−07 | T256E/M428L/N434Y |
| IgG1-F78 | 7.8E−07 | S254T/M428L/N434W |
| IgG1-F79 | 5.9E−06 | S254T/T256E/N434A |
| IgG1-F80 | 2.7E−06 | M252Y/T256Q/N434A |
| IgG1-F81 | 1.6E−06 | M252Y/T256E/N434A |
| IgG1-F82 | 1.1E−06 | T256Q/N434W |
| IgG1-F83 | 2.6E−06 | T256Q/N434Y |
| IgG1-F84 | 2.8E−06 | M252W/T256Q/N434W |
| IgG1-F85 | 5.5E−07 | M252W/T256Q/N434Y |
| IgG1-F86 | 1.5E−06 | S254T/T256Q/N434W |
| IgG1-F87 | 4.3E−06 | S254T/T256Q/N434Y |
| IgG1-F88 | 1.9E−07 | M252Y/S254T/T256Q/N434W |
| IgG1-F89 | 3.6E−07 | M252Y/S254T/T256Q/N434Y |
| IgG1-F90 | 1.9E−08 | M252Y/T256E/V308P/N434W |
| InG1-F91 | 4.8E−08 | M252Y/V308P/M428L/N434Y |
| IgG1-F92 | 1.1E−08 | M252Y/S254T/T256E/V308P/M428L/N434W |
| IgG1-F93 | 7.4E−07 | M252W/M428L/N434W |
| IgG1-F94 | 3.7E−07 | P257L/M428L/N434Y |
| IgG1-F95 | 2.6E−07 | M252Y/S254T/T256E/M428L/N434F |
| IgG1-F99 | 6.2E−07 | M252Y/T256E/N434H |

Such amino acid alterations can be appropriately introduced using known methods. For example, alterations in the Fc domain of human natural IgG1 are described in Drug Metab Dispos. 2007 January 35(1): 86-94; Int Immunol. 2006 Dec. 18, (12): 1759-69; J Biol Chem. 2001 Mar. 2, 276(9): 6591-604; J Biol Chem. (2007) 282(3): 1709-17; J Immunol. (2002) 169(9): 5171-80; J Immunol. (2009) 182 (12): 7663-71; Molecular Cell, Vol. 7, 867-877, April, 2001; Nat Biotechnol. 1997 Jul. 15, (7): 637-40; Nat Biotechnol. 2005 Oct. 23, (10): 1283-8; Proc Natl Acad Sci USA. 2006 Dec. 5, 103(49): 18709-14; EP 2154157; US 20070141052; WO 2000/042072; WO 2002/060919; WO 2006/020114; WO 2006/031370; WO 2010/033279; WO 2006/053301; and WO 2009/086320.

According to the Journal of Immunology (2009) 182: 7663-7671, the human FcRn-binding activity of human natural IgG1 in the acidic pH range (pH 6.0) is KD 1.7 μM, and the activity is almost undetectable in the neutral pH range. Thus, in a preferred embodiment, the antigen-binding molecule to be used in the methods of the present invention includes antigen-binding molecules whose human FcRn-binding activity in the acidic pH range is KD 20 μM or stronger, and is identical to or stronger than that of human natural IgG1 in the neutral pH range. In a more preferred embodiment, the antigen-binding molecule includes antigen-binding molecules whose human FcRn-binding activity is KD 2.0 μM or stronger in the acidic pH range and KD 40 μM or stronger in the neutral pH range. In a still more preferred embodiment, the antigen-binding molecule includes antigen-binding molecules whose human FcRn-binding activity is KD 0.5 μM or stronger in the acidic pH range and KD 15 μM or stronger in the neutral pH range. Specifically, it is preferred that the antigen-binding activity is lower under an acidic pH condition than under a neutral pH condition. The above KD values are determined by the method described in the Journal of Immunology (2009) 182: 7663-7671 (by immobilizing the antigen-binding molecule onto a chip and loading human FcRn as an analyte).

Dissociation constant (KD) can be used as a value of human FcRn-binding activity. However, human natural IgG1 has little human FcRn-binding activity in the neutral pH range (pH 7.4), and therefore it is difficult to calculate the activity as KD. Methods for assessing whether the human FcRn-binding activity is higher than that of human natural IgG1 at pH 7.4 include assessment methods by comparing the intensities of a Biacore™ response after loading analytes at the same concentration. Specifically, when the response after loading a human FcRn chip immobilized with an antigen-binding molecule at pH 7.4 is stronger than the response after loading human FcRn onto a chip immobilized with human natural IgG1 at pH 7.4, the human FcRn-binding activity of the antigen-binding molecule is judged to be higher than that of human natural IgG1 at pH 7.4.

pH 7.0 can also be used as a neutral pH range. Using pH 7.0 as a neutral pH can facilitate weak interaction between human FcRn and FcRn-binding domain. As a temperature employed in the assay condition, a binding affinity may be assessed at any temperature from 10° C. to 50° C. Preferably, a temperature at from 15° C. to 40° C. is employed in order to determine the binding affinity between human FcRn-binding domain and human FcRn. More preferably, any temperature at from 20° C. to 35° C., like any one of 20, 21, 22, 23, 24, 25, 26, 27, 28, 29, 30, 31, 32, 33, 34, and 35° C. is also employed in order to determine the binding affinity between human FcRn-binding domain and human FcRn. A temperature at 25° C. described in Example 5 is one of example for the embodiment of this invention. In a preferred embodiment, an interaction between human FcRn and FcRn-binding domain can be measured at pH 7.0 and at 25° C. as described in Example 5. Binding affinity of antigen-binding molecule to human FcRn can be measured by Biacore™ SPR analysis as described in Example 3.

In a more preferred embodiment, the antigen-binding molecules of the present invention have human FcRn-binding activity at pH 7.0 and at 25° C. which is stronger than natural human IgG. In a more preferred embodiment, human FcRn-binding activity at pH 7.0 and at 25° C. is 28-fold stronger than natural human IgG or stronger than KD 3.2 μM. In a more preferred embodiment, human FcRn-binding activity at pH 7.0 and at 25° C. is 38-fold stronger than natural human IgG or stronger than KD 2.3 μM.

A natural human IgG1, IgG2, IgG3 or IgG4 is preferably used as the intact human IgG for a purpose of a reference intact human IgG to be compared with the antigen-binding molecules for their human FcRn binding activity or in vivo binding activity. Preferably, a reference antigen-binding molecule comprising the same antigen-binding domain as an antigen-binding molecule of the interest and natural human IgG Fc region as a human FcRn-binding domain can be appropriately used. More preferably, a natural human IgG1 is used for a purpose of a reference natural human IgG to be compared with the antigen-binding molecules for their human FcRn binding activity or in vivo binding activity.

More specifically, the antigen-binding molecules with long term effect on activity for eliminating antigen in plasma described in the present invention have human FcRn-binding activity at pH 7.0 and at 25° C. within a range of 28-fold to 440-fold stronger than natural human IgG1 or KD within a range of 3.0 μM to 0.2 μM. A long term plasma antigen concentration is determined by measuring total or free antigen concentration in plasma and molar antigen/antigen-binding molecule ratio at 2, 4, 7, 14, 28, 56, or 84 days after administration of an antigen-binding molecule in order to evaluate the long term effect of the antigen-binding molecule of the present invention on activity for eliminating antigen in plasma. Whether the reduction of plasma antigen concentration or molar antigen/antigen-binding molecule ratio is achieved by antigen-binding molecule described in the present invention can be determined by the evaluation of the reduction at any one or more of the time points described above.

Still more specifically, the antigen-binding molecules with short term effect on activity for eliminating antigen in plasma described in the present invention have human FcRn-binding activity at pH 7.0 and at 25° C. 440-fold stronger than natural human IgG or KD stronger than 0.2 M. A short term plasma antigen concentration is determined by measuring total or free antigen concentration in plasma and molar antigen/antigen-binding molecule ratio at 15 min, 1, 2, 4, 8, 12, or 24 hours after administration of an antigen-binding molecule in order to evaluate the short term effect of the antigen-binding molecule of the present invention on activity for eliminating antigen in plasma.

The methods of the present invention are applicable to any antigen-binding molecules regardless of the type of target antigen.

For example, when the antigen-binding molecule is an antibody that binds to a membrane antigen, the antibody administered into the body binds to the antigen and then is taken up via internalization into endosomes in the cells together with the antigen while the antibody is kept bound to the antigen. Then, the antibody translocates to lysosomes while the antibody is kept bound to the antigen, and the antibody is degraded by the lysosome together with the antigen. The internalization-mediated elimination from the plasma is called antigen-dependent elimination, and such elimination has been reported with numerous antibody molecules (Drug Discov Today. 2006 January; 11(1-2): 81-8). When a single molecule of IgG antibody binds to antigens in a divalent manner, the single antibody molecule is internalized while the antibody is kept bound to the two antigen molecules, and degraded in the lysosome. Accordingly, in the case of common antibodies, one molecule of IgG antibody cannot bind to three or more molecules of antigen. For example, a single IgG antibody molecule having a neutralizing activity cannot neutralize three or more antigen molecules.

The relatively prolonged retention (slow elimination) of IgG molecules in the plasma is due to the function of human FcRn which is known as a salvage receptor of IgG molecules. When taken up into endosomes via pinocytosis, IgG molecules bind to human FcRn expressed in the endosomes under the acidic condition in the endosomes. While IgG molecules that did not bind to human FcRn transfer to lysosomes where they are degraded, IgG molecules that are bound to human FcRn translocate to the cell surface and return again in the plasma by dissociating from human FcRn under the neutral condition in the plasma.

Alternatively, when the antigen-binding molecule is an antibody that binds to a soluble antigen, the antibody administered into the body binds to the antigen and then is taken up into cells while the antibody is kept bound to the antigen. Many antibodies taken up into cells are released to the outside of the cell via FcRn. However, since the antibodies are released to the outside of the cell, with the antibodies kept bound to antigens, the antibodies cannot bind to antigens again. Thus, similar to antibodies that bind to membrane antigens, in the case of common antibodies, one molecule of IgG antibody cannot bind to three or more antigen molecules.

Calcium concentration-dependent antigen-binding antibodies that strongly bind to an antigen under high calcium concentration conditions in plasma but dissociate from the antigen under low calcium concentration conditions in the endosome can dissociate from the antigen in the endosome. Such calcium concentration-dependent antigen-binding antibodies can bind to antigens again when they are recycled to the plasma by FcRn after antigen dissociation; thus, each antibody can repeatedly bind to a number of antigens. Furthermore, the antigen bound to the antigen-binding molecule is dissociated in the endosome and not recycled to the plasma. This facilitates the antigen-binding molecule-mediated antigen uptake into cells. Thus, the administration of an antigen-binding molecule can enhance the antigen elimination and thereby reduces the plasma antigen concentration.

Antigen-Binding Molecules

The present invention provides antigen-binding molecules having an antigen-binding domain and a human FcRn-binding domain, wherein the antigen-binding activity of the antigen-binding molecules is different under two different calcium concentration conditions and is lower under a low calcium concentration condition than under a high calcium concentration condition.

The antigen-binding molecules of the present invention are not particularly limited, as long as they include an antigen-binding domain having a binding activity specific to a target antigen. Such preferred antigen-binding domains comprise, for example, domains having an antigen-binding region of an antibody. The antigen-binding region of an antibody comprises, for example, CDRs and variable regions. When the antigen-binding region of an antibody is CDR, it may contain all six CDRs from the whole antibody, or one, two, or more CDRs. When CDRs are contained as a binding region in an antibody, they may comprise amino acid deletions, substitutions, additions, and/or insertions, or may be a portion of a CDR.

On the other hand, antigen-binding molecules to be used in the methods of the present invention include antigen-binding molecules that have an antagonistic activity (antagonistic antigen-binding molecules), antigen-binding molecules that have an agonistic activity (agonistic antigen-binding molecule), and molecules having cytotoxicity. In a preferred embodiment, the antigen-binding molecules comprise antagonistic antigen-binding molecules, in particular, antagonistic antigen-binding molecules that recognize an antigen such as a receptor or cytokine.

In the present invention, the antigen-binding molecule of interest is not particularly limited, and may be any antigen-binding molecules. The antigen-binding molecule of the present invention preferably has both an antigen-binding activity (antigen-binding domain) and a human FcRn-binding domain. In particular, a preferred antigen-binding molecule of the present invention comprises a human FcRn-binding domain.

The antigen-binding molecule comprising both an antigen-binding domain and a human FcRn-binding domain includes, for example, antibodies. In the context of the present invention, a preferred example of antibody includes IgG antibodies. When the antibody to be used is an IgG antibody, the type of IgG is not limited; and an IgG belonging to any isotype (subclass) such as IgG1, IgG2, IgG3, or IgG4 can be used. Furthermore, the antigen-binding molecules of the present invention may comprise an antibody constant region, and amino acid mutations may be introduced into the constant region. Amino acid mutations to be introduced include, for example, those that potentiate or impair the binding to Fcγ receptor (Proc Natl Acad Sci USA. 2006 Mar. 14; 103(11): 4005-10), but are not limited to these examples. Alternatively, it is also possible to alter the pH-dependent binding by selecting an appropriate constant region such as that of IgG2.

When the antigen-binding molecule of interest in the present invention is an antibody, it may be an antibody derived from any animal, such as a mouse antibody, human antibody, rat antibody, rabbit antibody, goat antibody, or camel antibody. Furthermore, the antibody may be an altered antibody, for example, a chimeric antibody, and in particular, an altered antibody including amino acid substitutions in the sequence of a humanized antibody, and such. The antibodies also include bispecific antibodies, antibody modification products linked with various molecules, and polypeptides comprising antibody fragments.

"Chimeric antibodies" are antibodies prepared by combining sequences derived from different animals. Specifically, the chimeric antibody includes, for example, antibodies having heavy and light chain variable (V) regions from a mouse antibody and heavy and light chain constant (C) regions from a human antibody.

"Humanized antibodies", also referred to as reshaped human antibodies, are antibodies in which the complementarity determining regions (CDRs) of an antibody derived from a nonhuman mammal, for example, a mouse, are transplanted into the CDRs of a human antibody. Methods for identifying CDRs are known (Kabat et al., Sequence of Proteins of Immunological Interest (1987), National Institute of Health, Bethesda, Md.; Chothia et al., Nature (1989) 342: 877). General genetic recombination technologies suitable for this purpose are also known (see European Patent Application EP 125023; and WO 96/02576).

A bispecific antibody refers to an antibody that has variable regions in the same antibody molecule that recognize different epitopes. A bispecific antibody may be an antibody that recognizes two or more different antigens, or an antibody that recognizes two or more different epitopes on a same antigen.

Furthermore, polypeptides comprising antibody fragments include, for example, Fab fragments, F(ab')2 fragments, scFvs (Nat Biotechnol. 2005 September; 23(9): 1126-36), domain antibodies (dAbs) (WO 2004/058821; WO 2003/002609), scFv-Fc (WO 2005/037989), dAb-Fc, and Fc fusion proteins. The Fc region of a molecule comprising Fc region can be used as a human FcRn-binding domain. Alternatively, an FcRn-binding domain may be fused to these molecules.

Further, antigen-binding molecules that are applicable to the present invention may be antibody-like molecules. An antibody-like molecule (scaffold molecule, peptide molecule) is a molecule that can exhibit functions by binding to a target molecule (Current Opinion in Biotechnology (2006) 17: 653-658; Current Opinion in Biotechnology (2007) 18: 1-10; Current Opinion in Structural Biology (1997) 7: 463-469; Protein Science (2006) 15: 14-27), and includes, for example, DARPins (WO 2002/020565), Affibody (WO 1995/001937), Avimer (WO 2004/044011; WO 2005/040229), and Adnectin (WO 2002/032925). These antibody-like molecules can bind to target molecules in a calcium concentration-dependent manner, facilitate antigen uptake into cells by antigen-binding molecules, facilitate reduction of plasma antigen concentration by administering antigen-binding molecules, and improve plasma retention of antigen-binding molecules, and increase the number of times of antigen binding by a single antigen-binding molecule.

Furthermore, the antigen-binding molecule may be a protein resulting from fusion between a human FcRn-binding domain and a receptor protein that binds to a target, and includes, for example, TNFR-Fc fusion proteins, IL1R-Fc fusion proteins, VEGFR-Fc fusion proteins, and CTLA4-Fc fusion proteins (Nat Med. 2003, January; 9(1): 47-52; BioDrugs. (2006) 20(3): 151-60). If these fusion proteins of receptor and human FcRn-binding domain bind to a target molecule in a calcium concentration-dependent manner, it is possible to facilitate antigen uptake into cells by antigen-binding molecules, facilitate the reduction of plasma antigen concentration by administering antigen-binding molecules, and improve plasma retention of the antigen-binding molecules, and increase the number of times of antigen binding by a single antigen-binding molecule.

Moreover, the antigen-binding molecule may be a fusion protein between an artificial ligand protein that binds to a target and has a neutralizing effect and a human FcRn-binding domain; and an artificial ligand protein includes, for example, mutant IL-6 (EMBO J. 1994 Dec. 15; 13(24): 5863-70). If such artificial ligand fusion proteins can bind to target molecules in a calcium concentration-dependent manner, it is possible to facilitate antigen uptake into cells by antigen-binding molecules, facilitate reduction of plasma antigen concentration by administering antigen-binding molecules, improve plasma retention of antigen-binding molecules, and increase the number of times of antigen binding by a single antigen-binding molecule.

Furthermore, sugar chains may be modified in the antibodies of the present invention. Antibodies with altered sugar chains include, for example, antibodies with modified glycosylation (WO 99/54342 and such), antibodies that are deficient in sugar chain-attached fucose (WO 00/61739; WO 02/31140; WO 2006/067847; WO 2006/067913), and antibodies having sugar chains with bisecting GlcNAc (WO 02/79255).

Besides ionized calcium concentration, conditions used for measuring antigen-binding activity can be appropriately selected by those skilled in the art, and they are not particularly limited. For example, the conditions of using HEPES buffer at 37° C. may be used to determine the activity. For example, Biacore™ (GE Healthcare) SPR analysis or such can be used to determine the activity. When the antigen is a soluble antigen, the activity of an antigen-binding molecule to bind to the soluble antigen can be determined by loading the antigen as an analyte onto a chip immobilized with the antigen-binding molecule. Alternatively, when the antigen is a membrane-type antigen, the activity of the antigen-binding molecule to bind to the membrane-type antigen can be determined by loading the antigen-binding molecule as an analyte onto an antigen-immobilized chip.

In the antigen-binding molecules of the present invention, the ratio of antigen-binding activity under a low calcium concentration condition to that under a high calcium concentration condition is not particularly limited as long as the antigen-binding activity is lower under the low calcium concentration condition than under the high calcium concentration condition. However, the value of KD (Ca 3 µM)/KD (Ca 2 mM), which is a ratio of dissociation constant (KD) against an antigen under a low calcium concentration condition to that under a high calcium concentration condition, is preferably 2 or greater, more preferably 10 or greater, and still more preferably 40 or greater. The upper limit of the KD (Ca 3 µM)/KD (Ca 2 mM) value is not particularly limited, and may be any value, for example, 400, 1,000, or 10,000, as long as production is possible by using the technologies of those skilled in the art.

When the antigen is a soluble antigen, the value of antigen-binding activity can be presented in terms of the dissociation constant (KD). On the other hand, when the antigen is a membrane-type antigen, the activity can be presented in terms of apparent dissociation constant (apparent KD). The dissociation constant (KD) and apparent dissociation constant (apparent KD) can be determined by methods known to those skilled in the art, for example, using Biacore™ (GE Healthcare) SPR analysis, Scatchard plot, flow cytometer, or such.

In the antigen-binding molecules of the present invention, other parameters that are representative of the ratio between the antigen-binding activities under a low calcium concentration condition and a high calcium concentration condition include, for example, dissociation rate constant $k_d$. When the dissociation rate constant ($k_d$) is used instead of the dissociation constant (KD) as a parameter representative of the binding activity ratio, the value of $k_d$ (under a low calcium concentration condition)/$k_d$ (under a high calcium concentration condition), which is a ratio between the $k_d$ (dissociation rate constant) values against an antigen under a low calcium concentration condition and a high calcium concentration condition, is preferably 2 or greater, more preferably 5 or greater, even more preferably 10 or greater, and still more preferably 30 or greater. The upper limit of the $k_d$ (under the condition of low calcium concentration)/$k_d$ (under condition of high calcium condition) value is not particularly limited, and may be any value, for example, 50, 100, or 200, as long as production is possible by using the technologies of those skilled in the art.

When the antigen is a soluble antigen, the value of antigen-binding activity can be presented using the dissociation rate constant ($k_d$). Alternatively, when the antigen is a membrane-type antigen, the value can be presented in terms of apparent $k_d$ (apparent dissociation rate constant). The dissociation rate constant ($k_d$) and apparent dissociation rate constant (apparent $k_d$) can be determined by methods known to those skilled in the art, for example, using Biacore™ (GE Healthcare) SPR analysis, flow cytometer, or the like.

In the present invention, when measuring the antigen-binding activity of an antigen-binding molecule at a different calcium concentration, it is preferable to use the same conditions except for the calcium concentration.

There is no particular limitation on the method for reducing (weakening) the antigen-binding activity of an antigen-binding molecule under a low calcium concentration condition to be lower than that under a high calcium concentration condition (method for conferring a calcium concentration-dependent antigen-binding activity) in order to obtain an antigen-binding molecule that has a lower antigen-binding activity under a low calcium concentration condition than under a high calcium concentration condition. Antigen-binding molecules that have a lower (weaker) antigen-binding activity under a low calcium concentration condition than under a high calcium concentration condition (antigen-binding molecules that show calcium concentration-dependent binding) can be obtained directly, for example, by screening an in vitro-displayed antibody library using the above-mentioned calcium concentration-dependent binding to an antigen as an indicator.

Other methods include methods for directly isolating an antigen-binding molecule having the above-mentioned property. For example, it is possible to directly obtain an antibody having a property of interest by immunizing animals (mice, rats, hamsters, rabbits, human immunoglobulin transgenic mice, human immunoglobulin transgenic rats, human immunoglobulin transgenic rabbits, llamas, camels, etc.) with an antigen, and screening the obtained antibodies using the calcium concentration-dependent antigen binding as an indicator. Alternatively, random mutations may be introduced into the amino acid sequence of an antigen-binding molecule, and the antigen-binding activity of the antigen-binding molecule at different calcium concentration conditions is measured by the above-mentioned method to select an antigen-binding molecule that has a lower antigen-binding activity under a low calcium concentration condition than under a high calcium concentration condition in comparison to the antigen-binding molecule before modification.

When the antigen-binding activity of an antigen-binding molecule under a low calcium concentration condition is reduced (weakened) to be lower than that under a high calcium concentration condition (the value of KD (under a low calcium concentration condition)/KD (under a high calcium concentration condition) is increased) by the above-mentioned method or such, the value of KD (under a low calcium concentration condition)/KD (under a high calcium concentration condition) is, without particular limitation, typically twice or more, preferably five times or more, and more preferably ten times or more in comparison to the original antibody.

Furthermore, by using a method for conferring the calcium concentration-dependent antigen-binding activity of the present invention, in combination with a method of using an antigen-binding molecule having human FcRn-binding activity at neutral pH or a method of conferring or increasing the human FcRn-binding activity at neutral pH, it is possible to enhance the function of promoting antigen uptake into cells, function of increasing the number of times of antigen-binding by one antigen-binding molecule, function of promoting the reduction of plasma antigen concentration by administering an antigen-binding molecule, or function of improving the plasma retention of an antigen-binding molecule. The methods of conferring or increasing the human FcRn-binding activity at neutral pH include, for example, the above-described methods for modifying amino acids in the human-FcRn-binding domain. Herein, "human FcRn-binding activity at neutral pH" means the activity to bind to human FcRn at pH 6.7 to 10.0. A preferable human FcRn-binding activity is, for example, the human FcRn-binding activity at pH 7.0 to 8.0; and a more preferable human FcRn-binding activity is, for example, the human FcRn-binding activity at pH 7.4.

Furthermore, by using a method for conferring the calcium concentration-dependent antigen-binding activity of the present invention, in combination with a method of using an antigen-binding molecule having pH-dependent antigen-binding activity or a method of conferring a pH-dependent antigen-binding activity, it is possible to enhance the function of promoting antigen uptake into cells, function of increasing the number of times of antigen-binding by one antigen-binding molecule, function of promoting the reduction of plasma antigen concentration by administering an antigen-binding molecule, or function of improving the plasma retention of an antigen-binding molecule. The methods of conferring a pH-dependent antigen-binding activity include, for example, methods described in WO 2009/125825.

Specifically, for example, a calcium concentration-dependent antigen-binding molecule of the present invention can be used in combination with a method for reducing (weakening) the antigen-binding activity of an antigen-binding molecule at acidic pH to be lower than that at neural pH. Herein, "reducing (weakening) the antigen-binding activity at acidic pH to be lower than the antigen-binding activity at neural pH" means reducing the antigen-binding activity of an antigen-binding molecule at pH 4.0 to 6.5 to be lower than that at pH 6.7 to 10.0. It preferably means weakening the antigen-binding activity of an antigen-binding molecule at pH 5.5 to 6.5 to be lower than that at pH 7.0 to 8.0, and particularly preferably means weakening the antigen-binding activity of an antigen-binding molecule at pH 5.8 to be lower than that at pH 7.4. Herein, "acidic pH" typically refers to pH 4.0 to 6.5, preferably pH 5.5 to 6.5, and particularly preferably pH 5.8. Meanwhile, herein "neutral pH" typically refers to pH 6.7 to 10.0, preferably pH 7.0 to 8.0, and particularly preferably pH 7.4.

On the other hand, the phrase "reducing the antigen-binding activity of an antigen-binding molecule at acidic pH to be lower than that at neutral pH" is synonymous with "increasing the antigen-binding activity of an antigen-binding molecule at neutral pH to be greater than that at acidic pH". Specifically, in the present invention, one may increase the difference between the antigen-binding activities of an antigen-binding molecule at acidic pH and neutral pH (for example, one may increase the value of KD (pH5.8)/KD (pH7.4) as described below). The difference between the antigen-binding activities of an antigen-binding molecule at acidic pH and neutral pH may be increased, for example, by reducing the antigen-binding activity at acidic pH, or increasing the antigen-binding activity at neutral pH, or both.

In the present invention, the difference between the antigen-binding activities at acidic pH and neutral pH is not particularly limited as long as the antigen-binding activity is lower at acidic pH than at neutral pH. However, the value of KD (pH 5.8)/KD (pH 7.4), which is a ratio between the dissociation constants (KD) against an antigen at pH 5.8 and pH 7.4, is preferably 2 or greater, more preferably 10 or greater, and still more preferably 40 or greater. The upper limit of the KD (pH 5.8)/KD (pH 7.4) value is not particularly limited, and may be any value, for example, 400, 1,000, or 10,000, as long as production is possible by using the technologies of those skilled in the art.

In the present invention, other parameters that are representative of the ratio between antigen-binding activities at acidic pH and neutral pH include, for example, dissociation rate constant $k_d$. When the dissociation rate constant ($k_d$) is used instead of the dissociation constant (KD) as a parameter representative of the binding activity ratio, the value of $k_d$ (pH 5.8)/$k_d$ (pH 7.4), which is a ratio between the $k_d$ (dissociation rate constant) values against an antigen at pH 5.7 and pH 7.4, is preferably 2 or greater, more preferably 5 or greater, even more preferably 10 or greater, and still more preferably 30 or greater. The upper limit of the $k_d$ (pH 5.8)/$k_d$ (pH 7.4) value is not particularly limited, and may be any value, for example, 50, 100, or 200, as long as production is possible by using the technologies of those skilled in the art.

The methods for conferring a pH-dependent antigen-binding activity are not particularly limited. Such methods include, for example, methods for weakening the antigen-binding activity at pH 5.8 to be lower than that at pH 7.4 by substituting at least one amino acid in an antigen-binding molecule with histidine, or inserting at least one histidine into an antigen-binding molecule. It is already known that substitution of an amino acid in an antibody with histidine can confer a pH-dependent antigen-binding activity to the antibody (FEBS Letter, 309(1): 85-88, (1992)). In the present invention, sites of histidine mutation (substitution) or insertion in an antigen-binding molecule are not particularly limited, and any site can be used as long as the antigen-binding activity at pH 5.8 becomes weaker than that at pH 7.4 (the value of KD (pH5.8)/KD (pH7.4) becomes greater) in comparison to before the mutation or insertion. For example, when the antigen-binding molecule is an antibody, such sites include an antibody variable region. The number of histidine mutation or insertion sites introduced (or made) can be appropriately determined by those skilled in the art. Only one site may be substituted with histidine, or histidine may be inserted at only one site. Alternatively, two or more multiple sites may be substituted with histidine, or histidine may be inserted at two or more multiple sites. It is also possible to introduce a mutation besides histidine mutation (mutation into an amino acid besides histidine) at the same time. Furthermore, histidine mutation may be introduced simultaneously with histidine insertion. It is possible to substitute or insert histidine at random using a method such as histidine scanning, which uses histidine instead of alanine in alanine scanning known to those skilled in the art. Alternatively, an antigen-binding molecule whose KD (pH 5.8)/KD (pH 7.4) is increased compared to before mutation can be selected from a library of antigen-binding molecules into which a random histidine mutation or insertion has been introduced.

When at least one amino acid in an antigen-binding molecule is substituted with histidine, or at least one histidine is inserted into the amino acids of an antigen-binding molecule, while there is no particular limitation, it is preferred that the antigen-binding activity of the antigen-binding molecule at pH 7.4 after histidine substitution or insertion is comparable to that at pH 7.4 before histidine substitution or insertion. Herein, the phrase "the antigen-binding activity of an antigen-binding molecule at pH 7.4 after histidine substitution or insertion is comparable to that at pH 7.4 before histidine substitution or insertion" means that the antigen-binding molecule after histidine substitution or insertion retains 10% or more, preferably 50% or more, more preferably 80% or more, and still more preferably 90% or more of the antigen-binding activity before histidine substitution or insertion. When the antigen-binding activity of an antigen-binding molecule is impaired by a histidine substitution or insertion, the antigen-binding activity may be made to be comparable to that before the histidine substitution or insertion by introducing one or more amino acid substitutions, deletions, additions, and/or insertions into the antigen-binding molecule. The present invention also includes antigen-binding molecules having a comparable binding activity made by one or more amino acid substitutions, deletions, additions, and/or insertions after histidine substitution or insertion.

Alternative methods for weakening the antigen-binding activity of an antigen-binding molecule at pH 5.8 to be lower than that at pH 7.4 include methods of substituting an amino acid in an antigen-binding molecule with a non-natural amino acid, or inserting a non-natural amino acid into the amino acids of an antigen-binding molecule. It is known that pKa can be artificially controlled using non-natural amino acids (Angew. Chem. Int. Ed. 2005, 44, 34; Chem Soc Rev. 2004 Sep. 10; 33(7): 422-30; Amino Acids. 1999; 16(3-4): 345-79). Thus, in the present invention, non-natural amino acids can be used instead of histidine mentioned above. Substitution and/or insertion of a non-natural amino acid may be introduced simultaneously with the above-mentioned histidine substitution and/or insertion. Any non-natural amino acids may be used in the present invention. It is possible to use non-natural amino acids or such known to those skilled in the art.

Furthermore, when the antigen-binding molecule is a substance containing an antibody constant region, alternative methods for weakening the antigen-binding activity of the antigen-binding molecule at pH 5.8 to be lower than that at pH 7.4 include methods for modifying the antibody constant region contained in the antigen-binding molecule. Examples of modifying an antibody constant region include methods for substituting a constant region described in WO 2009/125825.

Meanwhile, methods for altering an antibody constant region include, for example, methods for assessing various constant region isotypes (IgG1, IgG2, IgG3, and IgG4) and selecting isotypes that reduce the antigen-binding activity at pH 5.8 (increase the dissociation rate at pH 5.8). Such methods also include methods for reducing the antigen-binding activity at pH 5.8 (increasing the dissociation rate at pH 5.8) by introducing amino acid substitutions into the amino acid sequences of wild-type isotypes (amino acid sequences of wild type IgG1, IgG2, IgG3, or IgG4). The sequence of hinge region in the antibody constant region is considerably different among isotypes (IgG1, IgG2, IgG3, and IgG4), and the difference in the hinge region amino acid sequence has a great impact on the antigen-binding activity. Thus, it is possible to select an appropriate isotype to reduce the antigen-binding activity pH 5.8 (increase the dissociation rate at pH 5.8) according to the type of antigen or epitope. Furthermore, since the difference in the hinge region amino acid sequence has a great impact on the antigen-binding activity, preferred amino acid substitution sites in the amino acid sequences of wild-type isotypes are assumed to be within the hinge region.

When the antigen-binding activity of an antigen-binding substance at pH 5.8 is weakened to be lower than that at pH 7.4 (when the value of KD (pH 5.8)/KD (pH 7.4) is increased) by the above-described method and the like, it is generally preferable that the KD (pH 5.8)/KD (pH 7.4) value is twice or more, preferably five times or more, and more preferably ten times or more in comparison to the original antibody, but it is not particularly limited thereto.

Antigen-Binding Molecules

Furthermore, the present invention provides antigen-binding molecules whose antigen-binding activity differs at two different calcium concentration conditions; i.e., the antigen-binding activity is lower under a low calcium concentration condition than under a high calcium concentration condition. Preferably, the present invention provides antigen-binding molecules that have a lower antigen-binding activity under a low calcium concentration condition (ionized calcium concentration of 0.1 μM to 30 μM) than under a high calcium concentration condition (ionized calcium concentration of 100 μM to 10 mM). More specifically, the antigen-binding molecules include antigen-binding molecules that have a lower antigen-binding activity at the ionized calcium concentration in the early endosome in vivo (a low calcium concentration such as 1 μM to 5 μM) than at the ionized calcium concentration in plasma in vivo (a high calcium concentration such as 0.5 mM to 2.5 mM).

With respect to the antigen-binding activity of an antigen-binding molecule of the present invention that has a lower antigen-binding activity under a low calcium concentration condition than under a high calcium concentration condition, there is no limitation on the difference in antigen-binding activity as long as the antigen-binding activity is lower under a low calcium concentration condition than under a high calcium concentration condition. It is even acceptable that the antigen-binding activity of an antigen-binding molecule is only slightly lower under a low calcium concentration condition.

In a preferred embodiment, for an antigen-binding molecule of the present invention that has a lower antigen-binding activity under a low calcium concentration condition than under a high calcium concentration condition, the value of KD (low Ca)/KD (high Ca), which is the KD ratio between low and high calcium concentration conditions, is 2 or more, preferably the value of KD (low Ca)/KD (high Ca) is 10 or more, and more preferably the value of KD (low Ca)/KD (high Ca) is 40 or more. The upper limit of the KD (low Ca)/KD (high Ca) value is not particularly limited, and may be any value such as 400, 1,000, and 10,000 as long as it can be produced by techniques known to those skilled in the art.

In another preferred embodiment, for an antigen-binding molecule of the present invention that has a lower antigen-binding activity under a low calcium concentration condition than under a high calcium concentration condition, the value of $k_d$ (low Ca)/$k_d$ (high Ca), which is a ratio between the $k_d$ values for an antigen at a low calcium concentration condition and high calcium concentration condition, is 2 or more, preferably the value of $k_d$ (low Ca)/$k_d$ (high Ca) is 5 or more, more preferably the value of $k_d$ (low Ca)/$k_d$ (high Ca) is 10 or more, and still more preferably the value of $k_d$ (low Ca)/$k_d$ (high Ca) is 30 or more. The upper limit of the $k_d$ (low Ca)/$k_d$ (high Ca) value is not particularly limited, and may be any value such as 50, 100, and 200 as long as it can be produced by techniques known to those skilled in the art.

An antigen-binding molecule of the present invention may additionally have the above-mentioned human FcRn-binding activity under a neutral pH condition. By using the human FcRn-binding activity under a neutral pH condition in combination with a calcium concentration-dependent antigen-binding activity, it is possible to enhance the function of promoting antigen uptake into cells, function of increasing the number of times of antigen binding by one antigen-binding molecule, function of promoting the reduction of plasma antigen concentration by administering an antigen-binding molecule, or function of improving the plasma retention of an antigen-binding molecule.

An antigen-binding molecule of the present invention may additionally have the above-mentioned pH-dependent antigen-binding activity, i.e., a lower antigen-binding activity under an acidic pH condition than under a neutral pH condition. By using the pH-dependent antigen-binding activity in combination with a calcium concentration-dependent antigen-binding activity, it is possible to enhance the function of promoting antigen uptake into cells, function of increasing the number of times of antigen binding by one antigen-binding molecule, function of promoting the reduction of plasma antigen concentration by administering an antigen-binding molecule, or function of improving the plasma retention of an antigen-binding molecule.

Furthermore, an antigen-binding molecule of the present invention may have any other property as long as it has a lower antigen-binding activity under a low calcium concentration condition than under a high calcium concentration condition. For example, the antigen-binding molecule may be an agonistic antigen-binding molecule or antagonistic antigen-binding molecule. Preferred antigen-binding molecules of the present invention include, for example, antagonistic antigen-binding molecules. Such antagonistic antigen-binding molecule is typically an antigen-binding molecule that inhibits receptor-mediated intracellular signal transduction by inhibiting the binding between a ligand (agonist) and its receptor.

Furthermore, an antigen-binding molecule to which the pH-dependent antigen-binding activity is conferred may have a substitution of histidine for at least one amino acid, or an insertion of at least one histidine.

Meanwhile, there is no particular limitation on the antigen to which an antigen-binding molecule of the present invention binds, and the antigen-binding molecule may bind to any antigen. Such antigens include, for example, membrane antigens such as receptor proteins (membrane-type receptors and soluble receptors) and cell surface markers, and soluble antigens such as cytokines. Specific examples of other antigens are described above.

Screening Methods

The present invention provides methods of screening for an antigen-binding molecule that has a lower antigen-binding activity under a low calcium concentration condition than under a high calcium concentration condition. The present invention also provides methods of screening for an antigen-binding molecule having at least one function selected from:
- (i) function of promoting uptake of an antigen into cells;
- (ii) function of binding to an antigen two or more times;
- (iii) function of promoting the reduction of plasma antigen concentration; and
- (iv) function of excellence in plasma retention.

Specifically, the present invention provides methods of screening for an antigen-binding molecule, which comprises the steps of (a) to (c) below:
- (a) determining the antigen-binding activity of an antigen-binding molecule under a low calcium concentration condition;
- (b) determining the antigen-binding activity of the antigen-binding molecule under a high calcium concentration condition; and
- (c) selecting an antigen-binding molecule that has a lower antigen-binding activity under a low calcium concentration condition than under a high calcium concentration condition.

The present invention also provides methods of screening for an antigen-binding molecule, which comprises the steps of (a) to (c) below:
- (a) contacting an antigen with an antigen-binding molecule or a library of antigen-binding molecules under a high calcium concentration condition;
- (b) placing an antigen-binding molecule that binds to the antigen in step (a) under a low calcium concentration condition; and
- (c) obtaining an antigen-binding molecule that dissociates in step (b).

The present invention also provides methods of screening for an antigen-binding molecule, which comprises the steps of (a) to (d) below:
- (a) contacting an antigen with an antigen-binding molecule or a library of antigen-binding molecules under a low calcium concentration condition;
- (b) selecting an antigen-binding molecule that does not bind to the antigen in step (a);
- (c) allowing the antigen-binding molecule selected in step (b) to bind to the antigen under a high calcium concentration condition; and
- (d) obtaining an antigen-binding molecule that binds to the antigen in step (c).

The present invention also provides methods of screening for an antigen-binding molecule, which comprises the steps of (a) to (c) below:
- (a) contacting an antigen-binding molecule or a library of antigen-binding molecules with an antigen-immobilized column under a high calcium concentration condition;
- (b) eluting an antigen-binding molecule that binds to the column in step (a) from the column under a low calcium concentration condition; and
- (c) obtaining the antigen-binding molecule eluted in step (b).

The present invention also provides methods of screening for an antigen-binding molecule, which comprises the steps of (a) to (d) below:
- (a) allowing an antigen-binding molecule or a library of antigen-binding molecules to pass through an antigen-immobilized column under a low calcium concentration condition;
- (b) collecting an antigen-binding molecule eluted without binding to the column in step (a);
- (c) allowing the antigen-binding molecule collected in step (b) to bind to the antigen under a high calcium concentration condition; and
- (d) obtaining an antigen-binding molecule that binds to the antigen in step (c).

The present invention also provides methods of screening for an antigen-binding molecule, which comprises the steps of (a) to (d) below:
- (a) contacting an antigen with an antigen-binding molecule or a library of antigen-binding molecules under a high calcium concentration condition;
- (b) obtaining an antigen-binding molecule that binds to the antigen in step (a);
- (c) placing the antigen-binding molecule obtained in step (b) under a low calcium concentration condition; and
- (d) obtaining an antigen-binding molecule whose antigen-binding activity in step (c) is lower than the an antigen-binding activity in step (b).

The above steps may be repeated two or more times. Thus, the present invention provides screening methods that further comprise the step of repeating the steps of (a) to (c), or (a) to (d) two or more times in the above-mentioned screening methods. The number of times steps (a) to (c) or (a) to (d) are repeated is not particularly limited, and it is generally ten or less.

In the screening methods of the present invention, the antigen-binding activity of an antigen-binding molecule under a low calcium concentration condition is not particularly limited, as long as it is an antigen-binding activity at an ionized calcium concentration of 0.1 µM to 30 µM. Preferably, the antigen-binding activity includes antigen-binding activities at an ionized calcium concentration of 0.5 µM to 10 µM. More preferable ionized calcium concentrations include ionized calcium concentrations in the early endosome in vivo. Specifically, the antigen-binding activity includes activities at 1 µM to 5 µM. Meanwhile, the antigen-binding activity of an antigen-binding molecule under a high calcium concentration condition is not particularly limited, as long as it is an antigen-binding activity at an ionized calcium concentration of 100 µM to 10 mM. Preferably, the antigen-binding activity includes antigen-binding activities at an ionized calcium concentration of 200 µM to 5 mM. More preferred ionized calcium concentrations include ionized calcium concentrations in plasma in vivo. Specifically, the antigen-binding activity includes activities at 0.5 mM to 2.5 mM.

The antigen-binding activity of an antigen-binding molecule can be determined by methods known to those skilled in the art. Appropriate conditions besides ionized calcium concentration can be selected by those skilled in the art. The antigen-binding activity of an antigen-binding molecule can be assessed by using KD (dissociation constant), apparent KD (apparent dissociation constant), dissociation rate $k_d$ (dissociation rate), apparent $k_d$ (apparent dissociation: apparent dissociation rate), or such. They can be determined by methods known to those skilled in the art, for example, using Biacore™ (GE Healthcare) SPR analysis, Scatchard plot, FACS, or such.

In the present invention, the step of selecting an antigen-binding molecule that has a greater antigen-binding activity under a high calcium concentration condition than under a low calcium concentration is synonymous with the step of selecting an antigen-binding molecule that has a lower antigen-binding activity under a low calcium concentration condition than under a high calcium concentration condition.

The difference between the antigen binding activity under a high calcium concentration condition and that under a low calcium concentration condition is not particularly limited, as long as the antigen-binding activity is greater under a high calcium concentration condition than under a low calcium concentration condition. However, the antigen-binding activity under a high calcium concentration condition is preferably twice or more, more preferably 10 times or more, and still more preferably 40 times or more of the antigen-binding activity under a low calcium concentration condition.

Antigen-binding molecules to be screened by the screening method of the present invention may be any antigen-binding molecules. For example, the above-described antigen-binding molecules can be screened. For example, it is possible to screen for antigen-binding molecules having a natural sequence or antigen-binding molecules having an amino acid sequence with a substitution.

Antigen-binding molecules to be screened by the screening method of the present invention may be prepared by any methods. It is possible to use, for example, pre-existing antibodies, pre-existing libraries (phage libraries, and such), and antibodies and libraries prepared from B cells of immunized animals or hybridomas prepared by immunizing animals, antibodies or libraries obtained by introducing amino acids capable of chelating calcium (for example, aspartic acid or glutamic acid) or non-natural amino acid mutations into such antibodies or libraries (libraries with high content of non-natural amino acids or amino acids capable of chelating calcium (for example, aspartic acid or glutamic acid), libraries introduced with non-natural amino acid mutations or mutations with amino acids capable of chelating calcium (for example, aspartic acid or glutamic acid) at specific sites, or such), or such.

An antigen-binding molecule having at least one function selected from:
  (i) function of promoting antigen uptake into cells,
  (ii) function of binding to an antigen two or more times,
  (iii) function to promoting the reduction of plasma antigen concentration, and
  (iv) function of excellence in plasma retention,
can be obtained by the screening methods of the present invention when administered to animals such as humans, mice, and monkeys. Thus, the screening methods of the present invention can be used as a screening method to obtain an antigen-binding molecule having at least one of the above-described functions.

Furthermore, such antigen-binding molecules obtained by the screening methods of the present invention are expected to be especially superior as pharmaceuticals, because the dose and frequency of administration in patients can be reduced, and as a result the total dosage can be reduced. Thus, the screening methods of the present invention can be used as methods of screening for antigen-binding molecules for use as pharmaceutical compositions.

Methods for Producing Antigen-Binding Molecules

The present invention provides methods of producing an antigen-binding molecule that has a lower antigen-binding activity under a low calcium concentration condition than under a high calcium concentration condition. The present invention also provides methods of producing an antigen-binding molecule having at least one function selected from:
  (i) function of promoting antigen uptake into cells,
  (ii) function of binding to an antigen two or more times,
  (iii) function of promoting the reduction of plasma antigen concentration, and
  (iv) function of excellence in plasma retention.

Specifically, the present invention provides methods of producing an antigen-binding molecule, which comprise the steps of (a) to (e) below:
  (a) determining the antigen-binding activity of an antigen-binding molecule under a low calcium concentration condition;
  (b) determining the antigen-binding activity of the antigen-binding molecule under a high calcium concentration condition;
  (c) selecting an antigen-binding molecule that has a lower antigen-binding activity under the low calcium concentration condition than under the high calcium concentration condition;
  (d) obtaining a gene encoding the antigen-binding molecule selected in step (c); and
  (e) producing the antigen-binding molecule using the gene obtained in step (d).

The present invention also provides methods of producing an antigen-binding molecule, which comprise the steps of (a) to (e) below:
  (a) contacting an antigen with an antigen-binding molecule or a library of antigen-binding molecules under a high calcium concentration condition;
  (b) placing the antigen-binding molecule bound to the antigen in step (a) under a low calcium concentration condition;
  (c) obtaining an antigen-binding molecule that dissociates in step (b);
  (d) obtaining a gene encoding the antigen-binding molecule obtained in step (c); and
  (e) producing the antigen-binding molecule using the gene isolated in step (d).

Steps (a) to (d) may be repeated two or more times. Thus, the present invention provides methods that further comprise the step of repeating steps (a) to (d) two or more times in the above-described methods. The number of times steps (a) to (d) are repeated is not particularly limited, and it is generally ten or less.

Furthermore, the present invention provides methods of producing an antigen-binding molecule, which comprise the steps of (a) to (f) below:
  (a) contacting an antigen with an antigen-binding molecule or a library of antigen-binding molecules under a low calcium concentration condition;
  (b) selecting an antigen-binding molecule that does not bind to the antigen in step (a);
  (c) contacting the antigen with the antigen-binding molecule selected in step (b) under a high calcium concentration condition;
  (d) obtaining an antigen-binding molecule that binds to the antigen in step (c);
  (e) obtaining a gene encoding the antigen-binding molecule obtained in step (d); and
  (f) producing the antigen-binding molecule using the gene obtained in step (e).

Steps (a) to (e) may be repeated two or more times. Thus, the present invention provides methods that further comprise the step of repeating steps (a) to (e) two or more times in the above-described methods. The number of times steps (a) to (e) are repeated is not particularly limited, and it is generally ten or less.

The present invention also provides methods of producing an antigen-binding molecule, which comprise the steps of (a) to (e) below:
  (a) contacting an antigen-binding molecule or a library of antigen-binding molecules with an antigen-immobilized column under a high calcium concentration condition;
  (b) eluting an antigen-binding molecule bound to the column in step (a) from the column under a low calcium concentration condition;
  (c) obtaining the antigen-binding molecule eluted in step (b);
  (d) obtaining a gene encoding the antigen-binding molecule obtained in step (c); and
  (e) producing the antigen-binding molecule using the gene obtained in step (e).

Steps (a) to (d) may be repeated two or more times. Thus, the present invention provides methods that further comprise the step of repeating steps (a) to (d) two or more times in the above-described methods. The number of times steps (a) to (d) are repeated is not particularly limited, and it is generally ten or less.

The present invention also provides methods of producing an antigen-binding molecule, which comprise the steps of (a) to (f) below:
  (a) allowing an antigen-binding molecule or a library of antigen-binding molecules to pass through an antigen-immobilized column under a low calcium concentration condition;
  (b) collecting an antigen-binding molecule eluted without binding to the column in step (a);
  (c) allowing the antigen-binding molecule collected in (b) to bind to the antigen under a high calcium concentration condition;
  (d) obtaining an antigen-binding molecule that binds to the antigen in step (c);
  (e) obtaining a gene encoding the antigen-binding molecule obtained in step (d); and
  (f) producing an antigen-binding molecule using the gene obtained in step (e).

Steps (a) to (e) may be repeated two or more times. Thus, the present invention provides methods that further comprise the step of repeating steps (a) to (e) two or more times in the above-described methods. The number of times steps (a) to (e) are repeated is not particularly limited, and it is generally ten or less.

The present invention also provides methods of producing an antigen-binding molecule, which comprise the steps of (a) to (f) below:
  (a) contacting an antigen with an antigen-binding molecule or a library of antigen-binding molecules under a high calcium concentration condition;
  (b) obtaining an antigen-binding molecule that binds to the antigen in step (a);
  (c) placing the antigen-binding molecule obtained in step (b) under a low calcium concentration condition;
  (d) obtaining an antigen-binding molecule that has lower antigen-binding activity in step (c) than an antigen-binding activity in step (b);
  (e) obtaining a gene encoding the antigen-binding molecule obtained in step (d); and
  (f) producing the antigen-binding molecule using the gene obtained in step (e).

Steps (a) to (e) may be repeated two or more times. Thus, the present invention provides methods that further comprise the step of repeating steps (a) to (e) two or more times in the above-described methods. The number of times steps (a) to (e) are repeated is not particularly limited, and it is generally ten or less.

Antigen-binding molecules used in production methods of the present invention may be prepared by any method, and include, for example, existing antibodies and libraries (phage libraries, etc.), antibodies and libraries that are prepared from hybridomas obtained by immunizing animals or from B cells of immunized animals, antibodies and libraries prepared by introducing amino acids capable of chelating calcium (for example, aspartic acid and glutamic acid) or non-natural amino acid mutations into libraries (libraries with increased content of amino acids capable of chelating calcium (for example, aspartic acid and glutamic acid) or non-natural amino acids, libraries introduced with amino acids capable of chelating calcium (for example, aspartic acid and glutamic acid) or non-natural amino acid mutations at specific sites, or such).

In the above-described production methods, the antigen-binding activity of an antigen-binding molecule under a low calcium concentration condition is not particularly limited, as long as it is an antigen-binding activity at an ionized calcium concentration of 0.1 µM to 30 µM. Preferably, the antigen-binding activity includes an antigen-binding activity at an ionized calcium concentration of 0.5 µM to 10 µM. More preferred ionized calcium concentrations include the ionized calcium concentration in the early endosome in vivo. Specifically, the antigen-binding activity includes antigen-binding activities at 1 µM to 5 µM. Meanwhile, the antigen-binding activity of an antigen-binding molecule under a high calcium concentration condition is not particularly limited, as long as it is an antigen-binding activity at an ionized calcium concentration of 100 µM to 10 mM. Preferably, the antigen-binding activity includes antigen-binding activities at an ionized calcium concentration of 200 µM to 5 mM. More preferred ionized calcium concentrations include the ionized calcium concentration in plasma in vivo. Specifically, the antigen-binding activity includes antigen-binding activities at 0.5 mM to 2.5 mM.

The antigen-binding activity of an antigen-binding molecule can be determined by methods known to those skilled in the art. Appropriate conditions other than the ionized calcium concentration may be determined by those skilled in the art.

The step of selecting an antigen-binding molecule that has greater antigen-binding activity under a high calcium concentration condition than under a low calcium concentration condition is synonymous with the step of selecting an antigen-binding molecule that has greater antigen-binding activity under a low calcium concentration condition than under a high calcium concentration condition.

The difference between the antigen binding activity under a high calcium concentration condition and that under a low calcium concentration condition is not particularly limited, as long as the antigen-binding activity is greater under a high calcium concentration condition than under a low calcium concentration condition. The antigen-binding activity under a high calcium concentration condition is preferably twice or more, more preferably 10 times or more, and still more preferably 40 times or more of the antigen-binding activity under a low calcium concentration condition.

In the production methods described above, the binding of an antigen and an antigen-binding molecule may be carried out in any state, and the state is not particularly limited. For example, the binding of an antigen and an antigen-binding molecule may be carried out by contacting an antigen with an immobilized antigen-binding molecule, or by contacting an antigen-binding molecule with an immobilized antigen. Alternatively, the binding can be carried out by contacting an antigen with an antigen-binding molecule in a solution.

Furthermore, the production method of the present invention may be used for an above-described antigen-binding molecule having the human FcRn-binding activity at neutral pH, or may be combined with a method of conferring or increasing the human FcRn-binding activity at neutral pH. When the production method of the present invention is combined with a method of conferring or increasing the human FcRn-binding activity at neutral pH, the method may additionally comprise the step of altering amino acids in the antigen-binding molecule to confer or increase the human FcRn-binding activity under a neutral pH condition. Meanwhile, the preferred human FcRn-binding domain of an antigen-binding molecule having the human FcRn-binding activity at neutral pH includes, for example, the above-described human FcRn-binding domains having the human FcRn-binding activity at neutral pH. Thus, the production methods of the present invention may additionally comprise the step of selecting in advance an antigen-binding molecule having a human-FcRn-binding domain with greater human FcRn-binding activity at neutral pH and/or altering amino acids in an antigen-binding molecule to confer or increase the human FcRn-binding activity at neutral pH.

Furthermore, the production method of the present invention may be used for an antigen-binding molecule having the above-described pH-dependent antigen-binding activity, or may be combined with a method of conferring pH-dependent antigen-binding activity (WO 2009/125825). When the production method of the present invention is combined with a method of conferring pH-dependent antigen-binding activity, the method may additionally comprise the step of selecting in advance an antigen-binding molecule that has a lower antigen-binding activity under an acidic pH condition than under a neutral pH condition, and/or altering amino acids in an antigen-binding molecule to reduce the antigen-binding activity under an acidic pH condition to be lower than that under a neutral pH condition.

Preferred antigen-binding molecules having a pH-dependent antigen-binding activity include, for example, antigen-binding molecules in which at least one amino acid of an antigen binding molecule is substituted with histidine or at least one histidine is inserted into an antigen-binding molecule. Thus, the production method of the present invention may additionally comprise the step of using an antigen-binding molecule in which at least one amino acid is substituted with histidine or at least one histidine is inserted as an antigen-binding molecule, or the step of substituting histidine for at least one amino acid or inserting at least one histidine into an antigen-binding molecule.

In the production method of the present invention, non-natural amino acids may be used instead of histidine. Thus, the present invention can be understood with non-natural amino acids in place of histidine described above.

The production methods of the present invention can produce antigen-binding molecules having at least one function selected from:
(i) function of promoting antigen uptake into cells,
(ii) function of binding to an antigen two or more times,
(iii) function of promoting the reduction of plasma antigen concentration, and
(iv) function of excellence in plasma retention, when administered to animals such as humans, mice, and monkeys. Thus, the production method of the present invention may be used as a method of producing an antigen-binding molecule having at least one of the above-described functions.

Furthermore, such antigen binding molecules are expected to be especially superior as pharmaceuticals, because the dose and frequency of administration in patients can be reduced and as a result the total dosage can be reduced. Thus, the production methods of the present invention can be used as methods for producing antigen-binding molecules for use as pharmaceutical compositions.

Genes obtained by the production methods of the present invention are typically carried by (inserted into) appropriate vectors, and then introduced into host cells. The vectors are not particularly limited as long as they stably retain the inserted nucleic acids. For example, when *E. coli* is used as the host, preferred cloning vectors include the pBluescript vector (Stratagene); however, various commercially available vectors may be used. When using vectors to produce the antigen-binding molecules of the present invention, expression vectors are particularly useful. The expression vectors are not particularly limited as long as the vectors express the antigen-binding molecules in vitro, in *E. coli*, in culture cells, or in the body of an organism. For example, the pBEST vector (Promega) is preferred for in vitro expression; the pET vector (Invitrogen) is preferred for *E. coli*; the pME18S-FL3 vector (GenBank Accession No. AB009864) is preferred for culture cells; and the pME18S vector (Mol Cell Biol. (1988) 8: 466-472) is preferred for bodies of organisms. DNAs of the present invention can be inserted into the vectors by conventional methods, for example, by ligation using restriction enzyme sites (Current protocols in Molecular Biology, edit. Ausubel et al., (1987) Publish. John Wiley & Sons, Section 11.4-11.11).

The above host cells are not particularly limited, and various host cells may be used depending on the purpose. Examples of cells for expressing the antigen-binding molecules include bacterial cells (such as those of *Streptococcus, Staphylococcus, E. coli, Streptomyces*, and *Bacillus subtilis*), eukaryotic cells (such as those of yeast and *Aspergillus*), insect cells (such as *Drosophila* S2 and *Spodoptera* SF9), animal cells (such as CHO, COS, HeLa, C127, 3T3, BHK, HEK293, and Bowes melanoma cells), and plant cells. Vectors can be introduced into a host cell by known methods, for example, calcium phosphate precipitation methods, electroporation methods (Current protocols in Molecular Biology edit. Ausubel et al. (1987) Publish. John Wiley & Sons, Section 9.1-9.9), lipofection methods, and microinjection methods.

The host cells can be cultured by known methods. For example, when using animal cells as a host, DMEM, MEM, RPMI1640, or IMDM may be used as the culture medium. They may be used with serum supplements such as FBS or fetal calf serum (FCS). The cells may be cultured in serum-free cultures. The preferred pH is about 6 to 8 during the course of culturing. Incubation is carried out typically at about 30 to 40° C. for about 15 to 200 hours. Medium is exchanged, aerated, or agitated, as necessary.

Appropriate secretion signals may be incorporated to polypeptides of interest so that the antigen-binding molecules expressed in the host cell are secreted into the lumen of the endoplasmic reticulum, periplasmic space, or extracellular environment. These signals may be endogenous to the antigen-binding molecules of interest or may be heterologous signals.

On the other hand, for example, production systems using animals or plants may be used as systems for producing polypeptides in vivo. A polynucleotide of interest is introduced into an animal or plant and the polypeptide is produced in the body of the animal or plant, and then collected. The "hosts" of the present invention include such animals and plants.

The production system using animals include those using mammals or insects. It is possible to use mammals such as goats, pigs, sheep, mice, and bovines (Vicki Glaser SPECTRUM Biotechnology Applications (1993)). The mammals may be transgenic animals.

For example, a polynucleotide encoding an antigen-binding molecule of the present invention is prepared as a fusion gene with a gene encoding a polypeptide specifically produced in milk, such as the goat β casein. Next, goat embryos are injected with polynucleotide fragments containing the fusion gene, and then transplanted to female goats. Desired antigen-binding molecules can be obtained from milk produced by the transgenic goats, which are born from the goats that received the embryos, or from their offspring. Hormones may be administered as appropriate to increase the volume of milk containing the antigen-binding molecule produced by the transgenic goats (Ebert et al., Bio/Technology (1994) 12: 699-702).

Insects such as silkworms may be used to produce the antigen-binding molecules of the present invention. When silkworms are used, baculoviruses carrying a polynucleotide encoding an antigen-binding molecule of interest can be used to infect silkworms, and the antigen-binding molecule of interest can be obtained from their body fluids.

Furthermore, when plants are used to produce the antigen-binding molecules of the present invention, for example, tobacco may be used. When tobacco is used, a polynucleotide encoding an antigen-binding molecule of interest is inserted into a plant expression vector, for example, pMON 530, and then the vector is introduced into bacteria, such as *Agrobacterium tumefaciens*. The bacteria are then allowed to infect tobacco such as *Nicotiana tabacum*, and the desired antigen-binding molecules can be collected from their leaves (Ma et al., Eur. J. Immunol. (1994) 24: 131-138). Alternatively, it is possible to infect duckweed (*Lemna minor*) with similar bacteria. After cloning, the desired antigen-binding molecules can be obtained from the duckweed cells (Cox K M et al., Nat. Biotechnol. 2006 December; 24(12): 1591-1597).

The thus obtained antigen-binding molecules may be isolated from the inside or outside (such as the medium and milk) of host cells, and purified as substantially pure and homogenous antigen-binding molecules. The methods for isolating and purifying antigen-binding molecules are not particularly limited, and isolation and purification methods usually used for polypeptide purification can be used. Antigen-binding molecules may be isolated and purified by appropriately selecting and combining, for example, chromatographic columns, filtration, ultrafiltration, salting out, solvent precipitation, solvent extraction, distillation, immunoprecipitation, SDS-polyacrylamide gel electrophoresis, isoelectric focusing, dialysis, and recrystallization.

Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., (1996) Cold Spring Harbor Laboratory Press). Such chromatographic methods can be conducted using liquid phase chromatography such as HPLC and FPLC. Columns used for affinity chromatography include, protein A columns and protein G columns. Columns using protein A include, for example, Hyper D, POROS, and Sepharose F. F. (Pharmacia).

If needed, an antigen-binding molecule can be modified arbitrarily, and peptides can be partially deleted by allowing an appropriate protein modification enzyme to act before or after purification of the antigen-binding molecule. Such protein modification enzymes include, for example, trypsin, chymotrypsin, lysyl endopeptidases, protein kinases, and glucosidases.

<Pharmaceutical Compositions>

The present invention also relates to pharmaceutical compositions that include antigen-binding molecules of the present invention, antigen-binding molecules isolated by the screening methods of the present invention, or antigen-binding molecules produced by the production methods of the present invention. Antigen-binding molecules of the present invention, antigen-binding molecules isolated by the screening method of the present invention, or antigen-binding molecules produced by the production method of the present invention are antigen-binding molecules having at least one function selected from:

(i) function of promoting antigen uptake into cells,
(ii) function of binding to an antigen two or more times,
(iii) function of promoting the reduction of plasma antigen concentration, and
(iv) function of excellence in plasma retention, are useful as pharmaceutical compositions, because it is expected that the administration frequency can be reduced. Furthermore, the pharmaceutical composition of the present invention may comprise a pharmaceutically acceptable carrier.

In the present invention, pharmaceutical compositions generally refer to agents for treating or preventing, or testing and diagnosing diseases.

The pharmaceutical compositions of the present invention can be formulated by methods known to those skilled in the art. For example, they can be used parenterally, in the form of injections of sterile solutions or suspensions including water or other pharmaceutically acceptable liquid. For example, such compositions may be formulated by mixing in the form of unit dose required in the generally approved medicine manufacturing practice, by appropriately combining with pharmacologically acceptable carriers or media, specifically with sterile water, physiological saline, vegetable oil, emulsifier, suspension, surfactant, stabilizer, flavoring agent, excipient, vehicle, preservative, binder, or such. In such formulations, the amount of active ingredient is adjusted to obtain an appropriate amount in a pre-determined range.

Sterile compositions for injection can be formulated using vehicles such as distilled water for injection, according to standard formulation practice.

Aqueous solutions for injection include, for example, physiological saline and isotonic solutions containing dextrose or other adjuvants (for example, D-sorbitol, D-mannose, D-mannitol, and sodium chloride). It is also possible to use in combination appropriate solubilizers, for example, alcohols (ethanol and such), polyalcohols (propylene glycol, polyethylene glycol, and such), non-ionic surfactants (polysorbate 80(TM), HCO-50, and such).

Oils include sesame oil and soybean oils. Benzyl benzoate and/or benzyl alcohol can be used in combination as solubilizers. It is also possible to combine buffers (for example, phosphate buffer and sodium acetate buffer), soothing agents (for example, procaine hydrochloride), stabilizers (for example, benzyl alcohol and phenol), and/or antioxidants. Appropriate ampules are filled with the prepared injections.

The pharmaceutical compositions of the present invention are preferably administered parenterally. For example, the compositions may be in the dosage form for injections, transnasal administration, transpulmonary administration, or transdermal administration. For example, they can be administered systemically or locally by intravenous injection, intramuscular injection, intraperitoneal injection, subcutaneous injection, or such.

Administration methods can be appropriately selected in consideration of the patient's age and symptoms. The dose of a pharmaceutical composition containing an antigen-binding molecule may be, for example, from 0.0001 to 1,000 mg/kg for each administration. Alternatively, the dose may be, for example, from 0.001 to 100,000 mg per patient. However, the present invention is not limited by the numeric values described above. The doses and administration methods vary depending on the patient's weight, age, symptoms, and such. Those skilled in the art can set appropriate doses and administration methods in consideration of the factors described above.

Furthermore, the pharmaceutical composition of the present invention may be a pharmaceutical composition used to promote antigen uptake into cells or reduction of antigen concentration in plasma.

The present invention also relates to methods of promoting antigen uptake into cells by an antigen-binding molecule and methods of promoting the reduction of antigen concentration in plasma by administering the antigen-binding molecule of the present invention or antigen-binding molecule produced by the production method of the present invention. The antigen-binding molecule may be administered in vivo or in vitro. The subject to be administered includes, for example, nonhuman animals (mice, monkeys, etc.) and humans.

The present invention also relates to methods of increasing the number of times of antigen binding by one antigen-binding molecule and methods of improving the plasma retention of an antigen-binding molecule by using an antigen-binding molecule of the present invention or an antigen-binding molecule produced by the production method of the present invention.

Amino acids contained in the amino acid sequences of the present invention may be post-translationally modified (for example, the modification of an N-terminal glutamine into a pyroglutamic acid by pyroglutamylation is well-known to those skilled in the art). Naturally, such post-translationally modified amino acids are included in the amino acid sequences in the present invention.

Furthermore, the present invention provides kits for use in the methods of the present invention, which comprise at least an antigen-binding molecule of the present invention. In addition to the above, pharmaceutically acceptable carriers, media, instruction manuals describing the using method, and such may be packaged into the kits.

The present invention also relates to agents for promoting antigen uptake into cells by antigen-binding molecules, agents for promoting the reduction of plasma antigen concentration, agents for increasing the number of times of antigen binding by one antigen-binding molecule, and agents for improving plasma retention of antigen-binding molecules, all of which comprise as an active ingredient an antigen-binding molecule of the present invention or an antigen-binding molecule produced by production methods of the present invention.

The present invention also relates to the use of antigen-binding molecules of the present invention or antigen-binding molecules produced by production methods of the present invention in producing agents for promoting antigen uptake into cells by antigen-binding molecules, agents for promoting the reduction of plasma antigen concentration, agents for increasing the number of times of antigen binding by one antigen-binding molecule, or agents for improving plasma retention of antigen-binding molecules.

The present invention also relates to antigen-binding molecules of the present invention or antigen-binding molecules produced by production methods of the present invention for use in methods for promoting antigen uptake into cells by the antigen-binding molecules, agents for promoting the reduction of plasma antigen concentration, methods for increasing the number of times of antigen binding by one antigen-binding molecule, and methods for improving plasma retention of antigen-binding molecules.

All prior art documents cited in the specification are incorporated herein by reference.

EXAMPLES

Herein below, the present invention will be specifically described with reference to the Examples, but it is not to be construed as being limited thereto.

Example 1

The Concept of Antigen Elimination-Accelerating Effect of Calcium-Dependent Antigen-Binding Antibodies (1-1) Effect of pH-Dependent Antigen-Binding Antibodies to Accelerate Antigen Elimination H54/L28-IgG1 described in WO 2009/125825 is a humanized anti-IL-6 receptor antibody. Fv4-IgG1 is a humanized anti-IL-6 receptor antibody that results from conferring H54/L28-IgG1 with the property to bind to soluble human IL-6 receptor in a pH-dependent manner (which binds under neutral condition but is dissociated under acidic condition). The in vivo test described in WO 2009/125825 using mice demonstrated that the elimination of soluble human IL-6 receptor could be greatly accelerated in a group administered with a mixture of Fv4-IgG1 and soluble human IL-6 receptor as antigen as compared to a group administered with a mixture of H54/L28-IgG1 and soluble human IL-6 receptor as antigen.

Soluble human IL-6 receptor bound to a general antibody that binds to soluble human IL-6 receptor is recycled to the plasma along with the antibody via FcRn. Meanwhile, an antibody that binds to soluble human IL-6 receptor in a pH-dependent manner dissociates from the soluble human IL-6 receptor that has been bound to the antibody under acidic conditions in the endosome. The dissociated soluble human IL-6 receptor is degraded in the lysosome. This can greatly accelerate the elimination of soluble human IL-6 receptor. Then, the antibody that binds to soluble human IL-6 receptor in a pH-dependent manner is recycled to the plasma via FcRn. The recycled antibody can bind to a soluble human IL-6 receptor again. By repeating this cycle, a single antibody molecule can repeatedly bind to soluble human IL-6 receptors multiple times (FIG. 1).

Meanwhile, as described in WO 2009/125825, after binding to membrane-type human IL-6 receptor, a general humanized anti-IL-6 receptor antibody is internalized in a complex of humanized anti-IL-6 receptor antibody and membrane-type human IL-6 receptor and then degraded in the lysosome. In contrast, a humanized anti-IL-6 receptor antibody that binds to IL-6 receptor in a pH-dependent manner is recycled to plasma via dissociation from the membrane-type human IL-6 receptor under the acidic condition in the endosome after internalization in a complex with membrane-type human IL-6 receptor. The recycled antibody can bind to membrane-type human IL-6 receptor again. By repeating this cycle, a single antibody molecule can repeatedly bind to membrane-type human IL-6 receptor multiple times (FIG. 2).

(1-2) pH and Calcium Concentrations in Plasma and Endosome

Figure 1:
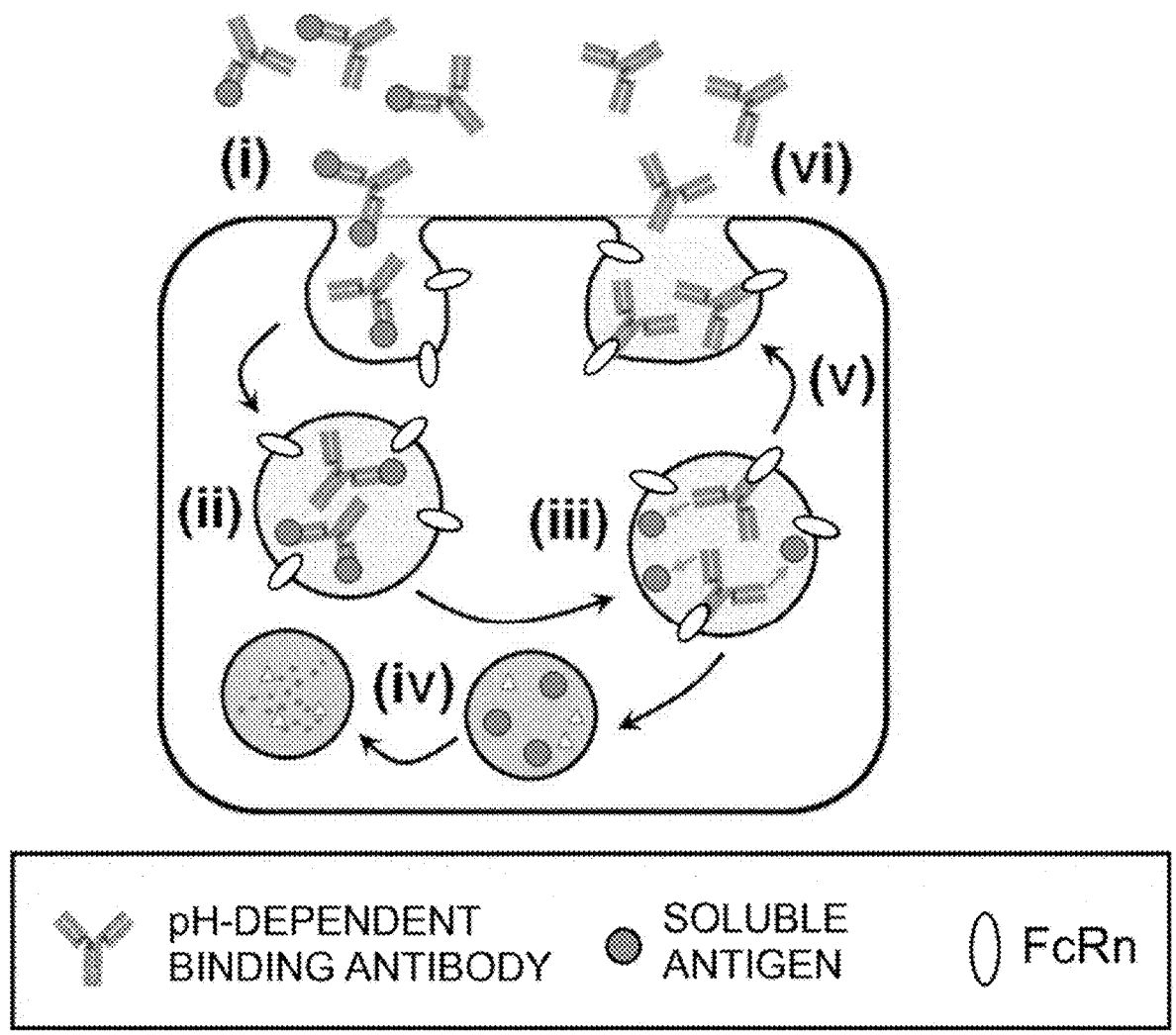
FIG. 1 is a diagram showing that an antibody with pH-dependent binding repeatedly binds to soluble antigens. (i) an antibody binds to soluble antigens; (ii) the antibody is non-specifically internalized into a cell via pinocytosis; (iii) the antibody binds to FcRn within the endosome, and then the soluble antigens dissociate from the antibody; (iv) the soluble antigens are transferred into the lysosome and degraded; (v) after dissociation from the soluble antigens, the antibody is recycled to the plasma via FcRn; (vi) the recycled antibody can bind to soluble antigens again.
Figure 2:
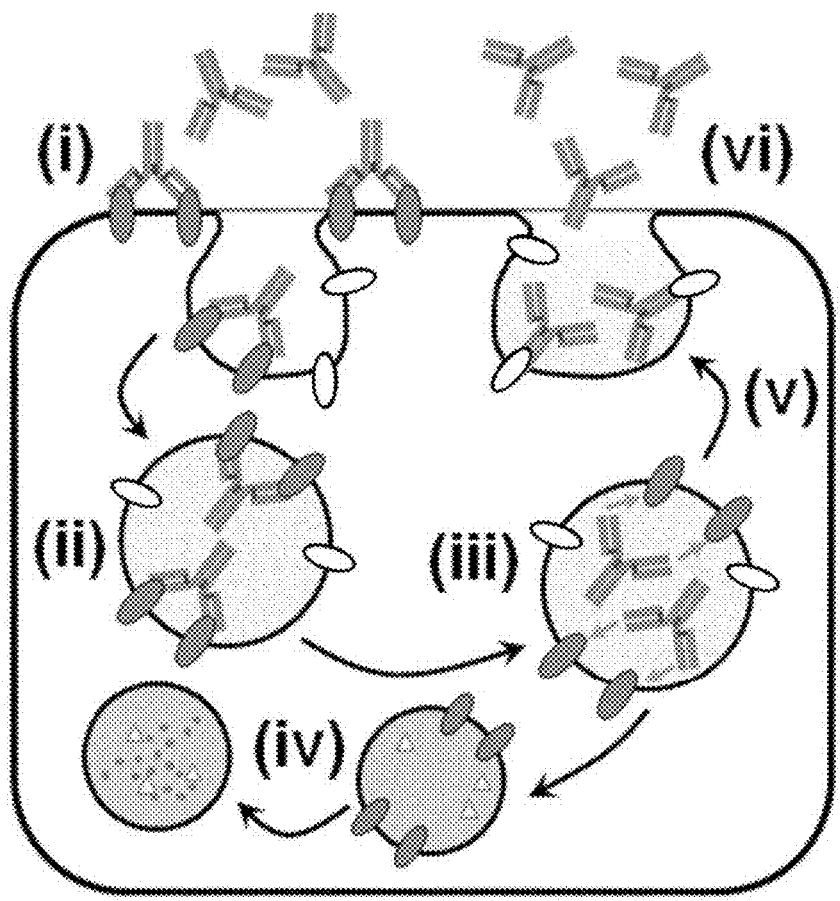
FIG. 2 is a diagram showing that an antibody with pH-dependent binding repeatedly binds to membrane antigens. (i) an antibody binds to membrane antigens; (ii) the antibody is internalized into a cell in a complex with the membrane antigens; (iii) the antibody dissociates from the membrane antigens within the endosome; (iv) the membrane antigens are transferred into the lysosome and degraded; (v) after dissociation from the membrane antigens, the antibody is recycled to the plasma; (vi) the recycled can bind to membrane antigens again.

In the mechanism of a pH-dependent binding antibody shown in FIGS. 1 and 2, it is important that the antibody strongly binds to an antigen in plasma and dissociates from the antigen in the endosome based on the environmental difference between plasma and endosome, i.e., pH difference (pH 7.4 in plasma; pH 6.0 in endosome). The degree of environmental difference between plasma and endosome is important for differentiating the antigen-binding ability of a pH-dependent binding antibody in plasma and endosome. A pH difference is due to a difference in the hydrogen ion concentration. Specifically, the hydrogen ion concentration in plasma (pH 7.4) is about 40 nM, while the concentration in the endosome (pH 6.0) is about 1,000 nM. The factor (hydrogen ion) concentration differs by about 25 times between plasma and endosome.

The present inventors conceived that, in order to achieve the mechanism illustrated in FIGS. 1 and 2 easily or to enhance the mechanism, it would be beneficial to use an antibody that depends on a factor that has a greater concentration difference between plasma and endosome than the difference of hydrogen ion concentration between the two. Thus, the inventors searched for a factor whose concentration is considerably different between plasma and endosome. As a result, calcium was identified. The ionized calcium concentration is about 1.1 to 1.3 mM in plasma and about 3 µM in the endosome. The factor (calcium) concentration differs by about 400 times between the two. Thus, the ratio was found to be greater than the difference in hydrogen ion concentration (25 times). Specifically, the mechanism illustrated in FIGS. 1 and 2 was expected to be achieved or enhanced more readily by using an ionized calcium concentration-dependent binding antibody, which binds to an antigen under a high calcium concentration condition (1.1 to 1.3 mM) but dissociates from the antigen under a low calcium concentration condition (3 µM).

Figure 3:
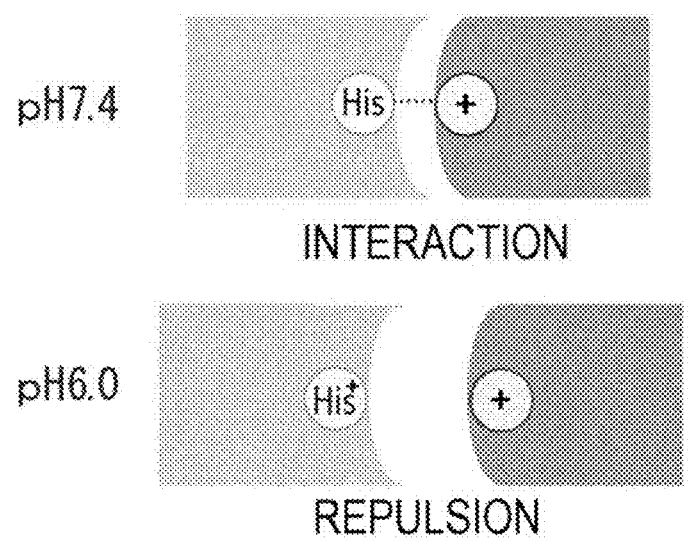
FIG. 3 is a diagram showing the modes of interaction in plasma (pH 7.4) and endosome (pH 6.0) between an antigen and an antibody with pH-dependent binding.

Furthermore, in WO 2009/125825, pH-dependent binding antibodies whose properties change between pH 7.4 and 6.0 were produced by introducing histidine. Histidine is electrically neutral under the neutral condition in plasma but is positively charged under the acidic condition in the endosome. The pH dependency can be conferred to antigen-antibody interaction by utilizing the change in the electric charge of histidine. Meanwhile, as shown in FIG. 3, when histidine is used, in order to bind to an antigen in plasma and to dissociate from the antigen in the endosome, histidine residues in the antibody need to interact with antigen's positively charged amino acids or amino acids that potentially serve as a donor for hydrogen bonding. Therefore, an antigen epitope, to which a pH-dependent binding antibody binds to exert a target effect, has to contain positively charged amino acids or amino acids that potentially serve as a donor for hydrogen bonding.

Figure 4:
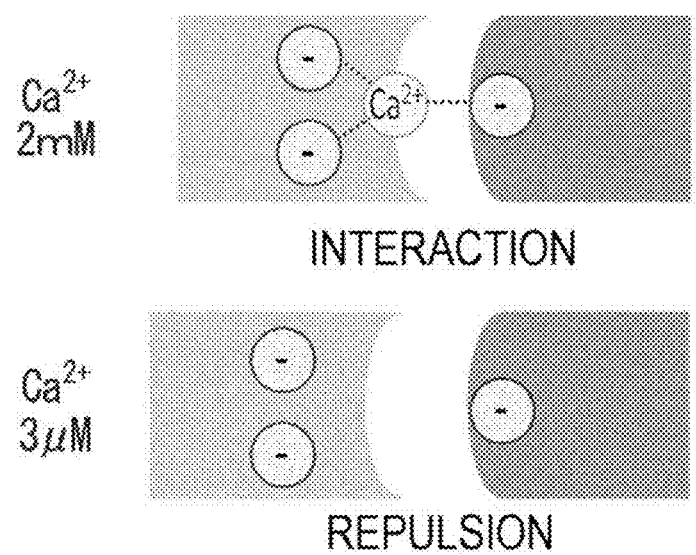
FIG. 4 is a diagram showing the modes of interaction in plasma ($Ca^{2+}$ 2 mM) and endosome ($Ca^{2+}$ 3 μM) between an antigen and an antibody with calcium-dependent binding.
Figure 5:
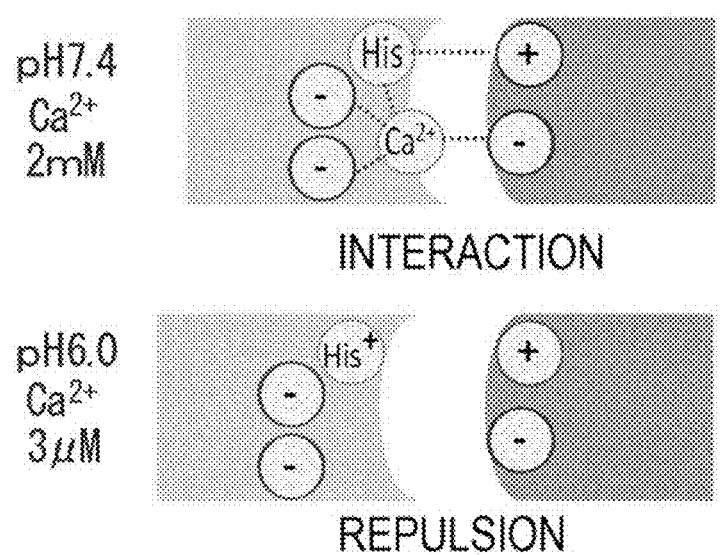
FIG. 5 is a diagram showing the modes of interaction in plasma (pH 7.4, $Ca^{2+}$ 2 mM) and endosome (pH 6.0, $Ca^{2+}$ 3 μM) between an antigen and an antibody with pH- and calcium-dependent binding.

On the other hand, as shown in FIG. 4, a calcium-dependent binding antibody is assumed to bind to an antigen via calcium ion. In this case, the antigen epitope contains negatively charged amino acids or amino acids that potentially serve as an acceptor for hydrogen bonding, which are capable of chelating calcium ion. Thus, such antibodies can target epitopes that are not targeted by pH-dependent binding antibodies produced by introducing histidine. Furthermore, as shown in FIG. 5, it is expected that epitopes that have a wide variety of properties can be targeted by using antibodies with both calcium dependency and pH dependency.

Example 2

Isolation of Ca-Dependent Binding Antibodies from Human Antibody Library Using Phage-Display Technique (2-1) Preparation of Phage-Display Library of Naive Human Antibodies Several human antibody phage-display libraries that present Fab domains comprising a human antibody sequence were constructed using as a template polyA-RNA prepared from human PBMC, human polyA RNA available on the market, or the like, according to Methods Mol Biol. 2002, 178: 87-100.

(2-2) Isolation of Ca-Dependent Binding Antibody Fragments from Libraries by Bead Panning The first selection from constructed human antibody phage-display libraries was achieved by enriching antibody fragments having antibody-binding ability or by enriching using the Ca-dependent binding ability as an indicator. Antibody fragments with a Ca-dependent binding ability were enriched by eluting phages via EDTA chelation of Ca ion after antibody fragments were bound to an antigen in the presence of Ca ion. Biotinylated human IL-6 receptor was used as the antigen.

Phages were produced with *E. coli* carrying phage-display phagemids constructed in the manner described above. The resulting culture medium was precipitated using 2.5 M NaCl/10% PEG. Then, the precipitate was diluted with TBS to prepare a phage library solution. BSA and $CaCl_2$) were added to the phage library solution so that the final concentrations of BSA and ionized calcium were 4% and 1.2 mM, respectively. Panning was carried out according to a conventional panning method using antigen-immobilized magnetic beads (J Immunol Methods. 2008 March 20, 332(1-2): 2-9; J Immunol Methods. 2001 January 1, 247(1-2): 191-203; Biotechnol Prog. 2002 March-April, 18(2): 212-20; Mol Cell Proteomics. 2003 February, 2(2): 61-9). The magnetic beads used were NeutrAvidin coated beads (Sera-Mag SpeedBeads NeutrAvidin-coated) and Streptavidin coated beads (Dynabeads M-280 Streptavidin).

Specifically, 250 pmol of the biotinylated antigen was added to the prepared phage library solution, and contacted with the antigen at room temperature for 60 minutes. BSA-blocked magnetic beads were added and incubated for binding at room temperature for 15 minutes. The beads were washed once with 1 mL of 1.2 mM $CaCl_2$/TBS (TBS containing 1.2 mM $CaCl_2$)). Then, the phages were harvested by elution using a standard method when enriching antibody fragments having binding ability, or by suspending the beads in 2 mM EDTA/TBS (TBS containing 2% EDTA) to enrich antibody fragments having Ca-dependent binding ability. *E. coli* was infected by adding 10 mL of the *E. coli* strain TG1 during the logarithmic growth phase (OD600 0.4-0.5) to the prepared phage suspension, and culturing at 37° C. for one hour with gentle stirring. The infected *E. coli* was plated onto plates (225 mm×225 mm). Again, the culture was started with this *E. coli* to cultivate the phages.

In the second and subsequent panning, the enrichment was achieved using Ca-dependent binding ability as an indicator. Specifically, 40 pmol of the biotinylated antigen was added to the prepared phage library solution. The phages were contacted with the antigen at room temperature for 60 minutes. BSA-blocked magnetic beads were added to the suspension and incubated for binding at room temperature for 15 minutes. The beads were washed once each with 1 mL of 1.2 mM $CaCl_2$/TBST (TBS containing 1.2 mM $CaCl_2$) and 0.1% Tween-20) and 1.2 mM $CaCl_2$/TBS. Then, 0.1 mL of 2 mM EDTA/TBS (TBS containing 2% EDTA) was added to suspend the beads at room temperature, and immediately after suspension, the beads were removed using Magnet Stand to collect the phage suspension. The resulting phage suspension was added to 10 mL of the *E. coli* stain TG1 during the logarithmic growth phase (OD600 0.4-0.5) to infect the *E. coli* which was then cultured at 37° C. for one hour with gentle stirring. The infected *E. coli* was plated onto plates (225 mm×225 mm). Again, the culture was started with this *E. coli*, and the phages were cultivated in the manner as described above. Panning was repeated twice.

(2-3) Assessment by Phage ELISA

From *E. coli* single colonies obtained by the method described above, phage-containing culture supernatants were prepared according to Methods Mol Biol. 2002, 178: 133-145.

BSA and $CaCl_2$) were added to the phage-containing culture supernatants so that the final concentrations of BSA and calcium were 4% and 1.2 mM, respectively. The supernatants were subjected to ELISA. StreptaWell 96 microtiter plates (Roche) were coated using 100 μL of PBS containing the biotinylated antigen. After washing with PBST (PBS containing 0.1% Tween®20 (polysorbate 20)) to remove the antigen, the plates were blocked with 250 μL of 4% BSA/ TBS for one hour or more. 4% BSA-TBS was removed, and then the prepared culture supernatants were added to the plates. The plates were allowed to stand at 37° C. for one hour to achieve the binding of phage-display antibody. Following wash with 1.2 mM $CaCl_2$/TBST (TBS containing 1.2 mM $CaCl_2$ and 0.1% Tween®20 (polysorbate 20)), 1.2 mM $CaCl_2$/TBS or 1 mM EDTA/TBS was added to the plates. The plates were allowed to stand at 37° C. for 30 minutes of incubation. After washing with 1.2 mM $CaCl_2$/ TBST, the plates were incubated for one hour with an HRP-conjugated anti-M13 antibody (Amersham Pharmacia Biotech) diluted with TBS containing 4% BSA and 1.2 mM ionized calcium. After washing with 1.2 mM $CaCl_2$)/TBST, detection was carried out with the TMB single solution (ZYMED). Absorbance at 450 nm was determined after the reaction was terminated by adding sulfuric acid. Antibody fragments judged to have a Ca-dependent binding ability were analyzed for their nucleotide sequences using specific primers.

(2-4) Antibody Expression and Purification

Clones judged to have a Ca-dependent binding ability by phage ELISA were introduced into animal cell expression plasmids. Antibodies were expressed using the following method. Cells of human fetal kidney-derived line FreeStyle 293-F(Invitrogen) were suspended in the FreeStyle 293 Expression Medium (Invitrogen), and 3-ml aliquots were plated to each well of 6-well plates at a cell density of $1.33×10^6$ cells/mL. The prepared plasmids were introduced into the cells by a lipofection method. The cells were cultured in a $CO_2$ incubator (37° C., 8% $CO_2$, 90 rpm) for four days. From the obtained culture supernatants, antibodies were purified using rProtein A Sepharose™ Fast Flow (Amersham Biosciences) by a method known to those skilled in the art. The concentrations of purified antibodies were determined by measuring absorbance at 280 nm using a spectrophotometer. The antibody concentrations were calculated from the determined values based on the extinction coefficient determined by PACE method (Protein Science 1995; 4: 2411-2423).

Example 3

Assessment of the Prepared Antibodies for their Ca-Dependent Binding Activity to Human IL-6 Receptor Antibodies 6RL #9-IgG1 (heavy chain SEQ ID NO: 1; light chain SEQ ID NO: 2), 6RK #12-IgG1 (heavy chain SEQ ID NO: 66; light chain SEQ ID NO: 67), and FH4-IgG1 (heavy chain SEQ ID NO: 3; light chain SEQ ID NO: 4) prepared in Example 2 were assessed for their binding activity to human interleukin 6 receptor (hIL6R) at pH 7.4 using Biacore™ T100 (GE Healthcare) SPR analysis. The assay was carried out using as a running buffer 0.05% Surfactant P20 (polysorbate 20), 10 mmol/L N-(2-acetamido)-2-aminoethanesulfonic acid (ACES), 150 mmol/L NaCl (pH 7.4 or 6.0) containing 3 μM or 2 mM $CaCl_2$).

Figure 6:
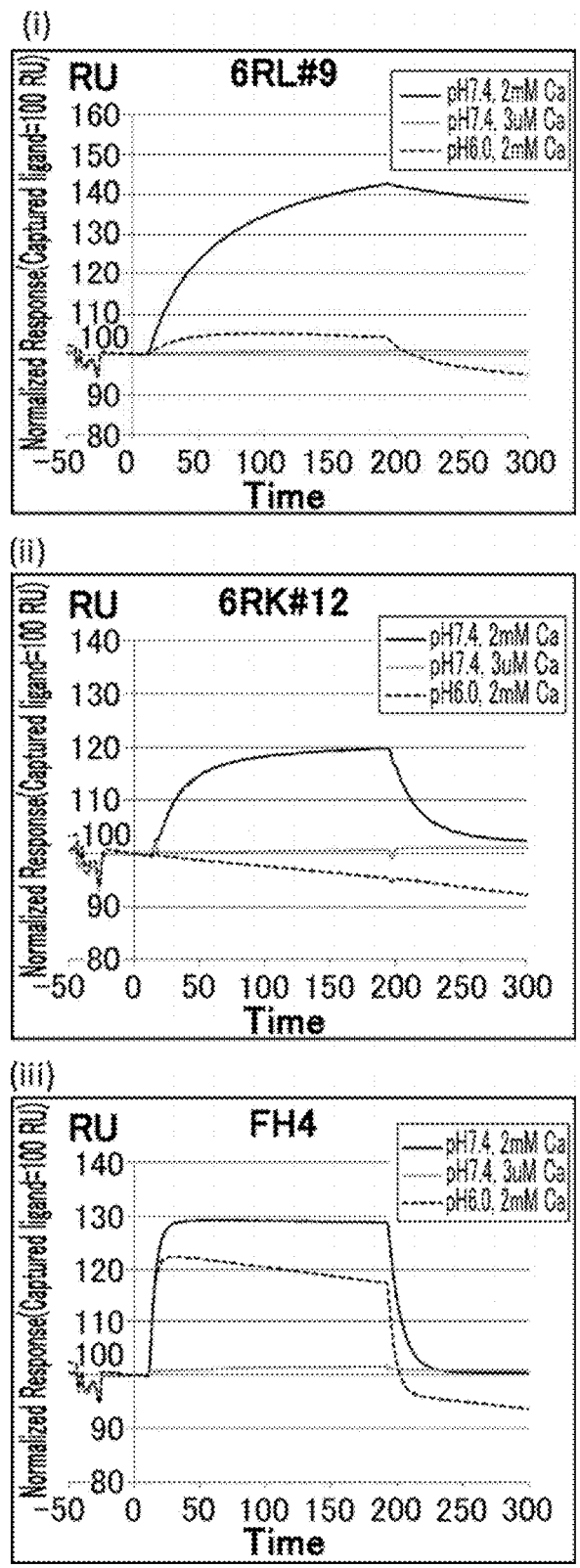
FIG. 6 presents Biacore™ sensorgrams showing the interaction of anti-human IL-6 receptor antibodies with soluble human IL-6 receptor under the conditions of ($Ca^{2+}$ 2 mM) and ($Ca^{2+}$ 3 μM).

After immobilizing an adequate amount of recombinant Protein A (Thermo Scientific) onto Sensor chip CM4 (GE Healthcare) by an amino coupling method, antibodies were allowed to bind onto the sensor chip. An appropriate concentration of hIL-6R was injected as an analyte to interact with antibodies on the sensor chip. Then, 10 mmol/L glycine-HCl (pH 1.5) was injected to regenerate the sensor chip. Measurements were carried out at 37° C. Sensorgrams obtained by the measurements are show in in FIG. 6. The result demonstrated that all of antibodies 6RL #9-IgG1, 6RK #12-IgG1, and FH4-IgG1 bound to hIL6R more weakly under the condition of 3 μM $Ca^{2+}$ concentration of than under the condition of 2 mM $Ca^{2+}$ concentration.

Of these antibodies, as antibodies exhibiting Ca dependency, 6RL #9-IgG1 (heavy chain SEQ ID NO: 1; light chain SEQ ID NO: 2) and FH4-IgG1 (heavy chain SEQ ID NO: 3; light chain SEQ ID NO: 4) were further analyzed kinetically. H54/L28-IgG1 (heavy chain SEQ ID NO: 5; light chain SEQ ID NO: 6) described in WO 2009/125825 was used as an antibody exhibiting no Ca dependency. The high and low calcium ion concentration conditions used were 2 mM and 3 μM, respectively. Human IL-6 receptor (IL-6R) was used as an antigen. An appropriate amount of protein A (Invitrogen) was immobilized onto Sensor chip CM4 (GE Healthcare) by the amine coupling method and antibodies of interest were captured on the chip. The two types of running buffers used were: [10 mmol/L ACES, 150 mmol/L NaCl, 0.05% (w/v) Tween®20 (polysorbate 20), 2 mmol/L $CaCl_2$) (pH 7.4)] or [10 mmol/L ACES, 150 mmol/L NaCl, 0.05% (w/v) Tween®20 (polysorbate 20), 3 μmol/L $CaCl_2$) (pH 7.4)]. All measurements were carried out at 37° C. Each buffer was also used to dilute IL-6R.

H54L28-IgG1 was assayed by injecting each running buffer as a blank and the diluted IL-6R solution at a flow rate of 20 μl/min for three minutes. Thus, IL-6R was allowed to interact with the antibody captured on the sensor chip. Then, the running buffer was injected at a flow rate of 20 μl/min for ten minutes to observe the dissociation of IL-6R. Next, 10 mmol/L glycine-HCl (pH 1.5) was injected at a flow rate of 30 μl/min for 30 seconds to regenerate the sensor chip. Association rate constant ka (1/Ms) and dissociation rate constant kd (1/s), which are kinetic parameters, were calculated from the sensorgram obtained by the measurement. Based on the values, the dissociation constant $K_D$ (M) between each antibody and human IL-6 receptor was calculated. Each parameter was calculated using the Biacore™ T100 Evaluation Software (GE Healthcare).

FH4-IgG1 and 6RL #9-IgG1 were assayed by injecting each running buffer as a blank and the diluted IL-6R solution at a flow rate of 5 µl/min for 15 minutes. Thus, IL-6R was allowed to interact with the antibody captured on the sensor chip. Then, 10 mmol/L glycine-HCl (pH 1.5) was injected at a flow rate of 30 µl/min for 30 seconds to regenerate the sensor chip. Based on the steady state affinity model, the dissociation constant KD (M) was calculated from the sensorgram obtained by the measurement. Each parameter was calculated using the Biacore™ T100 Evaluation Software (GE Healthcare).

Figure 7:
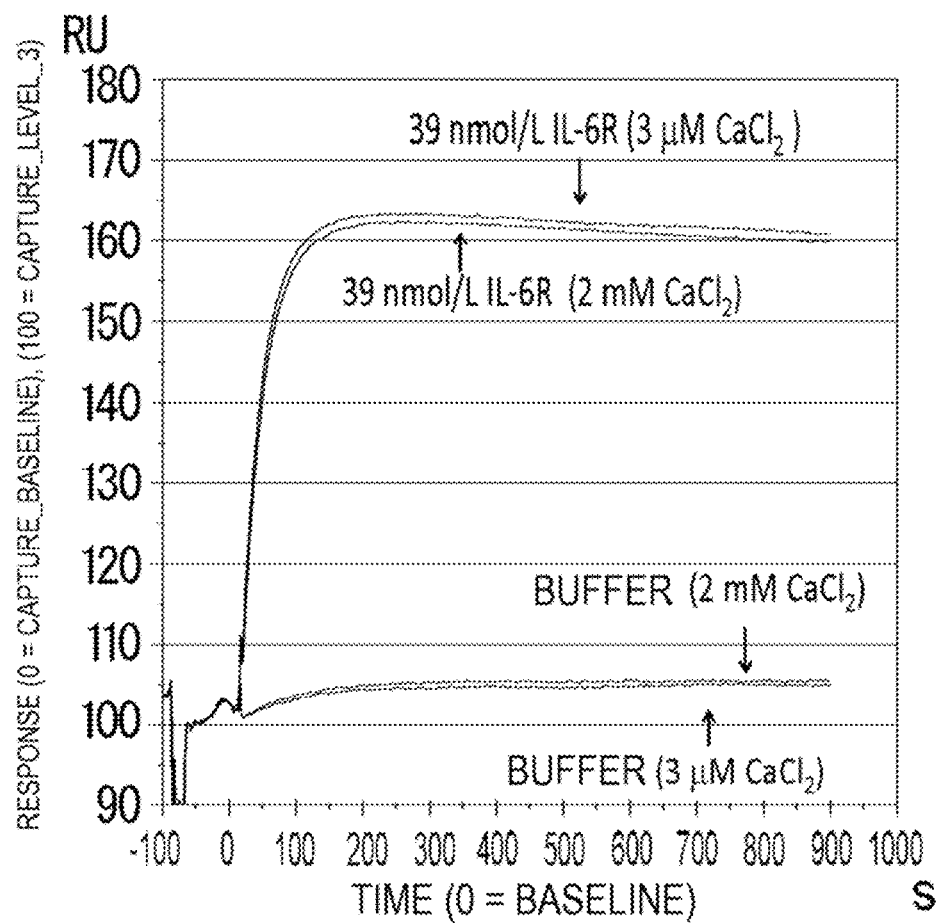
FIG. 7 presents a Biacore™ sensorgram showing the interaction of H54/L28-IgG1 with soluble human IL-6 receptor under the conditions of ($Ca^{2+}$ 2 mM) and ($Ca^{2+}$ 3 μM).
Figure 8:
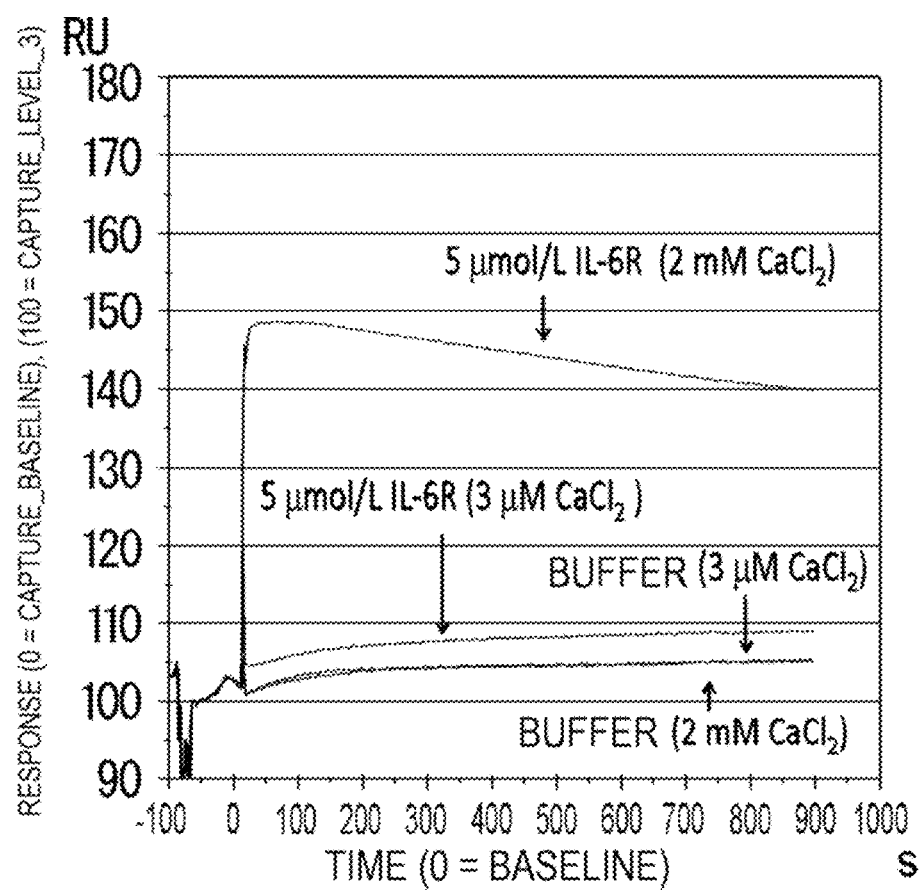
FIG. 8 presents a Biacore™ sensorgram showing the interaction of FH4-IgG1 with soluble human IL-6 receptor under the conditions of ($Ca^{2+}$ 2 mM) and ($Ca^{2+}$ 3 μM).
Figure 9:
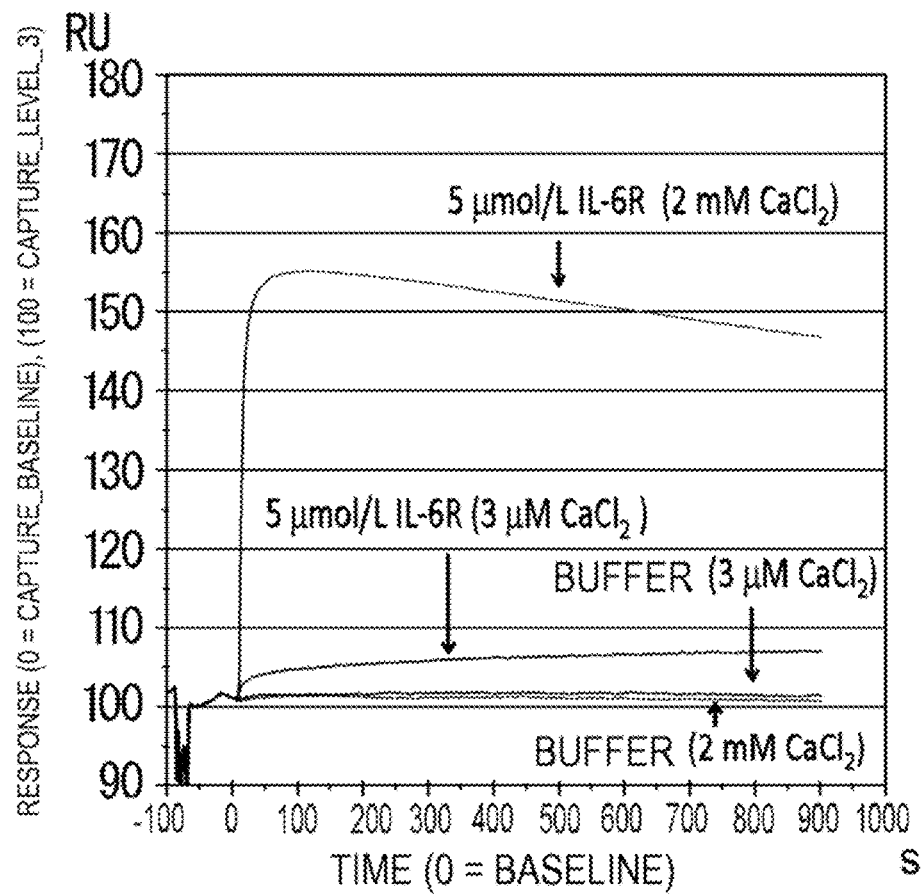
FIG. 9 presents a Biacore™ sensorgram showing the interaction of 6RL #9-IgG1 with soluble human IL-6 receptor under the conditions of ($Ca^{2+}$ 2 mM) and ($Ca^{2+}$ 3 μM).

The dissociation constants KD between IL-6R and each antibody in the presence of 2 mM $CaCl_2$), which was determined by the above-described methods, are shown in Table 7. H54/L28-IgG1 did not show any difference in the level of IL-6R binding due to the Ca concentration difference. Meanwhile, FH4-IgG1 and 6RL #9-IgG1 exhibited a significant impairment of binding at the low Ca concentration condition (FIGS. 7, 8, and 9).

TABLE 7

|  | H54/L28-IgG1 | FH4-IgG1 | 6RL#9-IgG1 |
|---|---|---|---|
| $K_D$ (M) | 1.9E−9 | 5.9E−7 | 2.6E−7 |

In the case of H54/L28-IgG1, $K_D$ at a Ca concentration of 3 µM can be calculated by similar methods used for determining $K_D$ at a Ca concentration of 2 mM. In the case of FH4-IgG1 and 6RL #9-IgG1, on the other hand, it is difficult to calculate $K_D$ at a Ca concentration of 3 M by similar methods described above, because the binding to IL-6R was almost undetectable at 3 µM Ca concentration. However, the $K_D$ can be predicted by using formula 1 shown below (Biacore™ T100 Software Handbook, BR-1006-48, AE 01/2007).

$$R_{eq} = C \cdot R_{max}/(K_D + C) + RI \quad \text{[Formula 1]}$$

Each symbol in formula 1 shown above is defined below.
$R_{eq}$ (RU): steady state binding levels
$R_{max}$ (RU): analyte binding capacity of the surface
RI (RU): bulk refractive index contribution in the sample
C (M): analyte concentration
$K_D$ (M): equilibrium dissociation constant The dissociation constant $K_D$ between IL-6R and each antibody at a Ca concentration of 3 µmol/L, which can be predicted by using formula 1 above, is shown as an approximate estimate in Table 8.

TABLE 8

|  | H54L28-IgG1 | FH4-IgG1 | 6RL#9-IgG1 |
|---|---|---|---|
| $R_{eq}$ (RU) |  | 5 | 10 |
| $R_{max}$ (RU) |  | 39 | 72 |
| RI (RU) |  | 0 | 0 |
| C (M) |  | 5E−06 | 5E−06 |
| $K_D$ (M) | 2.2E−9 | 3.4E−05 | 3.1E−05 |

In Table 8 shown above, the $R_{eq}$, $R_{max}$, RI, and C values are estimated based on the assay result.

Based on the findings described above, it was predicted that the $K_D$ between IL-6R and FH4-IgG1 or 6RL #9-IgG1 was increased by about 60 or 120 times (the affinity was reduced by 60 or 120 times or more) when the concentration of $CaCl_2$) was altered from 2 mM to 3 M. Table 9 summarizes the $K_D$ values at $CaCl_2$) concentrations of 2 mM and 3 µM and the Ca dependency for the three types of antibodies H54/L28-IgG1, FH4-IgG1, and 6RL #9-IgG1.

TABLE 9

|  | H54/L28-IgG1 | FH4-IgG1 | 6RL#9-IgG1 |
|---|---|---|---|
| $K_D$ (M) (2 mM $CaCl_2$) | 1.9E−9 | 5.9E−7 | 2.6E−7 |
| $K_D$ (M) (3 µM $CaCl_2$) | 2.2E−9 | 3.4E−5 OR HIGHER | 3.1E−5 OR HIGHER |
| Ca DEPENDENCY | ABOUT THE SAME | ABOUT 60 FOLD OR MORE | ABOUT 120 FOLD OR MORE |

Example 4

Assessment of the Obtained Antibodies for their Calcium Ion Binding

Next, antibodies were tested for their calcium ion binding by differential scanning calorimetry (DSC) (MicroCal VP-Capillary DSC; MicroCal) to assess the midpoint temperature of thermal denaturation (Tm value). The midpoint temperature of thermal denaturation (Tm value) serves as an indicator for stability. When a protein is stabilized by calcium ion binding, the midpoint temperature of thermal denaturation (Tm value) is elevated as compared to that when the protein is not bound to calcium ion (J Bio Chem. 2008 Sep. 12; Vol. 283; No. 37: pp 25140-25149). Based on this principle, antibodies were assessed for their calcium ion binding. Purified antibodies were dialyzed (EasySEP, TOMY) against a solution of [20 mM Tris-HCl, 150 mM NaCl, 2 mM $CaCl_2$) (pH 7.4)] or [20 mM Tris-HCl, 150 mM NaCl, 3 µM $CaCl_2$) (pH 7.4)]. The protein solutions were adjusted to 0.1 mg/ml using the same dialysis buffer as used in dialyzing the protein solution. DSC measurement was carried out at a heating rate of 240° C./hr from 20 to 115° C. Based on the obtained DSC denaturation curves, the midpoint temperature of thermal denaturation (Tm value) was calculated for the Fab domain of each antibody. The values are shown in Table 10.

TABLE 10

| VARIABLE REGION SEQUENCE | CALCIUM ION CONCENTRATION | | ΔTm[° C.] |
|---|---|---|---|
|  | 3 µM | 2 mM | 2 mM-3 µM |
| H54/L28 | 92.87 | 92.87 | 0.00 |
| FH4 | 74.71 | 78.97 | 4.26 |
| 6RL#9 | 77.77 | 78.98 | 1.21 |

The result shown in Table 10 demonstrates that for FH4 and 6RL #9, which exhibit calcium-dependent binding ability, the Tm values of their Fab vary depending on the calcium concentration, while the Tm value does not change in H54/L28, which does not exhibit calcium-dependent binding ability. The observed changes in the Tm values of Fab in FH4 and 6RL #9 suggest that the Fab domains of the antibodies were stabilized by calcium ion binding to the antibodies. This implies that calcium ion binds to FH4 and 6RL #9 whereas calcium ion does not bind to H54/L28.

Example 5

Assessment of Ca-Dependent Binding Antibodies for their Effect on Antigen Retention in Plasma Using Normal Mice (5-1) In Vivo Test Using Normal Mice Normal mice (57BL/6J mouse; Charles River Japan) were administered with hsIL-6R (soluble human IL-6 receptor: prepared as described in REFERENCE EXAMPLE 1) alone or in combination with an anti-human IL-6 receptor antibody, and then assessed for the in vivo dynamics of hsIL-6R and the anti-human IL-6 receptor antibody. An hsIL-6R solution (5 µg/ml) or a mixed solution of hsIL-6R and an anti-human IL-6 receptor antibody was administered at 10 ml/kg once into the caudal vein. The anti-human IL-6 receptor antibodies used were H54/L28-IgG1, 6RL #9-IgG1, and FH4-IgG1 described above.

The concentration of hsIL-6R was 5 µg/ml in all the mixed solutions. Meanwhile, the anti-human IL-6 receptor antibody concentration differs with each antibody. The concentration of H54/L28-IgG1 was 0.1 mg/mL, while those of 6RL #9-IgG1 and FH4-IgG1 were 10 mg/mL. The anti-human IL-6 receptor antibody is present in excess over hsIL-6R, and therefore almost every hsIL-6R is assumed to be bound by the antibody. Blood was collected 15 minutes, 7 hours, 1 day, 2 days, 4 days, 7 days, 14 days, 21 days, and 28 days after administration. The collected blood was immediately centrifuged at 4° C. and 12,000 rpm for 15 minutes to separate the plasma. The separated plasma was stored in a freezer at −20° C. or below until measurement.

Figure 10:
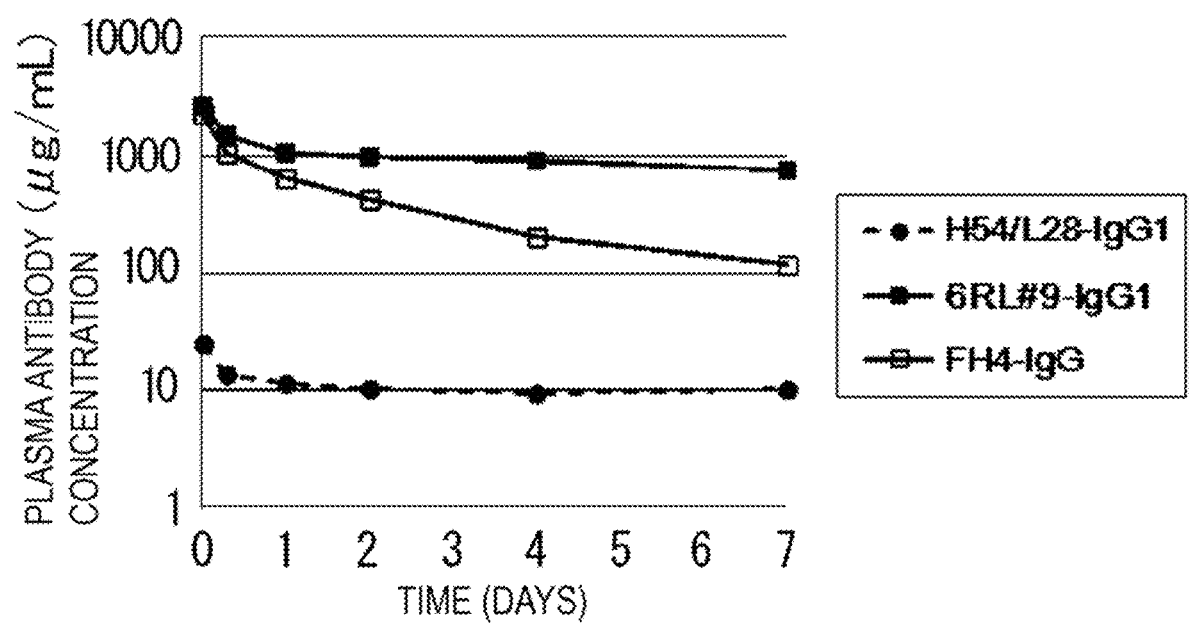
FIG. 10 describes a time course of the plasma antibody concentration in normal mice administered with H54/L28-IgG1, FH4-IgG1, or 6RL #9-IgG1.

(5-2) ELISA Determination of the Anti-Human IL-6 Receptor Antibody Concentration in Normal Mice Plasma The anti-human IL-6 receptor antibody concentration in mouse plasma was determined by ELISA. First, Anti-Human IgG (γ-chain specific) F(ab')2 Fragment of Antibody (SIGMA) was dispensed onto Nunc-Immuno Plates, MaxiSorp (Nalge nunc International) and allowed to stand overnight at 4° C. to prepare Anti-Human IgG-immobilized plates. Calibration curve samples having plasma concentrations of 0.64, 0.32, 0.16, 0.08, 0.04, 0.02, and 0.01 µg/mL, and mouse plasma assay samples diluted 100-fold or more were prepared and aliquoted into the Anti-Human IgG-immobilized plates. The plates were incubated at 25° C. for one hour, followed by incubation with biotinylated anti-human IL-6R antibody (R&D) at 25° C. for one hour. Then, Streptavidin-PolyHRP80 (Stereospecific Detection Technologies) was reacted at 25° C. for 0.5 hour. Color development was carried out using TMB One Component HRP Microwell Substrate (BioFX Laboratories) as a substrate. After stopping the reaction with 1N Sulfuric acid (Showa Chemical), absorbance at 450 nm was measured on a microplate reader. The plasma concentrations in the mice were calculated from the absorbance of the calibration curve using the analytical software SOFTmax PRO (Molecular Devices). Time courses for the plasma concentrations of antibodies H54/L28-IgG1, 6RL #9-IgG1, and FH4-IgG1 in normal mice after intravenous administration determined by this method are shown in FIG. 10.

Figure 11:
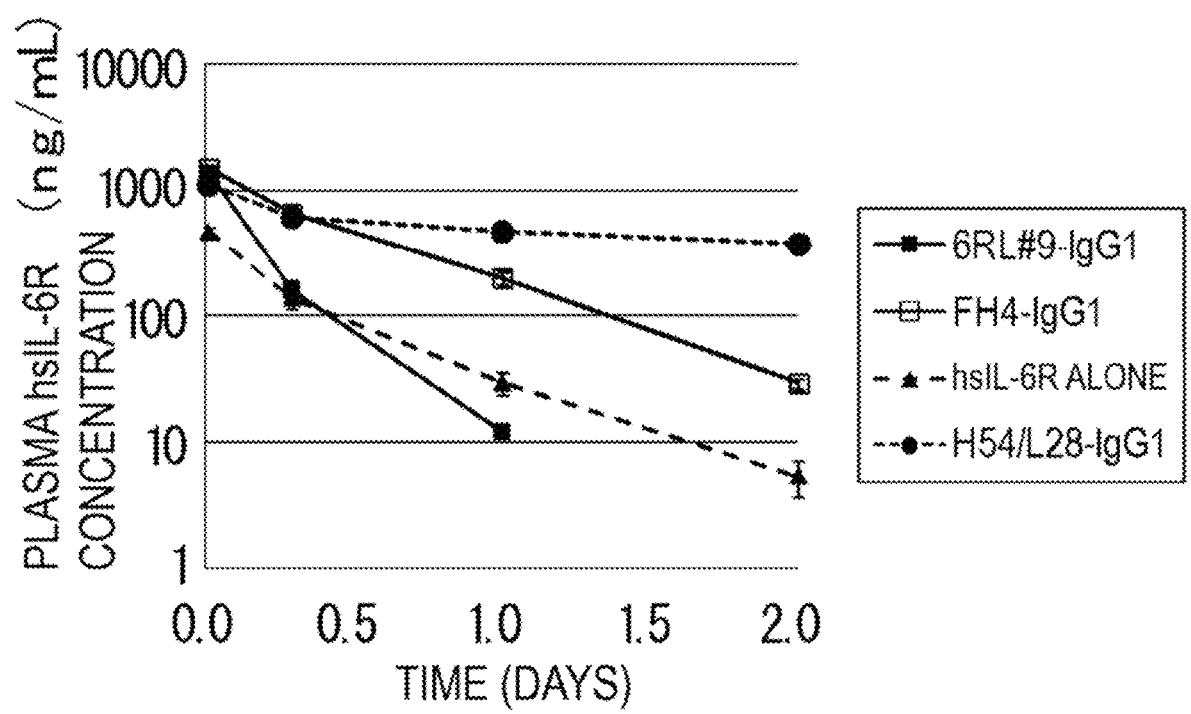
FIG. 11 describes a time course of the plasma level of soluble human IL-6 receptor (hsIL-6R) in normal mice administered with H54/L28-IgG1, FH4-IgG1, or 6RL #9-IgG1.

(5-3) Measurement of Plasma hsIL-6R Concentration by Electrochemiluminescence Method The hsIL-6R concentration in mouse plasma was measured by the electrochemiluminescence method. hsIL-6R calibration curve samples adjusted to concentrations of 2,000, 1,000, 500, 250, 125, 62.5, or 31.25 pg/mL and mouse plasma assay samples diluted 50-fold or more were prepared. The samples were mixed with a solution of monoclonal anti-human IL-6R antibody (R&D) ruthenium-labeled with SULFO-TAG NHS Ester (Meso Scale Discovery), Biotinylated Anti-human IL-6R Antibody (R&D), and tocilizumab (heavy chain SEQ ID NO: 13; light chain SEQ ID NO: 14), and then allowed to react overnight at 4° C. The assay buffer used for the reaction contains 10 mM EDTA for the purpose of reducing the free Ca concentration in the samples so that almost every hsIL-6R is dissociated from 6RL #9-IgG1 or FH4-IgG1 in the samples and binds to tocilizumab added. Then, the mixtures were aliquoted into the MA400 PR Streptavidin Plate (Meso Scale Discovery). After another hour of reaction at 25° C., the plate was washed. Immediately after Read Buffer T(×4) (Meso Scale Discovery) was aliquoted into the plate, measurement was carried out using the SECTOR PR 400 reader (Meso Scale Discovery). The hSIL-6R concentration was calculated based on the response in the calibration curve using the analytical software, SOFTmax PRO (Molecular Devices). Time courses of the plasma hsIL-6R concentration in normal mice after intravenous administration determined by the above-described method are shown in FIG. 11.

The findings described above demonstrated that hsIL-6R administered alone was eliminated very rapidly. Meanwhile, the elimination of hsIL-6R was considerably retarded when hsIL-6R was simultaneously administered with a general antibody H54/L28-IgG1 which does not exhibit Ca-dependent hsIL-6R binding. Meanwhile, the elimination of hsIL-6R was significantly accelerated when hsIL-6R was simultaneously administered with 6RL #9-IgG1 or FH4-IgG1, which has 100 times or higher hsIL-6R binding in a Ca-dependent manner. When hsIL-6R was administered in combination with 6RL #9-IgG1 or FH4-IgG1, the plasma hsIL-6R concentration on Day 1 could be reduced by 39 times or twice, respectively, in comparison to when hsIL-6R was administered in combination with H54/L28-IgG1. This demonstrates that calcium-dependent binding antibodies can accelerate the elimination of an antigen from the plasma.

Example 6

Trials to Improve the Antigen Elimination-Accelerating Effect of Antibody with Ca-Dependent Antigen-Binding (Preparation of Antibodies)

(6-1) Regarding the Binding of IgG Antibody to FcRn

IgG antibodies have longer plasma retention time as a result of FcRn binding. The binding between IgG and FcRn is observed only under an acidic condition (pH 6.0). By contrast, the binding is almost undetectable under a neutral condition (pH 7.4). An IgG antibody is taken up into cells in a nonspecific manner. The antibody returns to the cell surface by binding to endosomal FcRn under the endosomal acidic condition, and then dissociates from FcRn under the plasma neutral condition. When the FcRn binding under the acidic condition is lost by introducing mutations into the IgG Fc domain, the antibody retention time in plasma is markedly impaired because the antibody no longer recycles to the plasma from the endosome.

A reported method for improving the plasma retention of an IgG antibody is to enhance the FcRn binding under acidic conditions. Amino acid mutations are introduced into its Fc domain of an IgG antibody to improve its FcRn binding under acidic conditions. This increases the efficiency of recycling to the plasma from the endosome, resulting in improvement of the plasma retention. An important requirement in the amino acid substitution is not to augment the FcRn binding under neutral conditions. If an IgG antibody binds to FcRn under neutral conditions, the antibody does not dissociate from FcRn under the plasma neutral condition even if it returns to the cell surface by binding to FcRn under the endosomal acidic condition. In this case, the plasma retention is rather lost because the IgG antibody is not recycled to the plasma.

For example, as described in J Immunol. (2002) 169(9): 5171-80, an IgG1 antibody modified by introduction of amino acid substations so that the resulting antibody is capable of binding to mouse FcRn under a neutral condition (pH 7.4) was reported to exhibit very poor plasma retention when administered to mice. Furthermore, as described in J Immunol. (2009) 182(12): 7663-71; J Biol Chem. 2007 Jan. 19, 282(3): 1709-17; and J Immunol. 2002 Nov. 1, 169(9): 5171-80, an IgG1 antibody has been modified by introduction of amino acid substitutions so that the resulting antibody exhibits improved human FcRn binding under an acidic condition (pH 6.0) and at the same time becomes capable of binding to human FcRn under a neutral condition (pH 7.4). The resulting antibody was reported to show neither improvement nor alteration in plasma retention when administered to cynomolgus monkeys. Thus, the antibody engineering technology for improving antibody functions has only focused on the improvement of antibody plasma retention by enhancing human FcRn binding under acidic conditions without enhancing it under a neutral condition (pH 7.4). To date, there is no report describing the advantage of improving human FcRn binding under a neutral condition (pH 7.4) by introducing amino acid substitutions into the Fc domain of an IgG antibody.

Antibodies that bind to antigens in a pH-dependent manner accelerate the elimination of soluble antigen. The antibodies produce the effect by repeatedly binding to soluble antigens multiple times. Thus, such antibodies are very useful. A method for augmenting FcRn binding under a neutral condition (pH 7.4) was tested to further enhance the antigen elimination-facilitating effect.

(6-2) Preparation of Ca-Dependent Human IL-6 Receptor-Binding Antibodies Having FcRn-Binding Activity Under Neutral Conditions Amino acid mutations to enhance FcRn binding under a neutral condition (pH 7.4) were introduced into FH4-IgG1 and 6RL #9-IgG1 which have a calcium-dependent antigen-binding ability, and H54/L28-IgG1 as a control which does not have the calcium-dependent antigen-binding ability. Amino acid mutations were introduced by a PCR method known to those skilled in the art. Specifically, FH4-N434W (heavy chain SEQ ID NO: 7; light chain SEQ ID NO: 8), 6RL #9-N434W (heavy chain SEQ ID NO: 9; light chain SEQ ID NO: 10), and H54/L28-N434W (heavy chain SEQ ID NO: 11; light chain SEQ ID NO: 12) were constructed by substituting Trp for Asn at position 434 in the EU numbering system in the heavy chain constant region of IgG1. The method for substituting an amino acid is as follows. Mutants were prepared using the QuikChange Site-Directed Mutagenesis Kit (Stratagene) by the method described in the appended instruction manual. The resulting plasmid fragments were inserted into animal cell expression vectors to construct desired expression vectors. Antibody expression and purification, and determination of their concentrations were carried out by the methods described in Example 2.

Example 7

Assessment of the Elimination-Accelerating Effect of Ca-Dependent Binding Antibodies Using Normal Mice (7-1) In Vivo Test Using Normal Mice Normal mice (C57BL/6J mouse; Charles River Japan) were administered with hsIL-6R (soluble human IL-6 receptor: prepared as described in REFERENCE EXAMPLE 1) alone or in combination with an anti-human IL-6 receptor antibody, and then assessed for the in vivo dynamics of hsIL-6R and the anti-human IL-6 receptor antibody. An hsIL-6R solution (5 µg/ml) or a mixed solutions of hsIL-6R and an anti-human IL-6 receptor antibody was administered at 10 mL/kg once into the caudal vein. The anti-human IL-6 receptor antibodies used were the above-described H54/L28-N434W, 6RL #9-N434W, and FH4-N434W.

The concentration of hsIL-6R was 5 µg/mL in all the mixed solutions. Meanwhile, the anti-human IL-6 receptor antibody concentration differs with each antibody. The concentrations of H54/L28-N434W, 6RL #9-N434W, and FH4-N434W were 0.042, 0.55, and 1 mg/ml, respectively. In this case, the anti-human IL-6 receptor antibody is present in excess over hsIL-6R in the mixed solutions, and therefore almost every hsIL-6R is assumed to be bound by the antibody. Blood was collected 15 minutes, 7 hours, 1 day, 2 days, 4 days, 7 days, 14 days, 21 days, and 28 days after administration. The collected blood was immediately centrifuged at 4° C. and 12,000 rpm for 15 minutes to separate plasma. The separated plasma was stored in a freezer at −20° C. or below before assay.

Figure 12:
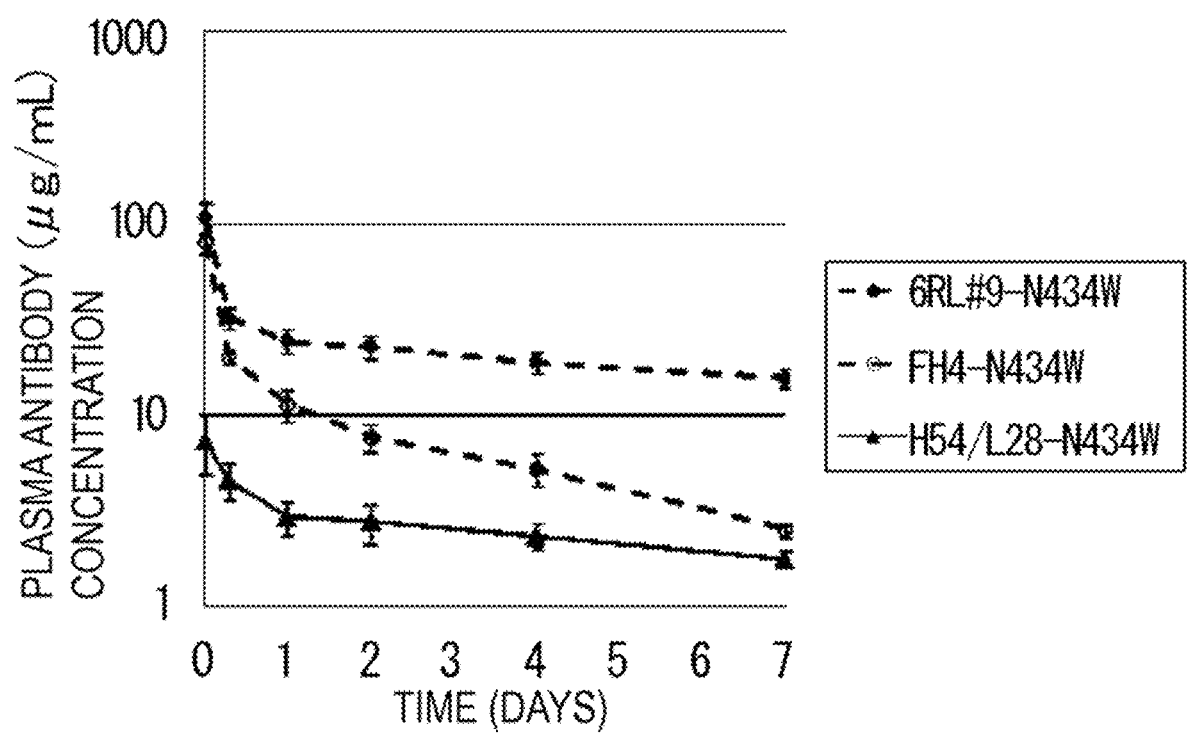
FIG. 12 describes a time course of the plasma antibody concentration in normal mice administered with H54/L28-N434W, FH4-N434W, or 6RL #9-N434W.

(7-2) ELISA Measurement of the Anti-Human IL-6 Receptor Antibody Concentration in Plasma in Normal Mice The anti-human IL-6 receptor antibody concentration in mouse plasma was measured by ELISA in the same manner as described in EXAMPLE 6. Time courses of the plasma concentrations of antibodies H54/L28-N434W, 6RL #9-N434W, and FH4-N434W in normal mice after intravenous administration determined by this method are shown in FIG. 12.

Figure 13:
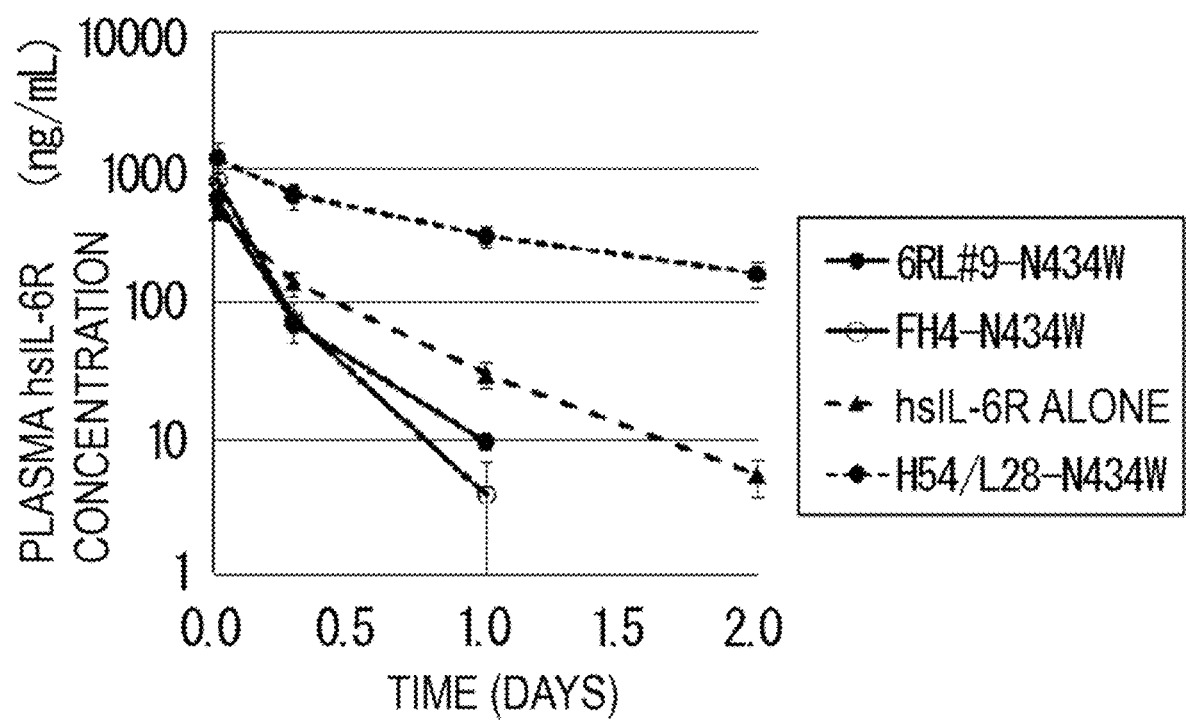
FIG. 13 describes a time course of the plasma level of soluble human IL-6 receptor (hsIL-6R) in normal mice administered with H54/L28-N434W, FH4-N434W, or 6RL #9-N434W.

(7-3) Measurement of the Plasma hsIL-6R Concentration by Electrochemiluminescence Assay The hsIL-6R concentration in mouse plasma was measured by the electrochemiluminescence method. hsIL-6R calibration curve samples adjusted to concentrations of 2,000, 1,000, 500, 250, 125, 62.5, and 31.25 pg/mL and mouse plasma assay samples diluted 50-fold or more were prepared. The samples were mixed with a solution of monoclonal anti-human IL-6R antibody (R&D) ruthenium-labeled with SULFO-TAG NHS Ester (Meso Scale Discovery) and biotinylated anti-human IL-6R antibody (R&D), and then allowed to react overnight at 4° C. The assay buffer used for the reaction contains 10 mM EDTA for the purpose of reducing the free Ca concentration in the samples so that almost every hsIL-6R dissociates from 6RL #9-N434W or FH4-N434W in the samples and exists in a free form. Then, the mixtures were aliquoted into the MA400 PR Streptavidin Plate (Meso Scale Discovery). After one hour of reaction at 25° C., the plate was washed. Immediately after Read Buffer T(×4) (Meso Scale Discovery) was aliquoted into the plate, measurement was carried out using the SECTOR PR 400 reader (Meso Scale Discovery). The hsIL-6R concentrations were calculated based on the response in the calibration curve using the analytical software, SOFTmax PRO (Molecular Devices). Time courses of the plasma hsIL-6R concentration in normal mice after intravenous administration determined by the above-described method are shown in FIG. 13.

The findings described above demonstrated that the FcRn binding at pH 7.4 was enhanced but, when hsIL-6R was simultaneously administered with a general antibody H54/L28-N434W, which does not exhibit Ca-dependent hsIL-6R binding, the elimination of hsIL-6R was considerably retarded as compared to when hsIL-6R was administered alone. Meanwhile, when hsIL-6R was simultaneously administered with 6RL #9-N434W or FH4-N434W which are antibodies that have enhanced FcRn binding at pH 7.4 and 100 times or higher hsIL-6R binding depending on Ca, the elimination of hsIL-6R was significantly accelerated as compared to when hsIL-6R was administered alone. When hsIL-6R was simultaneously administered with 6RL #9-N434W and FH4-N434W, the plasma hsIL-6R concentration on Day 1 could be reduced by 3 and 8 times, respectively, as compared to when hsIL-6R was administered alone. This demonstrates that the elimination of an antigen from the plasma can be further accelerated by enhancing the FcRn-binding ability of a calcium-dependent binding antibody at pH 7.4.

In comparison to a general antibody H54/L28-IgG1 which does not exhibit Ca-dependent hsIL-6R binding, antibody 6RL #9-IgG1 or FH4-IgG1 which has 100 times or higher Ca-dependent hsIL-6R binding were confirmed to have the effect to enhance the hsIL-6R elimination. Furthermore, in comparison to when hsIL-6R alone was administered, hsIL-6R and antibody 6RL #9-N434W or FH4-N434W which exhibits enhanced FcRn binding at pH 7.4 and has 100 times or higher hsIL-6R binding depending on Ca were confirmed to be able to accelerate hsIL-6R elimination. The data described above suggests that similar to an antibody that binds to an antigen in a pH-dependent manner, an antibody that binds to an antigen in a Ca-dependent manner dissociates from the antigen in the endosome, as illustrated in FIG. 1. As described in Example 1, there are limited types of epitopes targeted by antibodies with pH-dependent antigen binding (FIG. 3). However, by using antibodies with Ca-dependent antigen binding as revealed in the present invention, it is considered that one can expand the variety of epitopes to be targeted by antibodies capable of endosome-dependent antigen dissociation (FIGS. 4 and 5).

Example 8

Identification of Calcium Ion-Binding Site in Antibody 6RL #9 by X-Ray Crystallography (8-1) X-Ray Crystallography As described in Example 4, the measurements of thermal denaturation temperature Tm suggested that antibody 6RL #9 binds to calcium ion. However, it was unpredictable which portion of antibody 6RL #9 binds to calcium ion. Then, by using the technique of X-ray crystallography, residues of antibody 6RL #9 that interact with calcium ion were identified.

(8-2) Expression and Purification of Antibody 6RL #9

Antibody 6RL #9 was expressed and purified for X-ray crystallography. Specifically, animal expression plasmids constructed to be capable of expressing the heavy chain (SEQ ID NO: 1) and light chain (SEQ ID NO: 2) of antibody 6RL #9 were introduced transiently into animal cells. The constructed plasmids were introduced by the lipofection method into cells of human fetal kidney cell-derived Free-Style 293-F (Invitrogen) suspended in 800 ml of the Free-Style 293 Expression Medium (Invitrogen) (final cell density: $1\times10^6$ cells/mL). The plasmid-introduced cells were cultured in a $CO_2$ incubator (37° C., 8% $CO_2$, 90 rpm) for five days. From the culture supernatant obtained as described above, antibodies were purified by a method known to those skilled in the art using the rProtein A Sepharose™ Fast Flow (Amersham Biosciences). Absorbance at 280 nm of purified antibody solutions was measured using a spectrophotometer. Antibody concentrations were calculated from the measured values using an extinction coefficient calculated by the PACE method (Protein Science (1995) 4, 2411-2423).

(8-3) Purification of Antibody 6RL #9 Fab Fragment

Antibody 6RL #9 was concentrated to 21 mg/ml using an ultrafilter with a molecular weight cutoff of 10,000 MWCO. A 5 mg/mL antibody sample (2.5 mL) was prepared by diluting the antibody solution using 4 mM L-cysteine/5 mM EDTA/20 mM sodium phosphate buffer (pH 6.5). 0.125 mg of papain (Roche Applied Science) was added to the sample. After stirring, the sample was incubated at 35° C. for two hours. After incubation, a tablet of Protease Inhibitor Cocktail Mini, EDTA-free (Roche Applied Science) was dissolved in 10 ml of 25 mM MES buffer (pH 6) and added to the sample. The sample was incubated on ice to stop the papain proteolytic reaction. Then, the sample was loaded onto a 1-ml cation-exchange column HiTrap SP HP (GE Healthcare) equilibrated with 25 mM MES buffer (pH 6), downstream of which a 1-ml HiTrap MabSelect Sure Protein A column (GE Healthcare) was connected in tandem. A purified fraction of the Fab fragment of antibody 6RL #9 was obtained by performing elution with a linear NaCl concentration gradient up to 300 mM in the above-described buffer. Then, the resulting purified fraction was concentrated to about 0.8 ml using a 5000 MWCO ultrafilter. The concentrate was loaded onto a gel filtration column Superdex 200 10/300 GL (GE Healthcare) equilibrated with 100 mM HEPES buffer (pH 8) containing 50 mM NaCl. The purified Fab fragment of antibody 6RL #9 for crystallization was eluted from the column using the same buffer. All the column treatments described above were carried out at a low temperature of 6 to 7.5° C.

(8-4) Crystallization of the Antibody 6RL #9 Fab Fragment in the Presence of Ca

Seed crystals of the 6RL #9 Fab fragment were prepared in advance under general conditions. Then, the purified Fab fragment of antibody 6RL #9 in 5 mM $CaCl_2$) was concentrated to 12 mg/ml with a 5000 MWCO ultrafilter. Next, the sample concentrated as described above was crystallized by the hanging drop vapor diffusion method using 100 mM HEPES buffer (pH 7.5) containing 20% to 29% PEG4000 as a reservoir solution. The above-described seed crystals were crushed in 100 mM HEPES buffer (pH 7.5) containing 29% PEG4000 and 5 mM $CaCl_2$), and serially diluted to 100 to 10,000 folds. Then, 0.2 μL of diluted solutions were combined with a mixture of 0.8 μl of the reservoir solution and 0.8 μl of the concentrated sample to prepare crystallization drops on a glass cover slide. The crystal drops were allowed to stand at 20° C. for two to three days to prepare thin plate-like crystals. X-ray diffraction data were collected using the crystals.

(8-5) Crystallization of the Antibody 6RL #9 Fab Fragment in the Absence of Ca

The purified Fab fragment of antibody 6RL #9 was concentrated to 15 mg/ml using a 5000 MWCO ultrafilter. Then, the sample concentrated as described above was crystallized by the hanging drop vapor diffusion method using 100 mM HEPES buffer (pH 7.5) containing 18% to 25% PEG4000 as a reservoir solution. Crystals of the antibody 6RL #9 Fab fragment obtained in the presence of Ca were crushed in 100 mM HEPES buffer (pH 7.5) containing 25% PEG4000, and serially diluted to 100 to 10,000 folds. Then, 0.2 µL of diluted solutions were combined with a mixture of 0.8 µl of the reservoir solution and 0.8 µl of the concentrated sample to prepare crystallization drops on a glass cover slide. The crystal drops were allowed to stand at 20° C. for two to three days to prepare thin plate-like crystals. X-ray diffraction data were collected using the crystals.

(8-6) X-Ray Crystallographic Measurement of Fab Fragment Crystal from Antibody 6RL #9 in the Presence of Ca Crystals of the Fab fragment of antibody 6RL #9 prepared in the presence of Ca were soaked in 100 mM HEPES buffer (pH 7.5) solution containing 35% PEG4000 and 5 mM $CaCl_2$). By removing the exterior solution from the surface of a single crystal with a micro-nylon-loop pin, the single crystal was frozen in liquid nitrogen. X-ray diffraction data of the frozen crystal was collected from beam line BL-17A of the Photon Factory in the High Energy Accelerator Research Organization. The frozen crystal was maintained in the frozen state during the measurement by constantly placing it in a stream of nitrogen gas at −178° C. A total of 180 diffraction images were collected using the CCD detector Quantum315r (ADSC) attached to the beam line while rotating the crystal in 1° intervals. Lattice constant determination, diffraction spot indexing, and diffraction data analysis were performed using programs Xia2 (CCP4 Software Suite), XDS Package (Walfgang Kabsch), and Scala (CCP4 Software Suite). Finally, diffraction intensity data up to 2.2 angstrom resolution was obtained. The crystal belongs to space group P212121 with lattice constant a=45.47 angstrom, b=79.86 angstrom, c=116.25 angstrom, $\alpha=90°$, $\beta=90°$, and $\gamma=90°$.

(8-7) X-Ray Crystallographic Measurement of the Fab Fragment Crystal from Antibody 6RL #9 in the Absence of Ca Crystals of the Fab fragment of antibody 6RL #9 prepared in the absence of Ca were soaked in 100 mM HEPES buffer (pH 7.5) solution containing 35% PEG4000. By removing the exterior solution from the surface of a single crystal with a micro-nylon-loop pin, the single crystal was frozen in liquid nitrogen. X-ray diffraction data of the frozen crystal was collected from beam line BL-5A of the Photon Factory in the High Energy Accelerator Research Organization. The frozen crystal was maintained in the frozen state during the measurement by constantly placing it in a stream of nitrogen gas at −178° C. A total of 180 diffraction images were collected using the CCD detector Quantum210r (ADSC) attached to the beam line while rotating the crystal in 10 intervals. Lattice constant determination, diffraction spot indexing, and diffraction data analysis were performed using programs Xia2 (CCP4 Software Suite), XDS Package (Walfgang Kabsch), and Scala (CCP4 Software Suite). Finally, diffraction intensity data up to 2.3 angstrom resolution was obtained. The crystal belongs to space group P212121 with lattice constant a=45.40 angstrom, b=79.63 angstrom, c=116.07 angstrom, $\alpha=90°$, $\beta=90°$, $\gamma=90°$, and thus is structurally identical to the crystal prepared in the presence of Ca.

(8-8) X-Ray Crystallographic Measurement of the Fab Fragment Crystal from Antibody 6RL #9 in the Presence of Ca The crystal structure of the antibody 6RL #9 Fab fragment in the presence of Ca was determined by a molecular replacement method using the Phaser program (CCP4 Software Suite). The number of molecules in an asymmetrical unit was estimated to be one from the size of crystal lattice and molecular weight of the antibody 6RL #9 Fab fragment. Based on the primary sequence homology, a portion of amino acid positions 112 to 220 from A chain and a portion of amino acid positions 116 to 218 from B chain in the conformational coordinate of PDB code 1ZA6 were used as model molecules for analyzing the CL and CHI regions. Then, a portion of amino acid positions 1 to 115 from B chain in the conformational coordinate of PDB code 1ZA6 was used as a model molecule for analyzing the VH region. Finally, a portion of amino acid positions 3 to 147 of the light chain in the conformational coordinate of PDB code 2A9M was used as a model molecule for analyzing the VL region. Based on this order, an initial structure model for the antibody 6RL #9 Fab fragment was obtained by determining from translation and rotation functions the positions and orientations of the model molecules for analysis in the crystal lattice. The crystallographic reliability factor R for the reflection data at 25 to 3.0 angstrom resolution was 46.9% and Free R was 48.6% after rigid body refinement where the VH, VL, CHI, and CL domains were each allowed to deviate from the initial structure model. Then, model refinement was achieved by repeating structural refinement using program Refmac5 (CCP4 Software Suite) followed by model revision performed using program Coot (Paul Emsley) with reference to the Fo-Fc and 2Fo-F electron density maps where the coefficients Fo-Fc and 2Fo-Fc were calculated using experimentally determined structural factor Fo, structural factor Fc calculated based on the model, and the phases. The final refinement was carried out using program Refmac5 (CCP4 Software Suite) based on the Fo-Fc and 2Fo-F electron density maps by adding water molecule and Ca ion into the model. With 21,020 reflection data at 25 to 2.2 angstrom resolution, eventually the crystallographic reliability factor R became 20.0% and free R became 27.9% for the model consisting of 3440 atoms.

(8-9) Measurement of X-Ray Diffraction Data of the Fab Fragment Crystal from Antibody 6RL #9 in the Absence of Ca The crystal structure of the antibody 6RL #9 Fab fragment in the absence of Ca was determined based on the structure of the crystal prepared in the presence of Ca. Water and Ca ion molecules were omitted from the conformational coordinate of the crystal of the antibody 6RL #9 Fab fragment prepared in the presence of Ca. The crystallographic reliability factor R for the data of reflection at 25 to 3.0 angstrom resolution was 30.3% and Free R was 31.7% after the rigid body refinement where the VH, VL, CHI, and CL domains were each allowed to deviate. Then, model refinement was achieved by repeating structural refinement using program Refmac5 (CCP4 Software Suite) followed by model revision performed using program Coot (Paul Emsley) with reference to the Fo-Fc and 2Fo-Fc electron density maps where the coefficients Fo-Fc and 2Fo-Fc were calculated using experimentally determined structural factor Fo, structural factor Fc calculated based on the model, and the phases. The final refinement was carried out using program Refmac5 (CCP4 Software Suite) based on the Fo-Fc and 2Fo-F electron density maps by adding water molecule and Ca ion into the model. With 18,357 reflection data at 25 to 2.3 angstrom resolution, eventually the crystallographic reliability factor R became 20.9% and free R became 27.7% for the model consisting of 3351 atoms.

Figure 14:
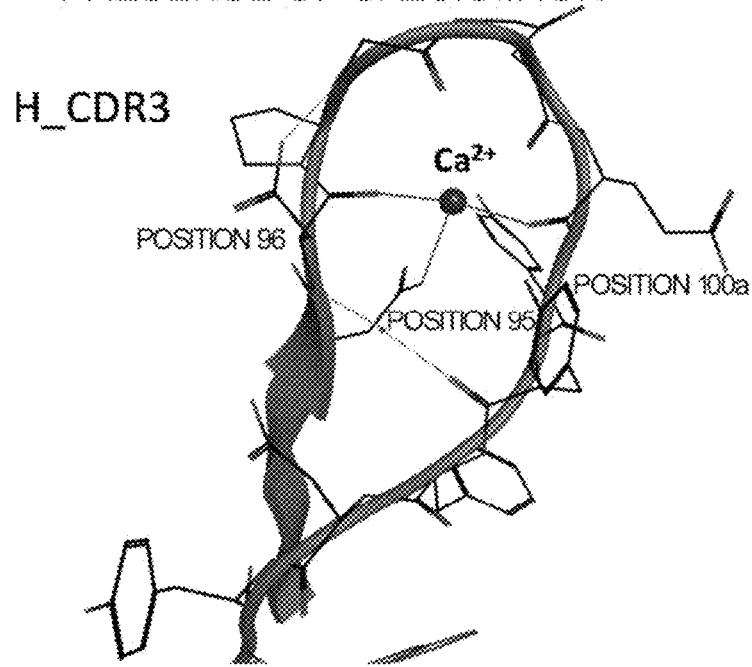
FIG. 14 shows the structure of heavy-chain CDR3 of an Fab fragment from antibody 6RL #9 determined by X-ray crystallography.
Figure 14:
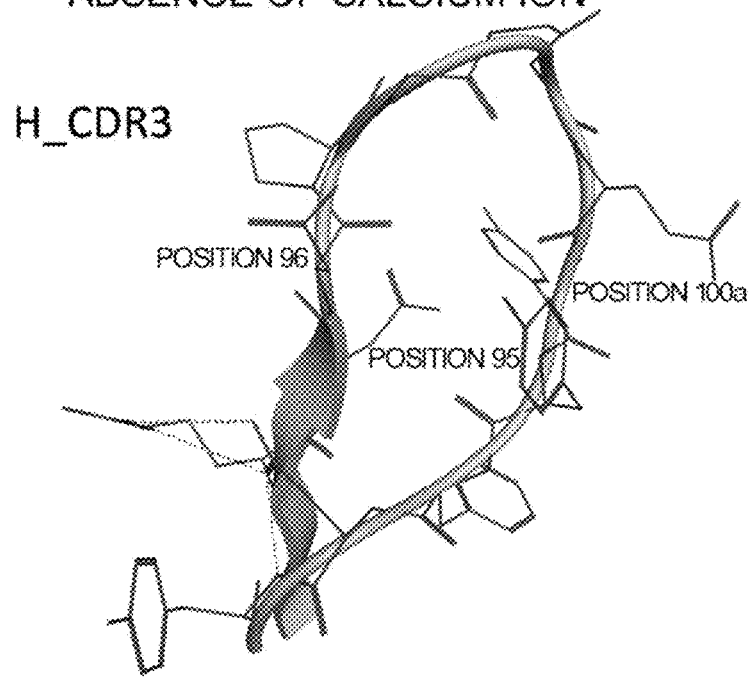

(8-10) Comparison of X-Ray Crystallographic Diffraction Data of the Fab Fragments of Antibody 6RL #9 Between in the Presence and Absence of Ca When the crystallographic structures of the Fab fragments of antibody 6RL #9 are compared between in the presence and absence of Ca, significant changes are seen in the heavy chain CDR3. The structure of the heavy chain CDR3 of the antibody 6RL #9 Fab fragment determined by X-ray crystallography is shown in FIG. 14. Specifically, a calcium ion resided at the center of the heavy chain CDR3 loop region of the antibody 6RL #9 Fab fragment prepared in the presence of Ca. The calcium ion was assumed to interact with positions 95, 96, and 100a (Kabat's numbering) of the heavy chain CDR3. It was believed that the heavy chain CDR3 loop which is important for the antigen binding was stabilized by calcium binding in the presence of Ca, and became an optimum structure for antigen binding. There is no report demonstrating that calcium binds to the antibody heavy chain CDR3. Thus, the calcium-bound structure of the antibody heavy chain CDR3 is a novel structure. The heavy chain CDR3 is known to be most important for antigen binding. The motif for which calcium ion is required for maintaining the structure of the heavy chain CDR3, revealed as described in the present Example, implies that calcium ion plays an important role in antigen binding. Specifically, it is highly plausible that antibodies with this motif bind to an antigen in a calcium ion-dependent manner. For example, when a synthetic library having this motif is prepared, one can efficiently isolate calcium-dependent binding antibodies from the library.

Example 9

Preparation of Antibodies that Bind to IL-6 in a Ca-Dependent Manner from a Human Antibody Library Using Phage Display Techniques (9-1) Construction of a Phage Display Library of Naïve Human Antibodies A human antibody phage display library containing multiple phages that display various human antibody Fab domain sequences was constructed by a method known to those skilled in the art using, as a template, polyA RNA prepared from human PBMC, commercially available human polyA RNA, and such.

(9-2) Preparation of Antibody Fragments that Bind to the Antigen in a Ca-Dependent Manner from Library by Bead Panning Primary selection from the constructed phage display library of naïve human antibodies was carried out by enriching antibody fragments that have antigen (IL-6)-binding activity. The antigen used was biotin-labeled IL-6.

Phages were produced from E. coli carrying the constructed phagemid for phage display. To precipitate the phages produced by E. coli, 2.5 M NaCl/10% PEG was added to the E. coli culture medium. The phage fraction was diluted with TBS to prepare a phage library solution. Then, BSA and CaCl$_2$) were added the phage library solution at final concentrations of 4% and 1.2 mM calcium ion concentration, respectively. The panning method used was a conventional panning method using antigen-immobilized magnetic beads (J. Immunol. Methods. (2008) 332(1-2): 2-9; J. Immunol. Methods. (2001) 247(1-2): 191-203; Biotechnol. Prog. (2002) 18(2): 212-20; Mol. Cell Proteomics (2003) 2(2): 61-9). The magnetic beads used were NeutrAvidin-coated beads (Sera-Mag SpeedBeads NeutrAvidin-coated) and Streptavidin-coated beads (Dynabeads M-280 Streptavidin).

Specifically, 250 pmol of the biotin-labeled antigen was added to the prepared phage library solution. Thus, the solution was contacted with the antigen at room temperature for 60 minutes. Magnetic beads blocked with BSA were added, and the antigen-phage complex was allowed to bind to the magnetic beads at room temperature for 15 minutes. The beads were washed three times with 1.2 mM CaCl$_2$)/TBST (TBST containing 1.2 mM CaCl$_2$)), and then twice with 1 ml of 1.2 mM CaCl$_2$)/TBS (TBS containing 1.2 mM CaCl$_2$)). Thereafter, 0.5 ml of 1 mg/ml trypsin was added to the beads. After 15 minutes of dispersion at room temperature, the beads were immediately separated using a magnetic stand to collect a phage suspension. The prepared phage suspension was added to 10 ml of E. coli of stain TG1 at the logarithmic growth phase (OD600=0.4 to 0.5). The E. coli was incubated with gentle stirring at 37° C. for one hour to infect the phages. The infected E. coli was seeded in a plate (225 mm×225 mm). Then, phages were collected from the culture medium of the seeded E. coli to prepare a phage library solution.

In the second round and subsequent panning, phages were enriched using the Ca-dependent binding activity as an indicator. Specifically, 40 pmol of the biotin-labeled antigen was added to the prepared phage library solution. Thus, the phage library was contacted with the antigen at room temperature for 60 minutes. Magnetic beads blocked with BSA were added, and the antigen-phage complex was allowed to bind to the magnetic beads at room temperature for 15 minutes. The beads were washed with 1 ml of 1.2 mM CaCl$_2$)/TBST and 1.2 mM CaCl$_2$)/TBS. Next, 0.1 ml of 2 mM EDTA/TBS was added to the beads. After dispersion at room temperature, the beads were immediately separated using a magnetic stand to collect a phage suspension. The pIII protein (helper phage-derived protein pIII) was cleaved from phages that did not display Fab by adding 5 μl of 100 mg/ml trypsin to the collected phage suspension to eliminate the ability of phages displaying no Fab to infect E. coli. Phages collected from the trypsinized liquid phage stock was added to 10 ml of E. coli cells of the TG1 strain at the logarithmic growth phase (OD600=0.4 to 0.7). The E. coli was incubated while gently stirring at 37° C. for one hour to infect phage. The infected E. coli was seeded in a plate (225 mm×225 mm). Then, phages were collected from the culture medium of the seeded E. coli to prepare a liquid stock of phage library. Panning was performed three times using the Ca-dependent binding activity as an indicator.

(9-3) Assessment by Phage ELISA

Culture supernatants containing phages were collected from single colonies of E. coli obtained by the method described above according to a conventional method (Methods Mol. Biol. (2002) 178, 133-145). BSA and CaCl$_2$) were added at final concentrations of 4% and 1.2 mM calcium ion concentration, respectively, to the phage-containing culture supernatants. The supernatants were subjected to ELISA by the following procedure. A StreptaWell 96-well microtiter plate (Roche) was coated overnight with 100 μl of PBS containing the biotin-labeled antigen. The antigen was removed by washing each well of the plate with PBST. Then, the wells were blocked with 250 μl of 4% BSA-TBS for one hour or more. After removal of 4% BSA-TBS, the prepared culture supernatants were added to the each well. The plate was incubated at 37° C. for one hour so that the antibody-displaying phages were allowed to bind to the antigen on each well. After each well was washed with 1.2 mM CaCl$_2$)/TBST, 1.2 mM CaCl$_2$)/TBS or 1 mM EDTA/TBS was added. The plate was left for incubation at 37° C. for 30 minutes. After washing with 1.2 mM CaCl$_2$)/TBST, an HRP-conjugated anti-M13 antibody (Amersham Pharmacia Biotech) diluted with TBS containing BSA and calcium ion at final concentrations of 4% and 1.2 mM calcium ion concentration was added to each well, and the plate was incubated for one hour. After washing with 1.2 mM CaCl$_2$)/

TBST, the TMB single solution (ZYMED) was added to each well. The chromogenic reaction in the solution of each well was stopped by adding sulfuric acid. Then, the developed color was assessed by measuring absorbance at 450 nm.

From the 96 clones isolated, antibodies 6KC4-1 #85, 6LC4-1 #15, and 6LC4-2 #16 having Ca-dependent IL-6-binding activity were obtained by phage ELISA. Using antibody fragments that were predicted to have a Ca-dependent antigen-binding activity based on the result of the phage ELISA described above as a template, genes were amplified with specific primers and their sequences were analyzed. The heavy-chain and light-chain variable region sequences of antibody 6KC4-1 #85 are shown in SEQ ID NOs: 25 and 26, respectively. The polynucleotide encoding the heavy-chain variable region of antibody 6KC4-1 #85 (SEQ ID NO: 25) was linked to a polynucleotide encoding an IgG1-derived sequence (SEQ ID NO: 65) by PCR method. The resulting DNA fragment was inserted into an animal cell expression vector to construct an expression vector for the heavy chain of SEQ ID NO: 27. A polynucleotide encoding the light-chain variable region of antibody 6KC4-1 #85 (SEQ ID NO: 26) was linked to a polynucleotide encoding the constant region of the natural Kappa chain (SEQ ID NO: 28) by PCR. A DNA fragment encoding the linked sequence shown in SEQ ID NO: 29 was inserted into an animal cell expression vector. Using the same method, antibody 6LC4-1 #15 (heavy chain SEQ ID NO: 68; light chain SEQ ID NO: 69) and antibody 6LC4-2 #16 (heavy chain SEQ ID NO: 70; light chain SEQ ID NO: 71) were also inserted into cell expression vectors. Sequences of the constructed variants were confirmed by a method known to those skilled in the art.

(9-4) Expression and Purification of Antibodies

Clones that were predicted to have a Ca-dependent antigen-binding activity based on the result of phage ELISA were inserted into animal cell expression plasmids. Antibody expression was carried out by the following method. Cells of human fetal kidney cell-derived FreeStyle 293-F (Invitrogen) were suspended in the FreeStyle 293 Expression Medium (Invitrogen), and plated at a cell density of $1.33 \times 10^6$ cells/ml (3 ml) into each well of a 6-well plate. The prepared plasmids were introduced into cells by a lipofection method. The cells were cultured for four days in a $CO_2$ incubator (37° C., 8% $CO_2$, 90 rpm). From the culture supernatants, antibodies were purified using the rProtein A Sepharose™ Fast Flow (Amersham Biosciences) by a method known to those skilled in the art. Absorbance at 280 nm of the purified antibody solutions was measured using a spectrophotometer. Antibody concentrations were calculated from the determined values using an extinction coefficient calculated by the PACE method (Protein Science (1995) 4: 2411-2423).

(9-5) Binding Assay of Calcium-Dependent Anti-IL6 Antibodies

Using Biacore™ T100 (GE Healthcare), the prepared antibodies were assessed for their binding activity (dissociation constant $K_D$ (M)) to human interleukin 6 (hIL6) at pH 7.4. The measurement was carried out using as a running buffer 0.05% Tween©20 (polysorbate 20), 10 mmol/L ACES, 150 mmol/L NaCl (pH 7.4) containing 3 µM or 1.2 mM $CaCl_2$).

Figure 15:
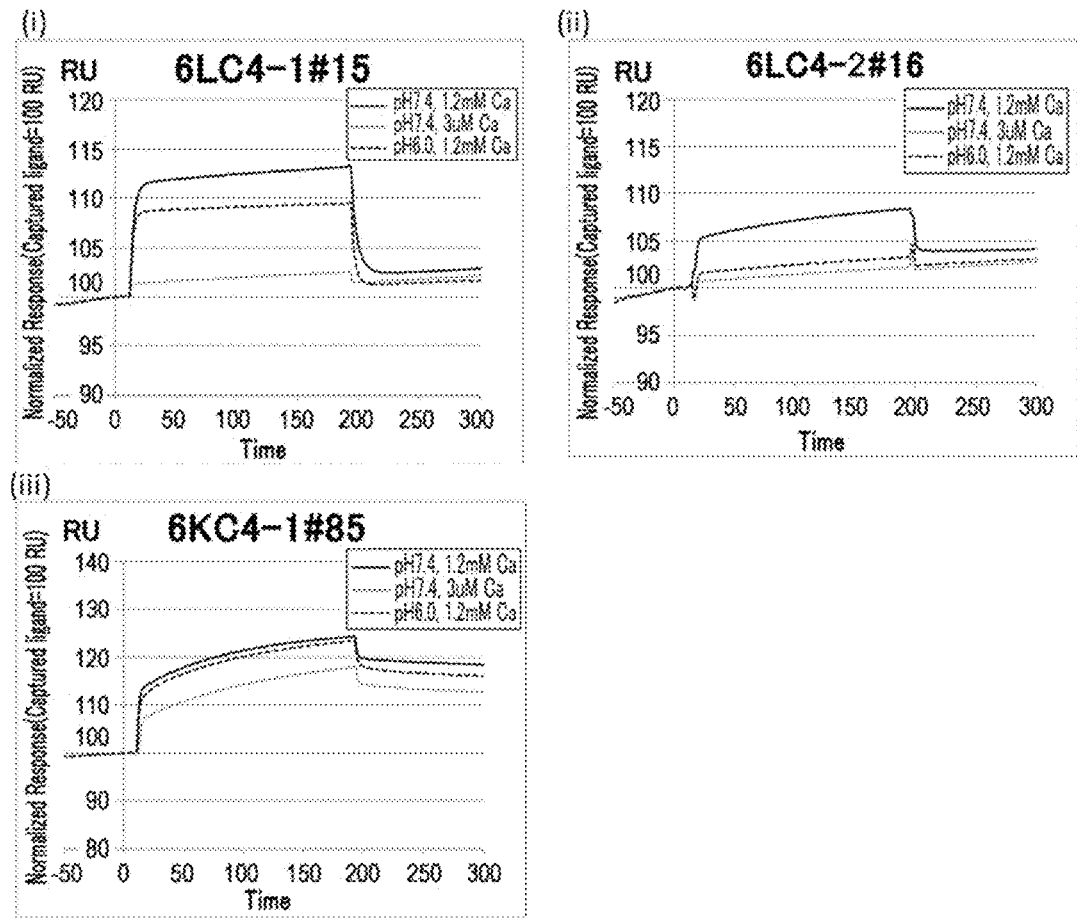
FIG. 15 presents Biacore™ sensorgrams showing the interaction of anti-human IL-6 antibodies with human IL-6 under the conditions of ($Ca^{2+}$ 1.2 mM) and ($Ca^{2+}$ 3 μM).

After an adequate amount of recombinant Protein A/G (Thermo Scientific) was immobilized onto Sensor chip CM5 (GE Healthcare) by an amino coupling method, antibodies were allowed to bind thereto. An appropriate concentration of hIL6 (human interleukin 6; Kamakura Techno-Science, Inc.) was injected as an analyte to interact with antibodies on the sensor chip. Then, the sensor chip was regenerated by injecting 10 mmol/L glycine-HCl (pH 1.5). The measurement was carried out at 37° C. The sensorgram resulting from the measurement is shown in FIG. 15. The result demonstrates that antibodies 6LC4-1 #15-IgG1, 6LC4-2 #16-IgG1, and 6KC4-1 #85-IgG1 had weaker hIL6 binding under the condition of 3 µM $Ca^{2+}$ concentration than at 1.2 mM. The finding described above suggests that this method is applicable to other antigens since the property of calcium-dependent antigen binding was proven for IL-6 as well as for IL-6R demonstrated in Example 3.

Example 10

Assessment of Antibody 6KC4-1 #85 for Calcium Ion Binding (10-1) Assessment of Antibody 6KC4-1 #85 for Calcium Ion Binding Calcium-dependent antigen-binding antibody 6KC4-1 #85 which was isolated from a human antibody library was assessed for its calcium binding. Whether the measured Tm value varies depending on the ionized calcium concentration condition was assessed by the method described in Example 4.

Tm values for the Fab domain of antibody 6KC4-1 #85 are shown in Table 11. As shown in Table 11, the Tm value of the 6KC4-1 #85 antibody Fab domain varied depending on the calcium ion concentration. This demonstrates that antibody 6KC4-1 #85 binds to calcium.

TABLE 11

| ANTIBODY | CALCIUM ION CONCENTRATION | | ΔTm(° C.) |
|---|---|---|---|
| | 3 µM | 2 mM | 2 mM-3 µM |
| 6KC4-1#85 | 71.49 | 75.39 | 3.9 |

(10-2) Identification of Calcium Ion-Binding Site in Antibody 6KC4-1 #85

As demonstrated in (10-1) of Example 10, antibody 6KC4-1 #85 binds to calcium ion. However, 6KC4-1 #85m does not have a calcium-binding motif such as the hVk5-2 sequence described below. Thus, to identify residues responsible for the calcium ion binding of antibody 6KC4-1 #85, altered heavy chains (6_H1-11 (SEQ ID NO: 30), 6_H1-12 (SEQ ID NO: 31), 6_H1-13 (SEQ ID NO: 32), 6_H1-14 (SEQ ID NO: 33), 6_H1-15 (SEQ ID NO: 34)) and altered light chains (6_L1-5 (SEQ ID NO: 35) and 6_L1-6 (SEQ ID NO: 36)) were constructed by substituting an Asp (D) residue in the CDR of antibody 6KC4-1 #85 with an Ala (A) residue which does not participate in the binding or chelation of calcium ion. By the method described in Example 2, altered antibodies were purified from the culture supernatants of animal cells introduced with expression vectors carrying the altered antibody genes. The purified altered antibodies were assessed for their calcium binding by the method described in Example 4. The measurement result is shown in Table 12.

TABLE 12

| HEAVY CHAIN | LIGHT CHAIN | ALTERED RESIDUE | CALCIUM ION CONCENTRATION | | ΔTm (° C.) |
|---|---|---|---|---|---|
| | | | 3 μM | 2 mM | 2 mM-3 μM |
| 6KC4-1#85 | 6KC4-1#85 | WILD-TYPE | 71.49 | 75.39 | 3.9 |
| 6H1-11 | 6KC4-1#85 | H CHAIN POSITION 61 (Kabat NUMBERING) | 71.73 | 75.56 | 3.83 |
| 6H1-12 | 6KC4-1#85 | H CHAIN POSITION 95 (Kabat NUMBERING) | 72.9 | 73.43 | 0.53 |
| 6H1-13 | 6KC4-1#85 | H CHAIN POSITION 100a (Kabat NUMBERING) | 70.94 | 76.25 | 5.31 |
| 6H1-14 | 6KC4-1#85 | H CHAIN POSITION 100g (Kabat NUMBERING) | 73.95 | 75.14 | 1.19 |
| 6H1-15 | 6KC4-1#85 | H CHAIN POSITION 101 (Kabat NUMBERING) | 65.37 | 66.25 | 0.87 |
| 6KC4-1#85 | 6L1-5 | L CHAIN POSITION 50 (Kabat NUMBERING) | 71.92 | 76.08 | 4.16 |
| 6KC4-1#85 | 6L1-6 | L CHAIN POSITION 92 (Kabat NUMBERING) | 72.13 | 78.74 | 6.61 |

As shown in Table 12, substitution of an Ala residue for the residue at position 95 or 101 (Kabat's numbering) in the heavy chain CDR3 of antibody 6KC4-1 #85 resulted in loss of the calcium-binding activity of antibody 6KC4-1 #85. This suggests that these residues are responsible for calcium binding. It was demonstrated that the calcium-binding motif around the base of the loop of the heavy chain CDR3 in antibody 6KC4-1 #85, which was identified based on the calcium-binding activity of antibodies altered from antibody 6KC4-1 #85, could also be used as a calcium-binding motif in the antigen-binding domain of an antigen-binding molecule of the present invention. Like the motif revealed as described in Example 8, this calcium-binding motif is located in the heavy chain CDR3. Thus, likewise, for example, when a synthetic library having this motif is constructed, calcium-dependent binding antibodies can be efficiently isolated from the library.

Example 11

Search for Human Germline Sequences that Bind to Calcium Ion (11-1) Isolation of Human Germline Sequences Calcium ion-binding antibodies containing human germline sequences have not been reported. Thus, the germline sequences of antibodies having human germline sequences were cloned using as a template cDNA prepared from Human Fetal Spleen Poly RNA (Clontech) to assess whether antibodies having human germline sequences bind to calcium ion. Cloned DNA fragments were inserted into animal cell expression vectors. The nucleotide sequences of the constructed expression vectors were determined by a method known to those skilled in the art. The SEQ IDs are shown in Table 13. By PCR, polynucleotides encoding SEQ ID NO: 37 (Vk1), SEQ ID NO: 38 (Vk2), SEQ ID NO: 39 (Vk3), SEQ ID NO: 40 (Vk4), and SEQ ID NO: 41 (Vk5) were linked to a polynucleotide encoding the natural Kappa chain constant region (SEQ ID NO: 28). The linked DNA fragments were inserted into animal cell expression vectors. Furthermore, polynucleotides encoding SEQ ID NO: 42 (Vk1), SEQ ID NO: 43 (Vk2), SEQ ID NO: 44 (Vk3), SEQ ID NO: 45 (Vk4), and SEQ ID NO: 46 (Vk5) were linked by PCR to a polynucleotide encoding a polypeptide (SEQ ID NO: 65) having a deletion of two amino acids at the C terminus of IgG1. The resulting DNA fragments were inserted into animal cell expression vectors. The sequences of the constructed variants were confirmed by a method known to those skilled in the art.

TABLE 13

| LIGHT CHAIN GERMLINE SEQUENCE | HEAVY CHAIN VARIABLE REGION SEQ ID NO | LIGHT CHAIN VARIABLE REGION SEQ ID NO |
|---|---|---|
| Vk1 | 42 | 37 |
| Vk2 | 43 | 38 |
| Vk3 | 44 | 39 |
| Vk4 | 45 | 40 |
| Vk5 | 46 | 41 |

(11-2) Expression and Purification of Antibodies

The constructed animal cell expression vectors inserted with the DNA fragments having the five types of human germ-line sequences were introduced into animal cells. Antibody expression was carried out by the following method. Cells of human fetal kidney cell-derived FreeStyle 293-F (Invitrogen) were suspended in the FreeStyle 293 Expression Medium (Invitrogen), and plated at a cell density of $1.33 \times 10^6$ cells/ml (3 ml) into each well of a 6-well plate. The prepared plasmids were introduced into cells by a lipofection method. The cells were cultured for four days in a C02 incubator (37° C., 8% $CO_2$, 90 rpm). From the culture supernatants prepared as described above, antibodies were purified using the rProtein A Sepharose™ Fast Flow (Amersham Biosciences) by a method known to those skilled in the art. Absorbance at 280 nm of the purified antibody solutions was measured using a spectrophotometer. Antibody concentrations were calculated from the determined values using an extinction coefficient calculated by the PACE method (Protein Science (1995) 4: 2411-2423).

(11-3) Assessment of Antibodies Having Human Germ-Line Sequences for their Calcium Ion-Binding Activity The purified antibodies were assessed for their calcium ion-binding activity. The purified antibodies were dialyzed (EasySEP, TOMY) against a solution containing 20 mM Tris-HCl, 150 mM NaCl, and 2 mM $CaCl_2$) (pH 7.4), or 20 mM Tris-HCl, 150 mM NaCl, and 3 µM $CaCl_2$) (pH 7.4). The antibody solutions as a test substance were adjusted to 0.1 mg/ml using the same solution used for dialysis, and DSC measurement was carried out at a rate of temperature increase of 240° C./hr from 20 to 115° C. Based on the obtained DSC denaturation curves, the midpoint temperature of thermal denaturation (Tm value) was calculated for the Fab domain of each antibody. The Tm values are shown in Table 14.

TABLE 14

| LIGHT CHAIN GERMLINE SEQUENCE | CALCIUM ION CONCENTRATION | | ΔTm (° C.) |
|---|---|---|---|
| | 3 µM | 2 mM | 2 mM-3 µM |
| Vk1 | 80.32 | 80.78 | 0.46 |
| Vk2 | 80.67 | 80.61 | −0.06 |
| Vk3 | 81.64 | 81.36 | −0.28 |
| Vk4 | 70.74 | 70.74 | 0 |
| Vk5 | 71.52 | 74.17 | 2.65 |

The result showed that the Tm values of the Fab domains of antibodies having the hVk1, hVk2, hVk3, or hVk4 sequence did not vary depending on the calcium ion concentration in the Fab domain-containing solutions. Meanwhile, the Tm value for the antibody Fab domain having the hVk5 sequence varied depending on the calcium ion concentration in the Fab domain-containing solution. This demonstrates that the hVk5 sequence binds to calcium ion.

Example 12

Assessment of the Human Vk5 (hVk5) Sequence (12-1) hVk5 Sequence

The only hVk5 sequence registered in Kabat's database is hVk5-2 sequence. Hereinafter, hVk5 and hVk5-2 are used synonymously.

(12-2) Construction, Expression, and Purification of a Non-Glycosylated Form of the hVk5-2 Sequence The hVk5-2 sequence has a sequence for N glycosylation at position 20 amino acid (Kabat's numbering). Sugar chains attached to proteins exhibit heterogeneity. Thus, it is desirable to lose the glycosylation from the viewpoint of substance homogeneity. In this context, variant hVk5-2_L65 (SEQ ID NO: 47) in which the Asn (N) residue at position 20 (Kabat's numbering) is substituted with Thr (T) was constructed. Amino acid substitution was carried out by a method known to those skilled in the art using the QuikChange Site-Directed Mutagenesis Kit (Stratagene). A DNA encoding the variant hVk5-2_L65 was inserted into an animal expression vector. The animal expression vector inserted with the constructed DNA encoding variant hVk5-2_L65, in combination with an animal expression vector having an insert to express CIM_H (SEQ ID NO: 48) as a heavy chain, was introduced into animal cells by the method described in Example 2. The antibody comprising hVk5-2_L65 and CIM_H, which was expressed in animal cells introduced with the vectors, was purified by the method described in Example 2.

Figure 16:
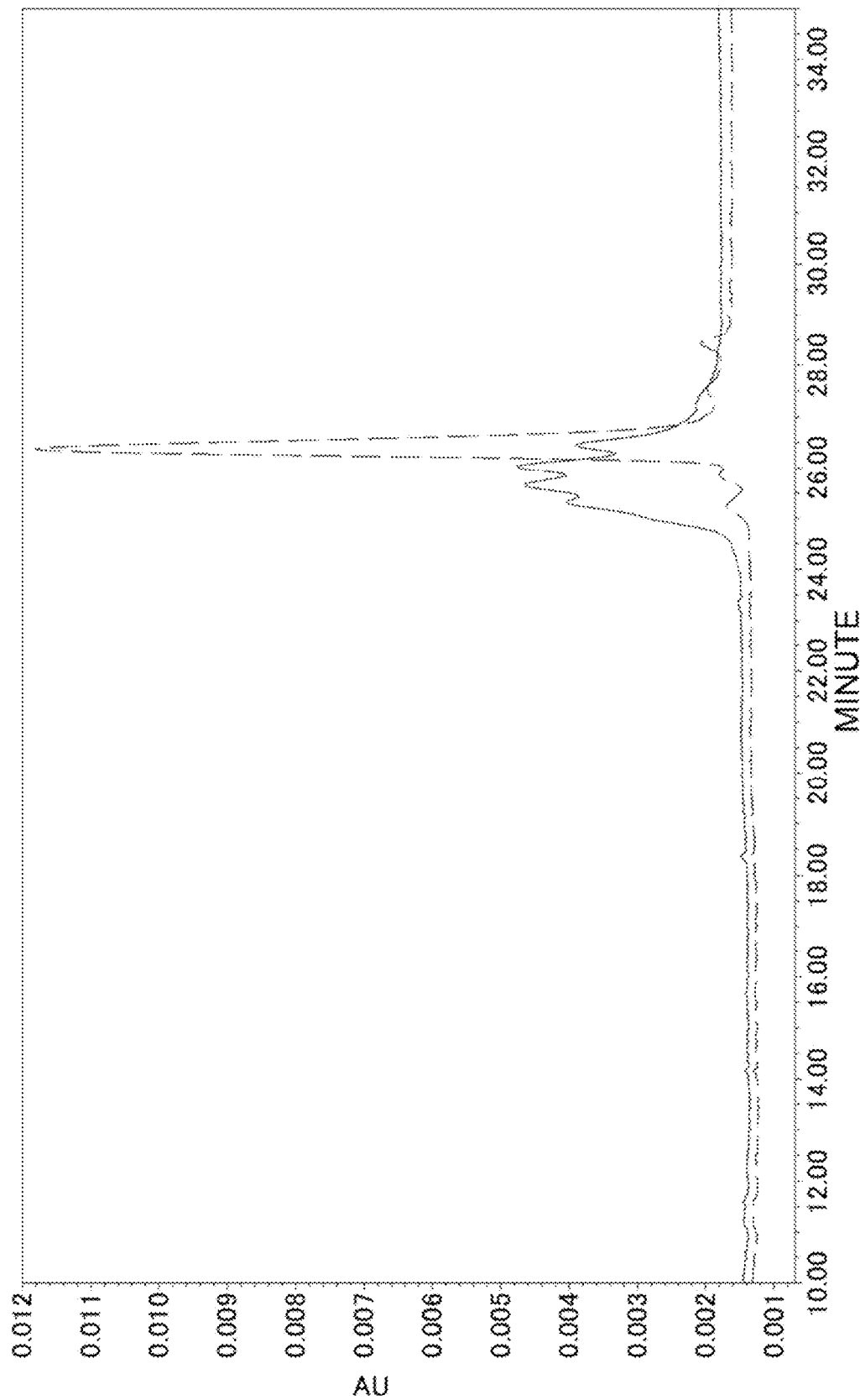
FIG. 16 shows ion-exchange chromatograms for an antibody having human Vk5-2 sequence and an antibody having h Vk5-2_L65 sequence which has a modified glycosylation sequence in the human Vk5-2 sequence. Solid line indicates a chromatogram for an antibody having human Vk5-2 sequence (heavy chain: CIM_H, SEQ ID NO: 48; light chain: hVk5-2, fusion molecule between SEQ ID NOs: 41 and 28); broken line indicates a chromatogram for an antibody having hVk5-2_L65 sequence (heavy chain: CIM_H (SEQ ID NO: 48); light chain: hVk5-2_L65 (SEQ ID NO: 47)).

(12-3) Assessment of the Antibody Having the Non-Glycosylated hVk5-2 Sequence for Physical Properties The isolated antibody having the modified sequence hVk5-2_L65 was analyzed by ion-exchange chromatography to test whether it is less heterogeneous than the antibody having the original sequence hVk5-2 before modification. The procedure of ion-exchange chromatography is shown in Table 15. The analysis result showed that hVk5-2_L65 modified at the glycosylation site was less heterogeneous than the original sequence hVk5-2, as shown in FIG. 16.

TABLE 15

| | CONDITION |
|---|---|
| COLUMN | TOSOH TSKgel DEAE-NPR |
| MOBILE PHASE | A; 10 mM Tris-HCl, 3 µM $CaCl_2$ (pH 8.0) |
| | B; 10 mM Tris-HCl, 500 mM NaCl, 3 µM $CaCl_2$ (pH 8.0) |
| GRADIENT SCHEDULE | % B = 0 − (5 min) − 0 − 2%/1 min |
| COLUMN TEMPERATURE | 40° C. |
| DETECTION | 280 nm |
| INJECTION VOLUME | 100 µL (5 µg) |

Next, whether the less-heterogeneous hVk5-2_L65 sequence-comprising antibody binds to calcium ion was assessed by the method described in Example 4. The result showed that the Tm value for the Fab domain of the antibody having hVk5-2_L65 with altered glycosylation site also varied depending on the calcium ion concentration in the antibody solutions, as shown in Table 16. Specifically, it was demonstrated that the Fab domain of the antibody having hVk5-2_L65 with altered glycosylation site binds to calcium ion.

TABLE 16

| LIGHT CHAIN | GLYCO-SYLATED SEQUENCE | CALCIUM ION CONCENTRATION | | ΔTm(° C.) |
|---|---|---|---|---|
| | | 3 µM | 2 mM | 2 mM-3 µM |
| hVk5-2 | YES | 71.52 | 74.17 | 2.65 |
| hVk5-2_L65 | NO | 71.51 | 73.66 | 2.15 |

Example 13

Assessment of the Calcium Ion-Binding Activity of Antibody Molecules Having CDR Sequence of the hVk5-2 Sequence (13-1) Construction, Expression, and Purification of Modified Antibodies Having a CDR Sequence from the hVk5-2 Sequence The hVk5-2_L65 sequence is a sequence with altered amino acids at a glycosylation site in the framework of human Vk5-2 sequence. As described in Example 12, it was demonstrated that calcium ion bound even after alteration of the glycosylation site. Meanwhile, from the viewpoint of immunogenicity, it is generally desirable that the framework sequence is a germ-line sequence. Thus, the present inventors assessed whether an antibody framework sequence could be substituted with the framework sequence of a non-glycosylated germline sequence while maintaining the calcium ion-binding activity of the antibody.

Polynucleotides encoding chemically synthesized sequences which comprise an altered framework sequence of the hVk5-2 sequence, hVk1, hVk2, hVk3, or hVk4

(CaVk1 (SEQ ID NO: 49), CaVk2 (SEQ ID NO: 50), CaVk3 (SEQ ID NO: 51), or CaVk4 (SEQ ID NO: 52), respectively) were linked by PCR to a polynucleotide encoding the constant region (SEQ ID NO: 28) of the natural Kappa chain. The linked DNA fragments were inserted into animal cell expression vectors. Sequences of the constructed variants were confirmed by a method known to those skilled in the art. Each plasmid constructed as described above was introduced into animal cells in combination with a plasmid inserted with a polynucleotide encoding CIM_H (SEQ ID NO: 48) by the method described in Example 2. The expressed antibody molecules of interest were purified from culture media of the animal cells introduced with the plasmids.

(13-2) Assessment of Altered Antibodies Having the CDR Sequence of the hVk5-2 Sequence for their Calcium Ion-Binding Activity Whether calcium ion binds to altered antibodies having the CDR sequence of the hVk5-2 sequence and the framework sequences of germline sequences other than hVk5-2 (hVk1, hVk2, hVk3, and hVk4) was assessed by the method described in Example 4. The assessment result is shown in Table 17. The Tm value of the Fab domain of each altered antibody was revealed to vary depending on the calcium ion concentration in the antibody solutions. This demonstrates that antibodies having a framework sequence other than the framework sequences of the hVk5-2 sequence also bind to calcium ion. Specifically, it was demonstrated that the motif in the CDR sequence of the hVk5-2 sequence is responsible for the calcium ion binding while the framework can be any framework sequence.

TABLE 17

| GERMLINE (LIGHT CHAIN FRAMEWORK SEQUENCE) | CALCIUM ION CONCENTRATION | | ΔTm (° C.) |
|---|---|---|---|
| | 3 μM | 2 mM | 2 mM-3 μM |
| hVk1 | 77.51 | 79.79 | 2.28 |
| hVk2 | 78.46 | 80.37 | 1.91 |
| hVk3 | 77.27 | 79.54 | 2.27 |
| hVk4 | 80.35 | 81.38 | 1.03 |
| hVk5-2 | 71.52 | 74.17 | 2.65 |

The thermal denaturation temperature (Tm value), as an indicator of thermal stability, of the Fab domain of each antibody altered to have the CDR sequence of the hVk5-2 sequence and the framework sequence of a germ-line sequence other than the hVk5-2 sequence (hVk1, hVk2, hVk3, or hVk4) was demonstrated to be greater than that of the Fab domain of the original antibody having the hVk5-2 sequence. This result shows that antibodies having the CDR sequence of the hVk5-2 sequence and the framework sequence of hVk1, hVk2, hVk3, or hVk4 not only have calcium ion-binding activity but also are excellent molecules from the viewpoint of thermal stability.

Example 14

Identification of the Calcium Ion-Binding Site in Human Germline hVk5-2 Sequence (14-1) Design of Mutation Site in the CDR Sequence of the hVk5-2 Sequence As described in Example 13, antibodies having the light chain resulting from introduction of the CDR domain of the hVk5-2 sequence into the framework sequence of a different germline sequence were also demonstrated to bind to calcium ion. This result suggests that in hVk5-2 a calcium ion-binding site is localized within its CDR. Amino acids that bind to calcium ion, i.e., chelate calcium ion, include negatively charged amino acids and amino acids that can be a hydrogen bond acceptor. Thus, it was tested whether antibodies having a mutant hVk5-2 sequence with a substitution of an Ala (A) residue for an Asp (D) or Glu (E) residue in the CDR sequence of the hVk5-2 sequence bind to calcium ion.

(14-2) Construction of Variant hVk5-2 Sequences with Ala Substitution, and Expression and Purification of Antibodies Antibody molecules were prepared to comprise a light chain with substitution of an Ala residue for Asp and/or Glu residue in the CDR sequence of the hVk5-2 sequence. As described in Example 12, non-glycosylated variant hVk5-2_L65 exhibited calcium ion binding and was assumed to be equivalent to the hVk5-2 sequence in terms of calcium ion binding. In this Example, amino acid substitutions were introduced into hVk5-2_L65 as a template sequence. Constructed variants are shown in Table 18. Amino acid substitutions were carried out by methods known to those skilled in the art such as using the QuikChange Site-Directed Mutagenesis Kit (Stratagene), PCR, or the In fusion Advantage PCR Cloning Kit (TAKARA) to construct expression vectors for altered light chains having an amino acid substitution.

TABLE 18

| LIGHT CHAIN VARIANT NAME | ALTERED POSITION (Kabat's NUMBERING) | SEQ ID NO |
|---|---|---|
| hVk5-2_L65 | WILDTYPE | 47 |
| hVk5-2_L66 | 30 | 53 |
| hVk5-2_L67 | 31 | 54 |
| hVk5-2_L68 | 32 | 55 |
| hVk5-2_L69 | 50 | 56 |
| hVk5-2_L70 | 30, 32 | 57 |
| hVk5-2_L71 | 30, 50 | 58 |
| hVk5-2_L72 | 30, 32, 50 | 59 |
| hVk5-2_L73 | 92 | 60 |

Nucleotide sequences of the constructed expression vectors were confirmed by a method known to those skilled in the art. The expression vectors constructed for the altered light chains were transiently introduced, in combination with an expression vector for the heavy chain CIM_H (SEQ ID NO: 48), into cells of the human fetal kidney cell-derived HEK293H line (Invitrogen) or FreeStyle293 (Invitrogen) to express antibodies. From the obtained culture supernatants, antibodies were purified using the rProtein A Sepharose™ Fast Flow (GE Healthcare) by a method known to those skilled in the art. Absorbance at 280 nm of the purified antibody solutions was measured using a spectrophotometer. Antibody concentrations were calculated from the determined values using an extinction coefficient calculated by the PACE method (Protein Science (1995) 4: 2411-2423).

(14-3) Assessment of the Calcium Ion-Binding Activity of Antibodies Having an Ala Substitution in the hVk5-2 Sequence Whether the obtained purified antibodies bind to calcium ion was tested. Specifically, the purified antibodies were dialyzed (EasySEP, TOMY) against 20 mM Tris-HCl/150 mM NaCl/2 mM CaCl$_2$) (pH 7.5) solution or 20 mM Tris-HCl/150 mM NaCl (pH 7.5) solution (in Table 19, indicated as 0 μM calcium ion concentration). DSC measurement was carried out at a rate of temperature increase of 240° C./hr from 20 to 115° C. using antibody solutions prepared at a concentration of 0.1 mg/mL by the same solution used for dialysis. Based on the obtained DSC denaturation curves, the intermediate temperature of thermal denaturation (Tm value) was calculated for the Fab domain of each antibody as shown in Table 19. Some antibodies having substitution of an Asp or Glu residue in the CDR sequence of the hVk5-2 sequence with an Ala residue which cannot be involved in calcium ion binding or chelation were revealed to have an Fab domain whose Tm did not vary by the calcium ion concentration in the antibody solutions. The substitution sites at which Ala substitution did not alter the Tm (positions 32 and 92 (Kabat's numbering)) were demonstrated to be greatly important for the calcium ion-antibody binding.

TABLE 19

| LIGHT CHAIN VARIANT NAME | ALTERED POSITION (Kabat's NUMBERING) | CALCIUM ION CONCENTRATION 0 μM | | ΔTm(° C.) 2 mM-0 μM |
|---|---|---|---|---|
| | | | 2 mM | |
| hVk5-2__L65 | WILDTYPE | 71.71 | 73.69 | 1.98 |
| hVk5-2__L66 | 30 | 71.65 | 72.83 | 1.18 |
| hVk5-2__L67 | 31 | 71.52 | 73.30 | 1.78 |
| hVk5-2__L68 | 32 | 73.25 | 74.03 | 0.78 |
| hVk5-2__L69 | 50 | 72.00 | 73.97 | 1.97 |
| hVk5-2__L70 | 30, 32 | 73.42 | 73.60 | 0.18 |
| hVk5-2__L71 | 30, 50 | 71.84 | 72.57 | 0.73 |
| hVk5-2__L72 | 30, 32, 50 | 75.04 | 75.17 | 0.13 |
| hVk5-2__L73 | 92 | 75.23 | 75.04 | −0.19 |

Example 15

Assessment of the Calcium Ion-Binding Activity of Antibodies Having hVk1 Sequence with Calcium Ion-Binding Motif (15-1) Construction of an hVk1 Sequence with Calcium Ion-Binding Motif, and Expression and Purification of Antibodies The result described in Example 14 on the calcium-binding activity of the Ala substitute demonstrates that Asp or Glu residues in the CDR sequence of the hVk5-2 sequence were important for calcium binding. Thus, the present inventors assessed whether an antibody can bind to calcium ion when the residues at positions 30, 31, 32, 50, and 92 (Kabat's numbering) alone were introduced into a different germline variable region sequence. Specifically, variant LfVk1_Ca (SEQ ID NO: 61) was constructed by substituting the residues at positions 30, 31, 32, 50, and 92 (Kabat's numbering) in the hVk5-2 sequence for the residues at positions 30, 31, 32, 50, and 92 (Kabat's numbering) in the hVk1 sequence (a human germline sequence). Specifically, it was tested whether antibodies having an hVk1 sequence introduced with only 5 residues from the hVk5-2 sequence can bind to calcium. The variants were produced by the same method as described in Example 2. The resulting light chain variant LfVk1_Ca and LfVk1 having the light-chain hVk1 sequence (SEQ ID NO: 62) were co-expressed with the heavy chain CIM_H (SEQ ID NO: 48). Antibodies were expressed and purified by the same method as described in Example 14.

(15-2) Assessment of the Calcium Ion-Binding Activity of Antibodies Having a Human hVk1 Sequence with Calcium Ion-Binding Motif Whether the purified antibody prepared as described above binds to calcium ion was assessed by the method described in Example 4. The result is shown in Table 20. The Tm value of the Fab domain of the antibody having LfVk1 with an hVk1 sequence did not vary depending on the calcium concentration in the antibody solutions. Meanwhile, Tm of the antibody having the LfVk1_Ca sequence was shifted by 1° C. or more upon change in the calcium concentration in the antibody solutions. Thus, it was shown that the antibody having LfVk1_Ca binds to calcium. The result described above demonstrates that the entire CDR sequence of hVk5-2 is not required, while the residues introduced for construction of the LfVk1_Ca sequence alone are sufficient for calcium ion binding.

TABLE 20

| LIGHT CHAIN VARIANT | CALCIUM ION CONCENTRATION | | ΔTm(° C.) |
|---|---|---|---|
| | 3 μM | 2 mM | 2 mM-3 μM |
| LfVk1 | 83.18 | 83.81 | 0.63 |
| LfVk1_Ca | 79.83 | 82.24 | 2.41 |

(15-3) Construction, Expression, and Purification of Degradation-Resistant LfVk1_Ca Sequence As described in (15-2) of Example 15, variant LfVk1_Ca (SEQ ID NO: 61) was constructed to have substitution of residues at positions 30, 31, 32, 50, and 92 (Kabat's numbering) in the hVk5-2 sequence for residues at positions 30, 31, 32, 50, and 92 (Kabat's numbering) in the hVk1 sequence (a human germline sequence). The variant was demonstrated to bind to calcium ion. Thus, one can consider Ca-dependent antibodies (Ca-binding antibodies) having the LfVk1_Ca sequence. However, since the LfVk1_Ca sequence is a novel sequence, its storage stability as pharmaceuticals is unclear. Thus, applicability of the LfVk1_Ca sequence as pharmaceuticals remains to be clarified. In this context, the stability of LfVk1_Ca was assessed by a thermal acceleration test. An antibody having LfVk1_Ca as an L chain was dialyzed against a solution of 20 mM histidine-HCl/150 mM NaCl (pH 6.0) overnight at 4° C. The dialyzed antibody concentration was adjusted to 0.5 mg/ml, and stored at 5° C. or 50° C. for three days. After storage, each antibody was subjected to ion-exchange chromatography by the method described in Example 12. The result demonstrated that LfVk1_Ca was significantly degraded during three days of storage at 50° C., as shown in FIG. 17. The LfVk1_Ca sequence has Asp at positions 30, 31, and 32 (Kabat's numbering) and thus its CDR1 sequence contains an Asp-Asp sequence which has been reported to be degraded under acidic conditions (J. Pharm. Biomed. Anal. (2008) 47(1): 23-30). This suggests that amino acids at positions 30, 31, and 32 (Kabat's numbering) are a possible degradation site. Then, to avoid degradation of LfVk1_Ca, variants LfVk1_Ca1 (SEQ ID NO: 72), LfVk1_Ca2 (SEQ ID NO: 73), and LfVk1_Ca3 (SEQ ID NO: 74) were constructed to have substitution of Ala (A) residues for the three Asp (D) residues that are possibly sensitive to degradation. Amino acid substitution was carried out by a method known to those skilled in the art using the QuikChange Site-Directed Mutagenesis Kit (Stratagene). DNAs encoding the variants were inserted into animal expression vectors. In combination with an animal expression vector having an insert to express GC H (SEQ ID NO: 102) as the heavy chain, the constructed animal expression vectors carrying DNA inserts for the variants were introduced into animal cells by the method described in Example 14. The antibodies expressed in the animal cells introduced with the vectors were purified by the method described in Example 14.

(15-4) Stability Assessment of Antibodies Having the Degradation-Resistant LfVk1_Ca Sequence Whether the antibodies prepared as described in (15-3) of Example 15 were more resistant to degradation in solutions at pH 6.0 than the original antibodies having the LfVk1_Ca sequence provided for modification was assessed by comparing the heterogeneity between respective antibodies after thermal acceleration. In the same manner as described above, antibodies were stored at 5° C. or 50° C. for three days. Each antibody after storage was subjected to ion-exchange chromatography using the method described in Example 12. As shown in FIG. 17, the analysis result demonstrates that LfVk1_Ca1 with an alteration at position 30 (Kabat's numbering) was less heterogeneous and much more resistant to degradation from thermal acceleration than the original LfVk1_Ca sequence. Specifically, it was demonstrated that degradation occurred at the Asp (D) residue of position 30 in the LfVk1_Ca sequence but it could be prevented by amino acid alteration.

(15-5) Construction of a Light Chain LfVk1_Ca Sequence Resistant to Degradation at the Asp Residue of Position 30, and Expression and Purification of Antibodies The result described in (15-4) of Example 15 on the degradation resistance of the Ala-substituted form demonstrates that under acidic conditions the LfVk1_Ca sequence was degraded at the Asp (D) residue of position 30 (Kabat's numbering) in its CDR sequence and the degradation could be prevented in the case substitution of a different amino acid (in (15-4), by substituting an Ala (A) residue for the Asp (D) residue at position 30 (Kabat's numbering). Then, the present inventors tested whether even a sequence with a substitution of Ser (S), a residue capable of chelating calcium ion, for the residue at position 30 (Kabat's numbering) (referred to as LfVk1_Ca6; SEQ ID NO: 75) was resistant to degradation while maintaining the calcium-binding activity. Variants were prepared by the same method as described in Example 14. The altered light chains LfVk1_Ca6 and LfVk1_Ca sequences were expressed in combination with a heavy chain GC_H (SEQ ID NO: 102). Antibodies were expressed and purified by the same method as described in Example 14.

(15-6) Assessment of a Light Chain LfVk1_Ca Sequence Resistant to Degradation at Asp Residue at Position 30

Purified antibodies prepared as described above were assessed for their storage stability under acidic conditions by the method described in (15-4) of Example 15. The result demonstrates that antibodies having the LfVk1_Ca6 sequence are more resistant to degradation than those having the original LfVk1_Ca sequence, as shown in FIG. 18.

Then, whether antibodies having the LfVk1_Ca sequence and antibodies having the LfVk1_Ca6 sequence bind to calcium ion was tested by the method described in Example 15. The result is shown in Table 21. The Tm values of the Fab domains of antibodies having LfVk1_Ca sequence and antibodies having the degradation-resistant LfVk1_Ca6 sequence were shifted by 1° C. or more upon change in the calcium concentration in antibody solutions.

TABLE 21

| LIGHT CHAIN | CALCIUM ION CONCENTRATION | | ΔTm (° C.) |
| --- | --- | --- | --- |
| VARIANT | 3 μM | 2 mM | 2 mM-3 μM |
| LfVk1_Ca | 78.45 | 80.06 | 1.61 |
| LfVk1_Ca6 | 78.44 | 79.74 | 1.30 |

Taking the stability into consideration, the result described above demonstrates that it is important for the calcium ion binding of antibodies that the amino acid at position 30 was an amino acid capable of interacting with calcium ion (Asn, Glu, Gln, Ser, Thr, His, Tyr, etc.) other than Asp, and all or some of the amino acids at positions 31, 32, 50, and 92 (Kabat's numbering) in the sequence were the same as hVk5-2 or amino acids capable of interacting with calcium (Asp, Asn, Glu, Gln, Ser, Thr, His, Tyr, etc.). For example, when a synthetic library is constructed to have such a motif, calcium-dependent binding antibodies can be efficiently isolated from the library.

Example 16

NMR Assessment of the Calcium Ion-Binding Activity of Antibodies Having the Human hVk1 Sequence with a Calcium Ion-Binding Motif (16-1) Expression and Purification of Antibodies An antibody having LfVk1_Ca and an antibody having LfVk1 were expressed and purified for NMR measurements. Specifically, animal expression plasmids for an antibody having LfVk1_Ca were constructed to be capable of expressing its heavy chain (SEQ ID NO: 13) and light chain (SEQ ID NO: 61), and they were introduced transiently into animal cells. Furthermore, animal expression plasmids for an antibody having LfVk1 were constructed to be capable of expressing its heavy chain (SEQ ID NO: 13) and light chain (SEQ ID NO: 62), and they were introduced transiently into animal cells. Labeled amino acids were added to 100 ml of cell suspensions prepared by suspending human fetal kidney cell-derived FreeStyle 293-F (Invitrogen) at a final cell density of $1 \times 10^6$ cells/ml in the FreeStyle 293 Expression Medium (Invitrogen). Specifically, a solution of L-aspartic acid-$^{13}C_4$, $^{15}N$ (10 mg), L-glutamic acid-$^{13}C_5$, $^{15}N$ (2.5 mg), L-glutamine-$^{13}C_5$, $^{15}N2$ (60 mg), L-asparagine-$^{13}C_4$, $^{15}N_2 \cdot H_2O$ (2.5 mg), and 3-chloro-L-alanine (6 mg) in 10 ml of water was filtered through a 0.22-m filter and added to prepare Asp/Glu/Gln/Asn-labeled antibodies. Meanwhile, a solution of L-leucine-$^{15}N$ (30 mg) and β-chloro-L-alanine (6 mg) in 10 ml of water was filtered through a 0.22-m filter and added to prepare Leu-labeled antibodies. Constructed plasmids were introduced into cells by the lipofection method. Cells introduced with the plasmids were cultured for five days in a $CO_2$ incubator (37° C., 8% $CO_2$, 90 rpm). From the culture supernatants prepared as described above, antibodies were purified using the rProtein A Sepharose™ Fast Flow (Amersham Biosciences) by a method known to those skilled in the art. Absorbance at 280 nm of purified antibody solutions was measured using a spectrophotometer. Antibody concentrations were calculated from the determined values using an extinction coefficient calculated by the PACE method (Protein Science (1995) 4: 2411-2423).

(16-2) Preparation of Fab Fragment

Each antibody was concentrated to 8.2 to 11.8 mg/ml using an ultrafilter with a molecular weight cut off of 30,000 MWCO. The antibodies were diluted to 8 mg/ml using 50 mM acetic acid/125 mM Tris buffer (pH 6.8) containing 1 mM L-cysteine and 2 mM EDTA to prepare samples. A 1/240 amount of papain (Roche Applied Science) was added to each antibody. After stirring, the samples were incubated at 37° C. for one hour. After incubation, each sample was loaded onto a 1-ml HiTrap NHS-activated HP (GE Healthcare) immobilized with Gly-Gly-Tyr-Arg peptide (Sigma) and equilibrated with 50 mM acetic acid/125 mM Tris buffer (pH 6.8), downstream of which a 1-ml HiTrap MabSelect Sure Protein A column (GE Healthcare) was connected in tandem. Purified Fab fragment fractions were obtained by removing Fc fragment and undigested antibodies by the downstream Protein A column while removing activated papain by the upstream Gly-Gly-Tyr-Arg peptide. Cysteine protease inhibitor E64 (Sigma) was added at 10 μM to the Fab fractions to prevent the activation of inactive papain in the Fab fractions. All the column operations described above were carried out at room temperature from 20 to 25° C.

(16-3) Preparation of Fab Fragments of Antibodies LfVk1_Ca and LfVk1 as NMR Samples Antibody solutions were concentrated to 0.5 ml by centrifugation using ultrafiltration device Vivaspin (Sartorius) with MWCO 5,000. Then, a diafiltration cup was placed in the ultrafiltration device described above, and the buffer was changed with NMR buffer: 5 mM d-BisTris/20 mM NaCl/ 0.001% (w/v) $NaN_3$/5% (v/v)$^2H_2O$ (pH 7.0) (the pH was adjusted using NaOH and HCl) (via three cycles of: addition of 5 ml of the above-described buffer to the diafiltration cup, followed by concentration to 0.5 ml by centrifugation). The antibody solutions were ultimately concentrated to 0.25 ml. Finally, the ultrafiltration device was washed with NMR buffer, and the buffer was combined with the concentrate. This yielded 420 μl and 270 μl of antibody solutions for antibody LfVk1_Ca and antibody LfVk1, respectively. At this stage, the pH of the solutions was again confirmed, and the pH was adjusted to pH 7.0 using NaOH and HCl if needed. The absorbance at 280 nm was measured using an UV spectrophotometer Nanodrop (Thermo Fisher Scientific) and concentrations of the Fab fragments were determined with molar extinction coefficient at 280 nm=70,000 $M^{-1}$ $cm^{-1}$. The concentrations of Leu-labeled antibodies LfVk1_Ca and LfVk1 were 0.12 mM, while the concentrations of Asp-, Glu-, Asn-, and Gln-labeled antibodies LfVk1_Ca and LfVk1 were 0.24 mM. Of the above-described samples, antibody LfVk1_Ca was filled in a 5 mm-diameter NMR sample tube (shigemi) and antibody LfVk1 was filled in a 5 mm-diameter symmetrical micro sample tube (shigemi) for aqueous solution using a Pasteur pipette. In $Ca^{2+}$ titration experiments for antibody LfVk1_Ca, $CaCl_2$) solutions were added to antibody solutions in succession so that $Ca^{2+}$ was 1, 2, 5, 10, or 20 molar equivalents to antibody. The $CaCl_2$) solutions added were prepared at 10, 20, 50, and 100 mM $CaCl_2$) using NMR buffer. Required volumes of $CaCl_2$) solutions were added directly to antibody solutions in the NMR sample tubes using a microsyringe (ITO), which was custom-tailored by extending the syringe portion of a ready-made product, so that the loading volume ranges from 3 to 10 μl. After stirring with a vortex mixer, the sample tubes were centrifuged using a manual centrifuge (Shimadzu).

(16-4) NMR Measurement to Observe Amide Group Signals from the Fab Fragments of Antibodies LfVk1_Ca and LfVk1_Ca NMR measurements were carried out using the NMR spectrometer DRX750 (Bruker Biospin) installed with TCI CryoProbe. The temperature was set at 307K (GasFlow 535 L/h). $^1H$-$^{15}N$ HSQC was used for observing amide group signals in NMR measurements. The measurement method was conducted by simultaneous $^{13}C$ decoupling of α and carbonyl carbons and subtraction of solvent water signals during the $^{15}N$ evolution period using $^1H$-$^{15}N$ FHSQC with a 3-9-19 pulse train. A standard program provided by the manufacturer (Bruker Biospin) was used as a pulse control scheme. The conditions of NMR measurement were as follows. Spectral width: 12019 Hz (f2), 1976 Hz (f1); the number of data points: 2048 (f2), 128 (f1). The data were processed using Topspin 3.0 (Bruker Biospin) in the following manner. A shifted square sine (QSINE) window function in both f2 and f1, and zero-filling to double the data size were applied prior to Fourier transformation. The chemical shifts of signals were calculated using an NMR analysis software Sparky (UCSF).

(16-5) NMR Signal Assignment of Main Chain Amide Groups

80% of the NMR signals from the main chain amide groups of the Fab fragment of tocilizumab (heavy chain SEQ ID NO: 13; light chain SEQ ID NO: 14) were assigned previously (data not disclosed). The amino acid sequence of the Fab fragment of antibody LfVk1_Ca is the same as that of the Fab fragment of tocilizumab, except some portions of light chain CDR1, CDR2, CDR3 and the amino acid residues at positions 73 and 83 in the light chain. Amino acid sequences shared by the two antibodies give NMR signals that exhibit the same or similar chemical shifts. Because of this, the assignment information on tocilizumab was applicable in such amino acid sequences. For Leu-labeled samples, assignments revealed to be applicable include: 11, (33), (46), (47), (54), (78), 125, 135, 136, 154, 175, 179, 181, and 201 in the light chain, and 18, 46, 64, 71, 81, 83, 114, 144, 147, 165, 176, 181, 184, and 195 in the heavy chain. In the above, numbers without parenthesis represent residue numbers at which the assignments are applicable because the chemical shifts are shared by tocilizumab; numbers in parentheses represent residue numbers at which the assignments are applicable because the chemical shifts are similar to those of tocilizumab and there are no other signals giving similar chemical shifts. Meanwhile, for the Asp-, Glu-, Asn-, Gln-labeled samples, four signals were newly observed in LfVk1_Ca when the spectra were compared between antibodies LfVk1_Ca and LfVk1. These were assumed to be assignable to four of the five residues, Asp30, Asp31, Asp32, Asp92, and Glu50, among Asp, Glu, Asn, and Gln residues in the light chain where the sequence introduced as a $Ca^{2+}$-binding motif is different between the two antibodies.

(16-6) Identification of $Ca^{2+}$ Binding Site in Antibody LfVk1_Ca

Signals with different chemical shift were extracted by comparing $^1H$-$^{15}N$ HSQC spectra of the Fab fragment of antibody LfVk1_Ca between in the presence and absence of 20 molar equivalents of $Ca^{2+}$. The result on the Leu-labeled samples showed that only Leu33, but no other Leu residues, in the light chain is involved in the binding. In addition, with the Asp-, Glu-, Asn-, Gln-labeled samples, four of the five residues, Asp30, Asp31, Asp32, Asp92, and Glu50, in the light chain were revealed to be involved in the binding, and all but except one of the other Asp, Glu, Asn, and Gln residues were not responsible for the binding. The finding described above demonstrates that in the amino acid sequence introduced as a $Ca^{2+}$-binding motif, some amino acids of at least light chain CDR1 and of both or either of light chain CDR2 and CDR3 were involved in the $Ca^{2+}$ binding. This is consistent with the finding described in Example 15 that it is important for the calcium ion binding that amino acids at four positions among positions 30, 31, 32, 50, and 92 (Kabat's numbering) are identical to those in the hVk5-2 sequence.

(16-7) Calculation of $Ca^{2+}$ Dissociation Constant by Titration Experiment

Based on $^1H$-$^{15}N$ HSQC spectra at $Ca^{2+}$ concentrations of 0, 1, 2, 5, 10, or 20 molar equivalents to the Fab fragment of antibody LfVk1_Ca, a graph was plotted with the molar equivalent of $Ca^{2+}$ in the horizontal axis and with $^1H$ or $^{15}N$ chemical shifts of the signal for light chain Leu33 identified as the binding site in the vertical axis. Using the function represented by formula 2 shown below, data fitting was performed with graphing software Gnuplot.

$$f(x)=s*[1-0.5/a*\{(a*x+a+Kd)-((a*x+a+Kd)^2-4*x*a^2)^{0.5}\}+t*[0.5/a*\{(a*x+a+Kd)-((a*x+a+Kd)^2-4*x*a^2)^{0.5}\}$$  [Formula 2]

In the function represented by formula 2, "s" and "t" represent the chemical shift [ppm] for the $Ca^{2+}$-unbound state and an estimated chemical shift [ppm] for the $Ca^{2+}$-bound, saturated state, respectively; "a" represents the concentration of the antibody Fab fragment [M]; "Kd" represents the dissociation constant; and "x" represents the molar equivalents of $Ca^{2+}$ added to the antibody Fab fragment. In the data fitting, s, t, and Kd were fitting parameters. As a result, based on $^1H$ and $^{15}N$ chemical shifts, Kd was estimated as follows: $Kd=7.1\times10^{-5}$ [M] and $Kd=5.9\times10^{-5}$ [M], respectively.

Example 17

Assessment of Variant Sequence hVk5-2 for Calcium Binding

Vk5-2 variant 1 (SEQ ID NO: 63) and Vk5-2 variant 2 (SEQ ID NO: 64) were obtained in addition to Vk5-2 (SEQ ID NO: 41), all of which are classified as Vk5-2. These variants were assessed for their calcium binding. DNA fragments for Vk5-2, Vk5-2 variant 1, and Vk5-2 variant 2 were each inserted into animal cell expression vectors. The nucleotide sequences of the constructed expression vectors were determined by a method known to those skilled in the art. By the method described in Example 13, the animal cell expression vectors inserted with DNA fragments for Vk5-2, Vk5-2 variant 1, and Vk5-2 variant 2 were introduced, in combination with animal expression vector carrying an insert to express CIM_H (SEQ ID NO: 48) as a heavy chain, into animal cells and antibodies were purified. The purified antibodies were assessed for their calcium ion-binding activity. The purified antibodies were dialyzed (EasySEP, TOMY) against 20 mM Tris-HCl/150 mM NaCl (pH 7.5) (in Table 22, indicated as 0 mM calcium ion concentration) or 20 mM Tris-HCl/150 mM NaCl/2 mM $CaCl_2$) (pH 7.5). DSC measurement was carried out at a rate of temperature increase of 240° C./hr from 20 to 115° C. using antibody solutions prepared at a concentration of 0.1 mg/mL by the same solution as used for dialysis. Based on the obtained DSC denaturation curves, the intermediate temperature of thermal denaturation (Tm value) was calculated for the Fab domain of each antibody. The Tm values are shown in Table 22.

TABLE 22

| LIGHT CHAIN | CALCIUM ION CONCENTRATION | | ΔTm (° C.) |
| --- | --- | --- | --- |
| | 0 mM | 2 mM | 2 mM-0 mM |
| Vk5-2 | 71.65 | 74.38 | 2.73 |
| Vk5-2 VARIANT 1 | 65.75 | 72.24 | 6.49 |
| Vk5-2 VARIANT 2 | 66.46 | 72.24 | 5.78 |

The result showed that the Tm value for the Fab domains of antibodies having the sequence of Vk5-2, Vk5-2 variant 1, or Vk5-2 variant 2 varied depending on the calcium ion concentration in solutions containing antibodies having the Fab domains. This demonstrates that antibodies having a sequence classified as Vk5-2 bind to calcium ion.

Example 18

Antibodies that Bind to Human CD4 in a Calcium-Dependent Manner (18-1) Preparation of Soluble Human CD4

Soluble human CD4 was prepared as follows. A DNA sequence encoding a sequence (SEQ ID NO: 76) in which Myc tag is attached to the amino acid sequence of human CD4 that lacks the transmembrane region was inserted into an animal cell expression vector. The sequence of the constructed recombinant human CD4 was confirmed by a method known to those skilled in the art.

(18-2) Expression and Purification of Antibodies that Bind to Soluble Human CD4

TNX355-IgG1 (heavy chain SEQ ID NO: 77; light chain SEQ ID NO: 78) and Q425 (heavy chain SEQ ID NO: 79; light chain SEQ ID NO: 80) are anti-human CD4 antibodies. Furthermore, Q425L9 (heavy chain SEQ ID NO: 81; light chain SEQ ID NO: 82) is an L chain variant from Q425. DNA sequences encoding the amino acids of TNX355-IgG1 (heavy chain SEQ ID NO: 77; light chain SEQ ID NO: 78), Q425 (heavy chain SEQ ID NO: 79; light chain SEQ ID NO: 80), and Q425L9 (heavy chain SEQ ID NO: 81; light chain SEQ ID NO: 82) were inserted into animal cell expression plasmids. Antibodies were expressed by the following method. Cells of human fetal kidney cell-derived FreeStyle 293-F (Invitrogen) were suspended in FreeStyle 293 Expression Medium (Invitrogen), and plated at a cell density of $1.33\times10^6$ cells/ml (3 ml) into each well of a 6-well plate. The prepared plasmids were introduced into cells by a lipofection method. The cells were cultured for four days in a $CO_2$ incubator (37° C., 8% $CO_2$, 90 rpm). From the culture supernatants prepared as described above, antibodies were purified using the rProtein A Sepharose™ Fast Flow (Amersham Biosciences) by a method known to those skilled in the art. Absorbance at 280 nm of purified antibody solutions was measured using a spectrophotometer. Antibody concentrations were calculated from the determined values using an extinction coefficient calculated by the PACE method (Protein Science (1995) 4: 2411-2423).

(18-3) Assessment of Prepared Antibodies for Calcium-Dependent Binding Activity to Human CD4

The prepared antibodies were assessed for their calcium-dependent binding activity to soluble human CD4 using Biacore™ T100 (GE Healthcare). The high calcium ion concentration used was 1.2 mM, while the low calcium ion concentration was 3 μM. Soluble human CD4 (prepared as described in 18-1) was used as antigen. An adequate amount of protein G (Invitrogen) was immobilized onto the Sensor chip CM4 (GE Healthcare) by the amine coupling method, and then antibodies of interest were allowed to capture. 10 mmol/L ACES, 150 mmol/L NaCl, 0.05% (w/v) Tween®20 (polysorbate 20), 1.2 mmol/L CaCl$_2$) (pH 7.4 or pH 6.0) containing 1.2 mmol/L or 3 µmol/L CaCl$_2$) was used as a running buffer. All measurements were carried out at 37° C. Human CD4 was diluted using the respective buffers. Antibody sensorgrams are shown in FIG. 19. As shown in FIG. 19, the shape of sensorgram of antibody TNX355-IgG1 did not change even when the running buffer condition was changed. This demonstrates that TNX355-IgG1 is a common antibody that does not show calcium-dependent binding activity to human CD4. Meanwhile, for both antibodies Q425 and Q425L9, the amount of antigen binding was smaller at a calcium ion concentration of 3 µM (low calcium ion concentration) than at 1.2 mM (high calcium ion concentration), and thus they exhibited Ca-dependent binding activity. In particular, no binding phase was observed for antibody Q425L9 at a calcium ion concentration of 3 µM even at an analyte (soluble human CD4) concentration of 200 nM. Specifically, Q425 and Q425L9 were demonstrated to be calcium-dependent binding antibodies that bind to human CD4 in a calcium-dependent manner.

Example 19

Assessment of Ca-Dependent Binding Antibodies for their Effect on Antigen Retention in Plasma Using Normal Mice (19-1) In Vivo Assay Using Normal Mice Q425 and Q425L9 prepared as described in Example 18 are antibodies that bind to soluble human CD4 in a calcium-dependent manner. As already described in Examples 5 and 6, regarding IL6R, it has been demonstrated that when administered in combination with an antigen, an antibody having the property of binding to an antigen in a calcium-dependent manner has a property to accelerate antigen elimination as compared to when an antibody that binds to an antigen in a calcium-independent manner is administered in combination with an antigen. However, whether antibodies against other antigens also have the property to accelerate antigen elimination remain to be clarified.

Then, soluble human CD4 (prepared as described in Example 18) was administered alone or in combination with an anti-human CD4 antibody to normal mice (C57BL/6J mouse; Charles River Japan). The mice were assessed for in vivo kinetics of soluble human CD4 and anti-human CD4 antibody after administration. A solution of soluble human CD4 (50 µg/ml) or a mixed solution of soluble human CD4 and an anti-human CD4 antibody was administered once at 10 ml/kg to the caudal vein. Anti-human CD4 antibodies used were TNX355-IgG1, Q425-IgG1, and Q425L9-IgG1 described above.

The concentration of soluble human CD4 in the mixed solution was 50 µg/ml. Meanwhile, the concentrations of anti-human CD4 antibodies varied depending on the antibody: 0.264 mg/ml for TNX355-IgG1; 0.197 mg/ml for Q425-IgG1; and 2.594 mg/ml for Q425L9-IgG1. In this case, the anti-human CD4 antibodies were present in an excess amount as compared to soluble human CD4, and soluble human CD4 was assumed to mostly bind to the antibodies. In the group administered with soluble human CD4 alone, blood was collected 2 minutes, 5 minutes, 15 minutes, 30 minutes, one hour, and two hours after administration. In the group administered with soluble human CD4 in combination with TNX355-IgG1 without calcium-dependent antigen-binding activity, blood was collected 5 minutes, 2 hours, 7 hours, 1 day, 3 days, 7 days, 14 days, and 28 days after administration. In the group administered with soluble human CD4 in combination with Q425-IgG1 or Q425L9-IgG1 having calcium-dependent antigen-binding activity, blood was collected 5 minutes, 30 minutes, 2 hours, 7 hours, 1 day, 3 days, 8 days, 14 days, and 28 days after administration. Immediately after collection, the blood was centrifuged at 4° C. and 12,000 rpm for 15 minutes to isolate plasma. The isolated plasma was stored in a freezer at −20° C. or below before measurements.

(19-2) Determination of Plasma Anti-Human CD4 Antibody Concentration in Normal Mice by ELISA Anti-human CD4 antibody concentrations in mouse plasma were determined by ELISA. First, Anti-Human IgG (γ-chain specific) F(ab')2 Fragment of Antibody (SIGMA) was aliquoted into Nunc-Immuno Plate, MaxiSorp (Nalge nunc International). The plate was allowed to stand overnight at 4° C. to prepare an anti-human IgG antibody-immobilized plate. Standard samples were prepared at concentrations of 0.64, 0.32, 0.16, 0.08, 0.04, 0.02, and 0.01 µg/ml in plasma. Mouse plasma assay samples were prepared by diluting 100 times or more. The samples were aliquoted into the anti-human IgG antibody-immobilized plate. The plate was incubated at 25° C. for one hour. After incubation, the samples were reacted with biotinylated anti-human IL-6R antibody (R&D) at 25° C. for one hour, and then with Streptavidin-PolyHRP80 (Stereospecific Detection Technologies) at 25° C. for 0.5 hour. Chromogenic reaction was carried out using TMB One Component HRP Microwell Substrate (BioFX Laboratories) as a substrate. After the reaction was terminated with 1N sulfuric acid (Showa Chemical), the absorbance at 450 nm was measured using a microplate reader. Using analysis software SOFTmax PRO (Molecular Devices), the concentrations in mouse plasma were calculated based on the absorbance from the standard curve.

A time course of plasma concentrations of antibodies TNX355-IgG1, Q425-IgG1, and Q425L9-IgG1 determined by the above-described method after intravenous administration to normal mice is shown in FIG. 20.

(19-3) Determination of Plasma Concentrations of Soluble Human CD4 by an Electrochemical Luminescence Method Soluble human CD4 concentrations in mouse plasma were determined by ELISA.

For the group administered with sCD4 alone and the group administered in combination with Q425 or Q425 L9, TNX was aliquoted into Nunc-Immuno Plate, MaxiSorp (Nalge nunc International). The plate was left overnight at 4° C. to prepare a TNX-immobilized plate. Standard samples were prepared at plasma concentrations of 10, 5, 2.5, 1.25, 0.625, 0.3125, and 0.156 µg/ml. Mouse plasma assay samples were prepared by diluting 100 times or more. The samples were prepared using a buffer containing 10 mM EDTA, and aliquoted into the TNX-immobilized plate. After three hours of incubation at 25° C., the samples were reacted with anti-c-myc-HRP (Miltenyi Biotech) at 25° C. for one hour. Chromogenic reaction was carried out using the TMB One Component HRP Microwell Substrate (BioFX Laboratories) as a substrate. After the reaction was terminated with 1N sulfuric acid (Showa Chemical), the absorbance at 450 nm was measured using a microplate reader. Using the analysis software SOFTmax PRO (Molecular Devices), the concentrations in mouse plasma were calculated based on the absorbance from the standard curve.

In the group administered in combination with TNX, Q425 was aliquoted into Nunc-Immuno Plate, MaxiSorp (Nalge nunc International). The plate was left overnight at 4° C. to prepare a Q425-immobilized plate. Standard samples were prepared at plasma concentrations of 20, 10, 5, 2.5, 1.25, 0.625, and 0.3125 µg/ml. Mouse plasma assay samples were prepared by diluting 100 times or more. The samples were prepared using a buffer containing 2 mM $Ca^{2+}$, and aliquoted into the TNX-immobilized plate. After three hours of incubation at 25° C., the samples were reacted with Anti-c-myc-HRP (Miltenyi Biotech) at 25° C. for one hour. Chromogenic reaction was carried out using the TMB One Component HRP Microwell Substrate (BioFX Laboratories) as a substrate. After the reaction was terminated with 1N sulfuric acid (Showa Chemical), the absorbance at 450 nm was measured using a microplate reader. Using the analysis software SOFTmax PRO (Molecular Devices), the concentrations in mouse plasma were calculated based on the absorbance from the standard curve.

A time course of plasma concentrations of soluble human CD4 determined by the above-described method after intravenous administration to normal mice is shown in FIG. 21.

The result showed that soluble human CD4 when administered alone was eliminated very rapidly. Meanwhile, the elimination of soluble human CD4 was greatly retarded when administered in combination with TNX355-IgG1, a common antibody without Ca-dependent binding activity to soluble human CD4. In contrast, the elimination of soluble human CD4 was significantly accelerated when administered in combination with Q425-IgG1 or Q425L9-IgG1 having Ca-dependent binding activity to soluble human CD4. The elimination of soluble human CD4 could be accelerated when administered in combination with Q425-IgG1 or Q425L9-IgG1 as compared to when administered in combination with TNX355-IgG1. This finding demonstrates that not only for IL-6R but also for human CD4, antigen elimination from plasma can be achieved with a calcium-dependent binding antibody.

Example 20

Antibodies that Bind to Human IgA in a Calcium-Dependent Manner (20-1) Preparation of Human IgA (hIgA)

An antigen, recombinant human IgA (hereinafter abbreviated as hIgA), was prepared as follows. hIgA comprising H(WT)-IgA1 (SEQ ID NO: 83) and L(WT) (SEQ ID NO: 14) was expressed, and purified by ion-exchange chromatography and gel filtration chromatography using a method known to those skilled in the art.

(20-2) Expression and Purification of Antibodies that Bind to Human IRA

GA1-IgG1 (heavy chain SEQ ID NO: 84; light chain SEQ ID NO: 85), GA2-IgG1 (heavy chain SEQ ID NO: 86; light chain SEQ ID NO: 87), GA3-IgG1 (heavy chain SEQ ID NO: 88; light chain SEQ ID NO: 89), and GA4-IgG1 (heavy chain SEQ ID NO: 90; light chain SEQ ID NO: 91) are antibodies that bind to human IgA. Then, for the purpose of further enhancing antigen (hIgA) elimination from plasma, in a similar way as described in Examples 6 and 7, GA2-N434W (heavy chain SEQ ID NO: 92; light chain SEQ ID NO: 87) was constructed by introducing amino acid substitution N434W into GA2-IgG1 to strengthen the binding to mouse FcRn at pH 7.4. DNA sequences encoding GA1-IgG1 (heavy chain SEQ ID NO: 84; light chain SEQ ID NO: 85), GA2-IgG1 (heavy chain SEQ ID NO: 86; light chain SEQ ID NO: 87), GA3-IgG1 (heavy chain SEQ ID NO: 88; light chain SEQ ID NO: 89), GA4-IgG1 (heavy chain SEQ ID NO: 90; light chain SEQ ID NO: 91), and GA2-N434W (heavy chain SEQ ID NO: 92; light chain SEQ ID NO: 87) were inserted into animal expression plasmids by a method known to those skilled in the art. Antibodies were expressed by the following method. Cells of human fetal kidney cell-derived FreeStyle 293-F (Invitrogen) were suspended in the FreeStyle 293 Expression Medium (Invitrogen), and plated at a cell density of $1.33 \times 10^6$ cells/ml (3 ml) into each well of a 6-well plate. The constructed plasmids were introduced into cells by a lipofection method. The cells were cultured for four days in a $CO_2$ incubator (37° C., 8% $CO_2$, 90 rpm). From the prepared culture supernatants, antibodies were purified using the rProtein A Sepharose™ Fast Flow (Amersham Biosciences) by a method known to those skilled in the art. The concentrations of purified antibodies were determined by measuring absorbance at 280 nm using a spectrophotometer. Antibody concentrations were calculated from the determined values using an extinction coefficient calculated by the PACE method (Protein Science (1995) 4: 2411-2423).

(20-3) Assessment of Prepared Antibodies for Ca-Dependent Human IgA-Binding Activity Using Biacore™ T200 (GE Healthcare), the obtained antibodies were assessed for their binding activity to human IgA (dissociation constant $K_D$ (M)). The measurement was carried out using as a running buffer 0.05% Tween®20 (polysorbate 20), 20 mmol/L ACES, 150 mmol/L NaCl (pH 7.4 or pH 5.8) containing 3 µM or 1.2 mM $CaCl_2$), or 0.05% Tween®20 (polysorbate 20), 20 mmol/L ACES, 150 mmol/L NaCl (pH 8.0) containing 0.1 µM or 10 mM $CaCl_2$).

After an adequate amount of recombinant Protein A/G (Thermo Scientific) was immobilized onto the Sensor chip CM5 (GE Healthcare) by an amino coupling method, antibodies were allowed to bind onto the sensor chip. An appropriate concentration of hIgA (described in (20-1)) was injected as an analyte to interact with antibodies on the sensor chip. Then, the sensor chip was regenerated by injecting 10 mmol/L glycine-HCl, pH 1.5. The measurement was carried out at 37° C. From the assay result, the dissociation constant $K_D$ (M) was calculated based on curve-fitting analysis and equilibrium constant analysis using Biacore™ T200 Evaluation Software (GE Healthcare). The result is shown in Table 23. The obtained sensorgram is shown in FIG. 22. GA2-IgG1, GA3-IgG1, and GA4-IgG1 were demonstrated to bind to human IgA strongly at a $Ca^2$ concentration of 1.2 mM and weakly at a Ca 1 concentration of 3 µM.

TABLE 23

| ANTIBODY NAME | CONDITION | Fit | ka | kd | KD |
|---|---|---|---|---|---|
| GA1-IgG1 | pH 8.0, 10 mM Ca | 1:1binding model | 1.10E+06 | 2.40E−01 | 2.20E−07 |
| | pH 8.0, 0.1 µM Ca | 1:1binding model | 1.20E+06 | 1.20E−01 | 1.00E−07 |
| | pH 7.4, 1.2 mM Ca | 1:1binding model | 5.70E+05 | 8.40E−02 | 1.50E−07 |
| | pH 7.4, 3 µM Ca | 1:1binding model | 6.40E+05 | 1.20E−01 | 1.90E−07 |
| | pH 5.8, 1.2 mM Ca | 1:1binding model | 6.80E+05 | 9.90E−02 | 1.40E−07 |
| | pH 5.8, 3 µM Ca | 1:1binding model | 7.10E+05 | 1.10E−01 | 1.50E−07 |

TABLE 23-continued

| ANTIBODY NAME | CONDITION | Fit | ka | kd | KD |
|---|---|---|---|---|---|
| GA2-IgG1 | pH 7.4, 1.2 mM Ca | 1:1binding model | 4.00E+05 | 1.60E−02 | 3.90E−08 |
| | pH 7.4, 3 µM Ca | Steady State Affinity | — | — | 6.70E−06 |
| | pH 5.8, 1.2 mM Ca | Steady State Affinity | — | — | 4.00E−06 |
| | pH 5.8, 3 µM Ca | Steady State Affinity | — | — | 5.00E−06 |
| GA3-IgG1 | pH 7.4, 1.2 mM Ca | 1:1binding model | 4.30E+05 | 3.30E−02 | 7.90E−08 |
| | pH 7.4, 3 µM Ca | Steady State Affinity | — | — | — |
| | pH 5.8 1.2 mM Ca | 1:1binding model | 4.40E+05 | 3.50E−02 | 8.10E−08 |
| | pH 5.8, 3 µM Ca | Steady State Affinity | — | — | 1.10E−06 |
| GA4-IgG1 | pH 7.4, 1.2 mM Ca | Steady State Affinity | — | — | 4.20E−07 |
| | pH 7.4, 3 µM Ca | Steady State Affinity | — | — | 8.90E−07 |
| | pH 5.8, 1.2 mM Ca | Steady State Affinity | — | — | 1.10E−06 |
| | pH 5.8, 3 µM Ca | Steady State Affinity | — | — | 1.50E−06 |

Example 21

Assessment of the Effect of Ca-Dependent Human IgA-Binding Antibodies on Antigen Retention in Plasma Using Normal Mice (21-1) In Vivo Assay Using-Normal Mice Human IgA (human IgA: prepared as described in Example 20) was administered alone or in combination with an anti-human IgA antibody to normal mice (C57BL/6J mouse; Charles River Japan). The mice were assessed for in vivo kinetics of human IgA and anti-human IgA antibody after administration. A human IgA solution (80 µg/ml) or a mixed solution of human IgA and anti-human IgA antibody was administered once at 10 ml/kg to the caudal vein. Anti-human IgA antibodies used were GA1-IgG1, GA2-IgG1, GA3-IgG1, and GA2-N434W described above.

The concentration of human IgA in the mixed solution was 80 µg/ml. Meanwhile, the concentrations of anti-human IgA antibodies vary depending on the affinity for hIgA: 100 mg/ml for GA1-IgG1; 28.9 mg/ml for GA2-IgG1; 53.8 mg/ml for GA3-IgG1; and 1 mg/ml for GA2-N434W. In this case, the anti-human IgA antibodies were present in an excess amount as compared to human IgA, and human IgA was assumed to mostly bind to the antibodies. Blood was collected 5 minutes, 7 hours, 1 day, 2 days, 3 days, and 7 days after administration. Immediately after the collection, the blood was centrifuged at 4° C. and 12,000 rpm for 15 minutes to isolate plasma. The isolated plasma was stored in a freezer at −20° C. or below before measurements.

(21-2) Determination of Plasma Concentration of Anti-Human IgA Antibody in Normal Mice by ELISA Anti-human IgA antibody concentrations in mouse plasma were determined by ELISA. First, Anti-Human IgG (γ-chain specific) F(ab')2 Fragment of Antibody (SIGMA) was aliquoted into Nunc-Immuno Plate, MaxiSorp (Nalge nunc International). The plate was left overnight at 4° C. to prepare an anti-human IgG antibody-immobilized plate. Standard samples were prepared at plasma concentrations of 0.5, 0.25, 0.125, 0.0625, 0.03125, 0.01563, and 0.07813 µg/ml. Mouse plasma assay samples were prepared by diluting 100 times or more. The samples were aliquoted into the Anti-Human IgG antibody-immobilized plate. After one hour of incubation at 25° C., the samples were reacted with the Goat Anti-Human IgG (γ chain specific) Biotin (BIOT) Conjugate (Southern Biotechnology Associats Inc.) at 25° C. for one hour. Then, the samples were reacted with Streptavidin-PolyHRP80 (Stereospecific Detection Technologies) at 25° C. for one hour. Chromogenic reaction was carried out using the TMB One Component HRP Microwell Substrate (BioFX Laboratories) as a substrate. After the reaction was terminated with 1N sulfuric acid (Showa Chemical), the absorbance at 450 nm was measured using a microplate reader. Using the analysis software SOFTmax PRO (Molecular Devices), the concentrations in mouse plasma were calculated based on the absorbance from the standard curve. A time course of plasma concentrations of antibodies GA1-IgG1, GA2-IgG1, GA3-IgG1, and GA2-N434W determined by the above-described method after intravenous administration to normal mice is shown in FIG. 23.

(21-3) Determination of Plasma Human IgA Concentration by ELISA

Human IgA concentrations in mouse plasma were determined by ELISA. First, Goat anti-Human IgA antibody (BETHYL) was aliquoted into a Nunc-Immuno Plate, MaxiSorp (Nalge nunc International). The plate was left at 4° C. overnight to prepare an anti-human IgA antibody-immobilized plate. Standard samples of human IgA were prepared at plasma concentrations of 0.4, 0.2, 0.1, 0.05, 0.025, 0.0125, and 0.00625 µg/ml. Mouse plasma assay samples were prepared by diluting 100 times or more. 200 µl of 500 ng/ml hsIL-6R was added to 100 µl of the standard and plasma samples. The resulting mixtures were allowed to stand at room temperature for one hour, and then aliquoted into the anti-human IgA antibody-immobilized plate and incubated at room temperature for one hour. After incubation, the mixtures were reacted with biotinylated Anti-human IL-6R antibody (R&D) at room temperature for one hour, and then with the Streptavidin-PolyHRP80 (Stereospecific Detection Technologies) at room temperature for one hour. Chromogenic reaction was carried out using the TMB One Component HRP Microwell Substrate (BioFX Laboratories) as a substrate. After the reaction was terminated with TN sulfuric acid (Showa Chemical), the absorbance at 450 nm was measured using a microplate reader. Using analysis software SOFTmax PRO (Molecular Devices), the concentrations in mouse plasma were calculated based on the absorbance from the standard curve. A time course of plasma concentrations of human IgA determined by the above-described method after intravenous administration to normal mice is shown in FIG. 24.

The result showed that when human IgA was administered in combination with GA1-IgG1, an antibody whose Ca dependency in the human IgA binding is weak (the degree of dependency is low), the elimination of human IgA was retarded as compared to when administered alone. Meanwhile, the elimination of human IgA was significantly accelerated when administered in combination with GA2-IgG1 which exhibits 100 times or more Ca-dependent human IgA-binding activity. The plasma concentration of unbound human IgA was determined from the plasma antibody concentration shown in FIG. 23, the plasma concentration of human IgA shown in FIG. 24, and the KD value of each antibody shown in Table 23. The result is shown in FIG. 25. As shown in FIG. 25, the concentration of unbound antigen (human IgA) in the group administered with GA2-IgG1 or GA3-IgG1 was lower as compared to the concentration of unbound antigen (human IgA) in the GA1-IgG1-administered group. This demonstrates that unbound antigen (human IgA) can be reduced by accelerating antigen elimination using calcium-dependent binding antibodies. Moreover, GA2-N434W that exhibited enhanced FcRn binding at pH 7.4 accelerated antigen elimination more than GA2-IgG1. The antigen was reduced to a level below the detection limit 7 hours after administration.

The finding described above demonstrates that calcium-dependent binding antibodies can accelerate antigen elimination from plasma as compared to common antibodies that bind to an antigen in a pH- or calcium-independent manner. It was revealed that this applies not only to human IL6R described in Example 5 or human CD4 described in Example 19 but also to human IgA. Furthermore, in addition to human IL6R described in Examples 6 and 7, it was demonstrated for human IgA that antigen elimination can be further accelerated by enhancing the FcRn binding of calcium-dependent binding antibodies at pH 7.4.

As shown in Reference Example 31, Fv4-IgG1, which binds to human IL-6 receptor in a pH-dependent manner, can accelerate the elimination of human IL-6 receptor as compared to H54/L28-IgG1 which binds to human IL-6 receptor in a pH-independent manner; however, Fv4-IgG1 cannot accelerate the elimination as compared to administration of human IL-6 receptor alone. Fv4-IgG1-v1 or Fv4-IgG1-v2 with enhanced FcRn binding activity in the neutral range should be used to accelerate the elimination as compared to administration of human IL-6 receptor alone.

Meanwhile, surprisingly, GA2-IgG1, which binds to human IgA in a Ca-dependent manner, was revealed to accelerate the elimination of human IgA as compared to administration of human IgA alone, although it has the constant region of natural IgG1 whose FcRn binding in the neutral range is not enhanced. The following mechanism is thought to account for what happened in GA2-IgG1.

In the case of monomeric antigens such as human IL-6 receptor, two antigens bind to a divalent antibody. This results in the formation of an antigen/antibody complex consisting of three molecules of antigen and antibody. On the other hand, since human IgA is a dimeric antigen and an antibody is divalent, the antigen/antibody complex between them is likely to form an antigen/antibody complex (immune complex) consisting of four or more molecules of antigen and antibody.

When a common antibody of natural IgG1 type against a multimeric antigen forms a bulky immune complex, the immune complex can bind to FcgR, FcRn, complement receptor, and such with avidity in a multivalent fashion via Fc domain. Thus, the immune complex is internalized into cells expressing such receptors. Meanwhile, a common pH/Ca-independent antibody against a monomeric antigen has insufficient affinity for the natural IgG1 type receptor, and thus the resulting immune complex is internalized into cells with low efficiency. FcRn originally has a role of recycling intracellularly internalized antibodies from the endosome to plasma. However, bulky immune complexes capable of binding to FcRn in a multivalent fashion are known to be transferred from the endosome by FcRn and degraded in the lysosome. Specifically, as shown in FIG. 26, a common antibody against a multimeric antigen, which forms a bulky immune complex, can accelerate the elimination of the antigen; however, the antigen is not dissociated from the antibody in the endosome, and the antibody is also eliminated simultaneously together with the antigen. Therefore, the antigen elimination efficiency per antibody molecule is low. In other words, a common pH/Ca-independent antibody against a monomeric antigen can accelerate antigen elimination; however, the efficiency is assumed to be low.

On the other hand, when a pH/Ca-dependent antibody that has a natula-IgG1-type constant region against a multimeric antigen forms a bulky immune complex, the immune complex binds to FcgR, FcRn, complement receptor, and such with avidity via multivalent Fc region as shown in FIG. 27, and is taken up by cells expressing the receptors. The immune complex dissolves by dissociation of the antigen from the pH/Ca-dependent antibody in the endosome. The antigen cannot bind to FcRn and is transferred to the lysosome for degradation. Meanwhile, the antibody is recycled to plasma by FcRn because it does not form an immune complex.

Specifically, when a pH/Ca-dependent antibody that has a natural-IgG1-type constant region against a multimeric antigen can bind to FcgR, FcRn, complement receptor, and such with avidity by forming a bulky immune complex, only antigen elimination can be selectively and greatly accelerated. The above described phenomenon was assumed to also occur with GA2-IgG1 against human IgA. This was expected to be useful as a method for significantly accelerating the elimination of multimeric antigen without using the amino acid substitution method for enhancing the FcRn binding of natural IgG1 in the neutral range such as shown in Reference Example 31.

In order to achieve the effect described above, an antigen and an antibody form a bulky immune complex and must tightly bind to FcgR/FcRn with avidity, even if the antibody is an IgG1. When the antigen is a dimeric or higher-order polymeric antigen, by screening for pH/Ca-dependent antibodies that form a bulky immune complex and bind to the above-described receptor, the antigen elimination can be accelerated efficiently by using the natural IgG1 constant region without performing any amino acid substitution. In general, it is considered that antigens have to be multimeric (for example, immunoglobulins such as IgA and IgE, and the TNF superfamily such as TNF and CD154) for antibodies and antigens to form bulky immune complexes. Even when an antigen is monomeric, a bulky immune complex can be formed by using a mixture of two or more types of appropriate pH/Ca-dependent antibodies that recognize two or more epitopes in a monomeric antigen. Alternatively, a bulky immune complex can be formed by using an appropriate multispecific pH/Ca-dependent antibody that recognizes two or more epitopes in a monomeric antigen (for example, a bispecific antibody having a natural IgG constant region with the right and left arms recognizing epitopes A and B, respectively, such as shown in FIG. 28). Specifically, if appropriate pH/Ca-dependent antibodies against monomeric antigens can be screened, antigen elimination can be accelerated efficiently by using a mixture of antibodies having a natural IgG1 constant region or a multispecific antibody having a natural IgG1 constant region, without using mutant IgG1 having an amino acid substitution.

Example 22

Antibodies that Bind to Human Glypican 3 in a Calcium-Dependent Manner (22-1) Preparation of Human Glypican 3 (GPC3)

Recombinant human glypican 3 (hereinafter abbreviated as GPC3) which is used as an antigen was prepared by the following procedure. CHO cells constitutively introduced with a plasmid that expresses a sequence to which six histidine residues are linked to the amino acid sequence of human glypican 3 without having the transmembrane domain (SEQ ID NO: 93) were cultured. Then, from the collected culture supernatant, GPC3 was purified by ion-exchange chromatography, followed by His tag-based affinity and gel filtration chromatography.

(22-2) Expression and Purification of Antibodies that Bind to Human GPC3

Anti-human glypican 3 antibodies CSCM-01_005 (heavy chain sequence: 94; light chain sequence: 95), CSCM-01_009 (heavy chain sequence: 96; light chain sequence: 97), CSCM-01_015 (heavy chain sequence: 98, light chain sequence: 99), CSCM-01_023 (heavy chain sequence: 100; light chain sequence: 101), and GC-IgG1 (heavy chain sequence: 102; light chain sequence: 103) were each inserted into animal expression plasmids. Antibodies were expressed by the following procedure. Cells of human fetal kidney cell-derived FreeStyle 293-F (Invitrogen) were suspended in the FreeStyle 293 Expression Medium (Invitrogen), and plated at a cell density of $1.33 \times 10^6$ cells/ml (3 ml) into each well of a 6-well plate. The prepared plasmids were introduced into cells by a lipofection method. The cells were cultured for four days in a $CO_2$ incubator (37° C., 8% $CO_2$, 90 rpm). From the prepared culture supernatants, antibodies were purified using the rProtein A Sepharose™ Fast Flow (Amersham Biosciences) by a method known to those skilled in the art. The concentrations of purified antibodies were determined by measuring absorbance at 280 nm using a spectrophotometer. Antibody concentrations were calculated from the determined values using an extinction coefficient calculated by the PACE method (Protein Science (1995) 4: 2411-2423). Furthermore, antibody GC-IgG1 was purified from culture supernatants of CHO cells constitutively expressing antibody GC-IgG1 and its concentration was determined by the same method as described above.

(22-3) Assessment of Isolated Antibodies for Ca-Dependent Human GPC3-Binding Activity Isolated antibodies were subjected to ELISA using the following procedure. StreptaWell 96-well microtiter plate (Roche) was coated overnight with 100 µl of PBS containing a biotin-labeled antigen. After the antigen was washed off from each well of the plate using ACES buffer (10 mM ACES, 150 mM NaCl, 100 mM $CaCl_2$), 0.05% Tween®20 (polysorbate 20), pH 7.4), the wells were blocked for one hour or more with 250 µl of an ACES Buffer containing 2% BSA. After removing the ACES Buffer containing 2% BSA from each well, a purified IgG serially diluted at a dilution ratio of 4 starting from 10 µg/ml was prepared in advance and aliquoted at 100 µl into the plate. The plate was allowed to stand for one hour to allow binding of IgG to the antigen in each well. Following wash with the ACES Buffer, "10 mM ACES, 150 mM NaCl, 1.2 mM $CaCl_2$), pH 7.4", "10 mM ACES, 150 mM NaCl, 3 M $CaCl_2$), pH 7.4", "10 mM ACES, 150 mM NaCl, 1.2 mM $CaCl_2$), pH 5.8", or "10 mM ACES, 150 mM NaCl, 3 µM $CaCl_2$), pH 5.8" was added to each well. The plate was incubated at 37° C. for 30 minutes. After washing with the ACES Buffer, an HRP-conjugated anti-human IgG antibody (BIOSOURCE) diluted with an ACES Buffer containing 2% BSA was added to each well. The plate was incubated for one hour. Following wash with ACES Buffer, the TMB single solution (ZYMED) was added to each well. The chromogenic reaction in the solution of each well was terminated by adding sulfuric acid. Then, the developed color was assessed by measuring absorbance at 450 nm.

The measurement result is shown in FIG. 29. In the case of GC-IgG1, the absorbance of GC-IgG1 did not change according to the calcium ion concentration. By contrast, as for CSCM-01_005, CSCM-01_009, CSCM-01_015, and CSCM-01_023, the absorbance was considerably lower at a calcium ion concentration of 3 µM (low calcium ion concentration) than at 1.2 mM (high calcium ion concentration). The result described above demonstrates that CSCM-01_005, CSCM-01_009, CSCM-01_015, and CSCM-01_023 have the property that their antigen binding varies according to the calcium ion concentration. This demonstrates that calcium-dependent antibodies against human glypican 3 are also obtainable. As compared to typical anti-human glypican 3 antibodies, it is considered that the calcium-dependent anti-human glypican 3 antibodies can accelerate elimination of human glypican 3, similarly to the case with human IL-6R, human CD4, or human IgA described in Examples above. Moreover, it is considered that the elimination of human glypican 3 can be further accelerated by enhancing the FcRn binding of the calcium-dependent anti-human glypican 3 antibodies at pH 7.4.

Example 23

Antibodies that Bind to IgE in a Calcium-Dependent Manner (23-1) Preparation of Biotinylated Human IgE Human IgE was prepared as an antigen by the following procedure. An animal cell expression vector inserted with a DNA sequence encoding IgE-H (SEQ ID NO: 104, a sequence for biotinylation is linked at the C terminus) and L(WT) (SEQ ID NO: 14) was prepared. Using the expression vector and FreeStyle293 (Invitrogen), the full-length human IgE protein to which a sequence for biotinylation is linked to the C terminus was expressed in the culture supernatant. From the isolated culture supernatant, a biotinylated human IgE was prepared by performing ion-exchange chromatography, avidin-affinity purification, and gel filtration chromatography purification.

(23-2) Expression and Purification of Antibodies that Bind to Human IgE

GEB0100 (heavy chain, SEQ ID NO: 105; light chain, SEQ ID NO: 106), GEB0220 (heavy chain, SEQ ID NO: 107; light chain, SEQ ID NO: 108), GEB0230 (heavy chain, SEQ ID NO: 109; light chain, SEQ ID NO: 110), and Xolair (heavy chain, SEQ ID NO: 111; light chain, SEQ ID NO: 112) were antibodies that bind to human IgE. GEB0100 (heavy chain, SEQ ID NO: 105; light chain, SEQ ID NO: 106), GEB0220 (heavy chain, SEQ ID NO: 107; light chain, SEQ ID NO: 108), GEB0230 (heavy chain, SEQ ID NO: 109; light chain, SEQ ID NO: 110), and Xolair (generic name: Omalizumab) (heavy chain, SEQ ID NO: 111; light chain, SEQ ID NO: 112) were each inserted into animal expression plasmids by a method known to those skilled in the art. Antibodies were expressed by the following procedure. The constructed plasmids were introduced into cells of human fetal kidney cell-derived FreeStyle 293-F (Invitrogen) by a lipofection method. The cells were cultured for four to seven days in a $CO_2$ incubator (37° C., 8% $CO_2$, 90 rpm). From the prepared culture supernatants, antibodies were purified using the rProtein A Sepharose™ Fast Flow (Amersham Biosciences) by a method known to those skilled in the art.

The concentrations of purified antibodies were determined by measuring absorbance at 280 nm using a spectrophotometer. Antibody concentrations were calculated from the determined values using an extinction coefficient calculated by the PACE method (Protein Science (1995) 4: 2411-2423).

(23-3) Assessment of Isolated Antibodies for Ca-Dependent Human IgE-Binding Activity Isolated antibodies were assessed for their Ca-dependent binding activity to human IgE by ELISA. Specifically, 40 μl of 1 μg/ml Goat anti-rabbit IgG-Fc polyclonal antibody (Bethyl laboratory; A120-111A) or 1 μg/ml Goat anti-human IgG-Fc polyclonal antibody (ICN biomedicals; 55071) was added to the NUNC Immuno 384-well Plate MaxiSorp (Thermo fisher scientific; 464718). After one hour of incubation at room temperature, the solution was removed and 50 μl of Blocking One Reagent (Nacalai Tesque; 03953-95) diluted to 20% was added. After one hour of incubation at room temperature, the solution was removed and 40 μl of purified antibodies diluted with Tris buffer containing 1.2 mM calcium chloride were added. After overnight incubation at 4° C., the plate was washed three times with 80 μl of Tris buffer containing 1.2 mM calcium chloride and 0.05% (w/v) Tween-20, and 40 μl of the biotinylated human IgE (prepared as described in (23-1)) diluted to 500 ng/ml with a Tris buffer containing 1.2 mM calcium chloride was added. After one hour of incubation at room temperature, the plate was washed three times with 80 μl of a Tris buffer containing 1.2 mM calcium chloride and 0.05% (w/v) Tween-20. 80 μl of an ACES buffer (pH 7.4) containing 2 mM or 3 μM calcium chloride was added and then immediately removed. Again, 80 μl of an ACES buffer (pH 7.4) containing 2 mM or 3 μM calcium chloride was added to the plate. After one hour of incubation at 37° C., the plate was washed three times with 80 μl of a Tris buffer containing 1.2 mM calcium chloride and 0.05% (w/v) Tween-20, and 40 μl of HRP-labeled streptavidin (Thermo fisher scientific; 21132) diluted to 25 ng/ml with a Tris buffer containing 1.2 mM calcium chloride was added. After one hour of incubation at room temperature, the plate was washed three times with 80 μl of a Tris buffer containing 1.2 mM calcium chloride and 0.05% (w/v) Tween-20. Then, 40 μl of a chromogenic substrate (KPL; 50-66-06: ABTS peroxidase substrate system 1 component) is added. Following 15 to 30 minutes of incubation at room temperature, the absorbance at 405 nm was measured (Molecular devices; SpectraMax Plus384).

The measurement result is shown in FIG. 30. In the case of Xolair, the absorbance did not change according to the calcium ion concentration. By contrast, as for GEB0100, GEB0220, and GEB0230, the absorbance was considerably lower at a calcium ion concentration of 3 μM (low calcium ion concentration) than at 1.2 mM (high calcium ion concentration). The result described above demonstrates that GEB0100, GEB0220, and GEB0230 have the property that their antigen binding varies according to the calcium ion concentration. This indicates that calcium-dependent antibodies against human IgE are also obtainable. As compared to typical anti-human IgE antibodies such as Xolair, it is considered that the calcium-dependent anti-human IgE antibodies can accelerate the elimination of human IgE, similarly to the case with human IL-6R, human CD4, or human IgA described in Examples above. Moreover, it is considered that the elimination of human IgE can be further accelerated by enhancing the FcRn binding of the calcium-dependent anti-human IgE antibodies at pH 7.4.

Reference Example 1

Preparation of Soluble Human IL-6 Receptor (hsIL-6R)

Recombinant human IL-6 receptor as an antigen was prepared as follows. A CHO cell line constitutively expressing soluble human IL-6 receptor (hereinafter referred to as hsIL-6R) having the amino acid sequence of positions 1 to 357 from the N terminus as reported in J. Immunol. 152: 4958-4968 (1994) was established by a method known to those skilled in the art. The cells were cultured to express hsIL-6R. The hsIL-6R was purified from the culture supernatant by two steps: Blue Sepharose 6 FF column chromatography and gel filtration column chromatography. A fraction eluted as the main peak in the final stage was prepared as the final purification product.

Reference Example 2

Preparation of Human FcRn

FcRn is a complex of FcRn and β2-microglobulin. Oligo-DNA primers were prepared based on the published human FcRn gene sequence (J Exp Med. 1994 Dec. 1; 180(6): 2377-81). A DNA fragment encoding the whole gene was prepared by PCR using human cDNA (Human Placenta Marathon-Ready cDNA, Clontech) as a template and the prepared primers. Using the obtained DNA fragment as a template, a DNA fragment encoding the extracellular domain containing the signal region (Met1-Leu290) was amplified by PCR, and inserted into a mammalian cell expression vector. Likewise, oligo-DNA primers were prepared based on the published human β2-microglobulin gene sequence (Proc. Natl. Acad. Sci. U.S.A. 99 (26): 16899-16903 (2002)). A DNA fragment encoding the whole gene was prepared by PCR using human cDNA (Human Placenta Marathon-Ready cDNA, Clontech) as a template and the prepared primers. Using the obtained DNA fragment as a template, a DNA fragment encoding the whole protein containing a signal region (Met1-Met119) was amplified by PCR and inserted into a mammalian cell expression vector.

Soluble human FcRn was expressed by the following procedure. The plasmids constructed for expressing human FcRn (SEQ ID NO: 17) and β2-microglobulin (SEQ ID NO: 18) were introduced into cells of the human embryonic kidney cancer-derived cell line HEK293H (Invitrogen) by the lipofection method using PEI (Polyscience). The resulting culture supernatant was collected, and FcRn was purified using IgG Sepharose 6 Fast Flow (Amersham Biosciences), followed by further purification using HiTrap Q HP (GE Healthcare) (J Immunol. 2002 Nov. 1; 169(9): 5171-80).

Reference Example 3

Studies to Improve the Antigen Elimination-Accelerating Effect of pH-Dependent Antigen-Binding Antibodies (In Vivo Test)

(3-1) Preparation of pH-Dependent Human IL-6 Receptor-Binding Antibodies that Bind to FcRn Under Neutral Condition Mutations were introduced into Fv4-IgG1 comprising VH3-IgG1 (SEQ ID NO: 19) and VL3-CK (SEQ ID NO: 20) to augment the FcRn binding under a neutral condition (pH 7.4). Specifically, VH3-IgG1-v1 (SEQ ID NO: 21) was prepared from the heavy chain constant region of IgG1 by substituting Tyr for Met at position 252, Thr for Ser at position 254, and Glu for Thr at position 256 in EU numbering, while VH3-IgG1-v2 (SEQ ID NO: 22) was constructed from the heavy chain constant region of IgG1 by substituting Trp for Asn at position 434 in EU numbering. The mutants were constructed by amino acid substitution using QuikChange Site-Directed Mutagenesis Kit (Stratagene) or In-Fusion HD Cloning Kit (Clontech) according to the method described in the provided manual. The prepared plasmid fragments were inserted into animal cell expression vectors to construct expression vectors for the H chain and L chain of interest. The nucleotide sequences of the constructed expression vectors were determined by a method known to those skilled in the art.

H54/L28-IgG1 comprising H54 (SEQ ID NO: 5) and L28 (SEQ ID NO: 6), Fv4-IgG1 comprising VH3-IgG1 (SEQ ID NO: 19) and VL3-CK (SEQ ID NO: 20), Fv4-IgG1-v1 comprising VH3-IgG1-v1 (SEQ ID NO: 21) and VL3-CK (SEQ ID NO: 20), and Fv4-IgG1-v2 comprising VH3-IgG1-v2 (SEQ ID NO: 22) and VL3-CK (SEQ ID NO: 20) were expressed and purified by the method described below. Antibodies were expressed by FreestyleHEK293 (Invitrogen) as described by the protocol provided by the manufacture or HEK293H cell line (Invitrogen). Human embryonic kidney cancer-derived HEK293H cell line (Invitrogen) was suspended in DMEM (Invitrogen) supplemented with 10% Fetal Bovine Serum (Invitrogen). The cells were plated at 10 ml per dish in dishes for adherent cells (10 cm in diameter; CORNING) at a cell density of 5 to 6×10$^5$ cells/ml and cultured in a $CO_2$ incubator (37° C., 5% $CO_2$) for one whole day and night. Then, the medium was removed by aspiration, and 6.9 ml of CHO-S-SFM-II medium (Invitrogen) was added. The prepared plasmid was introduced into the cells by the lipofection method. The resulting culture supernatants were collected, centrifuged (approximately 2,000×g, 5 min, room temperature) to remove cells, and sterilized by filtering through 0.22-μm filter MILLEX (registered trademark)-GV (Millipore) to obtain the supernatants. Antibodies were purified from the obtained culture supernatants by a method known to those skilled in the art using rProtein A Sepharose™ Fast Flow (Amersham Biosciences). To determine the concentration of the purified antibody, absorbance was measured at 280 nm using a spectrophotometer. Antibody concentrations were calculated from the determined values using an absorbance coefficient calculated by the method described in Protein Science (1995) 4: 2411-2423.

(3-2) In Vivo Test Using Human FcRn Transgenic Mice and Normal Mice

The in vivo kinetics of hsIL-6R (soluble human IL-6 receptor: prepared as described in Reference Example 1) and anti-human IL-6 receptor antibody was assessed after administering hsIL-6R alone or hsIL-6R and anti-human IL-6 receptor antibody in combination to human FcRn transgenic mice (B6.mFcRn −/−.hFcRn Tg line 276+/+ mouse, Jackson Laboratories; Methods Mol Biol. (2010) 602: 93-104) and normal mice (C57BL/6J mouse; Charles River Japan). An hsIL-6R solution (5 μg/ml) or a solution of mixture containing hsIL-6R and anti-human IL-6 receptor antibody (5 μg/ml and 0.1 mg/ml, respectively) was administered once at a dose of 10 ml/kg into the caudal vein. In this case, the anti-human IL-6 receptor antibody is present in excess over hsIL-6R, and therefore almost every hsIL-6R is assumed to be bound to the antibody. Blood was collected 15 minutes, seven hours, one day, two days, three days, four days, seven days, 14 days, 21 days, and 28 days after administration. The collected blood was immediately centrifuged at 15,000 rpm and 4° C. for 15 minutes to separate the plasma. The separated plasma was stored in a refrigerator at or below −20° C. before assay. The anti-human IL-6 receptor antibodies used are: above-described H54/L28-IgG1, Fv4-IgG1, and Fv4-IgG1-v2 for human FcRn transgenic mice, and above-described H54/L28-IgG1, Fv4-IgG1, Fv4-IgG1-v1, and Fv4-IgG1-v2 for normal mice.

(3-3) Measurement of Anti-Human IL-6 Receptor Antibody Plasma Concentration by ELISA The concentration of anti-human IL-6 receptor antibody in mouse plasma was measured by ELISA. Anti-human IgG (γ chain specific) F(ab')2 antibody fragment (Sigma) was dispensed onto a Nunc-ImmunoPlate MaxiSorp (Nalge Nunc International) and allowed to stand overnight at 4° C. to prepare anti-human IgG-immobilized plates. Calibration curve samples having plasma concentrations of 0.8, 0.4, 0.2, 0.1, 0.05, 0.025, and 0.0125 μg/ml, and mouse plasma samples diluted 100-fold or more were prepared. 200 μL of 20 ng/ml hsIL-6R was added to 100 μL of the calibration curve samples and plasma samples, and then the samples were allowed to stand for one hour at room temperature. Subsequently, the samples were dispensed into the anti-human IgG-immobilized plates, and allowed to stand for one hour at room temperature. Then, Biotinylated Anti-Human IL-6R Antibody (R&D) was added to react for one hour at room temperature. Subsequently, Streptavidin-PolyHRP80 (Stereospecific Detection Technologies) was added to react for one hour at room temperature, and chromogenic reaction was carried out using TMP One Component HRP Microwell Substrate (BioFX Laboratories) as a substrate. After stopping the reaction with 1N sulfuric acid (Showa Chemical), the absorbance at 450 nm was measured by a microplate reader. The concentration in mouse plasma was calculated from the absorbance of the calibration curve using the analytical software SOFTmax PRO (Molecular Devices). The time course of plasma concentration after intravenous administration as measured by this method is shown in FIG. 31 for human FcRn transgenic mice and FIG. 33 for normal mice.

(3-4) Measurement of hsIL-6R Plasma Concentration by Electrochemiluminescence Assay The concentration of hsIL-6R in mouse plasma was measured by electrochemiluminescence. hsIL-6R calibration curve samples adjusted to concentrations of 2,000, 1,000, 500, 250, 125, 62.5, and 31.25 pg/ml, and mouse plasma samples diluted 50-fold or more were prepared. The samples were mixed with a solution of Monoclonal Anti-human IL-6R Antibody (R&D) ruthenium-labeled with Sulfo-Tag NHS Ester (Meso Scale Discovery), Biotinylated Anti-human IL-6R Antibody (R&D), and WT-IgG1, and then allowed to react overnight at 37° C. The final concentration of WT-IgG1 as an anti-human IL-6 receptor antibody, comprising H (WT) (SEQ ID NO: 13) and L (WT) (SEQ ID NO: 14), was 333 μg/ml, which is in excess of the concentration of anti-human IL-6 receptor antibody contained in the samples, for the purpose of binding nearly all of the hsIL-6R molecules in the samples to WT-IgG1. Subsequently, the samples were dispensed into an MA400 PR Streptavidin Plate (Meso Scale Discovery), and allowed to react for one hour at room temperature, and washing was performed. Immediately after Read Buffer T (×4) (Meso Scale Discovery) was dispensed, the measurement was performed by the Sector PR 400 Reader (Meso Scale Discovery). The hsIL-6R concentration was calculated based on the response of the calibration curve using the analytical software SOFTmax PRO (Molecular Devices). The time course of plasma hsIL-6R concentration after intravenous administration as measured by this method is shown in FIG. 32 for human FcRn transgenic mice and FIG. 34 for normal mice.

(3-5) Determination of Free hsIL-6R Concentration in Plasma by Electrochemiluminescence Assay To assess the degree of neutralization of soluble human IL-6 receptor in plasma, the concentration of soluble human IL-6 receptor free of (non-neutralized by) anti-human IL-6 receptor antibody (free hsIL-6R concentration) in mouse plasma was determined by electrochemiluminescence assay. All IgG-type antibodies (mouse IgG, anti-human IL-6 receptor antibody, and anti-human IL-6 receptor antibody-soluble human IL-6 receptor complex) in plasma were adsorbed onto protein A by adding 12 µl each of hsIL-6R standard samples prepared at 10,000, 5,000, 2,500, 1,250, 625, 312.5, or 156.25 pg/ml and mouse plasma samples onto an appropriate amount of rProtein A Sepharose Fast Flow (GE Healthcare) resin dried on 0.22-m filter cup (Millipore). Then, the solution in a cup was spun down using a high-speed centrifuge to collect the solution that passed through. The passed-through solution does not contain Protein A-bound anti-human IL-6 receptor antibody-soluble human IL-6 receptor complex. Thus, the concentration of free hsIL-6R in plasma can be determined by measuring the concentration of hsIL-6R in the passed-through solution. Then, the passed-through solution was mixed with a monoclonal anti-human IL-6R antibody (R&D) ruthenium-labeled with SULFO-TAG NHS Ester (Meso Scale Discovery) and a biotinylated anti-human IL-6R antibody (R&D). The resulting mixture was incubated at room temperature for one hour, and then aliquoted to MA400 PR Streptavidin Plate (Meso Scale Discovery). After another hour of incubation at room temperature, the plate was washed and Read Buffer T (×4) (Meso Scale Discovery) was aliquoted thereto. Immediately, the plate was measured in SECTOR PR 400 reader (Meso Scale Discovery). The hsIL-6R concentration was calculated based on the response in the standard curve using the analysis software SOFTmax PRO (Molecular Devices). A time course of free hsIL-6R concentration in the plasma of normal mice after intravenous administration determined by the above-described method is shown in FIG. 35.

(3-6) Effect of pH-Dependent Binding to Human IL-6 Receptor

H54/L28-IgG1 and Fv4-IgG1 which binds to human IL-6 receptor in a pH-dependent manner were tested in vivo, and the results were compared between them. As shown in FIGS. 31 and 33, the antibody retention in plasma was comparable. Meanwhile, as shown in FIGS. 32 and 34, hsIL-6R simultaneously administered with Fv4-IgG1 which binds to human IL-6 receptor in a pH-dependent manner was found to accelerate the elimination of hsIL-6R as compared to hsIL-6R simultaneously administered with H54/L28-IgG1. The above tendency was observed in both human FcRn transgenic and normal mice; thus, it was demonstrated that by conferring a pH-dependent human IL-6 receptor-binding ability, the plasma hsIL-6R concentration four days after administration could be decreased by about 17 and 34 times, respectively.

(3-7) Effect of FcRn Binding Under Neutral Condition (pH 7.4)

Natural human IgG1 has been reported to hardly bind to (have extremely low affinity for) human FcRn under a neutral condition (pH 7.4). The human FcRn binding under a neutral condition (pH 7.4) was reported to be augmented by substituting Trp for Asn at position 434 (EU numbering) in natural human IgG1 (J Immunol. (2009) 182 (12): 7663-71). Fv4-IgG1-v2 which results from introducing the above amino acid substitution into Fv4-IgG1 was tested by an in vivo test using human FcRn transgenic mice. The test result was compared to that of Fv4-IgG1. As shown in FIG. 31, the antibody plasma retention was comparable between the two. Meanwhile, as shown in FIG. 32, hsIL-6R simultaneously administered with Fv4-IgG1-v2 that exhibits enhanced human FcRn binding under a neutral condition (pH 7.4) was found to be eliminated faster as compared to hsIL-6R simultaneously administered with Fv4-IgG1. Thus, it was demonstrated that by conferring the ability to bind to human FcRn under a neutral condition (pH 7.4), the plasma concentration of hsIL-6R four days after administration could be reduced by about four times.

Based on the homology between human FcRn and mouse FcRn, the substitution of Trp for Asn at position 434 in EU numbering is assumed to augment the binding to mouse FcRn under a neutral condition (pH 7.4). Meanwhile, the binding to mouse FcRn under a neutral condition (pH 7.4) has been reported to be augmented by substituting Tyr for Met at position 252, Thr for Ser at position 254, and Glu for Thr at position 256 in EU numbering (J Immunol. (2002) 169(9): 5171-80). Fv4-IgG1-v1 and Fv4-IgG1-v2 which result from introducing the above-described amino acid substitutions into Fv4-IgG1 were tested in vivo using normal mice. The test results were compared to that of Fv4-IgG1. As shown in FIG. 33, the plasma retention times of Fv4-IgG1-v1 and Fv4-IgG1-v2 which had also been improved to increase the binding to mouse FcRn under a neutral condition (pH 7.4) were slightly shortened (the neutralizing antibody concentrations in plasma one day after administration were reduced by about 1.5 and 1.9 times, respectively) as compared to Fv4-IgG1.

As shown in FIG. 34, hsIL-6R simultaneously administered with Fv4-IgG1-v1 or Fv4-IgG1-v2 which had been improved to increase the binding to mouse FcRn under a neutral condition (pH 7.4) was demonstrated to be eliminated markedly faster as compared to hsIL-6R simultaneously administered with Fv4-IgG1. Fv4-IgG1-v1 and Fv4-IgG1-v2 reduced the plasma hsIL-6R concentrations one day after administration by about 32 and 80 times, respectively. Thus, it was revealed that the plasma concentration could be reduced by conferring mouse FcRn-binding ability under a neutral condition (pH 7.4). As described above, by conferring the mouse FcRn-binding ability under a neutral condition (pH 7.4), the plasma antibody concentration was slightly reduced; however, the effect of reducing the plasma hsIL-6R concentration, which largely exceeded the decrease in antibody concentration, was produced. Furthermore, hsIL-6R simultaneously administered with Fv4-IgG1-v1 or Fv4-IgG1-v2 was found to be eliminated faster even when compared to the group administered with hsIL-6R alone. As shown in FIG. 34, it was demonstrated that hsIL-6R simultaneously administered with Fv4-IgG1-v1 or Fv4-IgG1-v2 could reduce the plasma hsIL-6R concentration one day after administration by about 4 or 11 times, respectively, as compared to hsIL-6R alone. Specifically, this means that the elimination of soluble IL-6 receptor could be accelerated by administering the antibody that binds to soluble IL-6 receptor in a pH-dependent manner and which is conferred with mouse FcRn-binding ability under a neutral condition (pH 7.4). Specifically, the plasma antigen concentration can be reduced in vivo by administering such an antibody to the body.

As shown in FIG. 35, free hsIL-6R was in a detectable concentration range for seven days after administration of H54/L28-IgG1, while free hsIL-6R was undetectable after one day following administration of Fv4-IgG1. On the other hand, free hsIL-6R was not detectable after seven hours following administration of Fv4-IgG1-v1 or Fv4-IgG1-v2. Specifically, the free hsIL-6R concentration was lower in the presence of Fv4-IgG1 that binds to hsIL-6R in a pH-dependent manner as compared to H54/L28-IgG1, suggesting that a strong hsIL-6R-neutralizing effect was produced by conferring the pH-dependent hsIL-6R-binding ability. Furthermore, the free hsIL-6R concentration was much lower in the presence of Fv4-IgG1-v1 or Fv4-IgG1-v2, both of which were modified from Fv4-IgG1 to increase the FcRn-binding ability at pH 7.4. This demonstrates that a much stronger hsIL-6R-neutralizing effect can be produced by increasing the FcRn-binding ability at pH 7.4.

When administered, an ordinary neutralizing antibody such as H54/L28-IgG1 reduces the clearance of a binding antigen, resulting in prolonged antigen plasma retention. It is not preferred that administered antibodies prolong the plasma retention of an antigen whose action is intended to be neutralized by the antibodies. The antigen plasma retention can be shortened by conferring the pH dependency to antigen binding (the antibody binds under neutral conditions but is dissociated under acidic conditions). In the present invention, the antigen retention time in plasma could be further shortened by additionally conferring human FcRn-binding ability under a neutral condition (pH 7.4). Furthermore, it was demonstrated that as compared to clearance of antigen alone, antigen clearance could be increased by administering an antibody that binds to an antigen in a pH dependent manner, and which is conferred with FcRn-binding ability under a neutral condition (pH 7.4). To date, there is no method available for increasing antigen clearance by antibody administration relative to clearance of antigen alone. Thus, the methods established as described in this EXAMPLE are very useful as a method for eliminating antigens from plasma by administering antibodies. Furthermore, the present inventors discovered for the first time the advantage of increasing the FcRn-binding ability under a neutral condition (pH 7.4). Furthermore, both v4-IgG1-v1 and Fv4-IgG1-v2 which have different amino acid substitutions that increase the FcRn-binding ability under a neutral condition (pH 7.4) produced comparable effects. This suggests that regardless of the type of amino acid substitution, every amino acid substitution that increases the human FcRn-binding ability under a neutral condition (pH 7.4) potentially has an effect of accelerating antigen elimination. Specifically, antibody molecules that eliminate antigens from plasma when administered can be produced using the following amino acid substitutions alone or in combination:

an amino acid substitution of Ile for Pro at position 257 and an amino acid substitution of Ile for Gln at position 311 in EU numbering, both of which have been reported in J Biol Chem. 2007, 282(3): 1709-17; an amino acid substitution of Ala, Tyr, or Trp for Asn at position 434, an amino acid substitution of Tyr for Met at position 252, an amino acid substitution of Gln for Thr at position 307, an amino acid substitution of Pro for Val at position 308, an amino acid substitution of Gln for Thr at position 250, an amino acid substitution of Leu for Met at position 428, an amino acid substitution of Ala for Glu at position 380, an amino acid substitution of Val for Ala at position 378, an amino acid substitution of Ile for Tyr at position 436 in EU numbering, all of which have been reported in J Immunol. (2009) 182(12): 7663-71; an amino acid substitution of Tyr for Met at position 252, an amino acid substitution of Thr for Ser at position 254, an amino acid substitution of Glu for Thr at position 256 in EU numbering, all of which have been reported in J Biol Chem. 2006 Aug. 18, 281(33): 23514-24; an amino acid substitution of Lys for His at position 433, an amino acid substitution of Phe for Asn at position 434, and an amino acid substitution of His for Tyr at position 436 in EU numbering, all of which have been reported in Nat Biotechnol. 2005 Oct. 23(10): 1283-8; and the like.

Reference Example 4

Assessment of Human FcRn-Binding Activity

For the Biacore-based assay system for testing the interaction between antibody and FcRn, a system that immobilizes antibody on a sensor chip and uses human FcRn as an analyte is reported in J Immunol. (2009) 182(12): 7663-71. For this purpose, human FcRn was prepared as described in Reference Example 2. Fv4-IgG1, Fv4-IgG1-v1, and Fv4-IgG1-v2 were assessed for the human FcRn-binding activity (dissociation constant (KD)) at pH 6.0 and pH 7.4 by using the above-described system. The antibodies were tested as a test substance after direct immobilization onto Series S Sensor Chip CM5. Using an amino-coupling kit according to the supplier's instruction manual, the antibodies were immobilized onto Sensor Chip so as to secure an immobilization amount of 500 RU. The running buffer used was 50 mmol/L Na-phosphate/150 mmol/L NaCl containing 0.05% (v/v %) Surfactant P20 (pH 6.0).

With the prepared sensor chips, assay was carried out using as a running buffer, 50 mmol/L Na-phosphate/150 mmol/L NaCl containing 0.05% Surfactant P20 (pH 6.0) or 50 mmol/L Na-phosphate/150 mmol/L NaCl containing 0.05% Surfactant P20 (pH 7.4). Assays were carried out exclusively at 25° C. The diluted human FcRn solutions and running buffer as a reference solution were injected at a flow rate of 5 µl/min for ten minutes to allow for human FcRn to interact with the antibody on the chip. Next, the running buffer was injected at a flow rate of 5 µl/min for one minute to monitor the dissociation of FcRn. Then, the sensor chip was regenerated by two rounds of injection of 20 mmol/L Tris-HCl/150 mmol/L NaCl (pH 8.1) at a flow rate of 30 µl/min for 15 seconds.

The assay results were analyzed using Biacore™ T100 Evaluation Software (Ver. 2.0.1). By a steady-state affinity method, the dissociation constant ($K_D$) was calculated from the assay results at six different FcRn concentrations. The results on the human FcRn-binding activities (dissociation constants (KD)) of Fv4-IgG1, Fv4-IgG1-v1, and Fv4-IgG1-v2 at pH 6.0 and pH 7.4 are shown in Table 24 below.

TABLE 24

|  | KD (μM) | |
| --- | --- | --- |
|  | pH 6.0 | pH 7.4 |
| Fv4-IgG1 | 1.99 | NA |
| Fv4-IgG1-v1 | 0.32 | 36.55 |
| Fv4-IgG1-v2 | 0.11 | 11.03 |

At pH 7.4, the binding of human FcRn to Fv4-IgG1 was too weak to determine the KD value (NA). Meanwhile, Fv4-IgG1-v1 and Fv4-IgG1-v2 were observed to bind to human FcRn at pH 7.4, and the KD values were determined to be 36.55 and 11.03 μM, respectively. The KD values for human FcRn at pH 6.0 were determined to be 1.99, 0.32, and 0.11 μM. As shown in FIG. 31, when compared to Fv4-IgG1, Fv4-IgG1-v2 accelerated the elimination of hsIL-6R in human FcRn transgenic mice. Thus, antigen elimination can be predicted to be accelerated by augmenting the human FcRn binding at pH 7.4 at least to be stronger than 11.03 μM by alteration of human IgG1. Meanwhile, as described in J Immunol. (2002) 169(9): 5171-80, human IgG1 binds about ten times more strongly to mouse FcRn than human FcRn. For this reason, Fv4-IgG1-v1 and Fv4-IgG1-v2 are also predicted to bind about ten times more strongly to mouse FcRn than human FcR at pH 7.4. Acceleration of the hsIL-6R elimination by Fv4-IgG1-v1 or Fv4-IgG1-v2 in normal mice shown in FIG. 34 is more significant than acceleration of the elimination by Fv4-IgG1-v2 in human FcRn transgenic mice shown in FIG. 32. This suggests that the degree of acceleration of hsIL-6R elimination is increased according to the strength of FcRn binding at pH 7.4.

Reference Example 5

Preparation of pH-Dependent Human IL-6 Receptor-Binding Antibodies with Enhanced Human FcRn Binding Under Neutral Condition (5-1) Preparation of Heavy Chain Constant Region Mutants of Fv4-12G1

Various alterations to augment the human FcRn binding under a neutral condition were introduced into Fv4-IgG1 to further enhance the antigen elimination effect of the pH-dependent human IL-6 receptor-binding antibody in human FcRn transgenic mice. Specifically, the amino acid alterations shown in Tables 25-1 and 25-2 were introduced into the heavy chain constant region of Fv4-IgG1 to produce various mutants (amino acid numbers of the mutation sites are presented according to EU numbering). The amino acid substitutions were introduced by methods known to those skilled in the art as described in Reference Example 3.

TABLE 25-1

| VARIANT NAME | KD (M) | AMINO ACID ALTERATION |
|---|---|---|
| IgG1 | ND | NONE |
| IgG1-v1 | 3.2E−06 | M252Y/S254T/T256E |
| IgG1-v2 | 8.1E−07 | N434W |
| IgG1-F3 | 2.5E−06 | N434Y |
| IgG1-F4 | 5.8E−06 | N434S |
| IgG1-F5 | 6.8E−06 | N434A |
| IgG1-F7 | 5.6E−06 | M252Y |
| IgG1-F8 | 4.2E−06 | M252W |
| IgG1-F9 | 1.4E−07 | M252Y/S254T/T256E/N434Y |
| IgG1-F10 | 6.9E−08 | M252Y/S254T/T256E/N434W |
| IgG1-F11 | 3.1E−07 | M252Y/N434Y |

TABLE 25-1-continued

| VARIANT NAME | KD (M) | AMINO ACID ALTERATION |
|---|---|---|
| IgG1-F12 | 1.7E−07 | M252Y/N434W |
| IgG1-F13 | 3.2E−07 | M252W/N434Y |
| IgG1-F14 | 1.8E−07 | M252W/N434W |
| IgG1-F19 | 4.6E−07 | P257L/N434Y |
| IgG1-F20 | 4.6E−07 | V308F/N434Y |
| IgG1-F21 | 3.0E−08 | M252Y/V308P/N434Y |
| IgG1-F22 | 2.0E−06 | M428L/N434S |
| IgG1-F25 | 9.2E−09 | M252Y/S254T/T256E/V308P/N434W |
| IgG1-F26 | 1.0E−06 | I332V |
| IgG1-F27 | 7.4E−06 | G237M |
| IgG1-F29 | 1.4E−06 | I332V/N434Y |
| IgG1-F31 | 2.8E−06 | G237M/V308F |
| IgG1-F32 | 8.0E−07 | S254T/N434W |
| IgG1-F33 | 2.3E−06 | S254T/N434Y |
| IgG1-F34 | 2.8E−07 | T256E/N434W |
| IgG1-F35 | 8.4E−07 | T256E/N434Y |
| IgG1-F36 | 3.6E−07 | S254T/T256E/N434W |
| IgG1-F37 | 1.1E−06 | S254T/T256E/N434Y |
| IgG1-F38 | 1.0E−07 | M252Y/S254T/N434W |
| IgG1-F39 | 3.0E−07 | M252Y/S254T/N434Y |
| IgG1-F40 | 8.2E−08 | M252Y/T256E/N434W |
| IgG1-F41 | 1.5E−07 | M252Y/T256E/N434Y |
| IgG1-F42 | 1.0E−06 | M252Y/S254T/T256E/N434A |
| IgG1-F43 | 1.7E−06 | M252Y/N434A |
| IgG1-F44 | 1.1E−06 | M252W/N434A |
| IgG1-F47 | 2.4E−07 | M252Y/T256Q/N434W |
| IgG1-F48 | 3.2E−07 | M252Y/T256Q/N434Y |
| IgG1-F49 | 5.1E−07 | M252F/T256D/N434W |
| IgG1-F50 | 1.2E−06 | M252F/T256D/N434Y |
| IgG1-F51 | 8.1E−06 | N434F/Y436H |
| IgG1-F52 | 3.1E−06 | H433K/N434F/Y436H |
| IgG1-F53 | 1.0E−06 | I332V/N434W |
| IgG1-F54 | 8.4E−08 | V308P/N434W |
| IgG1-F56 | 9.4E−07 | I332V/M428L/N434Y |
| IgG1-F57 | 1.1E−05 | G385D/Q386P/N389S |
| IgG1-F58 | 7.7E−07 | G385D/Q386P/N389S/N434W |
| IgG1-F59 | 2.4E−06 | G385D/Q386P/N389S/N434Y |
| IgG1-F60 | 1.1E−05 | G385H |
| IgG1-F61 | 9.7E−07 | G385H/N434W |
| IgG1-F62 | 1.9E−06 | G385H/N434Y |
| IgG1-F63 | 2.5E−06 | N434F |
| IgG1-F64 | 5.3E−06 | N434H |

Table 25-2 is the continuation of Table 25-1.

TABLE 25-2

| | | |
|---|---|---|
| IgG1-F65 | 2.9E−07 | M252Y/S254T/T256E/N434F |
| IgG1-F66 | 4.3E−07 | M252Y/S254T/T256E/N434H |
| IgG1-F67 | 6.3E−07 | M252Y/N434F |
| IgG1-F68 | 9.3E−07 | M252Y/N434H |
| IgG1-F69 | 5.1E−07 | M428L/N434W |
| IgG1-F70 | 1.5E−06 | M428L/N434Y |
| IgG1-F71 | 8.3E−08 | M252Y/S254T/T256E/M428L/N434W |
| IgG1-F72 | 2.0E−07 | M252Y/S254T/T256E/M428L/N434Y |
| IgG1-F73 | 1.7E−07 | M252Y/M428L/N434W |
| IgG1-F74 | 4.6E−07 | M252Y/M428L/N434Y |
| IgG1-F75 | 1.4E−06 | M252Y/M428L/N434A |
| IgG1-F76 | 1.0E−06 | M252Y/S254T/T256E/M428L/N434A |
| IgG1-F77 | 9.9E−07 | T256E/M428L/N434Y |
| IgG1-F78 | 7.8E−07 | S254T/M428L/N434W |
| IgG1-F79 | 5.9E−06 | S254T/T256E/N434A |
| IgG1-F80 | 2.7E−06 | M252Y/T256Q/N434A |
| IgG1-F81 | 1.6E−06 | M252Y/T256E/N434A |
| IgG1-F82 | 1.1E−06 | T256Q/N434W |
| IgG1-F83 | 2.6E−06 | T256Q/N434Y |
| IgG1-F84 | 2.8E−07 | M252W/T256Q/N434W |
| IgG1-F85 | 5.5E−07 | M252W/T256Q/N434Y |
| IgG1-F86 | 1.5E−06 | S254T/T256Q/N434W |
| IgG1-F87 | 4.3E−06 | S254T/T256Q/N434Y |
| IgG1-F88 | 1.9E−07 | M252Y/S254T/T256Q/N434W |
| IgG1-F89 | 3.6E−07 | M252Y/S254T/T256Q/N434Y |
| IgG1-F90 | 1.9E−08 | M252Y/T256E/V308P/N434W |
| IgG1-F91 | 4.8E−08 | M252Y/V308P/M428L/N434Y |
| IgG1-F92 | 1.1E−08 | M252Y/S254T/T256E/V308P/M428L/N434W |
| IgG1-F93 | 7.4E−07 | M252W/M428L/N434W |

TABLE 25-2-continued

| IgG1-F94 | 3.7E-07 | P257L/M428L/N434Y |
| IgG1-F95 | 2.6E-07 | M252Y/S254T/T256E/M428L/N434F |
| IgG1-F99 | 6.2E-07 | M252Y/T256E/N434H |

The variants each comprising a prepared heavy chain and L (WT) (SEQ ID NO: 14) were expressed and purified by methods known to those skilled in the art as described in Reference Example 3.

(5-2) Assessment of Human FcRn Binding

The binding between antibody and human FcRn was kinetically analyzed using Biacore™ T100 (GE Healthcare). For this purpose, human FcRn was prepared as described in Reference Example 2. An appropriate amount of protein L (ACTIGEN) was immobilized onto Sensor chip CM4 (GE Healthcare) by the amino coupling method, and the chip was allowed to capture an antibody of interest. Then, diluted FcRn solutions and running buffer (as a reference solution) were injected to allow human FcRn to interact with the antibody captured on the sensor chip. The running buffer used comprised 50 mmol/L sodium phosphate, 150 mmol/L NaCl, and 0.05% (w/v) Tween®20 (polysorbate 20) (pH 7.0). FcRn was diluted using each buffer. The chip was regenerated using 10 mmol/L glycine-HCl (pH 1.5). Assays were carried out exclusively at 25° C. The association rate constant ka (1/Ms) and dissociation rate constant kd (1/s), both of which are kinetic parameters, were calculated based on the sensorgrams obtained in the assays, and KD (M) of each antibody for human FcRn was determined from these values. Each parameter was calculated using Biacore™ T100 Evaluation Software (GE Healthcare).

The assessment result on the human FcRn binding under a neutral condition (pH 7.0) by Biacore™ SPR analysis is shown in Tables 6-1 and 6-2. The KD of the natural IgG1 could not be calculated because it exhibited only very weak binding. Thus, the KD is indicated as ND in Table 6-1.

Reference Example 6

In Vivo Test of pH-Dependent Human IL-6 Receptor-Binding Antibodies with Enhanced Human FcRn Binding Under the Neutral Condition pH-dependent human IL-6 receptor-binding antibodies having human FcRn binding ability under a neutral condition were produced using the heavy chains prepared as described in Reference Example 4 to have human FcRn binding ability under a neutral condition. The antibodies were assessed for their in vivo antigen elimination effect. Specifically, the antibodies listed below were expressed and purified by methods known to those skilled in the art as described in Reference Example 3:

Fv4-IgG1 comprising VH3-IgG1 and VL3-CK;
Fv4-IgG1-v2 comprising VH3-IgG1-v2 and VL3-CK;
Fv4-IgG1-F14 comprising VH3-IgG1-F14 and VL3-CK;
Fv4-IgG1-F20 comprising VH3-IgG1-F20 and VL3-CK;
Fv4-IgG1-F21 comprising VH3-IgG1-F21 and VL3-CK;
Fv4-IgG1-F25 comprising VH3-IgG1-F25 and VL3-CK;
Fv4-IgG1-F29 comprising VH3-IgG1-F29 and VL3-CK;
Fv4-IgG1-F35 comprising VH3-IgG1-F35 and VL3-CK;
Fv4-IgG1-F48 comprising VH3-IgG1-F48 and VL3-CK;
Fv4-IgG1-F93 comprising VH3-IgG1-F93 and VL3-CK; and
Fv4-IgG1-F94 comprising VH3-IgG1-F94 and VL3-CK.

By the same methods described in Reference Example 3, the prepared pH-dependent human IL-6 receptor-binding antibodies were tested in vivo using human FcRn transgenic mice (B6.mFcRn −/−.hFcRn Tg line 276+/+ mouse, Jackson Laboratories; Methods Mol Biol. (2010) 602: 93-104).

A time course of plasma concentration of soluble human IL-6 receptor after intravenous administration to human FcRn transgenic mice is shown in FIG. 36. The test result showed that the plasma concentration of soluble human IL-6 receptor remained low over time in the presence of any of the pH-dependent human IL-6 receptor-binding antibodies with augmented human FcRn binding under neutral condition, as compared to in the presence of Fv4-IgG1 which has almost no human FcRn binding ability under neutral condition. Among others, antibodies that produced the remarkable effect include, for example, Fv4-IgG1-F14. The plasma concentration of soluble human IL-6 receptor simultaneously administered with Fv4-IgG1-F14 was demonstrated to be reduced by about 54 times one day after administration as compared to that of soluble human IL-6 receptor simultaneously administered with Fv4-IgG1. Furthermore, the plasma concentration of soluble human IL-6 receptor simultaneously administered with Fv4-IgG1-F21 was demonstrated to be reduced by about 24 times seven hours after administration as compared to that of soluble human IL-6 receptor simultaneously administered with Fv4-IgG1. In addition, the plasma concentration of soluble human IL-6 receptor simultaneously administered with Fv4-IgG1-F25 seven hours after administration was below the detection limit (1.56 ng/ml). Thus, Fv4-IgG1-F25 was expected to enable a remarkable reduction of 200 or more times in the concentration of soluble human IL-6 receptor relative to the concentration of soluble human IL-6 receptor simultaneously administered with Fv4-IgG1. The findings described above demonstrate that augmentation of the human FcRn binding of pH-dependent antigen-binding antibodies under a neutral condition is highly effective for enhancing the antigen elimination effect. Meanwhile, the type of amino acid alteration to augment human FcRn binding under neutral condition, which is introduced to enhance the antigen elimination effect, is not particularly limited; and such alterations include those shown in Tables 6-1 and 6-2. The antigen elimination effect can be predicted to be enhanced in vivo by any introduced alteration.

Furthermore, the plasma concentration of soluble human IL-6 receptor simultaneously administered with one of the four types of pH-dependent human IL-6 receptor-binding antibodies, Fv4-IgG1-F14, Fv4-IgG1-F21, Fv4-IgG1-F25, and Fv4-IgG1-F48, remained lower over time than that of soluble human IL-6 receptor administered alone. Such a pH-dependent human IL-6 receptor-binding antibody can be administered to the body where the plasma concentration of soluble human IL-6 receptor is kept constant (steady state) to keep the plasma concentration of soluble human IL-6 receptor lower than the steady-state concentration in plasma. Specifically, the in vivo antigen concentration in plasma can be reduced by administering such an antibody to the body.

Reference Example 7

Assessment for the Effectiveness of Low-Dose (0.01 mg/kg) Fv4-IgG1-F14

Fv4-IgG1-F14 prepared as described in Reference Example 6 was tested at a low dose (0.01 mg/kg) by the same in vivo test method as described in Reference Example 6. The result (shown in FIGS. 37 and 38) was compared to that described in Reference Example 6, which was obtained by administering Fv4-IgG1 and Fv4-IgG1-F14 at 1 mg/kg.

The result showed that although the plasma antibody concentration in the group administered with Fv4-IgG1-F14 at 0.01 mg/kg was about 100 times lower as compared to the group administered at 1 mg/kg (FIG. 38), the time courses of plasma concentration of soluble human IL-6 receptor were comparable to each other (FIG. 37). In addition, it was demonstrated that the plasma concentration of soluble human IL-6 receptor seven hours after administration in the group administered with Fv4-IgG1-F14 at 0.01 mg/kg was reduced by about three times as compared to that in the group administered with Fv4-IgG1 at 1 mg/kg. Furthermore, in the presence of Fv4-IgG1-F14, the plasma concentration of soluble human IL-6 receptor was lower over time in both groups administered at different doses when compared to the group administered with soluble human IL-6 receptor alone (FIG. 37).

The finding demonstrates that even when administered at a dose one-hundredth of that of Fv4-IgG1, Fv4-IgG1-F14 which results from modification of Fv4-IgG1 to augment human FcRn binding under a neutral condition effectively reduces the plasma concentration of soluble human IL-6 receptor. Specifically, it is predicted that antigens can be efficiently eliminated even at a lower dose when a pH-dependent antigen-binding antibody is modified to augment its FcRn-binding ability under neutral condition.

Reference Example 8

In Vivo Test Based on the Steady-State Model Using Normal Mice (8-1) Assessment of the Binding to Mouse FcRn Under Neutral Condition VH3/L (WT)-IgG1 comprising VH3-IgG1 (SEQ ID NO: 19) and L (WT) (SEQ ID NO: 14), VH3/L (WT)-IgG1-v2 comprising VH3-IgG1-v2 (SEQ ID NO: 22) and L (WT) (SEQ ID NO: 14), and VH3/L (WT)-IgG1-F20 comprising VH3-IgG1-F20 (SEQ ID NO: 23) and L (WT) (SEQ ID NO: 14), all of which were prepared as described in Reference Example 5, were assessed for mouse FcRn binding under a neutral condition (pH 7.4) by the method described below.

The binding between antibody and mouse FcRn was kinetically analyzed using Biacore™ T100 SPR analysis (GE Healthcare). An appropriate amount of protein L (ACTIGEN) was immobilized onto Sensor chip CM4 (GE Healthcare) by the amino coupling method, and the chip was allowed to capture an antibody of interest. Then, diluted FcRn solutions and running buffer (as a reference solution) were injected to allow mouse FcRn to interact with the antibody captured on the sensor chip. The running buffer used contains 50 mmol/L sodium phosphate, 150 mmol/L NaCl, and 0.05% (w/v) Tween®20 (polysorbate 20) (pH 7.4). FcRn was diluted using each buffer. The chip was regenerated using 10 mmol/L glycine-HCl (pH 1.5). Assays were carried out exclusively at 25° C. The association rate constant ka (1/Ms) and dissociation rate constant $k_d$ (1/s), both of which are kinetic parameters, were calculated based on the sensorgrams obtained in the assays, and the KD (M) of each antibody for mouse FcRn was determined from these values. Each parameter was calculated using Biacore™ T100 Evaluation Software (GE Healthcare).

The result is shown in Table 26 (affinity for mouse FcRn at pH 7.4). VH3/L (WT)-IgG1 (IgG1 in Table 26) whose constant region is of the natural IgG1 exhibited only very weak binding to mouse FcRn. Thus, the KD could not be calculated and is indicated as ND in Table 26. The assay result showed that the altered antibodies with enhanced human FcRn binding under neutral condition also exhibited augmented binding to mouse FcRn under the neutral condition.

TABLE 26

|  | KD (M) |
| --- | --- |
| IgG1 | ND |
| IgG1-v2 | 1.04E−06 |
| IgG1-F20 | 1.17E−07 |

(8-2) In Vivo Test Using Normal Mice with a Constant Plasma Concentration of Soluble Human IL-6 Receptor Using H54/L28-IgG1, Fv4-IgG1, Fv4-IgG1-v2, and Fv4-IgG1-F20 prepared as described in Example 3 and Reference Example 5, an in vivo test was conducted by the method described below.

An infusion pump (MINI-OSMOTIC PUMP MODEL 2004; alzet) containing soluble human IL-6 receptor was implanted under the skin on the back of normal mice (C57BL/6J mice; Charles River Japan) to prepare model animals where the plasma concentration of soluble human IL-6 receptor was kept constant. Anti-human IL-6 receptor antibodies were administered to the model animals to assess the in vivo kinetics after administration of soluble human IL-6 receptor. Monoclonal anti-mouse CD4 antibody (R&D) was administered at 20 mg/kg once into the caudal vein to suppress the production of neutralizing antibody against soluble human IL-6 receptor. Then, an infusion pump containing 92.8 μg/ml soluble human IL-6 receptor was implanted under the skin on the back of the mice. Three days after implantation of an infusion pump, anti-human IL-6 receptor antibodies were administered at 1 mg/kg once into the caudal vein. Blood was collected 15 minutes, seven hours, one day, two days, three days, four days, seven days, 14 days, 21 days, and 28 days after administration of the anti-human IL-6 receptor antibody. The collected blood was immediately centrifuged at 15,000 rpm and 4° C. for 15 minutes to separate plasma. The separated plasma was stored in a refrigerator at or below −20° C. before assay.

(8-3) Determination of Plasma Concentration of Anti-Human IL-6 Receptor Antibodies by ELISA The method used was the same as described in Reference Example 3.

(8-4) Determination of Plasma hsIL-6R Concentration by Electrochemiluminescence Assay The method used was the same as described in Example 5.

As shown in FIG. 39, the plasma concentration of soluble human IL-6 receptor was elevated to 650 ng/ml (15 times before administration) when H54/L28-IgG1, a neutralizing antibody against soluble human IL-6 receptor, was administered to normal mice (hsIL-6R group) in which the plasma concentration of soluble human IL-6 receptor was kept constantly at about 40 ng/ml. On the other hand, the plasma concentration of soluble human IL-6 receptor was maintained at about 70 ng/ml in the group administered with Fv4-IgG1 which results from conferring H54/L28-IgG1 with a pH-dependent antigen binding ability. This suggests that the increase in the plasma concentration of soluble human IL-6 receptor caused by administration of H54/L28-IgG1, an ordinary neutralizing antibody, can be suppressed to about one tenth by conferring the pH-dependent binding ability.

Furthermore, the plasma concentration of soluble human IL-6 receptor was demonstrated to be maintained at or below one tenth of the steady-state concentration by administering Fv-IgG1-v2 or Fv-IgG1-F20, both of which resulted from introducing an alteration into a pH-dependent human IL-6 receptor-binding antibody to augment the FcRn binding under neutral condition. When Fv-IgG1-v2 was administered, the plasma concentration of soluble human IL-6 receptor 14 days after administration was about 2 ng/ml. Thus, Fv-IgG1-v2 could reduce the concentration to 1/20 of the level before administration. Meanwhile, when Fv-IgG1-F20 was administered, the plasma concentrations of soluble human IL-6 receptor seven hours, one day, two days, and four days after administration were below the detection limit (1.56 ng/ml). This suggests that Fv-IgG1-F20 reduced the concentration to or below 1/25 of the level before administration.

The findings described above demonstrate that the plasma antigen concentration can be significantly reduced by increasing the antigen elimination rate in plasma, by administering an antibody having both pH-dependent antigen-binding ability and FcRn-binding ability under the neutral condition to model animals in which the plasma antigen concentration is kept constant.

Common antibodies such as H54/L28-IgG1 can only neutralize the action of a target antigen by binding to the target antigen, and even worse they increase the plasma antigen concentration. By contrast, antibodies having both pH-dependent antigen-binding ability and FcRn-binding ability under neutral condition were found to be able to not only neutralize the target antigen but also reduce the plasma concentration of the target antigen. The effect of antigen removal from the plasma can be expected to be more beneficial than neutralization. In addition, antigen removal can also work for target antigens that are insufficiently effective by neutralization alone.

Reference Example 9

Identification of Threshold of the Binding Affinity to Human FcRn at Neutral pH Required to Enhance Antigen Elimination and Relationship Between Antigen Elimination and the Binding Affinity to Human FcRn at Neutral pH (9-1) Antibody Preparation for In Vivo Study Fc variants of Fv4-IgG1 comprising VH3-IgG1 (SEQ ID NO: 19) and VL3-CK (SEQ ID NO: 20) with increased FcRn binding under the neutral pH were generated. Specifically, VH3-M73 (SEQ ID NO: 24) and VH3-IgG1-v1 (SEQ ID NO: 21) was prepared. The amino acid substitutions were introduced by methods known to those skilled in the art as described in Reference Example 3.

H54/L28-IgG1 comprising $H_{54}$ (SEQ ID NO: 5) and L28 (SEQ ID NO: 6), Fv4-IgG1 comprising VH3-IgG1 (SEQ ID NO: 19) and VL3-CK (SEQ ID NO: 20), Fv4-M73 comprising VH3-M73 (SEQ ID NO: 24) and VL3-CK (SEQ ID NO: 20), Fv4-IgG1-v1 comprising VH3-IgG1-v1 (SEQ ID NO: 21) and VL3-CK (SEQ ID NO: 20), and Fv4-IgG1-v2 comprising VH3-IgG1-v2 (SEQ ID NO: 22) and VL3-CK (SEQ ID NO: 20), were expressed and purified by the method known to those skilled in the art described in Reference Example 3.

(9-2) Assessment of the Binding Affinity of Antibodies to Human FcRn Under Neutral pH Condition VH3/L (WT)-IgG1 comprising VH3-IgG1 (SEQ ID NO: 19) and L (WT) (SEQ ID NO: 14), VH3/L (WT)-M73 comprising VH3-M73 (SEQ ID NO: 24) and L (WT) (SEQ ID NO: 14), VH3/L (WT)-IgG1-v1 comprising VH3-IgG1-v1 (SEQ ID NO: 21) and L (WT) (SEQ ID NO: 14), and VH3/L (WT)-IgG1-v2 comprising VH3-IgG1-v2 (SEQ ID NO: 22) and L (WT) (SEQ ID NO: 14), all of which were prepared as described in Reference Example 3, were assessed for human FcRn binding under a neutral pH (pH 7.0).

The binding activity of VH3/L (WT)-IgG1-v1 and VH3/L (WT)-IgG1-v2 to human FcRn was measured using the method described in Reference Example 5. Due to the low binding activity of VH3/L (WT)-IgG1 and VH3/L (WT)-M73 to human FcRn, binding activity to human FcRn could not be measured using the method described in Example 5, therefore, these antibodies were assessed by the method described below. The binding between antibody and human FcRn was kinetically analyzed using Biacore™ T100(GE Healthcare). An appropriate amount of protein L (ACTIGEN) was immobilized onto Sensor chip CM4 (GE Healthcare) by the amine-coupling method, and the chip was allowed to capture an antibody of interest. Then, diluted FcRn solutions and running buffer as a reference solution were injected to allow for human FcRn to interact with the antibody captured on the sensor chip. The running buffer used comprised 50 mmol/L sodium phosphate, 150 mmol/L NaCl, and 0.05% (w/v) Tween®20 (polysorbate 20) (pH 7.0). FcRn was diluted using each buffer. The chip was regenerated using 10 mmol/L glycine-HCl (pH 1.5). Assays were carried out at 25° C.

KD (M) of each antibody was derived from the sensorgram data using Biacore™ T100 Evaluation Software (GE Healthcare), which simultaneously fits the association and dissociation phases of the sensorgrams and globally fits all curves in the working set. Sensorgrams were fit 15 to 1:1 binding model, the "Langmuir binding" model, supplied by Biacore™ T100 Evaluation Software. For some of the binding interactions, KD was derived by nonlinear regression analysis of plots of $R_{eq}$, the equilibrium binding response, versus the log of the analyte concentration using an equilibrium-based approach.

The result on the human FcRn binding under the neutral condition (pH 7.0) by Biacore™ SPR analysis is shown in Tables 27.

TABLE 27

|  | KD(M) |
| --- | --- |
| IgG1 | 8.8E−05 |
| M73 | 1.4E−05 |
| IgG1-v1 | 3.2E−06 |
| IgG1-v2 | 8.1E−07 |

(9-3) In Vivo Studies of Effect of Antibodies on Antigen Elimination in Co-Administration Model Using Human FcRn Transgenic Mouse Line 276

In vivo study of antibodies using co-administration model was performed as described in Reference Example 3. Anti-human IL-6 receptor antibodies used in this study are the above-described H54/L28-IgG1, Fv4-IgG1, Fv4-M73, Fv4-IgG1-v1 and Fv4-IgG1-v2. Mice used in this study is human FcRn transgenic mice (B6.mFcRn −/−.hFcRn Tg line 276+/+ mouse, Jackson Laboratories; Methods Mol Biol. (2010) 602: 93-104).

As shown in FIG. 40, pharmacokinetics of H54/L28-IgG1, Fv4-IgG1, Fv4-M73, Fv4-IgG1-v1 and Fv4-IgG1-v2 were comparable, and these antibodies maintained similar plasma concentration during the study.

Time course of plasma hsIL-6R concentration was show in FIG. 41. Compared to the hsIL-6R administered with Fv4-IgG1, hsIL-6R administered with Fv4-IgG1-v2 exhibited enhanced clearance, whereas hsIL-6R administered with Fv4-M73 and Fv4-IgG1-v1 exhibited reduced clearance. Although all Fc variant, M73, v1, and v2 have increased binding affinity to human FcRn at neutral pH condition (pH 7.0), it was demonstrated that only Fv4-IgG1-v2, but not Fv4-M73 and Fv4-IgG1-v1, exhibited enhanced hsIL-6R clearance. This indicates that in order to enhance antigen clearance, binding affinity of antibody to human FcRn at pH 7.0 needs to be at least stronger than IgG1-v1, whose binding affinity to human FcRn at pH 7.0 is KD 3.2 µM or 28-fold stronger than intact human IgG1 (binding affinity to human FcRn is KD 88 µM).

FIG. 42 describes the relationship between the binding affinity of Fc variants to human FcRn at pH7.0 and plasma hsIL-6R concentration at day 1 after co-administration of hsIL-6R and Fc variants. Fc variants described in this Example and Reference Example 6 (Fv4-IgG1, Fv4-M73, Fv4-IgG1-v1, Fv4-IgG1-v2, Fv4-IgG1-F14, Fv4-IgG1-F20, Fv4-IgG1-F21, Fv4-IgG1-F25, Fv4-IgG1-F29, Fv4-IgG1-F35, Fv4-IgG1-F48, Fv4-IgG1-F93, and Fv4-IgG1-F94) are plotted. By increasing the binding affinity of antibody to human FcRn at pH 7.0, plasma concentration of hsIL-6R, which reflects the clearance of antigen, increased at first, but then decreased rapidly. This demonstrates that in order to enhance the antigen clearance compared to intact human IgG1, binding affinity of antibody to human FcRn at pH 7.0 needs to be preferably stronger than KD 2.3 µM (value obtained from curve fitting of FIG. 42). Binding affinity of antibody to human FcRn between KD 88 µM and KD 2.3 µM would rather reduce the antigen clearance (higher hsIL-6R concentration). In other words, binding affinity of antibody to human FcRn at pH 7.0 needs to be preferably 38-fold stronger than natural human IgG1 to enhance antigen elimination, or otherwise would reduce the antigen clearance.

FIG. 43 describes the relationship between the binding affinity of Fc variants to human FcRn at pH 7.0 and plasma antibody concentration at day 1 after co-administration of hsIL-6R and Fc variants. Fc variants described in this Example and Reference Example 6 (Fv4-IgG1, Fv4-M73, Fv4-IgG1-v1, Fv4-IgG1-v2, Fv4-IgG1-F14, Fv4-IgG1-F20, Fv4-IgG1-F21, Fv4-IgG1-F25, Fv4-IgG1-F29, Fv4-IgG1-F35, Fv4-IgG1-F48, Fv4-IgG1-F93, and Fv4-IgG1-F94) are plotted. By increasing the binding affinity of antibody to human FcRn at pH 7.0, plasma concentration of antibody, which reflects antibody pharmacokinetics (clearance), is maintained at first, but then decreased rapidly. This demonstrates that in order to maintain pharmacokinetics of antibody similar to natural human IgG1 (binding affinity to human FcRn is KD 88 µM), affinity of antibody to human FcRn at pH 7.0 needs to be weaker than KD 0.2 µM (value obtained from curve fitting of FIG. 43). Binding affinity of antibody to human FcRn stronger than KD 0.2 µM increased the antibody clearance (i.e. more rapid antibody elimination from plasma). In other words, binding affinity of antibody to human FcRn at pH 7.0 needs to be within 440-fold stronger than natural human IgG1 to exhibit similar antibody pharmacokinetics as natural human IgG1, or otherwise would result in rapid antibody elimination from plasma.

Considering both FIGS. 42 and 43, in order to enhance antigen clearance (i.e., reduce antigen plasma concentration) compared to IgG1, while maintaining antibody pharmacokinetics similar to natural human IgG1, binding affinity of antibody to human FcRn at pH 7.0 needs to be between 2.3 µM and 0.2 µM, or in other words, binding affinity of antibody to human FcRn at pH 7.0 needs to be within a range of 38-fold to 440-fold stronger than intact human IgG1. Such antibody with similar pharmacokinetics as IgG1 with long-term antigen-elimination activity would be beneficial for antibody therapeutic which requires longer dosing interval such as chronic disease because of its long-acting property.

On the other hand, by increasing the binding affinity of antibody to human FcRn at pH 7.0 stronger than KD 0.2 µM, or in other words, by increasing the binding affinity of antibody to human FcRn at pH 7.0 more than 440-fold as compared to natural human IgG1, it would enhance antigen clearance to a large extent within a short-term, although antibody is eliminated from plasma faster than natural human IgG1. Such antibody with capability of inducing rapid and strong reduction of antigen concentration would be beneficial for antibody therapeutic such as acute disease in which disease related antigen needs to be removed from plasma because of its fast-acting property.

Amount of antigen eliminated from plasma per antibody is the important factor to evaluate the efficiency of antigen elimination by administrating the antibody Fc variants having increased binding affinity to human FcRn at pH 7.0. To evaluate the efficiency of antigen elimination per antibody, following calculation were conducted at each time point of in vivo study described in this Example and Reference Example 6.

value A: Molar antigen concentration at each time point
value B: Molar antibody concentration at each time point
value C: Molar antigen concentration per molar antibody concentration (molar antigen/antibody ratio) at each time point

C=A/B

Time courses of value C (molar antigen/antibody ratio) for each antibody were described in FIG. 44. Smaller value C indicates higher efficiency of antigen elimination per antibody whereas higher value C indicates lower efficiency of antigen elimination per antibody. Lower value C as compared to IgG1 indicates that higher antigen elimination efficiency was achieved by Fc variants, whereas higher value C as compared to IgG1 indicates that Fc variants have negative effect on antigen elimination efficiency. All the Fc variants except Fv4-M73 and Fv4-IgG1-v1 demonstrated enhanced antigen elimination efficiency as compared to Fv4-IgG1. Fv4-M73 and Fv4-IgG1-v1 demonstrated negative impact on antigen elimination efficiency, which was consistent with FIG. 42.

FIG. 45 describes the relationship between the binding affinity of Fc variants to human FcRn at pH 7.0 and value C (molar antigen/antibody ratio) at day 1 after co-administration of hsIL-6R and Fc variants. Fc variants described in this Example and Reference Example 6 (Fv4-IgG1, Fv4-M73, Fv4-IgG1-v1, Fv4-IgG1-v2, Fv4-IgG1-F14, Fv4-IgG1-F20, Fv4-IgG1-F21, Fv4-IgG1-F25, Fv4-IgG1-F29, Fv4-IgG1-F35, Fv4-IgG1-F48, Fv4-IgG1-F93, and Fv4-IgG1-F94) are plotted. This demonstrates that in order to achieve higher antigen elimination efficiency as compared to natural human IgG1, affinity of antibody to human FcRn at pH 7.0 needs to be stronger than KD 3.0 µM (value obtained from curve fitting of FIG. 45). In other words, binding affinity of antibody to human FcRn at pH 7.0 needs to be at least 29-fold stronger than natural human IgG1 to achieve higher antigen elimination efficiency as compared to natural human IgG1.

In conclusion, group of antibody variants having binding affinity to FcRn at pH 7.0 between KD 3.0 µM and 0.2 µM, or in other words, group of antibody variants having binding affinity to FcRn at pH 7.0 within a range of 29-fold to 440-fold stronger than natural human IgG1, have similar antibody pharmacokinetics to IgG1 but have enhanced capability to eliminate the antibody from plasma. Therefore, such antibody exhibits enhanced antigen elimination efficiency as compared to IgG1. Similar pharmacokinetics as IgG1 would enable long-term elimination of antigen from plasma (long-acting antigen elimination), and therefore long dosing intervals which would be preferable for antibody therapeutics for chronic disease. Group of antibody variants having binding affinity to FcRn at pH 7.0 stronger than KD 0.2 μM, or in other words, group of antibody variants having binding affinity to FcRn at pH 7.0 440-fold stronger than natural human IgG1, have rapid antibody clearance (short-term antibody elimination). Nevertheless, since such antibody enables even more rapid clearance of antigen (fast-acting antigen elimination), therefore, such antibody also exhibits enhanced antigen elimination efficiency as compared to IgG1. As shown in Reference Example 8, Fv4-IgG1-F20 in normal mouse would induce significant elimination of the antigen from plasma in a very short term, but the antigen elimination effect is not durable. Such profile would be preferable for acute diseases where disease related antigen is needed to be depleted from plasma rapidly and significantly in a very short term.

Reference Example 10

In Vivo Study of Fv4-IgG1-F14 by Steady-State Infusion Model Using Human FcRn Transgenic Mouse Line 276

In vivo study of Fv4-IgG1-F14 by steady-state infusion model using human FcRn transgenic mouse line 276 was performed as described below. Study group consists of control group (without antibody), Fv4-IgG1 at a dose of 1 mg/kg and Fv4-IgG1-F14 at a dose of 1 mg/kg, 0.2 mg/kg, and 0.01 mg/kg.

An infusion pump (MINI-OSMOTIC PUMP MODEL 2004; alzet) containing soluble human IL-6 receptor was implanted under the skin on the back of human FcRn transgenic mice 276 (B6.mFcRn −/−.hFcRn Tg line 276+/+ mouse (B6.mFcRn −/− hFCRN Tg276 B6.Cg-Fcgrt <tm1Dcr> Tg(FCGRT) 276Dcr (Jackson #4919)), Jackson Laboratories; Methods Mol Biol. (2010) 602: 93-104) to prepare model animals where the plasma concentration of soluble human IL-6 receptor was kept constant. Anti-human IL-6 receptor antibodies were administered to the model animals to assess the in vivo dynamics after administration of soluble human IL-6 receptor. Monoclonal anti-mouse CD4 antibody (R&D) was administered at 20 mg/kg before implanting infusion pump and 14 days after antibody administration into the caudal vein to suppress the production of neutralizing antibody against soluble human IL-6 receptor. Then, an infusion pump containing 92.8 μg/ml soluble human IL-6 receptor was implanted under the skin on the back of the mice. Three days after implantation of an infusion pump, anti-human IL-6 receptor antibodies (H54/L28-IgG1 and H54/L28-IgG1-F14) were administered at 1 mg/kg once into the caudal vein. Blood was collected 15 minutes, seven hours, one day, two days, three days, four days, seven days, 14 days, 21 days, and 28 days after administration of the anti-human IL-6 receptor antibody. The collected blood was immediately centrifuged at 15,000 rpm and 4° C. for 15 minutes to separate plasma. The separated plasma was stored in a refrigerator at −20° C. or below before assay.

The concentration of hsIL-6R in mouse plasma was measured by electrochemiluminescence. hsIL-6R calibration curve samples adjusted to concentrations of 2,000, 1,000, 500, 250, 125, 62.5, and 31.25 pg/ml, and mouse plasma samples diluted 50-fold or more were prepared. The samples were mixed with a solution of Monoclonal Anti-human IL-6R Antibody (R&D) ruthenium-labeled with Sulfo-Tag NHS Ester (Meso Scale Discovery), Biotinylated Anti-human IL-6R Antibody (R&D), and WT-IgG1, and then allowed to react overnight at 37° C. The final concentration of WT-IgG1 as an anti-human IL-6 receptor antibody, comprising tocilizumab (heavy chain SEQ ID NO: 13; light chain SEQ ID NO: 14), was 333 μg/ml, which is in excess of the concentration of anti-human IL-6 receptor antibody contained in the samples, for the purpose of binding nearly all of the hsIL-6R molecules in the samples to WT-IgG1. Subsequently, the samples were dispensed into an MA400 PR Streptavidin Plate (Meso Scale Discovery), and allowed to react for one hour at room temperature, and washing was performed. Immediately after Read Buffer T (×4) (Meso Scale Discovery) was dispensed, the measurement was performed by the Sector PR 400 Reader (Meso Scale Discovery). The hsIL-6R concentration was calculated based on the response of the calibration curve using the analytical software SOFTmax PRO (Molecular Devices).

FIG. 46 describes time profile of hsIL-6R plasma concentration after antibody administration. Compared to baseline hsIL-6R level without antibody, administration of 1 mg/kg of Fv4-IgG1 resulted in several fold increase in plasma hsIL-6R concentration. On the other hands, administration of 1 mg/kg of Fv4-IgG1-F14 resulted in significant reduction in plasma concentration in comparison with Fv4-IgG1 group and baseline group. At day 2, plasma hsIL-6R concentration was not detected (quantitation limit of plasma hsIL-6R concentration is 1.56 ng/mL in this measurement system), and this lasted up to day 14.

H54/L28-IgG1-F14 exhibited reduction of plasma hsIL-6R concentration as compared to H54/L28-IgG1, but the extent of the reduction was small. Extent of reduction was much higher for Fv4 variable region which has pH dependent binding property to hsIL-6R. This demonstrates that although increasing binding affinity to human FcRn at pH 7.0 is effective for reducing plasma antigen concentration, combination of pH dependent antigen binding and increased binding affinity to human FcRn at neutral pH significantly enhances the antigen elimination.

Study using lower dose of Fv4-IgG1-F14 exhibited that even at 0.01 mg/kg, 1/100 of 1 mg/kg, reduced the antigen plasma concentration below the baseline demonstrating significant efficiency of the molecule to deplete the antigen from plasma.

Reference Example 11

Comparison of Human FcRn Transgenic Mouse Lineage 276 and Lineage 32 in Co-Administration Model Previous in vivo studies have been conducted using human FcRn transgenic mouse line 276 (Jackson Laboratories). In order to compare the difference between human FcRn transgenic mouse lineage 276 and a different transgenic line, lineage 32, we conducted co-administration study of H54/L28-IgG1, Fv4-IgG1, and Fv4-IgG1-v2 using human FcRn transgenic mouse lineage 32 (B6.mFcRn −/−.hFcRn Tg lineage 32+/+ mouse (B6.mFcRn −/− hFCRN Tg32; B6.Cg-Fcgrt<tm1Dcr> Tg(FCGRT)32Dcr) (Jackson

4915)), Jackson Laboratories; Methods Mol Biol. (2010) 602: 93-104). Study method was same as that of Reference Example 3 but human FcRn transgenic mouse lineage 32 was used instead of human FcRn transgenic mouse lineage 276.

FIG. 47 describes the time course of plasma hsIL-6R concentration in both human FcRn transgenic mouse lineage 276 and lineage 32. H54/L28-IgG1, Fv4-IgG1, and Fv4-IgG1-v2 exhibited similar plasma hsIL-6R concentration time profile. In both mice, increasing binding affinity to human FcRn at pH 7.0 enhanced the antigen elimination from plasma (comparing Fv4-IgG1 and Fv4-IgG1-v2) to a same extent.

FIG. 48 describes the time course of plasma antibody concentration in both human FcRn transgenic mouse lineage 276 and lineage 32. H54/L28-IgG1, Fv4-IgG1, and Fv4-IgG1-v2 exhibited similar plasma antibody concentration time profile.

In conclusion, no significant difference were observed between lineage 276 and lineage 32, demonstrating that the Fc variant to increase the binding affinity to human FcRn at pH 7.0 was effective in two different transgenic mouse line expressing human FcRn for enhancing elimination of antigen plasma concentration.

Reference Example 12

Generation of Various Antibody Fc Variants Having Increased Binding Affinity to Human FcRn at Neutral pH (12-1) Generation of Fc Variants Various mutations to increase the binding affinity to human FcRn under the neutral pH were introduced into Fv4-IgG1 to further improve the antigen elimination profile. Specifically, the amino acid mutations shown in Table 15, were introduced into the heavy chain constant region of Fv4-IgG1 to generate Fc variants (amino acid numbers of the mutation sites are described according to the EU numbering). The amino acid substitutions were introduced by the method known to those skilled in the art described in Reference Example 3.

The additional variants (IgG1-F100 to IgG1-F1052) each comprising a prepared heavy chain and L (WT) (SEQ ID NO: 14) were expressed and purified by methods known to those skilled in the art as described in Reference Example 3.

(12-2) Assessment of Human FcRn Binding

The binding between antibody and human FcRn was kinetically analyzed as described in Reference Example 5 for IgG1-v1, IgG1-v2 and IgG1-F2 to IgG1-F1052 or Reference Example 9 for IgG1 and M73. The result on the human FcRn binding under a neutral condition (pH 7.0) by Biacore™ SPR analysis is shown in Tables 28-1 to 28-21.

TABLE 28-1

| VARIANT | KD (M) | AMINO ACID ALTERED POSITION |
|---|---|---|
| F1 | 8.10E−07 | N434W |
| F2 | 3.20E−06 | M252Y/S254T/T256E |
| F3 | 2.50E−06 | N434Y |
| F4 | 5.80E−06 | N434S |
| F5 | 6.80E−06 | N434A |
| F7 | 5.60E−06 | M252Y |
| F8 | 4.20E−06 | M252W |
| F9 | 1.40E−07 | M252Y/S254T/T256E/N434Y |
| F10 | 6.90E−08 | M252Y/S254T/T256E/N434W |
| F11 | 3.10E−07 | M252Y/N434Y |

TABLE 28-1-continued

| VARIANT | KD (M) | AMINO ACID ALTERED POSITION |
|---|---|---|
| F12 | 1.70E−07 | M252Y/N434W |
| F13 | 3.20E−07 | M252W/N434Y |
| F14 | 1.80E−07 | M252W/N434W |
| F19 | 4.60E−07 | P257L/N434Y |
| F20 | 4.60E−07 | V308F/N434Y |
| F21 | 3.00E−08 | M252Y/V308P/N434Y |
| F22 | 2.00E−06 | M428L/N434S |
| F25 | 9.20E−09 | M252Y/S254T/T256E/V308P/N434W |
| F26 | 1.00E−06 | I332V |
| F27 | 7.40E−06 | G237M |
| F29 | 1.40E−06 | I332V/N434Y |
| F31 | 2.80E−06 | G237M/V308F |
| F32 | 8.00E−07 | S254T/N434W |
| F33 | 2.30E−06 | S254T/N434Y |
| F34 | 2.80E−07 | T256E/N434W |
| F35 | 8.40E−07 | T256E/N434Y |
| F36 | 3.60E−07 | S254T/T256E/N434W |
| F37 | 1.10E−06 | S254T/T256E/N434Y |
| F38 | 1.00E−07 | M252Y/S254T/N434W |
| F39 | 3.00E−07 | M252Y/S254T/N434Y |
| F40 | 8.20E−08 | M252Y/T256E/N434W |
| F41 | 1.50E−07 | M252Y/T256E/N434Y |
| F42 | 1.00E−06 | M252Y/S254T/T256E/N434A |
| F43 | 1.70E−06 | M252Y/N434A |
| F44 | 1.10E−06 | M252W/N434A |
| F47 | 2.40E−07 | M252Y/T256Q/N434W |
| F48 | 3.20E−07 | M252Y/T256Q/N434Y |
| F49 | 5.10E−07 | M252F/T256D/N434W |
| F50 | 1.20E−06 | M252F/T256D/N434Y |
| F51 | 8.10E−06 | N434F/Y436H |

Table 28-2 is the continuation of Table 28-1.

TABLE 28-2

| VARIANT | KD (M) | AMINO ACID ALTERED POSITION |
|---|---|---|
| F52 | 3.10E−06 | H433K/N434F/Y436H |
| F53 | 1.00E−06 | I332V/N434W |
| F54 | 8.40E−08 | V308P/N434W |
| F56 | 9.40E−07 | I332V/M428L/N434Y |
| F57 | 1.10E−05 | G385D/Q386P/N389S |
| F58 | 7.70E−07 | G385D/Q386P/N389S/N434W |
| F59 | 2.40E−06 | G385D/Q386P/N389S/N434Y |
| F60 | 1.10E−05 | G385H |
| F61 | 9.70E−07 | G385H/N434W |
| F62 | 1.90E−06 | G385H/N434Y |
| F63 | 2.50E−06 | N434F |
| F64 | 5.30E−06 | N434H |
| F65 | 2.90E−07 | M252Y/S254T/T256E/N434F |
| F66 | 4.30E−07 | M252Y/S254T/T256E/N434H |
| F67 | 6.30E−07 | M252Y/N434F |
| F68 | 9.30E−07 | M252Y/N434H |
| F69 | 5.10E−07 | M428L/N434W |
| F70 | 1.50E−06 | M428L/N434Y |
| F71 | 8.30E−08 | M252Y/S254T/T256E/M428L/N434W |
| F72 | 2.00E−07 | M252Y/S254T/T256E/M428L/N434Y |
| F73 | 1.70E−07 | M252Y/M428L/N434W |
| F74 | 4.60E−07 | M252Y/M428L/N434Y |
| F75 | 1.40E−06 | M252Y/M428L/N434A |
| F76 | 1.00E−06 | M252Y/S254T/T256E/M428L/N434A |
| F77 | 9.90E−07 | T256E/M428L/N434Y |
| F78 | 7.80E−07 | S254T/M428L/N434W |
| F79 | 5.90E−06 | S254T/T256E/N434A |
| F80 | 2.70E−06 | M252Y/T256Q/N434A |
| F81 | 1.60E−06 | M252Y/T256E/N434A |
| F82 | 1.10E−06 | T256Q/N434W |
| F83 | 2.60E−06 | T256Q/N434Y |
| F84 | 2.80E−07 | M252W/T256Q/N434W |
| F85 | 5.50E−07 | M252W/T256Q/N434Y |
| F86 | 1.50E−06 | S254T/T256Q/N434W |
| F87 | 4.30E−06 | S254T/T256Q/N434Y |
| F88 | 1.90E−07 | M252Y/S254T/T256Q/N434W |
| F89 | 3.60E−07 | M252Y/S254T/T256Q/N434Y |
| F90 | 1.90E−08 | M252Y/T256E/V308P/N434W |
| F91 | 4.80E−08 | M252Y/V308P/M428L/N434Y |

TABLE 28-2-continued

| | | |
|---|---|---|
| F92 | 1.10E−08 | M252Y/S254T/T256E/V308P/M428L/N434W |
| F93 | 7.40E−07 | M252W/M428L/N434W |
| F94 | 3.70E−07 | P257L/M428L/N434Y |

Table 28-3 is the continuation of Table 28-2.

TABLE 28-3

| | | |
|---|---|---|
| F95 | 2.60E−07 | M252Y/S254T/T256E/M428L/N434F |
| F99 | 6.20E−07 | M252Y/T256E/N434H |
| F101 | 1.10E−07 | M252W/T256Q/P257L/N434Y |
| F103 | 4.40E−08 | P238A/M252Y/V308P/N434Y |
| F104 | 3.70E−08 | M252Y/D265A/V308P/N434Y |
| F105 | 7.50E−08 | M252Y/T307A/V308P/N434Y |
| F106 | 3.70E−08 | M252Y/V303A/V308P/N434Y |
| F107 | 3.40E−08 | M252Y/V308P/D376A/N434Y |
| F108 | 4.10E−08 | M252Y/V305A/V308P/N434Y |
| F109 | 3.20E−08 | M252Y/V308P/Q311A/N434Y |
| F111 | 3.20E−08 | M252Y/V308P/K317A/N434Y |
| F112 | 6.40E−08 | M252Y/V308P/E380A/N434Y |
| F113 | 3.20E−08 | M252Y/V308P/E382A/N434Y |
| F114 | 3.80E−08 | M252Y/V308P/S424A/N434Y |
| F115 | 6.60E−06 | T307A/N434A |
| F116 | 8.70E−06 | E380A/N434A |
| F118 | 1.40E−05 | M428L |
| F119 | 5.40E−06 | T250Q/M428L |
| F120 | 6.30E−08 | P257L/V308P/M428L/N434Y |
| F121 | 1.50E−08 | M252Y/T256E/V308P/M428L/N434W |
| F122 | 1.20E−07 | M252Y/T256E/M428L/N434W |
| F123 | 3.00E−08 | M252Y/T256E/V308P/N434Y |
| F124 | 2.90E−08 | M252Y/T256E/M428L/N434Y |
| F125 | 2.40E−08 | M252Y/S254T/T256E/V308P/M428L/N434Y |
| F128 | 1.70E−07 | P257L/M428L/N434W |
| F129 | 2.20E−07 | P257A/M428L/N434Y |
| F131 | 3.00E−06 | P257G/M428L/N434Y |
| F132 | 2.10E−07 | P257I/M428L/N434Y |
| F133 | 4.10E−08 | P257M/M428L/N434Y |
| F134 | 2.70E−07 | P257N/M428L/N434Y |
| F135 | 7.50E−07 | P257S/M428L/N434Y |
| F136 | 3.80E−07 | P257T/M428L/N434Y |
| F137 | 4.60E−07 | P257V/M428L/N434Y |
| F139 | 1.50E−08 | M252W/V308P/N434W |
| F140 | 3.60E−08 | S239K/M252Y/V308P/N434Y |
| F141 | 3.50E−08 | M252Y/S298G/V308P/N434Y |
| F142 | 3.70E−08 | M252Y/D270F/V308P/N434Y |
| F143 | 2.00E−07 | M252Y/V308A/N434Y |
| F145 | 5.30E−08 | M252Y/V308F/N434Y |
| F147 | 2.40E−07 | M252Y/V308I/N434Y |
| F149 | 1.90E−07 | M252Y/V308L/N434Y |
| F150 | 2.00E−07 | M252Y/V308M/N434Y |

TABLE 28-4

| | | |
|---|---|---|
| F152 | 2.70E−07 | M252Y/V308Q/N434Y |
| F154 | 1.80E−07 | M252Y/V308T/N434Y |
| F157 | 1.50E−07 | P257A/V308P/M428L/N434Y |
| F158 | 5.90E−08 | P257T/V308P/M428L/N434Y |
| F159 | 4.40E−08 | P257V/V308P/M428L/N434Y |
| F160 | 8.50E−08 | M252W/M428I/N434Y |
| F162 | 1.60E−07 | M252W/M428Y/N434Y |
| F163 | 4.20E−07 | M252W/M428F/N434Y |
| F164 | 3.70E−07 | P238A/M252W/N434Y |
| F165 | 2.90E−07 | M252W/D265A/N434Y |
| F166 | 1.50E−07 | M252W/T307Q/N434Y |
| F167 | 2.90E−07 | M252W/V303A/N434Y |
| F168 | 3.20E−07 | M252W/D376A/N434Y |
| F169 | 2.90E−07 | M252W/V305A/N434Y |
| F170 | 1.70E−07 | M252W/Q311A/N434Y |
| F171 | 1.90E−07 | M252W/D312A/N434Y |
| F172 | 2.20E−07 | M252W/K317A/N434Y |
| F173 | 7.70E−07 | M252W/E380A/N434Y |
| F174 | 3.40E−07 | M252W/E382A/N434Y |
| F175 | 2.70E−07 | M252W/S424A/N434Y |
| F176 | 2.90E−07 | S239K/M252W/N434Y |
| F177 | 2.80E−07 | M252W/S298G/N434Y |
| F178 | 2.70E−07 | M252W/D270F/N434Y |

TABLE 28-4-continued

| | | |
|---|---|---|
| F179 | 3.10E−07 | M252W/N325G/N434Y |
| F182 | 6.60E−08 | P257A/M428L/N434W |
| F183 | 2.20E−07 | P257T/M428L/N434W |
| F184 | 2.70E−07 | P257V/M428L/N434W |
| F185 | 2.60E−07 | M252W/I332Y/N434Y |
| F188 | 3.00E−06 | P257I/Q311I |
| F189 | 1.90E−07 | M252Y/T307A/N434Y |
| F190 | 1.10E−07 | M252Y/T307Q/N434Y |
| F191 | 1.60E−07 | P257L/T307A/M428L/N434Y |
| F192 | 1.10E−07 | P257A/T307A/M428L/N434Y |
| F193 | 8.50E−08 | P257T/T307A/M428L/N434Y |
| F194 | 1.20E−07 | P257V/T307A/M428L/N434Y |
| F195 | 5.60E−08 | P257L/T307Q/M428L/N434Y |
| F196 | 3.50E−08 | P257A/T307Q/M428L/N434Y |
| F197 | 3.30E−08 | P257T/T307Q/M428L/N434Y |
| F198 | 4.80E−08 | P257V/T307Q/M428L/N434Y |
| F201 | 2.10E−07 | M252Y/T307D/N434Y |
| F203 | 2.40E−07 | M252Y/T307F/N434Y |
| F204 | 2.10E−07 | M252Y/T307G/N434Y |

Table 28-5 is the continuation of Table 28-4.

TABLE 28-5

| | | |
|---|---|---|
| F205 | 2.00E−07 | M252Y/T307H/N434Y |
| F206 | 2.30E−07 | M252Y/T307I/N434Y |
| F207 | 9.40E−07 | M252Y/T307K/N434Y |
| F208 | 3.90E−07 | M252Y/T307L/N434Y |
| F209 | 1.30E−07 | M252Y/T307M/N434Y |
| F210 | 2.90E−07 | M252Y/T307N/N434Y |
| F211 | 2.40E−07 | M252Y/T307P/N434Y |
| F212 | 6.80E−07 | M252Y/T307R/N434Y |
| F213 | 2.30E−07 | M252Y/T307S/N434Y |
| F214 | 1.70E−07 | M252Y/T307V/N434Y |
| F215 | 9.60E−08 | M252Y/T307W/N434Y |
| F216 | 2.30E−07 | M252Y/T307Y/N434Y |
| F217 | 2.30E−07 | M252Y/K334L/N434Y |
| F218 | 2.60E−07 | M252Y/G385H/N434Y |
| F219 | 2.50E−07 | M252Y/T289H/N434Y |
| F220 | 2.50E−07 | M252Y/Q311H/N434Y |
| F221 | 3.10E−07 | M252Y/D312H/N434Y |
| F222 | 3.40E−07 | M252Y/N315H/N434Y |
| F223 | 2.70E−07 | M252Y/K360H/N434Y |
| F225 | 1.50E−06 | M252Y/L314R/N434Y |
| F226 | 5.40E−07 | M252Y/L314K/N434Y |
| F227 | 1.20E−07 | M252Y/N286E/N434Y |
| F228 | 2.30E−07 | M252Y/L309E/N434Y |
| F229 | 5.10E−07 | M252Y/R255E/N434Y |
| F230 | 2.50E−07 | M252Y/P387E/N434Y |
| F236 | 8.90E−07 | K248I/M428L/N434Y |
| F237 | 2.30E−07 | M252Y/M428A/N434Y |
| F238 | 7.40E−07 | M252Y/M428D/N434Y |
| F240 | 7.20E−07 | M252Y/M428F/N434Y |
| F241 | 1.50E−06 | M252Y/M428G/N434Y |
| F242 | 8.50E−07 | M252Y/M428H/N434Y |
| F243 | 1.80E−07 | M252Y/M428I/N434Y |
| F244 | 1.30E−06 | M252Y/M428K/N434Y |
| F245 | 4.70E−07 | M252Y/M428N/N434Y |
| F246 | 1.10E−06 | M252Y/M428P/N434Y |
| F247 | 4.40E−07 | M252Y/M428Q/N434Y |
| F249 | 6.40E−07 | M252Y/M428S/N434Y |
| F250 | 2.90E−07 | M252Y/M428T/N434Y |
| F251 | 1.90E−07 | M252Y/M428V/N434Y |
| F252 | 1.00E−06 | M252Y/M428W/N434Y |
| F253 | 7.10E−07 | M252Y/M428Y/N434Y |
| F254 | 7.50E−08 | M252W/T307Q/M428Y/N434Y |

Table 28-6 is the continuation of Table 28-5.

TABLE 28-6

| | | |
|---|---|---|
| F255 | 1.10E−07 | M252W/Q311A/M428Y/N434Y |
| F256 | 5.40E−08 | M252W/T307Q/Q311A/M428Y/N434Y |
| F257 | 5.00E−07 | M252Y/T307A/M428Y/N434Y |
| F258 | 3.20E−07 | M252Y/T307Q/M428Y/N434Y |
| F259 | 2.80E−07 | M252Y/D270F/N434Y |
| F260 | 1.30E−07 | M252Y/T307A/Q311A/N434Y |

TABLE 28-6-continued

| | | |
|---|---|---|
| F261 | 8.40E−08 | M252Y/T307Q/Q311A/N434Y |
| F262 | 1.90E−07 | M252Y/T307A/Q311H/N434Y |
| F263 | 1.10E−07 | M252Y/T307Q/Q311H/N434Y |
| F264 | 2.80E−07 | M252Y/E382A/M428Y |
| F265 | 6.80E−07 | M252Y/E382A/M428Y/N434Y |
| F266 | 4.70E−07 | M252Y/T307A/E382A/M428Y/N434Y |
| F267 | 3.20E−07 | M252Y/T307Q/E382A/M428Y/N434Y |
| F268 | 6.30E−07 | P238A/M252Y/M428F/N434Y |
| F269 | 5.20E−08 | M252Y/V305A/M428F/N434Y |
| F270 | 6.60E−07 | M252Y/N325G/M428F/N434Y |
| F271 | 6.90E−07 | M252Y/D376A/M428F/N434Y |
| F272 | 6.80E−07 | M252Y/E380A/M428F/N434Y |
| F273 | 6.50E−07 | M252Y/E382A/M428F/N434Y |
| F274 | 7.60E−07 | M252Y/E380A/E382A/M428F/N434Y |
| F275 | 4.20E−08 | S239K/M252Y/V308P/E382A/N434Y |
| F276 | 4.10E−08 | M252Y/D270F/V308P/E382A/N434Y |
| F277 | 1.30E−07 | S239K/M252Y/V308P/M428Y/N434Y |
| F278 | 3.00E−08 | M252Y/T307Q/V308P/E382A/N434Y |
| F279 | 6.10E−08 | M252Y/V308P/Q311H/E382A/N434Y |
| F280 | 4.10E−08 | S239K/M252Y/D270F/V308P/N434Y |
| F281 | 9.20E−08 | M252Y/V308P/E382A/M428F/N434Y |
| F282 | 2.90E−08 | M252Y/V308P/E382A/M428L/N434Y |
| F283 | 1.00E−07 | M252Y/V308P/E382A/M428Y/N434Y |
| F284 | 1.00E−07 | M252Y/V308P/M428Y/N434Y |
| F285 | 9.90E−08 | M252Y/V308P/M428F/N434Y |
| F286 | 1.20E−07 | S239K/M252Y/V308P/E382A/M428Y/N434Y |
| F287 | 1.00E−07 | M252Y/V308P/E380A/E382A/M428F/N434Y |
| F288 | 1.90E−07 | M252Y/T256E/E382A/N434Y |
| F289 | 4.80E−07 | M252Y/T256E/M428Y/N434Y |
| F290 | 4.60E−07 | M252Y/T256E/E382A/M428Y/N434Y |
| F292 | 2.30E−08 | S239K/M252Y/V308P/E382A/M428I/N434Y |
| F293 | 5.30E−08 | M252Y/V308P/E380A/E382A/M428I/N434Y |
| F294 | 1.10E−07 | S239K/M252Y/V308P/M428F/N434Y |
| F295 | 6.80E−07 | S239K/M252Y/E380A/E382A/M428F/N434Y |
| F296 | 4.90E−07 | M252Y/Q311A/M428Y/N434Y |
| F297 | 5.10E−07 | M252Y/D312A/M428Y/N434Y |

Table 28-7 is the continuation of Table 28-6.

TABLE 28-7

| | | |
|---|---|---|
| F298 | 4.80E−07 | M252Y/Q311A/D312A/M428Y/N434Y |
| F299 | 9.40E−08 | S239K/M252Y/V308P/Q311A/M428Y/N434Y |
| F300 | 8.30E−08 | S239K/M252Y/V308P/D312A/M428Y/N434Y |
| F301 | 7.20E−08 | S239K/M252Y/V308P/Q311A/D312A/M428Y/N434Y |
| F302 | 1.90E−07 | M252Y/T256E/T307P/N434Y |
| F303 | 6.70E−07 | M252Y/T307P/M428Y/N434Y |
| F304 | 1.60E−08 | M252W/V308P/M428Y/N434Y |
| F305 | 2.70E−08 | M252Y/T256E/V308P/E382A/N434Y |
| F306 | 3.60E−08 | M252W/V308P/E382A/N434Y |
| F307 | 3.60E−08 | S239K/M252W/V308P/E382A/N434Y |
| F308 | 1.90E−08 | S239K/M252W/V308P/E382A/M428Y/N434Y |
| F310 | 9.40E−08 | S239K/M252W/V308P/E382A/M428I/N434Y |
| F311 | 2.80E−08 | S239K/M252W/V308P/M428F/N434Y |
| F312 | 4.50E−07 | S239K/M252W/E380A/E382A/M428F/N434Y |
| F313 | 6.50E−07 | S239K/M252Y/T307P/M428Y/N434Y |
| F314 | 3.20E−07 | M252Y/T256E/Q311A/D312A/M428Y/N434Y |
| F315 | 6.80E−07 | S239K/M252Y/M428Y/N434Y |
| F316 | 7.00E−07 | S239K/M252Y/D270F/M428Y/N434Y |
| F317 | 1.10E−07 | S239K/M252Y/D270F/V308P/M428Y/N434Y |
| F318 | 1.80E−08 | S239K/M252Y/V308P/M428I/N434Y |
| F320 | 2.00E−08 | S239K/M252Y/V308P/N325G/E382A/M428I/N434Y |
| F321 | 3.20E−08 | S239K/M252Y/D270F/V308P/N325G/N434Y |
| F322 | 9.20E−08 | S239K/M252Y/D270F/T307P/V308P/N434Y |
| F323 | 2.70E−08 | S239K/M252Y/T256E/D270F/V308P/N434Y |
| F324 | 2.80E−08 | S239K/M252Y/D270F/T307Q/V308P/N434Y |
| F325 | 2.10E−08 | S239K/M252Y/D270F/T307Q/V308P/Q311A/N434Y |
| F326 | 7.50E−08 | S239K/M252Y/D270F/T307Q/Q311A/N434Y |
| F327 | 6.50E−08 | S239K/M252Y/T256E/D270F/T307Q/Q311A/N434Y |
| F328 | 1.90E−08 | S239K/M252Y/D270F/V308P/M428I/N434Y |
| F329 | 1.20E−08 | S239K/M252Y/D270F/N286E/V308P/N434Y |
| F330 | 3.60E−08 | S239K/M252Y/D270F/V308P/L309E/N434Y |
| F331 | 3.00E−08 | S239K/M252Y/D270F/V308P/P387E/N434Y |
| F333 | 7.40E−08 | S239K/M252Y/D270F/T307Q/L309E/Q311A/N434Y |
| F334 | 1.90E−08 | S239K/M252Y/D270F/V308P/N325G/M428I/N434Y |
| F335 | 1.50E−08 | S239K/M252Y/T256E/D270F/V308P/M428I/N434Y |
| F336 | 1.40E−08 | S239K/M252Y/D270F/T307Q/V308P/Q311A/M428I/N434Y |

TABLE 28-7-continued

| | | |
|---|---|---|
| F337 | 5.60E−08 | S239K/M252Y/D270F/T307Q/Q311A/M428I/N434Y |
| F338 | 7.70E−09 | S239K/M252Y/D270F/N286E/V308P/M428I/N434Y |
| F339 | 1.90E−08 | S239K/M252Y/D270F/V308P/L309E/M428I/N434Y |
| F343 | 3.20E−08 | S239K/M252Y/D270F/V308P/M428L/N434Y |
| F344 | 3.00E−08 | S239K/M252Y/V308P/M428L/N434Y |
| F349 | 1.50E−07 | S239K/M252Y/V308P/L309P/M428L/N434Y |

Table 28-8 is the continuation of Table 28-7.

TABLE 28-8

| | | |
|---|---|---|
| F350 | 1.70E−07 | S239K/M252Y/V308P/L309R/M428L/N434Y |
| F352 | 6.00E−07 | S239K/M252Y/L309P/M428L/N434Y |
| F353 | 1.10E−06 | S239K/M252Y/L309R/M428L/N434Y |
| F354 | 2.80E−08 | S239K/M252Y/T307Q/V308P/M428L/N434Y |
| F356 | 3.40E−08 | S239K/M252Y/D270F/V308P/L309E/P387E/N434Y |
| F357 | 1.60E−08 | S239K/M252Y/T256E/D270F/V308P/N325G/M428I/N434Y |
| F358 | 1.00E−07 | S239K/M252Y/T307Q/N434Y |
| F359 | 4.20E−08 | P257V/T307Q/M428I/N434Y |
| F360 | 1.30E−06 | P257V/T307Q/M428V/N434Y |
| F362 | 5.40E−08 | P257V/T307Q/N325G/M428L/N434Y |
| F363 | 4.10E−08 | P257V/T307Q/Q311A/M428L/N434Y |
| F364 | 3.50E−08 | P257V/T307Q/Q311A/N325G/M428L/N434Y |
| F365 | 5.10E−08 | P257V/V305A/T307Q/M428L/N434Y |
| F367 | 1.50E−08 | S239K/M252Y/E258H/D270F/T307Q/V308P/Q311A/N434Y |
| F368 | 2.00E−08 | S239K/M252Y/D270F/V308P/N325G/E382A/M428I/N434Y |
| F369 | 7.50E−08 | M252Y/P257V/T307Q/M428I/N434Y |
| F372 | 1.30E−08 | S239K/M252W/V308P/M428Y/N434Y |
| F373 | 1.10E−08 | S239K/M252W/V308P/Q311A/M428Y/N434Y |
| F374 | 1.20E−08 | S239K/M252W/T256E/V308P/M428Y/N434Y |
| F375 | 5.50E−08 | S239K/M252W/N286E/V308P/M428Y/N434Y |
| F376 | 9.60E−09 | S239K/M252Y/T256E/D270F/N286E/V308P/N434Y |
| F377 | 1.30E−07 | S239K/M252W/T307P/M428Y/N434Y |
| F379 | 9.00E−09 | S239K/M252W/T256E/V308P/Q311A/M428Y/N434Y |
| F380 | 5.60E−09 | S239K/M252W/T256E/N286E/V308P/M428Y/N434Y |
| F381 | 1.10E−07 | P257V/T307A/Q311A/M428L/N434Y |
| F382 | 8.70E−08 | P257V/V305A/T307A/M428L/N434Y |
| F386 | 3.20E−08 | M252Y/V308P/L309E/N434Y |
| F387 | 1.50E−07 | M252Y/V308P/L309D/N434Y |
| F388 | 7.00E−08 | M252Y/V308P/L309A/N434Y |
| F389 | 1.70E−08 | M252W/V308P/L309E/M428Y/N434Y |
| F390 | 6.80E−08 | M252W/V308P/L309D/M428Y/N434Y |
| F391 | 3.60E−08 | M252W/V308P/L309A/M428Y/N434Y |
| F392 | 6.90E−09 | S239K/M252Y/N286E/V308P/M428I/N434Y |
| F393 | 1.20E−08 | S239K/M252Y/N286E/V308P/N434Y |
| F394 | 5.30E−08 | S239K/M252Y/T307Q/Q311A/M428I/N434Y |
| F395 | 2.40E−08 | S239K/M252Y/T256E/V308P/N434Y |
| F396 | 2.00E−08 | S239K/M252Y/D270F/N286E/T307Q/Q311A/M428I/N434Y |
| F397 | 4.50E−08 | S239K/M252Y/D270F/T307Q/Q311A/P387E/M428I/N434Y |
| F398 | 4.40E−09 | S239K/M252Y/D270F/N286E/T307Q/V308P/Q311A/M428I/N434Y |
| F399 | 6.50E−09 | S239K/M252Y/D270F/N286E/T307Q/V308P/M428I/N434Y |
| F400 | 6.10E−09 | S239K/M252Y/D270F/N286E/V308P/Q311A/M428I/N434Y |

Table 28-9 is the continuation of Table 28-8.

TABLE 28-9

| | | |
|---|---|---|
| F401 | 6.90E−09 | S239K/M252Y/D270F/N286E/V308P/P387E/M428I/N434Y |
| F402 | 2.30E−08 | P257V/T307Q/M428L/N434W |
| F403 | 5.10E−08 | P257V/T307A/M428L/N434W |
| F404 | 9.40E−08 | P257A/T307Q/L309P/M428L/N434Y |
| F405 | 1.70E−07 | P257V/T307Q/L309P/M428L/N434Y |
| F406 | 1.50E−07 | P257A/T307Q/L309R/M428L/N434Y |
| F407 | 1.60E−07 | P257V/T307Q/L309R/M428L/N434Y |
| F408 | 2.50E−07 | P257V/N286E/M428L/N434Y |
| F409 | 2.00E−07 | P257V/P387E/M428L/N434Y |
| F410 | 2.20E−07 | P257V/T307H/M428L/N434Y |
| F411 | 1.30E−07 | P257V/T307N/M428L/N434Y |

TABLE 28-9-continued

| F412 | 8.80E-08 | P257V/T307G/M428L/N434Y |
|---|---|---|
| F413 | 1.20E-07 | P257V/T307P/M428L/N434Y |
| F414 | 1.10E-07 | P257V/T307S/M428L/N434Y |
| F415 | 5.60E-08 | P257V/N286E/T307A/M428L/N434Y |
| F416 | 9.40E-08 | P257V/T307A/P387E/M428L/N434Y |
| F418 | 6.20E-07 | S239K/M252Y/T307P/N325G/M428Y/N434Y |
| F419 | 1.60E-07 | M252Y/T307A/Q311H/K360H/N434Y |
| F420 | 1.50E-07 | M252Y/T307A/Q311H/P387E/N434Y |
| F421 | 1.30E-07 | M252Y/T307A/Q311H/M428A/N434Y |
| F422 | 1.80E-07 | M252Y/T307A/Q311H/E382A/N434Y |
| F423 | 8.40E-08 | M252Y/T307W/Q311H/N434Y |
| F424 | 9.40E-08 | S239K/P257A/V308P/M428L/N434Y |
| F425 | 8.00E-08 | P257A/V308P/L309E/M428L/N434Y |
| F426 | 8.40E-08 | P257V/T307Q/N434Y |
| F427 | 1.10E-07 | M252Y/P257V/T307Q/M428V/N434Y |
| F428 | 8.00E-08 | M252Y/P257V/T307Q/M428L/N434Y |
| F429 | 3.70E-08 | M252Y/P257V/T307Q/N434Y |
| F430 | 8.10E-08 | M252Y/P257V/T307Q/M428Y/N434Y |
| F431 | 6.50E-08 | M252Y/P257V/T307Q/M428F/N434Y |
| F432 | 9.20E-07 | P257V/T307Q/Q311A/N325G/M428V/N434Y |
| F433 | 6.00E-08 | P257V/T307Q/Q311A/N325G/N434Y |
| F434 | 2.00E-08 | P257V/T307Q/Q311A/N325G/M428Y/N434Y |
| F435 | 2.50E-08 | P257V/T307Q/Q311A/N325G/M428F/N434Y |
| F436 | 2.50E-07 | P257A/T307Q/M428V/N434Y |
| F437 | 5.70E-08 | P257A/T307Q/N434Y |
| F438 | 3.60E-08 | P257A/T307Q/M428Y/N434Y |
| F439 | 4.00E-08 | P257A/T307Q/M428F/N434Y |
| F440 | 1.50E-08 | P257V/N286E/T307Q/Q311A/N325G/M428L/N434Y |
| F441 | 1.80E-07 | P257A/Q311A/M428L/N434Y |
| F442 | 2.00E-07 | P257A/Q311H/M428L/N434Y |
| F443 | 5.50E-08 | P257A/T307Q/Q311A/M428L/N434Y |

Table 28-10 is the continuation of Table 28-9.

TABLE 28-10

| F444 | 1.40E-07 | P257A/T307A/Q311A/M428L/N434Y |
|---|---|---|
| F445 | 6.20E-08 | P257A/T307Q/Q311H/M428L/N434Y |
| F446 | 1.10E-07 | P257A/T307A/Q311H/M428L/N434Y |
| F447 | 1.40E-08 | P257A/N286E/T307Q/M428L/N434Y |
| F448 | 5.30E-08 | P257A/N286E/T307A/M428L/N434Y |
| F449 | 5.70E-07 | S239K/M252Y/D270F/T307P/N325G/M428Y/N434Y |
| F450 | 5.20E-07 | S239K/M252Y/T307P/L309E/N325G/M428Y/N434Y |
| F451 | 1.00E-07 | P257S/T307A/M428L/N434Y |
| F452 | 1.40E-07 | P257M/T307A/M428L/N434Y |
| F453 | 7.80E-08 | P257N/T307A/M428L/N434Y |
| F454 | 9.60E-08 | P257I/T307A/M428L/N434Y |
| F455 | 2.70E-08 | P257V/T307Q/M428Y/N434Y |
| F456 | 3.40E-08 | P257V/T307Q/M428F/N434Y |
| F457 | 4.00E-08 | S239K/P257V/V308P/M428L/N434Y |
| F458 | 1.50E-08 | P257V/T307Q/V308P/N325G/M428L/N434Y |
| F459 | 1.30E-08 | P257V/T307Q/V308P/Q311A/N325G/M428L/N434Y |
| F460 | 4.70E-08 | P257V/T307A/V308P/N325G/M428L/N434Y |
| F462 | 8.50E-08 | P257A/V308P/N325G/M428L/N434Y |
| F463 | 1.30E-07 | P257A/T307A/V308P/M428L/N434Y |
| F464 | 5.50E-08 | P257A/T307Q/V308P/M428L/N434Y |
| F465 | 2.10E-08 | P257A/N286E/T307Q/N325G/M428L/N434Y |
| F466 | 3.50E-07 | T256E/P257V/N434Y |
| F467 | 5.70E-07 | T256E/P257T/N434Y |
| F468 | 5.70E-08 | S239K/P257T/V308P/M428L/N434Y |
| F469 | 5.60E-08 | P257T/V308P/N325G/M428L/N434Y |
| F470 | 5.40E-08 | T256E/P257T/V308P/N325G/M428L/N434Y |
| F471 | 6.60E-08 | P257T/V308P/N325G/E382A/M428L/N434Y |
| F472 | 5.40E-07 | P257T/V308P/N325G/P387E/M428L/N434Y |
| F473 | 4.50E-07 | P257T/V308P/L309P/N325G/M428L/N434Y |
| F474 | 3.50E-07 | P257T/V308P/L309R/N325G/M428L/N434Y |
| F475 | 4.30E-08 | T256E/P257V/T307Q/M428L/N434Y |
| F476 | 5.50E-08 | P257V/T307Q/E382A/M428L/N434Y |
| F477 | 4.30E-08 | P257V/T307Q/P387E/M428L/N434Y |
| F480 | 3.90E-08 | P257L/V308P/N434Y |
| F481 | 5.60E-08 | P257T/T307Q/N434Y |
| F482 | 7.00E-08 | P257V/T307Q/N325G/N434Y |
| F483 | 5.70E-08 | P257V/T307Q/Q311A/N434Y |
| F484 | 6.20E-08 | P257V/V305A/T307Q/N434Y |
| F485 | 9.70E-08 | P257V/N286E/T307A/N434Y |

TABLE 28-10-continued

| F486 | 3.40E-07 | P257V/T307Q/L309R/Q311H/M428L/N434Y |
|---|---|---|
| F488 | 3.50E-08 | P257V/V308P/N325G/M428L/N434Y |
| F490 | 7.50E-08 | S239K/P257V/V308P/Q311H/M428L/N434Y |

Table 28-11 is the continuation of Table 28-10.

TABLE 28-11

| F492 | 9.80E-08 | P257V/V305A/T307A/N325G/M428L/N434Y |
|---|---|---|
| F493 | 4.90E-07 | S239K/D270F/T307P/N325G/M428Y/N434Y |
| F497 | 3.10E-06 | P257T/T307A/M428V/N434Y |
| F498 | 1.30E-06 | P257A/M428V/N434Y |
| F499 | 5.20E-07 | P257A/T307A/M428V/N434Y |
| F500 | 4.30E-08 | P257S/T307Q/M428L/N434Y |
| F506 | 1.90E-07 | P257V/N297A/T307Q/M428L/N434Y |
| F507 | 5.10E-08 | P257V/N286A/T307Q/M428L/N434Y |
| F508 | 1.10E-07 | P257V/T307Q/N315A/M428L/N434Y |
| F509 | 5.80E-08 | P257V/T307Q/N384A/M428L/N434Y |
| F510 | 5.30E-08 | P257V/T307Q/N389A/M428L/N434Y |
| F511 | 4.20E-07 | P257V/N434Y |
| F512 | 5.80E-07 | P257T/N434Y |
| F517 | 3.10E-07 | P257V/N286E/N434Y |
| F518 | 4.20E-07 | P257T/N286E/N434Y |
| F519 | 2.60E-08 | P257V/N286E/T307Q/N434Y |
| F521 | 1.10E-08 | P257V/N286E/T307Q/M428Y/N434Y |
| F523 | 2.60E-08 | P257V/V305A/T307Q/M428Y/N434Y |
| F526 | 1.90E-08 | P257T/T307Q/M428Y/N434Y |
| F527 | 9.40E-09 | P257V/T307Q/V308P/N325G/M428Y/N434Y |
| F529 | 2.50E-08 | P257T/T307Q/M428F/N434Y |
| F533 | 1.20E-08 | P257A/N286E/T307Q/M428F/N434Y |
| F534 | 1.20E-08 | P257A/N286E/T307Q/M428Y/N434Y |
| F535 | 3.90E-08 | T250A/P257V/T307Q/M428L/N434Y |
| F538 | 9.90E-08 | T250F/P257V/T307Q/M428L/N434Y |
| F541 | 6.00E-08 | T250I/P257V/T307Q/M428L/N434Y |
| F544 | 3.10E-08 | T250M/P257V/T307Q/M428L/N434Y |
| F549 | 5.40E-08 | T250S/P257V/T307Q/M428L/N434Y |
| F550 | 5.90E-08 | T250V/P257V/T307Q/M428L/N434Y |
| F551 | 1.20E-07 | T250W/P257V/T307Q/M428L/N434Y |
| F552 | 1.10E-07 | T250Y/P257V/T307Q/M428L/N434Y |
| F553 | 1.70E-07 | M252Y/Q311A/N434Y |
| F554 | 2.80E-08 | S239K/M252Y/S254T/V308P/N434Y |
| F556 | 1.50E-06 | M252Y/T307Q/Q311A |
| F559 | 8.00E-08 | M252Y/S254T/N286E/N434Y |
| F560 | 2.80E-08 | M252Y/S254T/V308P/N434Y |
| F561 | 1.40E-07 | M252Y/S254T/T307A/N434Y |
| F562 | 8.30E-08 | M252Y/S254T/T307Q/N434Y |
| F563 | 1.30E-07 | M252Y/S254T/Q311A/N434Y |
| F564 | 1.90E-07 | M252Y/S254T/Q311H/N434Y |
| F565 | 9.20E-08 | M252Y/S254T/T307A/Q311A/N434Y |
| F566 | 6.10E-08 | M252Y/S254T/T307Q/Q311A/N434Y |

Table 28-12 is the continuation of Table 28-11.

TABLE 28-12

| F567 | 2.20E-07 | M252Y/S254T/M428I/N434Y |
|---|---|---|
| F568 | 1.10E-07 | M252Y/T256E/T307A/Q311H/N434Y |
| F569 | 2.00E-07 | M252Y/T256Q/T307A/Q311H/N434Y |
| F570 | 1.30E-07 | M252Y/S254T/T307A/Q311H/N434Y |
| F571 | 8.10E-08 | M252Y/N286E/T307A/Q311H/N434Y |
| F572 | 1.00E-07 | M252Y/T307A/Q311H/M428I/N434Y |
| F576 | 1.60E-06 | M252Y/T256E/T307Q/Q311H |
| F577 | 1.30E-06 | M252Y/N286E/T307A/Q311A |
| F578 | 5.70E-07 | M252Y/N286E/T307Q/Q311A |
| F580 | 8.60E-08 | M252Y/N286E/T307Q/Q311H |
| F581 | 7.20E-08 | M252Y/T256E/N286E/N434Y |
| F582 | 7.50E-07 | S239K/M252Y/V308P |
| F583 | 7.80E-07 | S239K/M252Y/V308P/E382A |
| F584 | 6.30E-08 | S239K/M252Y/T256E/V308P |
| F585 | 2.90E-07 | S239K/M252Y/N286E/V308P |
| F586 | 1.40E-07 | S239K/M252Y/N286E/V308P/M428I |
| F587 | 1.90E-07 | M252Y/N286E/M428L/N434Y |
| F592 | 2.00E-07 | M252Y/S254T/E382A/N434Y |
| F593 | 3.10E-08 | S239K/M252Y/S254T/V308P/M428I/N434Y |
| F594 | 1.60E-08 | S239K/M252Y/T256E/V308P/M428I/N434Y |
| F595 | 1.80E-07 | S239K/M252Y/M428I/N434Y |
| F596 | 4.00E-07 | M252Y/D312A/E382A/M428Y/N434Y |

TABLE 28-12-continued

| | | |
|---|---|---|
| F597 | 2.20E−07 | M252Y/E382A/P387E/N434Y |
| F598 | 1.40E−07 | M252Y/D312A/P387E/N434Y |
| F599 | 5.20E−07 | M252Y/P387E/M428Y/N434Y |
| F600 | 2.80E−07 | M252Y/T256Q/E382A/N434Y |
| F601 | 9.60E−09 | M252Y/N286E/V308P/N434Y |
| F608 | | G236A/S239D/I332E |
| F611 | 2.80E−07 | M252Y/V305T/T307P/V308I/L309A/N434Y |
| F612 | 3.60E−07 | M252Y/T307P/V308I/L309A/N434Y |
| F613 | | S239D/A330L/I332E |
| F616 | | S239D/K326D/L328Y |
| F617 | 7.40E−07 | S239K/N434W |
| F618 | 6.40E−07 | S239K/V308F/N434Y |
| F619 | 3.10E−07 | S239K/M252Y/N434Y |
| F620 | 2.10E−07 | S239K/M252Y/S254T/N434Y |
| F621 | 1.50E−07 | S239K/M252Y/T307A/Q311H/N434Y |
| F622 | 3.50E−07 | S239K/M252Y/T256Q/N434Y |
| F623 | 1.80E−07 | S239K/M252W/N434W |
| F624 | 1.40E−07 | S239K/P257A/N286E/T307Q/M428L/N434Y |
| F625 | 7.60E−08 | S239K/P257A/T307Q/M428L/N434Y |
| F626 | 1.30E−06 | V308P |

Table 28-13 is the continuation of Table 28-12.

TABLE 28-13

| | | |
|---|---|---|
| F629 | 3.90E−08 | M252Y/V279L/V308P/N434Y |
| F630 | 3.70E−08 | S239K/M252Y/V279L/V308P/N434Y |
| F633 | 2.40E−08 | M252Y/V282D/V308P/N434Y |
| F634 | 3.20E−08 | S239K/M252Y/V282D/V308P/N434Y |
| F635 | 4.50E−08 | M252Y/V284K/V308P/N434Y |
| F636 | 4.80E−08 | S239K/M252Y/V284K/V308P/N434Y |
| F637 | 1.50E−07 | M252Y/K288S/V308P/N434Y |
| F638 | 1.40E−07 | S239K/M252Y/K288S/V308P/N434Y |
| F639 | 2.70E−08 | M252Y/V308P/G385R/N434Y |
| F640 | 3.60E−08 | S239K/M252Y/V308P/G385R/N434Y |
| F641 | 3.00E−08 | M252Y/V308P/Q386K/N434Y |
| F642 | 3.00E−08 | S239K/M252Y/V308P/Q386K/N434Y |
| F643 | 3.20E−08 | L235G/G236R/S239K/M252Y/V308P/N434Y |
| F644 | 3.00E−08 | G236R/S239K/M252Y/V308P/N434Y |
| F645 | 3.30E−08 | S239K/M252Y/V308P/L328E/N434Y |
| F646 | 3.80E−08 | S239K/M252Y/N297A/V308P/N434Y |
| F647 | 2.90E−08 | P238D/M252Y/V308P/N434Y |
| F648 | | P238D |
| F649 | 1.20E−07 | S239K/M252Y/N286E/N434Y |
| F650 | 1.70E−07 | S239K/M252Y/T256E/N434Y |
| F651 | 1.80E−07 | S239K/M252Y/Q311A/N434Y |
| F652 | 2.40E−07 | P238D/M252Y/N434Y |
| F654 | 3.20E−08 | L235K/S239K/M252Y/V308P/N434Y |
| F655 | 3.40E−08 | L235R/S239K/M252Y/V308P/N434Y |
| F656 | 3.30E−08 | G237K/S239K/M252Y/V308P/N434Y |
| F657 | 3.20E−08 | G237R/S239K/M252Y/V308P/N434Y |
| F658 | 3.20E−08 | P238K/S239K/M252Y/V308P/N434Y |
| F659 | 3.00E−08 | P238R/S239K/M252Y/V308P/N434Y |
| F660 | 3.10E−08 | S239K/M252Y/V308P/P329K/N434Y |
| F661 | 3.40E−08 | S239K/M252Y/V308P/P329R/N434Y |
| F663 | 6.40E−09 | S239K/M252Y/N286E/T307Q/V308P/Q311A/N434Y |
| F664 | 3.90E−08 | M252Y/N286A/V308P/N434Y |
| F665 | 2.00E−08 | M252Y/N286D/V308P/N434Y |
| F666 | 2.10E−08 | M252Y/N286F/V308P/N434Y |
| F667 | 3.00E−08 | M252Y/N286G/V308P/N434Y |
| F668 | 4.00E−08 | M252Y/N286H/V308P/N434Y |
| F669 | 3.50E−08 | M252Y/N286I/V308P/N434Y |
| F670 | 2.10E−07 | M252Y/N286K/V308P/N434Y |
| F671 | 2.20E−08 | M252Y/N286L/V308P/N434Y |
| F672 | 2.40E−08 | M252Y/N286M/V308P/N434Y |
| F673 | 2.30E−08 | M252Y/N286P/V308P/N434Y |
| F674 | 3.20E−08 | M252Y/N286Q/V308P/N434Y |

Table 28-14 is the continuation of Table 28-13.

TABLE 28-14

| | | |
|---|---|---|
| F675 | 5.10E−08 | M252Y/N286R/V308P/N434Y |
| F676 | 3.20E−08 | M252Y/N286S/V308P/N434Y |
| F677 | 4.70E−08 | M252Y/N286T/V308P/N434Y |
| F678 | 3.30E−08 | M252Y/N286V/V308P/N434Y |
| F679 | 1.70E−08 | M252Y/N286W/V308P/N434Y |
| F680 | 1.50E−08 | M252Y/N286Y/V308P/N434Y |
| F681 | 4.90E−08 | M252Y/K288A/V308P/N434Y |
| F682 | 8.20E−08 | M252Y/K288D/V308P/N434Y |
| F683 | 5.00E−08 | M252Y/K288E/V308P/N434Y |
| F684 | 5.10E−08 | M252Y/K288F/V308P/N434Y |
| F685 | 5.30E−08 | M252Y/K288G/V308P/N434Y |
| F686 | 4.60E−08 | M252Y/K288H/V308P/N434Y |
| F687 | 4.90E−08 | M252Y/K288I/V308P/N434Y |
| F688 | 2.80E−08 | M252Y/K288L/V308P/N434Y |
| F689 | 4.10E−08 | M252Y/K288M/V308P/N434Y |
| F690 | 1.00E−07 | M252Y/K288N/V308P/N434Y |
| F691 | 3.20E−07 | M252Y/K288P/V308P/N434Y |
| F692 | 3.90E−08 | M252Y/K288Q/V308P/N434Y |
| F693 | 3.60E−08 | M252Y/K288R/V308P/N434Y |
| F694 | 4.70E−08 | M252Y/K288V/V308P/N434Y |
| F695 | 4.00E−08 | M252Y/K288W/V308P/N434Y |
| F696 | 4.40E−08 | M252Y/K288Y/V308P/N434Y |
| F697 | 3.10E−08 | S239K/M252Y/V308P/N325G/N434Y |
| F698 | 2.20E−08 | M252Y/N286E/T307Q/Q311A/N434Y |
| F699 | 2.30E−08 | S239K/M252Y/N286E/T307Q/Q311A/N434Y |
| F700 | 5.20E−08 | M252Y/V308P/L328E/N434Y |
| F705 | 7.10E−09 | M252Y/N286E/V308P/M428I/N434Y |
| F706 | 1.80E−08 | M252Y/N286E/T307Q/Q311A/M428I/N434Y |
| F707 | 5.90E−09 | M252Y/N286E/T307Q/V308P/Q311A/N434Y |
| F708 | 4.10E−09 | M252Y/N286E/T307Q/V308P/Q311A/M428I/N434Y |
| F709 | 2.00E−08 | S239K/M252Y/N286E/T307Q/Q311A/M428I/N434Y |
| F710 | 1.50E−08 | P238D/M252Y/N286E/T307Q/Q311A/M428I/N434Y |
| F711 | 6.50E−08 | S239K/M252Y/T307Q/Q311A/N434Y |
| F712 | 6.00E−08 | P238D/M252Y/T307Q/Q311A/N434Y |
| F713 | 2.00E−08 | P238D/M252Y/N286E/T307Q/Q311A/N434Y |
| F714 | 2.30E−07 | P238D/M252Y/N325S/N434Y |
| F715 | 2.30E−07 | P238D/M252Y/N325M/N434Y |
| F716 | 2.70E−07 | P238D/M252Y/N325L/N434Y |
| F717 | 2.60E−07 | P238D/M252Y/N325I/N434Y |
| F718 | 2.80E−07 | P238D/M252Y/Q295M/N434Y |
| F719 | 7.40E−08 | P238D/M252Y/N325G/N434Y |
| F720 | 2.40E−08 | M252Y/T307Q/V308P/Q311A/N434Y |

Table 28-15 is a continuation of Table 28-14.

TABLE 28-15

| | | |
|---|---|---|
| F721 | 1.50E−08 | M252Y/T307Q/V308P/Q311A/M428I/N434Y |
| F722 | 2.70E−07 | P238D/M252Y/A327G/N434Y |
| F723 | 2.80E−07 | P238D/M252Y/L328D/N434Y |
| F724 | 2.50E−07 | P238D/M252Y/L328E/N434Y |
| F725 | 4.20E−08 | L235K/G237R/S239K/M252Y/V308P/N434Y |
| F726 | 3.70E−08 | L235K/P238K/S239K/M252Y/V308P/N434Y |
| F729 | 9.20E−07 | T307A/Q311A/N434Y |
| F730 | 6.00E−07 | T307Q/Q311A/N434Y |
| F731 | 8.50E−07 | T307A/Q311H/N434Y |
| F732 | 6.80E−07 | T307Q/Q311H/N434Y |
| F733 | 3.20E−07 | M252Y/L328E/N434Y |
| F734 | 3.10E−07 | G236D/M252Y/L328E/N434Y |
| F736 | 3.10E−07 | M252Y/S267M/L328E/N434Y |
| F737 | 3.10E−07 | M252Y/S267L/L328E/N434Y |
| F738 | 3.50E−07 | P238D/M252Y/T307P/N434Y |
| F739 | 2.20E−07 | M252Y/T307P/Q311A/N434Y |
| F740 | 2.90E−07 | M252Y/T307P/Q311H/N434Y |
| F741 | 3.10E−07 | P238D/T250A/M252Y/N434Y |
| F744 | 9.90E−07 | P238D/T250F/M252Y/N434Y |
| F745 | 6.60E−07 | P238D/T250G/M252Y/N434Y |
| F746 | 6.00E−07 | P238D/T250H/M252Y/N434Y |
| F747 | 2.80E−07 | P238D/T250I/M252Y/N434Y |
| F749 | 5.10E−07 | P238D/T250L/M252Y/N434Y |
| F750 | 3.00E−07 | P238D/T250M/M252Y/N434Y |
| F751 | 5.30E−07 | P238D/T250N/M252Y/N434Y |
| F753 | 1.80E−07 | P238D/T250Q/M252Y/N434Y |
| F755 | 3.50E−07 | P238D/T250S/M252Y/N434Y |
| F756 | 3.70E−07 | P238D/T250V/M252Y/N434Y |
| F757 | 1.20E−06 | P238D/T250W/M252Y/N434Y |
| F758 | 1.40E−06 | P238D/T250Y/M252Y/N434Y |
| F759 | | L235K/S239K |
| F760 | | L235R/S239K |
| F761 | 1.10E−06 | P238D/N434Y |
| F762 | 3.60E−08 | L235K/S239K/M252Y/N286E/T307Q/Q311A/N434Y |
| F763 | 3.50E−08 | L235R/S239K/M252Y/N286E/T307Q/Q311A/N434Y |
| F764 | 6.30E−07 | P238D/T307Q/Q311A/N434Y |

TABLE 28-15-continued

| | | |
|---|---|---|
| F765 | 8.50E−08 | P238D/M252Y/T307Q/L309E/Q311A/N434Y |
| F766 | 6.00E−07 | T307A/L309E/Q311A/N434Y |
| F767 | 4.30E−07 | T307Q/L309E/Q311A/N434Y |
| F768 | 6.40E−07 | T307A/L309E/Q311H/N434Y |
| F769 | 4.60E−07 | T307Q/L309E/Q311H/N434Y |
| F770 | 3.00E−07 | M252Y/T256A/N434Y |

Table 28-16 is a continuation of Table 28-15.

TABLE 28-16

| | | |
|---|---|---|
| F771 | 4.00E−07 | M252Y/E272A/N434Y |
| F772 | 3.80E−07 | M252Y/K274A/N434Y |
| F773 | 3.90E−07 | M252Y/V282A/N434Y |
| F774 | 4.00E−07 | M252Y/N286A/N434Y |
| F775 | 6.20E−07 | M252Y/K338A/N434Y |
| F776 | 3.90E−07 | M252Y/K340A/N434Y |
| F777 | 3.90E−07 | M252Y/E345A/N434Y |
| F779 | 3.90E−07 | M252Y/N361A/N434Y |
| F780 | 3.90E−07 | M252Y/Q362A/N434Y |
| F781 | 3.70E−07 | M252Y/S375A/N434Y |
| F782 | 3.50E−07 | M252Y/Y391A/N434Y |
| F783 | 4.00E−07 | M252Y/D413A/N434Y |
| F784 | 5.00E−07 | M252Y/L309A/N434Y |
| F785 | 7.40E−07 | M252Y/L309H/N434Y |
| F786 | 2.80E−08 | M252Y/S254T/N286E/T307Q/Q311A/N434Y |
| F787 | 8.80E−08 | M252Y/S254T/T307Q/L309E/Q311A/N434Y |
| F788 | 4.10E−07 | M252Y/N315A/N434Y |
| F789 | 1.50E−07 | M252Y/N315D/N434Y |
| F790 | 2.70E−07 | M252Y/N315E/N434Y |
| F791 | 4.40E−07 | M252Y/N315F/N434Y |
| F792 | 4.40E−07 | M252Y/N315G/N434Y |
| F793 | 3.30E−07 | M252Y/N315I/N434Y |
| F794 | 4.10E−07 | M252Y/N315K/N434Y |
| F795 | 3.10E−07 | M252Y/N315L/N434Y |
| F796 | 3.40E−07 | M252Y/N315M/N434Y |
| F798 | 3.50E−07 | M252Y/N315Q/N434Y |
| F799 | 4.10E−07 | M252Y/N315R/N434Y |
| F800 | 3.80E−07 | M252Y/N315S/N434Y |
| F801 | 4.40E−07 | M252Y/N315T/N434Y |
| F802 | 3.30E−07 | M252Y/N315V/N434Y |
| F803 | 3.60E−07 | M252Y/N315W/N434Y |
| F804 | 4.00E−07 | M252Y/N315Y/N434Y |
| F805 | 3.00E−07 | M252Y/N325A/N434Y |
| F806 | 3.10E−07 | M252Y/N384A/N434Y |
| F807 | 3.20E−07 | M252Y/N389A/N434Y |
| F808 | 3.20E−07 | M252Y/N389A/N390A/N434Y |
| F809 | 2.20E−07 | M252Y/S254T/T256S/N434Y |
| F810 | 2.20E−07 | M252Y/A378V/N434Y |
| F811 | 4.90E−07 | M252Y/E380S/N434Y |
| F812 | 2.70E−07 | M252Y/E382V/N434Y |
| F813 | 2.80E−07 | M252Y/S424E/N434Y |
| F814 | 1.20E−07 | M252Y/N434Y/Y436I |

Table 28-17 is a continuation of Table 28-16.

TABLE 28-17

| | | |
|---|---|---|
| F815 | 5.50E−07 | M252Y/N434Y/T437R |
| F816 | 3.60E−07 | P238D/T250V/M252Y/T307P/N434Y |
| F817 | 9.80E−08 | P238D/T250V/M252Y/T307Q/Q311A/N434Y |
| F819 | 1.40E−07 | P238D/M252Y/N286E/N434Y |
| F820 | 3.40E−07 | L235K/S239K/M252Y/N434Y |
| F821 | 3.10E−07 | L235R/S239K/M252Y/N434Y |
| F822 | 1.10E−06 | P238D/T250Y/M252Y/W313Y/N434Y |
| F823 | 1.10E−06 | P238D/T250Y/M252Y/W313F/N434Y |
| F828 | 2.50E−06 | P238D/T250V/M252Y/I253V/N434Y |
| F831 | 1.60E−06 | P238D/T250V/M252Y/R255A/N434Y |
| F832 | 2.60E−06 | P238D/T250V/M252Y/R255D/N434Y |
| F833 | 8.00E−07 | P238D/T250V/M252Y/R255E/N434Y |
| F834 | 8.10E−07 | P238D/T250V/M252Y/R255F/N434Y |
| F836 | 5.00E−07 | P238D/T250V/M252Y/R255H/N434Y |
| F837 | 5.60E−07 | P238D/T250V/M252Y/R255I/N434Y |
| F838 | 4.30E−07 | P238D/T250V/M252Y/R255K/N434Y |
| F839 | 3.40E−07 | P238D/T250V/M252Y/R255L/N434Y |
| F840 | 4.20E−07 | P238D/T250V/M252Y/R255M/N434Y |
| F841 | 1.10E−06 | P238D/T250V/M252Y/R255N/N434Y |
| F843 | 6.60E−07 | P238D/T250V/M252Y/R255Q/N434Y |
| F844 | 1.30E−06 | P238D/T250V/M252Y/R255S/N434Y |
| F847 | 3.40E−07 | P238D/T250V/M252Y/R255W/N434Y |
| F848 | 8.30E−07 | P238D/T250V/M252Y/R255Y/N434Y |
| F849 | 3.30E−07 | M252Y/D280A/N434Y |
| F850 | 2.90E−07 | M252Y/D280E/N434Y |
| F852 | 3.30E−07 | M252Y/D280G/N434Y |
| F853 | 3.20E−07 | M252Y/D280H/N434Y |
| F855 | 3.20E−07 | M252Y/D280K/N434Y |
| F858 | 3.20E−07 | M252Y/D280N/N434Y |
| F860 | 3.30E−07 | M252Y/D280Q/N434Y |
| F861 | 3.20E−07 | M252Y/D280R/N434Y |
| F862 | 3.00E−07 | M252Y/D280S/N434Y |
| F863 | 2.70E−07 | M252Y/D280T/N434Y |
| F867 | 2.80E−07 | M252Y/N384A/N389A/N434Y |
| F868 | 2.00E−08 | G236A/S239D/M252Y/N286E/T307Q/Q311A/N434Y |
| F869 | | G236A/S239D |
| F870 | 7.30E−08 | L235K/S239K/M252Y/T307Q/Q311A/N434Y |
| F871 | 7.10E−08 | L235R/S239K/M252Y/T307Q/Q311A/N434Y |
| F872 | 1.30E−07 | L235K/S239K/M252Y/N286E/N434Y |
| F873 | 1.20E−07 | L235R/S239K/M252Y/N286E/N434Y |
| F875 | 4.80E−07 | M252Y/N434Y/Y436A |
| F877 | 8.30E−07 | M252Y/N434Y/Y436E |

Table 28-18 is a continuation of Table 28-17.

TABLE 28-18

| | | |
|---|---|---|
| F878 | 1.90E−07 | M252Y/N434Y/Y436F |
| F879 | 9.20E−07 | M252Y/N434Y/Y436G |
| F880 | 3.90E−07 | M252Y/N434Y/Y436H |
| F881 | 3.10E−07 | M252Y/N434Y/Y436K |
| F882 | 1.30E−07 | M252Y/N434Y/Y436L |
| F883 | 2.10E−07 | M252Y/N434Y/Y436M |
| F884 | 4.00E−07 | M252Y/N434Y/Y436N |
| F888 | 4.80E−07 | M252Y/N434Y/Y436S |
| F889 | 2.20E−07 | M252Y/N434Y/Y436T |
| F890 | 1.10E−07 | M252Y/N434Y/Y436V |
| F891 | 1.70E−07 | M252Y/N434Y/Y436W |
| F892 | 7.10E−08 | M252Y/S254T/N434Y/Y436I |
| F893 | 9.80E−08 | L235K/S239K/M252Y/N434Y/Y436I |
| F894 | 9.20E−08 | L235R/S239K/M252Y/N434Y/Y436I |
| F895 | 2.10E−08 | L235K/S239K/M252Y/N286E/T307Q/Q311A/N315E/N434Y |
| F896 | 2.00E−08 | L235R/S239K/M252Y/N286E/T307Q/Q311A/N315E/N434Y |
| F897 | 9.70E−08 | M252Y/N315D/N384A/N389A/N434Y |
| F898 | 1.70E−07 | M252Y/N315E/N384A/N389A/N434Y |
| F899 | 1.10E−07 | M252Y/N315D/G316A/N434Y |
| F900 | 1.70E−07 | M252Y/N315D/G316D/N434Y |
| F901 | 1.30E−07 | M252Y/N315D/G316E/N434Y |
| F902 | 2.20E−07 | M252Y/N315D/G316F/N434Y |
| F903 | 2.30E−07 | M252Y/N315D/G316H/N434Y |
| F904 | 1.00E−07 | M252Y/N315D/G316I/N434Y |
| F905 | 1.30E−07 | M252Y/N315D/G316K/N434Y |
| F906 | 1.50E−07 | M252Y/N315D/G316L/N434Y |
| F907 | 1.30E−07 | M252Y/N315D/G316M/N434Y |
| F908 | 1.50E−07 | M252Y/N315D/G316N/N434Y |
| F909 | 1.30E−07 | M252Y/N315D/G316P/N434Y |
| F910 | 1.40E−07 | M252Y/N315D/G316Q/N434Y |
| F911 | 1.30E−07 | M252Y/N315D/G316R/N434Y |
| F912 | 1.20E−07 | M252Y/N315D/G316S/N434Y |
| F913 | 1.10E−07 | M252Y/N315D/G316T/N434Y |
| F914 | 1.50E−07 | M252Y/N315D/G316V/N434Y |
| F915 | 2.30E−07 | M252Y/N315D/G316W/N434Y |
| F917 | 2.50E−07 | M252Y/N286S/N434Y |
| F918 | 2.80E−07 | M252Y/D280E/N384A/N389A/N434Y |
| F919 | 3.30E−07 | M252Y/D280G/N384A/N389A/N434Y |
| F920 | 2.50E−07 | M252Y/N286S/N384A/N389A/N434Y |
| F921 | 1.20E−07 | M252Y/N286E/N384A/N389A/N434Y |
| F922 | 5.90E−08 | L235K/S239K/M252Y/N286E/N434Y/Y436I |
| F923 | 6.00E−08 | L235R/S239K/M252Y/N286E/N434Y/Y436I |

Table 28-19 is the continuation of Table 28-18.

TABLE 28-19

| | | |
|---|---|---|
| F924 | 3.40E-08 | L235K/S239K/M252Y/T307Q/Q311A/N434Y/Y436I |
| F925 | 3.20E-08 | L235R/S239K/M252Y/T307Q/Q311A/N434Y/Y436I |
| F926 | 1.10E-07 | L235K/S239K/M252Y/S254T/N434Y/Y436I |
| F927 | 1.00E-07 | L235R/S239K/M252Y/S254T/N434Y/Y436I |
| F928 | 2.90E-08 | M252Y/T307Q/Q311A/N434Y/Y436I |
| F929 | 2.90E-08 | M252Y/S254T/T307Q/Q311A/N434Y/Y436I |
| F930 | 1.40E-07 | P238D/T250V/M252Y/N286E/N434Y |
| F931 | 1.20E-07 | P238D/T250V/M252Y/N434Y/Y436I |
| F932 | 3.20E-07 | T250V/M252Y/N434Y |
| F933 | 3.00E-07 | L234R/P238D/T250V/M252Y/N434Y |
| F934 | 3.10E-07 | G236K/P238D/T250V/M252Y/N434Y |
| F935 | 3.20E-07 | G237K/P238D/T250V/M252Y/N434Y |
| F936 | 3.20E-07 | G237R/P238D/T250V/M252Y/N434Y |
| F937 | 3.10E-07 | P238D/S239K/T250V/M252Y/N434Y |
| F938 | 1.60E-07 | L235K/S239K/M252Y/N434Y/Y436V |
| F939 | 1.50E-07 | L235R/S239K/M252Y/N434Y/Y436V |
| F940 | 1.50E-07 | P238D/T250V/M252Y/N434Y/Y436V |
| F941 | 1.20E-08 | M252Y/N286E/T307Q/Q311A/N434Y/Y436V |
| F942 | 4.20E-08 | L235K/S239K/M252Y/T307Q/Q311A/N434Y/Y436V |
| F943 | 4.00E-08 | L235R/S239K/M252Y/T307Q/Q311A/N434Y/Y436V |
| F944 | 1.70E-07 | T250V/M252Y/N434Y/Y436V |
| F945 | 1.70E-08 | T250V/M252Y/V308P/N434Y/Y436V |

TABLE 28-19-continued

| | | |
|---|---|---|
| F946 | 4.30E-08 | T250V/M252Y/T307Q/Q311A/N434Y/Y436V |
| F947 | 1.10E-08 | T250V/M252Y/T307Q/V308P/Q311A/N434Y/Y436V |
| F954 | 5.30E-07 | M252Y/N434Y/H435K/Y436V |
| F957 | 7.70E-07 | M252Y/N434Y/H435N/Y436V |
| F960 | 8.00E-07 | M252Y/N434Y/H435R/Y436V |
| F966 | 3.10E-07 | M252Y/S254A/N434Y |
| F970 | 2.50E-06 | M252Y/S254G/N434Y |
| F971 | 2.60E-06 | M252Y/S254H/N434Y |
| F972 | 2.60E-07 | M252Y/S254I/N434Y |
| F978 | 1.30E-06 | M252Y/S254Q/N434Y |
| F980 | 1.80E-07 | M252Y/S254V/N434Y |
| F987 | 4.00E-08 | P238D/T250V/M252Y/T307Q/Q311A/N434Y/Y436V |
| F988 | 6.90E-08 | P238D/T250V/M252Y/N286E/N434Y/Y436V |
| F989 | 1.40E-08 | L235R/S239K/M252Y/V308P/N434Y/Y436V |
| F990 | 9.40E-09 | L235R/S239K/M252Y/T307Q/V308P/Q311A/N434Y/Y436V |
| F991 | 1.30E-08 | L235R/S239K/M252Y/N286E/T307Q/Q311A/N434Y/Y436V |
| F992 | 5.10E-08 | L235R/S239K/M252Y/T307Q/Q311A/M428I/N434Y/Y436V |
| F993 | 3.80E-08 | M252Y/T307Q/Q311A/N434Y/Y436V |
| F994 | 2.80E-07 | M252Y/N325G/N434Y |
| F995 | 2.90E-07 | L235R/P238D/S239K/M252Y/N434Y |

Table 28-20 is the continuation of Table 28-19.

TABLE 28-20

| | | |
|---|---|---|
| F996 | 1.30E-07 | L235R/P238D/S239K/M252Y/N434Y/Y436V |
| F997 | 3.80E-07 | K248I/T250V/M252Y/N434Y/Y436V |
| F998 | 8.50E-07 | K248Y/T250V/M252Y/N434Y/Y436V |
| F999 | 2.10E-07 | T250V/M252Y/E258H/N434Y/Y436V |
| F1005 | | N325G |
| F1008 | 1.70E-07 | L235R/S239K/T250V/M252Y/N434Y/Y436V |
| F1009 | 1.20E-08 | L235R/S239K/T250V/M252Y/T307Q/V308P/Q311A/N434Y/Y436V |
| F1010 | 1.90E-07 | L235R/S239K/M252Y/T307A/Q311H/N434Y |
| F1011 | 4.50E-08 | T250V/M252Y/V308P/N434Y |
| F1012 | 4.70E-08 | L235R/S239K/T250V/M252Y/V308P/N434Y |
| F1013 | 3.00E-08 | T250V/M252Y/T307Q/V308P/Q311A/N434Y |
| F1014 | 3.20E-08 | L235R/S239K/T250V/M252Y/T307Q/V308P/Q311A/N434Y |
| F1015 | 2.20E-08 | L235R/S239K/M252Y/T307Q/V308P/Q311A/N434Y |
| F1016 | 3.80E-09 | T250V/M252Y/N286E/T307Q/V308P/Q311A/N434Y/Y436V |
| F1017 | 4.20E-09 | L235R/S239K/T250V/M252Y/N286E/T307Q/V308P/Q311A/N434Y/Y436V |
| F1018 | 3.20E-09 | L235R/S239K/M252Y/N286E/T307Q/V308P/Q311A/N434Y/Y436V |
| F1019 | 3.40E-07 | P238D/T250V/M252Y/N325G/N434Y |
| F1020 | 8.50E-08 | P238D/T250V/M252Y/T307Q/Q311A/N325G/N434Y |
| F1021 | 3.30E-07 | P238D/T250V/M252Y/N325A/N434Y |
| F1022 | | K326D/L328Y |
| F1023 | 4.40E-08 | S239D/T250V/M252Y/T307Q/Q311A/N434Y/Y436V |
| F1024 | 4.00E-08 | T250V/M252Y/T307Q/Q311A/K326D/L328Y/N434Y/Y436V |
| F1025 | 3.60E-08 | S239D/T250V/M252Y/T307Q/Q311A/K326D/L328Y/N434Y/Y436V |
| F1026 | 8.40E-08 | M252Y/T307A/Q311H/N434Y/Y436V |
| F1027 | 8.60E-08 | L235R/S239K/M252Y/T307A/Q311H/N434Y/Y436V |
| F1028 | 4.60E-08 | G236A/S239D/T250V/M252Y/T307Q/Q311A/N434Y/Y436V |
| F1029 | 5.10E-08 | T250V/M252Y/T307Q/Q311A/I332E/N434Y/Y436V |
| F1030 | | I332E |
| F1031 | 5.30E-08 | G236A/S239D/T250V/M252Y/T307Q/Q311A/I332E/N434Y/Y436V |
| F1032 | 4.30E-08 | P238D/T250V/M252Y/T307Q/Q311A/N325G/N434Y/Y436V |
| F1033 | 1.00E-06 | P238D/N434W |
| F1034 | 1.50E-08 | L235K/S239K/M252Y/V308P/N434Y/Y436V |
| F1035 | 1.00E-08 | L235K/S239K/M252Y/T307Q/V308P/Q311A/N434Y/Y436V |
| F1036 | 1.40E-08 | L235K/S239K/M252Y/N286E/T307Q/Q311A/N434Y/Y436V |
| F1037 | 6.10E-08 | L235K/S239K/M252Y/T307Q/Q311A/M428I/N434Y/Y436V |
| F1038 | 2.80E-07 | L235K/P238D/S239K/M252Y/N434Y |
| F1039 | 1.30E-07 | L235K/P238D/S239K/M252Y/N434Y/Y436V |

Table 28-21 is the continuation of Table 28-20.

TABLE 28-21

| | | |
|---|---|---|
| F1040 | 2.00E-07 | L235K/S239K/T250V/M252Y/N434Y/Y436V |
| F1041 | 1.40E-08 | L235K/S239K/T250V/M252Y/T307Q/V308P/Q311A/N434Y/Y436V |
| F1042 | 2.00E-07 | L235K/S239K/M252Y/T307A/Q311H/N434Y |
| F1043 | 5.20E-08 | L235K/S239K/T250V/M252Y/V308P/N434Y |
| F1044 | 3.50E-08 | L235K/S239K/T250V/M252Y/T307Q/V308P/Q311A/N434Y |
| F1045 | 2.50E-08 | L235K/S239K/M252Y/T307Q/V308P/Q311A/N434Y |
| F1046 | 4.50E-09 | L235K/S239K/T250V/M252Y/N286E/T307Q/V308P/Q311A/N434Y/Y436V |
| F1047 | 3.40E-09 | L235K/S239K/M252Y/N286E/T307Q/V308P/Q311A/N434Y/Y436V |
| F1048 | 9.90E-08 | L235K/S239K/M252Y/T307A/Q311H/N434Y/Y436V |
| F1050 | 3.50E-09 | T250V/M252Y/N286E/T307Q/V308P/Q311A/M428I/N434Y/Y436V |
| F1051 | 3.90E-09 | L235R/S239K/T250V/M252Y/N286E/T307Q/V308P/Q311A/M428I/N434Y/Y436V |
| F1052 | 3.20E-09 | L235K/S239K/M252Y/N286E/T307Q/V308P/Q311A/M428I/N434Y/Y436V |

Reference Example 13

In Vivo Study of Various Fc Variant Antibodies by Steady-State Infusion Model Using Human FcRn Transgenic Mouse Lineage 32

Fc variants generated in Reference Example 12 was tested for their ability to eliminate antigen from plasma in steady-state infusion model using human FcRn transgenic mouse lineage 32. Steady-state infusion model in vivo study was performed as described in Example 1, but human FcRn transgenic mouse lineage 32 was used instead of lineage 276, and monoclonal anti-mouse CD4 antibody was administered twice (before infusion pump was implanted and 14 days after antibody administration) or three times (before infusion pump was implanted and 10 and 20 days after antibody administration).

From the Fc variants described in Tables 28-1 to 28-21, selected antibody Fc variants listed below were expressed and purified by methods known to those skilled in the art as described in Reference Example 3:

Fv4-IgG1 comprising VH3-IgG1 and VL3-CK;
Fv4-IgG1-F11 comprising VH3-IgG1-F11 and VL3-CK;
Fv4-IgG1-F14 comprising VH3-IgG1-F14 and VL3-CK;
Fv4-IgG1-F39 comprising VH3-IgG1-F39 and VL3-CK;
Fv4-IgG1-F48 comprising VH3-IgG1-F48 and VL3-CK;
Fv4-IgG1-F140 comprising VH3-IgG1-F140 and VL3-CK;
Fv4-IgG1-F157 comprising VH3-IgG1-F157 and VL3-CK;
Fv4-IgG1-F194 comprising VH3-IgG1-F194 and VL3-CK;
Fv4-IgG1-F196 comprising VH3-IgG1-F196 and VL3-CK;
Fv4-IgG1-F198 comprising VH3-IgG1-F198 and VL3-CK;
Fv4-IgG1-F262 comprising VH3-IgG1-F262 and VL3-CK;
Fv4-IgG1-F264 comprising VH3-IgG1-F264 and VL3-CK;
Fv4-IgG1-F393 comprising VH3-IgG1-F393 and VL3-CK;
Fv4-IgG1-F424 comprising VH3-IgG1-F434 and VL3-CK; and
Fv4-IgG1-F447 comprising VH3-IgG1-F447 and VL3-CK.

These antibodies were administered to the human FcRn transgenic mouse lineage 32 at a dose of 1 mg/kg.

FIG. 49 describes the time course of plasma hsIL-6R concentration in the mouse. Compared to Fv4-IgG1, all the Fc variants having increased binding affinity to human FcRn at pH 7.0 exhibited reduction of plasma hsIL-6R concentration, therefore enhanced antigen elimination from plasma. Although the extent and durability of antigen concentration reduction was different among the Fc variants, all the variant consistently reduced the plasma hsIL-6R concentration as compared to IgG1 demonstrating that increased binding affinity to human FcRn at pH 7.0 would universally enhance the antigen elimination from plasma. FIG. 50 describes the time course of plasma antibody concentration in the mouse. Antibody pharmacokinetics was different among the Fc variants.

As described in Reference Example 9, amount of antigen eliminated from plasma per antibody is the important factor to evaluate the efficiency of antigen elimination by administrating the antibody Fc variants having increased binding affinity to human FcRn at pH 7.0. Therefore, time courses of value C (molar antigen/antibody ratio) for each antibody were described in FIG. 51. FIG. 52 describes the relationship between the binding affinity of Fc variants to human FcRn at pH 7.0 and value C (molar antigen/antibody ratio) at day 1 after administration of antibodies. This demonstrates that all the antibody Fc variants tested in this study have lower value C as compared to Fv4-IgG1. Since all the Fc variants tested in this study have binding affinity to human FcRn at pH 7.0 stronger than KD 3.0 µM, they achieved higher antigen elimination efficiency as compared to natural human IgG1. This was consistent with the results obtained in Reference Example 9 (FIG. 42).

FIG. 53 describes that among the Fc variants tested in this study, antibodies having Fc variant of F11, F39, F48, and F264 exhibited similar pharmacokinetics to IgG1. Since this study is conducted using human FcRn transgenic mouse, these Fc variants is expected to have long half-life similar to IgG1 also in human. FIG. 54 describes the time course of plasma hsIL-6R concentration in mice administered with antibodies having similar pharmacokinetics to natural human IgG1 (F11, F39, F48, and F264). These variants reduced the plasma hsIL-6R concentration as compared to IgG1 approximately 10-fold. Moreover, these antibodies reduced the hsIL-6R concentration below the baseline hsIL-6R concentration (concentration without antibody). Therefore, these antibodies would enable long-term elimination of antigen from plasma, and therefore long dosing intervals which would be preferable for antibody therapeutics for chronic disease.

FIGS. 55 and 56 described the time course of plasma antibody concentration and plasma hsIL-6R concentration for IgG1, and Fc variant F157, F196 and F262, respectively. Surprisingly, although antibody pharmacokinetics of F157 and F262 showed significantly faster clearance from plasma as compared to natural human IgG1, F157 and F262 exhibited significant elimination of hsIL-6R from plasma. Specifically, plasma hsIL-6R concentration of F157 was below detection limit (1.56 ng/mL), from days 1 to 28 (except at day 14), and that of F262 was below detection limit (1.56 ng/mL) from days 14 to 28. On the other hand, for F196 with slower clearance of antibody compared to F157, antigen concentration started to increase at day 14 and returned back to baseline at day 28. Among the Fc variants tested in this study, F157 and F262 were the only Fc variants that were capable of reducing plasma hsIL-6R concentration below 1.56 ng/mL at day 28.

Such durable long-term effect of F157 and F262 is unexpected from the pharmacokinetics of the antibody, since antibodies were eliminated from plasma very rapidly as compared to natural human IgG1. In particular, plasma antibody concentration of F157 was not detected at day 21. Nevertheless, plasma hsIL-6R concentration continued to be reduced to a level lower than the detection limit of 1.56 ng/mL at days 21 and 28. The present invention is not limited to a particular theory, but this unexpected effect is considered to be due to the presence of the antibody at the surface of vascular endothelium cell as FcRn bound form. Although these antibodies showed low concentration in plasma, these antibodies is still present in the vascular compartment as FcRn bound form (which cannot be measured as a plasma antibody concentration). These FcRn bound antibody can still bind to the antigen in the plasma, and after FcRn mediated uptake of antigen/antibody complex, antigen is released within the endosome and degraded by the lysosome while the antibody is recycled back to the cell surface as FcRn bound form. Thus these FcRn bound antibody contribute to the antigen elimination. This explains the reason why these antibodies maintains antigen elimination capability even after the antibody concentration becomes low in plasma.

INDUSTRIAL APPLICABILITY

The present invention provides methods for promoting antigen uptake into cells by using antigen-binding molecules, methods for increasing the number of times of antigen binding by one antigen-binding molecule, methods for promoting the reduction of plasma antigen concentration by administering antigen-binding molecules, and methods for improving plasma retention of antigen-binding molecules. By promoting antigen uptake into cells by an antigen-binding molecule, it becomes possible to not only promote the reduction of plasma antigen by administration of the antigen-binding molecule, but also improve the plasma retention of the antigen-binding molecule and increase the number of times of antigen binding by each of the antigen-binding molecule. Such antigen-binding molecules can exhibit more beneficial effects in vivo than typical antigen-binding molecules.

The invention claimed is:

1. A method of removing a soluble antigen from plasma, the method comprising:
   (a) identifying an individual in need of having the antigen removed from the individual's plasma; and
   (b) administering to the individual an antibody that is able to remove the antigen from plasma, thereby removing the antigen from the individual's plasma,
   wherein the antibody comprises an antigen-binding domain and a human FcRn-binding domain,
   wherein the antibody binds to the antigen through the antigen-binding domain of the antibody and has a KD(Ca$^{2+}$3 μM)/KD(Ca$^{2+}$2 mM) value, defined as the ratio of KD for the antigen at a 3 μM calcium ion concentration and KD for the antigen at a 2 mM calcium ion concentration, of 2 to 10,000, when KD is measured using a surface plasmon resonance technique under the following conditions:
   37 degrees Celsius, pH 7.4, a running buffer comprising 0.05% polysorbate 20,
   10 mmol/L N-(2-acetamido)-2-aminoethanesulfonic acid (ACES), 150 mmol/L NaCl,
   and either 3 μM or 2 mM CaCl$_2$, and where the antibody is immobilized on a CM4 sensor chip, and the antigen serves as analyte,
   wherein the antibody binds to the antigen in plasma in vivo and dissociates from the bound antigen under conditions present in an endosome in vivo,
   wherein the antibody is a human IgG or a humanized IgG,
   wherein the antigen-binding domain comprises a light chain variable domain and a heavy chain variable domain,
   wherein at least four positions selected from Kabat numbering positions 30, 31, 32, 50, and 92 of the light chain variable domain are occupied by amino acids independently selected from serine, asparagine, aspartic acid, glutamic acid, histidine, and tyrosine, and
   wherein at least one of the at least four positions is occupied by glutamic acid or aspartic acid.

2. The method of claim 1, wherein three of the at least four positions are Kabat numbering positions 30, 31, and 32 of the light chain variable domain.

3. The method of claim 1, wherein one of the at least four positions is Kabat numbering position 50 of the light chain variable domain.

4. The method of claim 1, wherein one of the at least four positions is Kabat numbering position 92 of the light chain variable domain.

5. The method of claim 1, wherein the heavy chain variable domain comprises Kabat numbering positions 95, 96, 100a, and 101, and wherein at least three positions selected from Kabat numbering positions 95, 96, 100a and 101 of the heavy chain variable domain are occupied by amino acids independently selected from serine, threonine, asparagine, glutamine, aspartic acid, glutamic acid, histidine, and tyrosine.

6. The method of claim 1, wherein three of the at least four positions are Kabat numbering positions 30, 31, and 50 of the light chain variable domain.

7. The method of claim 1, wherein three of the at least four positions are Kabat numbering positions 30, 31, and 92 of the light chain variable domain.

8. The method of claim 1, wherein three of the at least four positions are Kabat numbering positions 31, 32, and 50 of the light chain variable domain.

9. The method of claim 1, wherein three of the at least four positions are Kabat numbering positions 31, 32, and 92 of the light chain variable domain.

10. The method of claim 1, wherein three of the at least four positions are Kabat numbering positions 30, 32, and 50 of the light chain variable domain.

11. The method of claim 1, wherein three of the at least four positions are Kabat numbering positions 30, 32, and 92 of the light chain variable domain.

12. The method of claim 1, wherein three of the at least four positions are Kabat numbering positions 30, 50, and 92 of the light chain variable domain.

13. The method of claim 1, wherein three of the at least four positions are Kabat numbering positions 31, 50, and 92 of the light chain variable domain.

14. The method of claim 1, wherein three of the at least four positions are Kabat numbering positions 32, 50, and 92 of the light chain variable domain.

15. The method of claim 1, wherein each of Kabat numbering positions 30, 31, 32, 50, and 92 of the light chain variable domain is occupied by an amino acid independently selected from serine, asparagine, aspartic acid, glutamic acid, histidine, and tyrosine.

16. The method of claim 1, wherein each of Kabat numbering positions 30, 31, 32, 50, and 92 of the light chain variable domain is occupied by an amino acid independently selected from glutamic acid and aspartic acid.

17. The method of claim 1, wherein each of at least two of the at least four positions is occupied by an amino acid independently selected from glutamic acid and aspartic acid.

18. The method of claim 1, wherein each of at least three of the at least four positions is occupied by an amino acid independently selected from glutamic acid and aspartic acid.

19. The method of claim 1, wherein each of the at least four positions is occupied by an amino acid independently selected from glutamic acid and aspartic acid.

20. The method of claim 5, wherein each of Kabat numbering positions 95, 96, 100a, and 101 of the heavy chain variable domain is occupied by an amino acid independently selected from serine, threonine, asparagine, glutamine, aspartic acid, glutamic acid, histidine, and tyrosine.

21. The method of claim 5, wherein each of Kabat numbering positions 95, 96, 100a, and 101 of the heavy chain variable domain is occupied by an amino acid independently selected from glutamic acid and aspartic acid.

22. The method of claim 5, wherein at least one of the at least three heavy chain variable domain positions is occupied by glutamic acid or aspartic acid.

23. The method of claim 5, wherein each of at least two of the at least three heavy chain variable domain positions is occupied by an amino acid independently selected from glutamic acid and aspartic acid.

24. The method of claim 5, wherein each of the at least three heavy chain variable domain positions is occupied by an amino acid independently selected from glutamic acid and aspartic acid.

25. The method of claim 1, wherein binding of the antigen to the antibody is lower at pH 5.8 than at pH 7.4.

26. The method of claim 1, wherein the FcRn-binding domain is a modified Fc domain that has FcRn-binding activity at pH 7.4, wherein the amino acid sequence of the modified Fc domain varies from the sequence of a wild type Fc domain at one or more of positions 248, 250, 252, 254, 255, 256, 257, 258, 265, 286, 289, 297, 303, 305, 307, 308, 309, 311, 312, 314, 315, 317, 332, 334, 360, 376, 380, 382, 384, 385, 386, 387, 389, 424, 428, 433, 434, and 436 (EU numbering).

27. The method of claim 1, wherein the antigen is human IL-6, a soluble form of human IL-6 receptor, a soluble form of human CD4, human IgA, a soluble form of human glypican 3, or human IgE.

28. The method of claim 1, wherein one or more of Kabat numbering positions 31, 32, and 92 in the light chain variable domain are occupied by aspartic acid.

29. The method of claim 1, wherein one or both of Kabat numbering positions 31 and 32 in the light chain variable domain are occupied by aspartic acid.

30. The method of claim 1, wherein Kabat numbering positions 31 and 32 in the light chain variable domain are both occupied by aspartic acid.

31. The method of claim 1, wherein Kabat numbering positions 31 and 32 in the light chain variable domain are both occupied by aspartic acid, and at least one of Kabat numbering positions 30, 50, and 92 in the light chain variable domain is occupied by aspartic acid or glutamic acid.

32. A method of removing a soluble antigen from plasma, the method comprising:
(a) identifying an individual in need of having the antigen removed from the individual's plasma; and
(b) administering to the individual an antibody comprising an antigen-binding domain and a human FcRn-binding domain,
wherein the antibody binds to the antigen through the antigen-binding domain of the antibody and has a KD(Ca$^{2+}$3 µM)/KD (Ca$^{2+}$2 mM) value, defined as the ratio of KD for the antigen at a 3 µM calcium ion concentration and KD for the antigen at a 2 mM calcium ion concentration, of 2 to 10,000, when KD is measured using a surface plasmon resonance technique under the following conditions:
37 degrees Celsius, pH 7.4, a running buffer comprising 0.05% polysorbate 20,
10 mmol/L ACES, 150 mmol/L NaCl, and either 3 µM or 2 mM CaCl$_2$), and where
the antibody is immobilized on a CM4 sensor chip, and the antigen serves as analyte,
wherein the antibody binds to the antigen in plasma in vivo and dissociates from the bound antigen under conditions present in an endosome in vivo,
wherein the antibody is a human IgG or a humanized IgG,
wherein the antigen-binding domain comprises a light chain variable domain and a heavy chain variable domain,
wherein the antigen is human IL-6, a soluble form of human IL-6 receptor, a soluble form of human CD4, human IgA, a soluble form of human glypican 3, or human IgE, and
wherein at least four positions selected from Kabat numbering positions 30, 31, 32, 50, and 92 of the light chain variable domain are occupied by amino acids independently selected from serine, threonine, asparagine, glutamine, aspartic acid, glutamic acid, histidine, and tyrosine.

* * * * *

SEQUENCE LISTING

```
<160> NUMBER OF SEQ ID NOS: 113

<210> SEQ ID NO 1
<211> LENGTH: 449
<212> TYPE: PRT
<213> ORGANISM: Artificial Sequence
<220> FEATURE:
<223> OTHER INFORMATION: an artificially synthesized sequence

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Pro Gly Gly Gly Glu Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro

<210> SEQ ID NO 2
<211> LENGTH: 216
<212> TYPE: PRT
<213> ORGANISM: Artificial Sequence
<220> FEATURE:
<223> OTHER INFORMATION: an artificially synthesized sequence

<400> SEQUENCE: 2

Gln Ser Val Leu Thr Gln Pro Pro Ser Val Ser Gly Ala Pro Gly Gln
1               5                   10                  15

Arg Val Thr Ile Ser Cys Thr Gly Ser Arg Ser Asn Met Gly Ala Gly
            20                  25                  30

Tyr Asp Val His Trp Tyr Gln Leu Leu Pro Gly Ala Ala Pro Lys Leu
            35                  40                  45

Leu Ile Ser His Asn Thr His Arg Pro Ser Gly Val Pro Asp Arg Phe
        50                  55                  60

Ser Gly Ser Lys Ser Gly Ala Ser Ala Ser Leu Ala Ile Thr Gly Leu
65                  70                  75                  80

Gln Ala Glu Asp Glu Ala Asp Tyr Tyr Cys Gln Ser His Asp Ser Ser
                85                  90                  95

Leu Ser Ala Val Val Phe Gly Gly Gly Thr Lys Leu Thr Val Leu Ser
```

```
            100                 105                 110
Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys
    210                 215

<210> SEQ ID NO 3
<211> LENGTH: 453
<212> TYPE: PRT
<213> ORGANISM: Artificial Sequence
<220> FEATURE:
<223> OTHER INFORMATION: an artificially synthesized sequence

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Asp Tyr Tyr Asp Ser Ser Gly Tyr Tyr Asp Ala Phe
            100                 105                 110

Asp Ile Trp Gly Gln Gly Thr Met Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
```

```
                    245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln Tyr
                290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
                355                 360                 365

Asn Gln Val Ser Leu Thr Cys Leu Val Lys Gly Phe Tyr Pro Ser Asp
                370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                    405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro
                450

<210> SEQ ID NO 4
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 4

Glu Thr Thr Val Thr Gln Ser Pro Ser Phe Leu Ser Ala Ser Val Gly
1               5                   10                  15

Asp Arg Val Thr Ile Thr Cys Ile Thr Thr Asp Ile Asp Asp Asp
                20                  25                  30

Met Asn Trp Phe Gln Gln Glu Pro Gly Lys Ala Pro Lys Leu Leu Ile
                35                  40                  45

Ser Glu Gly Asn Ile Leu Arg Pro Gly Val Pro Ser Arg Phe Ser Ser
            50                  55                  60

Ser Gly Tyr Gly Thr Asp Phe Thr Leu Thr Ile Ser Lys Leu Gln Pro
65                  70                  75                  80

Glu Asp Phe Ala Thr Tyr Tyr Cys Leu Gln Ser Asp Asn Leu Pro Phe
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
```

```
            145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 5
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 5

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
                20                  25                  30

Gln Ala Trp Ser Trp Val Arg Gln Pro Pro Gly Glu Gly Leu Glu Trp
            35                  40                  45

Ile Gly Tyr Ile Ser Tyr Ser Gly Ile Thr Asn Tyr Asn Pro Ser Leu
        50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
```

```
                290                 295                 300
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
                435                 440                 445

<210> SEQ ID NO 6
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 6

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
                20                  25                  30

Leu Asn Trp Tyr Gln Gln Lys Pro Gly Lys Ala Pro Glu Leu Leu Ile
            35                  40                  45

Tyr Tyr Gly Ser Glu Leu His Ser Gly Val Pro Ser Arg Phe Ser Gly
        50                  55                  60

Ser Gly Ser Gly Thr Asp Phe Thr Phe Thr Ile Ser Ser Leu Glu Ala
65              70                  75                  80

Glu Asp Ala Ala Thr Tyr Tyr Cys Gln Gln Gly Asn Ser Leu Pro Tyr
                85                  90                  95

Thr Phe Gly Gln Gly Thr Lys Val Glu Ile Glu Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
```

<210> SEQ ID NO 7
<211> LENGTH: 453
<212> TYPE: PRT
<213> ORGANISM: Artificial Sequence
<220> FEATURE:
<223> OTHER INFORMATION: an artificially synthesized sequence

<400> SEQUENCE: 7

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Asp Tyr Tyr Asp Ser Ser Gly Tyr Tyr Asp Ala Phe
            100                 105                 110

Asp Ile Trp Gly Gln Gly Thr Met Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
```

```
                355                 360                 365
Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Trp His Tyr Thr Gln Lys Ser
        435                 440                 445

Leu Ser Leu Ser Pro
    450

<210> SEQ ID NO 8
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 8

Glu Thr Thr Val Thr Gln Ser Pro Ser Phe Leu Ser Ala Ser Val Gly
1               5                   10                  15

Asp Arg Val Thr Ile Thr Cys Ile Thr Thr Asp Ile Asp Asp Asp
            20                  25                  30

Met Asn Trp Phe Gln Gln Glu Pro Gly Lys Ala Pro Lys Leu Leu Ile
        35                  40                  45

Ser Glu Gly Asn Ile Leu Arg Pro Gly Val Pro Ser Arg Phe Ser Ser
    50                  55                  60

Ser Gly Tyr Gly Thr Asp Phe Thr Leu Thr Ile Ser Lys Leu Gln Pro
65                  70                  75                  80

Glu Asp Phe Ala Thr Tyr Tyr Cys Leu Gln Ser Asp Asn Leu Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 449
<212> TYPE: PRT
<213> ORGANISM: Artificial Sequence
<220> FEATURE:
<223> OTHER INFORMATION: an artificially synthesized sequence
```

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Pro Gly Gly Gly Glu Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val

```
                        405                 410                 415
Asp Lys Ser Arg Trp Gln Gln Gly Asn Val Phe Ser Cys Ser Val Met
            420                 425                 430

His Glu Ala Leu His Trp His Tyr Thr Gln Lys Ser Leu Ser Leu Ser
        435                 440                 445

Pro

<210> SEQ ID NO 10
<211> LENGTH: 216
<212> TYPE: PRT
<213> ORGANISM: Artificial Sequence
<220> FEATURE:
<223> OTHER INFORMATION: an artificially synthesized sequence

<400> SEQUENCE: 10

Gln Ser Val Leu Thr Gln Pro Pro Ser Val Ser Gly Ala Pro Gly Gln
1               5                   10                  15

Arg Val Thr Ile Ser Cys Thr Gly Ser Arg Ser Asn Met Gly Ala Gly
            20                  25                  30

Tyr Asp Val His Trp Tyr Gln Leu Leu Pro Gly Ala Ala Pro Lys Leu
        35                  40                  45

Leu Ile Ser His Asn Thr His Arg Pro Ser Gly Val Pro Asp Arg Phe
    50                  55                  60

Ser Gly Ser Lys Ser Gly Ala Ser Ala Ser Leu Ala Ile Thr Gly Leu
65                  70                  75                  80

Gln Ala Glu Asp Glu Ala Asp Tyr Tyr Cys Gln Ser His Asp Ser Ser
                85                  90                  95

Leu Ser Ala Val Val Phe Gly Gly Gly Thr Lys Leu Thr Val Leu Ser
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys
    210                 215

<210> SEQ ID NO 11
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 11

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
```

```
                35                  40                  45
Ile Gly Tyr Ile Ser Tyr Ser Gly Ile Thr Asn Tyr Asn Pro Ser Leu
 50                  55                  60

Lys Gly Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Ala Tyr Tyr Cys
                 85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Trp His Tyr Thr Gln Lys Ser Leu Ser Leu Ser Pro
                435                 440                 445

<210> SEQ ID NO 12
```

```
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 12

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu His Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Ser Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 449
<212> TYPE: PRT
<213> ORGANISM: Artificial Sequence
<220> FEATURE:
<223> OTHER INFORMATION: an artificially synthesized sequence

<400> SEQUENCE: 13

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
```

```
                100             105                 110
Ser Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
        130                 135             140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys

<210> SEQ ID NO 14
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 14

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 15
<211> LENGTH: 468
<212> TYPE: PRT
<213> ORGANISM: Homo sapiens

<400> SEQUENCE: 15

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
```

```
                     165                 170                 175
Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp Ser Ser Val Pro Leu Pro Thr Phe Leu
        355                 360                 365

Val Ala Gly Gly Ser Leu Ala Phe Gly Thr Leu Leu Cys Ile Ala Ile
    370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
            420                 425                 430

Ser Pro Ser Ser Leu Gly Ser Asp Asn Thr Ser Ser His Asn Arg Pro
        435                 440                 445

Asp Ala Arg Asp Pro Arg Ser Pro Tyr Asp Ile Ser Asn Thr Asp Tyr
    450                 455                 460

Phe Phe Pro Arg
465

<210> SEQ ID NO 16
<211> LENGTH: 1407
<212> TYPE: DNA
<213> ORGANISM: Homo sapiens

<400> SEQUENCE: 16
atgctggccg tcggctgcgc gctgctggct gccctgctgg ccgcgccggg agcggcgctg      60
gccccaaggc gctgccctgc gcaggaggtg gcgagaggcg tgctgaccag tctgccagga     120
gacagcgtga ctctgacctg cccgggggta gagccggaag acaatgccac tgttcactgg     180
gtgctcagga agccggctgc aggctcccac cccagcagat gggctggcat gggaaggagg     240
ctgctgctga ggtcggtgca gctccacgac tctggaaact attcatgcta ccgggccggc     300
cgcccagctg ggactgtgca cttgctggtg atgttccccc cgaggagcc ccagctctcc     360
```

```
tgcttccgga agagccccct cagcaatgtt gtttgtgagt ggggtcctcg agcacccca      420
tccctgacga caaaggctgt gctcttggtg aggaagtttc agaacagtcc ggccgaagac      480
ttccaggagc cgtgccagta ttcccaggag tcccagaagt tctcctgcca gttagcagtc      540
ccggagggag acagctcttt ctacatagtg tccatgtgcg tcgccagtag tgtcgggagc      600
aagttcagca aaactcaaac cttctcaggg tgtggaatct tgcagcctga tccgcctgcc      660
aacatcacag tcactgccgt ggccagaaac cccgctggc tcagtgtcac ctggcaagac      720
ccccactcct ggaactcatc tttctacaga ctacggtttg agctcagata tcgggctgaa      780
cggtcaaaga cattcacaac atggatggtc aaggacctcc agcatcactg tgtcatccac      840
gacgcctgga gcggcctgag gcacgtggtg cagcttcgtg cccaggagga gttcgggcaa      900
ggcgagtgga gcgagtggag cccggaggcc atgggcacgc cttggacaga atccaggagt      960
cctccagctg agaacgaggt gtccacccc atgcaggcac ttactactaa taaagacgat     1020
gataatattc tcttcagaga ttctgcaaat gcgacaagcc tcccagtgca agattcttct     1080
tcagtaccac tgcccacatt cctggttgct ggagggagcc tggccttcgg aacgctcctc     1140
tgcattgcca ttgttctgag gttcaagaag acgtggaagc tgcgggctct gaaggaaggc     1200
aagacaagca tgcatccgcc gtactctttg gggcagctgg tccggagag gcctcgaccc     1260
accccagtgc ttgttcctct catctcccca ccggtgtccc ccagcagcct ggggtctgac     1320
aatacctcga gccacaaccg accagatgcc agggacccac ggagcccta tgacatcagc     1380
aatacagact acttcttccc cagatag                                        1407
```

<210> SEQ ID NO 17
<211> LENGTH: 365
<212> TYPE: PRT
<213> ORGANISM: Homo sapiens

<400> SEQUENCE: 17

```
Met Gly Val Pro Arg Pro Gln Pro Trp Ala Leu Gly Leu Leu Leu Phe
1               5                   10                  15
Leu Leu Pro Gly Ser Leu Gly Ala Glu Ser His Leu Ser Leu Leu Tyr
            20                  25                  30
His Leu Thr Ala Val Ser Ser Pro Ala Pro Gly Thr Pro Ala Phe Trp
        35                  40                  45
Val Ser Gly Trp Leu Gly Pro Gln Gln Tyr Leu Ser Tyr Asn Ser Leu
    50                  55                  60
Arg Gly Glu Ala Glu Pro Cys Gly Ala Trp Val Trp Glu Asn Gln Val
65                  70                  75                  80
Ser Trp Tyr Trp Glu Lys Glu Thr Thr Asp Leu Arg Ile Lys Glu Lys
                85                  90                  95
Leu Phe Leu Glu Ala Phe Lys Ala Leu Gly Gly Lys Gly Pro Tyr Thr
            100                 105                 110
Leu Gln Gly Leu Leu Gly Cys Glu Leu Gly Pro Asp Asn Thr Ser Val
        115                 120                 125
Pro Thr Ala Lys Phe Ala Leu Asn Gly Glu Glu Phe Met Asn Phe Asp
    130                 135                 140
Leu Lys Gln Gly Thr Trp Gly Gly Asp Trp Pro Glu Ala Leu Ala Ile
145                 150                 155                 160
Ser Gln Arg Trp Gln Gln Asp Lys Ala Ala Asn Lys Glu Leu Thr
                165                 170                 175
Phe Leu Leu Phe Ser Cys Pro His Arg Leu Arg Glu His Leu Glu Arg
            180                 185                 190
```

```
Gly Arg Gly Asn Leu Glu Trp Lys Glu Pro Ser Met Arg Leu Lys
        195                 200                 205

Ala Arg Pro Ser Ser Pro Gly Phe Ser Val Leu Thr Cys Ser Ala Phe
210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
            245                 250                 255

Phe His Ala Ser Ser Ser Leu Thr Val Lys Ser Gly Asp Glu His His
        260                 265                 270

Tyr Cys Cys Ile Val Gln His Ala Gly Leu Ala Gln Pro Leu Arg Val
    275                 280                 285

Glu Leu Glu Ser Pro Ala Lys Ser Ser Val Leu Val Val Gly Ile Val
290                 295                 300

Ile Gly Val Leu Leu Leu Thr Ala Ala Val Gly Gly Ala Leu Leu
305                 310                 315                 320

Trp Arg Arg Met Arg Ser Gly Leu Pro Ala Pro Trp Ile Ser Leu Arg
                325                 330                 335

Gly Asp Asp Thr Gly Val Leu Leu Pro Thr Pro Gly Glu Ala Gln Asp
            340                 345                 350

Ala Asp Leu Lys Asp Val Asn Val Ile Pro Ala Thr Ala
        355                 360                 365

<210> SEQ ID NO 18
<211> LENGTH: 119
<212> TYPE: PRT
<213> ORGANISM: Homo sapiens

<400> SEQUENCE: 18

Met Ser Arg Ser Val Ala Leu Ala Val Leu Ala Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 19
<211> LENGTH: 447
<212> TYPE: PRT
<213> ORGANISM: Homo sapiens

<400> SEQUENCE: 19

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30
```

```
His Ala Trp Ser Trp Val Arg Gln Pro Pro Gly Glu Gly Leu Glu Trp
             35                  40                  45

Ile Gly Phe Ile Ser Tyr Ser Gly Ile Thr Asn Tyr Asn Pro Ser Leu
 50                  55                  60

Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Leu Ala Arg Thr Thr Ala Met Asp Tyr Trp Gly Glu Gly
             100                 105                 110

Thr Leu Val Thr Val Ser Ser Ala Ser Thr Lys Gly Pro Ser Val Phe
             115                 120                 125

Pro Leu Ala Pro Ser Ser Lys Ser Thr Ser Gly Gly Thr Ala Ala Leu
             130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
             195                 200                 205

Ser Asn Thr Lys Val Asp Lys Lys Val Glu Pro Lys Ser Cys Asp Lys
             210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Ser His Glu Asp
             260                 265                 270

Pro Glu Val Lys Phe Asn Trp Tyr Val Asp Gly Val Glu Val His Asn
             275                 280                 285

Ala Lys Thr Lys Pro Arg Glu Glu Gln Tyr Asn Ser Thr Tyr Arg Val
         290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                 325                 330                 335

Thr Ile Ser Lys Ala Lys Gly Gln Pro Arg Glu Pro Gln Val Tyr Thr
             340                 345                 350

Leu Pro Pro Ser Arg Asp Glu Leu Thr Lys Asn Gln Val Ser Leu Thr
             355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                 405                 410                 415

Ser Arg Trp Gln Gln Gly Asn Val Phe Ser Cys Ser Val Met His Glu
             420                 425                 430

Ala Leu His Asn His Tyr Thr Gln Lys Ser Leu Ser Leu Ser Pro
             435                 440                 445
```

<210> SEQ ID NO 20
<211> LENGTH: 214
<212> TYPE: PRT
<213> ORGANISM: Homo sapiens

<400> SEQUENCE: 20

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 21
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 21

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly

```
                100             105             110
Thr Leu Val Thr Val Ser Ser Ala Ser Thr Lys Gly Pro Ser Val Phe
            115                 120             125

Pro Leu Ala Pro Ser Ser Lys Ser Thr Ser Gly Gly Thr Ala Ala Leu
130             135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Tyr Ile Thr
                245                 250                 255

Arg Glu Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 22
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 22

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
```

```
              20                  25                  30
His Ala Trp Ser Trp Val Arg Gln Pro Gly Glu Gly Leu Glu Trp
         35                  40                  45
Ile Gly Phe Ile Ser Tyr Ser Gly Ile Thr Asn Tyr Asn Pro Ser Leu
 50                  55                  60
Gln Gly Arg Val Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Ser Leu Ala Arg Thr Thr Ala Met Asp Tyr Trp Gly Glu Gly
             100                 105                 110
Thr Leu Val Thr Val Ser Ser Ala Ser Thr Lys Gly Pro Ser Val Phe
             115                 120                 125
Pro Leu Ala Pro Ser Ser Lys Ser Thr Ser Gly Gly Thr Ala Ala Leu
             130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                 165                 170                 175
Gln Ser Ser Gly Leu Tyr Ser Leu Ser Ser Val Val Thr Val Pro Ser
             180                 185                 190
Ser Ser Leu Gly Thr Gln Thr Tyr Ile Cys Asn Val Asn His Lys Pro
             195                 200                 205
Ser Asn Thr Lys Val Asp Lys Lys Val Glu Pro Lys Ser Cys Asp Lys
         210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                 245                 250                 255
Arg Thr Pro Glu Val Thr Cys Val Val Val Asp Val Ser His Glu Asp
             260                 265                 270
Pro Glu Val Lys Phe Asn Trp Tyr Val Asp Gly Val Glu Val His Asn
         275                 280                 285
Ala Lys Thr Lys Pro Arg Glu Glu Gln Tyr Asn Ser Thr Tyr Arg Val
         290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                 325                 330                 335
Thr Ile Ser Lys Ala Lys Gly Gln Pro Arg Glu Pro Gln Val Tyr Thr
             340                 345                 350
Leu Pro Pro Ser Arg Asp Glu Leu Thr Lys Asn Gln Val Ser Leu Thr
             355                 360                 365
Cys Leu Val Lys Gly Phe Tyr Pro Ser Asp Ile Ala Val Glu Trp Glu
         370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                 405                 410                 415
Ser Arg Trp Gln Gln Gly Asn Val Phe Ser Cys Ser Val Met His Glu
             420                 425                 430
Ala Leu His Trp His Tyr Thr Gln Lys Ser Leu Ser Leu Ser Pro
         435                 440                 445
```

<210> SEQ ID NO 23
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 23

| | | | | | | | | | | | | | | |
|---|---|---|---|---|---|---|---|---|---|---|---|---|---|---|
| Gln | Val | Gln | Leu | Gln | Glu | Ser | Gly | Pro | Gly | Leu | Val | Lys | Pro | Ser | Glu |
| 1 | | | | 5 | | | | | 10 | | | | | 15 | |
| Thr | Leu | Ser | Leu | Thr | Cys | Ala | Val | Ser | Gly | His | Ser | Ile | Ser | His | Asp |
| | | | 20 | | | | | 25 | | | | | 30 | | |
| His | Ala | Trp | Ser | Trp | Val | Arg | Gln | Pro | Pro | Gly | Glu | Gly | Leu | Glu | Trp |
| | | | 35 | | | | 40 | | | | | 45 | | | |
| Ile | Gly | Phe | Ile | Ser | Tyr | Ser | Gly | Ile | Thr | Asn | Tyr | Asn | Pro | Ser | Leu |
| | 50 | | | | | 55 | | | | | 60 | | | | |
| Gln | Gly | Arg | Val | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Ser | Leu | Ala | Arg | Thr | Thr | Ala | Met | Asp | Tyr | Trp | Gly | Glu | Gly |
| | | | 100 | | | | | 105 | | | | | 110 | | |
| Thr | Leu | Val | Thr | Val | Ser | Ser | Ala | Ser | Thr | Lys | Gly | Pro | Ser | Val | Phe |
| | | | 115 | | | | | 120 | | | | | 125 | | |
| Pro | Leu | Ala | Pro | Ser | Ser | Lys | Ser | Thr | Ser | Gly | Gly | Thr | Ala | Ala | Leu |
| | 130 | | | | | 135 | | | | | 140 | | | | |
| Gly | Cys | Leu | Val | Lys | Asp | Tyr | Phe | Pro | Glu | Pro | Val | Thr | Val | Ser | Trp |
| 145 | | | | | 150 | | | | | 155 | | | | | 160 |
| Asn | Ser | Gly | Ala | Leu | Thr | Ser | Gly | Val | His | Thr | Phe | Pro | Ala | Val | Leu |
| | | | | 165 | | | | | 170 | | | | | 175 | |
| Gln | Ser | Ser | Gly | Leu | Tyr | Ser | Leu | Ser | Ser | Val | Val | Thr | Val | Pro | Ser |
| | | | 180 | | | | | 185 | | | | | 190 | | |
| Ser | Ser | Leu | Gly | Thr | Gln | Thr | Tyr | Ile | Cys | Asn | Val | Asn | His | Lys | Pro |
| | | | 195 | | | | | 200 | | | | | 205 | | |
| Ser | Asn | Thr | Lys | Val | Asp | Lys | Lys | Val | Glu | Pro | Lys | Ser | Cys | Asp | Lys |
| | 210 | | | | | 215 | | | | | 220 | | | | |
| Thr | His | Thr | Cys | Pro | Pro | Cys | Pro | Ala | Pro | Glu | Leu | Leu | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | His | Glu | Asp |
| | | | 260 | | | | | 265 | | | | | 270 | | |
| Pro | Glu | Val | Lys | Phe | Asn | Trp | Tyr | Val | Asp | Gly | Val | Glu | Val | His | Asn |
| | | | 275 | | | | | 280 | | | | | 285 | | |
| Ala | Lys | Thr | Lys | Pro | Arg | Glu | Glu | Gln | Tyr | Asn | Ser | Thr | Tyr | Arg | Val |
| | 290 | | | | | 295 | | | | | 300 | | | | |
| Val | Ser | Val | Leu | Thr | Phe | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Ala | Leu | Pro | Ala | Pro | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Arg | Asp | Glu | Leu | Thr | Lys | Asn | Gln | Val | Ser | Leu | Thr |
| | | | 355 | | | | | 360 | | | | | 365 | | |

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445

<210> SEQ ID NO 24
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285
```

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Ala
            420                 425                 430

His Tyr Thr Gln Lys Ser Leu Ser Leu Ser Pro
    435                 440

<210> SEQ ID NO 25
<211> LENGTH: 126
<212> TYPE: PRT
<213> ORGANISM: Artificial Sequence
<220> FEATURE:
<223> OTHER INFORMATION: an artificially synthesized sequence

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Asp Ser Ser Gly Tyr Thr Asp Ala
            100                 105                 110

Phe Asp Ile Trp Gly Gln Gly Thr Met Val Thr Val Ser Ser
        115                 120                 125

<210> SEQ ID NO 26
<211> LENGTH: 106
<212> TYPE: PRT
<213> ORGANISM: Artificial Sequence
<220> FEATURE:
<223> OTHER INFORMATION: an artificially synthesized sequence

<400> SEQUENCE: 26

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr

```
                    20                  25                  30

Leu Ala Trp Tyr Gln Gln Lys Pro Gly Gln Ala Pro Arg Leu Leu Ile
            35                  40                  45

Phe Asp Ala Ser Asn Arg Ala Ala Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Phe Asp Lys Trp Val Thr
                 85                  90                  95

Phe Gly Gly Gly Thr Thr Val Glu Ile Arg
            100                 105

<210> SEQ ID NO 27
<211> LENGTH: 454
<212> TYPE: PRT
<213> ORGANISM: Artificial Sequence
<220> FEATURE:
<223> OTHER INFORMATION: an artificially synthesized sequence

<400> SEQUENCE: 27

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Glu Met Asn Trp Val Arg Gln Ala Pro Gly Lys Gly Leu Glu Trp Val
         35                  40                  45

Ser Tyr Ile Ser Ser Ser Gly Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ala Pro Tyr Tyr Asp Ser Ser Gly Tyr Thr Asp Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
        180                 185                 190

Ser Val Val Thr Val Pro Ser Ser Ser Leu Gly Thr Gln Thr Tyr Ile
    195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
        260                 265                 270

Val Asp Val Ser His Glu Asp Pro Glu Val Lys Phe Asn Trp Tyr Val
```

```
                    275                 280                 285
Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro
        450

<210> SEQ ID NO 28
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 28

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 29
<211> LENGTH: 213
<212> TYPE: PRT
<213> ORGANISM: Artificial Sequence
<220> FEATURE:
<223> OTHER INFORMATION: an artificially synthesized sequence

<400> SEQUENCE: 29

Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Phe Asp Ala Ser Asn Arg Ala Ala Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Asp Lys Trp Val Thr
                85                  90                  95

Phe Gly Gly Gly Thr Thr Val Glu Ile Arg Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 30
<211> LENGTH: 454
<212> TYPE: PRT
<213> ORGANISM: Artificial Sequence
<220> FEATURE:
<223> OTHER INFORMATION: an artificially synthesized sequence

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Glu Met Asn Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Ala Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Asp Ser Ser Gly Tyr Thr Asp Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160
```

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro
    450

<210> SEQ ID NO 31
<211> LENGTH: 454
<212> TYPE: PRT
<213> ORGANISM: Artificial Sequence
<220> FEATURE:
<223> OTHER INFORMATION: an artificially synthesized sequence

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Ala Ala Pro Tyr Tyr Tyr Asp Ser Ser Gly Tyr Thr Asp Ala
        100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro
    450

<210> SEQ ID NO 32
<211> LENGTH: 454
<212> TYPE: PRT

<213> ORGANISM: Artificial Sequence
<220> FEATURE:
<223> OTHER INFORMATION: an artificially synthesized sequence

<400> SEQUENCE: 32

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Ala Ser Ser Gly Tyr Thr Asp Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
```

```
                385                 390                 395                 400
Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro
        450

<210> SEQ ID NO 33
<211> LENGTH: 454
<212> TYPE: PRT
<213> ORGANISM: Artificial Sequence
<220> FEATURE:
<223> OTHER INFORMATION: an artificially synthesized sequence

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Asp Ser Ser Gly Tyr Thr Ala Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
```

```
            290                 295                 300
Tyr Asn Ser Thr Tyr Arg Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
                355                 360                 365

Lys Asn Gln Val Ser Leu Thr Cys Leu Val Lys Gly Phe Tyr Pro Ser
                370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
                435                 440                 445

Ser Leu Ser Leu Ser Pro
                450

<210> SEQ ID NO 34
<211> LENGTH: 454
<212> TYPE: PRT
<213> ORGANISM: Artificial Sequence
<220> FEATURE:
<223> OTHER INFORMATION: an artificially synthesized sequence

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Glu Met Asn Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Asp Ser Ser Gly Tyr Thr Asp Ala
                100                 105                 110

Phe Ala Ile Trp Gly Gln Gly Thr Met Val Thr Val Ser Ser Ala Ser
            115                 120                 125

Thr Lys Gly Pro Ser Val Phe Pro Leu Ala Pro Ser Ser Lys Ser Thr
            130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
```

```
            195                 200                 205
Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro
    450

<210> SEQ ID NO 35
<211> LENGTH: 213
<212> TYPE: PRT
<213> ORGANISM: Artificial Sequence
<220> FEATURE:
<223> OTHER INFORMATION: an artificially synthesized sequence

<400> SEQUENCE: 35

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Phe Ala Ala Ser Asn Arg Ala Ala Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Asp Lys Trp Val Thr
                85                  90                  95

Phe Gly Gly Gly Thr Thr Val Glu Ile Arg Arg Thr Val Ala Ala Pro
```

```
                100              105              110
Ser Val Phe Ile Phe Pro Ser Asp Glu Gln Leu Lys Ser Gly Thr
            115              120              125
Ala Ser Val Val Cys Leu Leu Asn Asn Phe Tyr Pro Arg Glu Ala Lys
    130              135              140
Val Gln Trp Lys Val Asp Asn Ala Leu Gln Ser Gly Asn Ser Gln Glu
145              150              155              160
Ser Val Thr Glu Gln Asp Ser Lys Asp Ser Thr Tyr Ser Leu Ser Ser
                165              170              175
Thr Leu Thr Leu Ser Lys Ala Asp Tyr Glu Lys His Lys Val Tyr Ala
            180              185              190
Cys Glu Val Thr His Gln Gly Leu Ser Ser Pro Val Thr Lys Ser Phe
            195              200              205
Asn Arg Gly Glu Cys
        210

<210> SEQ ID NO 36
<211> LENGTH: 213
<212> TYPE: PRT
<213> ORGANISM: Artificial Sequence
<220> FEATURE:
<223> OTHER INFORMATION: an artificially synthesized sequence

<400> SEQUENCE: 36

Glu Ile Val Leu Thr Gln Ser Pro Ala Thr Leu Ser Leu Ser Pro Gly
1               5                  10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Phe Asp Ala Ser Asn Arg Ala Ala Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Phe Ala Lys Trp Val Thr
                85                  90                  95
Phe Gly Gly Gly Thr Thr Val Glu Ile Arg Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210

<210> SEQ ID NO 37
<211> LENGTH: 107
<212> TYPE: PRT
```

<213> ORGANISM: Artificial Sequence
<220> FEATURE:
<223> OTHER INFORMATION: an artificially synthesized sequence

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 38
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 38

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asp Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu Arg Asn Pro Leu Thr Phe Gly Gly Gly Thr Lys Val Glu Ile Gln
            100                 105                 110

<210> SEQ ID NO 39
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 39

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Thr Phe Gly Gln Gly Thr Lys Val Glu Ile Lys
            100                 105
```

<210> SEQ ID NO 40
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 40

```
Asp Ile Val Met Thr Gln Ser Pro Glu Ser Leu Val Leu Ser Leu Gly
 1               5                  10                  15

Gly Thr Ala Thr Ile Asn Cys Arg Ser Ser Gln Ser Val Leu Tyr Ser
                20                  25                  30

Ser Asn Asn Lys Asn Tyr Leu Thr Trp Tyr Gln Gln Lys Pro Gly Gln
             35                  40                  45

Pro Pro Thr Leu Leu Phe Ser Trp Ala Ser Ile Arg Asp Ser Gly Val
         50                  55                  60

Pro Asp Arg Phe Ser Ala Ser Gly Ser Gly Thr Glu Phe Thr Leu Thr
 65                  70                  75                  80

Ile Ser Asp Leu Gln Ala Glu Asp Ala Ala Val Tyr Tyr Cys Gln Gln
                 85                  90                  95

Tyr Tyr Arg Ala Pro Ser Phe Gly Gln Gly Thr Lys Leu Gln Ile Lys
            100                 105                 110
```

<210> SEQ ID NO 41
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 41

```
Glu Thr Thr Leu Thr Gln Ser Pro Ala Phe Met Ser Ala Thr Pro Gly
 1               5                  10                  15

Asp Lys Val Asn Ile Ser Cys Lys Ala Ser Gln Asp Ile Asp Asp Asp
                20                  25                  30

Met Asn Trp Tyr Gln Gln Lys Pro Gly Glu Ala Ala Ile Phe Ile Ile
             35                  40                  45

Gln Glu Ala Thr Thr Leu Val Pro Gly Ile Ser Pro Arg Phe Ser Gly
         50                  55                  60

Ser Gly Tyr Gly Thr Asp Phe Thr Leu Thr Ile Asn Asn Ile Glu Ser
 65                  70                  75                  80

Glu Asp Ala Ala Tyr Tyr Phe Cys Leu Gln His Asp Asn Phe Pro Tyr
                 85                  90                  95

Thr Phe Gly Gln Gly Thr Lys Leu Glu Ile Lys
            100                 105
```

<210> SEQ ID NO 42
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Thr Leu Tyr Asp Phe Trp Ser Gly Tyr Tyr Ser Tyr
                100                 105                 110

Asp Ala Phe Asp Ile Trp Gly Gln Gly Thr Met Val Thr Val Ser Ser
                115                 120                 125

<210> SEQ ID NO 43
<211> LENGTH: 122
<212> TYPE: PRT
<213> ORGANISM: Artificial Sequence
<220> FEATURE:
<223> OTHER INFORMATION: an artificially synthesized sequence

<400> SEQUENCE: 43

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Leu Asp Thr Gly Pro Tyr Tyr Tyr Gly Met Asp Val Trp
                100                 105                 110

Gly Gln Gly Thr Met Val Thr Val Ser Ser
                115                 120

<210> SEQ ID NO 44
<211> LENGTH: 124
<212> TYPE: PRT
<213> ORGANISM: Artificial Sequence
<220> FEATURE:
<223> OTHER INFORMATION: an artificially synthesized sequence

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

```
Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Pro Val Pro Gly Val Tyr Tyr Tyr Gly Met Asp
                100                 105                 110

Val Trp Gly Gln Gly Thr Met Val Thr Val Ser Ser
                115                 120
```

<210> SEQ ID NO 45
<211> LENGTH: 119
<212> TYPE: PRT
<213> ORGANISM: Artificial Sequence
<220> FEATURE:
<223> OTHER INFORMATION: an artificially synthesized sequence

<400> SEQUENCE: 45

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Arg Ala Gly Asp Leu Gly Gly Asp Tyr Trp Gly Gln Gly
                100                 105                 110

Thr Leu Val Thr Val Ser Ser
            115
```

<210> SEQ ID NO 46
<211> LENGTH: 121
<212> TYPE: PRT
<213> ORGANISM: Artificial Sequence
<220> FEATURE:
<223> OTHER INFORMATION: an artificially synthesized sequence

<400> SEQUENCE: 46

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Ile Met Asn Trp Val Arg Gln Ala Pro Gly Gln Gly Leu Glu Trp Met
            35                  40                  45

Gly Leu Ile Asn Pro Tyr Asn Gly Gly Thr Tyr Tyr Asn Pro Gln Phe
        50                  55                  60

Gln Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
```

```
                    100                 105                 110

Gln Gly Thr Leu Val Thr Val Ser Ser
        115                 120

<210> SEQ ID NO 47
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 47

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 48
<211> LENGTH: 445
<212> TYPE: PRT
<213> ORGANISM: Artificial Sequence
<220> FEATURE:
<223> OTHER INFORMATION: an artificially synthesized sequence

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60
```

```
Gln Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Asn Phe Gly Thr Gln Thr Tyr Thr Cys Asn Val Asp His
                195                 200                 205

Lys Pro Ser Asn Thr Lys Val Asp Lys Thr Val Glu Arg Lys Ser Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Pro
435                 440                 445

<210> SEQ ID NO 49
<211> LENGTH: 107
<212> TYPE: PRT
<213> ORGANISM: Artificial Sequence
<220> FEATURE:
<223> OTHER INFORMATION: an artificially synthesized sequence
```

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asp Asp Asp
            20                  25                  30

Met Asn Trp Tyr Gln Gln Lys Pro Gly Lys Ala Pro Lys Leu Leu Ile
        35                  40                  45

Tyr Glu Ala Thr Thr Leu Val Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asp Asn Phe Pro Tyr
                85                  90                  95

Thr Phe Gly Gln Gly Thr Lys Val Glu Ile Lys
            100                 105

<210> SEQ ID NO 50
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 50

Asp Ile Val Met Thr Gln Ser Pro Leu Ser Leu Pro Val Thr Pro Gly
1               5                   10                  15

Glu Pro Ala Ser Ile Ser Cys Lys Ala Ser Gln Asp Ile Asp Asp Asp
            20                  25                  30

Met Asn Trp Tyr Leu Gln Lys Pro Gly Gln Ser Pro Gln Leu Leu Ile
        35                  40                  45

Tyr Glu Ala Thr Thr Leu Val Pro Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Leu Gln His Asp Asn Phe Pro Tyr
                85                  90                  95

Thr Phe Gly Gln Gly Thr Lys Leu Glu Ile Lys
            100                 105

<210> SEQ ID NO 51
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 51

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asp Asp Asp
            20                  25                  30

Met Asn Trp Tyr Gln Gln Lys Pro Gly Gln Ala Pro Arg Leu Leu Ile
        35                  40                  45

Tyr Glu Ala Thr Thr Leu Val Pro Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

```
Glu Asp Phe Ala Val Tyr Tyr Cys Leu Gln His Asp Asn Phe Pro Tyr
                85                  90                  95

Thr Phe Gly Gln Gly Thr Lys Val Glu Ile Lys
            100                 105

<210> SEQ ID NO 52
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 52

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Ile Asp Asp Asp
            20                  25                  30

Met Asn Trp Tyr Gln Gln Lys Pro Gly Gln Pro Pro Lys Leu Leu Ile
        35                  40                  45

Tyr Glu Ala Thr Thr Leu Val Pro Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Leu Gln His Asp Asn Phe Pro Tyr
                85                  90                  95

Thr Phe Gly Gln Gly Thr Lys Leu Glu Ile Lys
            100                 105

<210> SEQ ID NO 53
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 53

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Ala Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

-continued

```
                165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 54
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 54

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Ala Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 55
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 55

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Asp Ala
            20                  25                  30
```

Met Asn Trp Tyr Gln Gln Lys Pro Gly Glu Ala Ala Ile Phe Ile Ile
           35                  40                  45

Gln Glu Ala Thr Thr Leu Val Pro Gly Ile Ser Pro Arg Phe Ser Gly
 50                  55                  60

Ser Gly Tyr Gly Thr Asp Phe Thr Leu Thr Ile Asn Asn Ile Glu Ser
 65                  70                  75                  80

Glu Asp Ala Ala Tyr Tyr Phe Cys Leu Gln His Asp Asn Phe Pro Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 56
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 56

Glu Thr Thr Leu Thr Gln Ser Pro Ala Phe Met Ser Ala Thr Pro Gly
 1               5                  10                  15

Asp Lys Val Thr Ile Ser Cys Lys Ala Ser Gln Asp Ile Asp Asp Asp
             20                  25                  30

Met Asn Trp Tyr Gln Gln Lys Pro Gly Glu Ala Ala Ile Phe Ile Ile
           35                  40                  45

Gln Ala Ala Thr Thr Leu Val Pro Gly Ile Ser Pro Arg Phe Ser Gly
 50                  55                  60

Ser Gly Tyr Gly Thr Asp Phe Thr Leu Thr Ile Asn Asn Ile Glu Ser
 65                  70                  75                  80

Glu Asp Ala Ala Tyr Tyr Phe Cys Leu Gln His Asp Asn Phe Pro Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 57
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 57

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Ala Asp Ala
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 58
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 58

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Ala Asp Asp
            20                  25                  30

Met Asn Trp Tyr Gln Gln Lys Pro Gly Glu Ala Ala Ile Phe Ile Ile
        35                  40                  45
```

Gln Ala Ala Thr Thr Leu Val Pro Gly Ile Ser Pro Arg Phe Ser Gly
        50                  55                  60

Ser Gly Tyr Gly Thr Asp Phe Thr Leu Thr Ile Asn Asn Ile Glu Ser
 65                  70                  75                  80

Glu Asp Ala Ala Tyr Tyr Phe Cys Leu Gln His Asp Asn Phe Pro Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 59
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 59

Glu Thr Thr Leu Thr Gln Ser Pro Ala Phe Met Ser Ala Thr Pro Gly
 1               5                  10                  15

Asp Lys Val Thr Ile Ser Cys Lys Ala Ser Gln Asp Ile Ala Asp Ala
                20                  25                  30

Met Asn Trp Tyr Gln Gln Lys Pro Gly Glu Ala Ala Ile Phe Ile Ile
            35                  40                  45

Gln Ala Ala Thr Thr Leu Val Pro Gly Ile Ser Pro Arg Phe Ser Gly
        50                  55                  60

Ser Gly Tyr Gly Thr Asp Phe Thr Leu Thr Ile Asn Asn Ile Glu Ser
 65                  70                  75                  80

Glu Asp Ala Ala Tyr Tyr Phe Cys Leu Gln His Asp Asn Phe Pro Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 60
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 60

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Ala Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 61
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asp Asp
            20                  25                  30

Leu Asn Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asp Ser Thr Pro Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 62
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 62

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

```
                195                 200                 205
Phe Asn Arg Gly Glu Cys
    210

<210> SEQ ID NO 63
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 63

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 64
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 64

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Glu Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60
```

```
Ser Gly Tyr Gly Thr Asp Phe Thr Leu Thr Ile Asn Asn Ile Glu Ser
 65                  70                  75                  80

Glu Asp Ala Ala Tyr Tyr Phe Cys Leu Gln His Asp Asn Phe Pro Leu
             85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 65
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 65

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
             85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 66
<211> LENGTH: 462
<212> TYPE: PRT
<213> ORGANISM: Artificial Sequence
<220> FEATURE:
<223> OTHER INFORMATION: an artificially synthesized sequence

<400> SEQUENCE: 66

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Leu Gly Asp Ile Val Val Val Pro Ala Ala Pro Asp Met
            100                 105                 110

Pro Lys Gly Tyr Tyr Tyr Gly Met Asp Val Trp Gly Gln Gly Thr
        115                 120                 125

Met Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240
```

His Thr Cys Pro Pro Cys Pro Ala Pro Glu Leu Leu Gly Gly Pro Ser
              245                 250                 255

Val Phe Leu Phe Pro Pro Lys Pro Lys Asp Thr Leu Met Ile Ser Arg
        260                 265                 270

Thr Pro Glu Val Thr Cys Val Val Val Asp Val Ser His Glu Asp Pro
    275                 280                 285

Glu Val Lys Phe Asn Trp Tyr Val Asp Gly Val Glu Val His Asn Ala
290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro
450                 455                 460

<210> SEQ ID NO 67
<211> LENGTH: 215
<212> TYPE: PRT
<213> ORGANISM: Artificial Sequence
<220> FEATURE:
<223> OTHER INFORMATION: an artificially synthesized sequence

<400> SEQUENCE: 67

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Asn Asp Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Tyr Gln Tyr Trp Pro Pro
                85                  90                  95

Ile Thr Phe Gly Gln Gly Thr Arg Leu Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 68
<211> LENGTH: 446
<212> TYPE: PRT
<213> ORGANISM: Artificial Sequence
<220> FEATURE:
<223> OTHER INFORMATION: an artificially synthesized sequence

<400> SEQUENCE: 68

Gln Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ala Gly Ser Ser Asn Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

```
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro
                435                 440                 445

<210> SEQ ID NO 69
<211> LENGTH: 216
<212> TYPE: PRT
<213> ORGANISM: Artificial Sequence
<220> FEATURE:
<223> OTHER INFORMATION: an artificially synthesized sequence

<400> SEQUENCE: 69

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
                35                  40                  45

Met Ile Tyr Asp Val Ser Lys Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Trp Val Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
                115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
                195                 200                 205
```

```
Thr Val Ala Pro Thr Glu Cys Ser
    210                 215
```

<210> SEQ ID NO 70
<211> LENGTH: 452
<212> TYPE: PRT
<213> ORGANISM: Artificial Sequence
<220> FEATURE:
<223> OTHER INFORMATION: an artificially synthesized sequence

<400> SEQUENCE: 70

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Leu Ile Ala Ala Gly Gly Asp Phe Asp
            100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350
```

Pro Gln Val Tyr Thr Leu Pro Pro Ser Arg Asp Glu Leu Thr Lys Asn
                355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro
    450

<210> SEQ ID NO 71
<211> LENGTH: 217
<212> TYPE: PRT
<213> ORGANISM: Artificial Sequence
<220> FEATURE:
<223> OTHER INFORMATION: an artificially synthesized sequence

<400> SEQUENCE: 71

Gln Ser Val Leu Thr Gln Pro Pro Ser Val Ser Gly Ala Pro Gly Gln
1               5                   10                  15

Arg Val Thr Ile Ser Cys Thr Gly Ser Arg Ser Asn Ile Gly Ala Gly
            20                  25                  30

Phe Asp Val His Trp Tyr Arg Gln Leu Pro Gly Thr Ala Pro Lys Leu
        35                  40                  45

Leu Ile Tyr Gly Ile Ser Asn Arg Pro Ser Gly Val Pro Asp Arg Phe
    50                  55                  60

Ser Gly Ser Lys Ser Asp Thr Ser Val Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 72
<211> LENGTH: 214
<212> TYPE: PRT
<213> ORGANISM: Artificial Sequence
<220> FEATURE:

<223> OTHER INFORMATION: an artificially synthesized sequence

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Asp Asp
            20                  25                  30

Leu Asn Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 73
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Ala Asp
            20                  25                  30

Leu Asn Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 74
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asp Ala
            20                  25                  30

Leu Asn Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 75
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 75

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Asp
            20                  25                  30

Leu Asn Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 76
<211> LENGTH: 383
<212> TYPE: PRT
<213> ORGANISM: Artificial Sequence
<220> FEATURE:
<223> OTHER INFORMATION: an artificially synthesized sequence

<400> SEQUENCE: 76

```
Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
```

```
            130                 135                 140
Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Val Tyr Lys Lys Glu Gly Glu
            180                 185                 190

Gln Val Glu Phe Ser Phe Pro Leu Ala Phe Thr Val Glu Lys Leu Thr
        195                 200                 205

Gly Ser Gly Glu Leu Trp Trp Gln Ala Glu Arg Ala Ser Ser Ser Lys
    210                 215                 220

Ser Trp Ile Thr Phe Asp Leu Lys Asn Lys Glu Val Ser Val Lys Arg
225                 230                 235                 240

Val Thr Gln Asp Pro Lys Leu Gln Met Gly Lys Lys Leu Pro Leu His
                245                 250                 255

Leu Thr Leu Pro Gln Ala Leu Pro Gln Tyr Ala Gly Ser Gly Asn Leu
            260                 265                 270

Thr Leu Ala Leu Glu Ala Lys Thr Gly Lys Leu His Gln Glu Val Asn
        275                 280                 285

Leu Val Val Met Arg Ala Thr Gln Leu Gln Lys Asn Leu Thr Cys Glu
    290                 295                 300

Val Trp Gly Pro Thr Ser Pro Lys Leu Met Leu Ser Leu Lys Leu Glu
305                 310                 315                 320

Asn Lys Glu Ala Lys Val Ser Lys Arg Glu Lys Ala Val Trp Val Leu
                325                 330                 335

Asn Pro Glu Ala Gly Met Trp Gln Cys Leu Leu Ser Asp Ser Gly Gln
            340                 345                 350

Val Leu Leu Glu Ser Asn Ile Lys Val Leu Pro Thr Trp Glu Gln Lys
        355                 360                 365

Leu Ile Ser Glu Glu Asp Leu Asp Tyr Lys Asp Asp Asp Asp Lys
    370                 375                 380
```

<210> SEQ ID NO 77
<211> LENGTH: 450
<212> TYPE: PRT
<213> ORGANISM: Artificial Sequence
<220> FEATURE:
<223> OTHER INFORMATION: an artificially synthesized sequence

<400> SEQUENCE: 77

```
Gln Val Gln Leu Gln Gln Ser Gly Pro Glu Val Val Lys Pro Gly Ala
1               5                   10                  15

Ser Val Lys Met Ser Cys Lys Ala Ser Gly Tyr Thr Phe Thr Ser Tyr
                20                  25                  30

Val Ile His Trp Val Arg Gln Lys Pro Gly Gln Gly Leu Asp Trp Ile
            35                  40                  45

Gly Tyr Ile Asn Pro Tyr Asn Asp Gly Thr Asp Tyr Asp Glu Lys Phe
        50                  55                  60

Lys Gly Lys Ala Thr Leu Thr Ser Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Lys Asp Asn Tyr Ala Thr Gly Ala Trp Phe Ala Tyr Trp
            100                 105                 110

Gly Gln Gly Thr Leu Val Thr Val Ser Ser Ala Ser Thr Lys Gly Pro
```

```
                115                 120                 125
Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro
    450

<210> SEQ ID NO 78
<211> LENGTH: 219
<212> TYPE: PRT
<213> ORGANISM: Artificial Sequence
<220> FEATURE:
<223> OTHER INFORMATION: an artificially synthesized sequence

<400> SEQUENCE: 78

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Leu Tyr Ser
```

```
                20                  25                  30
Thr Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Val Gln Ala Glu Asp Val Ala Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 79
<211> LENGTH: 448
<212> TYPE: PRT
<213> ORGANISM: Artificial Sequence
<220> FEATURE:
<223> OTHER INFORMATION: an artificially synthesized sequence

<400> SEQUENCE: 79

Glu Val Gln Leu Val Glu Ser Gly Gly Asp Leu Val Lys Pro Gly Gly
 1               5                  10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Gly Leu Glu Trp Val
            35                  40                  45

Ala Thr Ile Ser Ser Gly Gly Ser Tyr Thr Tyr Tyr Pro Asp Asn Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                85                  90                  95

Ala Arg His Glu Asp Gly Asn Trp Asn Tyr Phe Asp Tyr Trp Gly Gln
            100                 105                 110

Gly Thr Thr Leu Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

```
                165                 170                 175
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

<210> SEQ ID NO 80
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 80

Glu Thr Thr Val Thr Gln Ser Pro Ala Ser Leu Ser Val Ala Ile Gly
1               5                   10                  15

Glu Lys Val Thr Ile Arg Cys Ile Thr Ser Thr Asp Ile Asp Asp Asp
            20                  25                  30

Met Asn Trp Tyr Gln Gln Lys Pro Gly Glu Pro Pro Lys Phe Phe Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Thr Leu Pro Leu
```

```
                85                  90                  95
Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 81
<211> LENGTH: 448
<212> TYPE: PRT
<213> ORGANISM: Artificial Sequence
<220> FEATURE:
<223> OTHER INFORMATION: an artificially synthesized sequence

<400> SEQUENCE: 81

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Gly Leu Glu Trp Val
        35                  40                  45

Ala Thr Ile Ser Ser Gly Gly Ser Tyr Thr Tyr Tyr Pro Asp Asn Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Glu Asp Gly Asn Trp Asn Tyr Phe Asp Tyr Trp Gly Gln
            100                 105                 110

Gly Thr Thr Leu Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
```

```
                225                 230                 235                 240
        Pro Ser Val Phe Leu Phe Pro Lys Pro Lys Asp Thr Leu Met Ile
                            245                 250                 255

Ser Arg Thr Pro Glu Val Thr Cys Val Val Asp Val Ser His Glu
                        260                 265                 270

Asp Pro Glu Val Lys Phe Asn Trp Tyr Val Asp Gly Val Glu Val His
                    275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
        305                 310                 315                 320

Glu Tyr Lys Cys Lys Val Ser Asn Lys Ala Leu Pro Ala Pro Ile Glu
                            325                 330                 335

Lys Thr Ile Ser Lys Ala Lys Gly Gln Pro Arg Glu Pro Gln Val Tyr
                        340                 345                 350

Thr Leu Pro Pro Ser Arg Asp Glu Leu Thr Lys Asn Gln Val Ser Leu
                    355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Lys Leu Thr Val Asp
                            405                 410                 415

Lys Ser Arg Trp Gln Gln Gly Asn Val Phe Ser Cys Ser Val Met His
                        420                 425                 430

Glu Ala Leu His Asn His Tyr Thr Gln Lys Ser Leu Ser Leu Ser Pro
                    435                 440                 445

<210> SEQ ID NO 82
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 82

Glu Thr Thr Val Thr Gln Ser Pro Ala Ser Leu Ser Val Ala Ile Gly
        1               5                   10                  15

Glu Lys Val Thr Ile Arg Cys Ile Thr Ser Thr Asp Ile Asp Asp Asp
                        20                  25                  30

Met Asn Trp Tyr Gln Gln Lys Pro Gly Glu Pro Pro Lys Phe Phe Ile
                    35                  40                  45

Ser Asn Gly Asn Thr Leu Arg Pro Gly Val Pro Ser Arg Phe Ser Ser
                50                  55                  60

Ser Gly Tyr Gly Thr Asp Phe Val Phe Thr Ile Glu Asn Met Leu Ser
        65                  70                  75                  80

Glu Asp Val Ala Asp Tyr Tyr Cys Leu Gln Ser Asp Thr Leu Pro Leu
                        85                  90                  95

Thr Phe Gly Ser Gly Thr Lys Leu Glu Ile Lys Arg Thr Val Ala Ala
                    100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
```

```
145                 150                 155                 160
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 83
<211> LENGTH: 464
<212> TYPE: PRT
<213> ORGANISM: Artificial Sequence
<220> FEATURE:
<223> OTHER INFORMATION: an artificially synthesized sequence

<400> SEQUENCE: 83

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
        50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
                100                 105                 110

Ser Leu Val Thr Val Ser Ser Ala Ser Pro Thr Ser Pro Lys Val Phe
                115                 120                 125

Pro Leu Ser Leu Cys Ser Thr Gln Pro Asp Gly Asn Val Val Ile Ala
                130                 135                 140

Cys Leu Val Gln Gly Phe Phe Pro Gln Glu Pro Leu Ser Val Thr Trp
145                 150                 155                 160

Ser Glu Ser Gly Gln Gly Val Thr Ala Arg Asn Phe Pro Pro Ser Gln
                165                 170                 175

Asp Ala Ser Gly Asp Leu Tyr Thr Thr Ser Ser Gln Leu Thr Leu Pro
                180                 185                 190

Ala Thr Gln Cys Leu Ala Gly Lys Ser Val Thr Cys His Val Lys His
                195                 200                 205

Tyr Thr Asn Pro Ser Gln Asp Val Thr Val Pro Cys Pro Val Pro Ser
                210                 215                 220

Thr Pro Pro Thr Pro Ser Pro Ser Thr Pro Pro Thr Pro Ser Pro Ser
225                 230                 235                 240

Cys Cys His Pro Arg Leu Ser Leu His Arg Pro Ala Leu Glu Asp Leu
                245                 250                 255

Leu Leu Gly Ser Glu Ala Asn Leu Thr Cys Thr Leu Thr Gly Leu Arg
                260                 265                 270

Asp Ala Ser Gly Val Thr Phe Thr Trp Thr Pro Ser Ser Gly Lys Ser
                275                 280                 285

Ala Val Gln Gly Pro Pro Glu Arg Asp Leu Cys Gly Cys Tyr Ser Val
```

```
                290                 295                 300
Ser Ser Val Leu Pro Gly Cys Ala Glu Pro Trp Asn His Gly Lys Thr
305                 310                 315                 320

Phe Thr Cys Thr Ala Ala Tyr Pro Glu Ser Lys Thr Pro Leu Thr Ala
                325                 330                 335

Thr Leu Ser Lys Ser Gly Asn Thr Phe Arg Pro Glu Val His Leu Leu
                340                 345                 350

Pro Pro Pro Ser Glu Glu Leu Ala Leu Asn Glu Leu Val Thr Leu Thr
                355                 360                 365

Cys Leu Ala Arg Gly Phe Ser Pro Lys Asp Val Leu Val Arg Trp Leu
                370                 375                 380

Gln Gly Ser Gln Glu Leu Pro Arg Glu Lys Tyr Leu Thr Trp Ala Ser
385                 390                 395                 400

Arg Gln Glu Pro Ser Gln Gly Thr Thr Thr Phe Ala Val Thr Ser Ile
                405                 410                 415

Leu Arg Val Ala Ala Glu Asp Trp Lys Lys Gly Asp Thr Phe Ser Cys
                420                 425                 430

Met Val Gly His Glu Ala Leu Pro Leu Ala Phe Thr Gln Lys Thr Ile
                435                 440                 445

Asp Arg Leu Ala Gly Lys Glu Gln Lys Leu Ile Ser Glu Glu Asp Leu
                450                 455                 460

<210> SEQ ID NO 84
<211> LENGTH: 450
<212> TYPE: PRT
<213> ORGANISM: Artificial Sequence
<220> FEATURE:
<223> OTHER INFORMATION: an artificially synthesized sequence

<400> SEQUENCE: 84

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
                35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Ala Pro Gly Asn Trp Gly Ser Pro Tyr Phe Asp Tyr Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
                130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
```

```
                195                 200                 205
    His Lys Pro Ser Asn Thr Lys Val Asp Lys Val Glu Pro Lys Ser
        210                 215                 220

Cys Asp Lys Thr His Thr Cys Pro Pro Cys Pro Ala Pro Glu Leu Leu
    225                 230                 235                 240

Gly Gly Pro Ser Val Phe Leu Phe Pro Pro Lys Pro Lys Asp Thr Leu
                    245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
    305                 310                 315                 320

Gly Lys Glu Tyr Lys Cys Lys Val Ser Asn Lys Ala Leu Pro Ala Pro
                    325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
    385                 390                 395                 400

Pro Val Leu Asp Ser Asp Gly Ser Phe Phe Leu Tyr Ser Lys Leu Thr
                    405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro
        450

<210> SEQ ID NO 85
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Asp Ser Ser Pro Leu
                85                  90                  95

Thr Phe Gly Gln Gly Thr Lys Val Glu Ile Lys Arg Thr Val Ala Ala
```

-continued

```
                100                 105                 110
Pro Ser Val Phe Ile Phe Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 86
<211> LENGTH: 451
<212> TYPE: PRT
<213> ORGANISM: Artificial Sequence
<220> FEATURE:
<223> OTHER INFORMATION: an artificially synthesized sequence

<400> SEQUENCE: 86

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
                20                  25                  30
Ala Ile Ser Trp Val Arg Gln Ala Pro Gly Gln Gly Leu Glu Trp Met
            35                  40                  45
Gly Gly Ile Ile Pro Ile Phe Gly Thr Ala Asn Tyr Ala Gln Lys Phe
        50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Pro Arg Trp Glu Thr Ala Ile Ser Ser Asp Ala Phe Asp Ile
            100                 105                 110
Trp Gly Gln Gly Thr Met Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
```

```
                     245                 250                 255
Leu Met Ile Ser Arg Thr Pro Glu Val Thr Cys Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
                370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro
        450

<210> SEQ ID NO 87
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Asp
                20                  25                  30

Leu Asn Trp Tyr Gln Gln Lys Pro Gly Lys Ala Pro Lys Leu Leu Ile
            35                  40                  45

Tyr Glu Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Ser Ser Ser Pro Leu
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
```

```
              145                 150                 155                 160
        Glu Ser Val Thr Glu Gln Asp Ser Lys Asp Ser Thr Tyr Ser Leu Ser
                            165                 170                 175
        Ser Thr Leu Thr Leu Ser Lys Ala Asp Tyr Glu Lys His Lys Val Tyr
                            180                 185                 190
        Ala Cys Glu Val Thr His Gln Gly Leu Ser Ser Pro Val Thr Lys Ser
                    195                 200                 205
        Phe Asn Arg Gly Glu Cys
                    210

<210> SEQ ID NO 88
<211> LENGTH: 448
<212> TYPE: PRT
<213> ORGANISM: Artificial Sequence
<220> FEATURE:
<223> OTHER INFORMATION: an artificially synthesized sequence

<400> SEQUENCE: 88

Gln Val Gln Leu Val Gln Ser Gly Ala Glu Val Lys Lys Pro Gly Ser
        1               5                   10                  15
        Ser Val Lys Val Ser Cys Lys Ala Ser Gly Gly Thr Phe Ser Ser Tyr
                        20                  25                  30
        Ala Ile Ser Trp Val Arg Gln Ala Pro Gly Gln Gly Leu Glu Trp Met
                    35                  40                  45
        Gly Gly Ile Ile Pro Ile Phe Gly Thr Ala Asn Tyr Ala Gln Lys Phe
                50                  55                  60
        Gln Gly Arg Val Thr Ile Thr Ala Asp Glu Ser Thr Ser Thr Ala Tyr
        65                  70                  75                  80
        Met Glu Leu Ser Ser Leu Arg Ser Glu Asp Thr Ala Val Tyr Tyr Cys
                        85                  90                  95
        Ala Arg Gly Asn Gly Asp Tyr Leu Glu Tyr Phe Gln His Trp Gly Gln
                    100                 105                 110
        Gly Thr Leu Val Thr Val Ser Ser Ala Ser Thr Lys Gly Pro Ser Val
                    115                 120                 125
        Phe Pro Leu Ala Pro Ser Ser Lys Ser Thr Ser Gly Gly Thr Ala Ala
                130                 135                 140
        Leu Gly Cys Leu Val Lys Asp Tyr Phe Pro Glu Pro Val Thr Val Ser
        145                 150                 155                 160
        Trp Asn Ser Gly Ala Leu Thr Ser Gly Val His Thr Phe Pro Ala Val
                        165                 170                 175
        Leu Gln Ser Ser Gly Leu Tyr Ser Leu Ser Ser Val Val Thr Val Pro
                    180                 185                 190
        Ser Ser Ser Leu Gly Thr Gln Thr Tyr Ile Cys Asn Val Asn His Lys
                    195                 200                 205
        Pro Ser Asn Thr Lys Val Asp Lys Lys Val Glu Pro Lys Ser Cys Asp
                210                 215                 220
        Lys Thr His Thr Cys Pro Pro Cys Pro Ala Pro Glu Leu Leu Gly Gly
        225                 230                 235                 240
        Pro Ser Val Phe Leu Phe Pro Pro Lys Pro Lys Asp Thr Leu Met Ile
                        245                 250                 255
        Ser Arg Thr Pro Glu Val Thr Cys Val Val Val Asp Val Ser His Glu
                    260                 265                 270
        Asp Pro Glu Val Lys Phe Asn Trp Tyr Val Asp Gly Val Glu Val His
                    275                 280                 285
        Asn Ala Lys Thr Lys Pro Arg Glu Glu Gln Tyr Asn Ser Thr Tyr Arg
```

```
        290                 295                 300
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

<210> SEQ ID NO 89
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Asp
                20                  25                  30

Leu Ala Trp Tyr Gln Gln Lys Pro Gly Lys Ala Pro Lys Leu Leu Ile
                35                  40                  45

Tyr Glu Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Arg Asp Ser Ser Pro Leu
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
```

<210> SEQ ID NO 90
<211> LENGTH: 452
<212> TYPE: PRT
<213> ORGANISM: Artificial Sequence
<220> FEATURE:
<223> OTHER INFORMATION: an artificially synthesized sequence

<400> SEQUENCE: 90

```
Gln Val Gln Leu Gln Gln Ser Gly Pro Gly Leu Val Lys Pro Ser Glu
1               5                   10                  15

Thr Leu Ser Leu Thr Cys Thr Ile Leu Gly Gly Ser Ile Ser Gly His
            20                  25                  30

Tyr Trp Ser Trp Ile Arg Gln Thr Pro Gly Lys Gly Leu Glu Trp Ile
        35                  40                  45

Gly Tyr Ile Asp Tyr Ser Gly Ser Thr His Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Met Tyr Tyr Cys Ala
                85                  90                  95

Arg Asp Asn Trp Asp Phe Gly Ser Gly Ser Tyr Tyr Asn Trp Phe Asp
            100                 105                 110

Pro Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
```

```
                355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro
    450

<210> SEQ ID NO 91
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 91

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Glu Asp Asp
            20                  25                  30
Leu Ala Trp Tyr Gln Gln Lys Pro Gly Lys Ala Pro Lys Leu Leu Ile
        35                  40                  45
Tyr His Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Asp Asn Ser Pro Leu
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 92
<211> LENGTH: 451
<212> TYPE: PRT
<213> ORGANISM: Artificial Sequence
<220> FEATURE:
<223> OTHER INFORMATION: an artificially synthesized sequence
```

<400> SEQUENCE: 92

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Arg Trp Glu Thr Ala Ile Ser Ser Asp Ala Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu

```
                        405                 410                 415
Thr Val Asp Lys Ser Arg Trp Gln Gln Gly Asn Val Phe Ser Cys Ser
            420                 425                 430

Val Met His Glu Ala Leu His Trp His Tyr Thr Gln Lys Ser Leu Ser
            435                 440                 445

Leu Ser Pro
    450

<210> SEQ ID NO 93
<211> LENGTH: 545
<212> TYPE: PRT
<213> ORGANISM: Artificial Sequence
<220> FEATURE:
<223> OTHER INFORMATION: an artificially synthesized sequence

<400> SEQUENCE: 93

Gln Pro Pro Pro Pro Pro Asp Ala Thr Cys His Gln Val Arg Ser
1               5                   10                  15

Phe Phe Gln Arg Leu Gln Pro Gly Leu Lys Trp Val Pro Glu Thr Pro
            20                  25                  30

Val Pro Gly Ser Asp Leu Gln Val Cys Leu Pro Lys Gly Pro Thr Cys
            35                  40                  45

Cys Ser Arg Lys Met Glu Glu Lys Tyr Gln Leu Thr Ala Arg Leu Asn
        50                  55                  60

Met Glu Gln Leu Leu Gln Ser Ala Ser Met Glu Leu Lys Phe Leu Ile
65                  70                  75                  80

Ile Gln Asn Ala Ala Val Phe Gln Glu Ala Phe Glu Ile Val Val Arg
                85                  90                  95

His Ala Lys Asn Tyr Thr Asn Ala Met Phe Lys Asn Asn Tyr Pro Ser
            100                 105                 110

Leu Thr Pro Gln Ala Phe Glu Phe Val Gly Glu Phe Phe Thr Asp Val
        115                 120                 125

Ser Leu Tyr Ile Leu Gly Ser Asp Ile Asn Val Asp Asp Met Val Asn
    130                 135                 140

Glu Leu Phe Asp Ser Leu Phe Pro Val Ile Tyr Thr Gln Leu Met Asn
145                 150                 155                 160

Pro Gly Leu Pro Asp Ser Ala Leu Asp Ile Asn Glu Cys Leu Arg Gly
                165                 170                 175

Ala Arg Arg Asp Leu Lys Val Phe Gly Asn Phe Pro Lys Leu Ile Met
            180                 185                 190

Thr Gln Val Ser Lys Ser Leu Gln Val Thr Arg Ile Phe Leu Gln Ala
        195                 200                 205

Leu Asn Leu Gly Ile Glu Val Ile Asn Thr Thr Asp His Leu Lys Phe
    210                 215                 220

Ser Lys Asp Cys Gly Arg Met Leu Thr Arg Met Trp Tyr Cys Ser Tyr
225                 230                 235                 240

Cys Gln Gly Leu Met Met Val Lys Pro Cys Gly Gly Tyr Cys Asn Val
                245                 250                 255

Val Met Gln Gly Cys Met Ala Gly Val Val Glu Ile Asp Lys Tyr Trp
            260                 265                 270

Arg Glu Tyr Ile Leu Ser Leu Glu Glu Leu Val Asn Gly Met Tyr Arg
        275                 280                 285

Ile Tyr Asp Met Glu Asn Val Leu Leu Gly Leu Phe Ser Thr Ile His
    290                 295                 300

Asp Ser Ile Gln Tyr Val Gln Lys Asn Ala Gly Lys Leu Thr Thr Thr
```

-continued

```
                305                 310                 315                 320
            Ile Gly Lys Leu Cys Ala His Ser Gln Gln Arg Gln Tyr Arg Ser Ala
                            325                 330                 335

Tyr Tyr Pro Glu Asp Leu Phe Ile Asp Lys Lys Val Leu Lys Val Ala
                            340                 345                 350

His Val Glu His Glu Thr Leu Ser Ser Arg Arg Arg Glu Leu Ile
                            355                 360                 365

Gln Lys Leu Lys Ser Phe Ile Ser Phe Tyr Ser Ala Leu Pro Gly Tyr
                            370                 375                 380

Ile Cys Ser His Ser Pro Val Ala Glu Asn Asp Thr Leu Cys Trp Asn
            385                 390                 395                 400

Gly Gln Glu Leu Val Glu Arg Tyr Ser Gln Lys Ala Ala Arg Asn Gly
                            405                 410                 415

Met Lys Asn Gln Phe Asn Leu His Glu Leu Lys Met Lys Gly Pro Glu
                            420                 425                 430

Pro Val Val Ser Gln Ile Ile Asp Lys Leu Lys His Ile Asn Gln Leu
                            435                 440                 445

Leu Arg Thr Met Ser Met Pro Lys Gly Arg Val Leu Asp Lys Asn Leu
                            450                 455                 460

Asp Glu Glu Gly Phe Glu Ala Gly Asp Cys Gly Asp Asp Glu Asp Glu
            465                 470                 475                 480

Cys Ile Gly Gly Ala Gly Asp Gly Met Ile Lys Val Lys Asn Gln Leu
                            485                 490                 495

Arg Phe Leu Ala Glu Leu Ala Tyr Asp Leu Asp Val Asp Asp Ala Pro
                            500                 505                 510

Gly Asn Ser Gln Gln Ala Thr Pro Lys Asp Asn Glu Ile Ser Thr Phe
                            515                 520                 525

His Asn Leu Gly Asn Val His Ser Pro Leu Lys His His His His
                            530                 535                 540

His
            545

<210> SEQ ID NO 94
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 94

Glu Val Gln Leu Val Glu Thr Gly Gly Gly Val Val Gln Pro Gly Arg
            1               5                   10                  15

Ser Leu Arg Leu Ser Cys Ala Ala Ser Gly Phe Thr Phe Ser Ser Tyr
                            20                  25                  30

Ala Met His Trp Val Arg Gln Ala Pro Gly Lys Gly Leu Glu Trp Val
                            35                  40                  45

Ala Val Ile Ser Tyr Asp Gly Ser Asn Lys Tyr Tyr Ala Asp Ser Val
                            50                  55                  60

Lys Gly Arg Phe Thr Ile Ser Arg Asp Asn Ser Lys Asn Thr Leu Tyr
            65                  70                  75                  80

Leu Gln Met Asn Ser Leu Arg Ala Glu Asp Thr Ala Val Tyr Tyr Cys
                            85                  90                  95

Ala Arg Gly Ala Gly Met Asp Val Trp Gly Gln Gly Thr Thr Val Thr
                            100                 105                 110

Val Ser Ser Ala Ser Thr Lys Gly Pro Ser Val Phe Pro Leu Ala Pro
```

```
            115                 120                 125
Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro
            435                 440

<210> SEQ ID NO 95
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
```

```
            35                  40                  45
Tyr Glu Ala Ser Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Asp Ser Tyr Pro Leu
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 96
<211> LENGTH: 459
<212> TYPE: PRT
<213> ORGANISM: Artificial Sequence
<220> FEATURE:
<223> OTHER INFORMATION: an artificially synthesized sequence

<400> SEQUENCE: 96

Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Pro Ala Gly Arg His Tyr Tyr Asp Ser Ser Gly Tyr Tyr
                100                 105                 110

Asp Tyr Tyr Tyr Gly Met Asp Val Trp Gly Gln Gly Thr Met Val Thr
            115                 120                 125

Val Ser Ser Ala Ser Thr Lys Gly Pro Ser Val Phe Pro Leu Ala Pro
        130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
```

```
                180             185                 190
Leu Tyr Ser Leu Ser Ser Val Val Thr Val Pro Ser Ser Leu Gly
            195                 200                 205

Thr Gln Thr Tyr Ile Cys Asn Val Asn His Lys Pro Ser Asn Thr Lys
            210                 215                 220

Val Asp Lys Lys Val Glu Pro Lys Ser Cys Asp Lys Thr His Thr Cys
225                 230                 235                 240

Pro Pro Cys Pro Ala Pro Glu Leu Leu Gly Gly Pro Ser Val Phe Leu
            245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
            275                 280                 285

Phe Asn Trp Tyr Val Asp Gly Val Glu Val His Asn Ala Lys Thr Lys
            290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
                340                 345                 350

Ala Lys Gly Gln Pro Arg Glu Pro Gln Val Tyr Thr Leu Pro Pro Ser
            355                 360                 365

Arg Asp Glu Leu Thr Lys Asn Gln Val Ser Leu Thr Cys Leu Val Lys
            370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro
            450                 455

<210> SEQ ID NO 97
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Asp
                20                  25                  30

Leu Asn Trp Tyr Gln Gln Lys Pro Gly Lys Ala Pro Lys Leu Leu Ile
            35                  40                  45

Tyr Glu Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Leu
```

```
                85                  90                  95
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 98
<211> LENGTH: 451
<212> TYPE: PRT
<213> ORGANISM: Artificial Sequence
<220> FEATURE:
<223> OTHER INFORMATION: an artificially synthesized sequence

<400> SEQUENCE: 98

Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Thr Pro Tyr Asp Phe Trp Ser Gly Tyr Leu Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Leu
```

```
              225                 230                 235                 240
Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
                370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro
        450

<210> SEQ ID NO 99
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
                20                  25                  30

Leu Ala Trp Tyr Gln Gln Lys Pro Gly Lys Ala Pro Lys Leu Leu Ile
                35                  40                  45

Tyr Glu Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Asp Ser Ser Pro Leu
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
```

```
            130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 100
<211> LENGTH: 451
<212> TYPE: PRT
<213> ORGANISM: Artificial Sequence
<220> FEATURE:
<223> OTHER INFORMATION: an artificially synthesized sequence

<400> SEQUENCE: 100

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Pro Leu Leu Trp Phe Gly Pro Phe Phe Asp Tyr
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
```

```
                275                 280                 285
Glu Val His Asn Ala Lys Thr Lys Pro Arg Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
                370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro
         450

<210> SEQ ID NO 101
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
                20                  25                  30

Leu Ala Trp Tyr Gln Gln Lys Pro Gly Lys Ala Pro Lys Leu Leu Ile
                35                  40                  45

Tyr His Ala Ser Thr Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Tyr Pro Leu
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
                180                 185                 190
Ala Cys Glu Val Thr His Gln Gly Leu Ser Ser Pro Val Thr Lys Ser
            195                 200                 205

Phe Asn Arg Gly Glu Cys
        210

<210> SEQ ID NO 102
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
```

325                 330                 335
Ala Lys Gly Gln Pro Arg Glu Pro Gln Val Tyr Thr Leu Pro Pro Ser
                    340                 345                 350

Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro
                435                 440

<210> SEQ ID NO 103
<211> LENGTH: 219
<212> TYPE: PRT
<213> ORGANISM: Artificial Sequence
<220> FEATURE:
<223> OTHER INFORMATION: an artificially synthesized sequence

<400> SEQUENCE: 103

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Arg Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 104
<211> LENGTH: 567
<212> TYPE: PRT

<213> ORGANISM: Artificial Sequence
<220> FEATURE:
<223> OTHER INFORMATION: an artificially synthesized sequence

<400> SEQUENCE: 104

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Gln Ser Pro Ser Val Phe
        115                 120                 125

Pro Leu Thr Arg Cys Cys Lys Asn Ile Pro Ser Asn Ala Thr Ser Val
    130                 135                 140

Thr Leu Gly Cys Leu Ala Thr Gly Tyr Phe Pro Glu Pro Val Met Val
145                 150                 155                 160

Thr Trp Asp Thr Gly Ser Leu Asn Gly Thr Thr Met Thr Leu Pro Ala
                165                 170                 175

Thr Thr Leu Thr Leu Ser Gly His Tyr Ala Thr Ile Ser Leu Leu Thr
            180                 185                 190

Val Ser Gly Ala Trp Ala Lys Gln Met Phe Thr Cys Arg Val Ala His
        195                 200                 205

Thr Pro Ser Ser Thr Asp Trp Val Asp Asn Lys Thr Phe Ser Val Cys
    210                 215                 220

Ser Arg Asp Phe Thr Pro Pro Thr Val Lys Ile Leu Gln Ser Ser Cys
225                 230                 235                 240

Asp Gly Gly Gly His Phe Pro Pro Thr Ile Gln Leu Leu Cys Leu Val
                245                 250                 255

Ser Gly Tyr Thr Pro Gly Thr Ile Asn Ile Thr Trp Leu Glu Asp Gly
            260                 265                 270

Gln Val Met Asp Val Asp Leu Ser Thr Ala Ser Thr Thr Gln Glu Gly
        275                 280                 285

Glu Leu Ala Ser Thr Gln Ser Glu Leu Thr Leu Ser Gln Lys His Trp
    290                 295                 300

Leu Ser Asp Arg Thr Tyr Thr Cys Gln Val Thr Tyr Gln Gly His Thr
305                 310                 315                 320

Phe Glu Asp Ser Thr Lys Lys Cys Ala Asp Ser Asn Pro Arg Gly Val
                325                 330                 335

Ser Ala Tyr Leu Ser Arg Pro Ser Pro Phe Asp Leu Phe Ile Arg Lys
            340                 345                 350

Ser Pro Thr Ile Thr Cys Leu Val Asp Leu Ala Pro Ser Lys Gly
    355                 360                 365

Thr Val Asn Leu Thr Trp Ser Arg Ala Ser Gly Lys Pro Val Asn His
370                 375                 380

Ser Thr Arg Lys Glu Glu Lys Gln Arg Asn Gly Thr Leu Thr Val Thr
```

```
                385                 390                 395                 400
Ser Thr Leu Pro Val Gly Thr Arg Asp Trp Ile Glu Gly Glu Thr Tyr
                405                 410                 415

Gln Cys Arg Val Thr His Pro His Leu Pro Arg Ala Leu Met Arg Ser
                420                 425                 430

Thr Thr Lys Thr Ser Gly Pro Arg Ala Ala Pro Glu Val Tyr Ala Phe
                435                 440                 445

Ala Thr Pro Glu Trp Pro Gly Ser Arg Asp Lys Arg Thr Leu Ala Cys
        450                 455                 460

Leu Ile Gln Asn Phe Met Pro Glu Asp Ile Ser Val Gln Trp Leu His
465                 470                 475                 480

Asn Glu Val Gln Leu Pro Asp Ala Arg His Ser Thr Thr Gln Pro Arg
                485                 490                 495

Lys Thr Lys Gly Ser Gly Phe Phe Val Phe Ser Arg Leu Glu Val Thr
                500                 505                 510

Arg Ala Glu Trp Glu Gln Lys Asp Glu Phe Ile Cys Arg Ala Val His
                515                 520                 525

Glu Ala Ala Ser Pro Ser Gln Thr Val Gln Arg Ala Val Ser Val Asn
        530                 535                 540

Pro Gly Lys Gly Gly Gly Ser Gly Leu Asn Asp Ile Phe Glu Ala
545                 550                 555                 560

Gln Lys Ile Glu Trp His Glu
                565
```

<210> SEQ ID NO 105
<211> LENGTH: 438
<212> TYPE: PRT
<213> ORGANISM: Artificial Sequence
<220> FEATURE:
<223> OTHER INFORMATION: an artificially synthesized sequence

<400> SEQUENCE: 105

```
Gln Ser Leu Glu Glu Ser Gly Gly Asp Leu Val Lys Pro Gly Gly Thr
1               5                   10                  15

Leu Thr Leu Thr Cys Thr Ala Ser Gly Tyr Asp Phe Ser Ser Ala Tyr
                20                  25                  30

Asp Met Cys Trp Val Arg Gln Ala Pro Gly Lys Gly Leu Glu Trp Ile
                35                  40                  45

Ala Cys Ile Tyr Thr Gly Asp Gly Val Thr Tyr Tyr Ala Ser Trp Ala
        50                  55                  60

Lys Gly Arg Phe Thr Ile Ser Lys Thr Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Gly Gly Asp Tyr Tyr Asp Leu Trp Gly Pro Gly Thr Leu Val Thr
                100                 105                 110

Val Ser Ser Gly Gln Pro Lys Ala Pro Ser Val Phe Pro Leu Ala Pro
                115                 120                 125

Cys Cys Gly Asp Thr Pro Ser Ser Thr Val Thr Leu Gly Cys Leu Val
        130                 135                 140

Lys Gly Tyr Leu Pro Glu Pro Val Thr Val Thr Trp Asn Ser Gly Thr
145                 150                 155                 160

Leu Thr Asn Gly Val Arg Thr Phe Pro Ser Val Arg Gln Ser Ser Gly
                165                 170                 175

Leu Tyr Ser Leu Ser Ser Val Val Ser Val Thr Ser Ser Ser Gln Pro
```

```
            180                 185                 190
Val Thr Cys Asn Val Ala His Pro Ala Thr Asn Thr Lys Val Asp Lys
            195                 200                 205

Thr Val Ala Pro Ser Thr Cys Ser Lys Pro Met Cys Pro Pro Pro Glu
            210                 215                 220

Leu Leu Gly Gly Pro Ser Val Phe Ile Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser Gln Asp Asp Pro Glu Val Gln Phe Thr Trp Tyr Ile Asn Asn
            260                 265                 270

Glu Gln Val Arg Thr Ala Arg Pro Pro Leu Arg Glu Gln Gln Phe Asn
            275                 280                 285

Ser Thr Ile Arg Val Val Ser Thr Leu Pro Ile Ala His Gln Asp Trp
            290                 295                 300

Leu Arg Gly Lys Glu Phe Lys Cys Lys Val His Asn Lys Ala Leu Pro
305                 310                 315                 320

Ala Pro Ile Glu Lys Thr Ile Ser Lys Ala Arg Gly Gln Pro Leu Glu
                325                 330                 335

Pro Lys Val Tyr Thr Met Gly Pro Pro Arg Glu Glu Leu Ser Ser Arg
            340                 345                 350

Ser Val Ser Leu Thr Cys Met Ile Asn Gly Phe Tyr Pro Ser Asp Ile
            355                 360                 365

Ser Val Glu Trp Glu Lys Asn Gly Lys Ala Glu Asp Asn Tyr Lys Thr
            370                 375                 380

Thr Pro Thr Val Leu Asp Ser Asp Gly Ser Tyr Phe Leu Tyr Ser Lys
385                 390                 395                 400

Leu Ser Val Pro Thr Ser Glu Trp Gln Arg Gly Asp Val Phe Thr Cys
                405                 410                 415

Ser Val Met His Glu Ala Leu His Asn His Tyr Thr Gln Lys Ser Ile
            420                 425                 430

Ser Arg Ser Pro Gly Lys
            435

<210> SEQ ID NO 106
<211> LENGTH: 215
<212> TYPE: PRT
<213> ORGANISM: Artificial Sequence
<220> FEATURE:
<223> OTHER INFORMATION: an artificially synthesized sequence

<400> SEQUENCE: 106

Ala Ile Val Met Thr Gln Thr Pro Ser Ser Lys Ser Val Pro Val Gly
1               5                   10                  15

Asp Thr Val Thr Ile Asn Cys Gln Ala Ser Glu Ser Val Tyr Ser Asn
            20                  25                  30

Tyr Leu Ala Trp Phe Gln Gln Lys Pro Gly Pro Pro Lys Arg Leu
            35                  40                  45

Ile Tyr Gly Ala Ser Thr Leu Asp Ser Gly Val Ser Ser Arg Phe Lys
        50                  55                  60

Gly Ser Gly Ser Gly Thr Gln Phe Thr Leu Thr Ile Asn Asp Val Gln
65                  70                  75                  80

Cys Asp Asp Ala Ala Thr Tyr Tyr Cys Ala Gly Tyr Lys Ser Asp Asn
                85                  90                  95

Thr Asp Gly Ile Ala Phe Gly Gly Gly Thr Glu Val Val Val Lys Gly
```

```
            100                 105                 110
Asp Pro Val Ala Pro Thr Val Leu Ile Phe Pro Pro Ala Ala Asp Gln
        115                 120                 125

Val Ala Thr Gly Thr Val Thr Ile Val Cys Val Ala Asn Lys Tyr Phe
130                 135                 140

Pro Asp Val Thr Val Thr Trp Glu Val Asp Gly Thr Thr Gln Thr Thr
145                 150                 155                 160

Gly Ile Glu Asn Ser Lys Thr Pro Gln Asn Ser Ala Asp Cys Thr Tyr
                165                 170                 175

Asn Leu Ser Ser Thr Leu Thr Leu Thr Ser Thr Gln Tyr Asn Ser His
            180                 185                 190

Lys Glu Tyr Thr Cys Lys Val Thr Gln Gly Thr Thr Ser Val Val Gln
        195                 200                 205

Ser Phe Asn Arg Gly Asp Cys
    210                 215

<210> SEQ ID NO 107
<211> LENGTH: 448
<212> TYPE: PRT
<213> ORGANISM: Artificial Sequence
<220> FEATURE:
<223> OTHER INFORMATION: an artificially synthesized sequence

<400> SEQUENCE: 107

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Asp
            20                  25                  30

Met Ser Trp Val Arg Gln Ala Pro Gly Lys Gly Leu Glu Trp Ile Gly
        35                  40                  45

Asp Ile Asp Thr Thr Thr Gly Thr Thr Ile Tyr Ala Thr Trp Ala Lys
    50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Arg Cys
                85                  90                  95

Ala Gly Gly Thr Gly Tyr Cys Glu Asp Gly Leu Asp Pro Trp Gly Pro
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
```

```
                    245                 250                 255
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

<210> SEQ ID NO 108
<211> LENGTH: 217
<212> TYPE: PRT
<213> ORGANISM: Artificial Sequence
<220> FEATURE:
<223> OTHER INFORMATION: an artificially synthesized sequence

<400> SEQUENCE: 108

Ala Phe Asp Met Thr Gln Thr Pro Ala Ser Val Glu Val Ala Val Gly
1               5                   10                  15

Gly Thr Val Thr Ile Asn Cys Gln Ala Ser Gln Ser Ile Gly Ser Tyr
            20                  25                  30

Leu Thr Trp Tyr Gln Gln Lys Pro Gly Gln Pro Pro Lys Leu Leu Ile
        35                  40                  45

Tyr Arg Ala Ser Thr Leu Ala Ser Gly Val Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gln Asp Tyr Ser Gly Ser Asn
                85                  90                  95

Val Asp Asn Ile Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
```

```
                    165                 170                 175
Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 109
<211> LENGTH: 448
<212> TYPE: PRT
<213> ORGANISM: Artificial Sequence
<220> FEATURE:
<223> OTHER INFORMATION: an artificially synthesized sequence

<400> SEQUENCE: 109

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Asp
            20                  25                  30

Met Ser Trp Val Arg Gln Ala Pro Gly Lys Gly Leu Glu Trp Ile Gly
        35                  40                  45

Asp Ile Asp Thr Ala Ser Gly Thr Thr Ile Tyr Ala Ser Trp Ala Lys
    50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Arg Cys
                85                  90                  95

Ala Gly Ser Ser Gly Tyr Cys Glu Asn Gly Leu Asp Pro Trp Gly Pro
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
```

```
                305                 310                 315                 320
        Glu Tyr Lys Cys Lys Val Ser Asn Lys Ala Leu Pro Ala Pro Ile Glu
                        325                 330                 335

Lys Thr Ile Ser Lys Ala Lys Gly Gln Pro Arg Glu Pro Gln Val Tyr
                        340                 345                 350

Thr Leu Pro Pro Ser Arg Glu Glu Met Thr Lys Asn Gln Val Ser Leu
                        355                 360                 365

Thr Cys Leu Val Lys Gly Phe Tyr Pro Ser Asp Ile Ala Val Glu Trp
                        370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Lys Leu Thr Val Asp
                        405                 410                 415

Lys Ser Arg Trp Gln Gln Gly Asn Val Phe Ser Cys Ser Val Met His
                        420                 425                 430

Glu Ala Leu His Asn His Tyr Thr Gln Lys Ser Leu Ser Leu Ser Pro
                        435                 440                 445

<210> SEQ ID NO 110
<211> LENGTH: 217
<212> TYPE: PRT
<213> ORGANISM: Artificial Sequence
<220> FEATURE:
<223> OTHER INFORMATION: an artificially synthesized sequence

<400> SEQUENCE: 110

Ala Ile Glu Met Thr Gln Thr Pro Phe Ser Val Ser Ala Thr Val Gly
        1               5                   10                  15

Gly Thr Val Thr Ile Asn Cys Gln Ala Ser Gln Asn Ile Asn Asp Tyr
                        20                  25                  30

Leu Ser Trp Tyr Gln Gln Lys Pro Gly Gln Pro Pro Lys Leu Leu Ile
                        35                  40                  45

Tyr Lys Ala Ser Thr Leu Ala Ser Gly Val Ser Arg Phe Lys Gly Ser
                50                  55                  60

Ser Gly Ser Gly Thr Glu Phe Thr Leu Thr Ile Ser Asp Leu Glu Cys
        65                  70                  75                  80

Ala Asp Ala Ala Thr Tyr Tyr Cys Gln Gln Asp Tyr Ser Gly Ser Asp
                        85                  90                  95

Val Asp Asn Ile Phe Gly Gly Gly Thr Glu Val Val Val Lys Arg Thr
                        100                 105                 110

Val Ala Ala Pro Ser Val Phe Ile Phe Pro Pro Ser Asp Glu Gln Leu
                        115                 120                 125

Lys Ser Gly Thr Ala Ser Val Val Cys Leu Leu Asn Asn Phe Tyr Pro
                130                 135                 140

Arg Glu Ala Lys Val Gln Trp Lys Val Asp Asn Ala Leu Gln Ser Gly
        145                 150                 155                 160

Asn Ser Gln Glu Ser Val Thr Glu Gln Asp Ser Lys Asp Ser Thr Tyr
                        165                 170                 175

Ser Leu Ser Ser Thr Leu Thr Leu Ser Lys Ala Asp Tyr Glu Lys His
                        180                 185                 190

Lys Val Tyr Ala Cys Glu Val Thr His Gln Gly Leu Ser Ser Pro Val
                        195                 200                 205

Thr Lys Ser Phe Asn Arg Gly Glu Cys
                210                 215
```

<210> SEQ ID NO 111
<211> LENGTH: 449
<212> TYPE: PRT
<213> ORGANISM: Artificial Sequence
<220> FEATURE:
<223> OTHER INFORMATION: an artificially synthesized sequence

<400> SEQUENCE: 111

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Asn Pro Ser Val
    50                  55                  60

Lys Gly Arg Ile Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Gly Ser His Tyr Phe Gly His Trp His Phe Ala Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
```

370                 375                 380
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro

<210> SEQ ID NO 112
<211> LENGTH: 218
<212> TYPE: PRT
<213> ORGANISM: Artificial Sequence
<220> FEATURE:
<223> OTHER INFORMATION: an artificially synthesized sequence

<400> SEQUENCE: 112

Asp Ile Gln Leu Thr Gln Ser Pro Ser Leu Ser Ala Ser Val Gly
1               5                   10                  15

Asp Arg Val Thr Ile Thr Cys Arg Ala Ser Gln Ser Val Asp Tyr Asp
                20                  25                  30

Gly Asp Ser Tyr Met Asn Trp Tyr Gln Gln Lys Pro Gly Lys Ala Pro
            35                  40                  45

Lys Leu Leu Ile Tyr Ala Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
                210                 215

```
<210> SEQ ID NO 113
<211> LENGTH: 19
<212> TYPE: PRT
<213> ORGANISM: Artificial sequence
<220> FEATURE:
<223> OTHER INFORMATION: an artificially synthesized sequence

<400> SEQUENCE: 113

Met Gly Trp Ser Cys Ile Ile Leu Phe Leu Val Ala Thr Ala Thr Gly
1               5                   10                  15

Val His Ser
```